US011760984B2

(12) United States Patent
Choudhary et al.

(10) Patent No.: US 11,760,984 B2
(45) Date of Patent: Sep. 19, 2023

(54) CRISPR PROTEIN INHIBITORS

(71) Applicants:THE BROAD INSTITUTE, INC., Cambridge, MA (US); THE BRIGHAM AND WOMEN'S HOSPITAL, INC., Boston, MA (US); THE REGENTS OF THE UNIVERSITY OF CALIFORNIA, Oakland, CA (US)

(72) Inventors: Amit Choudhary, Boston, MA (US); Kurt Cox, Cambridge, MA (US); Basudeb Maji, Cambridge, MA (US); Peng Wu, Boston, MA (US); Hari Subramanian, Oakland, CA (US); Elisa Franco, Oakland, CA (US)

( * ) Notice: Subject to any disclaimer, the term of this patent is extended or adjusted under 35 U.S.C. 154(b) by 254 days.

(21) Appl. No.: 16/760,425

(22) PCT Filed: Oct. 31, 2018

(86) PCT No.: PCT/US2018/058466
§ 371 (c)(1),
(2) Date: Apr. 29, 2020

(87) PCT Pub. No.: WO2019/089761
PCT Pub. Date: May 9, 2019

(65) Prior Publication Data
US 2020/0354701 A1 Nov. 12, 2020

Related U.S. Application Data

(60) Provisional application No. 62/579,836, filed on Oct. 31, 2017, provisional application No. 62/579,727, filed on Oct. 31, 2017.

(51) Int. Cl.
*C12N 9/22* (2006.01)
*C12Q 1/6837* (2018.01)
(52) U.S. Cl.
CPC ............. *C12N 9/22* (2013.01); *C12Q 1/6837* (2013.01); *C12N 2310/20* (2017.05)
(58) Field of Classification Search
None
See application file for complete search history.

(56) References Cited

U.S. PATENT DOCUMENTS

| 6,207,397 | B1 | 3/2001 | Lynch |
| 2012/0252699 | A1 | 10/2012 | Jaffrey |
| 2014/0220560 | A1 | 8/2014 | Jaffrey |
| 2015/0356239 | A1 | 12/2015 | Zhang |

FOREIGN PATENT DOCUMENTS

| WO | 2010131115 | A1 | 11/2010 |
| WO | 2016205745 | A2 | 12/2016 |
| WO | 2017035416 | A2 | 3/2017 |
| WO | 2018085288 | A1 | 5/2018 |

OTHER PUBLICATIONS

Burke, et al., "A Planning Strategy for Diversity-Oriented Synthesis", Angewandte Chemie International Edition, vol. 43, No. 1, Jan. 2004, 46-58.
Comer, et al., "Fragment-Based Domain Shuffling Approach for the Synthesis of Pyran-Based Macrocycles", PNAS, vol. 108, No. 17, Apr. 26, 2011, 6751-6756.
Davis, et al., "Small Molecule-Triggered Cas9 Protein with Improved Genome-Editing Specificity", Nature Chemical Biology, vol. 11, No. 5, May 2015, 9 pages.
Fu, et al., "High-Frequency Off-Target Mutagenesis Induced by CRISPR-Cas Nucleases in Human Cells", Nature Biotechnology, vol. 31, No. 9, Sep. 2013, 822-826.
Gonzalez, et al., "An iCRISPR Platform for Rapid, Multiplexable, and Inducible Genome Editing in Human Pluripotent Stem Cells", Cell Stem Cell, vol. 15, No. 2, Aug. 7, 2014, 27 pages.
Heler, et al., "Cas9 Specifies Functional Viral Targets During CRISPR-Cas Adaptation", Nature, vol. 519, No. 7542, Mar. 12, 2015, 31 pages.
Jinek, et al., "A Programmable Dual-RNA-Guided DNA Endonuclease in Adaptive Bacterial Immunity", Science, vol. 337, No. 6096, Aug. 17, 2012, 816-821.
Kleinstiver, et al., "Engineered Crispr-Cas9 Nucleases with Altered Pam Specificities", Nature, vol. 523, No. 7561, Jul. 23, 2015, 17 pages.
Lowe, et al., "Synthesis and Profiling of a Diverse Collection of Azetidine-Based Scaffolds for the Development of CNS-Focused Lead-Like Libraries", The Journal of Organic Chemistry, vol. 77, No. 17, Sep. 7, 2012, 58 pages.
Lundblad, et al., "Fluorescence Polarization Analysis of Protein-DNA and Protein-Protein Interactions", Molecular Endocrinology, vol. 10, No. 6, Jun. 1996, 607-612.
Maji, et al., "Multidimensional Chemical Control of CRISPR-Cas9", Nature Chemical Biology, vol. 13, No. 1, Jan. 2017, 11 pages.
Marcaurelle, et al., "An Aldol-Based Build/Couple/Pair Strategy for the Synthesis of Medium- and Large-Sized Rings: Discovery of Macrocyclic Histone Deacetylase Inhibitors", Journal of the American Chemical Society, vol. 132, No. 47, Dec. 1, 2010, 35 pages.
Moore, et al., "CRISPR-Based Self-Cleaving Mechanism for Controllable Gene Delivery in Human Cells", Nucleic Acids Research, vol. 43, No. 2, 2015, 1297-1303.

(Continued)

*Primary Examiner* — Richard G Hutson
(74) *Attorney, Agent, or Firm* — F. Brent Nix, Esq.; Johnson, Marcou, Isaacs & Nix, LLC

(57) ABSTRACT

The embodiments disclosed herein utilize fluorescence polarization based preliminary screen to identify a putative set of Cas inhibitors from an initial set of candidate inhibitors. The primary screening assay is followed by secondary screening assay to validate the putative set of inhibitors selected by the preliminary screen. In some embodiments, the present disclosure includes compositions and methods are provided for the inhibition of the function of RNA guided endonucleases, including the identification and use of such inhibitors.

14 Claims, 136 Drawing Sheets
Specification includes a Sequence Listing.

(56) References Cited

OTHER PUBLICATIONS

Nguyen, et al., "Ligand-Binding Domains of Nuclear Receptors Facilitate Tight Control of Split CRISPR Activity", Nature Communications, vol. 7, No. 12009, Jul. 1, 2016, 10 pages.
Niesen, et al., "The Use of Differential Scanning Fluorimetry to Detect Ligand Interactions that Promote Protein Stability", Nature Protocols, vol. 2, No. 9, Sep. 13, 2007, 2212-2221.
Nishimasu, et al., "Crystal Structure of Cas9 in Complex with Guide RNA and Target DNA", Cell, vol. 156, No. 5, Feb. 27, 2014, 25 pages.
Nunez, et al., "Chemical and Biophysical Modulation of Cas9 for Tunable Genome Engineering", ACS Chemical Biology, vol. 11, Issue 3, Feb. 9, 2016, 8 pages.
Nunez, et al., "Integrase-Mediated Spacer Acquisition during CRISPR-Cas Adaptive Immunity", Nature, vol. 519, No. 7542, Mar. 12, 2015, 17 pages.
Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 16 pages.
Pawluk, et al., "Inactivation of CRISPR-Cas Systems by Anti-CRISPR Proteins in Diverse Bacterial Species", Nature Microbiology, vol. 1, No. 16085, Jun. 13, 2016, 6 pages.
Pawluk, et al., "Naturally Occurring Off-Switches for CRISPR-Cas9", Cell, vol. 167, No. 7, Dec. 15, 2016, 19 pages.
Rauch, et al., "Inhibition of CRISPR-Cas9 with Bacteriophage Proteins", Cell, vol. 168, No. (1-2), Jan. 12, 2017, 26 pages.
Richardson, et al., "Enhancing Homology-Directed Genome Editing by Catalytically Active and Inactive Crispr-Cas9 using Asymmetric Donor DNA", Nature Biotechnology, vol. 34, No. 3, Mar. 2016, 339-344.
Senis, et al., "CRISPR/Cas9-Mediated Genome Engineering: An Adeno-Associated Viral (AAV) Vector Toolbox", Biotechnology Journal, vol. 9, No. 11, Nov. 2014, 32 pages.
Shortridge, et al., "Estimating Protein-Ligand Binding Affinity using High-Throughput Screening by NMR", Journal of Combinatorial Chemistry, vol. 10, No. 6, 24 pages., Nov.-Dec. 2008.
Tan, et al., "Indium-Mediated Asymmetric Allylation of Acylhydrazones using a Chiral Urea Catalyst", Angewandte Chemie International Edition, vol. 46, No. 8, Jan. 9, 2007, 1315-1317.

Wright, et al., "Rational Design of a Split-Cas9 Enzyme Complex", Proceedings of the National Academy of Sciences of the United States of America, vol. 112, No. 10, Mar. 10, 2015, 2984-2989.
Zetsche, et al., "A Split-Cas9 Architecture for Inducible Genome Editing and Transcription Modulation", Nature Biotechnology, vol. 33, No. 2, Feb. 2015, 139-142.
International Search Report and Written Opinion issued by the U.S. Patent Office dated Jan. 16, 2019 for PCT/US2018/058466.
Harrington, et al., "A Broad-Spectrum Inhibitor of CRISPR-Cas9," Cell, Aug. 24, 2017 (Aug. 24, 2017), vol. 170, No. 6, pp. 1224-1233.
Hirano, et al., "Structural Basis for the Altered PAM Specificities of Engineered CRISPR-Cas9," Mol. Cell, Mar. 17, 2016 (Mar. 17, 2016), vol. 61, No. 6, pp. 886-894.
Hirano, et al., "Structure and Engineering of Francisella novicida Cas9," Cell, Feb. 11, 2016 (Feb. 11, 2016), vol. 164, No. 5, pp. 950-961.
Malina, et al., "PAM multiplicity marks genomic target sites as inhibitory to CRISPR-Cas9 editing," Nat. Commun, Dec. 8, 2015 (Dec. 8, 2015), vol. 6, No. 10124, pp. 1-6.
Nishimasu, et al., "Crystal Structure of *Staphylococcus aureus* Cas9," Cell, Aug. 27, 2015 (Aug. 27, 2015), vol. 162, No. 5, pp. 1113-1126., Aug. 27, 2015.
Nishimasu, et al., "Structural Basis for the Altered PAM Recognition by Engineered CRISPR-Cpf1," Mol. Cell, Jun. 6, 2017 (Jun. 6, 2017), vol. 67, No. 1, pp. 139-147.
Shin, et al., "Disabling Cas9 by an anti-CRISPR DNA mimic," Science Advances, Jul. 12, 2017 (Jul. 12, 2017), vol. 3, No. 7, e1701620, pp. 1-9.
Sternberg, et al., "DNA interrogation by the CRISPR RNA-guided endonuclease Cas9," Nature, Jan. 29, 2014 (Jan. 29, 2014), vol. 507, No. 7490, pp. 62-67.
Yamano, et al., "Structural Basis for the Canonical and Non-canonical PAM Recognition by CRISPR-Cpf1," Mol. Cell, Aug. 3, 2017 (Aug. 3, 2017), vol. 67, No. 4, pp. 633-645.
"International Preliminary Report on Patentability", PCT/US2018/058466.
Cox, et al., "A universal method for sensitive and cell-free detection of CRISPR-associated nucleases", Chem. Sci., vol. 10, pp. 2653-2662, Accepted: Dec. 28, 2018.
Maji, et al., "A high-throughput platform to identify small-molecule inhibitors of CRISPR-Cas9", Cell, vol. 177, No. 4, May 2, 2019, pp. 1067-1079.

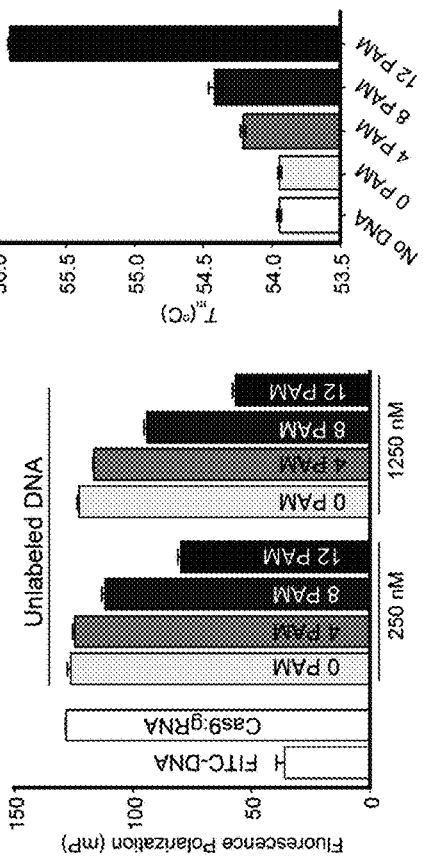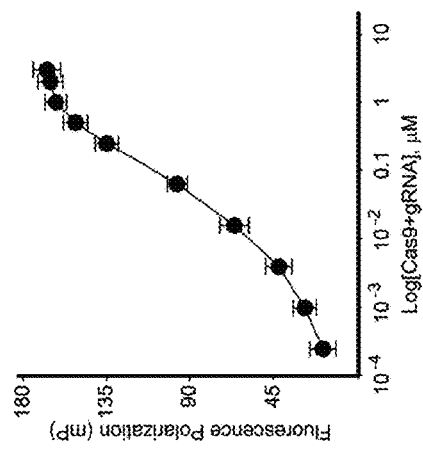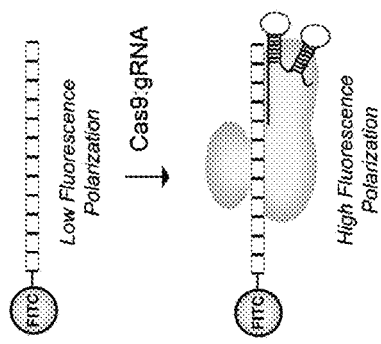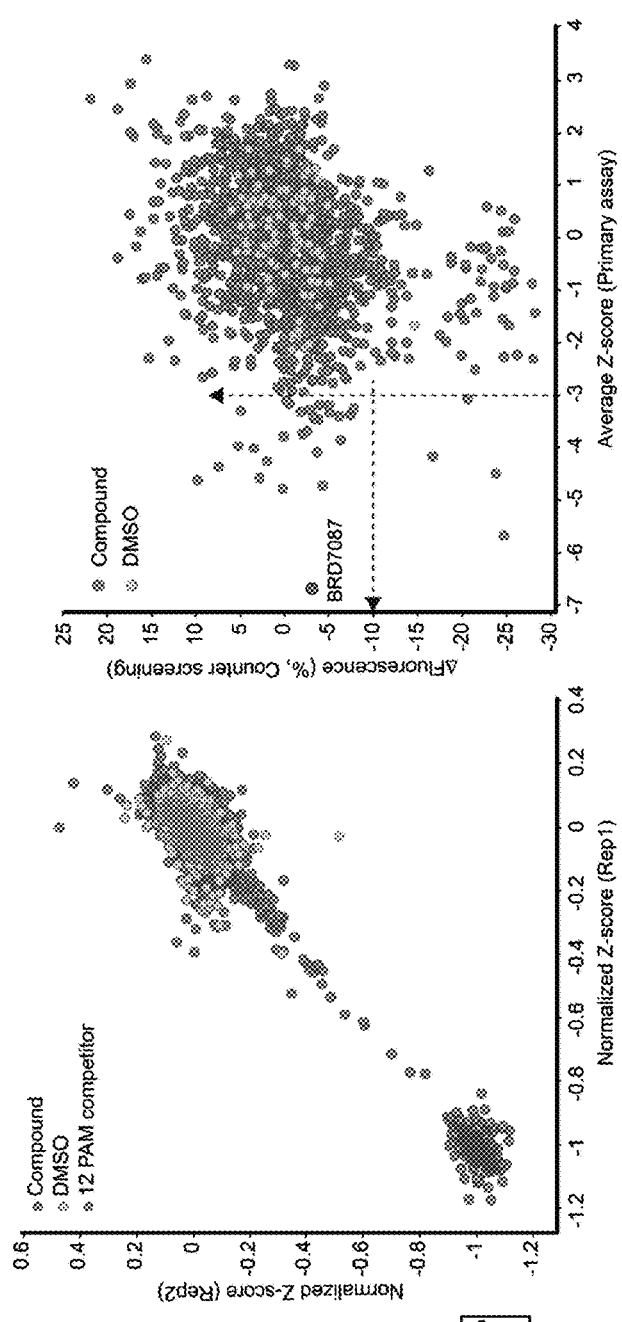

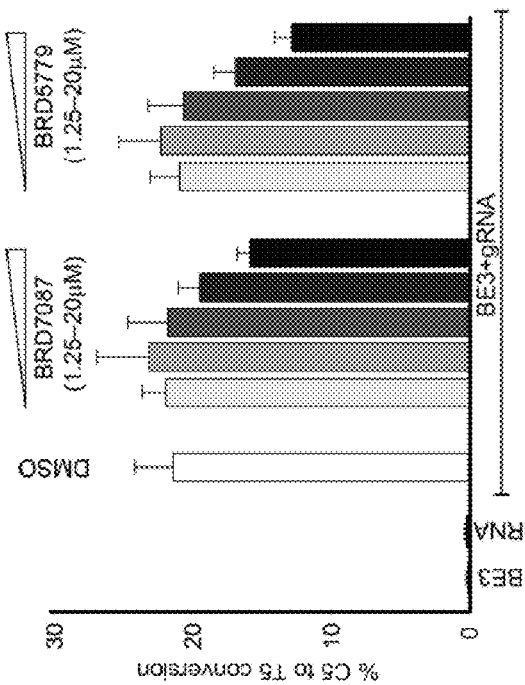
FIG. 3A
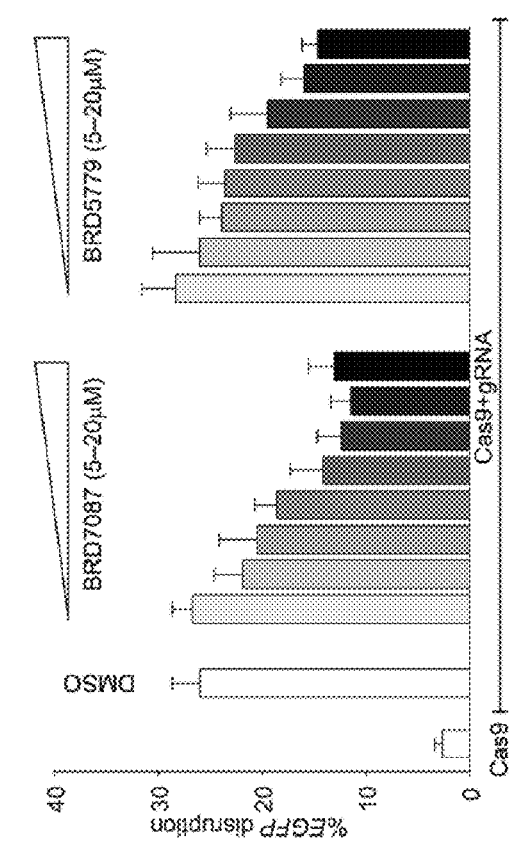
FIG. 3B
FIG. 3C
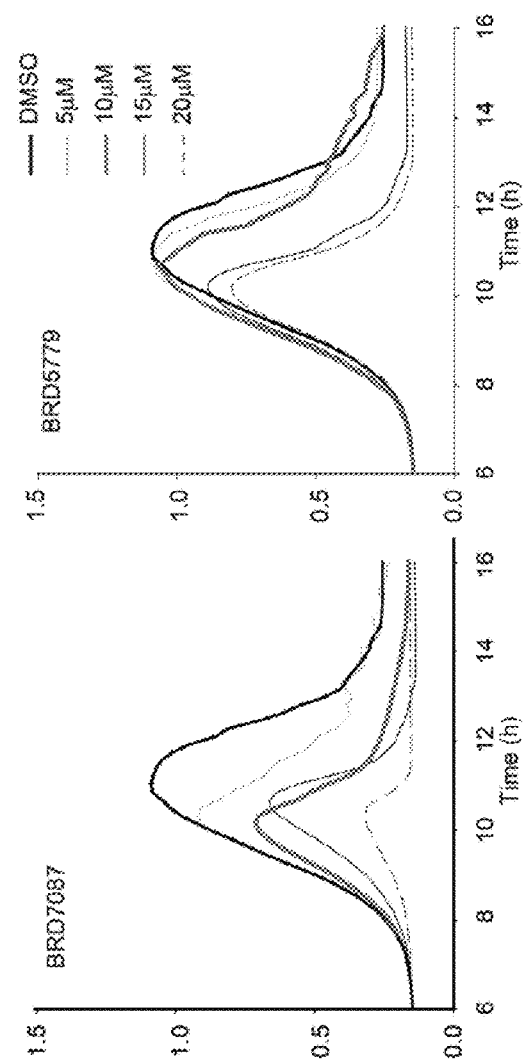
FIG. 3D
FIG. 3E
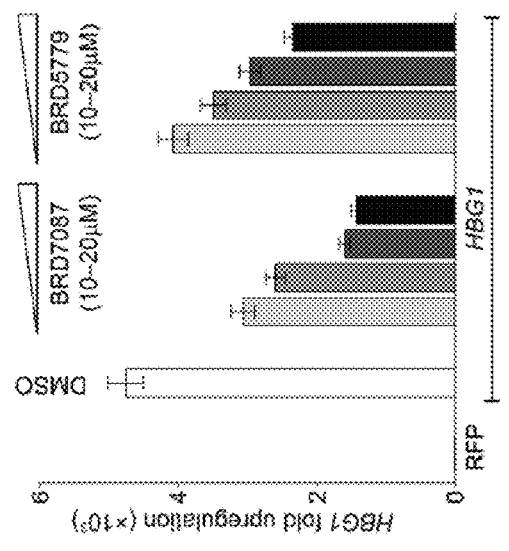

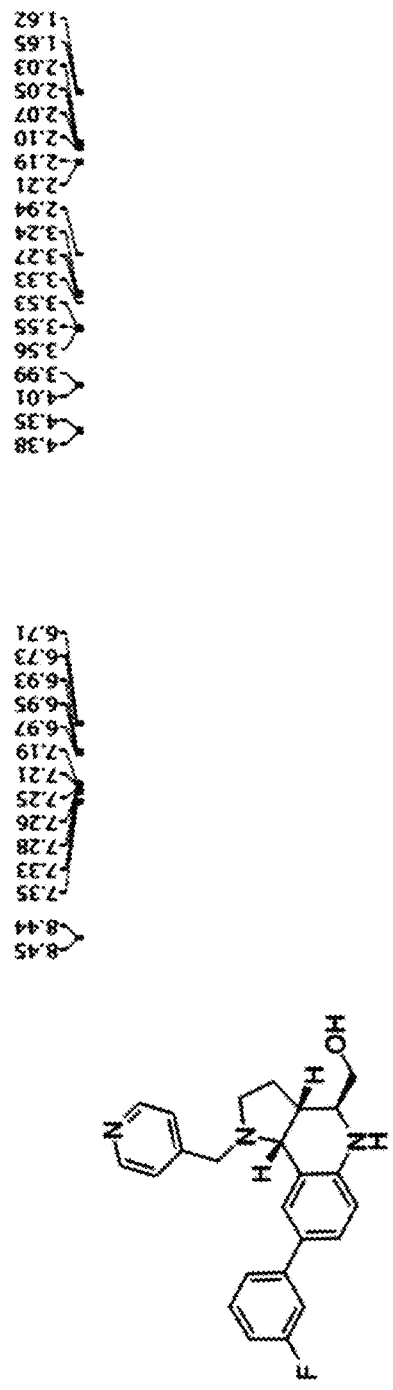
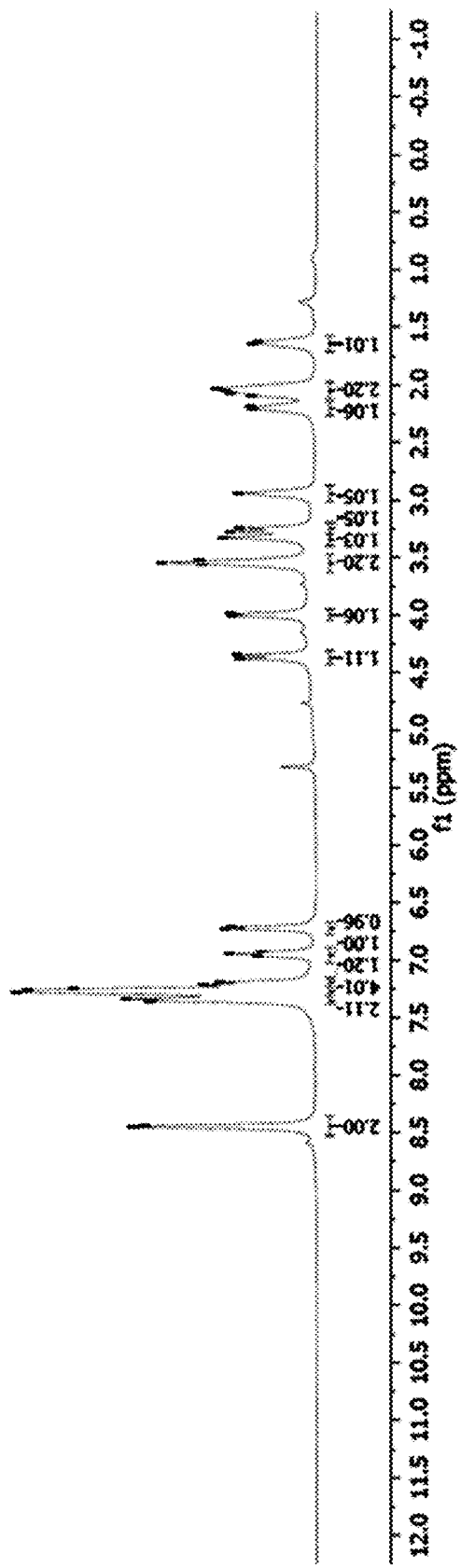
FIG. 46B

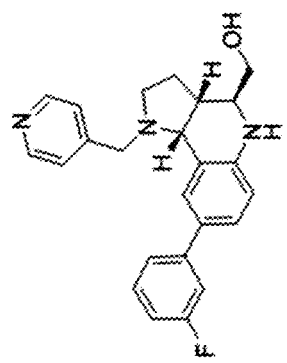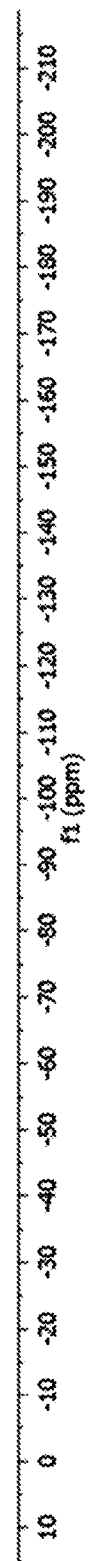
FIG. 46E

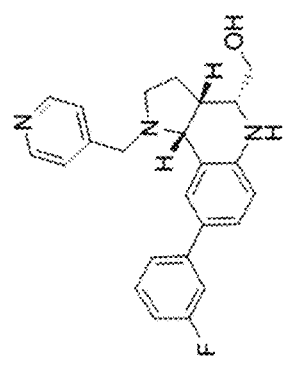
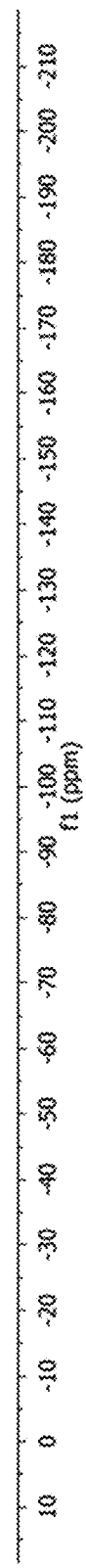
FIG. 46N

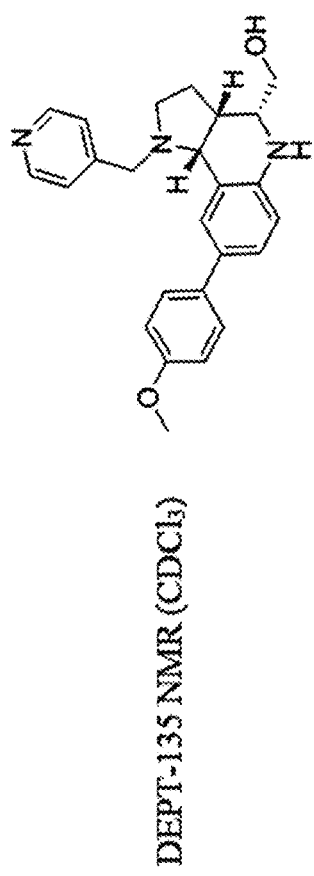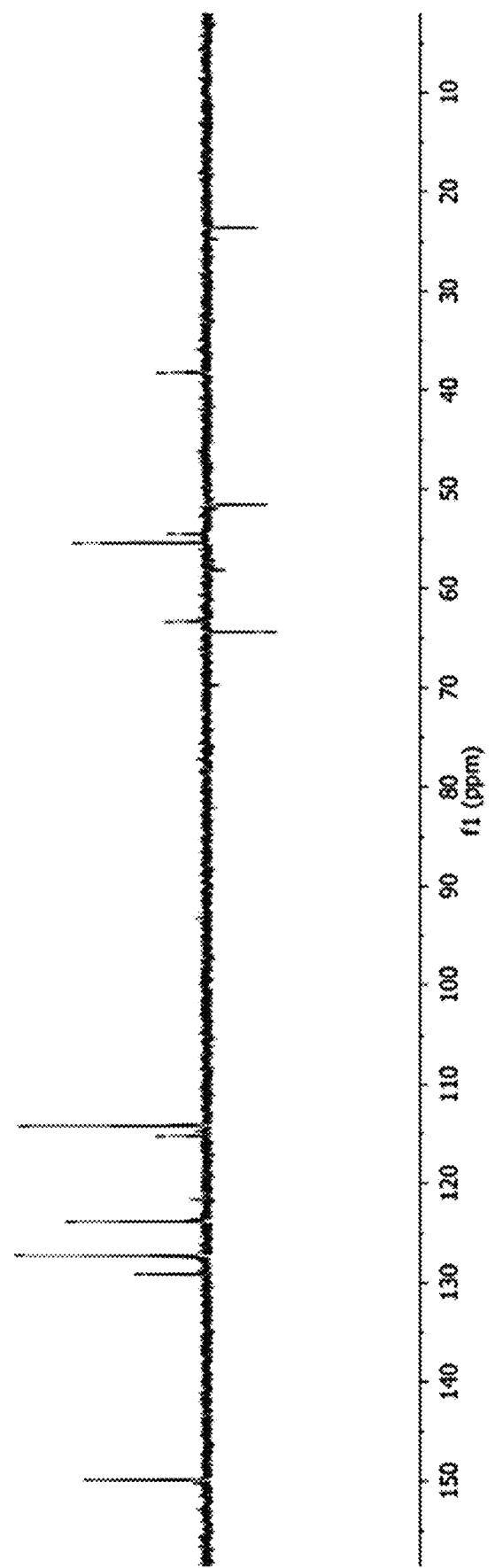
FIG. 46R

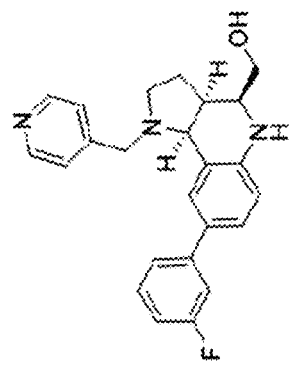
FIG. 46W

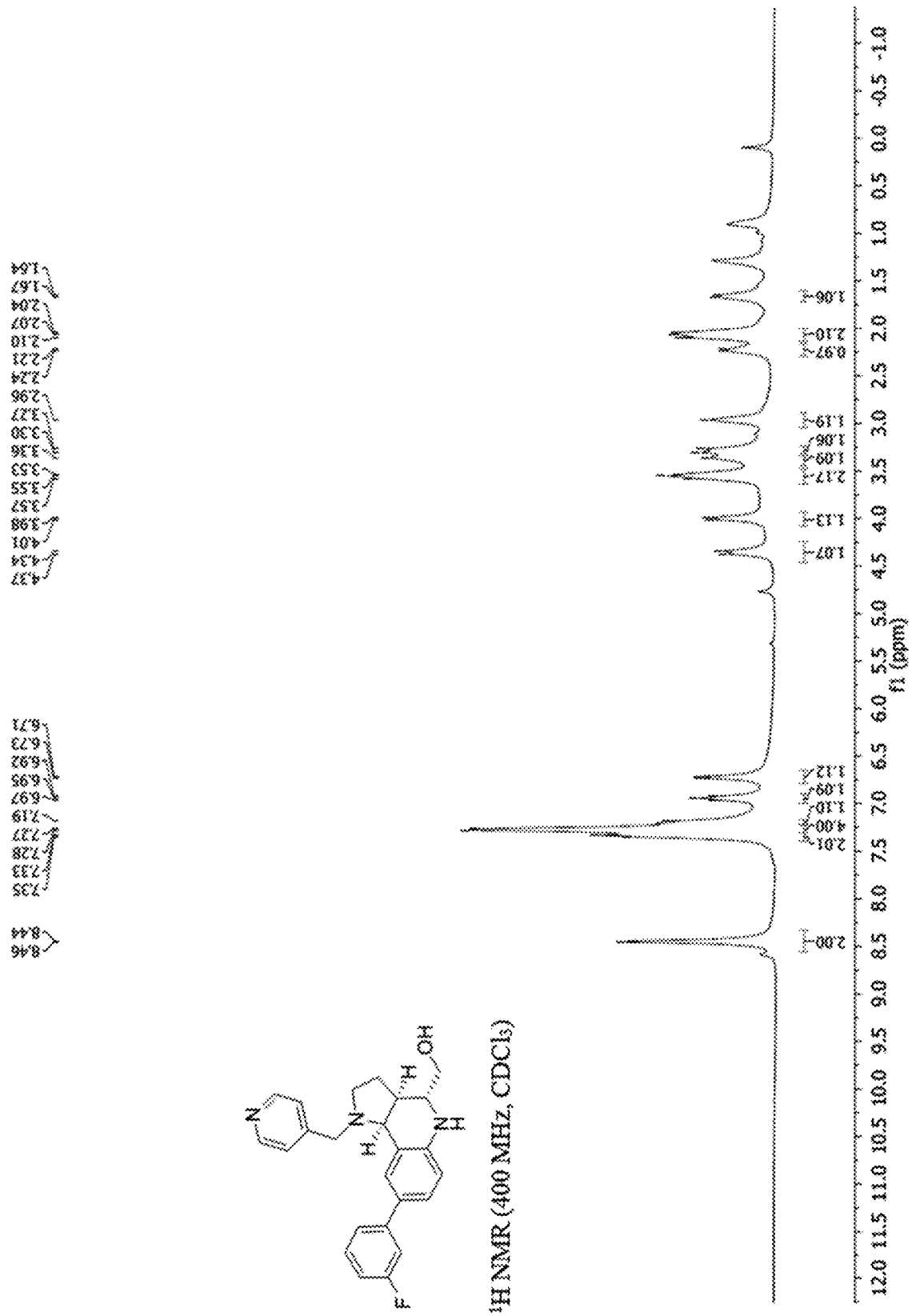

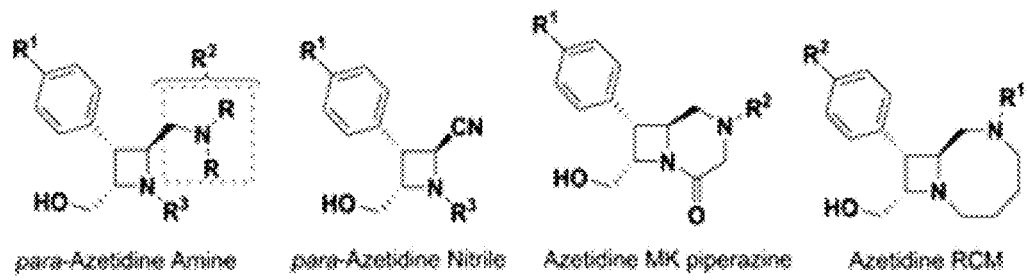
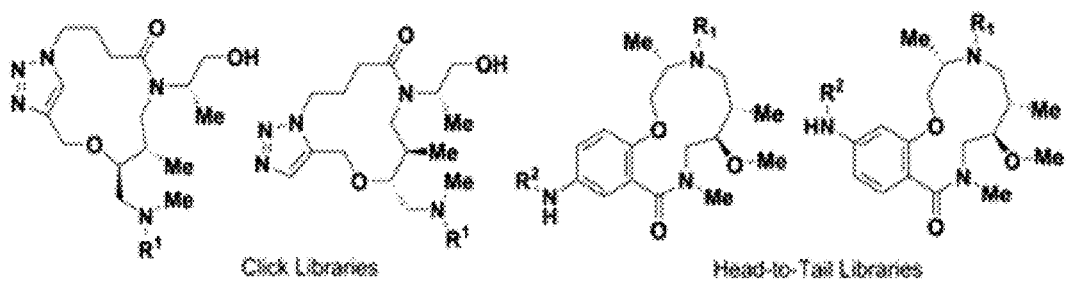
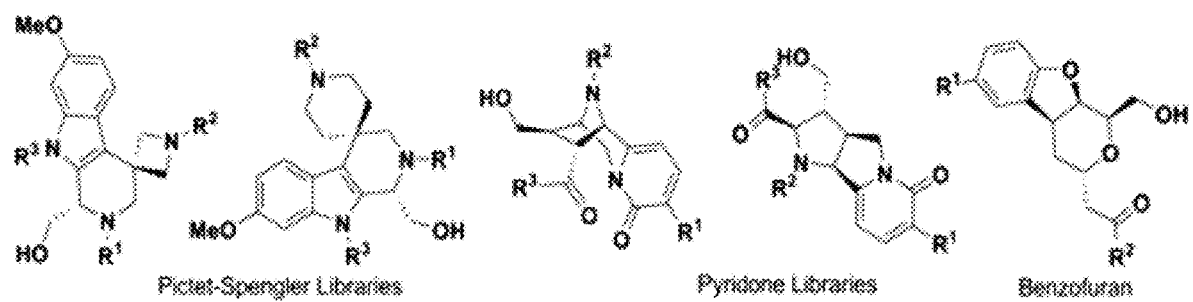
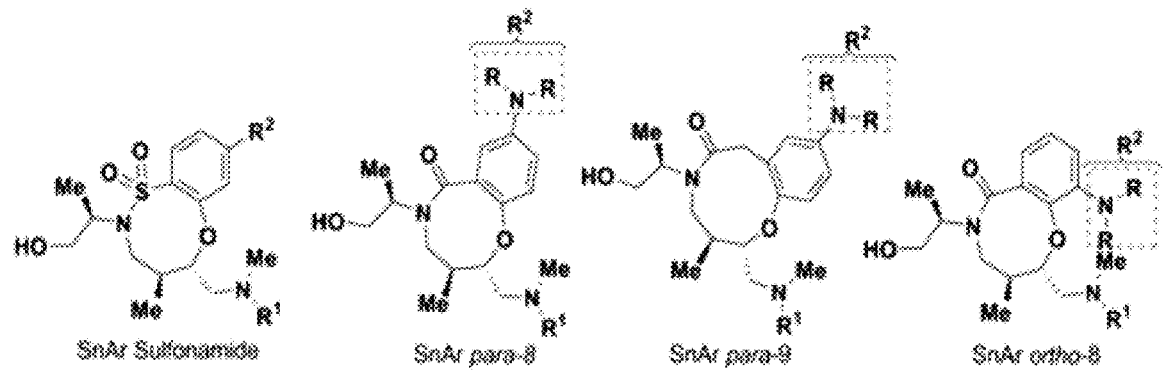
FIG. 52

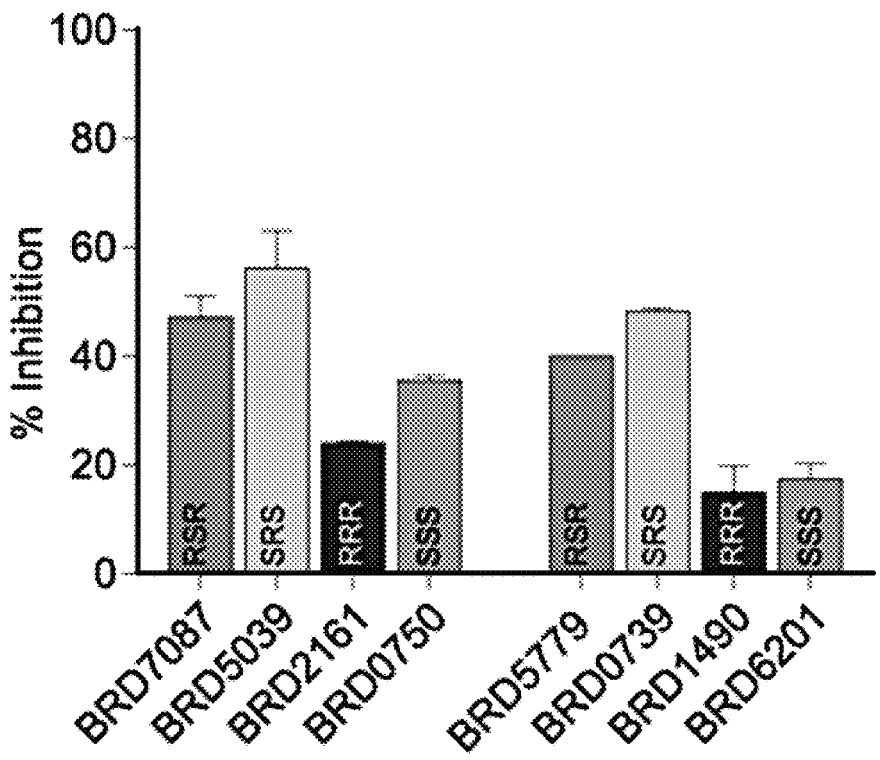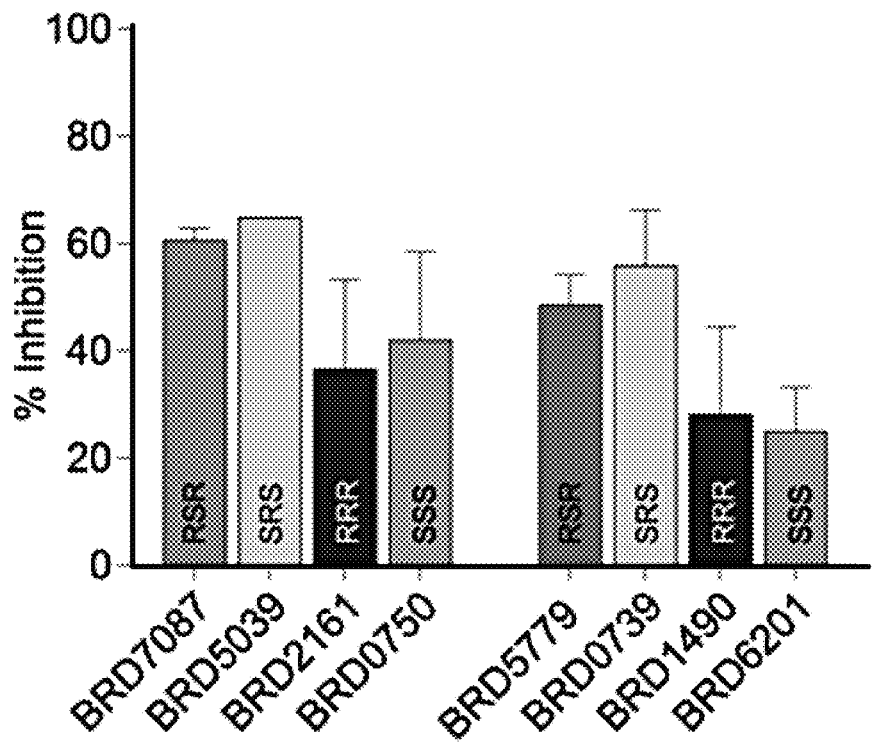
FIG. 81

US 11,760,984 B2

CRISPR PROTEIN INHIBITORS

CROSS-REFERENCE TO RELATED APPLICATION

This application is a National Stage application of International Application No. PCT/US2018/058466, filed Oct. 31, 2018, which claims the benefit of U.S. Provisional Application Nos. 62/579,727, filed Oct. 31, 2017, and 62/579,836, filed Oct. 31, 2017. The entire contents of the above-identified applications are hereby fully incorporated herein by reference.

STATEMENT REGARDING FEDERALLY SPONSORED RESEARCH

This invention was made with government support under Grant No. AI126239 awarded by the National Institutes of Health, Grant No. N66001-17-2-4055 awarded by the Defense Advanced Research Projects Agency, Grant No. W911NF1610586 awarded by the Army Research Office, and Grant No. DE-SC0010595and DE-SC0010426 awarded by the Department of Energy. The government has certain rights in the invention.

REFERENCE TO AN ELECTRONIC SEQUENCE LISTING

The contents of the electronic sequence listing ("BROD-2940WP_consolidated_ST25.txt"; Size is 8,006 bytes and it was created on Oct. 30, 2018) is herein incorporated by reference in its entirety.

TECHNICAL FIELD

The subject matter disclosed herein is generally directed to compositions and methods for the inhibition of the function of RNA guided endonucleases, including the identification and use of such inhibitors.

BACKGROUND

The CRISPR (clustered regularly interspaced short palindromic repeat) system is an adaptive immune system used by bacteria and archaea to defend against invading phages or mobile genetic elements. The most studied CRISPR system employs an RNA-guided endonuclease Cas9, which can cleave double-stranded target DNA in multiple cell types. Cas9 identifies the target sequence by two recognition mechanisms: (i) Watson-Crick base-pairing between the target DNA sequence and guide RNA and (ii) Protospacer Adjacent Motif (PAM) sequence on the target DNA. Upon target recognition, Cas9 induces double-strand breaks in the target gene, which when repaired by non-homologous end joining (NHEJ) can result in frameshift mutations and gene knockdown. Alternatively, homology-directed repair (HDR) at the double-strand break site can allow insertion of the desired sequence.

Two common variants of Cas9 are SpCas9 and SaCas9, which naturally occur in *S pyogenes* and *S aureus*, respectively, and recently another endonuclease called Cpf1 has been reported. The relative ease of targeting Cas9/Cpf1 to specific genomic loci has enabled the development of revolutionary biomedical technologies. For example, catalytically inactive Cas9 (called dCas9), when fused to transcriptional activators, has enabled genome-wide screening of gene targets. Further, by targeting dCas9 to the promoter or exonic sequences, transcriptional repression has been accomplished. In yet another example, a fusion of dCas9 to acetyltransferases has enabled epigenome editing. Imaging of specific genomic loci has been accomplished by fusing dCas9 to GFP.

There are multiple reasons to establish controls on Cas9 activity. First, as described by Paracelsus' "The dose makes the poison", dosable control of the therapeutic activity is important for effective therapeutic strategies. Indeed, Cas9 exhibits undesirable off-target editing and chromosomal translocations when present at high concentrations. Second, most gene delivery systems have constitutively active Cas9, which is important to be terminated rapidly following on-target gene-editing. Third, Cas9-based technologies (e.g., transcriptional regulation) would benefit from dosable and temporal control of Cas9 activity.

The rapid ascension of CRISPR-based genome editing technologies has raised serious biosafety and bioterrorism concerns, leading to calls for a moratorium and responsible conduct. In particular, much concern has surrounded CRISPR-based gene drives. In sexual reproduction, the progenies receive two versions of a gene, one from each parent. Gene drives enable replacement of one version of the gene with the other "selfish" version of the gene, thereby converting a heterozygous individual to homozygous individual. In laboratory settings, CRISPR-based gene drives have successfully enabled self-propagation of engineered genes in multiple organisms (e.g., mosquitoes) and complete annihilation of wild-type genes. For example, using gene drives engineered mosquitoes have been generated that can wipe out the entire species by ensuring that every female progeny is infertile. Gene drives can be used to propagate a particular trait in the entire ecosystem, which may find use in the elimination of diseases (e.g., malaria, dengue fever) or invasive species, and reversing pesticide resistance in plants. On the other hand, there exists the malevolent use of gene drives in entomological and agricultural settings.

Reports of small-molecule controlled Cas9 activity are present in literature and involve fusing Cas9 to small-molecule controlled protein domains. Genetic-fusions of Cas9 to small-molecule controlled degrons (e.g., Wandless' destabilized domains) may allow aforementioned controls, but such fusions to have unacceptably high background activity presumably owing to the large size of Cas9. These systems also do not ensure dosage control—the small molecules act merely as an inducer of Cas9 activity. Further, these "inducer" small molecules cannot control gene drives containing wild-type Cas9/Cpf1. A general approach would be desirable to control all variants of Cas9/Cpf1, including the wild type and engineered versions. The use of "inducible" systems to control gene drives is also questionable given that the "inducer" small molecules are toxic at the organismal level (albeit not at the cellular level, where these systems were developed).

More importantly, large-sized genetic-fusion constructs are incompatible with the most common Cas9 gene delivery systems under investigation for therapeutic gene therapy. The application of these "inducible systems" in a therapeutic setting will be challenging as they involve fusion of large genes to Cas9 gene. Since Cas9 is a large protein, fitting even Cas9 gene into virus delivery systems (e.g., AAV) has been an enormous challenge. Even the smallest of the small-molecule controlled systems will aggrandize the delivery problems. Finally, many small-molecule "inducible" Cas9 constructs exist, but none allow dosable control.

The reported "inducible" systems are not reversible upon removal of the small molecule, and therefore, do not allow complete temporal control.

Currently, no method exists for rapid, reversible dosage and temporal control of CRISPR-based technologies or to thwart the malevolent use of gene drives. Accordingly, a need exists for compositions and methods for inhibiting one or more activities of RNA guided endonuclease (e.g., Cas9, Cpf1). Such compositions and methods are useful for regulating the activity of RNA guided endonucleases (e.g., in genome editing).

Since its discovery, the RNA guided endonuclease cas9 has found a wide variety of applications owing to the ease of targeting it to any genomic locus of interest using a single guide RNA. The recognition of the target DNA by Cas9 is based on complementary base-pairing between the target DNA and the guide RNA as well as presence of a protospacer adjacent motif (PAM) sequence adjacent to the target sequence in DNA. Till date, several Cas9 based technologies have been developed which lead to knock-in or knock-out of a specific gene. Catalytically inactive Cas9 (dCas9) has been fused to a variety of effectors for applications in transcriptional activation and repression, genome imaging, epigenome editing as well as base editing. Further, Cas9 based alterations can also be robustly propagated throughout a species population via gene drives. SpCas9 has been extensively investigated for gene therapy in pathologies such as Duchenne Muscular dystrophy (DMD), HIV, hereditary tyrosinemia and vision disorders. In order to be effectively used for therapeutic applications, it is essential to have a dosable control of the therapeutic agent. This is an extremely important consideration for gene editing using Cas9, owing to the high off-target effects and chromosomal translocations observed at elevated Cas9 levels. Furthermore, the delivery systems used in gene therapy applications deliver constitutively active Cas9 whose activity must be terminated following the desired gene editing activity. From a gene drive perspective, it is important to develop methods to counter the nefarious use of gene drives or to facilitate its dosable, reversible and temporal control. These controls can be achieved through the precise regulation of Cas9 activity. Previous studies to control Cas9 activity have focused on developing fusions of Cas9 to proteins domains that can be regulated by small molecules. However, such systems will to be difficult to adapt for therapeutic applications, since fitting these large fusion proteins into currently available delivery systems will be challenging. Further, most of these systems act merely as 'turn-on' switches for the Cas9 systems and several are not reversible which hinder temporal control. Small molecule inhibitors of Cas9 will allow both dose and temporal control of its activity and aid in the better application of this system in gene therapy. Given that Cas9 is vital to several bacterial processes including immunity, inhibitors of this protein have the potential to afford novel anti-infective agents to counter the ever-growing challenge of antibiotic resistance.

Recent studies have described the discovery of certain 'anti-CRISPR' proteins from phages that inhibit SpCas9 in *E. coli* and human cells. However, development of protein inhibitors of Cas9 for therapeutic purposes may prove tedious since proteins are highly sensitive to pH and temperature making them difficult to produce on a large scale and characterize. Additionally, optimizing the potency of such protein-based inhibitors may involve mutagenesis which can prove to be challenging as well as time-consuming. Further, from a therapeutic standpoint, the immunogenicity of proteins becomes a significant challenge. Small molecules, on the other hand, are quite stable under reasonably small changes in pH, temperature, and humidity as well as to the presence of cellular proteases. They are considerably easier to deliver since most enter cells through passive diffusion. Small molecule inhibitors exhibit their effects rapidly which is in stark contrast to genetic methods. Besides offering efficient dose and temporal control, small molecules are cheaper to synthesize and have little variability amongst batches. Finally, the inhibition resulting from a non-covalent small molecule can be readily reversed. All these attributes make small molecule inhibitors of Cas9 a very attractive avenue to pursue.

Citation or identification of any document in this application is not an admission that such document is available as prior art to the present invention.

SUMMARY

The invention provides compositions and methods for inhibiting the activity of RNA guided endonucleases (e.g., Cas9, Cpf1), and methods of use therefor, including rapid, reversible, dosage, and/or temporal control of RNA guided endonuclease technologies. Also provided are high-throughput biochemical and cellular assays for detecting one or more activities of RNA guided endonucleases, and methods of using them to identify or screen agents that inhibit RNA guided nucleases.

In one aspect, the present disclosure provides a method for screening inhibitors of CRISPR-Cas systems comprising: incubating a set of candidate inhibitors in individual discrete volumes, each individual discrete volume comprising (i) a different candidate inhibitor, different concentration of a inhibitor, different combination of inhibitors, or different concentrations of the combination of inhibitors, and (ii) a labeled PAM-rich target oligonucleotide, a CRISPR-Cas effector protein, and a guide molecule, wherein the guide molecule targets binding of the CRISPR-Cas effector protein to the labeled PAM-rich target oligonucleotide; selecting one or more putative inhibitors from the set of candidate inhibitors at least in part by detecting change in fluorescence polarization of the labeled PAM-rich target oligonucleotide, wherein inhibition of formation of a complex of the CRISPR-Cas and the guide molecule by the one or more of the candidate inhibitors leads to a decrease in fluorescence polarization of the labeled PAM-rich target oligonucleotide; validating the one or more putative inhibitors based on a cell-based knockdown assay and a cell-based nuclease activity assay comprising use of a frame-shift reporter; and selecting one or more final inhibitors based at least in part on the cell-based knockdown assay and the cell-based nuclease activity assay.

In some embodiments, the method further comprises a counter-screen of the one or more putative inhibitors comprising measuring change in fluorescence polarization of the labeled PAM-rich target oligonucleotide in presence of the one or more putative inhibitors alone, and candidate inhibitors that increase fluorescence polarization beyond a defined cut-off value are excluded from the one or more putative inhibitors. In some embodiments, the cell-based knockdown assay is performed by: delivering the CRISPR-Cas effector protein, a nucleotide sequence encoding a polypeptide reporter, and a guide sequence targeting the nucleotide sequence encoding the polypeptide reporter to a population of cells in the individual discrete volumes, each individual discrete volume comprising the one or more putative inhibitors; and detecting inhibitor activity by measuring changes in fluorescence, wherein an increase in fluorescence relative to a control indicates inhibition of CRISPR-Cas mediated knockdown of the polypeptide reporter.

In some embodiments, the cell-based nuclease activity assay comprises: delivering a first construct and a second construct to a population of cells in individual discrete volumes, each individual discrete volume comprising the one or more putative inhibitors, wherein the first construct encodes an out-of-frame first reporter and a downstream in-frame second reporter separated by a linker comprising a stop codon, and the second construct encodes the CRISPR-Cas effector protein and a guide molecule targeting the linker, wherein the CRISPR-Cas effector protein introduces a frameshift edit at the stop codon that shifts the first reporter in-frame; and detecting inhibitor activity by measuring changes in expression of the first reporter, wherein decreased expression of the first reporter relative to a control indicates inhibition of CRISPR-Cas mediated nuclease activity.

In some embodiments, detecting inhibitor activity is performed using high-content imaging and automated data analysis. In some embodiments, the polypeptide reporter is a fluorescent protein. In some embodiments, the fluorescent protein is mKate2. In some embodiments, the first construct and the second construct are delivered in equimolar ratios. In some embodiments, the first reporter is a first fluorescent polypeptide detectable at a first wavelength or range of wavelengths, and the second reporter is a second fluorescent polypeptide detectable at a second wavelength or range of wavelengths. In some embodiments, the CRISPR-Cas effector protein, the nucleotide sequence encoding the polypeptide reporter, and the guide sequence targeting the nucleotide sequence encoding the polypeptide reporter are all encoded on a single construct. In some embodiments, the labeled PAM-rich target oligonucleotide comprises between 2 and 20 PAM regions per oligonucleotide. In some embodiments, the labeled PAM-rich target oligonucleotide comprises 12 PAM regions. In some embodiments, the individual discrete volumes are droplets or wells of a multi-well plate. In some embodiments, the method further comprises performing a transcription assay and/or a strand displacement assay to identify one or more final inhibitors.

In another aspect, the disclosure provides a method of designing or identifying an inhibitor of a CRISPR protein, the method comprising
  (a) fitting a candidate molecule to the three-dimensional structure of one or more target regions of a PAM interaction (PI) domain, and
  (b) evaluating the results of the fitting step (a) to determine the ability of the candidate molecule to interact with the one or more target regions of the PI domain.

In an embodiment, step (a) is carried out on a computer.

In an embodiment, the method further comprises determining the candidate as an inhibitor of target nucleic acid modification by a CRISPR system which comprises the CRISPR protein.

In an embodiment, the target nucleic acid modification comprises cleavage of a target nucleic acid. In another embodiment, the target nucleic acid modification comprises non-homologous end joining (NHEJ). In another embodiment, the target nucleic acid modification comprises homologous repair (HR).

In an embodiment, the CRISPR protein is Cas9 and the target region comprises one or more amino acid residues of the PI domain of the Cas9.

In an embodiment, the CRISPR protein is *Streptococcus pyogenes* Cas9 (SpCas9) and the target region comprises one or more of Lys1107, Arg1333, and Arg1335. In another embodiment, the target region comprises interacting amino acids having an alpha-carbon within 20 angstroms of Lys1107, Arg1333, and/or Arg1335.

In an embodiment, the CRISPR protein is *Staphylococcus aureus* Cas9 (SaCas9) and the target region comprises one or more of Asn985, Asn986, Arg991, Glu993, and Arg1015. In another embodiment, the target region comprises interacting amino acids having an alpha-carbon within 20 angstroms of Asn985, Asn986, Arg991, Glu993, and/or Arg1015. In another embodiment, the target region further comprises Tyr789, Tyr882, Lys886, Ans888, Ala889, and/or Leu909.

In an embodiment, the CRISPR protein is *Francisella novicida* Cas9 (FnCas9) and the target region comprises one or more of Ser1473, Arg1474, Arg1556, and Arg1585. In another embodiment, the target region further comprises interacting amino acids having an alpha-carbon within 20 angstroms of Ser1473, Arg1474, Arg1556, and/or Arg1585. In another embodiment, the target region further comprises Glu1449, Asp1470, and/or Lys1451.

In an embodiment, the CRISPR protein is *Campylobacter jejuni* Cas9 (CjCas9) and the target region comprises one or more of Arg866, Thr913, Ser915, and/or Ser951.

In an embodiment, the protein is a Cas9 ortholog and the target region comprises one or more amino acids corresponding to Lys1107, Arg1333, or Arg1335 of SpCas9, or Asn985, Asn986, Arg991, Glu993, or Arg1015 of SaCas9, or Ser1473, Arg1474, Arg1556, of Arg1585 of FnCas9.

In an embodiment, the CRISPR protein is *Acidaminococcus* sp. Cpf1 (AsCpf1) and the target region comprises one or more of Thr167, Ser542, Lys548, Asn552, Met604, and Lys607. In another embodiment, the target region further comprises interacting amino acids having an alpha-carbon within 20 angstroms of Thr167, Ser542, Lys548, Asn552, Met604, and/or Lys607.

In an embodiment, the CRISPR protein is *Lachnospiraceae bacterium* Cpf1 (LsCpf1) and the target region comprises one or more of Gly532, Lys538, Tyr542, and Lys595. In another embodiment, the target region further comprises interacting amino acids having an alpha-carbon within 20 angstroms of Gly532, Lys538, Tyr542, and/or Lys595.

In an embodiment, the protein is a Cpf1 ortholog and the target region comprises one or more amino acids corresponding to Thr167, Ser542, Lys548, Asn552, Met604, or Lys607 of AsCpf1, or Gly532, Lys538, Tyr542, or Lys595 of LsCpf1.

The invention provides a method for inhibiting a CRISPR protein comprising an inhibitor that interacts with the PAM interacting domain. The following compounds provide examples of CRISPR protein inhibitors, including PI domain interacting ligands.

TABLE 1

| Index | Compound ID | Structure |
|---|---|---|
| 1 | BRD3326 | |
| 2 | BRD1701 | 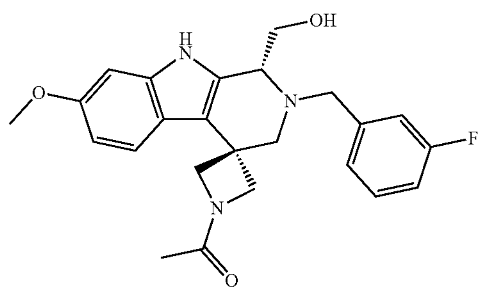 |
| 3 | BRD2911 | 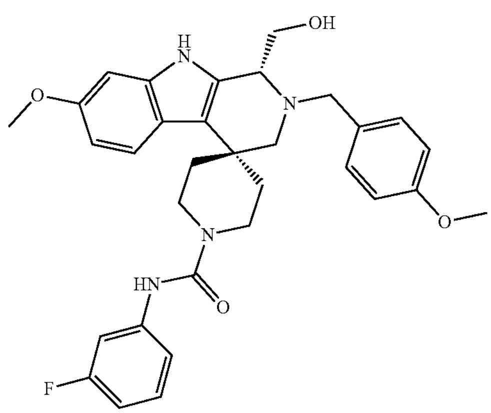 |
| 4 | BRD1368 | 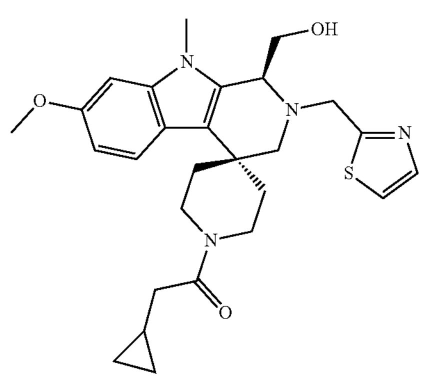 |
| 5 | BRD7682 | 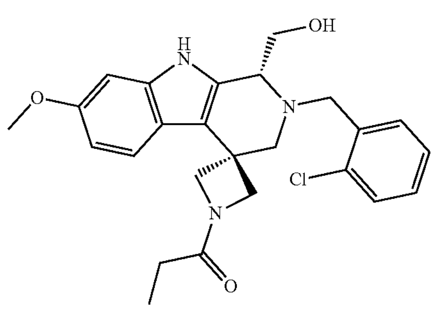 |

TABLE 1-continued

| Index | Compound ID | Structure |
|-------|-------------|-----------|
| 6 | BRD1830 | 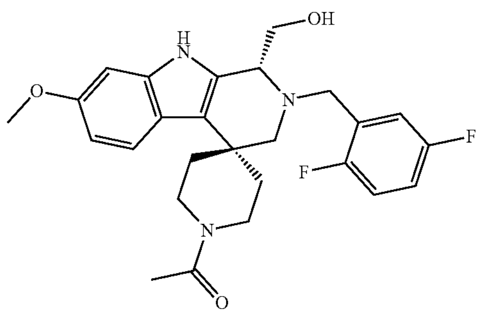 |
| 7 | BRD2473 | 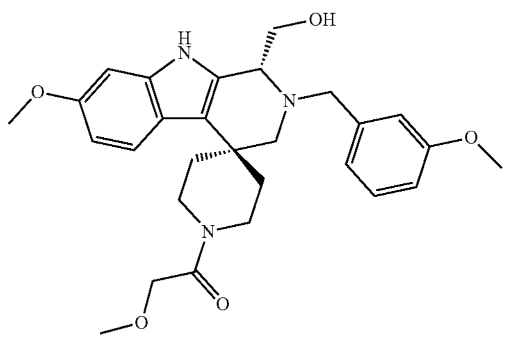 |
| 8 | BRD0159 | |
| 9 | BRD5813 | 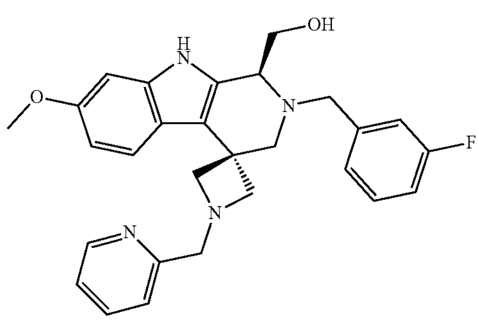 |
| 10 | BRD4249 | |
| 11 | BRD7299 | |
| 12 | BRD8786 | 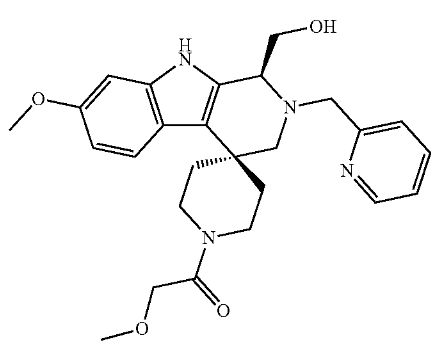 |

TABLE 1-continued
| Index | Compound ID | Structure |
|---|---|---|
| 13 | BRD0568 | |
| 14 | BRD7713 | 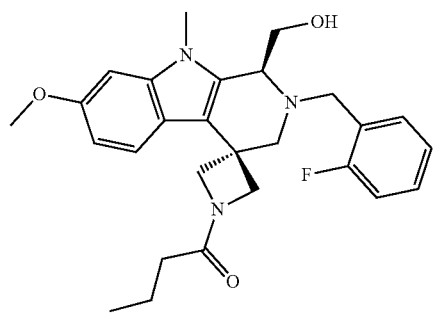 |
| 15 | BRD3389 | 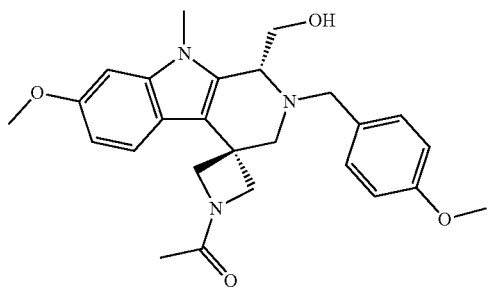 |
| 16 | BRD4048 | 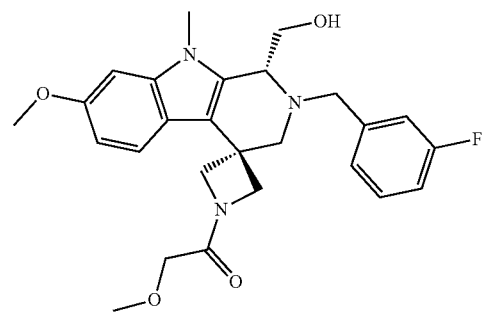 |
| 17 | BRD2679 | 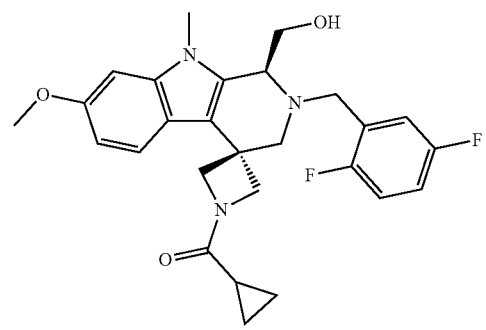 |

TABLE 1-continued
| Index | Compound ID | Structure |
|---|---|---|
| 18 | BRD3326 | |
| 1 | BRD7087 | 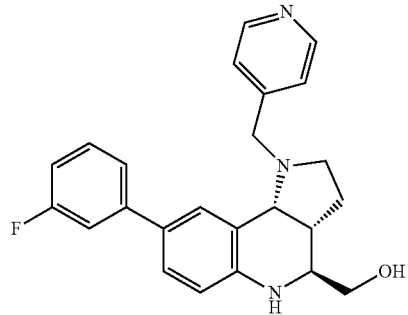 [SMILES: OC[C@H]1Nc2ccc(-c3cccc(F)c3)cc2[C@H]2[C@@H]1CCN2Cc1ccncc1] |
| 2 | BRD5779 | 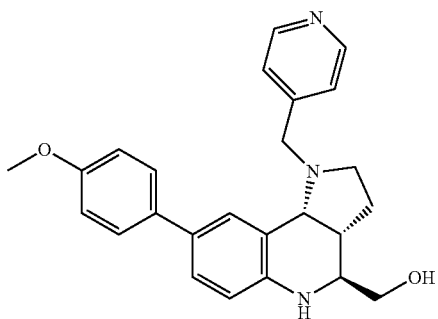 [SMILES: COc1ccc(-c2ccc3c(c2)[C@H]2[C@H](CCN2Cc2ccncc2)[C@@H](CO)N3)cc1] |
| 3 | BRD4592 | 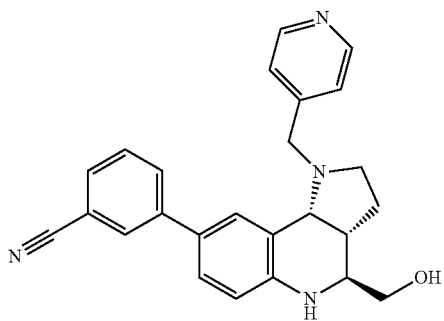 [SMILES: N#Cc1cccc(-c2ccc3c(c2)[C@H]2[C@H](CCN2Cc2ccncc2)[C@@H](CO)N3)c1] |
| 4 | BRD1098 | 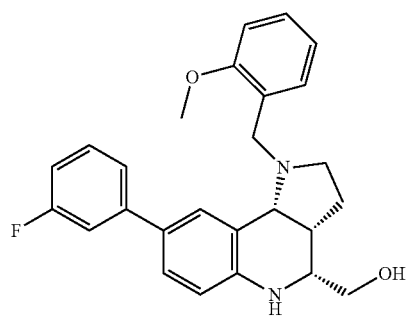 [SMILES: COc1ccccc1CN1CC[C@@H]2[C@H](CO)Nc3ccc(-c4cccc(F)c4)cc3[C@@H]21] |

TABLE 1-continued

| Index | Compound ID | Structure |
|---|---|---|
| 5 | BRD7032 | 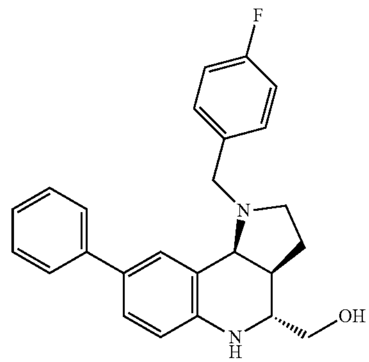 [SMILES: OC[C@@H]1Nc2ccc(-c3ccccc3)cc2[C@@H]2[C@H]1CCN2Cc1ccc(F)cc1] |
| 6 | BRD6688 | 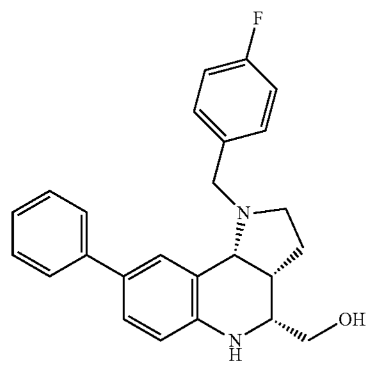 [SMILES: OC[C@@H]1Nc2ccc(-c3ccccc3)cc2[C@H]2[C@@H]1CCN2Cc1ccc(F)cc1] |
| 7 | BRD5737 | 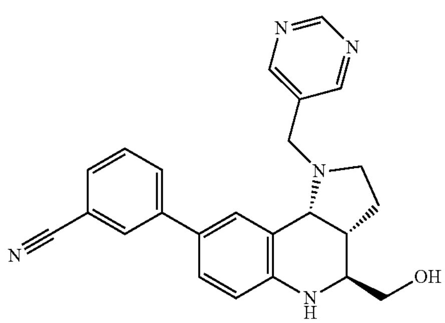 [SMILES: N#Cc1cccc(-c2ccc3c(c2)[C@H]2[C@H](CCN2Cc2cncnc2)[C@@H](CO)N3)c1] |
| 8 | BRD7801 | 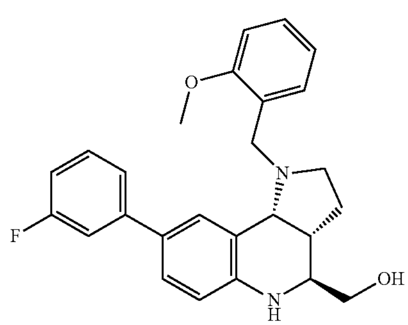 [SMILES: COc1ccccc1CN1CC[C@@H]2[C@@H](CO)Nc3ccc(-c4cccc(F)c4)cc3[C@@H]21] |

TABLE 1-continued
| Index | Compound ID | Structure |
|---|---|---|
| 9 | BRD1476 | 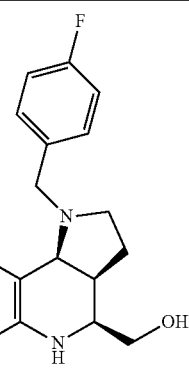 |
| 10 | BRD2810 | |
| 11 | BRD6201 | 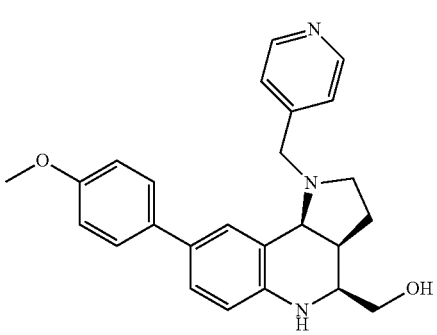 [SMILES: COc1ccc(-c2ccc3c(c2)[C@@H]2[C@@H](CCN2Cc2ccncc2)[C@@H](CO)N3)cc1] |
| 12 | BRD5762 | 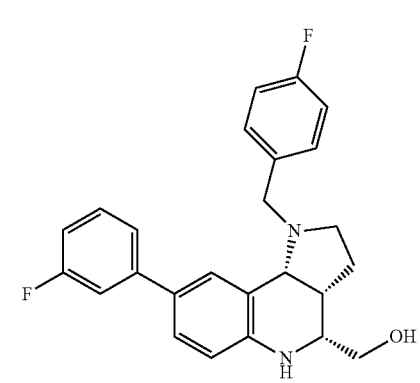 |
| 13 | BRD8312 | 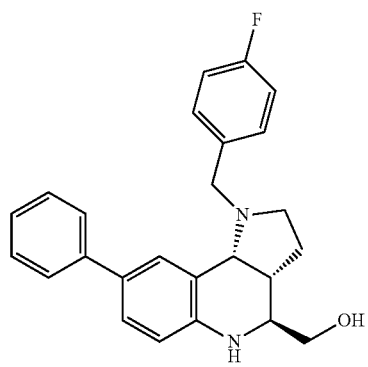 [SMILES: OC[C@H]1Nc2ccc(-c3ccccc3)cc2[C@H]2[C@@H]1CCN2Cc1ccc(F)cc1] |

TABLE 1-continued

| Index | Compound ID | Structure |
|-------|-------------|-----------|
| 14 | BRD7804 | 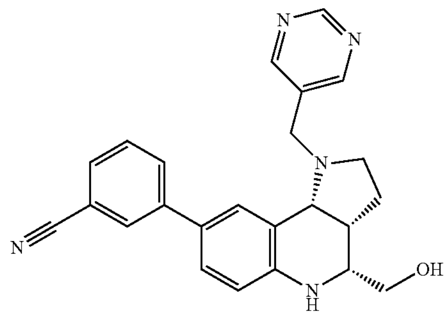 [SMILES: N#Cc1cccc(-c2ccc3c(c2)[C@H]2[C@H](CCN2Cc2cncnc2)[C@H](CO)N3)c1] |
| 15 | BRD2878 | 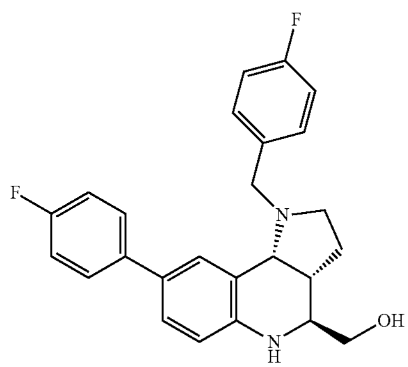 [SMILES: OC[C@H]1Nc2ccc(-c3ccc(F)cc3)cc2[C@H]2[C@@H]1CCN2Cc1ccc(F)cc1] |
| 16 | BRD8575 | 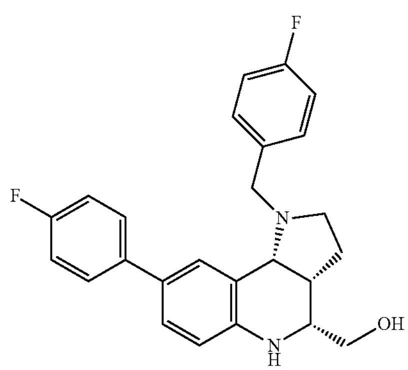 [SMILES: OC[C@@H]1Nc2ccc(-c3ccc(F)cc3)cc2[C@H]2[C@@H]1CCN2Cc1ccc(F)cc1] |
| 17 | BRD7481 | 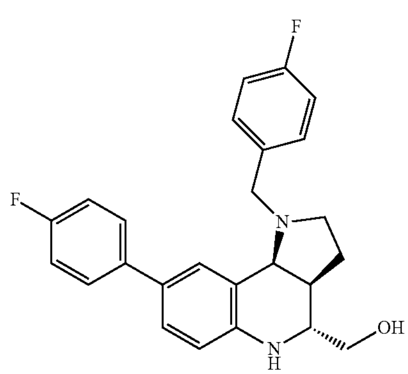 [SMILES: OC[C@@H]1Nc2ccc(-c3ccc(F)cc3)cc2[C@@H]2[C@H]1CCN2Cc1ccc(F)cc1] |

TABLE 1-continued
| Index | Compound ID | Structure |
|---|---|---|
| 18 | BRD5903 | 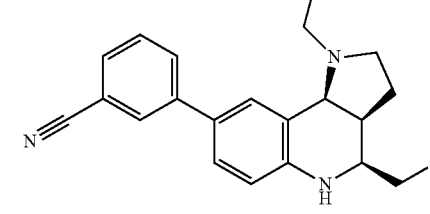 |
| 19 | BRD3119 | 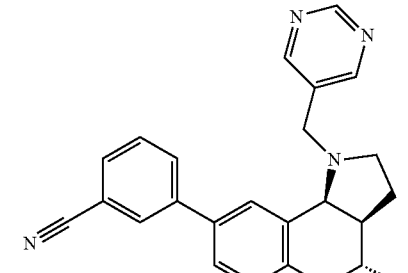 |
| 20 | BRD2161 | 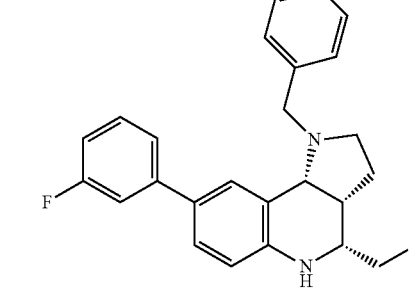 |
| 21 | BRD8480 | 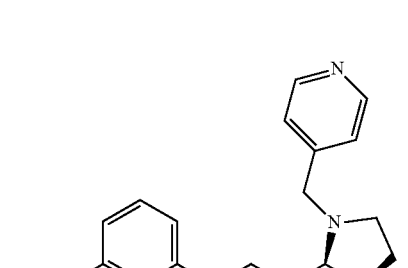 |

TABLE 1-continued

| Index | Compound ID | Structure |
|---|---|---|
| 22 | BRD3978 | 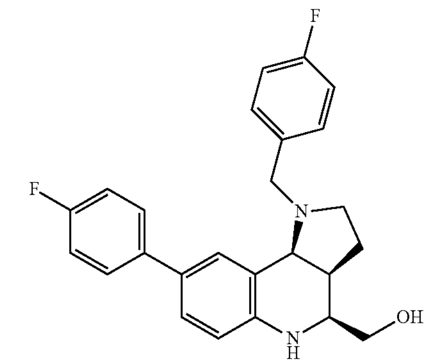 [SMILES: OC[C@H]1Nc2ccc(-c3ccc(F)cc3)cc2[C@@H]2[C@H]1CCN2Cc1ccc(F)cc1] |
| 23 | BRD6467 | 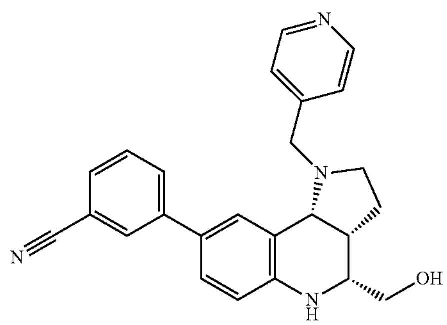 [SMILES: N#Cc1cccc(-c2ccc3c(c2)[C@H]2[C@H](CCN2Cc2ccncc2)[C@H](CO)N3)c1] |
| 24 | BRD5039 | 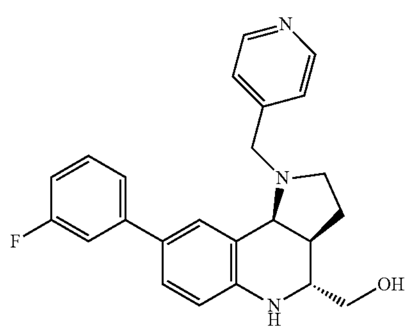 [SMILES: OC[C@@H]1Nc2ccc(-c3cccc(F)c3)cc2[C@@H]2[C@H]1CCN2Cc1ccncc1] |
| 25 | BRD0489 | 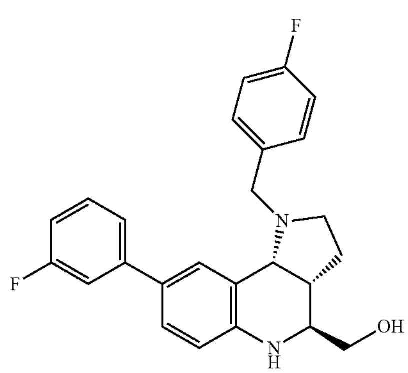 [SMILES: OC[C@H]1Nc2ccc(-c3cccc(F)c3)cc2[C@H]2[C@@H]1CCN2Cc1ccc(F)cc1] |

TABLE 1-continued

| Index | Compound ID | Structure |
|---|---|---|
| 26 | BRD1794 | 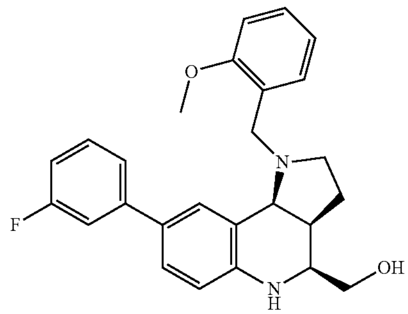 [SMILES: COc1ccccc1CN1CC[C@@H]2[C@H]1c1cc(-c3cccc(F)c3)ccc1N[C@@H]2CO] |
| 27 | BRD4326 | 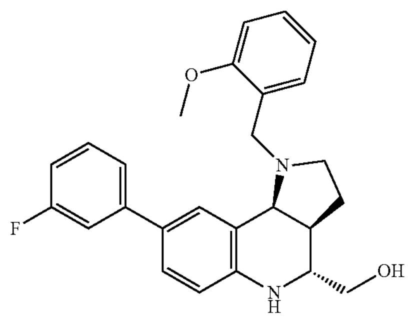 [SMILES: COc1ccccc1CN1CC[C@H]2[C@H](CO)Nc3ccc(-c4cccc(F)c4)cc3[C@H]21] |
| 28 | BRD0750 | 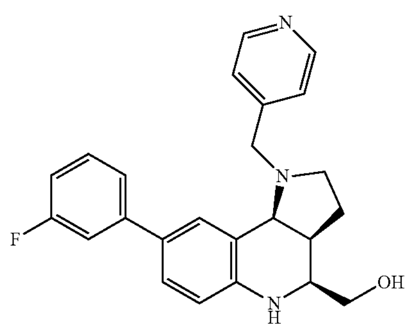 [SMILES: OC[C@H]1Nc2ccc(-c3cccc(F)c3)cc2[C@@H]2[C@H]1CCN2Cc1ccncc1] |
| 29 | BRD7037 | 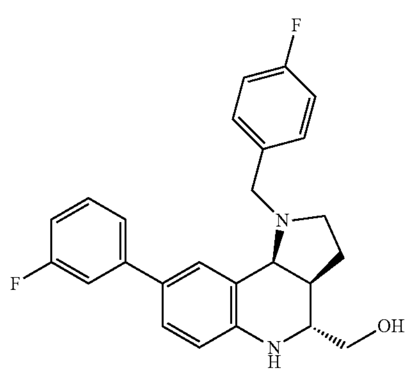 [SMILES: OC[C@@H]1Nc2ccc(-c3cccc(F)c3)cc2[C@@H]2[C@H]1CCN2Cc1ccc(F)cc1] |
| 30 | BRD7147 | |

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1G—Development of screening pipeline for identifying SpCas9 inhibitor. FIG. 1A) Schematic representation of fluorescence polarization-based assay for monitoring DNA-SpCas9:gRNA binding. FIG. 1B) Validation of FP-assay depicting dose-dependent enhancement in the FP-signal upon FITC-labeled DNA and SpCas9:gRNA complex. Error bars for each data point represent standard deviation from technical replicates (n=3). FIG. 1C) A competitive experiment demonstrating PAM sequence-specific DNA-SpCas9:gRNA binding as a readout in the FP-assay. Label 0-12 PAM represents the FITC-unlabeled competitive DNA with different number of PAM stretches (NGG) on the ds-DNA. Error bars for each data point represent standard deviation from technical replicates (n=3). FIG. 1D) Differential scanning fluorimetry assay depicting an increase in the thermal stability of SpCas9:gRNA ribonucleoprotein complex upon binding with the ds-DNA containing an incremental number of PAM sequence. Error bars for each data point represent standard deviation from technical replicates (n=3). FIG. 1E) An overview of the Screening workflow from identification to validation of SpCas9 inhibitors. FIG. 1F) Scatter plot representing the high throughput screening result of 10,000 compounds in FP-based DNA-SpCas9:gRNA binding assay. Dots in yellow, blue, and green represent DMSO control, compound results, and 12 PAM competitors respectively. FIG. 1G) Scatter plot of specific library Povarov in FP-based DNA-SpCas9:gRNA binding screening assay and counter-screening assays. The X-axis represents screening results and Y-axis represents counter-screening results. Dots in yellow and blue represent DMSO control and compound results respectively.

FIG. 2A) The molecular structure of the identified inhibitors BRD7087 and BRD5779 for SpCas9. The BRD7087-Biotin compound was developed by conjugating BRD7087-scaffold with Biotin. FIG. 2B) Bio-Layer Interferometry (BLI) study of biotinylated BRD7087 binding with SpCas9:gRNA complex. Streptavidin sensors were loaded with 1 µM BRD7087-Biotin and the interaction was followed by varying the SpCas9:gRNA complex from 1-0.15 µM. Global fitting of the response curves against ribonucleoprotein concentration provides the dissociation constant. The experiment was performed in three replicates. FIG. 2C) Binding interaction of BRD7087 and SpCas9:gRNA ribonucleoprotein complex probed under 19F NMR spectrometry. Line broadening in the $^{19}$F peak signal indicates the association of BRD7087 with Cas9. The experiments were performed in three replicates.

FIGS. 3A-3E—Cellular activity of small molecule inhibitors of SpCas9. (FIG. 3A) Dose-dependent inhibition activity of BRD7087 and BRD5779 against SpCas9 in U2OS.eGFP.PEST cells. Inhibitors were tested in 5-20 µM concentration range with 1.22× dilution. U2OS.eGFP.PEST cells were nucleofected by SpCas9 (JDS242) and sgRNA (egfp1320) plasmids and incubated with the compounds at the indicated concentration for 24 h before imaging. Error bars for each panel represent standard deviation from technical replicates (n=4). (FIG. 3B) Dose-dependent inhibition of the dCas9-based base-editing activity of cytidine deaminase (BE3) targeting EMX1 gene in HEK293T cells. Small molecule preincubated with BE3:gRNA ribonucleoprotein was delivered into the adhered HEK293T cells and incubated in the presence of either DMSO or compound at the indicated concentration for 72 h. The cells were then harvested and processed for DNA sequencing to evaluate the extent of C5→T5 conversion. The experiment was performed in three biological replicates and data are reported as mean±S.D. for technical replicates (n=3). (FIG. 3C) Dose-dependent inhibition of dCas9-based transcriptional activation of HBG1 gene in HEK293FT cells. Cells were transfected with dCas9, MS2.p65.HSF1.GFP plasmids along with either RFP or HBG1 plasmid and incubated in the presence of the compounds at the indicated concentration before processing for RT-qPCR. The experiments were performed in three biological replicates and each biological replicates were processed in six technical replicates. The data are reported as mean±S.E.M. for technical replicates. (FIG. 3D, FIG. 3E) Bacterial resistance study against pages in the presence of either DMSO or compound BRD7087 (FIG. 3D) and BRD5779 (FIG. 3E) at the indicated concentration. Growth curves demonstrate a dose-dependent blockage of CRISPR-Cas9 based immunity in bacteria by small molecules against phage. The experiment was performed in three technical replicates.

(FIG. 6A) Schematic representation of mKate2 expression assay showing Cas9 mediated knockdown of reporter mKate2 RFP expression. First step, delivery of the single plasmid containing SpCas9, gRNA, and reporter gene mKate2. In the second stage, both SpCas9, gRNA, and mKate2 getting expressed. In the final stage, depending upon the guide sequences in the gRNA, Cas9 may target the mKate2 gene and knockdown its expression level. (FIG. 6B) Quantification of mKate2 expression assay in HEK293T cells. A plasmid containing non-targeting guide (CgRNA) showed high mKate2 positive cells while the plasmid containing targeting guide (T1gRNA) showed a significant reduction in the mKate2 positive cells number after 24 h. Error bars represent ±S.D. from technical replicates (n=4).

(FIG. 35A) Schematic representation of fluorescence polarization-based assay for monitoring DNA-SpCas9:gRNA binding. (FIG. 35B). Validation of FP-assay depicting dose-dependent enhancement in the FP-signal upon FITC-labeled DNA and SpCas9:gRNA complex. Error bars for each data point represent standard deviation from technical replicates (n=3). (FIG. 35C). A competitive experiment demonstrating PAM sequence-specific DNA-SpCas9:gRNA binding as a readout in the FP-assay. Label 0-12 PAM represents the FITC-unlabeled competitive DNA with different number of PAM stretches (NGG) on the ds-DNA. Error bars for each data point represent standard deviation from technical replicates (n=3). (FIG. 35D). Differential scanning fluorimetry assay depicting an increase in the thermal stability of SpCas9:gRNA ribonucleoprotein complex upon binding with the ds-DNA containing an incremental number of PAM sequence. Error bars for each data point represent standard deviation from technical replicates (n=3). (FIG. 35E). An overview of the Screening workflow from identification to validation of SpCas9 inhibitors. (FIG. 35F). Scatter plot representing the high throughput screening result of 10,000 compounds in FP-based DNA-SpCas9:gRNA binding assay. Dots in yellow, blue, and green represent DMSO control, compound results, and 12 PAM competitors respectively. (FIG. 35G). Scatter plot of specific library Povarov in FP-based DNA-SpCas9:gRNA binding screening assay and counter-screening assays. The X-axis represents screening results and Y-axis represents counter-screening results. Dots in yellow and blue represent DMSO control and compound results respectively.

(FIG. 36A) The molecular structure of the identified inhibitors BRD7087 and BRD5779 for SpCas9. The BRD7087-Biotin compound was developed by conjugating BRD7087-scaffold with Biotin. (FIG. 36B) Bio-Layer Interferometry (BLI) study of biotinylated BRD7087 binding with SpCas9:gRNA complex. Streptavidin sensors were loaded with 1 µM BRD7087-Biotin and the interaction was followed by varying the SpCas9:gRNA complex from 1-0.15 µM. Global fitting of the response curves against ribonucleoprotein concentration provides the dissociation constant. The experiment was performed in three replicates. (FIG. 36C) Binding interaction of BRD7087 and SpCas9:gRNA ribonucleoprotein complex probed under 19F NMR spectrometry. Line broadening in the $^{19}F$ peak signal indicates the association of BRD7087 with Cas9. The experiments were performed in three replicates.

(FIG. 37A). Dose-dependent inhibition activity of BRD7087 and BRD5779 against SpCas9 in U2OS.eGFP.PEST cells. Inhibitors were tested in 5-20 µM concentration range with 1.22× dilution. U2OS.eGFP.PEST cells were nucleofected by SpCas9 (JDS242) and sgRNA (egfp1320) plasmids and incubated with the compounds at the indicated concentration for 24 h before imaging. Error bars for each panel represent standard deviation from technical replicates (n=4). (FIG. 37B). Dose-dependent inhibition of the dCas9-based base-editing activity of cytidine deaminase (BE3) targeting EMX1 gene in HEK293T cells. Small molecule preincubated with BE3:gRNA ribonucleoprotein was delivered into the adhered HEK293T cells and incubated in the presence of either DMSO or compound at the indicated concentration for 72 h. The cells were then harvested and processed for DNA sequencing to evaluate the extent of C5→T5 conversion. The experiment was performed in three biological replicates and data are reported as mean±S.D. for technical replicates (n=3). (FIG. 37C). Dose-dependent inhibition of dCas9-based transcriptional activation of HBG1 gene in HEK293FT cells. Cells were transfected with dCas9, MS2.p65.HSF1.GFP plasmids along with either RFP or HBG1 plasmid and incubated in the presence of the compounds at the indicated concentration before processing for RT-qPCR. The experiments were performed in three biological replicates and each biological replicates were processed in six technical replicates. The data are reported as mean±S.E.M. for technical replicates. (FIG. 37D, FIG. 37E) Bacterial resistance study against pages in the presence of either DMSO or compound BRD7087 (FIG. 37D) and BRD5779 (FIG. 37E) at the indicated concentration. Growth curves demonstrate a dose-dependent blockage of CRISPR-Cas9 based immunity in bacteria by small molecules against phage. The experiment was performed in three technical replicates.

(FIG. 38A) Schematic of a fluorescence-based strand displacement assay for monitoring Cas9 nuclease activity. Following Cas9 cleavage, a fluorophore bearing double stranded oligo (DS-oligo) is displaced by a quencher (Q)-baring displacer strand (Q-oligo), resulting in a decrease in fluorescent signal. (FIG. 38B). Gel-monitored cleavage of fluorophore labeled oligos (100 nM) are cleaved by SpCas9 (500 nM) in a PAM-dependent manner. Gel is representative of 2 biological replicates. (FIG. 38C). DS-oligo fluorescence is not quenched in the presence of Q-oligo unless the duplex is disrupted by cleavage via an active Cas9:gRNA complex. A single DNA strand with fluorophore (SS-Oligo) can be completely quenched by the Q-oligo in the absence of a duplex. Error bars represent standard deviation from 3 technical replicates (n=3), and is representative of 2 biological replicates. (FIG. 38D). Quenching via strand displacement is dependent on the presence of a NGG PAM in the DS-oligo when using SpCas9, indicating the specificity of the interaction. Error bars represent standard deviation from 3 technical replicates (n=3), and is representative of 2 biological replicates. (FIG. 38E). Strand displacement is generalizable to SaCas9 with comparable efficiency to SpCas9, and is dependent on an NNGGGT PAM sequence. Error bars represent standard deviation from 3 technical replicates (n=3), and is representative of 2 biological replicates.

(FIG. 39A). Optimization of the relative ratio of the SpCas9:gRNA complex (1-200 nM) to DS-oligo (fixed at 1 nM) while holding the Q-oligo concentration fixed (5 nM). Using a 5-fold excess of SpCas9:gRNA maximizes activity while minimizing background quenching from SpCas9 simply binding to DNA. Data is presented as the average background-subtracted fluorescence from 3 technical replicates. Error bars represent standard deviation (n=3). (FIG. 39B). Optimization of the relative amounts of Q-oligo (1-200 nM) and DS-oligo (fixed at 1 nM) while holding the SpCas9:gRNA concentration fixed (5 nM). A 2-fold excess of Q-oligo is sufficient to displace the cut strand. Data is presented as the average background-subtracted fluorescence from 3 technical replicates. Error bars represent standard deviation (n=3). (FIG. 39C). Determination of the DS-oligo limit of detection, fixing [SpCas9] and [Q-oligo] at 5-fold relative amount of DS-oligo and conducting the reaction for 120 min. Data is presented as the average background-subtracted fluorescence from 3 technical replicates, and is representative of 2 biological replicates. Error bars represent standard deviation (n=3). Inset is enlarged view of the 1, 0.3, and 0.1 nM points. (FIG. 39D). Time course of strand displacement, fixing [SpCas9] and [Q-oligo] at 5-fold relative amount of DS-oligo (1 nM). Reactions were incubated at either 25° C. or 37° C. Data is presented as fraction with 3 technical replicates, and is representative of 2 biological replicates. Error bars represent standard deviation (n=3).

(FIG. 40A). Schematic of a spinach-based in vitro transcription assay for monitoring Cas9 nuclease activity. In absence of Cas9, T7 RNA polymerase is recruited to a T7 promoter-containing DNA template to transcribe the spinach RNA aptamer, which can bind to the fluorogenic molecule DFHBI. Cleavage of the DNA by Cas9 results in complete termination of transcription or production of unproductive RNA, resulting in loss of fluorescence. Cas9 can recognize PAM sites native to the T7 and spinach sequences, or variable PAMs proximal and distal to the T7 promoter. (FIG. 40B). Schematic of the DNA template detailing gRNA sites, both engineered and native. (FIG. 40C). SpCas9:gRNA targeting site Sp g-2 causes dose-dependent loss of spinach fluorescence. ApoCas9 at 5 nM did not result in cleavage, indicating that this loss is due to cleavage of the spinach DNA template. Error bars represent the standard deviation from n=3 technical replicates. (FIG. 40D). SpCas9:gRNA-mediated fluorescence loss is dependent on the position of the gRNA, with PAM sites closer to the T7 promoter (in order: Sp g-2, g-3, g-4, and g-5) being more efficient. ApoCas9 at 2 nM did not result in cleavage. Error bars represent the standard deviation from n=3 technical replicates. (FIG. 40E). Generalization of Cas nuclease-mediated inhibition of IVT to SaCas9. Active SaCas9:gRNA (5 nM) can be used at both an endogenous PAM site (Sa g-1) and an installed GGGT proximal PAM site (Sa g-2). ApoSaCas9 (5 nM) did not result in cleavage. Error bars represent the standard deviation from n=3 technical replicates.

(FIG. 41A). Generalization of Cas nuclease-mediated inhibition of IVT to AsCpf1. Active AsCpf1:gRNA can cleave an installed distal TTTC PAM site (Cpf1 gRNA-1) or native TTTC site (Cpf1 gRNA-2) in a dose dependent manner, albeit with lower efficiency compared to other tested Cas nucleases. Error bars represent the standard deviation from n=3 technical replicates. (FIG. 41B). Similar to (FIG. 41A), but testing LbCpf1. (FIG. 41C). Similar to (FIG. 41A), but testing FnCpf1.

(FIG. 42A). Surface show depicting the binding pose for a Cas9-inhibitor with a Povarov scaffold determined by Glide docking. (FIG. 42B). Ribbon show depicting the binding pose for a Cas9-inhibitor with a Povarov scaffold determined by Glude docking. Key hydrogen-bond interactions are depicted by dashed lines. The Cas9-inhibitor and the PAM-interacting residues Arg1333 and Arg1335 are depicted as sticks.

(FIG. 46A). ((3aR, 4S, 9bR)-8-(3-Fluorophenyl)-1-(pyridin-4-ylmethyl)-2,3,3a,4,5,9b-hexahydro-1H-pyrrolo[3,2-c]quinolin-4-yl)methanol (BRD7087) UPLC Spectrum (210 nm). (FIG. 46B). ((3aR, 4S, 9bR)-8-(3-Fluorophenyl)-1-(pyridin-4-ylmethyl)-2,3,3a,4,5,9b-hexahydro-1H-pyrrolo[3,2-c]quinolin-4-yl)methanol (BRD7087)$^1$H NMR (400 MHz, CDCl$_3$). (FIG. 46E). ((3aR, 4S, 9bR)-8-(3-Fluorophenyl)-1-(pyridin-4-ylmethyl)-2,3,3a,4,5,9b-hexahydro-1H-pyrrolo[3,2-c]quinolin-4-yl)methanol (BRD7087)$^{19}$F NMR (376 MHz, CDCl$_3$). (FIG. 46R). ((3aR,4R,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD1490) DEPT-135 NMR (CDCl$_3$). (FIG. 46W). ((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD 0750)$^{19}$F NMR (376 MHz, CDCl$_3$). (FIG. 46AA). ((3aS,4R,9bS)-8-(4-Methoxyphenyl)-1-(pyridin-4-ylmethyl)-2,3,3a,4,5,9b-hexahydro-1H-pyrrolo[3,2-c] quinolin-4-yl)methanol (BRD0739) DEPT-135 NMR (CDCl$_3$). (FIG. 46AB). ((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD5039) UPLC Spectrum (210 nm). (FIG. 46AC). ((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD5039)$^1$H NMR (400 MHz, CDCl$_3$). (FIG. 46AD). ((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl) methanol (BRD5039)$^{13}$C NMR (100 MHz, CDCl$_3$). (FIG. 46AE). ((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD5039) DEPT-135 NMR (CDCl$_3$). (FIG. 46AF). ((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD5039)$^{19}$F NMR (376 MHz, CDCl$_3$). (FIG. 46AG). ((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (BRD6201) UPLC Spectrum (210 nm). (FIG. 46AH). ((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (BRD6201)$^1$H NMR (400 MHz, CDCl$_3$). (FIG. 46AI).

((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (BRD6201) $^{13}$C NMR (100 MHz, CDCl$_3$). (FIG. 46AJ). ((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (BRD6201) DEPT-135 NMR (CDCl$_3$).

(FIG. 47A). tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14) UPLC Spectrum (210 nm). (FIG. 47B). tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14) $^1$H NMR (400 MHz, CDCl$_3$). (FIG. 47C). tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14) $^{13}$C NMR (100 MHz, CDCl$_3$). (FIG. 47D). tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14) DEPT-135 NMR (CDCl$_3$). (FIG. 47E). 1H-pyrrolo[3,2-c]quinolin-8-yl)phenyl)amino)-3-oxopropoxy)ethoxy)ethyl)-5-((3aS,4S,6aR)-2-oxohexahydro-1H-thieno[3,4-d]imidazol-4-yl)pentanamide (15) UPLC Spectrum (210 nm). (FIG. 47F). 1H-pyrrolo[3,2-c]quinolin-8-yl)phenyl)amino)-3-oxopropoxy)ethoxy)ethoxy)ethyl)-5-((3aS,4S,6aR)-2-oxohexahydro-1H-thieno[3,4-d]imidazol-4-yl)pentanamide (15) $^1$H NMR (400 MHz, D$_2$O). (FIG. 47G). 1H-pyrrolo[3,2-c]quinolin-8-yl)phenyl)amino)-3-oxopropoxy)ethoxy)ethyl)-5-((3aS,4S,6aR)-2-oxohexahydro-1H-thieno[3,4-d]imidazol-4-yl)pentanamide (15) $^{13}$C NMR (100 MHz, D$_2$O). (FIG. 47H). 1H-pyrrolo[3,2-c]quinolin-8-yl)phenyl)amino)-3-oxopropoxy)ethoxy)ethyl)-5-((3aS,4S,6aR)-2-oxohexahydro-1H-thieno[3,4-d]imidazol-4-yl)pentanamide (15) DEPT-135 NMR (D$_2$O).

(FIG. 50A) Schematic representation of mKate2 expression assay showing Cas9 mediated knockdown of reporter mKate2 RFP expression. First step, delivery of the single plasmid containing SpCas9, gRNA, and reporter gene mKate2. In the second stage, both SpCas9, gRNA, and mKate2 getting expressed. In the final stage, depending upon the guide sequences in the gRNA, Cas9 may target the mKate2 gene and knockdown its expression level. (FIG. 50B) Quantification of mKate2 expression assay in HEK293T cells. A plasmid containing non-targeting guide (CgRNA) showed high mKate2 positive cells while the plasmid containing targeting guide (T1gRNA) showed a significant reduction in the mKate2 positive cells number after 24 h. Error bars represent ±S.D. from technical replicates (n=4).

FIG. 81. Effect of stereo-isomers in Cas9 inhibition activity. Evaluation of the SpCas9 activity of compound BRD7087 and BRD5779 and their stereo-isomers in the EGFP-knockdown assay in U2OS.eGFP.PEST cells. Cells were Nucleofected with SpCas9 and gRNA expressing plasmids and incubated with either DMSO or 15 µM of the compound for 24 h before processing for imaging and analysis. Error bars represent ±S.D. from biological replicates (n=2).

Figure 2C:
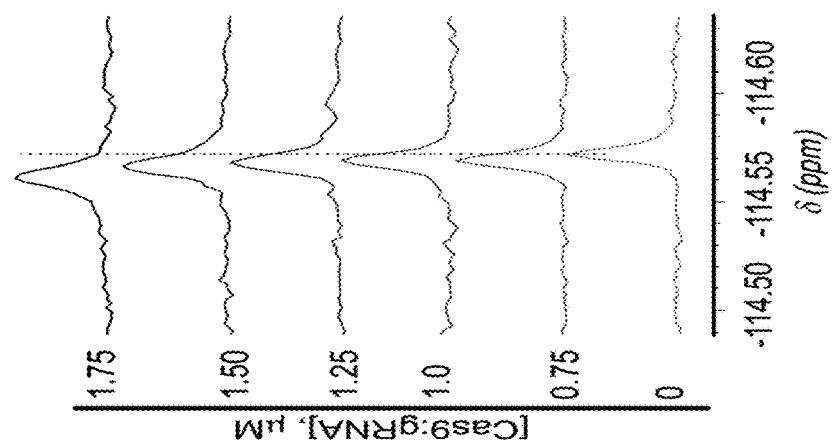
FIGS. 2A-2C—Biochemical characterization of small molecule-SpCas9 binding.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination. Unless specifically stated or obvious from context, as used herein, the term "or" is understood to be inclusive. The term "including" is used herein to mean, and is used interchangeably with, the phrase "including but not limited to."

Reference is made to U.S. Provisional Patent Application No. 62/416,017, filed Nov. 1, 2016.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide compositions, systems and methods screening assay that exploit PAM recognition by CRISPR-Cas effector proteins to identify inhibitors of CRISPR-Cas proteins. As discussed above, an active search is ongoing for "off-switches" of SpCas9. Currently, the best SpCas9 inhibitor (reported by Rauch et al.) is an "Anti-CRISPR" protein with a paltry efficacy of ~25% inhibition in mammalian cells.50 Further, this protein is highly-negatively charged with poor PK/PD properties, and has shown delivery and immunogenicity problems. Identification of small-molecule CRISPR-Cas inhibitors may resolve some of these issues. However, the identification of small molecule inhibitors of Cas proteins poses many challenges. First, inhibitor identification requires robust, orthogonal, sensitive, high-throughput, miniature, and inexpensive assays, which are currently unavailable. Second, Cas proteins are single turnover enzymes that hold on to its DNA substrate with pM affinity, making the development of such assays challenging.51 Third, the inhibition of some Cas protein activity requires inhibition of two nuclease domains.3 Fourth, Cas proteins have many novel protein folds that limit the ability to leverage existing rational design approaches.52 To circumvent these challenges, the embodiments provided herein may focus on targeting the Cas-substrate PAM motif interaction as a way to identify novel small molecule inhibitors of Cas proteins. To this end, several high-throughput biochemical assays for Cas proteins were developed and a preliminary screen was performed to identify small molecules that inhibit Cas protein activity.

The embodiments disclosed herein utilize fluorescence polarization based preliminary screen to identify a putative set of Cas inhibitors from an initial set of candidate inhibitors. The primary screening assay is followed by secondary screening assay to validate the putative set of inhibitors selected by the preliminary screen. In certain example embodiments, the first cell-based assay is a knockdown assay that measures changes in Cas-mediated knockdown of a reporter gene relative to control. In certain other example embodiments, the second cell-based assay measures changes in Cas editing activity using a frame-shift reporter. The first cell based assay, when deployed to identify inhibitors, is a gain-of-signal assay which has a much lower probability of false positives and are complementary to the second cell-based loss-of-signal assay. In certain example embodiments, a further screening step may be employed to assess inhibition of nuclease activity in eukaryotic or prokaryotic cells.

Further provided herein include computer-based methods and systems for designing and/or identifying inhibitors of a CRISPR-Cas effector protein (CRISPR protein). In general, the methods may include fitting (e.g., using a computer) a candidate molecule to one or more target regions in a three-dimensional structure of a PAM interaction (PI) domain of the CRISPR protein. The fitting results may then be evaluated to determine the ability of the candidate molecule to interact with the target region(s).

The present disclosure provides compositions and methods for inhibiting the activity of RNA guided endonucleases (e.g., Cas9, Cpf1), and methods of use therefore, as well as to inhibit or prevent Cas9 genome editing. The invention is based, at least in part, on the discovery of small molecule inhibitors of RNA guided endonucleases. As described herein, high-throughput biochemical and cellular assays, and workflows comprising combinations of such assays, were developed for screening and identifying small molecules with the ability to inhibit one or more activities of RNA guided endonucleases. Methods involving small molecule inhibitors of RNA guided endonucleases are useful for the modulation of RNA guided endonuclease activity, including rapid, reversible, dosage, and/or temporal control of RNA guided endonuclease technologies.

Methods of Screening Compounds

In one aspect, the present disclosure provides a method for screening inhibitors of a CRISPR-Cas system. In general, the method may comprise one or more of: incubating a set of candidate inhibitors with components of a CRISPR-Cas system, selecting one or more putative inhibitors (e.g., based on a preliminary screen), validating the putative inhibitors (e.g., using cell-based assays), and selecting one or more final inhibitors based on the validation.

Preliminary Screen

In certain example embodiments, the method may comprise a preliminary screen. The preliminary screen comprises incubating a set of candidate inhibitors in individual discrete volumes. Each individual discrete volume may comprise a different candidate inhibitor, different combination of candidate inhibitors, and/or different concentrations thereof. Each individual volume may further comprise a Cas protein to be screened, a guide molecule, and a labeled PAM-rich target oligonucleotide. The guide molecule targets binding of the CRISPR-Cas effector protein to the labeled PAM-rich target oligonucleotide. The assay may be conducted in a cellular, acellular, or cell-free environment. The Cas protein and guide molecule may be delivered as a ribonucleoprotein complex, or may delivered to the individual discrete volumes as an inducible construct. The Cas protein and guide molecule may be on the same or different guide constructs. In certain example embodiments, the Cas protein may be delivered directly to the individual discrete volumes and the guide molecule may delivered as a construct. The Cas protein and guide molecule to be screened may be any combination of Cas protein and guide molecule described above.

High-Throughput Screening

In some embodiments, the method may comprise incubating a set of candidate inhibitors in individual discrete volumes. The embodiments disclosed herein are designed to allow for screening multiple inhibitor in a high throughput manner. Accordingly, for both the preliminary screen and the cell-based screens multiple individual inhibitors, combinations of inhibitors, and/or different concentrations thereof may screen in individual discrete volumes.

Discrete Volumes

An "individual discrete volume" may be a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electromagnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents maybe passed in our through the discrete volume, while other material, such as target molecules, maybe maintained in the discrete volume or space.

Typically, a discrete volume may include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate. In certain examples, the individual discrete volumes are droplets. In certain examples, the individual discrete volumes are wells of a multi-well plate.

Selection of Putative Inhibitors

The method may further comprise selecting one or more putative inhibitors from the set of candidate inhibitors. In some examples, the selection of the putative inhibitors may be performed by measuring the effect of an inhibitor on the interaction between the Cas protein and the guide sequence, and/or the interaction between the Cas protein and the PAM-rich target oligonucleotide. For example, the putative inhibitors may be selected at least in part by detecting change in fluorescence polarization of the labeled PAM-rich target oligonucleotide, where inhibition of formation of a complex of the CRISPR-Cas and the guide molecule by the one or more of the candidate inhibitors leads to a decrease in fluorescence polarization of the labeled PAM-rich target oligonucleotide.

Disrupting PAM-sequence binding by Cas (or mutating Cas or the PAM-site) can render Cas inactive.53 Further, Cas proteins generally have a low affinity for the PAM-sequence, making the Cas-PAM interaction an Achille's heel for inhibitor discovery. However, the low affinity creates a challenge in developing robust Cas-PAM binding assays, which are overcome in the present application by leveraging the principle of multi-valency. A DNA sequence bearing multiple PAM sites has high affinity for Cas proteins. Fluorescence polarization may be used to monitor protein-DNA interaction.54 The binding of the labeled PAM-rich target molecule to a much larger Cas:guide molecule complex lowers the target molecule's tumbling rate, which can be monitored by fluorescence polarization (FIG. 1A). A preliminary assay was developed that measures changes in fluorescence polarization of the fluorophore-labeled PAM-rich target molecule as it binds to the Cas:guide sequence complex. Differential scanning fluorimetry (FIG. 1D) and bio-lary interferometry experiments (FIG. 4) confirm that Cas:guide molecule interaction with the labeled PAM-rich target molecule were PAM specific.

The labeled PAM-rich target oligonucleotide comprises multiple PAM sites. In certain example embodiments, the labeled PAM-rich target oligonucleotide comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 PAM regions per molecule. In certain example embodiments, the labeled PAM-rich target oligonucleotide comprises between 2 and 40, e.g., 2 and 30, 2 and 20, 4 and 20, 5 and 20, 6 and 20, 7 and 20, 8 and 20, 9 and 20, 10 and 20, 11 and 20, 12 and 20, 13 and 20, 14 and 20, 15 and 20, PAM sites per molecule. In one example embodiment, the labeled PAM-rich target sequence comprises 12 PAM sites per molecule. The labeled PAM-rich target oligonucleotide may be double stranded DNA, RNA, or hybrid thereof.

The labeled PAM-rich target oligonucleotide may be labeled with any fluorophore known in the art and recognized by one of ordinary skill in the art as suitable for use in a fluorescence polarization assay. In certain example embodiments, the fluorophore is FAM. In certain other example embodiments, the fluorophore is FITC. An exemplary labeled PAM rich target oligonucleotide is provided in and further shown below. (SEQ ID Nos. 7 and 8)

```
5'-GGCTGGACCACGCGGGAAAATCCACCTAGGTGGTTC

CTCTTCGGATGTTCCATCCTTT/36-FAM-3'

3'-CCGACCTGGTGCGCCCTTTTAGGTGGATCCACCAAG

GAGAAGCCTACAAGGTAGGAAA-5'
```

As understood by one of ordinary skill in the art the composition of each PAM site will depend on the Cas protein to be screened, as different Cas proteins are recognized as having different PAM site preferences. The guide molecule used in the preliminary assay is designed to target the Cas:guide molecule complex to the labeled PAM-rich target oligonucleotide. The size of the labeled PAM-rich target oligonucleotide may vary. Design considerations include the number of PAM sites to be included and the size of any target sequence adjacent to the PAM site to facilitate formation of the Cas:guide-molecule:target-sequence complex. The size of any target sequence adjacent to each PAM may vary based on the guide molecule used.

After incubating the inhibitors in the presence of Cas, guide molecule, and labelled PAM-rich target molecule for time sufficient to allow Cas:guide molecule complex formation and binding with the target molecule, changes in fluorescence polarization are measured in each individual discrete volume. For example, the fluorescence polarization may be measured using a standard fluorescence microplate reader. In certain example embodiment, the Cas protein and inhibitor are added to each individual volume first and incubated. In certain example embodiments, the incubation is at room temperature. Then, the candidate inhibitors and labeled PAM-rich target molecule are added to each individual discrete volume and incubated further. In certain example embodiments, the second incubation takes place at room temperature. In certain example embodiments putative inhibitors are defined as those compounds have > than 3σ of Z-score.

Counter Screen

In certain example embodiment, the method may further comprise performing a counter-screening assay. A counter-screening assay may be performed after the preliminary screen. A counter-screening assay may be performed in a similar format as the preliminary compound screen. For example, a counter-screening assay may comprise measuring change in fluorescence polarization of the labeled PAM-rich target oligonucleotide in presence of the one or more putative inhibitors alone, wherein candidate inhibitors that increase fluorescence polarization beyond a defined cut-off value are excluded from the one or more putative inhibitors.

In the counter screen the labelled PAM-rich target molecule is first transferred to each individual discrete volume and then incubated with the candidate inhibitor compounds prior to acquiring a fluorescence polarization signal. The change in the fluorescence polarization signal may be calculated in percentile and plotted against compounds' average Z-score values obtained from the original compound-screening assay. Compounds that resulted in greater than 3σ change in the Z-score but do not alter the fluorescence polarization signal by greater than 1%, 2%, 3%, 4%, 5%, 6%, 7%, 8%, 9%, 10%, 11%, 12%, 13%, 14%, or 15% are selected as putative inhibitor compounds and subjected to further cell-based screening as described herein.

Validating Assays

After the preliminary screen, an optionally after the counter screen, the set of identified putative compounds may be further assessed by one or more validating assays. When there are multiple validating assays, the assays may be performed in any order. The method may then comprise selecting one or more final inhibitors based at least in part on the validating assay(s). In some examples, a validating assay may be performed by delivering one or more components of a CRISPR-Cas system manipulating expression and/or activity of a reporter gene, and detecting inhibitor activity by measuring the change of expression and/or activity of the reporter gene. IN certain examples, detecting inhibitor activity is performed using high-content imaging and automated data analysis.

Knockdown Assay

In some cases, the validating assay may be a cell-based knock-down assay. In general, a cell-based knock-down assay may be performed by delivering a CRISPR-Cas effector protein, a guide sequence, and a nucleotide sequence encoding a reporter (e.g., a polypeptide reporter) into one or more cells (e.g., a population of cells) in a discrete volume with putative inhibitor(s). The knock-down assay may further comprise detecting a change in the expression and/or activity of the reporter. In some cases, the guide sequence targets the nucleotide sequence encoding the reporter and recruits the Cas effector protein to knock-down the expression of the reporter. In these cases, an increase in the expression and/or activity may indicate the inhibitor activity. In some cases, the CRISPR-Cas effector protein, the nucleotide sequence encoding the polypeptide reporter, and the guide sequence targeting the nucleotide sequence encoding the polypeptide reporter are all encoded on a single construct.

Figure 5:
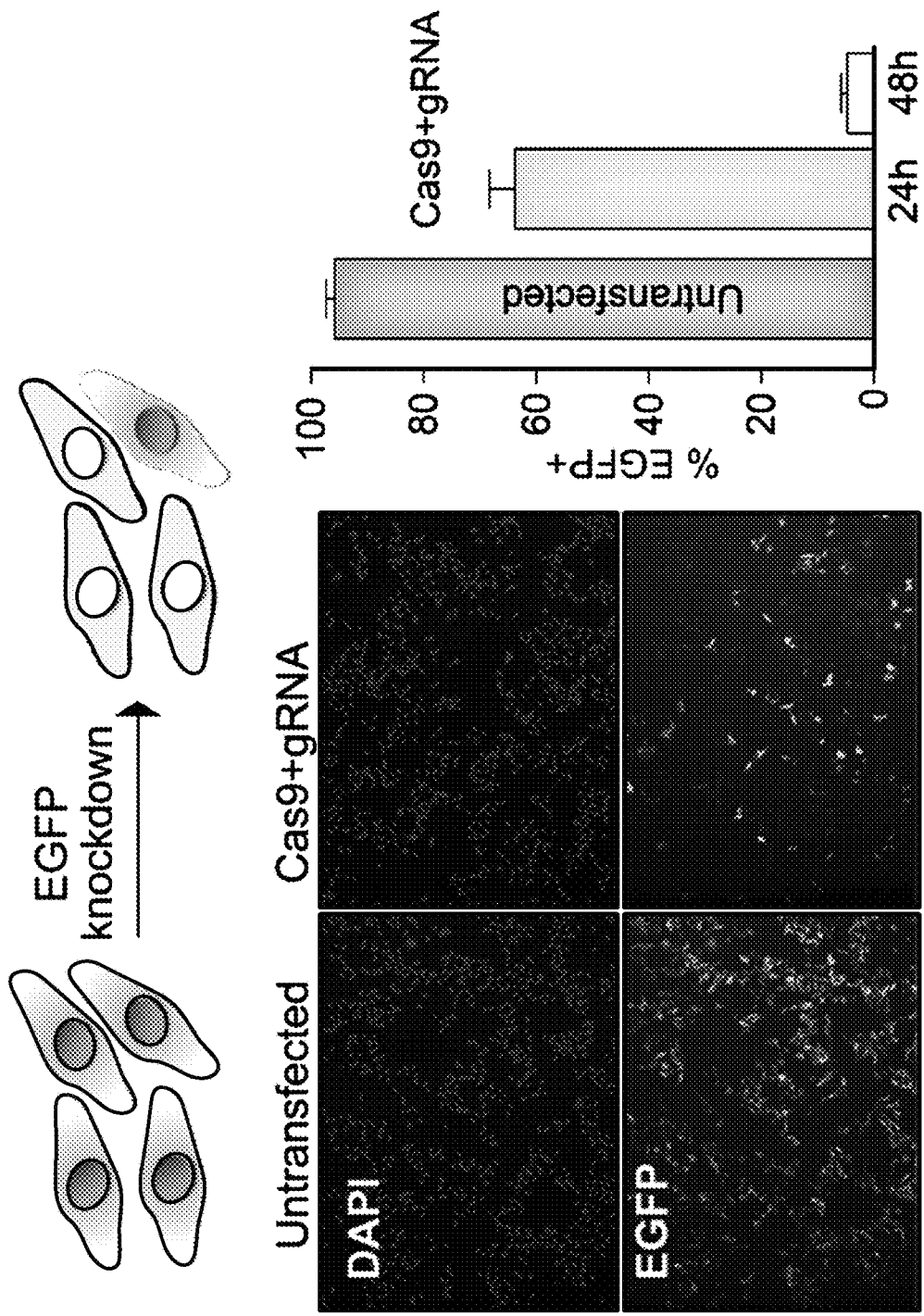
FIG. 5—Schematic representation and validation of EGFP-knockdown assay. (Top) Schematic representation of the EGFP-knockdown by SPCas9 targeting the stably expressing EGFP.PEST gene in U2OS.eGFP.PEST cells. SpCas9 induced knockout of EGFP.PEST results in the GFP fluorescence signal. (Bottom left) Representative images of the EGFP-knockdown assay in U2OS.eGFP.PEST cells. Left panels represent untransfected cells and the right panels represent post-nucleofected U2OS.eGFP.PEST cells with SpCas9 and gRNA expressing plasmids for 48 h. Scale bar=100 µm. (Bottom right) Quantified image analysis of the EGFP-knockdown assay at 24 and 48 h. Error bars represent ±S.D. from technical replicates (n=4).

The assay may use high-throughput readout using a high content, automated microscope and automated image analysis (FIG. 5). In some cases, the Cas protein to be screened, a reporter molecule and a guide molecule targeting the Cas protein to the target molecule are added to the individual discrete volumes in which cells are cultured. Various cell lines may be used. A putative inhibitor or combination of inhibitors is then added to each individual discrete volume. In certain example embodiments, the reporter molecule is a nucleic acid encoding a fluorescent polypeptide. In certain example embodiments, the reporter molecule is GFP, YFP, or RFP. In certain other example embodiments, the reporter molecule encodes mKate2. Other fluorescent proteins may be used. After incubation with the compounds, the cells may be fixed and counterstained with a nuclear stain. Image analysis of each individual discrete volume may be then obtained under the appropriate excitation channel to determine differences in reporter molecule expression. Inhibitory activity may limit Cas-mediated knockdown of the reporter genes.

In certain example embodiments, compounds showing at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 8100, 82%, 83%, 84%, 85%, 86%, 87%, 88%, 89%, or 90% inhibition relative to a control are selected for further analysis. In certain example embodiments, compounds showing at least 60% inhibition relative to control are selected for further analysis. In some examples, a control may be one or more cells that contain the nucleotide sequence encoding the polypeptide reporter, but does not contain the Cas effector protein or the guide sequence, or contains neither the Cas effector protein nor the guide sequence. Alternatively or additionally, the control may be one or more cells in a discrete volume that does not have any inhibitor.

Nuclease Activity Assay

In some cases, the validating assay may be a cell-based nuclease activity assay. It should be understood the knockdown assay and nuclease activity assay may be conducted in any order. In general, a nuclease activity assay (also referred to as a Cas activity assay) may comprise delivering a first construct and a second construct in one or more cells (e.g., a population of cells). The one or more cells may be in individual discrete volumes. Each of the discrete volumes may comprise one or more putative inhibitors. The first construct may encode an out-of-frame first reporter. The second construct may encode a CRISPR-Cas effector protein and a guide molecule. In certain examples, the nuclease activity assay may comprise a first construct as described herein, a second construct encoding a CRISPR-Cas effector protein and a third construct encoding a guide molecule. The guide molecule may target the first reporter or a regulatory element thereof, thereby recruiting the CRISPR-Cas effector protein to introduce a frameshift that shifts the first reporter in-frame. In certain examples, the first construct encodes an out-of-frame first reporter and a downstream in-frame second reporter separated by a linker comprising a stop codon, and the second construct encodes the CRISPR-Cas effector protein and a guide molecule targeting the linker, wherein the CRISPR-Cas effector protein introduces a frameshift edit at the stop codon that shifts the first reporter in-frame. The nuclease activity assay may further comprise detecting inhibitor activity by measuring changes in the expression and/or activity of the first reporter relative to a control. Decreased expression of the first reporter relative to the control may indicate inhibition of CRISPR-Cas mediated nuclease activity.

The first construct and the second construct may be delivered at a suitable molar ratio. For example, the molar ratio between the first construct and the second construct may be from 1:10 to 10:1, e.g., from 1:5 to 5:1, from 1:3 to 3:1, or from 1:2 to 2:1. For example, the molar ratio between the first construct and the second construct may be 1:10, 1:5, 1:3, 1:2, 1:1, 2:1, 3:1 5:1 or 10:1. In certain cases, the molar ratio between the first construct and the second construct may be 1:1, i.e., equimolar ratio.

In some cases, a nuclease activity assay may be a frameshift reporter assay, e.g., performed using a frame-shift reporter. Cells are cultured in individual discrete volumes. As above multiple cell lines may be used including the same cell line as used in the Knock-down assay. Cells are transfected with a frameshift reporter, the Cas protein to be screen, and guide molecules. The frameshift reporter is a nucleic acid construct encoding a first type of reporter molecule that is out-of-frame and not initially expressed, and a second type of reporter molecule that is in frame and initially expressed. A linker sequence separate the first type and second type of reporter molecule and encodes a stop codon. The guide molecules direct the Cas protein to the linker comprising the stop codon in the frameshift reporters. Introduction of a frameshift edit at the stop codon by the Cas protein results in the first type of reporter molecule being shifted in frame. Thus, inhibitory activity will limit expression of the first type of reporter molecule by limiting Cas-mediated frameshift edits.

In certain example embodiments, the first type of reporter molecule is a first type of fluorescent polypeptide detectable at a first wavelength or range of wavelengths, and the second type of reporter molecule is a second type of fluorescent polypeptide detectable at a second wavelength or range of wavelengths. After an initial incubation, the cells may be fixed and counterstained with a nucleus counterstain. As with the knockdown assay an automated high content microscope may be used to obtain images at different excitation wavelengths of each individual discrete volumes and those images analysis, for example using the MetaXpress or similar software, to determine the % NHEJ. In certain example embodiments, compounds showing at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% inhibition relative to control are selected for further analysis. In certain example embodiments, compounds showing at least 60% inhibition relative to control are selected. In certain cases, the control may be a population cells contain the first construct but does not contain the construct encoding the CRISPR-Cas effector protein or the guide molecule. Alternatively or additionally, the control may be one or more cells in a discrete volume that does not have any inhibitor.

The final inhibitor set may comprise those inhibitors passing the preliminary compound screen and exhibiting the desire level of inhibitory activity in one or both cell-based assays.

Additional Inhibitor Screens

In addition to the screens described above, the methods may further comprise one or more of the following screens. The assays described below are further described in U.S. Provisional Application No. 62/416,017 filed Nov. 1, 2016 and a PCT application to be filed claiming priority thereto and entitled "Inhibitors of RNA Guided Nucleases And Uses Thereof". The contents of both applications are incorporated herein by reference. In some examples, the method may further comprise performing a transcription assay (e.g., a spinach transcription assay), a strand displacement assay, or both. These assay(s) may be performed to identify one or more final inhibitors.

Spinach Transcription Assay

In one aspect, the invention provides a transcription assay to detect the activity of an RNA guided endonuclease. In one embodiment, the level of transcription is suppressed by Cas9 nuclease activity in an in vitro assay. In various embodiments, the transcription assay involves expression of a nucleic acid aptamer that binds a molecular fluorophore to generate a fluorescent signal. Such aptamer-fluorophore combinations are known in the art, including for example, the Spinach aptamer having the sequence

5'-GGGAGACGCAACUGAAUGAAAUGGUGAAGGACGGGUCCAGGUGU

GGCUGCUUCGGCAGUGCAGCUUGUUGAGUAGAGUGUGAGCUCCGCGU

AACUAGUCGCGUCAC-3'

(SEQ. I.D No. 14) and the fluorophore 4-(3,5-difluoro-4-hydroxybenzylidene)-1,2-dimethyl-1H-imidazol-5-one (DFHBI) (see, e.g., US20120252699 and US20140220560, each of which is incorporated herein in their entirety). In the Spinach assay, Cas9 can cleave the DNA template and thus inhibit in vitro transcription of the nucleic acid aptamer. In certain embodiments, the guide RNA targeting the Spinach aptamer has the sequence (SEQ ID No. 15)

```
5'-GCUAUAGGACGCGACCGAAAGUUUUAGAGCUAGAAAUAGCAAG

UUAAAAUAAGGCUAGUCCGUUAUCAACUUGAAAAAGUGGCACCGAG

UCGGUGCUUUU-3'
```

In the presence of fluorophore, suppression in transcription results in the reduction of RNA aptamer-fluorophore concentration and hence in the fluorescence signal. In vitro transcription reactions may comprise a purified linear DNA template containing a promoter operatively linked to a nucleic acid sequence encoding an RNA aptamer, ribonucleotide triphosphates, a buffer system (e.g., including DTT and magnesium ions, and an appropriate phage RNA polymerase (e.g., T7 polymerase).

In certain other example embodiments, the DNA templates for the Spinach IVT transcription assay are:

```
(SEQ ID No. 16)
GCGCGCTTTCTAATACGACTCACTATAGGGTGACGCGACCGAAATGGTG

AAGGACGGGTCCAGTGCTTCGGCACTGTTGAGTAGAGTGTGAGCTCCGT

AACTGGTCGCGTC
Red = T7 Promoter
Green = Cpf1 PAM
Blue = SpCas9 PAM
Orange = SaCas9 PAM
```

Produces a Spinach RNA aptamer upon transcription with the sequence

```
(SEQ ID No. 17)
5'GGUGACGCGACCGAAAUGGUGAAGGACGGGUCCAGUGCUUCGGCACU

GUUGAGUAGAGUGUGAGCUCCGUAACUGGUCGCGUC-3'
```

A more generalizable DNA Template for Spinach IVT transcription:

```
(SEQ ID No. 18)
GCGCGCNNNNTAATACGACTCACTATAGGGNNNNGACGCGACCGAAATG

GTGAAGGACGGGTCCAGTGCTTCGGCACTGTTGAGTAGAGTGTGAGCTC

CGTAACTGGTCGCGTC
```

Produces a Spinach RNA aptamer upon transcription with the sequence

```
(SEQ ID No. 19)
5'GGNNNNGACGCGACCGAAAUGGUGAAGGACGGGUCCAGUGCUUCGGC

ACUGUUGAGUAGAGUGUGAGCUCCGUAACUGGUCGCGUC-3'
```

Where either NNNN represents any nucleotide A, G, T, or C. The length of the string of NNNN is arbitrary, and can be expanded to accommodate the PAM consensus motif of any RNA-programmable DNA nuclease. The first "NNNN" site accommodates distal-PAM binding nucleases such as those of the Cpf1 family, while the second "NNNN" site accommodates both distal and proximal PAM binding nucleases (such as those of the Cpf1 family and Cas9 family, respectively).

Strand Invasion Assay

Figure 4:
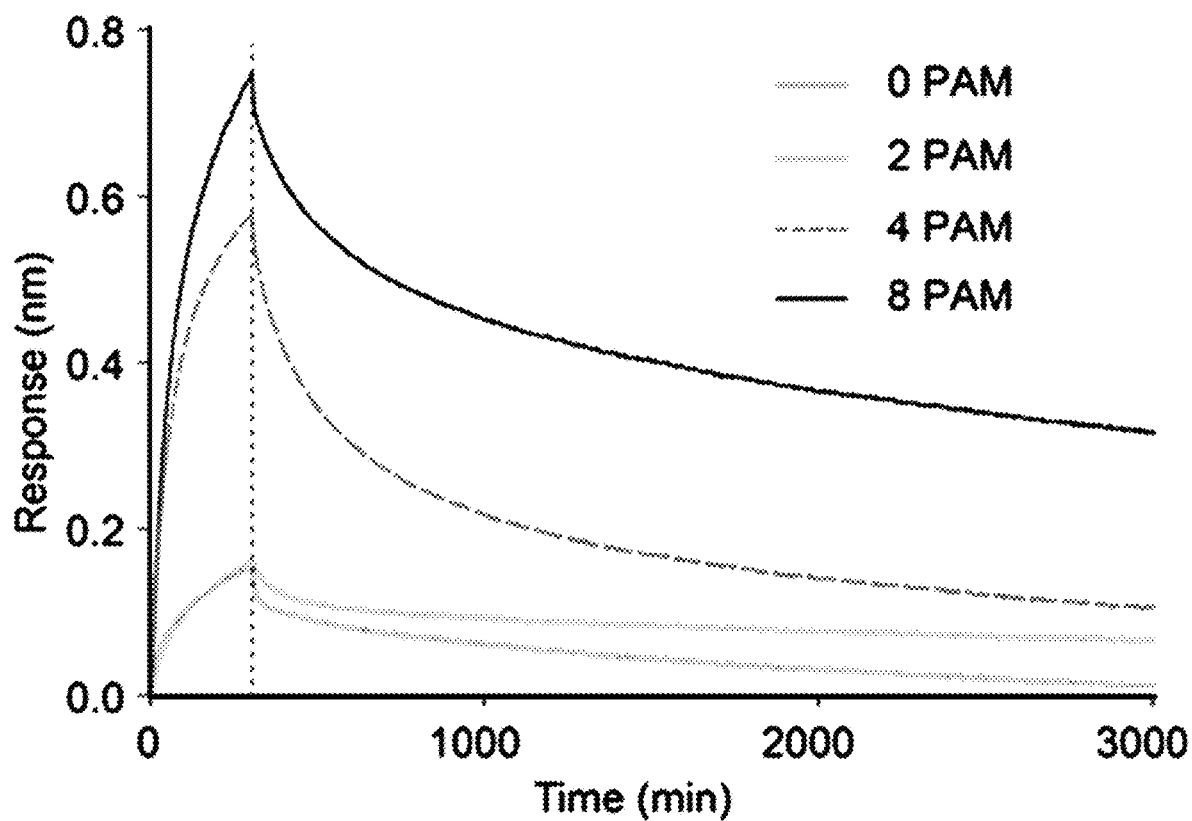
FIG. 4—Interaction of SpCas9 with ds-DNA containing a variable number of PAM sequence. Bio-Layer Interferometry (BLI) study of SpCas9:gRNA complex with ds-DNA with varying PAM sequence. Increase in the PAM number resulted in a concomitant increase in the response signal depicting higher binding affinity.

To measure the Cas9 nuclease activity, a technique was designed based on DNA strand invasion. It was hypothesized that, after a DSB by Cas9 on the substrate DNA, the fluorophore labeled (FAM) 5'-end of the non-target strand can be replaced by a corresponding single-stranded cold DNA (FIG. 4). Without being bound by theory, the displacement of the cleaved fluorophore labeled 5'-end by cold DNA leads to the loss of fluorophore from the Cas9:gRNA-DNA ternary complex which results in a decrease in the fluorescence polarization signal (FIG. 4). Thus, the extent of loss in the fluorescence polarization signal provides a readout of the Cas9 nuclease activity. It is anticipated that this assay would be useful to evaluate the potency of a Cas9 inhibitor and screen Cas9 inhibitors in a high throughput manner.

Strand Displacement Assay

In another approach, the previously described strand invasion assay may be modified to make it more sensitive and effective with an orthogonal readout of fluorescence instead of fluorescence polarization. In this assay, the substrate DNA remained the same as the strand invasion assay, though the sequence of the invading cold DNA is changed so that it can hybridize with the 5'-end free DNA available only after the Cas9 mediated cleavage. Moreover, the DNA strand may be conjugated with a fluorescence quencher at the 3'-end which can readily quench FAM fluorescence only when it hybridizes with the labile non-target strand.

In certain example embodiments, DNA substrates for the strand displacement assay are shown below and are double stranded, and only include a fluorophore (6-FAM) on the strand shown:

SpCas9:

```
SpCas9:
                                    (SEQ ID No. 20)
5'-6-FAM/TAATACGACTCACTATAGGACGCGACCGAAA

TGGTGAAGGACGGGT-3'

SaCas9:
                                    (SEQ ID No. 21)
5'-6-FAM/ACTCACTATAGGGACGCGACCGAAATGGTGA

AGGACGGGTCCAGTGCTTCGG-3'

Cpf1 (all species):
                                    (SEQ ID No. 22)
5'CGTCCTTCACCATTTCGGTCGCGTCCCTATAGTGAGTC GTATTAGTTCCAT/6-FAM-3'
And
                                    (SEQ ID No. 23)
5'-6-FAM/ATGGAACTAATACGACTCACTATAGGGACGC

GACCGAAATGGTGAAGGACG-3'
```

Quencher strand sequences for the strand displacement assay shown below are single stranded, and include a quencher (Iowa Black® FQ):

```
SpCas9:
                                    (SEQ ID No. 24)
5'-ATAGTGAGTCGTATTA/3IABkFQ-3'

SaCas9:
                                    (SEQ ID No. 25)
5'-CGTCCCTATAGTGAGT/3IABkFQ-3'

Cpf1 (all species):
                                    (SEQ ID No. 26)
```

```
                         -continued
            5'-5IABkFQ/ATGGAACTAATACGAC-3'
            And (SEQ ID No. 27)
            5'-GTCGTATTAGTTCCAT/3IABkFQ-3'
```

Cell Cas Inhibition Assays

In certain example embodiments, further screening may be done by measuring the inhibitory activity in a eukaryotic or prokaryotic cell, for example, using the assays described in further detail below Methods of Designing and/or Identifying Compounds Provided herein includes a method for designing or identifying a compound that regulates a CRISPR protein's activity. In some cases, the compound may be an inhibitor that inhibits (partially or completely) one or more activities (e.g., nuclease activity) of the CRISPR protein. In certain cases, the compound may be an activator that increases one or more activities (e.g., nuclease activity) of the CRISPR protein.

In some aspects, the method may be a computer-based method of rational design of CRISPR ligands. This rational design can comprise: providing the structure of the CRISPR protein or complex as defined by some or all (e.g., at least 2 or more, e.g., at least 5, advantageously at least 10, more advantageously at least 50 and even more advantageously at least 100 atoms) of the structure co-ordinates. The method or fitting of the method may use the co-ordinates of atoms of interest of the CRISPR complex as defined by some or all co-ordinates which are in the vicinity of an active site or binding region (e.g., at least 2 or more, e.g., at least 5, advantageously at least 10, more advantageously at least 50 and even more advantageously at least 100 atoms) of the structure in order to model the vicinity of the active site or binding region. These co-ordinates may be used to define a space which is then screened "in silico" against a desired or candidate nucleic acid molecule. Thus, the invention provides a computer-based method of rational design of CRISPR complexes. This method may include: providing the co-ordinates of at least two atoms of the CRISPR protein or complex; providing the structure of a candidate or desired ligand; and fitting the structure of the candidate to the selected co-ordinates. In this fashion, the skilled person may also fit a functional group and a candidate or desired nucleic acid molecule. For example, providing the structure of the CRISPR complex as defined by some or all (e.g., at least 2 or more, e.g., at least 5, advantageously at least 10, more advantageously at least 50 and even more advantageously at least 100) atoms of the structure co; providing a structure of a desired ligand as to which a CRISPR complex is desired; fitting the structure of the CRISPR complex as defined by some or all co-ordinates to the desired ligand, including in said fitting obtaining putative modification(s) of the CRISPR complex. The methods of the invention can employ a sub-domain of interest of the CRISPR protein or complex.

The methods can optionally include synthesizing the candidate or desired ligand and/or the CRISPR systems from the "in silico" output and testing binding and/or activity of "wet" or actual a functional group linked to a "wet" or actual CRISPR system bound to a "wet" or actual candidate or desired ligand. The methods can include synthesizing the CRISPR systems (including a functional group) from the "in silico" output and testing binding and/or activity of "wet" or actual a functional group linked to a "wet" or actual CRISPR system bound to an in vivo "wet" or actual candidate or desired nucleic acid molecule, e.g., contacting "wet" or actual CRISPR system including a functional group from the "in silico" output with a cell containing the desired or candidate ligand. These methods can include observing the cell or an organism containing the cell for a desired reaction, e.g., reduction of symptoms or condition or disease. The step of providing the structure of a candidate ligand may involve selecting the compound by computationally screening a database containing ligand data, e.g., such data as to conditions or diseases. A 3-D descriptor for binding of the candidate ligand may be derived from geometric and functional constraints derived from the architecture and chemical nature of the CRISPR protein or complex or domains or regions thereof from the herein crystal structure. In effect, the descriptor can be a type of virtual modification(s) of the CRISPR complex structure for binding CRISPR to the candidate or desired nucleic acid molecule. The descriptor may then be used to interrogate the ligand database to ascertain those ligands of the database that have putatively good binding to the descriptor. The herein "wet" steps can then be performed using the descriptor and ligands that have putatively good binding.

Fitting

The methods herein may comprise fitting a candidate molecule to a three-dimensional structure of one or more target regions. The target regions may be on a PAM interaction (PI) domain of a CRISPR protein.

"Fitting" can mean determining, by automatic or semi-automatic means, interactions between at least one atom of the candidate and at least one atom of the CRISPR protein or complex and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure.

Computational modeling technologies can be used to assess the potential modulating or binding effect of a PI domain ligand on a CRISPR protein or complex. If computer modeling indicates a strong interaction, the molecule may then be synthesized and tested for its ability to bind to a CRISPR PI domain and inhibit its activity. Modulating or other binding agents may be computationally evaluated and designed by means of a series of steps in which chemical groups or fragments are screened and selected for their ability to associate with the individual binding pockets or other areas of a CRISPR protein. This process may begin by visual inspection of, for example, the CRISPR PI domain based on the structural coordinates. Selected fragments or chemical groups may then be positioned in a variety of orientations, or docked. Manual docking may be accomplished using software such as Insight II (Accelrys, San Diego, Calif.) MOE; CE (Shindyalov, Ind., Bourne, P E, "Protein Structure Alignment by Incremental Combinatorial Extension (CE) of the Optimal Path," Protein Engineering, 11:739-47, 1998); and SYBYL (Molecular Modeling Software, Tripos Associates, Inc., St. Louis, Mo., 1992), followed by energy minimization and molecular dynamics with standard molecular mechanics force fields, such as CHARMM (Brooks, et al., J. Comp. Chem. 4:187-217, 1983). More automated docking may be accomplished by using programs such as DOCK (Kuntz et al., J. Mol. Biol., 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., J. Mol. Biol. 245:43-53, 1995); and FLEXX (Tripos, St. Louis, Mo.;

Rarey, M., et al., J. Mol. Biol. 261:470-89, 1996); AMBER (Weiner, et al., J. Am. Chem. Soc. 106: 765-84, 1984) and C²MMFF (Merck Molecular Force Field; Accelrys, San Diego, Calif.). In a preferred embodiment, Glide docking can be used.

PAM Interacting Domains

The target regions(s) for fitting the candidate molecules may be on the PI domain of the CRISPR protein.

In some examples, the PI domain is a PI domain of SaCas9. SaCas9 recognizes the 5'-NNGRRN-3' PAM with a preference for a thymine base at the 6th position (Ran et al., 2015), which is distinct from the 5'-NGG-3' PAM of SpCas9. In the present structures containing either the 5'-TTGAAT-3' PAM or the 5'-TTGGGT-3' PAM, the PAM duplex is sandwiched between the WED and PI domains, and the PAM in the non-target DNA strand is read out from the major groove side by the PI domain. dT1* and dT2* form no direct contact with the protein. Consistent with the observed requirement for the 3rd G in the 5'-NNGRRT-3' PAM, the O6 and N7 of dG3* forms bidentate hydrogen bonds with the side chain of Arg1015, which is anchored via salt bridges with Glu993 in both complexes. In the 5'-TTGAAT-3' PAM complex, the N7 atoms of dA4* and dA5* form direct and water-mediated hydrogen bonds with Asn985 and Asn985/Asn986/Arg991, respectively. In addition, the N6 of dA5* forms a water-mediated hydrogen bond with Asn985. Similarly, in the 5'-TTGGGT-3' PAM complex, the N7 atoms of dG4* and dG5* form direct and water-mediated hydrogen bonds with Asn985 and Asn985/Asn986/Arg991, respectively. The O6 of dG5* forms a water-mediated hydrogen bond with Asn985. These structural findings explain the ability of SaCas9 to recognize the purine nucleotides at positions 4 and 5 in the 5'-NNGRRT-3' PAM. The O4 of dT6* hydrogen bonds with Arg991, explaining the preference of SaCas9 to the 6th T in the 5'-NNGRRT-3' PAM. Single alanine mutants of these PAM-interacting residues reduced cleavage activities in vivo, and double mutations abolished the activity, confirming the importance of Asn985, Asn986, Arg991, Glu993 and Arg1015 for PAM recognition. In addition, the phosphate backbone of the PAM duplex is recognized from the minor groove side by the WED domain (Tyr789, Tyr882, Lys886, Ans888, Ala889 and Leu909) in a manner distinct from SpCas9. Together, our structural and functional data reveal the mechanism of relaxed recognition of the 5'-NNGRRT-3' PAM by SaCas9.

WO 2014/093635 provides phylogenetic analyses of families of Cas9 orthologs and a sequence alignment of 12 Cas9 orthologs.

In FnCas9 the PAM duplex is sandwiched between the WED and PI domains and the PAM sequences are read by the PI domain. The O6 and N7 of dG2* form bidentate hydrogen bonds with Arg1585 in the PI domain, while the N3 of dG2* forms a hydrogen bond with Ser1473 in the WED-PI linker. In the 5'-TGG-3' PAM complex, the O6 and N7 of dG3* form bidentate hydrogen bonds with Arg1556, whereas in the 5'-TGA-3' PAM complex, the N7 of dA3* forms only a single hydrogen bond with Arg1556, consistent with the higher activity of FnCas9 with the 5'-NGG-3' PAM compared to the 5'-NGA-3' PAM. In addition, dA(-1) in the target DNA strand forms a stacking interaction with Arg1474 in the WED-PI linker. The mutations of these residues reduced the in vitro DNA cleavage activity of FnCas9, confirming the functional significance of Ser1473, Arg1474, Arg1556, and Arg1585. In addition to these direct interactions, dC(-2), dG2*, and dG3* form water-mediated hydrogen bonds with Glu1449, Asp1470, and Lys1451 in the WED domain, respectively. Together, these structural findings explain the mechanism of the 5'-NGG-3' PAM recognition by FnCas9.

The PI domains of SpCas9 and SaCas9 share a similar core fold comprising two distorted, anti-parallel R sheets (β1-β3 and β4-β9), with the β5-β7 region responsible for the PAM recognition. In SpCas9, the 5'-NGG-3' PAM is recognized by Arg1333/Arg1335 in the β7 loop, whereas in SaCas9, the 5'-NNGRRT-3' PAM is recognized by Asn985/Asn986/Arg991/Arg1015 in the β5-β7 region. The PI domain of FnCas9 adopts a similar core fold to those of SpCas9 and SaCas9. Whereas, in SpCas9 and SaCas9, the β8 and β9 strands in the PI domain are responsible for the interaction with the RuvC domain, the FnCas9 PI domain lacks the equivalent strands, consistent with the structural observation that the RuvC and PI domains do not interact in FnCas9.

Figure 83:
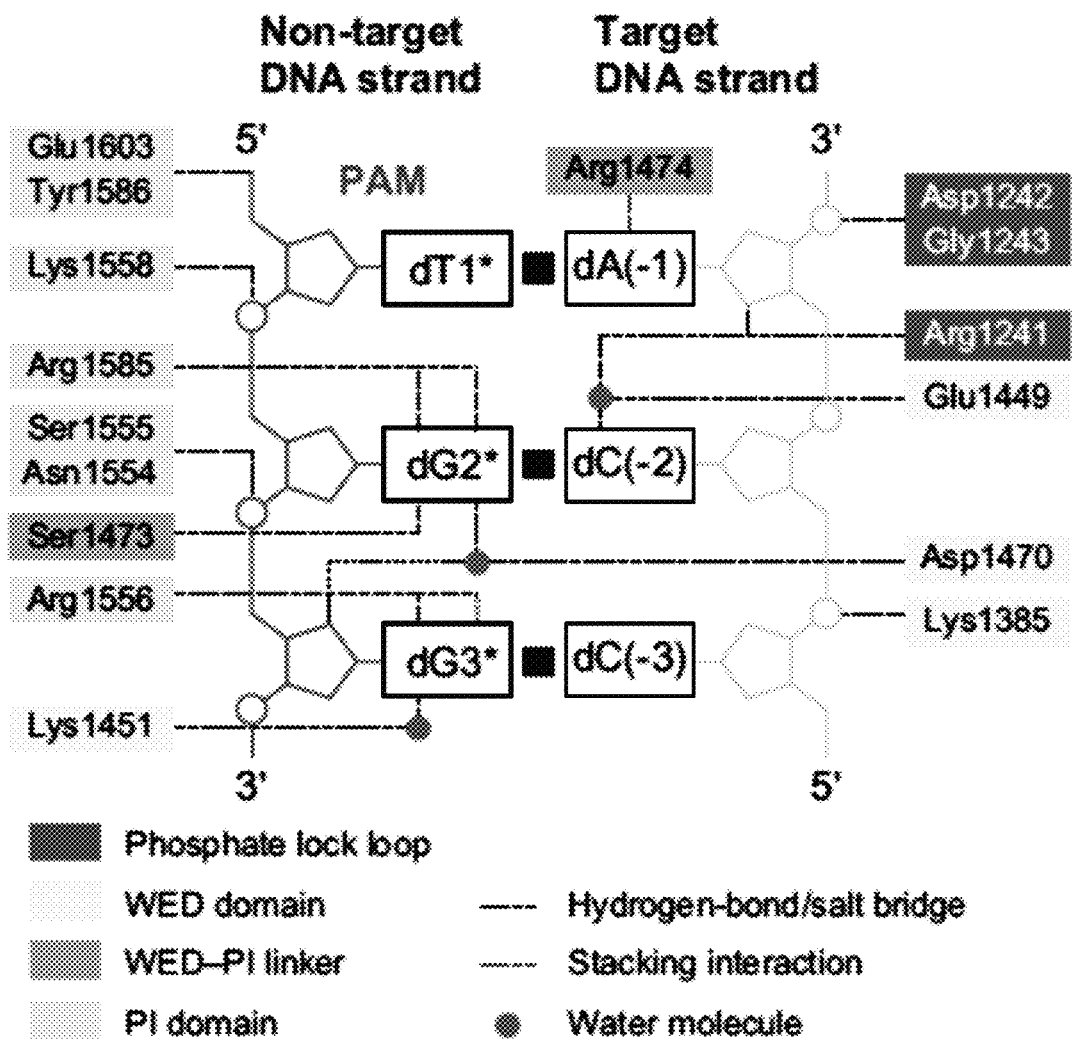
FIG. 83. Interactions of FnCas9 and PAM.

In FnCas9, the 5'-NGG-3' PAM is recognized by Arg1556 in the β5-β6 loop and Arg1585 in the β6-β7 loop. Although both SpCas9 and FnCas9 recognize the 5'-NGG-3' PAM with a pair of arginine residues (Arg1333/Arg1335 in SpCas9 and Arg1585/Arg1556 in FnCas9), these arginine pairs are located at different positions, due to the substantial difference in their relative arrangement between the PI domain and the PAM duplex. In SpCas9, the third G in the 5'-NGG-30 PAM is recognized by the Arg1335 side chain, which is anchored by a salt bridge with Glu1219, consistent with the specific recognition of the third G by SpCas9. In contrast, in FnCas9, the Arg1556 side chain does not form such a contact with the proximal residues, explaining why, unlike SpCas9, FnCas9 can also recognize the third A in the PAM, albeit with low efficiency. Together, these structural findings reinforced the notion that the Cas9 orthologs recognize diverse PAM sequences using distinct sets of PAM-interacting residues in the PI domains. See FIG. 83.

In the present structure, the 5'-AGAAACC-3' PAM-containing DNA duplex is bound to the cleft between the WED and PI domains. The nucleobases of dA1*-dA3* do not directly contact the protein, consistent with the lack of specificity for positions 1-3 in the 5'-NNNVRYM-3' PAM. The N7 of dA4* in the non-target strand forms a water-mediated hydrogen bond with the side-chain hydroxyl group of Thr913. Modeling suggested that a steric clash could occur between the methyl group of dT4* and the side chain of Thr913, consistent with the preference of CjCas9 for the fourth V (A/G/C). The N7 of dA5* in the nontarget strand forms a hydrogen bond with the side-chain hydroxyl group of Ser915. Because N7 is common among the purine nucleotides, the interaction can explain the requirement for the fifth R (A/G). Notably, the nucleobase of dC6* in the non-target strand is not recognized by the protein. Instead, the N7 of dG(-6) in the target strand forms a hydrogen bond with the side-chain hydroxyl group of Ser951. These structural findings revealed that CjCas9 does not recognize the Y (T/C) nucleotides at position 6 in the non-target strand as the PAM but detects their complementary R (A/G) nucleotides in the target strand. Similarly, the nucleobase of dC7* in the non-target strand is not recognized by the protein, whereas the O6 and N7 of dG(-7) in the target strand form bidentate hydrogen bonds with the side chain of Arg866. In addition to the 5'-AGAAACC-3' PAM complex, we determined the crystal structure of CjCas9-DHNH in complex with the sgRNA and the DNA target containing the 5'-AGAAACA-3' PAM. In the 5'-AGAAACA-3' PAM complex, the dT(-7): dA7* pair in the PAM duplex undergoes a slight displacement toward the PI domain, compared with the dG(-7): dC7* pair in the 5'-AGAAACC-3' PAM complex. This displacement in the PAM duplex allows Arg866 to form a hydrogen bond with the O4 of dT(−7) in the target strand. These observations revealed that CjCas9 does not recognize the M (A/C) nucleotides at position 7 in the non-target strand as the PAM but detects their complementary K (T/G) nucleotides in the target strand. The preference of CjCas9 for C over A at position 7 can be explained by the bidentate hydrogen-bonding interaction between dG(−7) and Arg866, in contrast to the single hydrogen-bonding interaction between dT(−7) and Arg866. The single mutations of Arg866, Thr913, Ser915, and Ser951 reduced or abolished the in vitro cleavage activity, confirming their functional importance. Together, our structural and functional data revealed that CjCas9 forms sequence-specific contacts with both the target and non-target DNA strands, to achieve the recognition of the 5'-NNNVRYM-3' PAM.

In AsCpf1, the PAM duplex adopts a distorted conformation with a narrow minor groove, as often observed in AT-rich DNA, and is bound to the groove formed by the WED, REC1 and PI domains. The PAM duplex is recognized by the WED-REC1 and PI domains from the major and minor groove sides, respectively. The dT(−1):dA(−1*) base pair in the PAM duplex does not form base-specific contacts with the protein, consistent with the lack of specificity in the 4th position of the 5'-TTTN-3' PAM. Lys607 in the PI domain is inserted into the narrow minor groove, and plays critical roles in the PAM recognition. The O2 of dT(−2*) forms a hydrogen bond with the side chain of Lys607, whereas the nucleobase and deoxyribose moieties of dA(−2) form van der Waals interactions with the side chains of Lys607 and Pro599/Met604, respectively. Modeling of the dG(−2):dC(−2*) base pair indicated that there is a steric clash between the N2 of dG(−2) and the side chain of Lys607, suggesting that dA(−2):dT(−2*), but not dG(−2):dC(−2*), is accepted at this position. These structural observations can explain the requirement of the 3rd T in the 5'-TTTN-3' PAM. The 5-methyl group of dT(−3*) forms a van der Waals interaction with the side-chain methyl group of Thr167, whereas the N3 and N7 of dA(−3) form hydrogen bonds with Lys607 and Lys548, respectively. Modeling of the dG(−3):dC(−3*) base pair indicated that there is a steric clash between the N2 of dG(−3) and the side chain of Lys607. These observations are consistent with the requirement of the 2nd T in the PAM. The 5-methyl group of dT(−4*) is surrounded by the side-chain methyl groups of Thr167 and Thr539, whereas the O4' of dA(−4) forms a hydrogen bond with the side chain of Lys607. Notably, the N3 and O4 of dT(−4*) form hydrogen bonds with the N1 of dA(−4) and the N6 of dA(−3), respectively. Modeling indicated that dA(−3) would form steric clashes with the modeled base pairs, dT(−4):dA(−4*), dG(−4):dC(−4*) and dC(−4):dG(−4*). These structural observations are consistent with the requirement of the 1st T in the PAM. The K548A and M604A mutants exhibited reduced activities, confirming that Lys548 and Met604 participate in the PAM recognition. More importantly, the K607A mutant showed almost no activity, indicating that Lys607 is critical for the PAM recognition. Together, these results indicate that AsCpf1 recognizes the 5'-TTTN-3' PAM via a combination of base and shape readout mechanisms. Thr167 and Lys607 are conserved throughout the Cpf1 family, and Lys548, Pro599, and Met604 are partially conserved. These observations indicate that the Cpf1 homologs from diverse bacteria recognize their T-rich PAMs in similar manners, although the fine details of the interaction could vary.

WO 2016/205711 provides a set of Cpf1 orthologs and consensus sequence. Preferred mutated Cpf1 and associated recognized PAM sequences are indicated in the Table 2 below of AsCpf1 and LbCpf1.

TABLE 2

Exemplary mutations of amino acid residues and associated PAMs of AsCpf1 and LbCpf1

| AsCpf1 | | LbCpf1 | |
|---|---|---|---|
| amino acid residue | PAM | amino acid residue | PAM |
| S542 (or S542R) | TYCN and TTTN (SEQ ID NO: 28 and 29) | G532 (or G532R) | TYCN and TTTN (SEQ ID NO: 28 and 29) |
| S542 (or S542R) and K548 (or K548V) | AYV and TYV and TGYV (SEQ ID NO: 30) | G532 (or G532R) and K538 (or K538V) | YCN and TTTN (SEQ ID NO: 29) |
| S542 (or S542R) and K548 (or K548V) and N552 (or N552R) | RCN and TTTN | G532 (or G532R) and K538 (or K538V) and Y542 (or Y542R) | RCN and TTTN |
| S542 (or S542R) and K607 (or K607R) | YCV and TYCV and VYCV (and TYTV) (SEQ ID NO: 31-33) | G532 (or G532R) and K595 (or K595R) | RCN and TTTN |

Interacting amino acids refers to amino acids of a CRISPR protein that interact with a ligand such as but not limited to an inhibitor. The interaction may include any subatomic element, atom or groups of atoms that form, for example, but not limited to, hydrogen bond donors, hydrogen bond acceptors, hydrophobic regions, hydrophilic regions, ionizable regions, aromatic rings. The interaction can comprise ionic, polar, and/or van der Waals interactions. The interaction may further be described by distance. For example, an interaction may involve a hydrogen bond donor that is 3 Angstroms away from a hydrogen bond acceptor. Interactions may be arranged in three-dimensional space with points of interaction defined by residues lining a binding site. In addition, interactions may further be described by torsional degrees of freedom of an atom or groups of atoms that define distinct, low energy conformations.

Nucleic Acid Modifications

In some further comprising determining the candidate molecule as an inhibitor of target nucleic acid modification by a CRISPR system which comprises the CRISPR protein. In some cases, the target nucleic acid modification comprises cleavage of the target nucleic acid. The target nucleic acid modification may comprise non-homologous end joining (NHEJ). Alternatively or additionally, the target nucleic acid modification may comprise the target nucleic acid modification comprises homologous repair (HR).

Target Regions

The target region(s) may comprise one or more amino acids. Alternatively or additionally, the target region(s) may comprise one or more first amino acids having or within certain distance of one or more second amino acids. For example, the target region(s) may comprise one or more first amino acids with certain distance, e.g., within about 1 angstroms, within about 5 angstroms, within about 10 angstroms, within about 15 angstroms, within about 20 angstroms, within about 25 angstroms, or within about 30 angstroms of one or more second amino acids.

In some examples, the CRISPR protein is *Streptococcus pyogenes* Cas9 (SpCas9) and the one or more target regions comprises one or more of Lys1107, Arg1333, and Arg1335. Alternatively or additionally, the one or more target regions comprises interacting amino acids having an alpha-carbon within 20 angstroms of Lys1107, Arg1333, and/or Arg1335.

In some examples, the CRISPR protein is *Staphylococcus aureus* Cas9 (SaCas9) and the one or more target region comprises one or more of Asn985, Asn986, Arg991, Glu993, and Arg1015. Alternatively or additionally, the one or more target regions comprises interacting amino acids having an alpha-carbon within 20 angstroms of Asn985, Asn986, Arg991, Glu993, and/or Arg1015. In some cases, the one or more target regions further comprises Tyr789, Tyr882, Lys886, Ans888, Ala889, and/or Leu909.

In some examples, the CRISPR protein is *Francisella novicida* Cas9 (FnCas9) and the one or more target regions comprises one or more of Ser1473, Arg1474, Arg1556, and Arg1585.

Alternatively or additionally, the one or more target regions further comprises interacting amino acids having an alpha-carbon within 20 angstroms of Ser1473, Arg1474, Arg1556, and/or Arg1585. In some cases, the one or more target regions further comprises Glu1449, Asp1470, and/or Lys1451. In some cases, wherein the protein is a Cas9 ortholog and the one or more target regions comprises one or more amino acids corresponding to Lys1107, Arg1333, or Arg1335 of SpCas9, or Asn985, Asn986, Arg991, Glu993, or Arg1015 of SaCas9, or Ser1473, Arg1474, Arg1556, of Arg1585 of FnCas9.

In some examples, the CRISPR protein is *Acidaminococcus* sp. Cpf1 (AsCpf1) and the one or more target regions comprises one or more of Thr167, Ser542, Lys548, Asn552, Met604, and Lys607. Alternatively or additionally, wherein the one or more target regions further comprises interacting amino acids having an alpha-carbon within 20 angstroms of Thr167, Ser542, Lys548, Asn552, Met604, and/or Lys607.

In some examples, the CRISPR protein is *Lachnospiraceae bacterium* Cpf1 (LsCpf1) and the one or more target regions comprises one or more of Gly532, Lys538, Tyr542, and Lys595. Alternatively or additionally, wherein the one or more target regions further comprises interacting amino acids having an alpha-carbon within 20 angstroms of Gly532, Lys538, Tyr542, and/or Lys595. In some cases, the protein is a Cpf1 ortholog and the target region comprises one or more amino acids corresponding to Thr167, Ser542, Lys548, Asn552, Met604, or Lys607 of AsCpf1, or Gly532, Lys538, Tyr542, or Lys595 of LsCpf1.

Uses of Crystal Structures and Atomic Structure Co-Ordinates

Crystal structures of the CRISPR protein or a part thereof may be used for the fitting. In some cases, the fitting takes advantage the crystal structure of the PI domain or a part thereof of a CRISPR protein.

Compounds disclosed herein have been discovered to interact to CRISPR proteins and inhibit CRISPR function. In certain embodiments, the compounds interact with amino acids of a PAM interacting (PI) domain of a CRISPR protein and inhibit function. The compounds can be used with CRISPR protein structure information to identify, measure, and/or model such interactions. Moreover, the interactions can be used to identify new compounds capable of inhibiting CRISPR function. In an embodiment of the invention, a compound is compared to the atomic coordinates of the PAM of a CRISPR protein. The atomic coordinates of the CRISPR protein can be from, e.g., crystallography or NMR studies, or in silico models.

Atomic coordinates and models of CRISPR proteins include, without limitation:

TABLE 3

| Model | PDB Ref. |
| --- | --- |
| *S. pyogenes* Cas9 | 4CMP |
| *Streptococcus pyogenes* Cas9 in complex with guide RNA and target DNA | 4OO8 |
| *S. aureus* Cas9 (TTGGGT PAM) | 5AXW |
| *S. aureus* Cas9 (TTGAAT PAM) | 5CZZ |
| *F. novicida* Cas9 (TGG PAM) | 5B2O |
| *F. novicida* Cas9 (TGA PAM) | 5B2P |
| *F. novicida* Cas9 (TGG PAM) | 5B2Q |
| *C. Jejuni* Cas9 (AGAAACC PAM) | 5X2G |
| *C. Jejuni* Cas9 (AGAAACA PAM) | 5X2H |
| AsCpf1 | 5B43 |
| *Acidaminococcus* sp. BV3L6 Cpf1 (TATA PAM) | 5XH6 |
| *Acidaminococcus* sp. BV3L6 Cpf1 (TCCA PAM) | 5XH7 |
| LbCpf1 (TTTA PAM) | 5XUS |
| LbCpf1 (TCTA PAM) | 5XUT |
| LbCpf1 (TCCA PAM) | 5XUU |
| LbCpf1 (CCCA PAM) | 5XUZ |

It will be recognized that there is variability among naturally occurring CRISPR proteins as to PAM specificity and further that changes in PAM specificity can be engineered. Thus, in certain embodiments, PI amino acids are identified in the art. In other embodiments, PI amino acids can be identified by their location in a CRISPR protein, for example at a position near to or in contact with PAM nucleotides in a CRISPR complex. In other embodiments, PI amino acids are evident from sequence alignments to CRISPR proteins whose structures have been solved. In still other embodiments, PI amino acids are evident from mutations which shift PAM specificity. Accordingly, the invention provides methods of designing or identifying inhibitors of naturally occurring and engineered CRISPR proteins.

The three-dimensional structures and atomic structure co-ordinates obtained therefrom, have a wide variety of uses. The crystals and structure co-ordinates are particularly useful for identifying compounds that interact with and/or bind to CRISPR-Cas9, CRISPR-Cpf1, and orthologs thereof. The structures of CRISPR proteins complexed with guides and target nucleic acids further provide the skilled artisan with insights into mechanisms of action of CRISPR proteins.

CRISPR Systems

The embodiments disclosed herein may be used to screen a wide array of CRISPR-Cas proteins. The molecules identified and/or designed using the methods herein may modulate activities of one or more components of a CRISPR system, e.g., a CRISPR protein. "CRISPR protein", "Cas protein" "CRISPR-Cas enzyme", and "CRISPR effector protein) may be used interchangeably.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of Homologous proteins may but need not be structurally related, or are only partially structurally related. An "orthologue" of a protein as used herein is a protein of a different species which performs the same or a similar function as the protein it is an orthologue of: Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base-pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl (cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J Med. Chem. 2005, 48:901-904; Bramsen et al., Front. Genet., 2012, 3:154; Deng et al., PNAS, 2015, 112:11870-11875; Sharma et al., MedChemComm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromouridine, pseudouridine (Ψ), N1-methylpseudouridine (meΨ), 5-methoxyuridine (5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU (SEQ ID Nos. 1-4).

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotrizines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y base-pairing sequence (e.g., as to length) is tolerated, so long as the secondary structure of the entire guide molecule is preserved. In one aspect, the loop that connects the stem made of X:Y base pairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer base pairs are also contemplated. In one aspect, non-Watson Crick base-pairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary base pairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions.

Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched base pairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527(7577): 192-7 (Nov. 12, 2015) doi: 10.1038/nature15521. Epub 2015 September 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 216 January 1351(6268): 84-88 doi: 10.1126/science.aad5227. Epub 2015 Dec. 1.

Gao et al, "Engineered Cpf1 Enzymes with Altered PAM Specificities," bioRxiv 091611; doi: dx.doi.org/10.1101/091611 (Dec. 4, 2016).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM (SEQ ID Nos. 5 and 6). A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from Francisella novicida U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of Streptococcus pyogenes Cas9 (SpCas9). The authors developed "enhanced specificity" SpCas9 (eSpCas9) variants which maintained robust on-target cleavage with reduced off-target effects.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/ 093661 (PCT/US2013/074743), WO2014/093694 (PCT/ US2013/074790), WO2014/093595 (PCT/US2013/ 074611), WO2014/093718 (PCT/US2013/074825), WO2014/093709 (PCT/US2013/074812), WO2014/093622 (PCT/US2013/074667), WO2014/093635 (PCT/US2013/ 074691), WO2014/093655 (PCT/US2013/074736), WO2014/093712 (PCT/US2013/074819), WO2014/093701 (PCT/US2013/074800), WO2014/018423 (PCT/US2013/ 051418), WO2014/204723 (PCT/US2014/041790), WO2014/204724 (PCT/US2014/041800), WO2014/204725 (PCT/US2014/041803), WO2014/204726 (PCT/US2014/ 041804), WO2014/204727 (PCT/US2014/041806), WO2014/204728 (PCT/US2014/041808), WO2014/204729 (PCT/US2014/041809), WO2015/089351 (PCT/US2014/ 069897), WO2015/089354 (PCT/US2014/069902), WO2015/089364 (PCT/US2014/069925), WO2015/089427 (PCT/US2014/070068), WO2015/089462 (PCT/US2014/ 070127), WO2015/089419 (PCT/US2014/070057), WO2015/089465 (PCT/US2014/070135), WO2015/089486 (PCT/US2014/070175), WO2015/058052 (PCT/US2014/ 061077), WO2015/070083 (PCT/US2014/064663), WO2015/089354 (PCT/US2014/069902), WO2015/089351 (PCT/US2014/069897), WO2015/089364 (PCT/US2014/ 069925), WO2015/089427 (PCT/US2014/070068), WO2015/089473 (PCT/US2014/070152), WO2015/089486 (PCT/US2014/070175), WO2016/049258 (PCT/US2015/ 051830), WO2016/094867 (PCT/US2015/065385), WO2016/094872 (PCT/US2015/065393), WO2016/094874 (PCT/US2015/065396), WO2016/106244 (PCT/US2015/ 067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17-Jun. 202015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTION- ALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24-Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

The embodiment disclosed herein may be used to screen a wide array of CRISPR-systems. In certain example embodiments, the Cas protein is Cas9 or an orthologue thereof, an engineered Cas9, Cpf1 ortholog thereof, an engineered Cpf1, a naturally occurring or engineered single strand or double strand nickase. In certain example embodiments, the Cas protein is a Cpf1 variant with altered PAM specificities such as those disclosed in Gao et al. Nature Biotechnology, 2017. 35(8):789-792.

CRISPR Evolution

An extension of the embodiment disclosed herein, is CRISPR evolution of new Cas variants. For example, once a set of inhibitors is identified a given CRISPR system may be expressed in a prokaryotic cell in growth media containing said inhibitors. Screening of the CRISPR system, for example by sequencing, may be used to assess for development of new CRISPR variants that evolve in the presence of the inhibitors.

Compounds

The candidate and/or the final inhibitors may be chemical compounds. Disclosed herein are inhibitors of a CRISPR protein, e.g., Cas9, Cpf1, etc., an RNA-guided DNA endonuclease that naturally occurs in, e.g., *S. pyogenes* (SpCas9), *S. aureus* (SaCas9), *F. novicida* (FnCas9), *Acidaminococcus* sp. (AsCpf1), *Lachnospiraceae bacterium* (LbCpf1), etc. Cas9 recognizes foreign DNA using Protospacer Adjacent Motif (PAM) sequence and the base-pairing of the target DNA by the guide RNA (gRNA). The relative ease of inducing targeted strand breaks at any genomic loci by a CRISPR protein has enabled efficient genome editing in multiple cell types and organisms. CRISPR protein derivatives can also be used as transcriptional activators/repressors.

A challenge posed by CRISPR protein is that its cleavage selectivity is low. Off-target editing activity can result in undesired undesirable chromosomal translocation. This activity limits the use of a CRISPR protein in a therapeutic setting due to unreliable gene manipulation and lack of ability to control the action of the CRISPR protein. The CRISPR protein inhibitors disclosed herein provide rapid, dosable, and/or temporal control of the CRISPR protein that increases CRISPR protein specificity and enables external control and manipulation of gene targeting.

The compounds disclosed herein can be in free base form unassociated with other ions or molecules, or they can be a pharmaceutically acceptable salt, solvate, or prodrug thereof. One aspect provides a disclosed compound or a pharmaceutically acceptable salt. One aspect provides a disclosed compound or a pharmaceutically acceptable salt or solvate thereof. One aspect provides a pharmaceutically acceptable salt of a disclosed compound. One aspect provides a solvate of a disclosed compound. One aspect provides a hydrate of a disclosed compound. One aspect provides a prodrug of a disclosed compound.

The disclosed compounds can be in free base form unassociated with other ions or molecules, or they can be a pharmaceutically acceptable salt, solvate, or prodrug thereof. One aspect provides a disclosed compound or a pharmaceutically acceptable salt. One aspect provides a disclosed compound or a pharmaceutically acceptable salt or solvate thereof. One aspect provides a pharmaceutically acceptable salt of a disclosed compound. One aspect provides a solvate of a disclosed compound. One aspect provides a hydrate of a disclosed compound. One aspect provides a prodrug of a disclosed compound.

Forms of Compounds

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof, and other mixtures thereof, as falling within the scope of this disclosure.

Geometric isomers can be represented by the symbol ----- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, a disclosed compound can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

All chiral, diastereomeric, racemic, and geometric isomeric forms of a structure are intended, unless specific stereochemistry or isomeric form is specifically indicated. All processes used to prepare compounds and intermediates made therein are encompassed by the present disclosure. All tautomers of shown or described compounds are also encompassed by the present disclosure.

Any compounds, compositions, or methods provided herein can be combined with one or more of any of the other compositions and methods provided herein.

Test Compounds and Extracts

In general, small molecule compounds are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. For example, a library of 8,000 novel small molecules is available, which was created using combinatorial methods of Diversity-Oriented Synthesis (DOS) (Comer et al, Proc Natl Acad Sci USA 108, 6751 (Apr. 26, 2011; Lowe et al, J Org Chem 77, 7187 (Sep. 7, 2012); Marcaurelle et al, J Am Chem Soc 132, 16962 (Dec. 1, 2010)) to investigate chemical compounds not represented in traditional pharmaceutical libraries (Schreiber, S. L. (2000). Science 287, 1964-1969; Schreiber et al, Nat Biotechnol 28, 904 (September, 2010), each of which is herein incorporated by reference in their entirety). Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

SURVEYOR Nuclease Assay

In various embodiments, SURVEYOR nuclease assay is used to assess genome modification (see e.g., US20150356239, which is herein incorporated by reference in its entirety. In one protocol, 293FT cells are transfected with plasmid DNA. Cells were incubated at 37° C. for 72 hours post-transfection prior to genomic DNA extraction. Genomic DNA is extracted using the QuickExtract DNA Extraction Solution (Epicentre) following the manufacturer's protocol. Briefly, pelleted cells are resuspended in QuickExtract solution and incubated at 65° C. for 15 minutes and 98° C. for 10 minutes.

The genomic region flanking the CR1SPR target site for each gene is PCR amplified, and products are purified using QiaQuick Spin Column (Qiagen) following the manufacturer's protocol. 400 ng total of the purified PCR products are mixed with 2 µl 10× Taq DNA Polymerase PCR buffer (Enzytrsaties) and ultrapure water to a final volume of 201, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products are treated with SURVEYOR nuclease and SURVEYOR enhancer S (Transgenomics) following the manufacturer's recommended protocol, and analyzed on 4-20% Novex TBE poly-acrylamide gels (Life Technologies). Gels re stained with SYBR Gold DNA stain (Life Technologies) for 30 minutes and imaged with a Gel Doe gel imaging system (Bio-rad). Quantification is based on relative band intensities.

Methods of Use

The present disclosure may also include using the compounds that regulating one or more activities of a CRISPR protein designed or identified using the methods described herein. In some cases, the compounds may be used for treating or diagnosing a health condition, e.g., a disease. For example, the present disclosure may include a method for treating a health condition, e.g., a disease using a CRISPR protein with one or more of the compounds identified or designed using the methods herein. In some examples, the method may comprise further screening and/or validating the designed or identified compound(s) with one or more additional assays, e.g., assays for testing a CRISPR activity and the effect of the compound(s) on the activity. Examples of such assay include affinity assay, knock-down assay, nuclease activity assay, spinach transcription assay, strand invasion assay, strand displacement assay, cell cas inhibition assay, or any combination thereof.

Small molecule inhibitors of RNA guided endonucleases (e.g., Cas9, Cpf1) were developed that have the potential to allow rapid, dosable, and/or temporal control of CRISPR protein activities. Reports of small-molecule controlled CRISPR protein activity are present in literature (Senis et al., *Biotechnol J* 2014, 9, 1402-12; Wright et al., *Proc Natl Acad Sci USA*. 2015 Mar. 10; 112(10):2984-9; Gonzalez et al., *Cell Stem Cell* 2014, 15, 215-26; Davis et al., *Nat Chem Biol* 2015, 11, 316-8). However, none of them ensure dosability—the small molecules act merely as inducers of CRISPR protein activity. Further, most of these small molecule systems are not reversible upon removal of the small molecule (Zetsche et al., *Nat Biotech* 2015, 33, 139-142;

Davis et al., *Nat Chem Biol* 2015, 11, 316-8), and therefore, do not allow precise temporal control in transcriptional regulatory technologies.

Small molecule inhibitors of RNA guided endonucleases (e.g., Cas9, Cpf1) have potential therapeutic uses for regulating genome editing technologies involving RNA guided endonucleases. Dosable control of the therapeutic activity of RNA guided endonucleases introduced into a subject or cell of a subject is important for effective genome editing therapeutic strategies. Small molecule inhibitors of RNA guided endonucleases can be administered to a subject undergoing RNA guided endonuclease based gene therapy or any other RNA guided endonuclease based therapy. In certain embodiments, the subject is a human or mammal. Small molecule inhibitors of RNA guided endonucleases eliminate or reduce undesirable off-target editing and chromosomal translocations when present at high concentrations Furthermore, small molecule inhibitors of RNA guided endonucleases can be used to rapidly terminate constitutively active CRISPR protein, following on-target gene-editing.

Small molecule inhibitors of RNA guided endonucleases can also be used to regulate genome editing technologies in other organisms, including invertebrates, plants, and unicellular organisms (e.g., bacteria). Potential uses include regulating gene drives for entomological and agricultural uses. In addition, it is anticipated that CRISPR protein inhibitors will be valuable probes to understand the role of the protein in CRISPR-mediated bacterial immunity (e.g., spacer acquisition) (Nunez et al., *Nature*. 2015 Mar. 12; 519(7542):193-8; Heler et al., *Nature* 2015, 519, 199-202). Along similar lines, CRISPR protein inhibitors can be deployed for directed evolution of the CRISPR protein. It is hypothesized that CRISPR protein inhibitors will disrupt bacterial immunity against bacteriophages (or toxic DNA) by interfering with the CRISPR-Cas-based immune surveillance system in bacteria. Akin to the development of antibiotic resistance, bacteria will be forced to evolve CRISPR protein.

Formulations

Agents described herein, including analogs thereof, and/or agents discovered to have medicinal value using the methods described herein are useful as a drug for treating diabetes. For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms. Generally, amounts will be in the range of those used for other agents used in the treatment of other diseases associated with diabetes.

The disclosed compounds may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus calmette-guerin, Shigella, Lactobacillus*); Live viral vectors (e.g., Vaccinia, adenovirus, Herpes Simplex); Microspheres; Nucleic acid vaccines; Polymers; Polymer rings; Proteasomes; Sodium Fluoride; Transgenic plants; Virosomes; Virus-like particles. Other delivery vehicles are known in the art and some additional examples are provided below.

The disclosed compounds may be administered by any route known, such as, for example, orally, transdermally, intravenously, cutaneously, subcutaneously, nasally, intramuscularly, intraperitoneally, intracranially, and intracerebroventricularly.

In certain embodiments, disclosed compounds are administered at dosage levels greater than about 0.001 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than about 0.001 mg/kg or greater than about 50 mg/kg (for example about 50-100 mg/kg) can also be administered to a subject.

In one embodiment, the compound is administered once-daily, twice-daily, or three-times daily. In one embodiment, the compound is administered continuously (i.e., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds can be administered on a non-regular basis e.g., whenever symptoms begin. For any compound described herein the effective amount can be initially determined from animal models.

Toxicity and efficacy of the compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices may have a greater effect when practicing the methods as disclosed herein. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds disclosed herein for use in humans. The dosage of such agents lies within a range of circulating concentrations that include the $ED_{50}$ with little or no toxicity. The dosage may vary within this range depending upon the dosage form employed and the route of administration utilized. For any compound used in the disclosed methods, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Multiple doses of the compounds are also contemplated.

The formulations disclosed herein are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more disclosed compounds can be administered to a subject by any mode that delivers the compound(s) to the desired surface, e.g., mucosal, systemic. Administering the pharmaceutical composition of the present disclosure may be accomplished by any means known to the skilled artisan. Disclosed compounds may be administered orally, transdermally, intravenously, cutaneously, subcutaneously, nasally, intramuscularly, intraperitoneally, intracranially, or intracerebroventricularly.

For oral administration, one or more compounds can be formulated readily by combining the active compound(s) with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of one or more disclosed compounds. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. In some aspects for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. In some aspects, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The disclosed compounds can be included in the formulation as fine multiparticulates in the form of granules or pellets of particle size about 1 mm. The formulation of the material for capsule administration could also be as a powder, lightly compressed plugs or even as tablets. The compound could be prepared by compression.

Colorants and flavoring agents may all be included. For example, the compound may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, $\alpha$-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultra-amylopecting, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the disclosure. The compound is delivered to the lungs of a mammal while inhaling and traverses across the lung epithelial lining to the blood stream using methods well known in the art.

Contemplated for use in the practice of methods disclosed herein are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of these methods are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to about 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., about 50 to about 90% by weight of the formulation. The compound should most advantageously be prepared in particulate form with an average particle size of less than 10 mm (or microns), such as about 0.5 to about 5 mm, for an effective delivery to the distal lung.

Nasal delivery of a disclosed compound is also contemplated. Nasal delivery allows the passage of a compound to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition solution into a chamber of defined volume, which chamber has an aperture dimensioned to aerosolize and aerosol formulation by forming a spray when a liquid in the chamber is compressed. The chamber is compressed to administer the pharmaceutical composition. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. In some aspects, the nasal inhaler will provide a metered amount of the aerosol formulation, for administration of a measured dose of the drug.

The compound, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (about 1-2% w/v); citric acid and a salt (about 1-3% w/v); boric acid and a salt (about 0.5-2.5% w/v); and phosphoric acid and a salt (about 0.8-2% w/v). Suitable preservatives include benzalkonium chloride (about 0.003-0.03% w/v); chlorobutanol (about 0.3-0.9% w/v); parabens (about 0.01-0.25% w/v) and thimerosal (about 0.004-0.02% w/v).

The pharmaceutical compositions contain an effective amount of a disclosed compound optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds, and with each other, in a manner such that there is no interaction which would substantially impair the desired pharmaceutical efficiency.

Provided herein are methods of synthesizing disclosed compounds. A compound provided herein can be synthesized using a variety of methods known in the art. The schemes and description below depict general routes for the preparation of disclosed compounds.

Kits

The present compositions may be assembled into kits or pharmaceutical systems. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996);

"Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Although the present invention and its advantages have been described in detail, it should be understood that various changes, substitutions and alterations can be made herein without departing from the spirit and scope of the invention as defined in the appended claims.

Example embodiments are further described in the following numbered statements.

1. A method for screening inhibitors of CRISPR-Cas systems comprising:
    incubating a set of candidate inhibitors in individual discrete volumes, each individual discrete volume comprising (i) a different candidate inhibitor, different concentration of a inhibitor, different combination of inhibitors, or different concentrations of the combination of inhibitors, and (ii) a labeled PAM-rich target oligonucleotide, a CRISPR-Cas effector protein, and a guide molecule, wherein the guide molecule targets binding of the CRISPR-Cas effector protein to the labeled PAM-rich target oligonucleotide;
    selecting one or more putative inhibitors from the set of candidate inhibitors at least in part by detecting change in fluorescence polarization of the labeled PAM-rich target oligonucleotide, wherein inhibition of formation of a complex of the CRISPR-Cas and the guide molecule by the one or more of the candidate inhibitors leads to a decrease in fluorescence polarization of the labeled PAM-rich target oligonucleotide;
    validating the one or more putative inhibitors based on a cell-based knockdown assay and a cell-based nuclease activity assay comprising use of a frame-shift reporter; and
    selecting one or more final inhibitors based at least in part on the cell-based knockdown assay and the cell-based nuclease activity assay.
2. The method of statement 1, further comprising a counter-screen of the one or more putative inhibitors comprising measuring change in fluorescence polarization of the labeled PAM-rich target oligonucleotide in presence of the one or more putative inhibitors alone, wherein candidate inhibitors that increase fluorescence polarization beyond a defined cut-off value are excluded from the one or more putative inhibitors.
3. The method of statement 1 or 2, wherein the cell-based knockdown assay is performed by:
    delivering the CRISPR-Cas effector protein, a nucleotide sequence encoding a polypeptide reporter, and a guide sequence targeting the nucleotide sequence encoding the polypeptide reporter to a population of cells in the individual discrete volumes, each individual discrete volume comprising the one or more putative inhibitors; and
    detecting inhibitor activity by measuring changes in fluorescence, wherein an increase in fluorescence relative to a control indicates inhibition of CRISPR-Cas mediated knockdown of the polypeptide reporter.
4. The method of any one of statements 1-3, wherein the cell-based nuclease activity assay comprises:
    delivering a first construct and a second construct to a population of cells in individual discrete volumes, each individual discrete volume comprising the one or more putative inhibitors, wherein the first construct encodes an out-of-frame first reporter and a downstream in-frame second reporter separated by a linker comprising a stop codon, and the second construct encodes the CRISPR-Cas effector protein and a guide molecule targeting the linker, wherein the CRISPR-Cas effector protein introduces a frame-shift edit at the stop codon that shifts the first reporter in-frame; and
    detecting inhibitor activity by measuring changes in expression of the first reporter, wherein decreased expression of the first reporter relative to a control indicates inhibition of CRISPR-Cas mediated nuclease activity.
5. The method of any one of statements 1-4, wherein detecting inhibitor activity is performed using high-content imaging and automated data analysis.
6. The method of any one of statements 1-5, wherein the polypeptide reporter is a fluorescent protein.
7. The method of statement 6, wherein the fluorescent protein is mKate2.
8. The method of any one of statements 1-7, wherein the first construct and the second construct are delivered in equimolar ratios.
9. The method of any one of statements 1-8, wherein the first reporter is a first fluorescent polypeptide detectable at a first wavelength or range of wavelengths, and the second reporter is a second fluorescent polypeptide detectable at a second wavelength or range of wavelengths.
10. The method of any one of statements 1-9, wherein the CRISPR-Cas effector protein, the nucleotide sequence encoding the polypeptide reporter, and the guide sequence targeting the nucleotide sequence encoding the polypeptide reporter are all encoded on a single construct.
11. The method of any one of statements 1-10, wherein the labeled PAM-rich target oligonucleotide comprises between 2 and 20 PAM regions per oligonucleotide.
12. The method of statement 11, wherein the labeled PAM-rich target oligonucleotide comprises 12PAM regions.
13. The method of any one of statements 1-12, where in the individual discrete volumes are droplets or wells of a multi-well plate.
14. The method of any one of statements 1-13, further comprising performing a transcription assay and/or a strand displacement assay to identify one or more final inhibitors.
15. A method of designing or identifying an inhibitor of a CRISPR protein, the method comprising:
    fitting a candidate molecule to a three-dimensional structure of one or more target regions of a PAM interaction (PI) domain of the CRISPR protein; and
    evaluating results of the fitting to determine ability of the candidate molecule to interact with the one or more target regions of the PI domain.
16. The method of statement 15, wherein the fitting is carried out on a computer.

17. The method of statement 15 or 16, further comprising determining the candidate molecule as an inhibitor of target nucleic acid modification by a CRISPR system which comprises the CRISPR protein.
18. The method of any one of statements 15-17, wherein the target nucleic acid modification comprises cleavage of the target nucleic acid.
19. The method of any one of statements 15-18, wherein the target nucleic acid modification comprises non-homologous end joining (NHEJ).
20. The method of any one of statements 15-19, wherein the target nucleic acid modification comprises homologous repair (HR).
21. The method of any one of statements 15-20, wherein the CRISPR protein is Cas9 and the PI domain is a PI domain of Cas9.
22. The method of any one of statements 15-21, wherein the CRISPR protein is *Streptococcus pyogenes* Cas9 (SpCas9) and the one or more target regions comprises one or more of Lys1107, Arg1333, and Arg1335.
23. The method of statement 22, wherein the one or more target regions comprises interacting amino acids having an alpha-carbon within 20 angstroms of Lys1107, Arg1333, and/or Arg1335.
24. The method of any one of statements 15-23, wherein the CRISPR protein is *Staphylococcus aureus* Cas9 (SaCas9) and the one or more target region comprises one or more of Asn985, Asn986, Arg991, Glu993, and Arg1015.
25. The method of statement 24, wherein the one or more target regions comprises interacting amino acids having an alpha-carbon within 20 angstroms of Asn985, Asn986, Arg991, Glu993, and/or Arg1015.
26. The method of statement 24 or 25, wherein the one or more target regions further comprises Tyr789, Tyr882, Lys886, Ans888, Ala889, and/or Leu909.
27. The method of any one of statements 15-26, wherein the CRISPR protein is *Francisella novicida* Cas9 (FnCas9) and the one or more target regions comprises one or more of Ser1473, Arg1474, Arg1556, and Arg1585.
28. The method of statement 27, wherein the one or more target regions further comprises interacting amino acids having an alpha-carbon within 20 angstroms of Ser1473, Arg1474, Arg1556, and/or Arg1585.
29. The method of statement 27 or 28, wherein the one or more target regions further comprises Glu1449, Asp1470, and/or Lys1451.
30. The method of any one of statements 15-29, wherein the protein is a Cas9 ortholog and the one or more target regions comprises one or more amino acids corresponding to Lys1107, Arg1333, or Arg1335 of SpCas9, or Asn985, Asn986, Arg991, Glu993, or Arg1015 of SaCas9, or Ser1473, Arg1474, Arg1556, of Arg1585 of FnCas9.
31. The method of any one of statements 15-29, wherein the CRISPR protein is *Acidaminococcus* sp. Cpf1 (AsCpf1) and the one or more target regions comprises one or more of Thr167, Ser542, Lys548, Asn552, Met604, and Lys607.
32. The method of statement 31, wherein the one or more target regions further comprises interacting amino acids having an alpha-carbon within 20 angstroms of Thr167, Ser542, Lys548, Asn552, Met604, and/or Lys607.
33. The method of any one of statements 15-32, wherein the CRISPR protein is *Lachnospiraceae bacterium* Cpf1 (LsCpf1) and the one or more target regions comprises one or more of Gly532, Lys538, Tyr542, and Lys595.
34. The method of statement 33, wherein the one or more target regions further comprises interacting amino acids having an alpha-carbon within 20 angstroms of Gly532, Lys538, Tyr542, and/or Lys595.
35. The method of any one of statements 15-34, wherein the protein is a Cpf1 ortholog and the target region comprises one or more amino acids corresponding to Thr167, Ser542, Lys548, Asn552, Met604, or Lys607 of AsCpf1, or Gly532, Lys538, Tyr542, or Lys595 of LsCpf1.

The invention is further described in the following examples, which do not limit the scope of the invention described in the claims.

EXAMPLES

Example 1—Assay Development and Identification of Small Molecule Inhibitors of Cas9

Rationale and Preliminary Studies. As discussed above, an active search is ongoing for "off-switches" of SpCas9. Currently, the best SpCas9 inhibitor (reported by Rauch et al.) is an "Anti-CRISPR" protein with a paltry efficacy of ~25% inhibition in mammalian cells.50 Further, this protein is highly-negatively charged with poor PK/PD properties, and has shown delivery and immunogenicity problems. We believe that a small-molecule SpCas9 inhibitor will resolve some of these issues. However, the identification of small molecule inhibitors of SpCas9 poses many challenges. First, inhibitor identification requires robust, orthogonal, sensitive, high-throughput, miniature, and inexpensive assays, which are currently unavailable. Second, SpCas9 is a single turnover enzyme that holds on to its DNA substrate with pM affinity, making the development of such assays challenging.51 Third, the inhibition of SpCas9 activity requires inhibition of two nuclease domains.3 Fourth, SpCas9 has many novel protein folds that limit our ability to leverage existing rational design approaches.52 To circumvent these challenges, we focused on targeting the SpCas9-substrate PAM motif interaction as a way to identify novel small molecule inhibitors of Cas9. To this end, we developed a several high-throughput biochemical assays for SpCas9 and performed a preliminary screen to identify small molecules that inhibit >50% of SpCas9 activity. Further, we also found these molecules to inhibit SpCas9 activity in mammalian and bacterial cells at low micromolar concentrations.

Development of High-Throughput Primary and Secondary Assays.

SpCas9-PAM binding assays. Disrupting PAM-sequence binding by SpCas9 (e.g., by mutating SpCas9 or the PAM-site) renders SpCas9 inactive.53 Further, SpCas9 has a low affinity for the PAM-sequence, making the SpCas9-PAM interaction an Achilles' heel for inhibitor discovery. However, the low affinity creates a challenge in developing robust SpCas9-PAM binding assays, which we overcame by leveraging the principle of multivalency; a DNA sequence bearing multiple PAM sites will have high affinity for SpCas9. Fluorescence polarization can be used to monitor protein-DNA interaction.54 The binding of this PAM-rich DNA to a much larger SpCas9:gRNA complex will lower DNA's tumbling rate, which can be monitored by fluorescence polarization (FIG. 1A). We developed an assay that measures the change in fluorescence polarization of the fluorophore-labeled PAM-rich target DNA (henceforth called 12PAM-DNA) as it binds to the SpCas9:gRNA complex. As expected, the complexation of SpCas9:gRNA to 12PAM-DNA showed a dose-dependent increase in fluorescence polarization (FIG. 1B). We confirmed that SpCas9: gRNA interaction were PAM dependent and not unspecific DNA binding, and we validated this fluorescence polarization assay using competition experiments, differential scanning fluorimetry,[55] and bio-layer interferometry[56]. In the competition experiment, 12PAM-DNA competed with unlabelled DNA sequences containing a varying number of PAM-sites. As expected, the decrease in fluorescence polarization signal of 12PAM-DNA correlated with the number of PAM-sites on the competitor DNA (FIG. 1C) as well as the concentration of the competitor DNA. Next, we used differential scanning fluorimetry, which detects ligand-induced changes in protein stability. We found that the melting temperature of the SpCas9:gRNA complex increases with the number of PAM-sites on the DNA (FIG. 1D) albeit the number of bases in the DNA remained the same. Finally, bio-layer interferometry (BLI) also confirmed higher affinity for SpCas9 toward DNA sequences with more PAM-sites (FIG. 4). All these studies confirm that SpCas9:gRNA interaction with the DNA substrate were PAM specific.

Figure 6B:
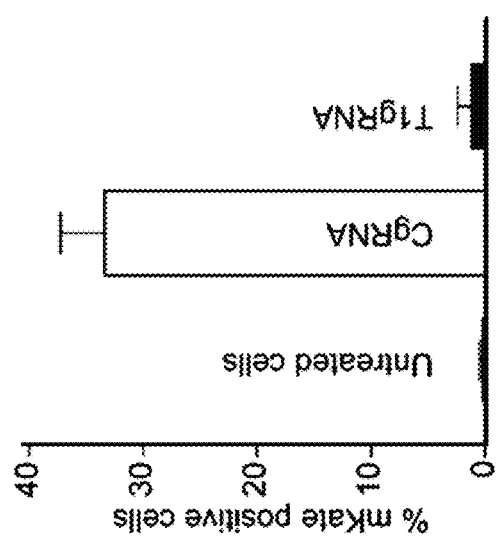
FIGS. 6A-6B—Schematic representation of mKate2 assay.
Figure 6A:
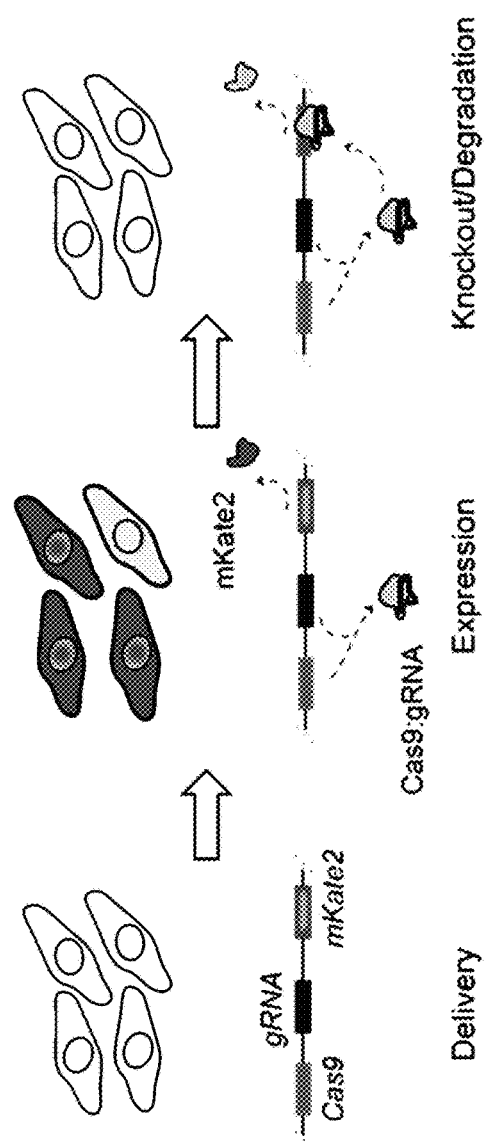
Figure 7:
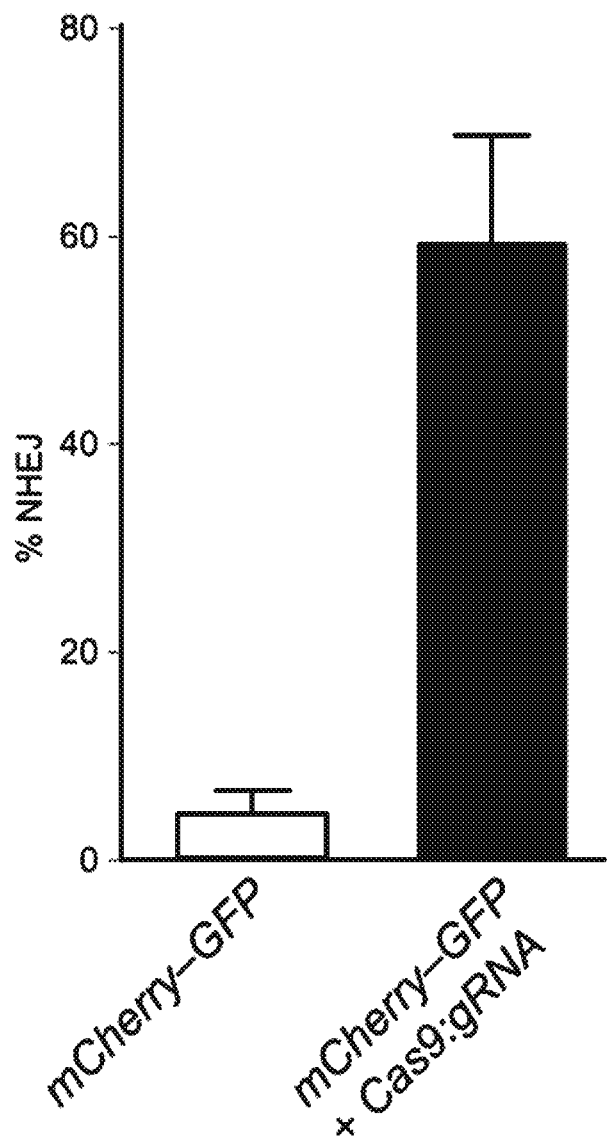
FIG. 7—Validation of mCherry-GFP expression NHEJ assay. Quantification of Cas9 induced NHEJ as measured by mCherry-GFP expression assay in HEK293T cells. The reporter constructs DN66 (mCherry-TAG-GFP) alone gave a basal level of NHEJ after 24 h. However, Cas9:gRNA induced GFP expression increased NHEJ significantly. Error bars represent ±S.D. from technical replicates (n=4).

Cell-based SpCas9 Activity Assays. We have also optimized several cell-based high-throughput assays to measure SpCas9 activity. Recently, Joung and co-workers have reported a U2OS.eGFP.PEST cell-line where eGFP knockout by SpCas9 leads to loss of fluorescence.[53, 57] By quantifying the percentage of eGFP negative cells using flow cytometry, one can estimate SpCas9 activity. We have modified this assay by replacing the flow-cytometry readout with a more reproducible and high-throughput readout using a high-content, automated microscope and automated image analysis (FIG. 5) using MetaXpress, which allows for high-throughput data analysis. In the mkate2 knockdown assay, the cells are transiently transfected with a single plasmid construct (Cas9-mKate-gRNA) that encodes for both Cas9 and gRNA components along with their target mKate2, a red fluorescent protein (FIG. 6A).[58] SpCas9-mediated knockdown of mKate2 expression level results in a loss of mKate signal that can be quantified using high-content imaging and automated data analysis using MetaXpress (FIG. 6B). We also optimized a fluorescence-based NHEJ measurement was employed to determine SpCas9 nuclease activity.[59] In this assay, cells are transfected with two plasmids in an equimolar ratio, where one plasmid has an out-of-frame reporter eGFP gene downstream of mCherry gene separated by a stop codon, while the other plasmid has SpCas9 and gRNA genes that can target the stop codon linker and make the eGFP gene in-frame. Thus, SpCas9 mediated DNA cleavage induces eGFP expression which can be quantified by a high-content imaging and automated data analysis (FIG. 7). We note that both eGFP-disruption and mKate2 expression assays, when deployed to identify inhibitors, are gain-of-signal assays which have much lower probability of false positives and these assays are complementary to the loss-of-signal NHEJ assay. All of these assays have been optimized to be conducted in 384-well plate format and have good Z-scores (FIG. 1E). In summary, we have built up a screening pipeline with FP-based primary screening assay followed by a counter screening and subsequent cell-based secondary screening for identifying and validating SpCas9 inhibitors.

Figure 8:
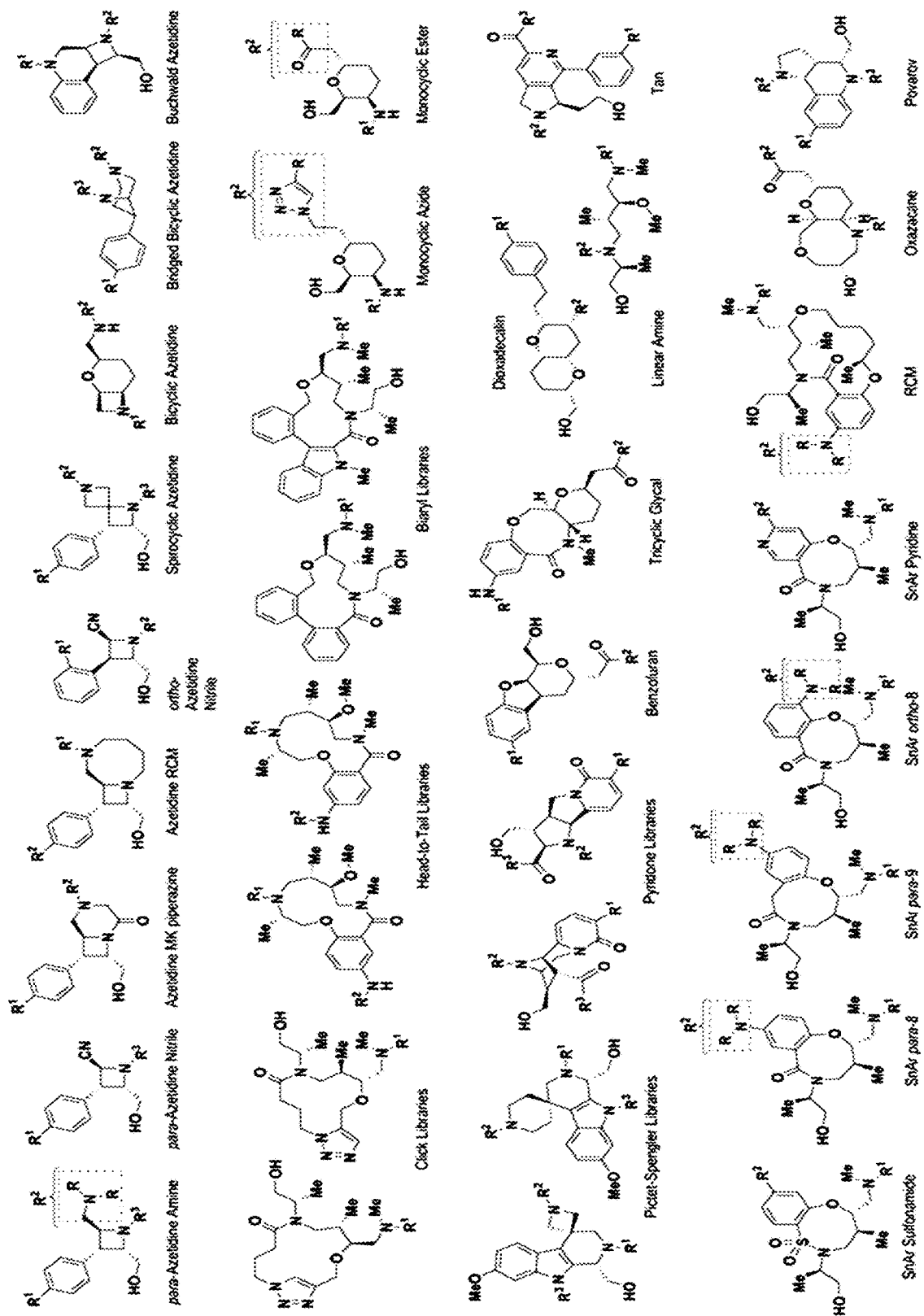
FIG. 8—Structural diversity of the DOS informer library set of compounds. Structures are the core-scaffold corresponding to each of the library and the R-groups represents the different functional moieties.

Small Molecule Screening and Hit Validation. We decided to leverage Broad Institute's performance diverse set as well as ~100,000 diversity-oriented synthetic (DOS) compound library as these natural-product like molecules have proved effective against microbial proteins.[60] However, screening all of these compounds will be inefficient as compounds within a single library are relatively similar to each other, and may perform similarly in assays. The Computational Chemical Biology group at the Broad Institute has established a list of ~10,000 compounds, called the "Informer set," that maximally represent the diversity across all DOS compounds. For the pilot screening, we decided to use this "informer set" (FIG. 8) that consists of 10,000 compounds. Using fluorescence polarization-based primary assay, we screened ~1x,000 compounds (informer set and performance diverse set) in two replicates (FIG. 1F) considering 12PAM-DNA without fluorophore as a positive control.

Figure 9:
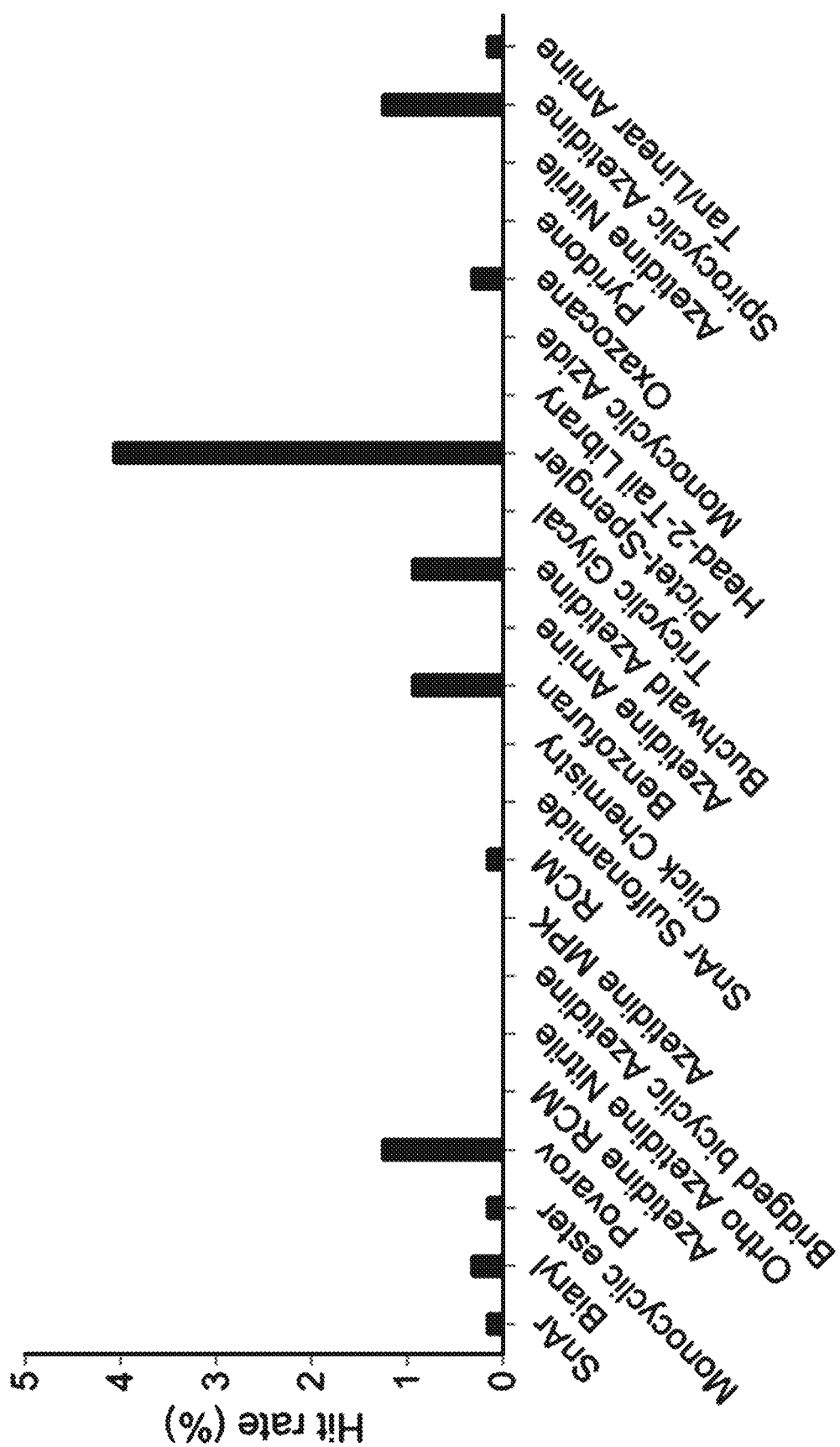
FIG. 9—Hit rate distribution of FP-based primary assay. Enrichment plot of the sub-libraries Povarov, Pictet-Spengler, and Spirocyclic Azetidine.
Figure 10:
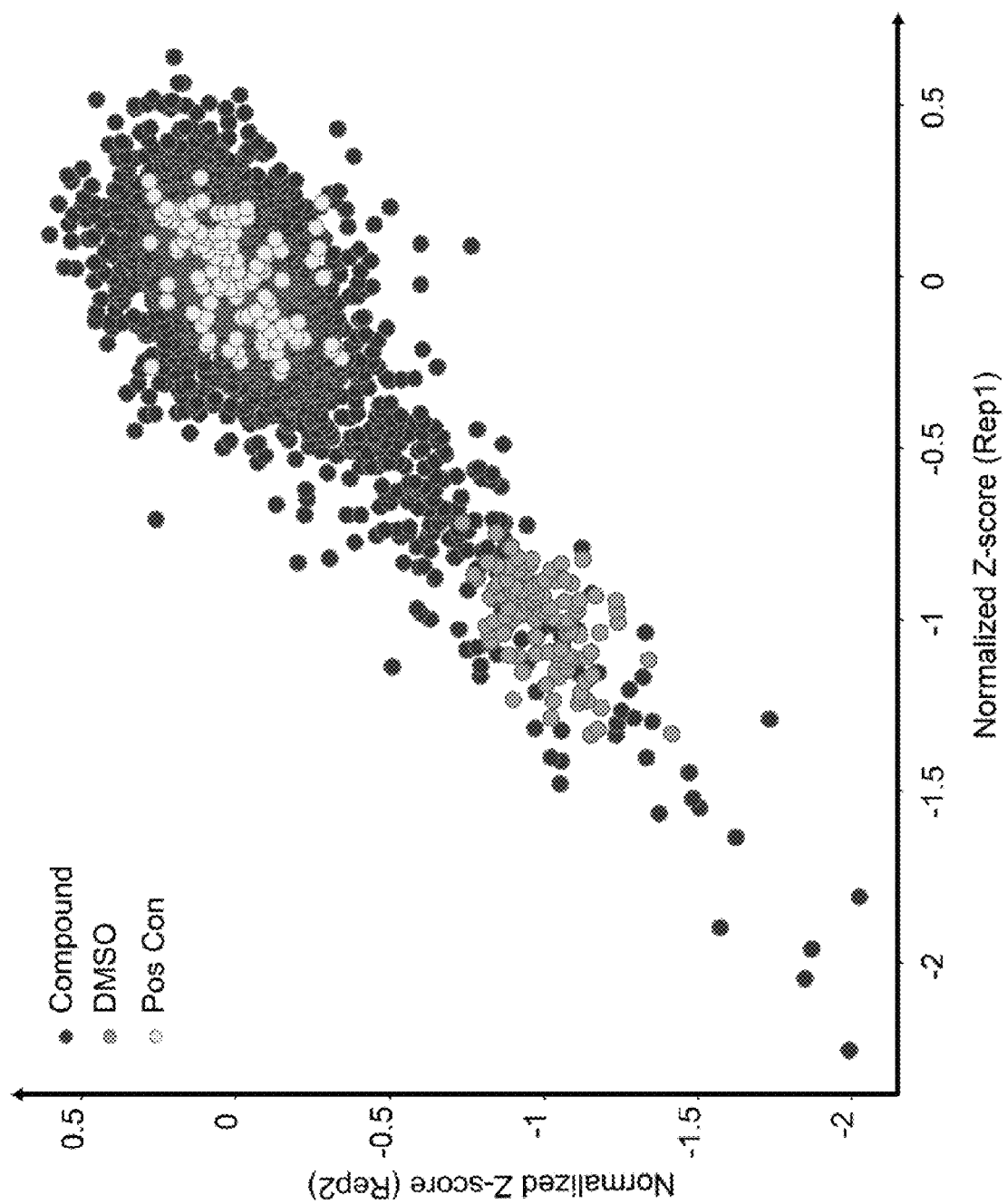
FIG. 10—Primary assay screening of specific library. Primary screening assay results of specific library Pictet-Spengler in an FP-based assay. The assay was performed in duplicate and each of the replicate data was plotted on two different axes.
Figure 11:
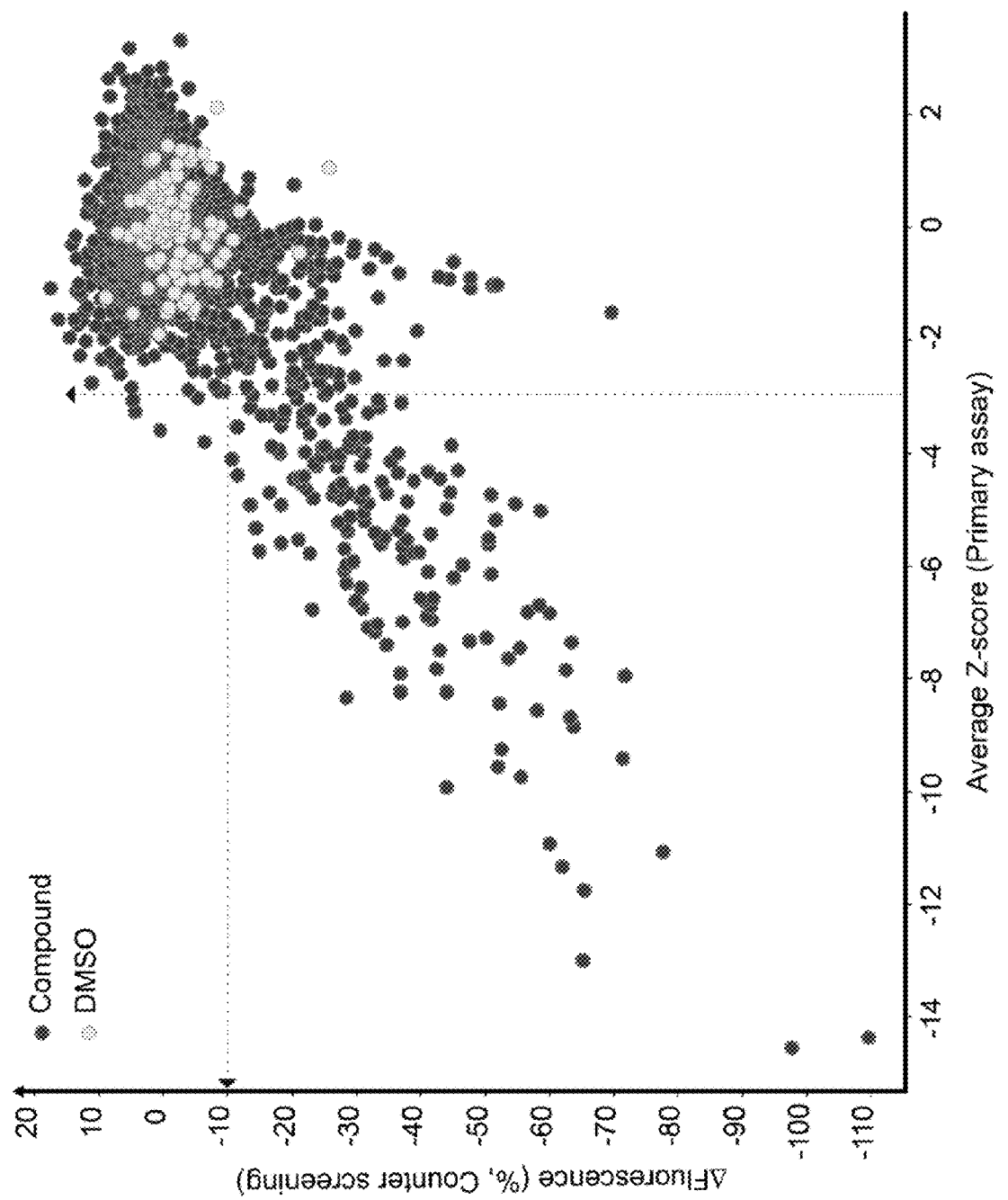
FIG. 11—Counter-screening data for specific Pictet-Spengler. FP-assay results of specific library Pictet-Spengler in the primary assay and counter-screening assay. The screening assay was performed in duplicate and the counter-screening assay was performed in singlicate. The average Z-score value from two-replicate screening data was plotted along the X-axis while the counter-screening data was plotted along the Y-axis.
Figure 12:
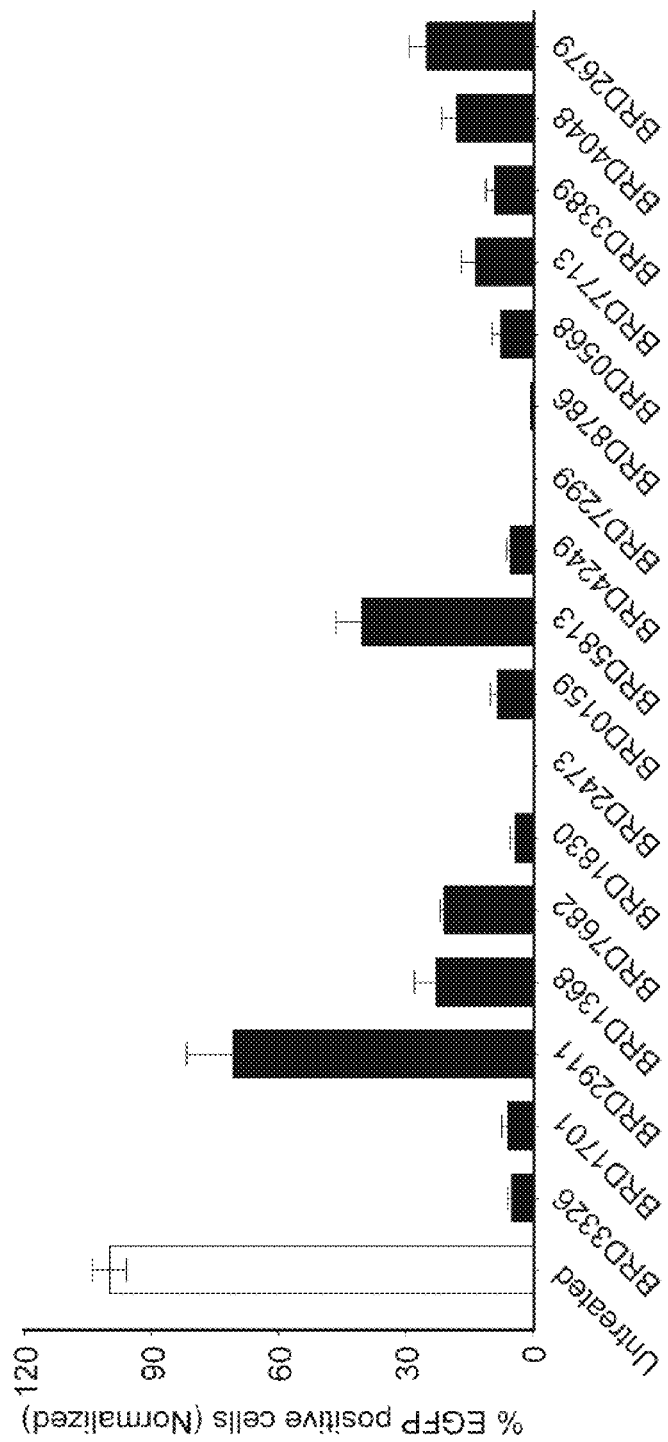
FIG. 12—Testing of counter-screened Pictet-Spengler hit compounds in EGFP-knockdown based secondary assay. Recovery of EGFP signal by compounds in the Cas9-mediated EGFP-knockdown assay. U2OS.eGFP.PEST cells were nucleofected with SpCas9 and gRNA plasmids and incubed either in the presence of vehicle or 20 µM compounds for 48 h. Error bars represent ±S.D. from technical replicates (n=4).
Figure 13:
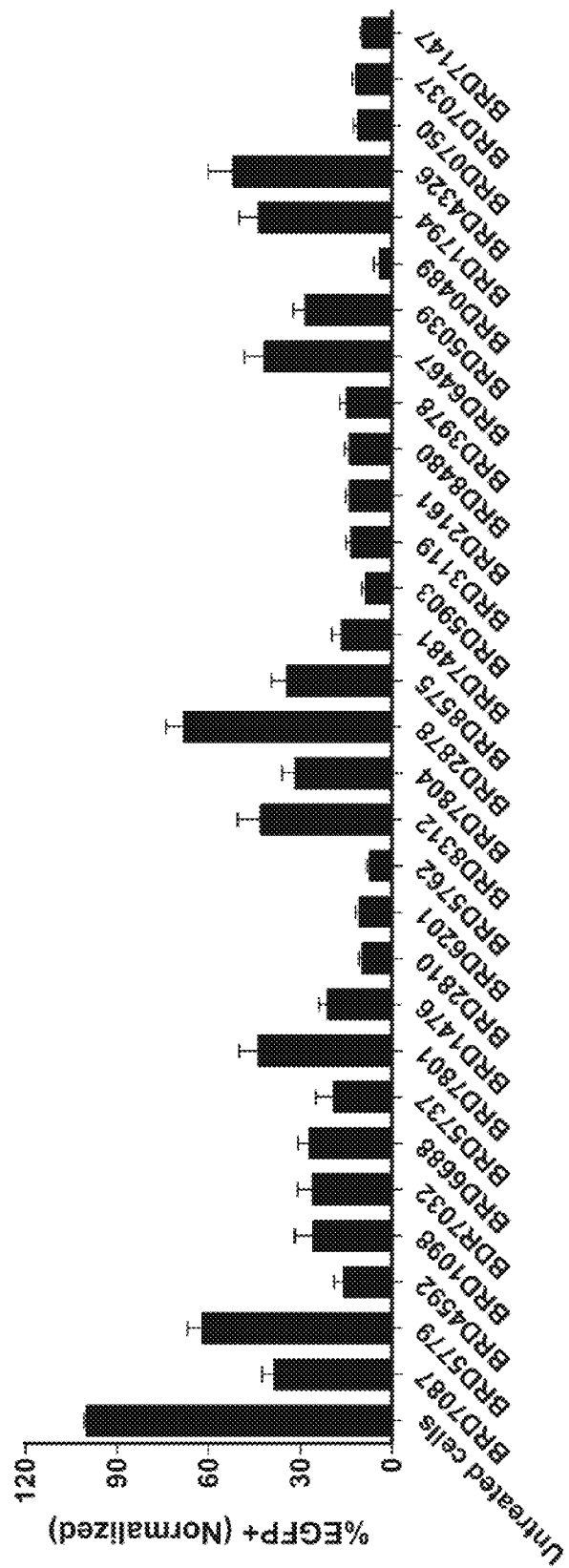
FIG. 13—Testing of counter-screened Povarov hit compounds in EGFP-knockdown based secondary assay. Recovery of EGFP signal by compounds in the Cas9-mediated EGFP-knockdown assay. U2OS.eGPF.PEST cells were Nucleofected with SpCas9 and gRNA plasmids and incubated either in the presence of vehicle or 20 µM compounds for 48 h. Error bars represent ±S.D. from technical replicates (n=4).
Figure 14:
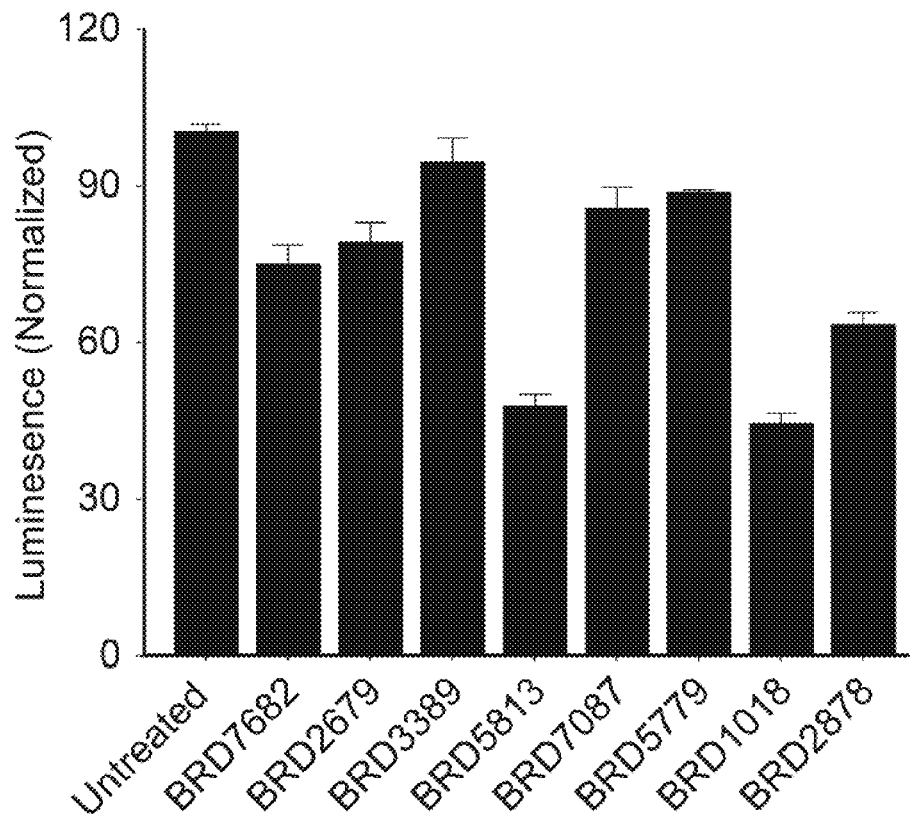
FIG. 14—Cell viability assay (ATP content) of U2OS.eGPF.PEST cells in the presence of compounds. Measurement of ATP content of U2OS.eGFP.PEST cells upon incubating with 20 µM compounds for 48 h. Error bars represent ±S.D. from technical replicates (n=3).

Following the conventional norm, we selected small molecules that lowered the fluorescence polarization signal by >3σ of that of DMSO as "candidates" and categorized them according to their compound-class to generate an enrichment plot (FIG. 9). The majority of the candidates belonged to two compound libraries, Povarov and Pictet-Spengler, suggesting a strong structure-activity relationship. We initiated the structure-activity studies to identify the key pharmacophore required for SpCas9 inhibition by these candidates. Traditionally, this process involves synthesis and potency evaluation of the structural analogs of the candidate compounds iteratively and is low throughput, tedious, labor-intensive, expensive, and time-consuming. Conveniently, >5,000 analogs of our candidate compounds already existed at the Broad Institute as a part of their compound library, and we tested all of these specific library analogs in our FP-based screening assay (FIG. 10). Moreover, we also tested the compounds by a counter-screen assay that measures the inherent fluorescence of these compounds to eliminate false positives (FIG. 1G and FIG. 11). Subsequently, we performed a structure based computational similarity search to widen the pharmacological scope. We then tested all the hit compounds and their similar analogs (Tables 2 and 3) in cell-based secondary assays. We tested the short-listed compounds in a cell-based eGFP-disruption assay and identified the most potent candidates based on both eGFP signal recovery (FIGS. 12 and 13) and cytotoxicity (FIG. 14). We resynthesized and thoroughly characterized the most potent and non-toxic compounds, BRD7087 and BRD5779 (FIG. 2A), by $^1$H and $^{13}$C NMR, $^{19}$F NMR, HRMS, Chiral SFC, and IR to validate the analytical integrity. We determined the solubilities of the synthesized compounds by mass spectroscopy and found that both the compounds showed no detectable aggregation up to ~75 µM concentration in PBS (FIG. 14).

Figure 2B:
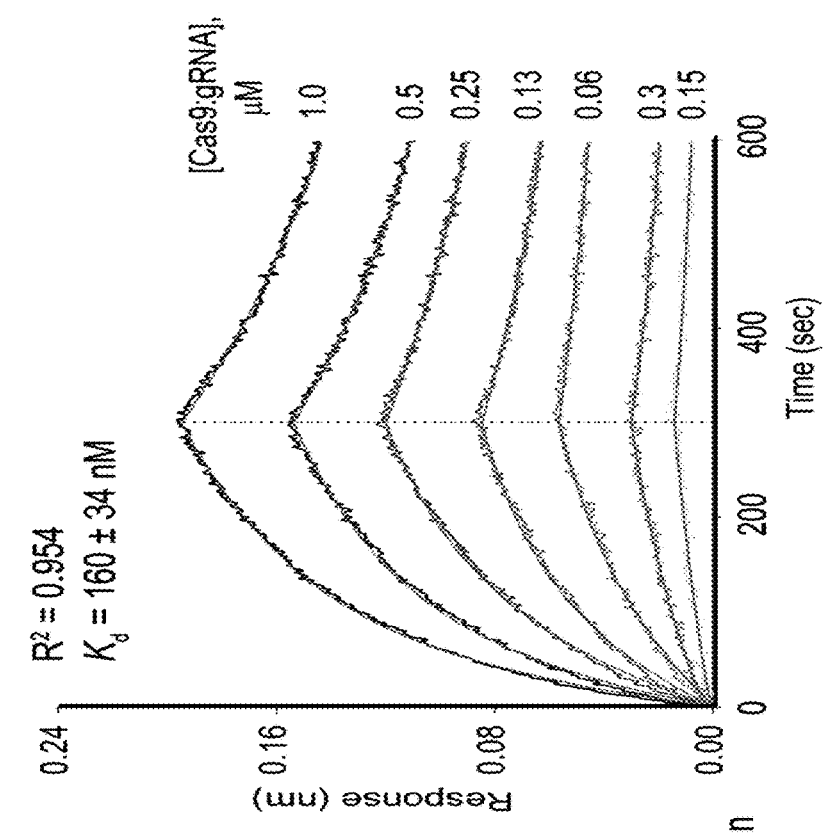
Figure 2A:
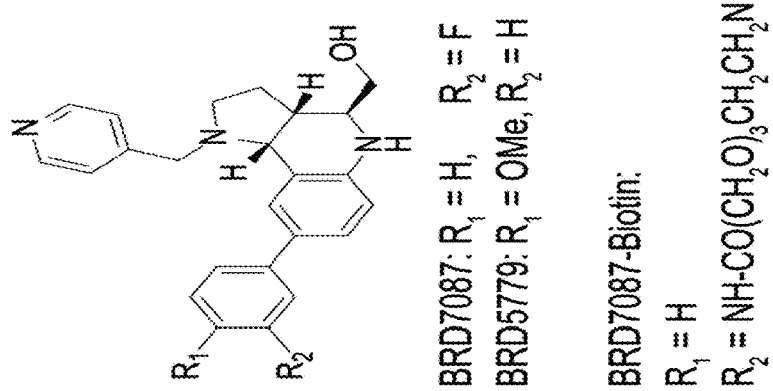
Figure 15:
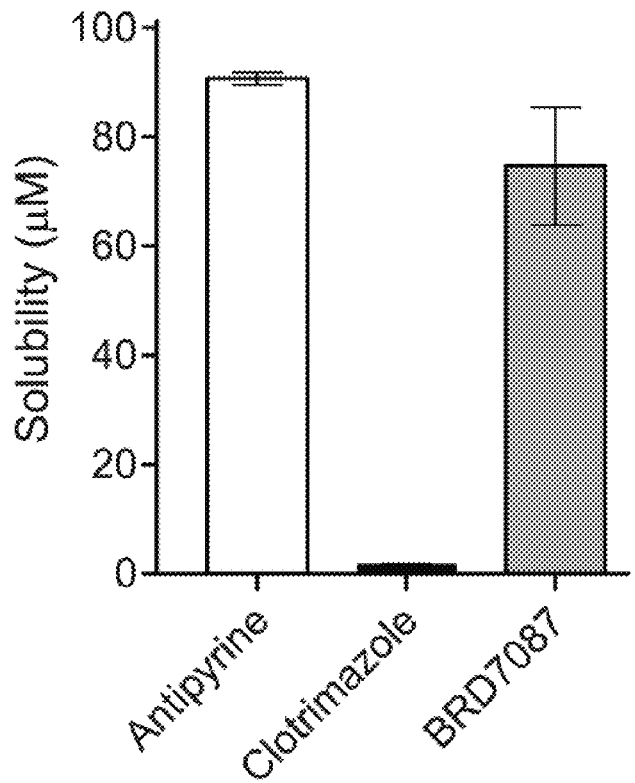
FIG. 15—The solubility of BRD7087 compound in PBS as determined by mass spectroscopy after 24 h of incubation at room temperature. Compounds Antipyrine and Clotrimazole were used as positive controls.
Figure 16A:
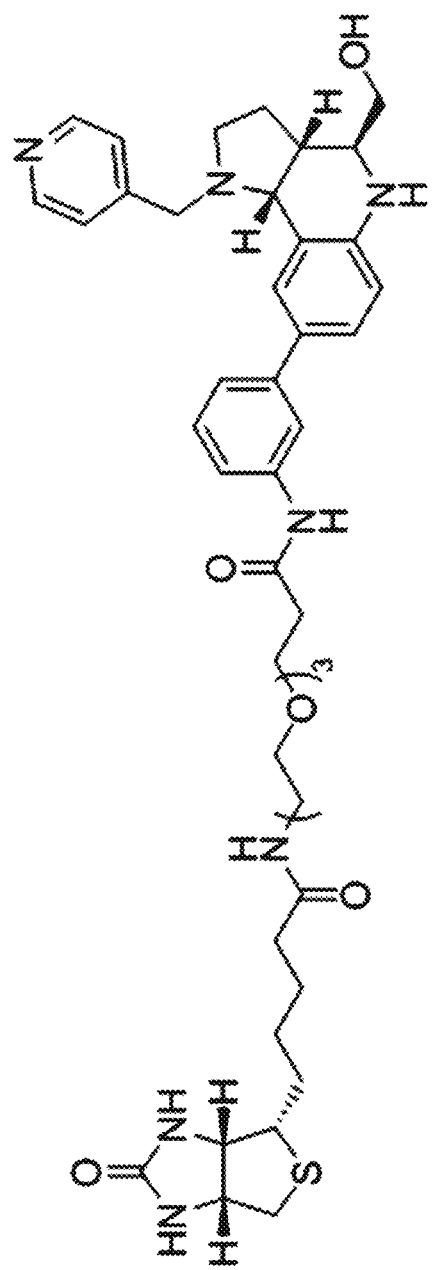
FIGS. 16—Structure of compound (FIG. 16A) BRD7087-Biotin conjugate and (FIG. 16B) biotin linker.
Figure 16B:
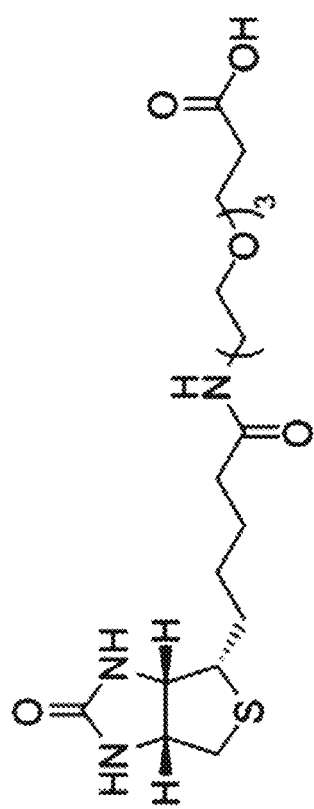
Figure 17:
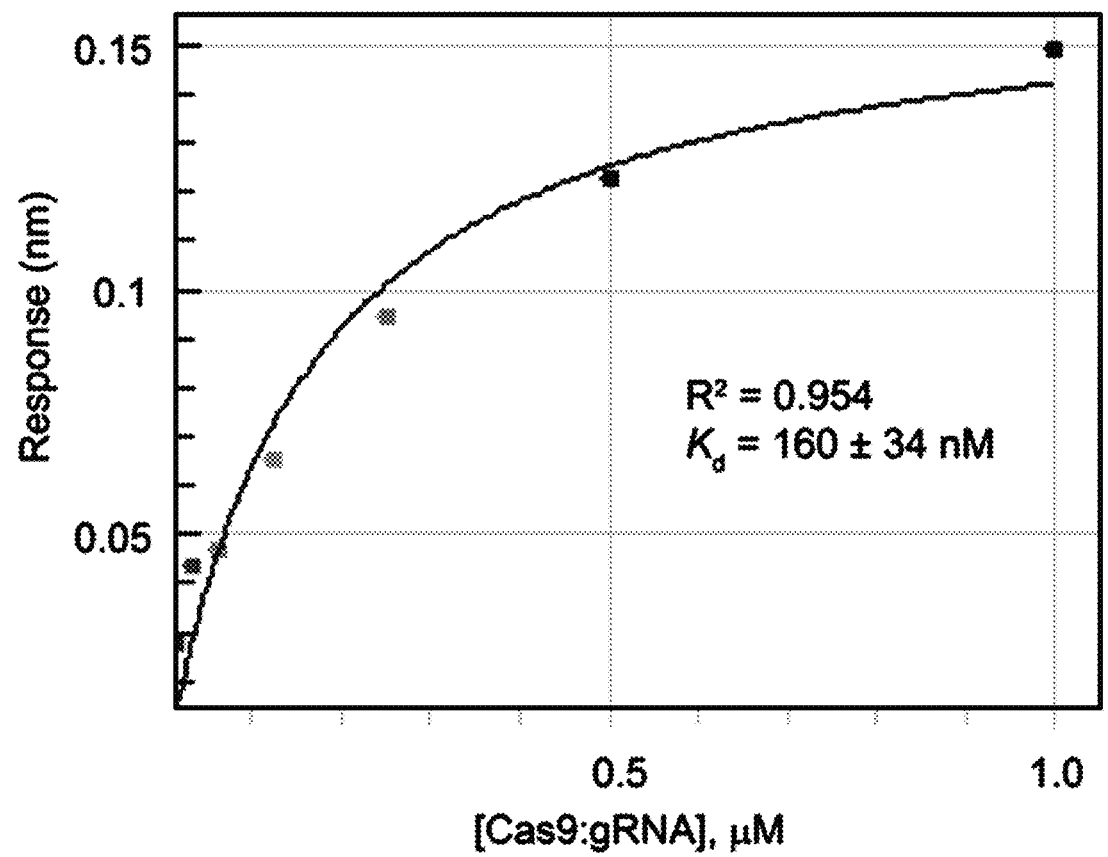
FIG. 17—Binding isotherm of BRD7087-Biotin and SpCas9:gRNA complex in BLI. The steady-state plot for BLI binding study of BRD7087-Biotin and SpCas9:gRNA complex. BLI experiment was performed using 1 µM BRD7087-Biotin onto streptavidin sensors followed by association with different concentration of SpCas9:gRNA complex and subsequent dissociation. Response data were plotted along X-axis and concentration of SpCas9:gRNA complex was plotted along Y-axis. A global 2:1 (small molecule:protein) model was used to plot the steady state and determine the binding constant.
Figure 18:
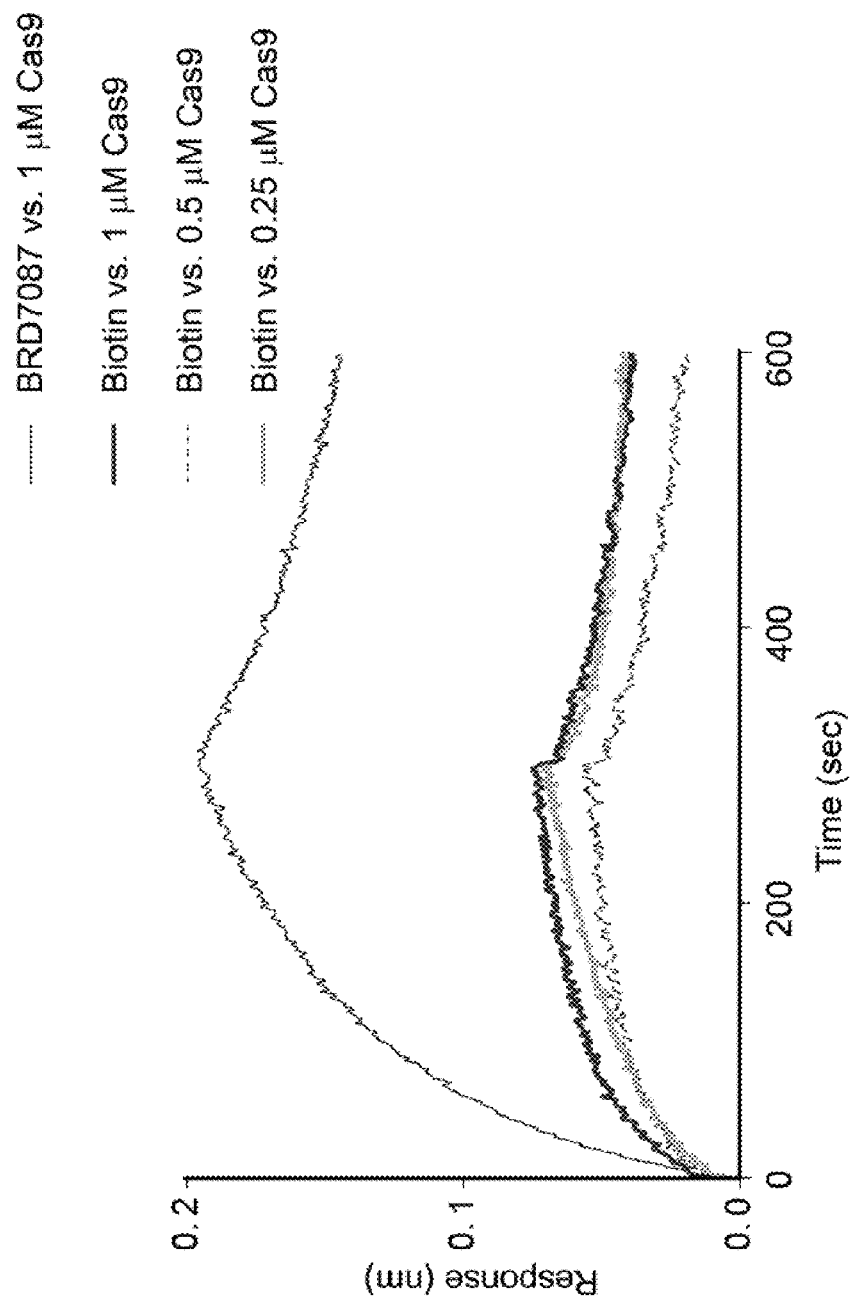
FIG. 18—BLI study of Biotin loaded streptavidin sensors with SpCas9:gRNA complex. Bio-Layer Interferometry study of streptavidin sensors loaded either with 1 µM BRD7087-Biotin or 10 µM of Biotin in 20 mM Tris buffer of pH 7.4, 100 mM KCl, 5 mM MgCl$_2$, 1 mM DTT, 0.01% Tween®. SpCas9:gRNA complex concentration was varied from 1-0.25 µM.
Figure 19:
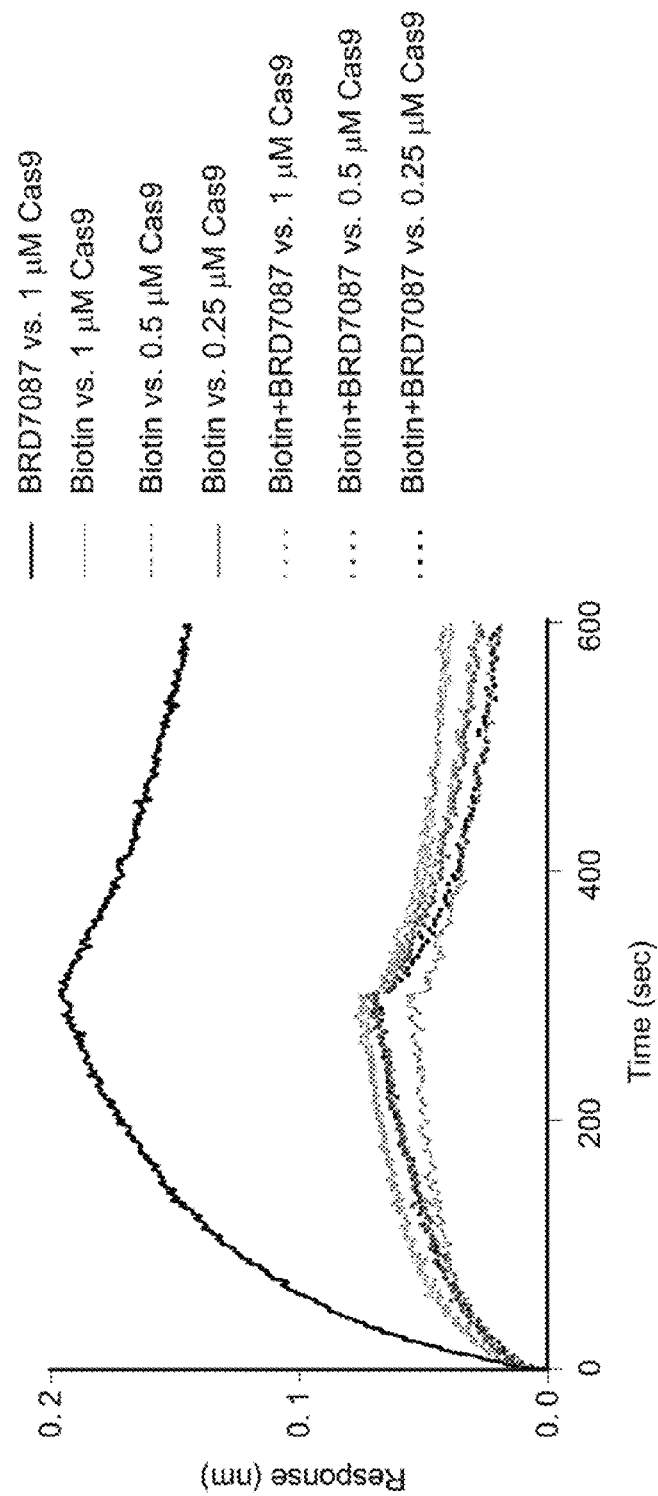
FIG. 19—Competitive BLI study of BRD7087-Biotin in the presence of 10 fold excess of Biotin. Bio-Layer Interferometry study of streptavidin sensors loaded with either with 1 µM BRD7087-Biotin or 10 µM of Biotin or Biotin as a competitor in 20 mM Tris buffer of pH 7.4, 100 mM KCl, 5 mM MgCl$_2$, 1 mM DTT, 0.01% Tween®. In the competition assay, streptavidin sensors were pre-loaded with 10 µM of Biotin followed by loading of 1 µM BRD7087-Biotin. SpCas9:gRNA complex concentration was varied from 1-0.25 µM.
Figure 20:
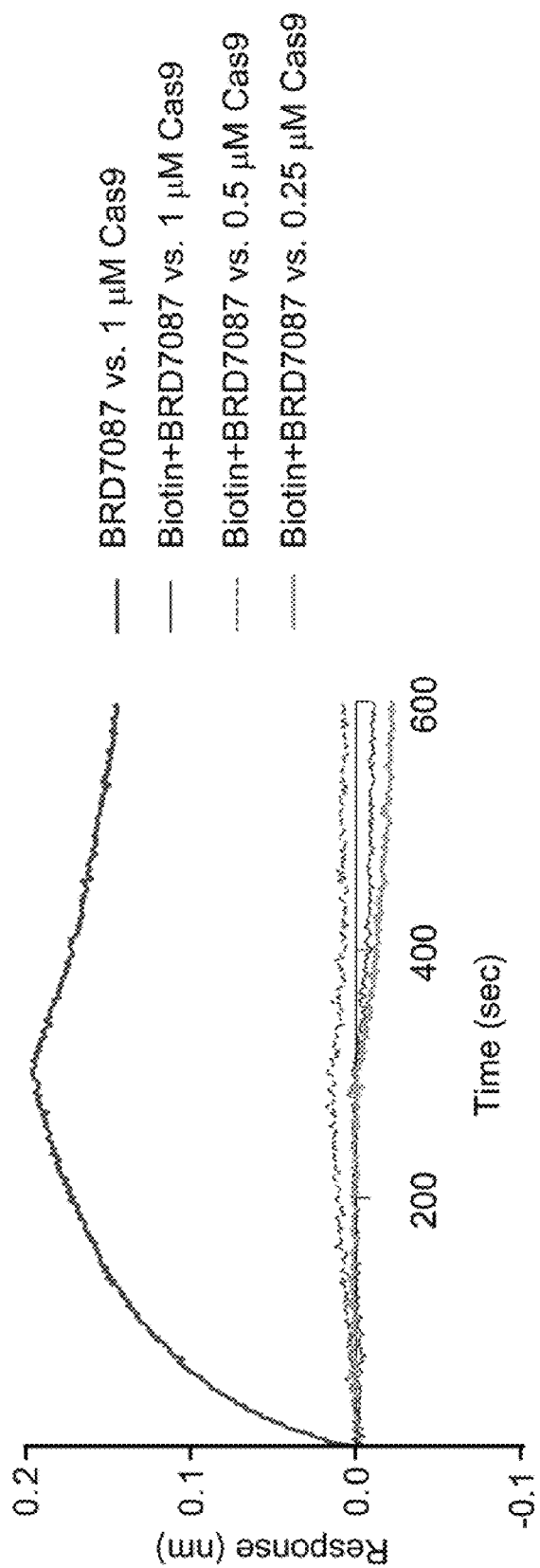
FIG. 20—Competitive BLI study of BRD7087-Biotin in the presence of 10 fold excess of Biotin. Background subtracted BLI responses of BRD7087-Biotin with SpCas9:gRNA in the presence of 10-fold excess Biotin as the competitor in 20 mM Tris buffer of pH 7.4, 100 mM KCl, 5 mM MgCl$_2$, 1 mM DTT, 0.01% Tween®. SpCas9:gRNA complex concentration was varied from 1-0.25 µM.

We deployed biolayer interferometry (BLI) to determine the binding affinity of BRD7087 and SpCas9:gRNA complex by tethering the compound onto the sensor. Towards this end, we synthesized a biotin-conjugate of BRD7087 (FIG. 15) and loaded this compound on the streptavidin sensors of BLI. The compound loaded sensors were allowed to interact with SpCas9:gRNA complex generating the response curves (FIG. 2B). A 2:1 compound to Cas9 binding isotherm indicated a dissociation constant of ~160 nM (FIG. 16). In a competitive experiment performed in the presence of excess (10×) of biotin to BRD7087 loading, we observed no substantial response signal upon incubation with the SpCas9:gRNA solution, confirming the specific nature of BRD7087 and SpCas9:gRNA interaction (FIGS. 17-19). Furthermore, the BRD7087 has a fluorine moiety which allowed us to investigate the interaction of compound and SpCas9:gRNA by $^{19}$F NMR. Binding of BRD7087 was confirmed using differential line broadening of $^{19}$F signal upon titration of SpCas9:gRNA; the signal corresponding to 50 µM ligand broadens in a dose-dependent manner as expected (Table 4). While small amounts of protein showed a negligible effect, significant broadening is observed with SpCas9:gRNA concentrations as low as 0.75 µM (67-fold excess of ligand), indicating relatively tight binding. Using peak intensities obtained by fitting for these datapoints, the method of Shortridge et. al. indicates a binding constant $K_d$~2.2 µM.[61] Allowing for the inclusion of a nonspecific binding term does not alter the binding constant value but slightly improves the fit (FIG. 20).

Figure 21:
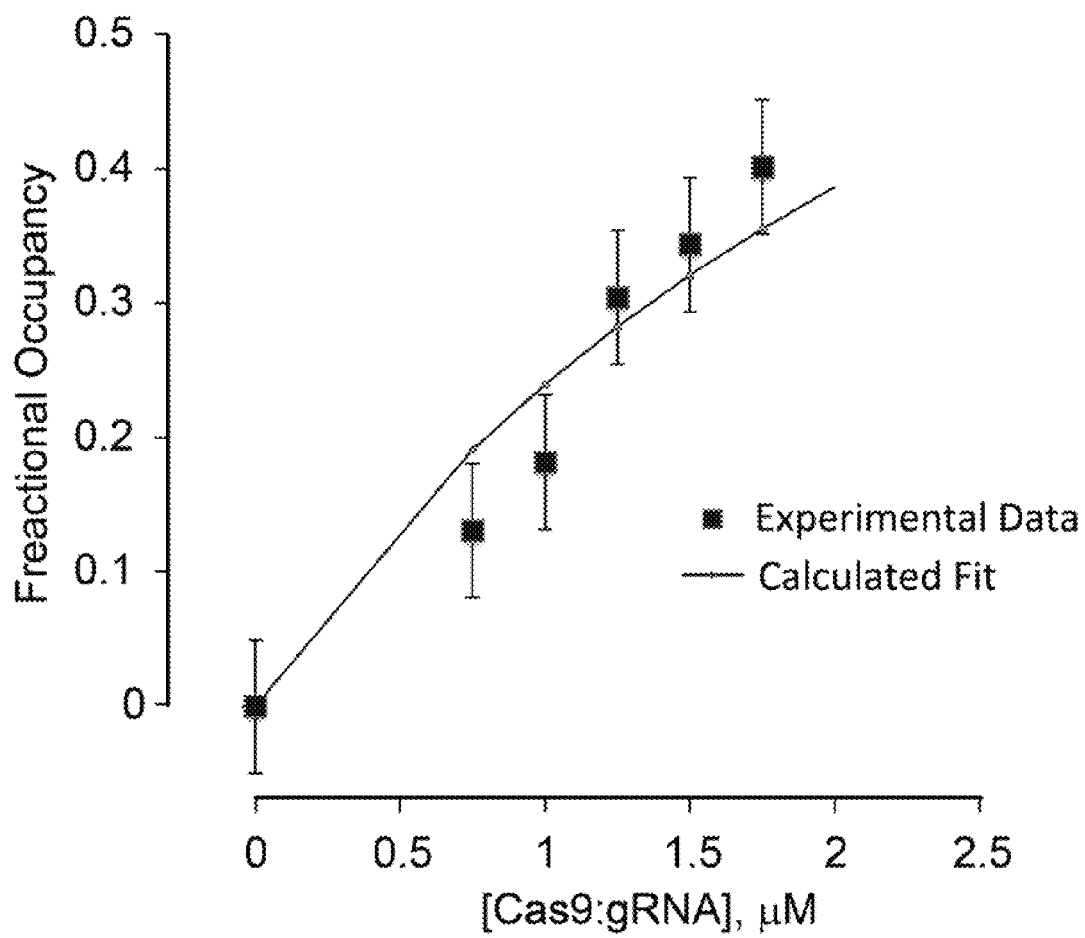
FIG. 21—NMR binding data of BRD7087 and SpCas9:gRNA complex. 19F NMR titration data were fitted following a reported protocol to calculate the binding constant of BRD7087 with SpCas9:gRNA complex in 20 mM Tris buffer of pH 7.4, 100 mM KCl, 5 mM MgCl$_2$, 1 mM DTT. A 50 µM Compound BRD7087 was titrated against increasing amount of SpCas9:gRNA ribonucleoprotein complex.
Figure 22:
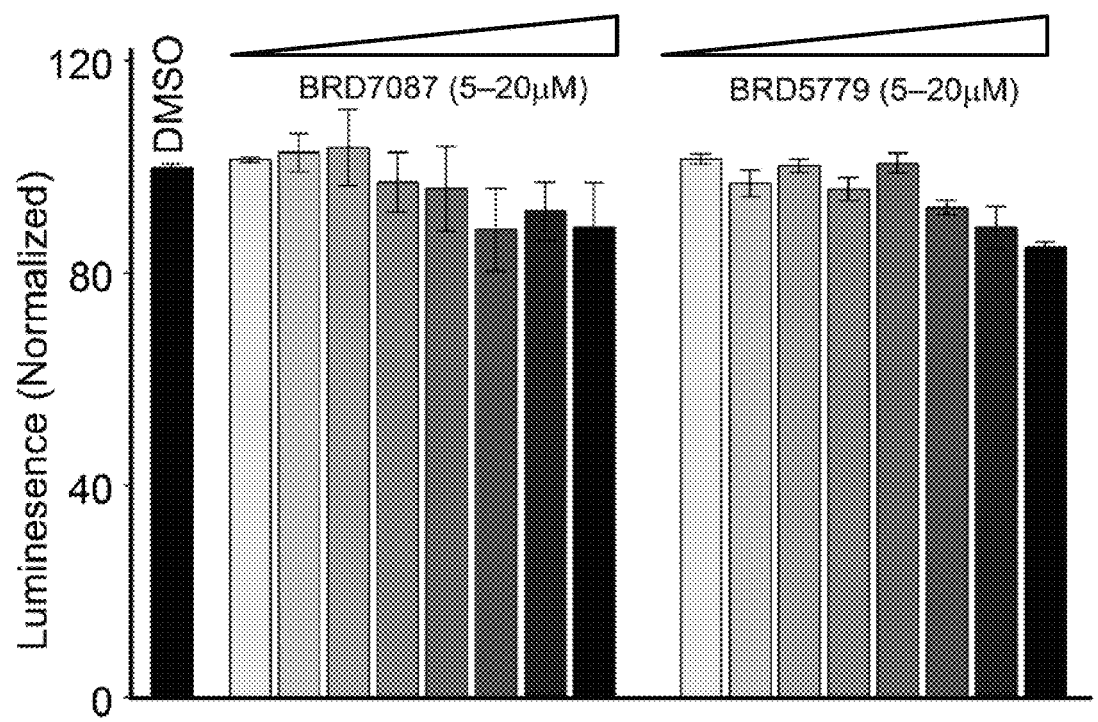
FIG. 22—Cell viability assay (ATP content) of U2OS.eGFP.PEST cells in the presence of compounds. Measurement ATP content of U2OS.eGFP.PEST cells upon incubating with BRD7087 and BRD5779 (5-20 µM) for 24 h. Error bars represent ±S.D. from technical replicates (n=3).
Figure 23:
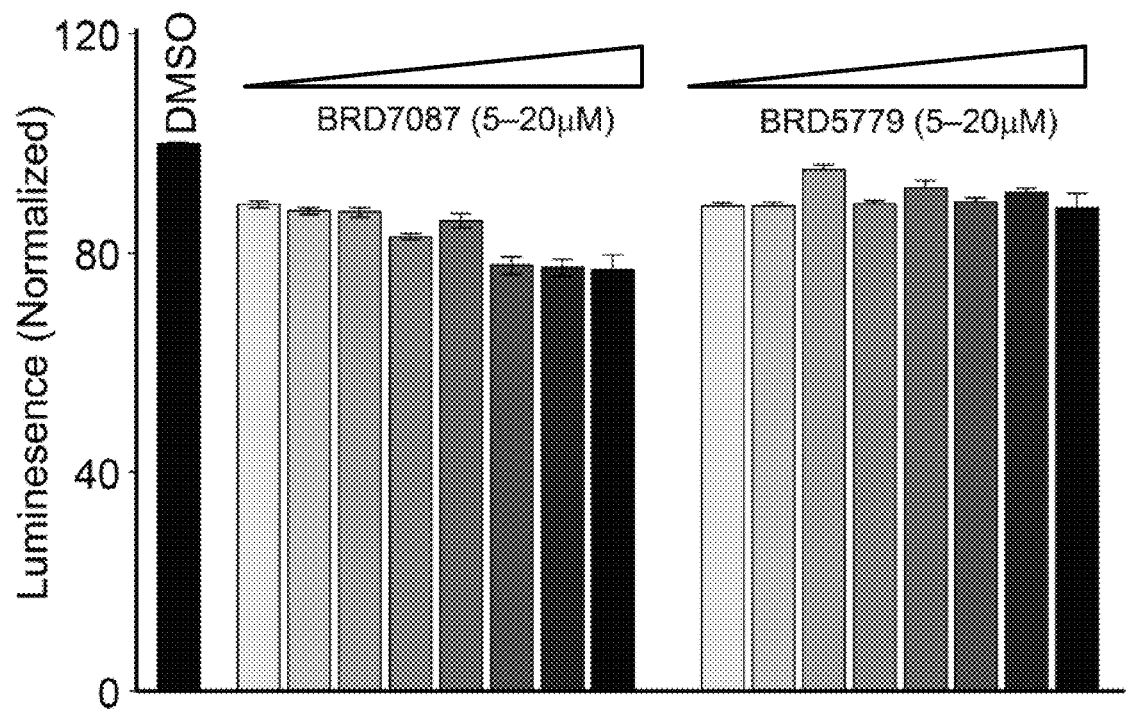
FIG. 23—Cell viability assay (ATP content) of KE293T cells in the presence of compounds. Measurement of ATP content of HEK293T cells upon incubating with BRD7087 and BRD5779 (5-20 µM) for 24 h. Error bars represent ±S.D. from technical replicates (n=3).
Figure 24:
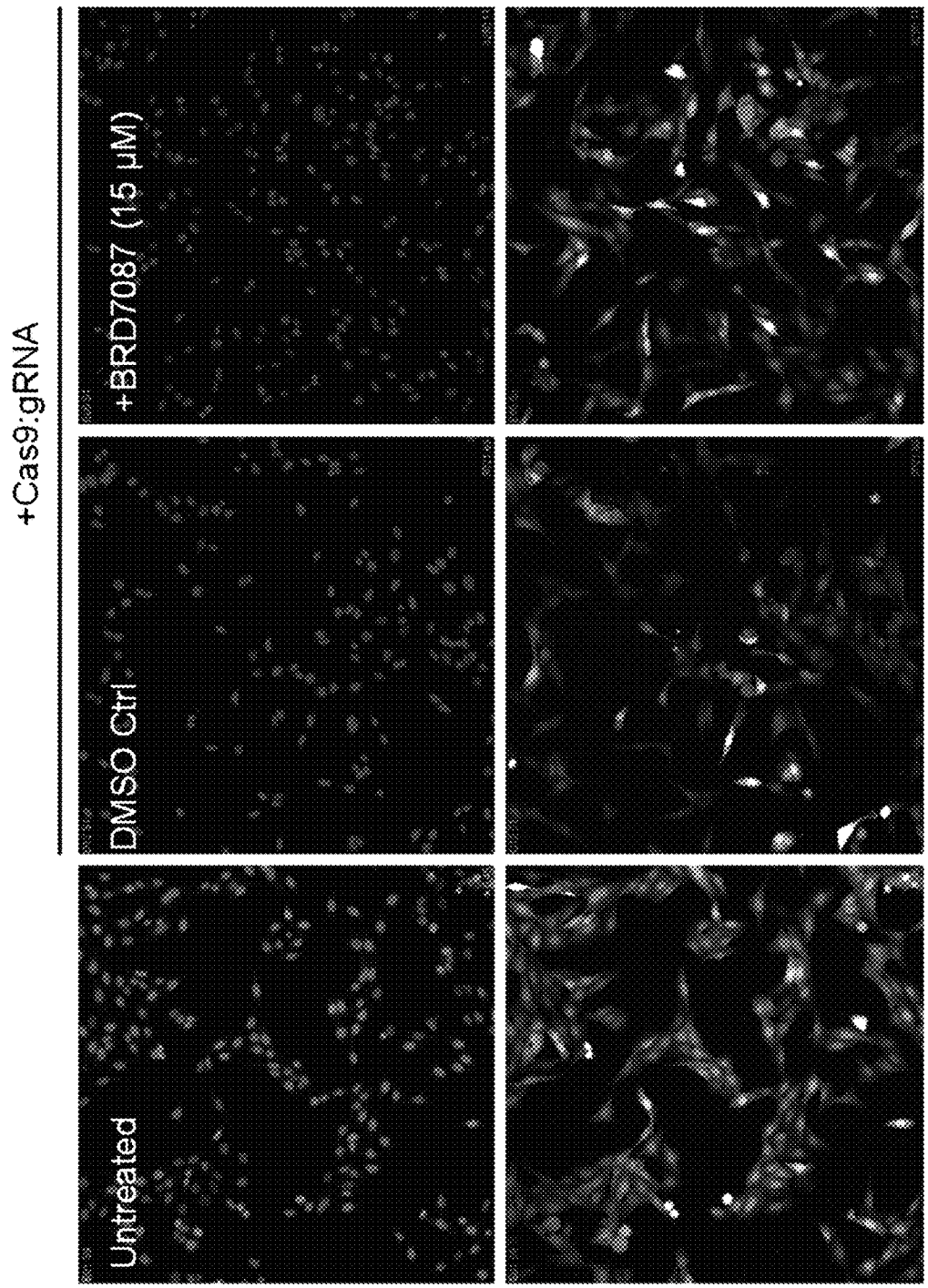
FIG. 24—Representative images of EGFP-knockdown assay. Representative images of U2OS.eGFP.PESt cells nucleofected with either SpCas9 expressing plasmid alone or SpCas9 and gRNA plasmids treated with vehicle or compound. Left panel represents cells nucleofected with SpCas9 expressing plasmid alone. Middle panel represents cells nucleofected with SpCas9 and gRNA expressing plasmids and treated with vehicle. Right panel represents cells nucleofected with SpCas9 and gRNA expressing plasmids and treated with 15 µM BRD7087 for 24 h. Scale bar=100 µm.
Figure 25:
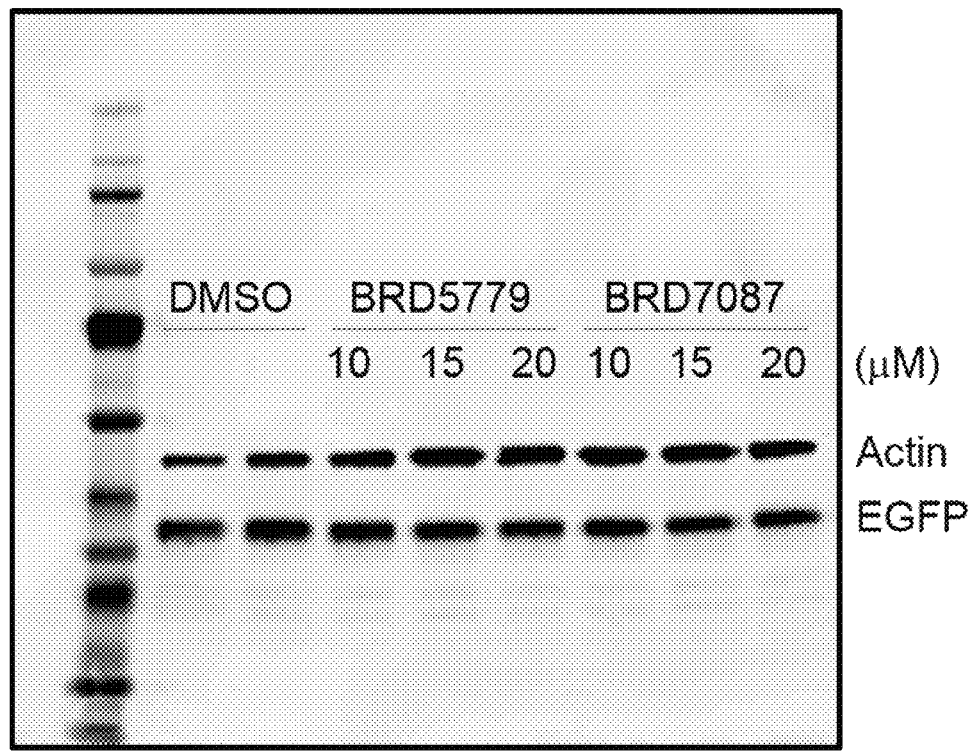
FIG. 25—Western blot analysis of EGFP protein in U2OS.eGFP.PEST cells in presence of compound. Western blot analysis of EGFP gene expression in U2OS.eGFP.PEST cells in the presence of DMSO and compound. Cells were incubated with compound BRD5779 and BRD7087 with an indicated concentration for 24 h before harvesting and processing for Western blot analysis.
Figure 26:
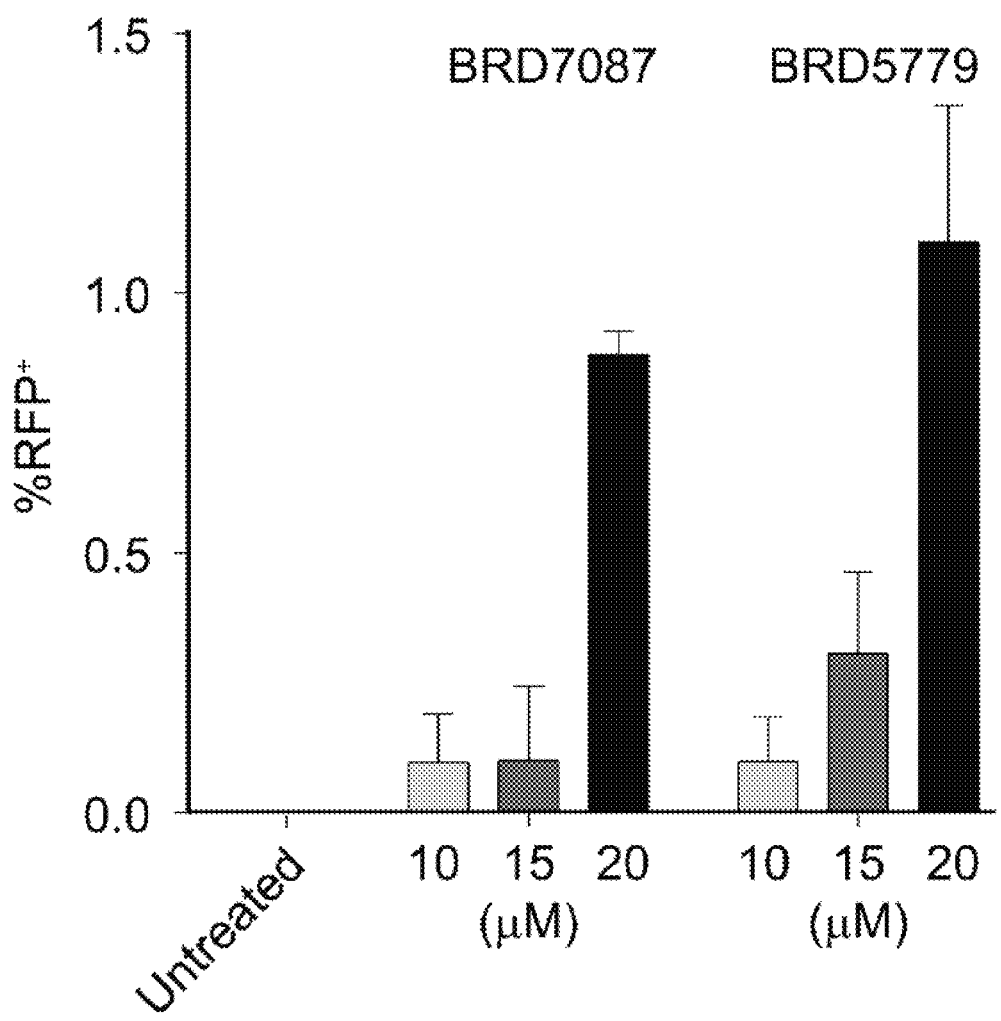
FIG. 26—Auto-fluorescence of cells treated with the compound in the EGFP-knockdown assay. Measurement of the auto-fluorescence level of compound-treated U2OS.eGFP.PEST cells. Cells were imaged in RFP channel with a same exposure time that has been used in the EGFP-knockdown assay for measuring compound mediated recovery of GFP signal. Compound-treated cells showed maximum 1% auto-fluorescence population indicating no significant contribution of auto-fluorescence in compound mediated GFP recovery. Error bars represent ±S.D. from technical replicates (n=4).
Figure 27:
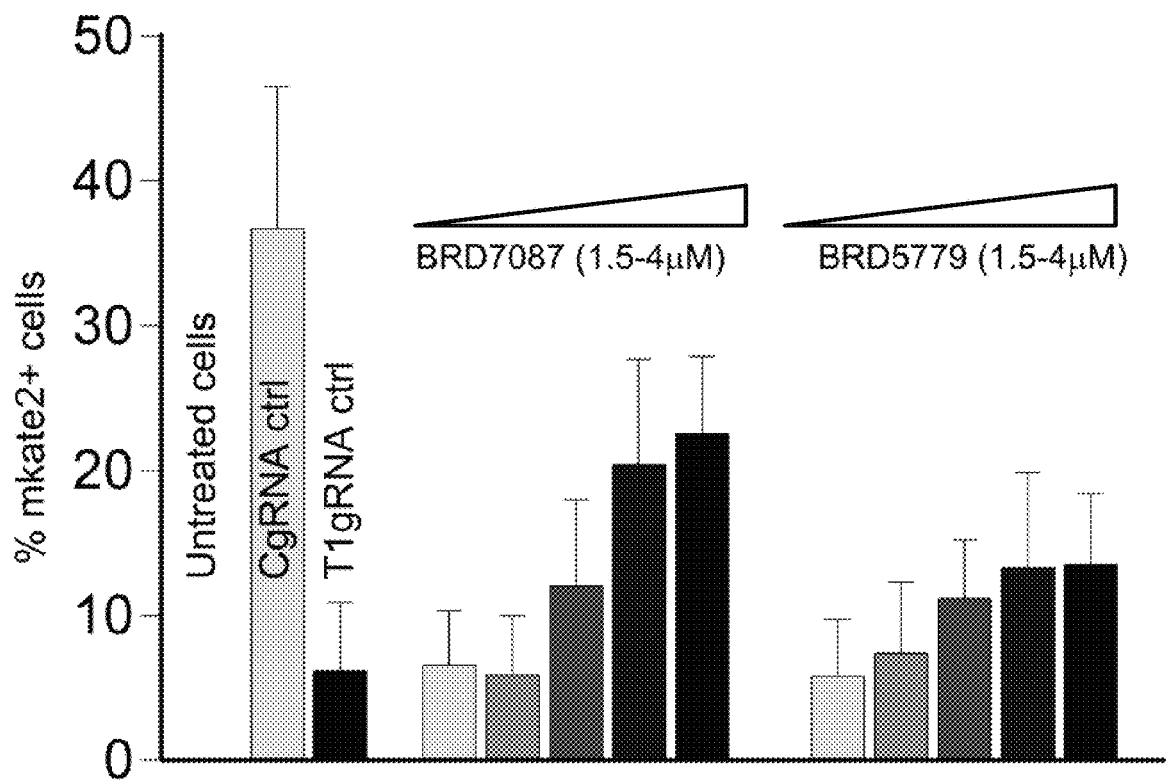
FIG. 27—Dose-dependent inhibition of SpCas9 by the compound in mKate2 expression assay. Dose-dependent recovery of the mKate2 signal by compound BRD7087 and BRD5779 in the mKate2-knockdown assay. HEK293 cells were transfected with a single plasmid containing SpCas9, gRNA, and mKate2 expressing genes. Plasmid without a non-targeting gRNA (CgRNA) was used as the positive control. Cells transfected with the targeting guide plasmid (T1gRNA) was incubated either in presence of DMSO or compound (1.5-5 µM) for 24 h. Error bars represent ±S.D. from technical replicates (n=3).
Figure 28:
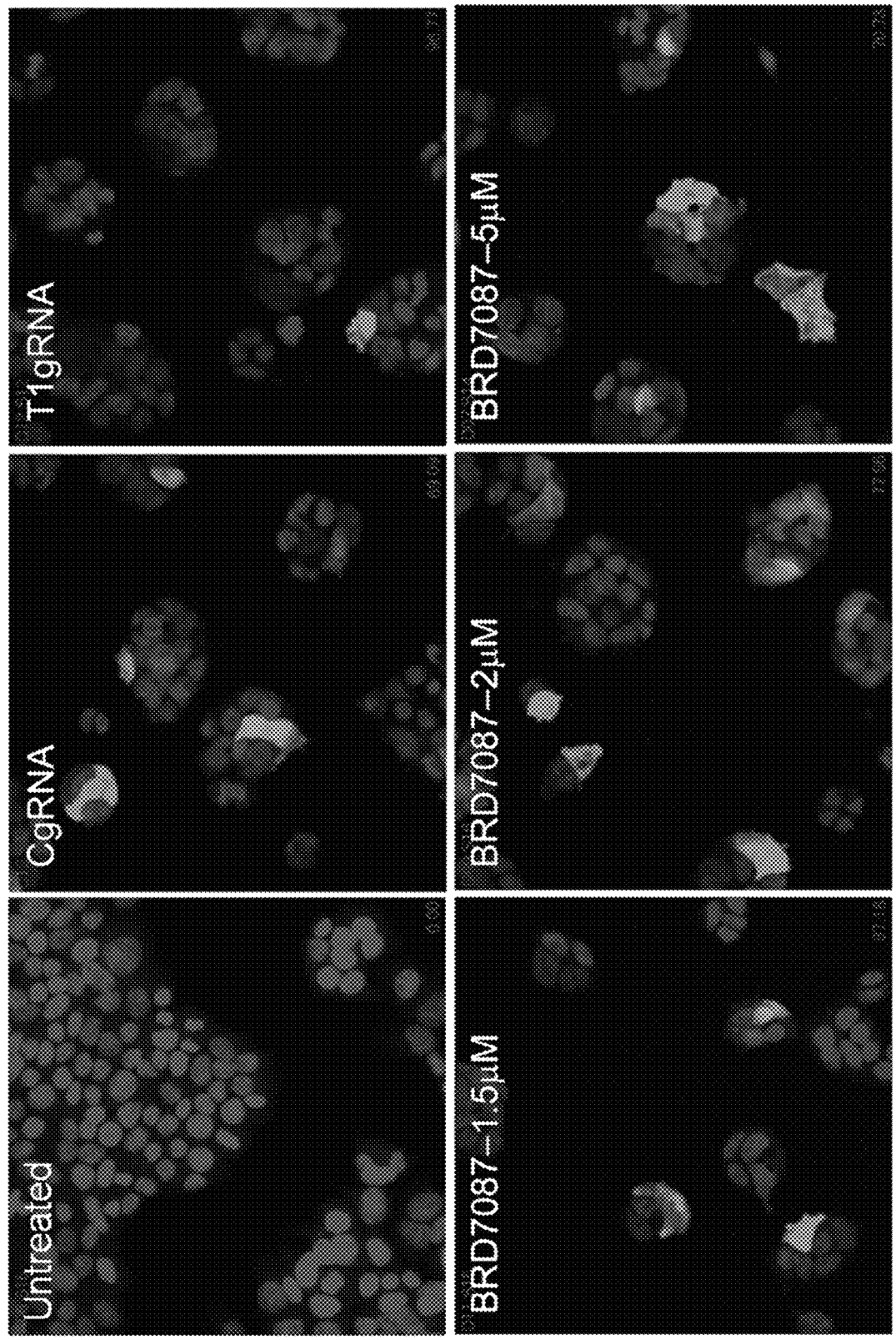
FIG. 28—Representative images of the mKate2-knockdown assay. Representative images of HEK293 cells transfected with a single plasmid containing SpCas9, gRNA, and mKate2 expressing genes. The Nuclei are counter-stained with DAPI and the red channel represents the expression level of mKate2. While control panel (CgRNA) was transfected with a plasmid with a non-targeting gRNA. Other panels represent cells transfected with targeting gRNA (T1gRNA) incubated with either DMSO or compound BRD7087 with indicated concentration. Error bars represent ±S.D. from technical replicates (n=3). Scale bar=100 µm.
Figure 29:
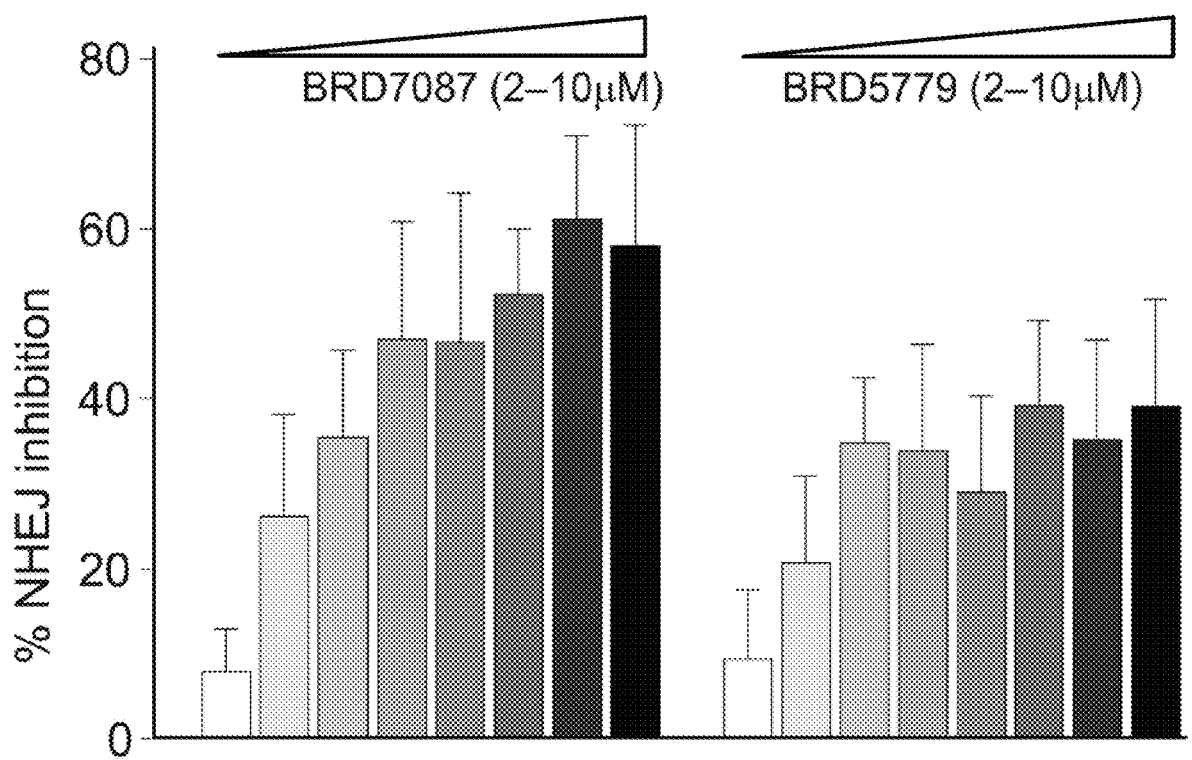
FIG. 29—Dose-dependent inhibition of SpCas9 mediated NHEJ by compounds. Dose-dependent inhibition of SpCas9-mediated NHEJ by compound BRD7087 and BRD5779 in HEK293T cells. HEK293 cells were transfected with a plasmid containing SpCas9, gRNA and another plasmid containing reporter gene mCherry-GFP. Transfected cells were incubated with either DMSO or compound (2-10 µM) for 24 h. Error bars represent ±S.D. from technical replicates (n=3).
Figure 30:
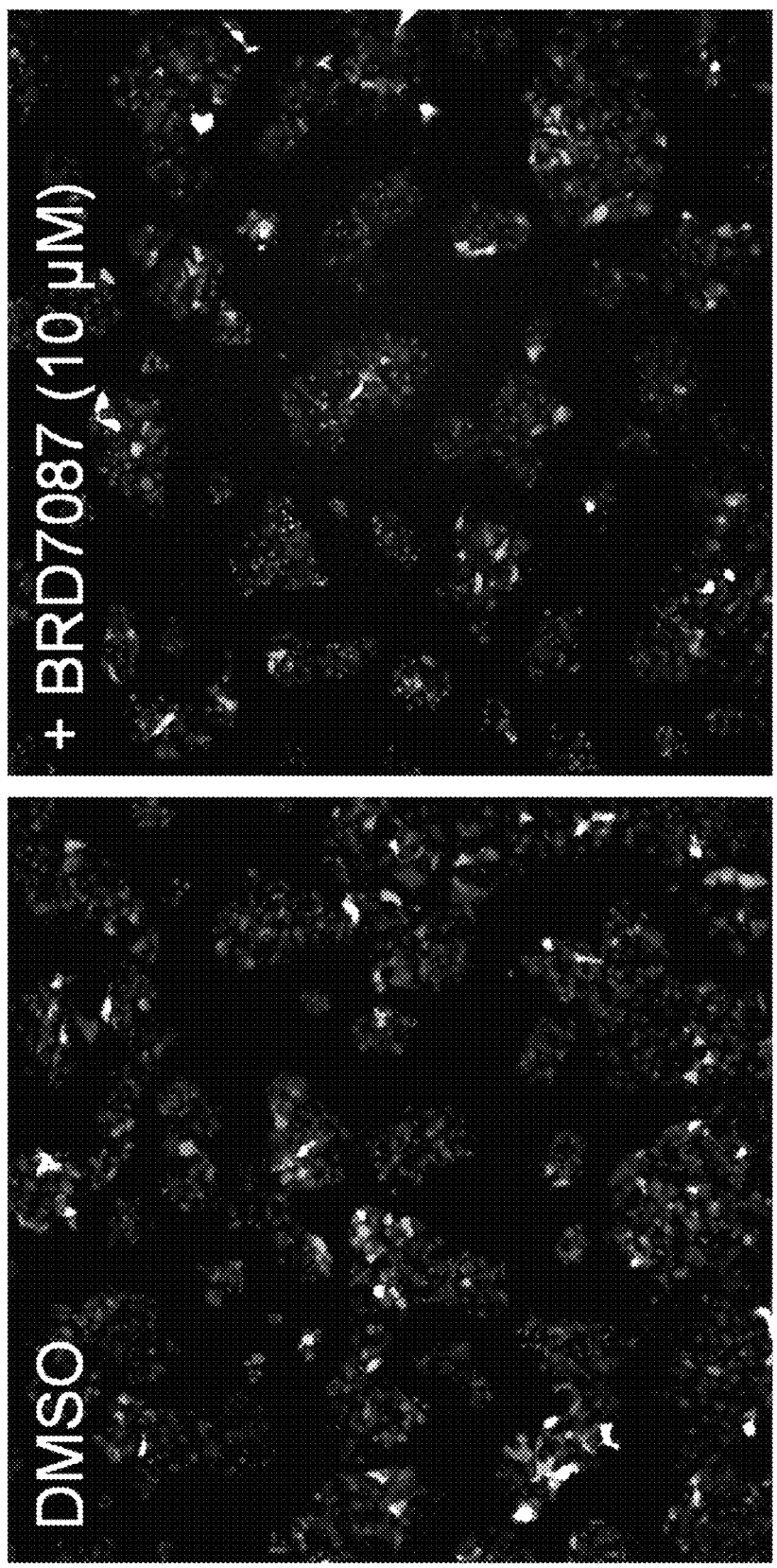
FIG. 30—Representative images of HEK293 cells transfected with a reporter plasmid mCherry and GFP genes and another plasmid with SpCas9 and gRNA genes. The Nuclei are counter-stained with DAPI and the red and green channels represent the expression level of mCherry and GFP respectively. Cells were incubated either with DMSO or compound BRD7087 with the indicated concentration. Error bars represent ±S.D. from technical replicates (n=3). Scale bar=100 µm.
Figure 31:
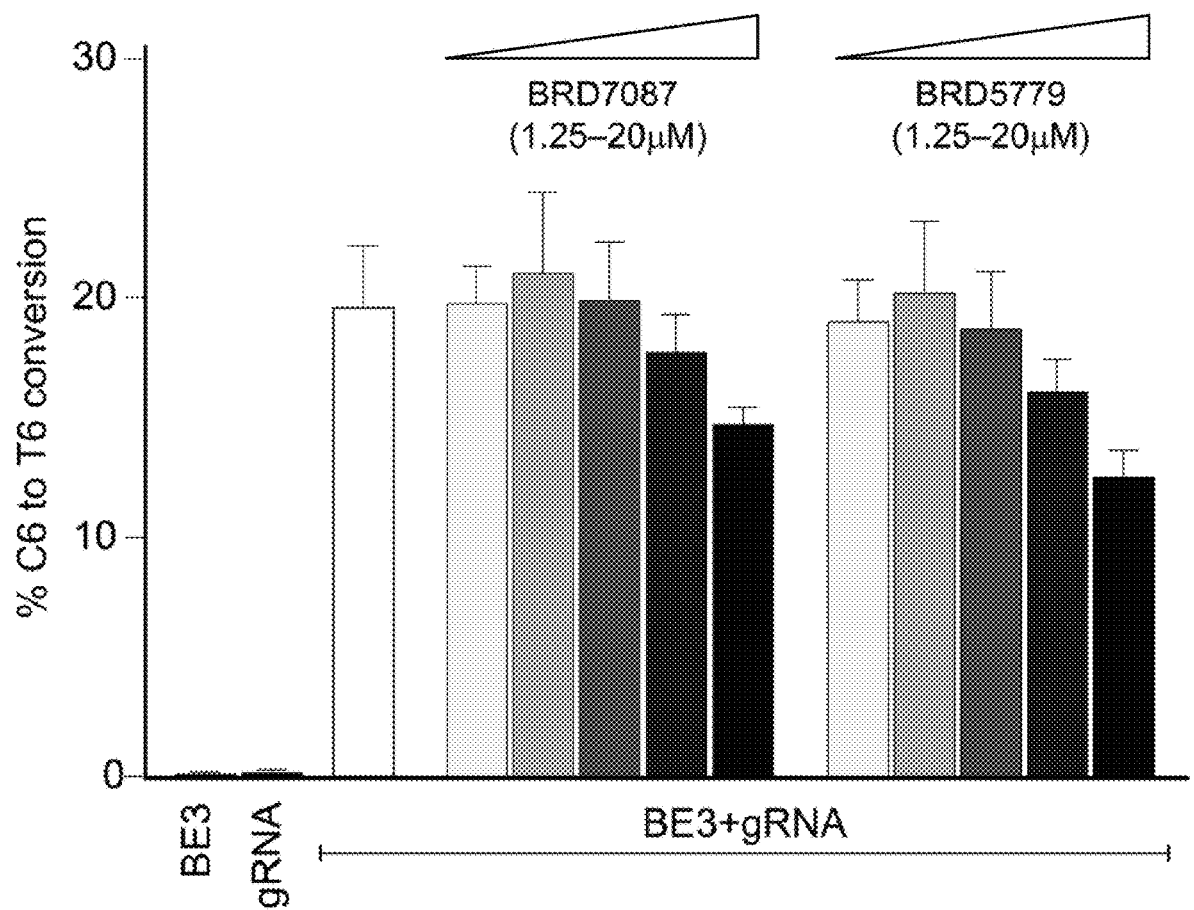
FIG. 31—Dose-dependent inhibition of base-editing activity by compounds. Dose-dependent inhibition of the dCas9-based base-editing activity of cytidine deaminase (BE3) targeting EMX1 gene in HEK293T cells. Ribonucleoprotein BE3:gRNA preincubated with small molecule was delivered into the adhered HEK293T cells and incubated in the presence of either DMSO or compound at the indicated concentration for 72 h. The cells were then harvested and processed for DNA sequencing to evaluate the extent of C6→T6 conversion. Error bars represent ±S.D. from technical replicates (n=3).
Figure 32:
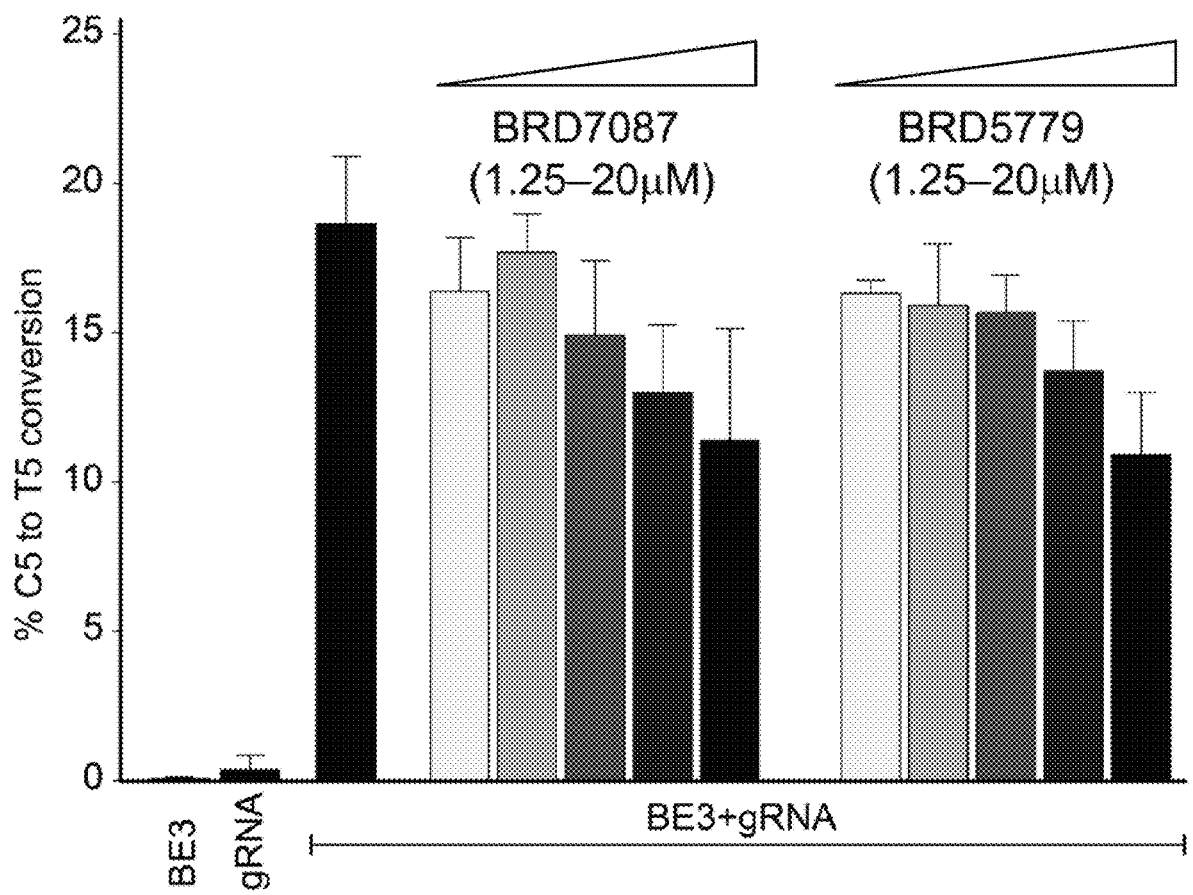
FIG. 32—Dose-dependent inhibition of base-editing by compounds. Dose-dependent inhibition of the dCas9-based base-editing activity of cytidine deaminase (BE3) targeting EMX1 gene in HEK293T cells. Ribonucleoprotein BE3:gRNA pre-incubated with small molecule was delivered into the adhered HEK293T cells and incubated in the presence of either DMSO or compound at the indicated concentration for 72 h. The cells were then harvested and processed for DNA sequencing to evaluate the extent of C5→T5 conversion. Error bars represent ±S.D. from biological replicates (n=3).

After biophysical validation of the interaction of BRD7087 with SpCas9, we performed cellular studies with this compound. First, we determined if BRD7087 and BRD5779 were cytotoxic. Treatment of U2OS and HEK293T cells with these compounds did not significantly alter the cellular ATP-levels upon incubation up to 20 µM concentration for 24 h (FIGS. 21-22). We then tested the compounds at different doses in EGFP-disruption assay in U2OS.eGFP.PEST cell and measured the recovery of EGFP signal. Both the compounds showed a dose-dependent SpCas9 inhibition activity as quantified by the recovery of the EGFP signal (FIGS. 3A and 23). Compound BRD7087 showed an inhibition of SpCas9 activity by 44% at 10 µM. We also confirmed that these compounds do not alter proteasomal degradation of EGFP when incubated with U2OS.eGFP.PEST cells (FIG. 24). The compounds also did not induce any notable auto-fluorescence in cells (FIG. 25). We further employed both the mKate2 expression assay and NHEJ assay to validate the activity of the compounds BRD7087 and BRD5779. Compound BRD7087 was found to be more active than BRD5779 with a 50% inhibition activity at ~5 µM in mKate2 disruption assay (FIGS. 26 and 27). Both compounds were also active in the NHEJ assay (FIGS. 28 and 29).

Figure 33:
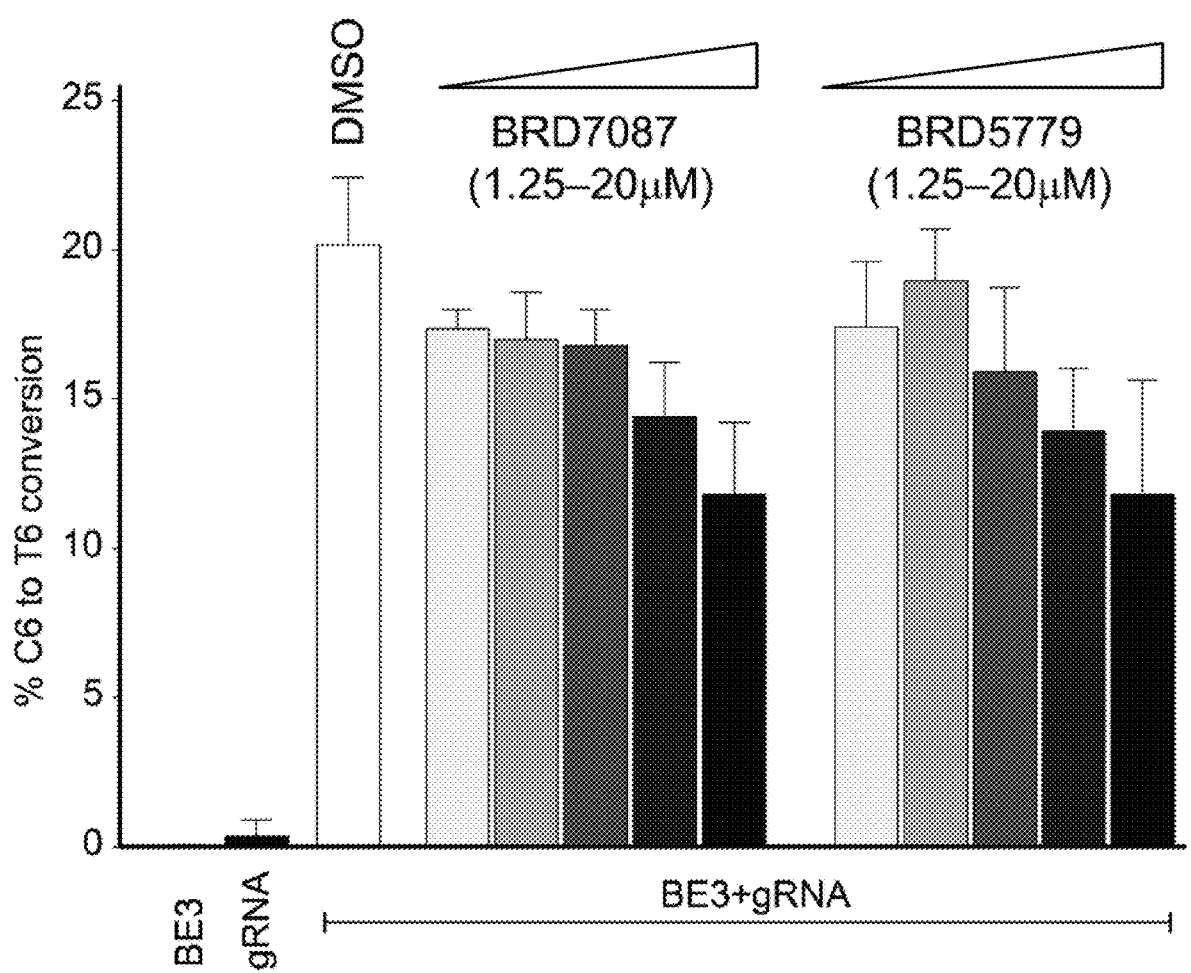
FIG. 33—Dose-dependent inhibition of base-editing activity by compounds. Dose-dependent inhibition of the dCas9-based base-editing activity of cytidine deaminase (BE3) targeting EMX1 gene in HEK293T cells. Ribonucleoprotein BE3:gRNA preincubated with small molecule was delivered into the adhered HEK293T cells and incubated in the presence of either DMSO or compound at the indicated concentration for 72 h. The cells were then harvested and processed for DNA sequencing to evaluate the extent of C6→T6 conversion. Error bars represent ±S.D. from biological replicates (n=3).

Since BRD7087 and BRD5779 alter PAM-binding, they should inhibit dCas9-based technologies, including baseediting and transcriptional activation technologies. We undertook the dCas9-cytidine deaminase conjugate (BE3)[19] targeting the EMX1 gene toward C→T conversion in the presence and absence of inhibitors at different concentrations. In this assay a ribonucleoprotein complex (BE3: gRNA) was incubated with either DMSO or compound at the specified concentration and delivered into HEK239T cells maintaining the corresponding compound concentration in the media. The base-editing efficiency was determined by isolating the genomic DNA followed by two-step barcoding the EMX1 gene and running on the MiSeq (Illumina) sequencer. Both the compounds BRD7087 and BRD5779 showed an efficient and dose-dependent inhibition of BE3-mediated base-editing (FIG. 3B and FIGS. 30-32). We observed similar inhibition of base editing when plasmid transfection was used in place of protein delivery. Next, we tested BRD7087 and BRD5779 in a dCas9-based transcriptional activation assay targeting the HBG1 gene. A dose-dependent inhibition of the HBG1 transcriptional activation further corroborated the inhibitory activity of BRD7087 and BRD5779 (FIG. 3C and FIG. 33). Compound BRD7087 showed >60% inhibition of transcriptional activation at 10 µM concentration (FIG. 3C).

Figure 34:
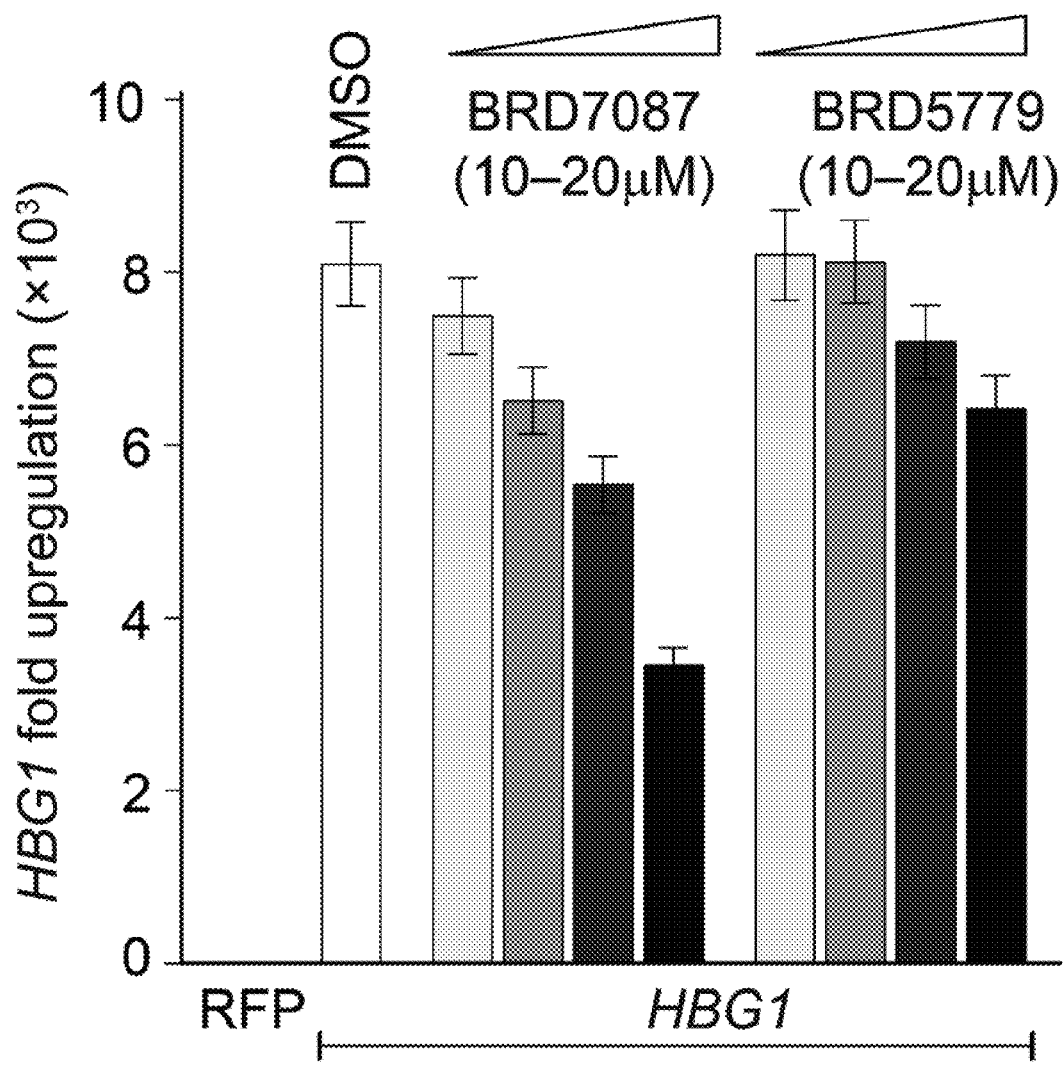
FIG. 34—Dose-dependent inhibition of base-editing activity by compounds. Dose-dependent inhibition of dCas9-based transcriptional activation of HBG1 gene in HEK293FT cells. Cells were transfected with dCas9, MS2.p65.HSF1.GFP plasmids along with either RFP or HBG1 plasmid and incubated in the presence of the compounds at the indicated concentration before processing for RT-qPCR. The experiments were performed in three biological replicates and each biological replicates were processed in six technical replicates. The data are reported as mean±S.E.M. for technical replicates.

After demonstrating inhibition of Cas9 and dCas9-based technologies, we determined if BRD7087 and BRD5779 can block CRISPR-immunity of bacteria from phages. We anticipated that SpCas9 inhibitors will disrupt the bacterial immunity and trigger lysis in the presence of phage. To test this hypothesis, we exposed the immune bacterial cell S. aureus RN4220 strain 62 to CRISPR targeting lytic phage φNM4ɣ 4 in the presence and absence of SpCas9 inhibitor BRD7087 and BRD5779 at different concentrations. Bacterial cell lysis, which was followed by OD600 measurements, was observed in the presence of our SpCas9 inhibitors and phage (FIG. 3D), but not in the presence of inhibitor alone (FIG. 34), suggesting that the inhibitors disrupt CRISPR-immunity and are non-toxic in the absence of phage. Both the compounds BRD7087 and BRD5779 were able to sensitize the immune bacterial cells against target phage in a dose-dependent manner, however, BRD7087 showed higher activity as was observed in the mammalian cells.

BRD7087 and BRD5779 possess three chiral centers (3aR,4S,9bR) and we wished to determine if different stereoisomers have similar nuclease inhibition activity. We tested four isomers of each compound BRD7087 and BRD5779 in EGFP-disruption assay (not shown). Strikingly, the enantiomer of BRD7087 (3aR,4S,9bR), that is BRD5039 (3aS,4R,9bS), was equipotent as BRD7087 in EGFP-disruption assay. However, the other two diastereomers BRD2161 (3aR,4R,9bR) and BRD0750 (3aS,4S,9bS) were less potent (not shown). Similar trend was observed for BRD5779 and its stereoisomers (not shown).

Small molecule inhibitors of CRISPR-Cas9 will find multifactorial use in basic, biomedical, and defense research. We report a suite of assays and workflow for discovery of small molecule inhibitors of SpCas9, and demonstrate the utility of these assays by identifying small molecule inhibitors of SpCas9. The availability of such workflow will catalyze discovery of inhibitors for not only SpCas9 but also several other next-generation CRISPR-associated nucleases. Our screening strategy involved disrupting PAM-binding by SpCas9 and we were able to demonstrate >60% inhibition of nuclease activity of SpCas9 in mammalian and bacterial cells, as well as inhibition of dCas9 based transcriptional and base editing technologies. Thus, we envision our SpCas9 inhibitors to find utility in wide variety of applications. Our future studies will involve identification of binding sites of our inhibitors and structure-guided potency optimization. Further, we are interested in determining if the disruption of CRISPR-immunity by our SpCas9 inhibitors will propel bacteria to evolve CRISPR system.

Materials and Methods

SpCas9 expression and purification. SpCas9 was expressed and purified following a previously reported protocol 1.

BL21 Star (DE3)-competent E. coli cells were transformed with plasmids encoding the bacterial codon-optimized SpCas9 with a His6 N-terminal purification tag. A single colony was grown overnight in TB containing 25 µg ml-1 kanamycin at 37° C. The cells were diluted 1:1000 into 1 L of the same media and grown at 37° C. until OD600=0.60-0.7. The cultures were cooled down to 18° C. for 30 min and protein expression was induced with 1 mM isopropyl-β-D-1-thiogalactopyranoside (GoldBio). Expression was sustained for 16-18 h with shaking at 18° C. The subsequent purification steps were carried out at 4° C. Cells were collected by centrifugation and resuspended in cell collection buffer (100 mM tris(hydroxymethyl)-aminomethane (Tris)-HCl, pH 8.0, 1 M KCl, 20% glycerol, 5 mM tris(2-carboxyethyl)phosphine (TCEP; GoldBio), 1 mM phenylmethane sulfonyl fluoride (Sigma-Aldrich) and 1 mg/mL Lysozyme. Cells were lysed by sonication (10 min total, 30 s on, 30 s off) and the lysate cleared by centrifugation at 15,000 g (1 h).

The cleared lysate was incubated with HisPur nickel-nitriloacetic acid (nickel-NTA) resin with rotation at 4° C. for 2 h. The resin was washed with 2 ×15 column volumes of cell collection buffer before bound protein was eluted with elution buffer (100 mM tris(hydroxymethyl)-aminomethane (Tris)-HCl, pH 8.0, 100 mM KCl, 20% glycerol, 5 mM TCEP (GoldBio), 250 mM imidazole). The resulting protein fraction was further treated with TEV protease at 4° C. for 24 h in 20 mM (Tris)-HCl, pH 8.0, 100 mM KCl, 20% glycerol, 5 mM TCEP and then purified on a 5 mL Hi-Trap HP SP (GE Healthcare) cation exchange column with KCl gradient from 0.1 M to 1 M using an Akta Pure FPLC. Protein-containing fractions were concentrated using a column with a 100 kDa cutoff (Millipore) centrifuged at 3,000 g. The Hi-Trap purified followed by running through a HiLoad Superdex 200 column using 20 mM (Tris)-HCl, pH 8.0, 100 mM KCl, 20% glycerol, 5 mM TCEP buffer. The purified protein was validated by running a denaturing gel and snap-frozen in liquid nitrogen and stored at −80° C.

In vitro transcription of sgRNA. Linear DNA fragments containing the T7 RNA polymerase promoter sequence upstream of the desired 20 bp sgRNA protospacer and the sgRNA backbone were generated by PCR (Q5 Hot Start MasterMix, New England Biolabs) using primers forward: AAAAGCACCGACTCGGTGCCACTTTTTCAAGTT-GATAACGGACTAGCCTTATTTTAACTTGCTAT-TTCTAGCTCTAAAAC-3' and reverse: 5'-TAATACGACT-CACTATAGCTATAGGACGCGACCGAAAGTTTTAGAG CTAGAAAT-3' (SEQ ID Nos. 9 and 10). sgRNA was transcribed with the HiScribe T7 High Yield RNA Synthesis Kit (New England Biolabs) at 37° C. for 16 h with 150 ng of linear template per 20 l reaction. sgRNA was purified using the MEGAClear Transcription Clean Up Kit (Thermo Fisher), according to the manufacturer's instructions. Purified sgRNAs were stored in aliquots at −80° C.

FP Assay. Fluorescence Polarization assay was performed in a 384-well plate (Corning 3575) format using a total reaction volume of 30 µL. A 25 nM FITC-labeled 12PAM DNA was titrated against increasing concentration of Cas9:gRNA (1:1.2) complex in a 20 mM Tris-HCl buffer of pH 7.5 containing 150 mM KCl, 5 mM $MgCl_2$, 1 mM DTT. The fluorescence polarization signal was measured using a microplate reader (PerkinElmer, EnVision). The experiments were performed in triplicates and the data were processed in GraphPad Prism 7. The Z'-value was calculated following the formula:

$$Z' = \frac{3(\sigma 1 + \sigma 2)}{|\mu 1 - \mu 2|}$$

Where σ1 and σ2 are the standard deviations of DMSO control and Cas9:gRNA control respectively. µ1 and µ2 are the mean FP-signal intensities for DMSO control and Cas9:gRNA control respectively.

Competition Assay. In a 384-well plate (Corning 3575), 25 nM FITC-labeled 12PAM DNA was incubated with 50 nM SpCas9:gRNA (1:1.2) complex in the presence and absence of unlabeled DNA in excess (10× and 50×) in a 20 mM Tris-HCl buffer of pH 7.5 containing 150 mM KCl, 5 mM $MgCl_2$, 1 mM DTT. The fluorescence polarization signal was measured using a microplate reader (PerkinElmer, EnVision). The number of PAM sequence in the unlabeled competitor DNA was varied from 0, 4, 8, and 12 PAMs. The experiments were performed in triplicates and the data were processed in GraphPad Prism 7.

Differential Scanning Fluorimetry (DSF). Protein melting experiments were performed in a 384-well format using a 6 µL reaction volume in a LightCycler 480 instrument. A 3.7 µM SpCas9:gRNA (1:1.2) was incubated with equimolar concentration of DNA with different PAM density (0, 4, 8, and 12) for 15 min in a 20 mM Tris-HCl buffer of pH 7.5 containing 150 mM KCl, 5 mM $MgCl_2$, 1 mM DTT. Then, 2 µL of 50× SYPRO® Orange was added before running the melting cycle with a temperature gradient of 4.8° C./min. The experiments were performed in triplicates and data were processed in Roche LightCycler® 480 Protein Melting software.

Bio-Layer Interferometry (BLI). DNA-Cas9 interactions were also probed using BLI experiments in an Octet Red384 (Pall ForteBio) instrument. The experiments were performed in a 96-well format with 180 µL reaction volume using biotinylated ds-DNA and streptavidin sensors. A 300 nM of biotinylated DNA with different PAM density (0, 2, 4, and 8) were loaded onto the sensors for 180 s in 20 mM Tris buffer of pH 7.4, 100 mM KCl, 5 mM MgCl2, 1 mM DTT, 0.01% Tween®, 50 µg/mL Heparin. Excess DNA was washed off for 60 s in reaction buffer followed by association with 200 nM of Cas9-gRNA (1:1.2) for 300 s. The complex was then allowed to dissociate for 3600 s in the reaction buffer. All the response curves were normalized against the reference sensor without Cas9:gRNA.

Compound Screening. The compound library screening was performed in two steps. Initially, the DOS informer set of library (10,000 compounds) was screened in the FP-based assay to identify the enriched hit libraries. Then, the specific enriched libraries were also screened using the same assay. The screening assay was performed in a 384-well plate format with a total reaction volume of 30 µL. Initially, a 25 µL of 60 nM of SpCas9 was transferred to the compound testing lanes of the 384-well plate except for the positive control wells. However, a 25 µL of solution containing 60 nM SpCas9 and 300 nM unlabeled 12PAM ds-DNA was transferred to the positive control wells. In the next step, 25 nL of DMSO alone or 10 mM compounds in DMSO were transferred to the reaction mixture and incubated for 30 min at room temperature. Next, a 5 µL solution containing 360 nM gRNA and 150 nM FAM-labeled 12PAM ds-DNA was added and incubated for 15 min at room temperature before acquiring the fluorescence polarization signal under a microplate reader (PerkinElmer, EnVision). Compounds were screened in duplicates and the data were processed to calculate the Z-score (σ) values and plotted in Spotfire analysis software (TIBCO). The hit compounds (Z-score >3σ) were then clustered according to the class of compound and a hit-rate plot was generated. The entire specific libraries of the enriched ones were then screened in the same FP-assay.

Counter-screening. Counter-screening assay was performed in a similar format as followed in the compound-screening assay. In a 384-well plate, a 30 µL of 25 nM FAM-labeled 12PAM ds-DNA was transferred to each well. Next, 25 nL of either DMSO or compound in DMSO were transferred and incubated for 15 min before the fluorescence polarization signal was acquired in a microplate reader (PerkinElmer, EnVision). The change in the FP signal was calculated in percentile and plotted against compounds' average Z-score values obtained from the original compound-screening assay. Compound that resulted in a >3σ change in the Z-score but did not alter the FP-signal by >10% in the counter-screen assay were selected as the potential hits. A molecular structure based similarity search was also performed and compounds with >0.8 similarity index was included in the hit list.

Compound-Cas9 interaction in BLI. The experiments were performed in a 96-well format with 180 µL reaction volume using biotinylated compound BRD7087-Biotin and streptavidin sensors. 1 µM of the biotinylated compound was loaded onto the sensors for 180 s in 20 mM Tris buffer of pH 7.4, 100 mM KCl, 5 mM $MgCl_2$, 1 mM DTT, 0.01% Tween®. The compound loaded sensors were then allowed to associate with the different concentration of SpCas9: gRNA complex (1-0.15 µM) for 300 s followed by dissociation in the reaction buffer. Reference sensor was loaded with compound and allowed to associate and dissociate in the reaction buffer alone. The response curves were fitted with a 2:1 stoichiometric model and a global fit steady-state analysis were performed using manufacturer inbuilt protocol. The experiment was performed in three replicates.

The competitive experiments were performed using Biotin-linker fragment. In this experiment, streptavidin sensors were pre-incubated with 10 µM of Biotin-linker before dipping into a solution of either 1 µM BRD7087-Biotin or reaction buffer alone. Sensors were then allowed to associate with different concentration of SpCas9:gRNA complex or buffer alone.

NMR binding assay. All samples were prepared with 50 µM BRD7087 in 20 mM Tris buffer (pH=7.4) with varying concentrations of SpCas9:gRNA in a 3 mm NMR tube. Experiments were performed on a 600 MHz (19F: 564.71 MHz) Bruker Avance III NMR spectrometer equipped with a 5 mm QCI-F CryoProbe and a SampleJet for automated sample handling. To acquire spectra, a standard one-pulse 19F experiment with WALTZ-16 for proton decoupling during acquisition, a 5 second recycle delay, and 256 scans was used. All spectra were recorded at 280 K. NMR data were apodized with a 1 Hz exponential function prior to Fourier transformation. All spectra were baseline corrected; peak widths and intensities were extracted using the automated line-fitting feature provided with the MNova software package. Determination of the value of Kd was accomplished using least squares fitting to the expression given in Equation 8 in the paper by Shortridge et al.2.

Kd values obtained by NMR rely on the assumption that ligand binding is in fast-exchange, which typically holds true for ligands with Kd in the 0.5 µM to 20 mM range. Additional sources of error could be variations in the concentrations of the protein and ligand, an incomplete curve that does not reach complete occupancy, or incomplete relaxation leading to underestimation of the fractional occupancy.

Cell culture. All cells were cultured at 37° C. in a humidified 5% CO2 atmosphere. HEK293T cells (Life Technologies) used in transcriptional activation, NHEJ, and mCherry expression assays were cultured in Dulbecco's modified Eagle's medium (CellGro) supplemented with 10% fetal bovine serum (CellGro) and 1× penicillin/streptomycin/glutamax (CellGro). U2OS.eGFP-PEST cells stably integrated with an eGFP-PEST fusion gene were maintained in Dulbecco's modified Eagle's medium (Life Technologies) supplemented with 10% FBS, 1×penicillin/streptomycin/glutamax (Life Technologies) and 400 µg/mL of the selection antibiotic G418. Cells were continuously maintained at <90% confluency. All cell lines were sourced commercially or were functionally validated. Cells were periodically tested for *Mycoplasma* contamination using the MycoAlert PLUS *Mycoplasma* Detection Kit (Lonza).

Cas9 Nuclease activity in EGFP disruption assay. Approximately 200,000 U2OS.eGFP-PEST cells were nucleofected with 400 ng of SpCas9 (Addgene Plasmid #43861) and 40 ng of sgRNA (pFYF1320 EGFP Site #1, Addgene Plasmid #47511) expressing plasmids along with a Td-tomato-encoding plasmid using the SE Cell Line 4D-Nucleofector™ X Kit (Lonza) according to the manufacturer's protocol. Approximately 20,000 transfected cells/well in 3 replicates were plated in a 96-well plate (Corning® 3904). Cells were allowed to grow in the indicated amount of compound or DMSO for 24 h post transfection. Cells were then fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 10× magnification under three excitation channels (blue, green and red) with 9 acquiring sites per well. Images were analyzed in the MetaXpress software and data were plotted using GraphPad Prism 6. The Z'-value was calculated following the formula:

$$Z' = \frac{3(\sigma1 + \sigma2)}{|\mu1 - \mu2|}$$

Where σ1 and σ2 are the standard deviations of DMSO control and Cas9:gRNA control respectively. µ1 and µ2 are the mean % GFP-cell population for DMSO control and Cas9:gRNA control respectively.

Western blot analysis. U2OS.eGFP.PEST cells stably expressing EGFP were incubated either in the absence or presence of compound BRD7087 and BRD5779 for 24 h at 37° C. prior to harvesting the cells. Cell suspensions were spun down at 1000×g for 5 min and processed for cell lysis. Cells were resuspended in RIPA total cell lysis buffer (abcam) and incubated at 4° C. for 10 min. The cell suspensions were then vortexed for 10 min at 4° C. followed by spinning down at 16,000×g for 15 min at 4° C. The supernatant was transferred to a fresh tube and processed for western-blotting.

Western blotting was performed following SDS-PAGE gel electrophoresis. In a typical experimental protocol, 40 µg of normalized proteins were electrophoresed on a 4-12% Bis/Tris gel. The protein bands were transferred to a PVDF membrane and probed with primary α-HSF1(c) (Abcam #ab52757) and/or α-CRISPR/Cas9 antibody (Abcam #ab191468). α-Actin antibody (Sigma) was used as a protein loading control.

NHEJ assay. Approximately 8,000 cells/well were plated in a 96-well format 24 h before transiently transfected with a total 100 ng of DN66 (mCherry-TAG-GFP reporter) and DN78 (SpCas9 and gRNA) plasmids (1:1) using lipofectamine 2000 (Life Technologies) 3. Transfected cells were allowed to grow in the indicated amount of compound or DMSO for 24 h. Cells were then fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 20× magnification under three excitation channels (blue, green and red) with 9 acquiring sites per well. Images were analyzed in the MetaXpress software to determine the % NHEJ and the data were plotted using GraphPad Prism 6. The Z'-value was calculated following the formula:

$$Z' = \frac{3(\sigma 1 + \sigma 2)}{|\mu 1 - \mu 2|}$$

Where σ1 and σ2 are the standard deviations of DN66 transfected wells and (DN66+DN78) transfected wells respectively. μ1 and μ2 are the mean % GFP⁻ cell population for DN66 transfected wells and (DN66+DN78) transfected wells respectively.

mKate2 expression assay. Approximately 8,000 cells/well were plated in a 96-well format 24 h before transiently transfected with 100 ng of either CgRNA (Addgene Plasmid #64955) or T1gRNA (Addgene Plasmid #62717) plasmids using lipofectamine 2000 (Life Technologies). Transfected cells were allowed to grow in the indicated amount of compound or DMSO for 24 h. Cells were then fixed using 4% paraformaldehyde and imaged with the HCS Nuclear-Mask™ Blue Stain (Life Technologies) as the nuclear counter-staining agent. Imaging was performed with an IXM 137204 ImageXpress Automated High Content Microscope (Molecular Devices) at 20× magnification under two excitation channels (blue and red) with 9 acquiring sites per well. Images were analyzed in the MetaXpress software to determine the % mKate2 positive cells and the % NHEJ was calculated following a reported protocol and plotted using GraphPad Prism 6. The Z'-value was calculated following the formula:

$$Z' = \frac{3(\sigma 1 + \sigma 2)}{|\mu 1 - \mu 2|}$$

Where σ1 and σ2 are the standard deviations of cgRNA transfected wells and T1-gRNA transfected wells respectively. μ1 and μ2 are the mean % RFP+ cell population for CgRNA transfected wells and T1gRNA transfected wells respectively.

Transcription activation experiments and quantitative RT-PCR analyses. For transcription activation experiments 250,000 cells/well were plated in a 12 well plate. The cells were transiently transfected with a 1:1:1 mass ratio of the dCas9 plasmid, MS2-P65-HSF1 effector plasmid and the sgRNA plasmid targeting the HBG1 gene or an RFP control plasmid. A total of 1.6 μg plasmid DNA was transfected using Lipofectamine 2000 (Life Technologies) according to manufacturer's protocol. Immediately after transfection, the cells were treated with an appropriate dose of the small molecule inhibitors for 48 hours following which the cells were harvested and RNA was extracted using the EZNA Total RNA kit I (Omega) as per manufacturer's instructions. 1 μg total cellular RNA was used to perform reverse transcription using the High-Capacity cDNA Reverse Transcription Kit (Applied Biosystems) or the qScript cDNA Synthesis Kit (QuantaBio). qPCR reactions were performed to quantify RNA expression using the TaqMan probes (Life Technologies, HBG1/HBG2: Hs00361131_g1 and ACTB: Hs01060665_g1) and TaqMan Fast Advanced Master Mix (Life Technologies) in 5 μL multiplexed reactions and 384-well format using the LightCycler 480 Instrument II (Roche). For each sample, six technical replicates were performed. Data were analyzed using the LightCycler 480 software (Roche) by the ΔΔCt method: Ct values for the gene of interest (HBG1) were normalized to Ct values for the housekeeping gene (ACTB) and fold-changes in the expression level of the gene of interest were normalized to RFP-transfected control. The data are reported as mean±S.E.M. for technical replicates.

Base-Editing Experiment.

BE3 expression and purification. BE3 was expressed and purified as previously reported 4. BL21 Star (DE3)-competent E. coli cells were transformed with plasmids encoding the bacterial codon-optimized base editor with a His6 N-terminal purification tag. A single colony was grown overnight in 2×YT broth containing 50 μg ml-1 kanamycin at 37° C. The cells were diluted 1:400 into 4 L of the same media and grown at 37° C. until OD600=0.70-0.75. The cultures were incubated on ice for 3 h and protein expression was induced with 1 mM isopropyl-β-D-1-thiogalactopyranoside (Gold-Bio). Expression was sustained for 16-18 h with shaking at 18° C. The subsequent purification steps were carried out at 4° C. Cells were collected by centrifugation and resuspended in cell collection buffer (100 mM tris(hydroxymethyl)-aminomethane (Tris)-HCl, pH 8.0, 1 M NaCl, 20% glycerol, 5 mM tris(2-carboxyethyl)phosphine (TCEP; GoldBio), 0.4 mM phenylmethane sulfonyl fluoride (Sigma-Aldrich) and 1 EDTA-free protease inhibitor pellet (Roche)). Cells were lysed by sonication (6 min total, 3 s on, 3 s off) and the lysate cleared by centrifugation at 25,000 g (20 min).

The cleared lysate was incubated with HisPur nickel-nitriloacetic acid (nickel-NTA) resin with rotation at 4° C. for 90 min. The resin was washed with 2 ×15 column volumes of cell collection buffer before bound protein was eluted with elution buffer (100 mM tris(hydroxymethyl)-aminomethane (Tris)-HCl, pH 8.0, 0.5 M NaCl, 20% glycerol, 5 mM TCEP (GoldBio), 200 mM imidazole). The resulting protein fraction was further purified on a 5 ml Hi-Trap HP SP (GE Healthcare) cation exchange column using an Akta Pure FPLC. Protein-containing fractions were concentrated using a column with a 100 kDa cutoff (Millipore) centrifuged at 3,000 g, and the concentrated solution was sterile-filtered through a 22-μm polyvinylidene difluoride membrane (Millipore).

After sterile filtration, proteins were quantified with Reducing Agent Compatible Bicinchoninic acid assay (Pierce Biotechnology), snap-frozen in liquid nitrogen and stored in aliquots at −80° C.

In vitro transcription of sgRNA. Linear DNA fragments containing the T7 RNA polymerase promoter sequence upstream of the desired 20 bp sgRNA protospacer and the sgRNA backbone were generated by PCR (Q5 Hot Start MasterMix, New England Biolabs) using primers forward: (SEQ ID Nos. 11 and 12) 5'-TAATACGACTCACTATAGG-GAGTCCGAGCAGAAGAAGAAGTTT-TAGAGCTAGAAATAGCA-3' and reverse: 5'-AAAAAAAGCACCGACTCGGTGCCAC-3' and concentrated on minelute columns (Qiagen). sgRNA was transcribed with the HiScribe T7 High Yield RNA Synthesis Kit (New England Biolabs) at 37° C. for 14-16 h with 400 ng of linear template per 20 μl reaction. sgRNA was purified using the MEGAClear Transcription Clean Up Kit (Thermo Fisher), according to the manufacturer's instructions. Purified sgRNAs were stored in aliquots at −80° C.

Protein transfection of base editor BE3 into HEK293T cells. HEK293T cells were seeded on 48-well BioCoat poly-D-lysine plates (Corning) in 250 μL of antibiotic-free medium and transfected at ~70% confluency. Prior to protein transfection, cells were incubated with 2 μL of DMSO-suspended BRD7087 or BRD5779 at the indicated concentration for 2-3 hours. BE3 protein was incubated with 1.1× molar excess of EMX1-targeting sgRNA at a final concentration ratio of 200 nM. 220 nM (based on a total well volume of 275 μL). The complex was mixed with 0.2 μL of compound for five minutes, incubated with 1.5 μL Lipofectamine 2000 (Thermo Fisher) and transfected according to the manufacturer's protocol plasmid delivery. The cells and ribonucleoprotein complex were incubated with compounds at final concentrations of 1.25 μM, 2.5 μM, 5 μM, 10 μM or 20 μM.

Purifications and sequencing of genomic DNA. Transfected cells were harvested after 72 h in 50 μL of lysis buffer (10 mM Tris-HCl pH 8.0, 0.05% SDS, 25 μg/mL proteinase K) and incubated at 37° C. for 1 h. Cell lysates were heated at 85° C. for 15 min to denature proteinase K. For the first PCR, genomic DNA was amplified to the top of the linear range using Phusion Hot Start II DNA polymerase (New England Biolabs) according to the manufacturer's instructions. For all amplicons, the PCR protocol used was an initial heating step for 1 min at 98° C. followed by an optimized number of amplification cycles (10 s at 98° C., 20 s at 68° C., 15 s at 72° C.). qPCR was performed to determine the optimum number of cycles for each amplicon. Amplified DNA was purified using RapidTip2 (Diffinity Genomics) and barcoded with a further PCR. Sequencing adapters and dual-barcoding sequences are based on the TruSeq Indexing Adapters (Illumina). Barcoded samples were pooled and purified by gel extraction (Qiagen) before quantification using the Qubit dsDNA HS Kit (Thermo Fisher) and qPCR (KAPA BioSystems) according to the manufacturer's instructions. Sequencing of pooled samples was performed using a single-end read from 260 to 300 bases on the MiSeq (Illumina) according to the manufacturer's instructions.

Analysis of base-edited sequences. Nucleotide frequencies were analyzed using a previously described MATLAB script 5. Briefly, the reads were aligned to the reference sequence via the Smith-Waterman algorithm. Base calls with Q-scores below 30 were replaced with a placeholder nucleotide (N). This quality threshold results in nucleotide frequencies with an expected theoretical error rate of 1 in 1,000.

To distinguish small molecule-induced inhibition of C→T editing from artefactual C→T editing, we compared the sequencing reads from cells treated with base-editor in the presence of small molecule to the sequencing reads from base-edited cells not exposed to small molecule. A Student's two-tailed t-test was used to determine if inhibition of C→T editing by small-molecule is statistically significant with $P<0.05$ as the threshold.

Bacterial study. Plasmid pRH248 harboring SpCas9, tracrRNA and a single-spacer array (CGTGTAAAGACAT-ATTAGATCGAGTCAAGG) (SEQ ID 13) No. targeting phage (DNM474 was constructed via BsaI cloning onto pDB114 as described in Heler et al 6. Plate reader growth curves of bacteria infected with phage were conducted as described previously with minor modifications 7. Overnight cultures were diluted 1:100 into 2 ml of fresh BHI supplemented with appropriate antibiotics and 5 mM CaCl2) and grown to an OD600 of ~0.2. Immune cells carrying pRH248 were diluted with cells lacking CRISPR-Cas in a 1:10,000 ratio. Following a 15-minute pre-incubation with DMSO or with varying amounts of inhibitors (5-20 μM), the cultures were infected with <DNM474 at an initial MOI of 1. To produce plate reader growth curves, 200 μL of infected cultures, normalized for OD600, were transferred to a 96-well plate in triplicate. OD600 measurements were collected every 10 minutes for 16 hours. Similarly, growth curves to evaluate the toxicity of the compounds at 20 μM (FIG. 32) were conducted on cultures lacking CRISPR in the absence of phage.

TABLE 4

List of hit compounds from the counter-screening assay of Pictet-Spengler library and their structurally similar analogs.

| Index | Compound ID | Structure |
|---|---|---|
| 1 | BRD3326 | |
| 2 | BRD1701 | |
| 3 | BRD2911 | |
| 4 | BRD1368 | |
| 5 | BRD7682 | |
| 6 | BRD1830 | |
| 7 | BRD2473 | |
| 8 | BRD0159 | |
| 9 | BRD5813 | |
| 10 | BRD4249 | |
| 11 | BRD7299 | |
| 12 | BRD8786 | |
| 13 | BRD0568 | |
| 14 | BRD7713 | |
| 15 | BRD3389 | |
| 16 | BRD4048 | |
| 17 | BRD2679 | |
| 18 | BRD3326 | |

TABLE 3

List of hit compounds from the counter-screening assay of Povarov library and their structurally similar analogs.

| Index | Compound ID | Structure |
|---|---|---|
| 1 | BRD7087 | |
| 2 | BRD5779 | |
| 3 | BRD4592 | |
| 4 | BRD1098 | |
| 5 | BRD7032 | |
| 6 | BRD6688 | |
| 7 | BRD5737 | |
| 8 | BRD7801 | |
| 9 | BRD1476 | |
| 10 | BRD2810 | |
| 11 | BRD6201 | |
| 12 | BRD5762 | |
| 13 | BRD8312 | |
| 14 | BRD7804 | |
| 15 | BRD2878 | |
| 16 | BRD8575 | |
| 17 | BRD7481 | |
| 18 | BRD5903 | |
| 19 | BRD3119 | |
| 20 | BRD2161 | |
| 21 | BRD8480 | |
| 22 | BRD3978 | |
| 23 | BRD6467 | |
| 24 | BRD5039 | |
| 25 | BRD0489 | |
| 26 | BRD1794 | |
| 27 | BRD4326 | |
| 28 | BRD0750 | |
| 29 | BRD7037 | |
| 30 | BRD7147 | |

TABLE 5

Table containing data that was used to estimate the ligand binding affinity based on the method described by Shortridge et. al. The linewidth (LW) increases with increasing protein concentration, as expected. Peak intensity values were used to measure the Fractional Occupancy using the relationship given in the paper ($1-I_{bound}/I_0$), where $I_0$ is the intensity of the peak with no protein in the sample. The peak area remains relatively constant, as expected for a fixed concentration of ligand. The value of $K_d$ was estimated by nonlinear least-squares fitting of expression from the reference.

RAW DATA EXTRACTED FROM SPECTRA

| [Ligand], (µM) | [Protein:gRNA], (µM) | LW (Hz) | Peak Intensity | Peak Area | Fractional Occupancy |
|---|---|---|---|---|---|
| 50 | 0 | 4.1 | 572470.95 | 3151271.718 | 0 |
| 50 | 0.75 | 4.3 | 497630.81 | 2968891.536 | 0.130731769 |
| 50 | 1.0 | 4.6 | 468481.06 | 2999269.636 | 0.181650947 |
| 50 | 1.25 | 5.3 | 398322.72 | 2964107.303 | 0.304204484 |
| 50 | 1.5 | 5.9 | 375769.97 | 3176044.761 | 0.343599933 |
| 50 | 1.75 | 6.3 | 342640.49 | 3020022.312 | 0.401470957 |

REFERENCES

1. Doudna, J. A.; Charpentier, E., Genome editing. The new frontier of genome engineering with CRISPR-Cas9. *Science* 2014, 346 (6213), 1258096.
2. Hsu, P. D.; Lander, E. S.; Zhang, F., Development and applications of CRISPR-Cas9 for genome engineering. *Cell* 2014, 157 (6), 1262-78.
3. Jinek, M.; Chylinski, K.; Fonfara, I.; Hauer, M.; Doudna, J. A.; Charpentier, E., A programmable dual-RNA-guided DNA endonuclease in adaptive bacterial immunity. *Science* 2012, 337 (6096), 816-21.
4. Jinek, M.; East, A.; Cheng, A.; Lin, S.; Ma, E.; Doudna, J., RNA-programmed genome editing in human cells. *eLife* 2013, 2, e00471.
5. Cong, L.; Ran, F. A.; Cox, D.; Lin, S.; Barretto, R.; Habib, N.; Hsu, P. D.; Wu, X.; Jiang, W.; Marraffini, L. A.; Zhang, F., Multiplex genome engineering using CRISPR/Cas systems. *Science* 2013, 339 (6121), 819-23.
6. Mali, P.; Yang, L.; Esvelt, K. M.; Aach, J.; Guell, M.; DiCarlo, J. E.; Norville, J. E.; Church, G. M., RNA-guided human genome engineering via Cas9. *Science* 2013, 339 (6121), 823-6.
7. Gasiunas, G.; Barrangou, R.; Horvath, P.; Siksnys, V., Cas9-crRNA ribonucleoprotein complex mediates specific DNA cleavage for adaptive immunity in bacteria. *Proceedings of the National Academy of Sciences of the United States of America* 2012, 109 (39), E2579-86.
8. Dahlman, J. E.; Abudayyeh, O. O.; Joung, J.; Gootenberg, J. S.; Zhang, F.; Konermann, S., Orthogonal gene knockout and activation with a catalytically active Cas9 nuclease. *Nat Biotechnol* 2015, 33 (11), 1159-61.
9. Merkle, F. T.; Neuhausser, W. M.; Santos, D.; Valen, E.; Gagnon, J. A.; Maas, K.; Sandoe, J.; Schier, A. F.; Eggan, K., Efficient CRISPR-Cas9-mediated generation of knockin human pluripotent stem cells lacking undesired mutations at the targeted locus. *Cell reports* 2015, 11 (6), 875-883.
10. He, X.; Tan, C.; Wang, F.; Wang, Y.; Zhou, R.; Cui, D.; You, W.; Zhao, H.; Ren, J.; Feng, B., Knock-in of large reporter genes in human cells via CRISPR/Cas9-induced homology-dependent and independent DNA repair. *Nucleic Acids Res* 2016, 44 (9), e85.
11. Lin, S.; Staahl, B. T.; Alla, R. K.; Doudna, J. A., Enhanced homology-directed human genome engineering by controlled timing of CRISPR/Cas9 delivery. *eLife* 2014, 3, e04766.
12. Shalem, O.; Sanjana, N. E.; Hartenian, E.; Shi, X.; Scott, D. A.; Mikkelson, T.; Heckl, D.; Ebert, B. L.; Root, D. E.; Doench, J. G.; Zhang, F., Genome-scale CRISPR-Cas9 knockout screening in human cells. *Science* 2014, 343 (6166), 84-87.
13. Chen, B.; Gilbert, L. A.; Cimini, B. A.; Schnitzbauer, J.; Zhang, W.; Li, G. W.; Park, J.; Blackburn, E. H.; Weissman, J. S.; Qi, L. S.; Huang, B., Dynamic imaging of genomic loci in living human cells by an optimized CRISPR/Cas system. *Cell* 2013, 155 (7), 1479-91.
14. Hilton, I. B.; D'Ippolito, A. M.; Vockley, C. M.; Thakore, P. I.; Crawford, G. E.; Reddy, T. E.; Gersbach, C. A., Epigenome editing by a CRISPR-Cas9-based acetyltransferase activates genes from promoters and enhancers. *Nat Biotechnol* 2015, 33 (5), 510-7.
15. Dominguez, A. A.; Lim, W. A.; Qi, L. S., Beyond editing: repurposing CRISPR-Cas9 for precision genome regulation and interrogation. *Nat Rev Mol Cell Biol* 2016, 17 (1), 5-15.
16. Shalem, O.; Sanjana, N. E.; Zhang, F., High-throughput functional genomics using CRISPR-Cas9. *Nature reviews. Genetics* 2015, 16 (5), 299-311.
17. Ma, H.; Naseri, A.; Reyes-Gutierrez, P.; Wolfe, S. A.; Zhang, S.; Pederson, T., Multicolor CRISPR labeling of chromosomal loci in human cells. *Proceedings of the National Academy of Sciences of the United States of America* 2015, 112 (10), 3002-7.
18. Fujita, T.; Fujii, H., Efficient isolation of specific genomic regions and identification of associated proteins by engineered DNA-binding molecule-mediated chromatin immunoprecipitation (enChIP) using CRISPR. *Biochemical and biophysical research communications* 2013, 439 (1), 132-6.
19. Komor, A. C.; Kim, Y. B.; Packer, M. S.; Zuris, J. A.; Liu, D. R., Programmable editing of a target base in genomic DNA without double-stranded DNA cleavage. *Nature* 2016, 533 (7603), 420-4.
20. Gantz, V. M.; Bier, E., The dawn of active genetics. *BioEssays: news and reviews in molecular, cellular and developmental biology* 2016, 38 (1), 50-63.
21. Esvelt, K. M.; Smidler, A. L.; Catteruccia, F.; Church, G. M., Concerning RNA-guided gene drives for the alteration of wild populations. *Elife* 2014, 3.
22. Champer, J.; Buchman, A.; Akbari, O. S., Cheating evolution: engineering gene drives to manipulate the fate of wild populations. *Nature reviews. Genetics* 2016, 17 (3), 146-59.
23. Cox, D. B.; Platt, R. J.; Zhang, F., Therapeutic genome editing: prospects and challenges. *Nat Med* 2015, 21 (2), 121-31.
24. Yin, H.; Xue, W.; Chen, S.; Bogorad, R. L.; Benedetti, E.; Grompe, M.; Koteliansky, V.; Sharp, P. A.; Jacks, T.; Anderson, D. G., Genome editing with Cas9 in adult mice corrects a disease mutation and phenotype. *Nature biotechnology* 2014, 32 (6), 551-3.
25. Doudna, J. A., Genomic engineering and the future of medicine. *Jama* 2015, 313 (8), 791-2.
26. Ding, Q.; Strong, A.; Patel, K. M.; Ng, S. L.; Gosis, B. S.; Regan, S. N.; Cowan, C. A.; Rader, D. J.; Musunuru, K., Permanent alteration of PCSK9 with in vivo CRISPR-Cas9 genome editing. *Circulation research* 2014, 115 (5), 488-92.
27. Saayman, S.; Ali, S. A.; Morris, K. V.; Weinberg, M. S., The therapeutic application of CRISPR/Cas9 technologies for HIV. *Expert Opin Biol Ther* 2015, 15 (6), 819-30.
28. Nelson, C. E.; Hakim, C. H.; Ousterout, D. G.; Thakore, P. I.; Moreb, E. A.; Castellanos Rivera, R. M.; Madhavan, S.; Pan, X.; Ran, F. A.; Yan, W. X.; Asokan, A.; Zhang, F.; Duan, D.; Gersbach, C. A., In vivo genome editing improves muscle function in a mouse model of Duchenne muscular dystrophy. *Science* 2016, 351 (6271), 403-7.
29. Tabebordbar, M.; Zhu, K.; Cheng, J. K. W.; Chew, W. L.; Widrick, J. J.; Yan, W. X.; Maesner, C.; Wu, E. Y.; Xiao, R.; Ran, F. A.; Cong, L.; Zhang, F.; Vandenberghe, L. H.; Church, G. M.; Wagers, A. J., In vivo gene editing in dystrophic mouse muscle and muscle stem cells. *Science* 2016, 351 (6271), 407-411.
30. Long, C.; Amoasii, L.; Mireault, A. A.; McAnally, J. R.; Li, H.; Sanchez-Ortiz, E.; Bhattacharyya, S.; Shelton, J. M.; Bassel-Duby, R.; Olson, E. N., Postnatal genome editing partially restores dystrophin expression in a mouse model of muscular dystrophy. *Science* 2016, 351 (6271), 400-3.
31. Bakondi, B.; Lv, W.; Lu, B.; Jones, M. K.; Tsai, Y.; Kim, K. J.; Levy, R.; Akhtar, A. A.; Breunig, J. J.; Svendsen, C. N.; Wang, S., In Vivo CRISPR/Cas9 Gene Editing Corrects Retinal Dystrophy in the S334ter-3 Rat Model of Autosomal Dominant Retinitis Pigmentosa. *Molecular therapy: the journal of the American Society of Gene Therapy* 2016, 24 (3), 556-63.
32. Wu, W. H.; Tsai, Y. T.; Justus, S.; Lee, T. T.; Zhang, L.; Lin, C. S.; Bassuk, A. G.; Mahajan, V. B.; Tsang, S. H., CRISPR Repair Reveals Causative Mutation in a Preclinical Model of Retinitis Pigmentosa. *Molecular therapy: the journal of the American Society of Gene Therapy* 2016, 24 (8), 1388-94.
33. Zhong, H.; Chen, Y.; Li, Y.; Chen, R.; Mardon, G., CRISPR-engineered mosaicism rapidly reveals that loss of Kcnj13 function in mice mimics human disease phenotypes. *Scientific reports* 2015, 5, 8366.
34. Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat Biotechnol* 2013, 31 (9), 822-6.
35. Hsu, P. D.; Scott, D. A.; Weinstein, J. A.; Ran, F. A.; Konermann, S.; Agarwala, V.; Li, Y.; Fine, E. J.; Wu, X.; Shalem, O.; Cradick, T. J.; Marraffini, L. A.; Bao, G.; Zhang, F., DNA targeting specificity of RNA-guided Cas9 nucleases. *Nat Biotechnol* 2013, 31 (9), 827-32.
36. Pattanayak, V.; Lin, S.; Guilinger, J. P.; Ma, E.; Doudna, J. A.; Liu, D. R., High-throughput profiling of off-target DNA cleavage reveals RNA-programmed Cas9 nuclease specificity. *Nature biotechnology* 2013, 31 (9), 839-43.
37. Pattanayak, V.; Guilinger, J. P.; Liu, D. R., Determining the specificities of TALENs, Cas9, and other genome-editing enzymes. *Methods Enzymol* 2014, 546, 47-78.
38. Frock, R. L.; Hu, J.; Meyers, R. M.; Ho, Y. J.; Kii, E.; Alt, F. W., Genome-wide detection of DNA double-stranded breaks induced by engineered nucleases. *Nature biotechnology* 2015, 33 (2), 179-86.
39. Tsai, S. Q.; Zheng, Z.; Nguyen, N. T.; Liebers, M.; Topkar, V. V.; Thapar, V.; Wyvekens, N.; Khayter, C.; Iafrate, A. J.; Le, L. P.; Aryee, M. J.; Joung, J. K., GUIDE-seq enables genome-wide profiling of off-target cleavage by CRISPR-Cas nucleases. *Nature biotechnology* 2015, 33 (2), 187-97.
40. Davis, K. M.; Pattanayak, V.; Thompson, D. B.; Zuris, J. A.; Liu, D. R., Small molecule-triggered Cas9 protein with improved genome-editing specificity. *Nat Chem Biol* 2015, 11 (5), 316-8.
41. Nunez, J. K.; Lee, A. S.; Engelman, A.; Doudna, J. A., Integrase-mediated spacer acquisition during CRISPR-Cas adaptive immunity. *Nature* 2015, 519 (7542), 193-8.
42. Maji, B.; Moore, C. L.; Zetsche, B.; Volz, S. E.; Zhang, F.; Shoulders, M. D.; Choudhary, A., Multidimensional chemical control of CRISPR-Cas9. *Nature chemical biology* 2017, 13 (1), 9-11.
43. Senis, E.; Fatouros, C.; Grosse, S.; Wiedtke, E.; Niopek, D.; Mueller, A. K.; Borner, K.; Grimm, D., CRISPR/Cas9-mediated genome engineering: an adeno-associated viral (AAV) vector toolbox. *Biotechnol J* 2014, 9 (11), 1402-12.
44. Nunez, J. K.; Harrington, L. B.; Doudna, J. A., Chemical and Biophysical Modulation of Cas9 for Tunable Genome Engineering. *ACS Chem Biol* 2016, 11 (3), 681-8.
45. Westra, E. R.; Buckling, A.; Fineran, P. C., CRISPR-Cas systems: beyond adaptive immunity. *Nature reviews. Microbiology* 2014, 12 (5), 317-26.
46. Barrangou, R., The roles of CRISPR-Cas systems in adaptive immunity and beyond. *Current opinion in immunology* 2015, 32, 36-41.
47. Pawluk, A.; Staals, R. H.; Taylor, C.; Watson, B. N.; Saha, S.; Fineran, P. C.; Maxwell, K. L.; Davidson, A. R., Inactivation of CRISPR-Cas systems by anti-CRISPR proteins in diverse bacterial species. *Nature microbiology* 2016, 1 (8), 16085.
48. Pawluk, A.; Amrani, N.; Zhang, Y.; Garcia, B.; Hidalgo-Reyes, Y.; Lee, J.; Edraki, A.; Shah, M.; Sontheimer, E. J.; Maxwell, K. L.; Davidson, A. R., Naturally Occurring Off-Switches for CRISPR-Cas9. *Cell* 2016, 167 (7), 1829-1838.e9.
49. Shin, J.; Jiang, F.; Liu, J. J.; Bray, N. L.; Rauch, B. J.; Baik, S. H.; Nogales, E.; Bondy-Denomy, J.; Corn, J. E.; Doudna, J. A., Disabling Cas9 by an anti-CRISPR DNA mimic. *Science advances* 2017, 3 (7), e1701620.
50. Rauch, B. J.; Silvis, M. R.; Hultquist, J. F.; Waters, C. S.; McGregor, M. J.; Krogan, N. J.; Bondy-Denomy, J., Inhibition of CRISPR-Cas9 with Bacteriophage Proteins. *Cell* 2017, 168 (1-2), 150-158.e10.
51. Sternberg, S. H.; Redding, S.; Jinek, M.; Greene, E. C.; Doudna, J. A., DNA interrogation by the CRISPR RNA-guided endonuclease Cas9. *Nature* 2014, 507 (7490), 62-7.
52. Nishimasu, H.; Ran, F. A.; Hsu, P. D.; Konermann, S.; Shehata, S. I.; Dohmae, N.; Ishitani, R.; Zhang, F.; Nureki, O., Crystal structure of Cas9 in complex with guide RNA and target DNA. *Cell* 2014, 156 (5), 935-49.
53. Kleinstiver, B. P.; Prew, M. S.; Tsai, S. Q.; Topkar, V. V.; Nguyen, N. T.; Zheng, Z.; Gonzales, A. P.; Li, Z.; Peterson, R. T.; Yeh, J. R.; Aryee, M. J.; Joung, J. K., Engineered CRISPR-Cas9 nucleases with altered PAM specificities. *Nature* 2015, 523 (7561), 481-5.
54. Lundblad, J. R.; Laurance, M.; Goodman, R. H., Fluorescence polarization analysis of protein-DNA and protein-protein interactions. *Mol Endocrinol* 1996, 10 (6), 607-12.
55. Niesen, F. H.; Berglund, H.; Vedadi, M., The use of differential scanning fluorimetry to detect ligand interactions that promote protein stability. *Nature protocols* 2007, 2 (9), 2212-21.
56. Richardson, C. D.; Ray, G. J.; DeWitt, M. A.; Curie, G. L.; Corn, J. E., Enhancing homology-directed genome editing by catalytically active and inactive CRISPR-Cas9 using asymmetric donor DNA. *Nature biotechnology* 2016, 34 (3), 339-44.
57. Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat. Biotechnol.* 2013, 31 (9), 822-6.

58. Moore, R.; Spinhirne, A.; Lai, M. J.; Preisser, S.; Li, Y.; Kang, T.; Bleris, L., CRISPR-based self-cleaving mechanism for controllable gene delivery in human cells. *Nucleic Acids Res* 2015, 43 (2), 1297-303.
59. Nguyen, D. P.; Miyaoka, Y.; Gilbert, L. A.; Mayerl, S. J.; Lee, B. H.; Weissman, J. S.; Conklin, B. R.; Wells, J. A., Ligand-binding domains of nuclear receptors facilitate tight control of split CRISPR activity. *Nat Commun* 2016, 7, 12009.
60. Burke, M. D.; Schreiber, S. L., A planning strategy for diversity-oriented synthesis. *Angew Chem Int Ed Engl* 2004, 43 (1), 46-58.
61. Shortridge, M. D.; Hage, D. S.; Harbison, G. S.; Powers, R., Estimating protein-ligand binding affinity using high-throughput screening by NMR. *J Comb Chem* 2008, 10 (6), 948-58.
62. Heler, R.; Samai, P.; Modell, J. W.; Weiner, C.; Goldberg, G. W.; Bikard, D.; Marraffini, L. A., Cas9 specifies functional viral targets during CRISPR-Cas adaptation. *Nature* 2015, 519 (7542), 199-202.

Example 2—Methods

SpCas9 expression and purification. SpCas9 was expressed and purified following a previously reported protocol. See, Pattanayak et al., "High-throughput profiling of off-target DNA cleavage reveals RNA-programmed Cas9 nuclease specificity," *Nature biotechnology* 2013, 31 (9), 839-43.

BL21 Star (DE3)-competent *E. coli* cells were transformed with plasmids encoding the bacterial codon-optimized SpCas9 with a His$_6$ N-terminal purification tag. A single colony was grown overnight in TB containing 25 μg ml$^{-1}$ kanamycin at 37° C. The cells were diluted 1:1000 into 1 L of the same media and grown at 37° C. until OD$_{600}$=0.60-0.7. The cultures were cooled down to 18° C. for 30 min and protein expression was induced with 1 mM isopropyl-β-D-1-thiogalactopyranoside (GoldBio). Expression was sustained for 16-18 h with shaking at 18° C. The subsequent purification steps were carried out at 4° C. Cells were collected by centrifugation and resuspended in cell collection buffer (100 mM tris(hydroxymethyl)-aminomethane (Tris)-HCl, pH 8.0, 1 M KCl, 20% glycerol, 5 mM tris(2-carboxyethyl)phosphine (TCEP; GoldBio), 1 mM phenylmethane sulfonyl fluoride (Sigma-Aldrich) and 1 mg/mL Lysozyme. Cells were lysed by sonication (10 min total, 30 s on, 30 s off) and the lysate cleared by centrifugation at 15,000 g (1 h).

The cleared lysate was incubated with HisPur nickel-nitriloacetic acid (nickel-NTA) resin with rotation at 4° C. for 2 h. The resin was washed with 2 ×15 column volumes of cell collection buffer before bound protein was eluted with elution buffer (100 mM tris(hydroxymethyl)-aminomethane (Tris)-HCl, pH 8.0, 100 mM KCl, 20% glycerol, 5 mM TCEP (GoldBio), 250 mM imidazole). The resulting protein fraction was further treated with TEV protease at 4° C. for 24 h in 20 mM (Tris)-HCl, pH 8.0, 100 mM KCl, 20% glycerol, 5 mM TCEP and then purified on a 5 mL Hi-Trap HP SP (GE Healthcare) cation exchange column with KCl gradient from 0.1 M to 1 M using an Akta Pure FPLC. Protein-containing fractions were concentrated using a column with a 100 kDa cutoff (Millipore) centrifuged at 3,000 g. The Hi-Trap purified followed by running through a HiLoad Superdex 200 column using 20 mM (Tris)-HCl, pH 8.0, 100 mM KCl, 20% glycerol, 5 mM TCEP buffer. The purified protein was validated by running a denaturing gel and snap-frozen in liquid nitrogen and stored at −80° C.

In vitro transcription of sgRNA. Linear DNA fragments containing the T7 RNA polymerase promoter sequence upstream of the desired 20 bp sgRNA protospacer and the sgRNA backbone were generated by PCR (Q5 Hot Start MasterMix, New England Biolabs) using primers forward: AAAAGCACCGACTCGGTGCCACTTTTTCAAGTTGATAACGGACTAGCCTTATTTTAACTTGCTATTTCTAGCTCTAAAAC-3' (SEQ ID NO:34) and reverse: 5'-TAATACGACTCACTATAGCTATAGGACGCGACCGAAAGTTTTAGAGCTAGAAAT-3' (SEQ ID NO:35). sgRNA was transcribed with the HiScribe T7 High Yield RNA Synthesis Kit (New England Biolabs) at 37° C. for 16 h with 150 ng of linear template per 20 l reaction. sgRNA was purified using the MEGAClear Transcription Clean Up Kit (Thermo Fisher), according to the manufacturer's instructions. Purified sgRNAs were stored in aliquots at −80° C.

FP Assay. In one aspect, the invention provides an assay that monitors the change in the fluorescence polarization of the fluorophore-labelled PAM-rich target DNA (henceforth called 12PAM-DNA) upon binding to [Cas9:guideRNA] complex. Fluorescence Polarization assay was performed in a 384-well plate (Corning 3575) format using a total reaction volume of 30 μL. A 25 nM FITC-labeled 12PAM DNA was titrated against increasing concentration of Cas9:gRNA (1:1.2) complex in a 20 mM Tris-HCl buffer of pH 7.5 containing 150 mM KCl, 5 mM MgCl$_2$, 1 mM DTT. The fluorescence polarization signal was measured using a microplate reader (PerkinElmer, EnVision). The experiments were performed in triplicates and the data were processed in GraphPad Prism 7. The Z'-value was calculated following the formula:

$$Z' = \frac{3(\sigma 1 + \sigma 2)}{|\mu 1 - \mu 2|}$$

Where σ1 and σ2 are the standard deviations of DMSO control and Cas9:gRNA control respectively. μ1 and μ2 are the mean FP-signal intensities for DMSO control and Cas9:gRNA control respectively.

Competition Assay. In a 384-well plate (Corning 3575), 25 nM FITC-labeled 12PAM DNA was incubated with 50 nM SpCas9:gRNA (1:1.2) complex in the presence and absence of unlabeled DNA in excess (10× and 50×) in a 20 mM Tris-HCl buffer of pH 7.5 containing 150 mM KCl, 5 mM MgCl$_2$, 1 mM DTT. The fluorescence polarization signal was measured using a microplate reader (PerkinElmer, EnVision). The number of PAM sequence in the unlabeled competitor DNA was varied from 0, 4, 8, and 12 PAMs. The experiments were performed in triplicates and the data were processed in GraphPad Prism 7.

Differential Scanning Fluorimetry (DSF). Protein melting experiments were performed in a 384-well format using a 6 μL reaction volume in a LightCycler 480 instrument. A 3.7 μM SpCas9:gRNA (1:1.2) was incubated with equimolar concentration of DNA with different PAM density (0, 4, 8, and 12) for 15 min in a 20 mM Tris-HCl buffer of pH 7.5 containing 150 mM KCl, 5 mM MgCl$_2$, 1 mM DTT. Then, 2 μL of 50× SYPRO® Orange was added before running the melting cycle with a temperature gradient of 4.8° C./min. The experiments were performed in triplicates and data were processed in Roche LightCycler® 480 Protein Melting software.

Bio-Layer Interferometry (BLI). DNA-Cas9 interactions were also probed using BLI experiments in an Octet Red384

(Pall ForteBio) instrument. The experiments were performed in a 96-well format with 180 µL reaction volume using biotinylated ds-DNA and streptavidin sensors. A 300 nM of biotinylated DNA with different PAM density (0, 2, 4, and 8) were loaded onto the sensors for 180 s in 20 mM Tris buffer of pH 7.4, 100 mM KCl, 5 mM $MgCl_2$, 1 mM DTT, 0.01% Tween®, 50 µg/mL Heparin. Excess DNA was washed off for 60 s in reaction buffer followed by association with 200 nM of Cas9-gRNA (1:1.2) for 300 s. The complex was then allowed to dissociate for 3600 s in the reaction buffer. All the response curves were normalized against the reference sensor without Cas9:gRNA.

Compound Screening. The compound library screening was performed in two steps. Initially, the DOS informer set of library (10,000 compounds) was screened in the FP-based assay to identify the enriched hit libraries. Then, the specific enriched libraries were also screened using the same assay. The screening assay was performed in a 384-well plate format with a total reaction volume of 30 µL. Initially, a 25 µL of 60 nM of SpCas9 was transferred to the compound testing lanes of the 384-well plate except for the positive control wells. However, a 25 µL of solution containing 60 nM SpCas9 and 300 nM unlabeled 12PAM ds-DNA was transferred to the positive control wells. In the next step, 25 nL of DMSO alone or 10 mM compounds in DMSO were transferred to the reaction mixture and incubated for 30 min at room temperature. Next, a 5 µL solution containing 360 nM gRNA and 150 nM FAM-labeled 12PAM ds-DNA was added and incubated for 15 min at room temperature before acquiring the fluorescence polarization signal under a microplate reader (PerkinElmer, EnVision). Compounds were screened in duplicates and the data were processed to calculate the Z-score (a) values and plotted in Spotfire analysis software (TIBCO). The hit compounds (Z-score >3a) were then clustered according to the class of compound and a hit-rate plot was generated. The entire specific libraries of the enriched ones were then screened in the same FP-assay.

Counter-screening. Counter-screening assay was performed in a similar format as followed in the compound-screening assay. In a 384-well plate, a 30 µL of 25 nM FAM-labeled 12PAM ds-DNA was transferred to each well. Next, 25 nL of either DMSO or compound in DMSO were transferred and incubated for 15 min before the fluorescence polarization signal was acquired in a microplate reader (PerkinElmer, EnVision). The change in the FP signal was calculated in percentile and plotted against compounds' average Z-score values obtained from the original compound-screening assay. Compound that resulted in a >3a change in the Z-score but did not alter the FP-signal by >10% in the counter-screen assay were selected as the potential hits. A molecular structure based similarity search was also performed and compounds with >0.8 similarity index was included in the hit list.

Compound-Cas9 interaction in BLL The experiments were performed in a 96-well format with 180 µL reaction volume using biotinylated compound BRD7087-Biotin and streptavidin sensors. 1 µM of the biotinylated compound was loaded onto the sensors for 180 s in 20 mM Tris buffer of pH 7.4, 100 mM KCl, 5 mM $MgCl_2$, 1 mM DTT, 0.01% Tween®. The compound loaded sensors were then allowed to associate with the different concentration of SpCas9: gRNA complex (1-0.15 µM) for 300 s followed by dissociation in the reaction buffer. Reference sensor was loaded with compound and allowed to associate and dissociate in the reaction buffer alone. The response curves were fitted with a 2:1 stoichiometric model and a global fit steady-state analysis were performed using manufacturer inbuilt protocol. The experiment was performed in three replicates.

The competitive experiments were performed using Biotin-linker fragment. In this experiment, streptavidin sensors were pre-incubated with 10 µM of Biotin-linker before dipping into a solution of either 1 µM BRD7087-Biotin or reaction buffer alone. Sensors were then allowed to associate with different concentration of SpCas9:gRNA complex or buffer alone.

NMR binding assay. All samples were prepared with 50 µM BRD7087 in 20 mM Tris buffer (pH=7.4) with varying concentrations of SpCas9:gRNA in a 3 mm NMR tube. Experiments were performed on a 600 MHz ($^{19}$F: 564.71 MHz) Bruker Avance III NMR spectrometer equipped with a 5 mm QCI-F CryoProbe and a SampleJet for automated sample handling. To acquire spectra, a standard one-pulse $^{19}$F experiment with WALTZ-16 for proton decoupling during acquisition, a 5 second recycle delay, and 256 scans was used. All spectra were recorded at 280 K. NMR data were apodized with a 1 Hz exponential function prior to Fourier transformation. All spectra were baseline corrected; peak widths and intensities were extracted using the automated line-fitting feature provided with the MNova software package. Determination of the value of $K_d$ was accomplished using least squares fitting to the expression given in Equation 8 in the paper by Shortridge et al.[2].

$K_d$ values obtained by NMR rely on the assumption that ligand binding is in fast-exchange, which typically holds true for ligands with $K_d$ in the 0.5 µM to 20 mM range. Additional sources of error could be variations in the concentrations of the protein and ligand, an incomplete curve that does not reach complete occupancy, or incomplete relaxation leading to underestimation of the fractional occupancy.

Cell culture. All cells were cultured at 37° C. in a humidified 5% $CO_2$ atmosphere. HEK293T cells (Life Technologies) used in transcriptional activation, NHEJ, and mCherry expression assays were cultured in Dulbecco's modified Eagle's medium (CellGro) supplemented with 10% fetal bovine serum (CellGro) and 1× penicillin/streptomycin/glutamax (CellGro). U2OS.eGFP-PEST cells stably integrated with an eGFP-PEST fusion gene were maintained in Dulbecco's modified Eagle's medium (Life Technologies) supplemented with 10% FBS, 1×penicillin/streptomycin/glutamax (Life Technologies) and 400 µg/mL of the selection antibiotic G418. Cells were continuously maintained at <90% confluency. All cell lines were sourced commercially or were functionally validated. Cells were periodically tested for *Mycoplasma* contamination using the MycoAlert PLUS *Mycoplasma* Detection Kit (Lonza).

Cas9 Nuclease activity in EGFP disruption assay. In some embodiments, a quantitative human cell-based reporter assay that enables rapid quantitation of targeted nuclease activities is used to characterize off-target cleavage of CRISPR protein-based RNA guided endonucleases. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end-joining (NHEJ) repair of nuclease-induced double-stranded breaks (DSBs).

Approximately 200,000 U2OS.eGFP-PEST cells were nucleofected with 400 ng of SpCas9 (Addgene Plasmid #43861) and 40 ng of sgRNA (pFYF1320 EGFP Site #1, Addgene Plasmid #47511) expressing plasmids along with a Td-tomato-encoding plasmid using the SE Cell Line 4D-Nucleofector™ X Kit (Lonza) according to the manufacturer's protocol. Approximately 20,000 transfected cells/well in 3 replicates were plated in a 96-well plate (Corning® 3904). Cells were allowed to grow in the indicated amount of compound or DMSO for 24 h post transfection. Cells were then fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 10× magnification under three excitation channels (blue, green and red) with 9 acquiring sites per well. Images were analyzed in the MetaXpress software and data were plotted using GraphPad Prism 6. The Z'-value was calculated following the formula:

$$Z' = \frac{3(\sigma 1 + \sigma 2)}{|\mu 1 - \mu 2|}$$

Where σ1 and σ2 are the standard deviations of DMSO control and Cas9:gRNA control respectively. μ1 and μ2 are the mean % GFP⁻ cell population for DMSO control and Cas9:gRNA control respectively.

Western Blot Analysis

U2OS.eGFP.PEST cells stably expressing EGFP were incubated either in the absence or presence of compound BRD7087 and BRD5779 for 24 h at 37° C. prior to harvesting the cells. Cell suspensions were spun down at 1000×g for 5 min and processed for cell lysis. Cells were resuspended in RIPA total cell lysis buffer (abcam) and incubated at 4° C. for 10 min. The cell suspensions were then vortexed for 10 min at 4° C. followed by spinning down at 16,000×g for 15 min at 4° C. The supernatant was transferred to a fresh tube and processed for western-blotting.

Western blotting was performed following SDS-PAGE gel electrophoresis. In a typical experimental protocol, 40 μg of normalized proteins were electrophoresed on a 4-12% Bis/Tris gel. The protein bands were transferred to a PVDF membrane and probed with primary α-HSF1(c) (Abcam #ab52757) and/or α-CRISPR/Cas9 antibody (Abcam #ab191468). α-Actin antibody (Sigma) was used as a protein loading control.

NHEJ assay. Approximately 8,000 cells/well were plated in a 96-well format 24 h before transiently transfected with a total 100 ng of DN66 (mCherry-TAG-GFP reporter) and DN78 (SpCas9 and gRNA) plasmids (1:1) using lipofectamine 2000 (Life Technologies) 3. Transfected cells were allowed to grow in the indicated amount of compound or DMSO for 24 h. Cells were then fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 20× magnification under three excitation channels (blue, green and red) with 9 acquiring sites per well. Images were analyzed in the MetaXpress software to determine the % NHEJ and the data were plotted using GraphPad Prism 6. The Z'-value was calculated following the formula:

$$Z' = \frac{3(\sigma 1 + \sigma 2)}{|\mu 1 - \mu 2|}$$

Where σ1 and σ2 are the standard deviations of DN66 transfected wells and (DN66+DN78) transfected wells respectively. μ1 and μ2 are the mean % GFP⁻ cell population for DN66 transfected wells and (DN66+DN78) transfected wells respectively.

mKate2 expression assay. Approximately 8,000 cells/well were plated in a 96-well format 24 h before transiently transfected with 100 ng of either CgRNA (Addgene Plasmid #64955) or T1gRNA (Addgene Plasmid #62717) plasmids using lipofectamine 2000 (Life Technologies). Transfected cells were allowed to grow in the indicated amount of compound or DMSO for 24 h. Cells were then fixed using 4% paraformaldehyde and imaged with the HCS NuclearMask™ Blue Stain (Life Technologies) as the nuclear counter-staining agent. Imaging was performed with an IXM 137204 ImageXpress Automated High Content Microscope (Molecular Devices) at 20× magnification under two excitation channels (blue and red) with 9 acquiring sites per well. Images were analyzed in the MetaXpress software to determine the % mKate2 positive cells and the % NHEJ was calculated following a reported protocol and plotted using GraphPad Prism 6. The Z'-value was calculated following the formula:

$$Z' = \frac{3(\sigma 1 + \sigma 2)}{|\mu 1 - \mu 2|}$$

Where σ1 and σ2 are the standard deviations of cgRNA transfected wells and T1-gRNA transfected wells respectively. μ1 and μ2 are the mean % RFP⁺ cell population for CgRNA transfected wells and T1gRNA transfected wells respectively.

Transcription activation experiments and quantitative RT-PCR analyses.

For transcription activation experiments 250,000 cells/well were plated in a 12 well plate. The cells were transiently transfected with a 1:1:1 mass ratio of the dCas9 plasmid, MS2-P65-HSF1 effector plasmid and the sgRNA plasmid targeting the HBG1 gene or an RFP control plasmid. A total of 1.6 μg plasmid DNA was transfected using Lipofectamine 2000 (Life Technologies) according to manufacturer's protocol. Immediately after transfection, the cells were treated with an appropriate dose of the small molecule inhibitors for 48 hours following which the cells were harvested and RNA was extracted using the EZNA Total RNA kit I (Omega) as per manufacturer's instructions. 1 μg total cellular RNA was used to perform reverse transcription using the High-Capacity cDNA Reverse Transcription Kit (Applied Biosystems) or the qScript cDNA Synthesis Kit (QuantaBio). qPCR reactions were performed to quantify RNA expression using the TaqMan probes (Life Technologies, HBG1/HBG2: Hs00361131_g1 and ACTB: Hs01060665_g1) and TaqMan Fast Advanced Master Mix (Life Technologies) in 5 μL multiplexed reactions and 384-well format using the LightCycler 480 Instrument II (Roche). For each sample, six technical replicates were performed. Data were analyzed using the LightCycler 480 software (Roche) by the ΔΔCt method: Ct values for the gene of interest (HBG1) were normalized to Ct values for the housekeeping gene (ACTB) and fold-changes in the expression level of the gene of interest were normalized to RFP-transfected control. The data are reported as mean±S.E.M. for technical replicates.

Base-Editing Experiment.

BE3 expression and purification. BE3 was expressed and purified as previously reported[4].

BL21 Star (DE3)-competent *E. coli* cells were transformed with plasmids encoding the bacterial codon-optimized base editor with a $His_6$ N-terminal purification tag. A single colony was grown overnight in 2×YT broth containing 50 µg ml$^{-1}$ kanamycin at 37° C. The cells were diluted 1:400 into 4 L of the same media and grown at 37° C. until $OD_{600}$=0.70-0.75. The cultures were incubated on ice for 3 h and protein expression was induced with 1 mM isopropyl-β-D-1-thiogalactopyranoside (GoldBio). Expression was sustained for 16-18 h with shaking at 18° C. The subsequent purification steps were carried out at 4° C. Cells were collected by centrifugation and resuspended in cell collection buffer (100 mM tris(hydroxymethyl)-aminomethane (Tris)-HCl, pH 8.0, 1 M NaCl, 20% glycerol, 5 mM tris(2-carboxyethyl)phosphine (TCEP; GoldBio), 0.4 mM phenylmethane sulfonyl fluoride (Sigma-Aldrich) and 1 EDTA-free protease inhibitor pellet (Roche)). Cells were lysed by sonication (6 min total, 3 s on, 3 s off) and the lysate cleared by centrifugation at 25,000 g (20 min).

The cleared lysate was incubated with HisPur nickel-nitriloacetic acid (nickel-NTA) resin with rotation at 4° C. for 90 min. The resin was washed with 2 ×15 column volumes of cell collection buffer before bound protein was eluted with elution buffer (100 mM tris(hydroxymethyl)-aminomethane (Tris)-HCl, pH 8.0, 0.5 M NaCl, 20% glycerol, 5 mM TCEP (GoldBio), 200 mM imidazole). The resulting protein fraction was further purified on a 5 ml Hi-Trap HP SP (GE Healthcare) cation exchange column using an Akta Pure FPLC. Protein-containing fractions were concentrated using a column with a 100 kDa cutoff (Millipore) centrifuged at 3,000 g, and the concentrated solution was sterile-filtered through a 22-µm polyvinylidene difluoride membrane (Millipore).

After sterile filtration, proteins were quantified with Reducing Agent Compatible Bicinchoninic acid assay (Pierce Biotechnology), snap-frozen in liquid nitrogen and stored in aliquots at −80° C.

In vitro transcription of sgRNA. Linear DNA fragments containing the T7 RNA polymerase promoter sequence upstream of the desired 20 bp sgRNA protospacer and the sgRNA backbone were generated by PCR (Q5 Hot Start MasterMix, New England Biolabs) using primers forward: 5'-TAATACGACTCACTATAGG-GAGTCCGAGCAGAAGAAGAAGTTT-TAGAGCTAGAAATAGCA-3' (SEQ ID NO:36) and reverse: 5'-AAAAAAAGCACCGACTCGGTGCCAC-3' (SEQ ID NO:37) and concentrated on minelute columns (Qiagen). sgRNA was transcribed with the HiScribe T7 High Yield RNA Synthesis Kit (New England Biolabs) at 37° C. for 14-16 h with 400 ng of linear template per 20 µl reaction. sgRNA was purified using the MEGAClear Transcription Clean Up Kit (Thermo Fisher), according to the manufacturer's instructions. Purified sgRNAs were stored in aliquots at −80° C.

Protein transfection of base editor BE3 into HEK293T cells. HEK293T cells were seeded on 48-well BioCoat poly-D-lysine plates (Corning) in 250 µL of antibiotic-free medium and transfected at ~70% confluency. Prior to protein transfection, cells were incubated with 2 µL of DMSO-suspended BRD7087 or BRD5779 at the indicated concentration for 2-3 hours. BE3 protein was incubated with 1.1× molar excess of EMX1-targeting sgRNA at a final concentration ratio of 200 nM:220 nM (based on a total well volume of 275 µL). The complex was mixed with 0.2 µL of compound for five minutes, incubated with 1.5 µL Lipofectamine 2000 (Thermo Fisher) and transfected according to the manufacturer's protocol plasmid delivery. The cells and ribonucleoprotein complex were incubated with compounds at final concentrations of 1.25 µM, 2.5 µM, 5 µM, 10 µM or 20 µM.

Purifications and sequencing of genomic DNA. Transfected cells were harvested after 72 h in 50 µL of lysis buffer (10 mM Tris-HCl pH 8.0, 0.05% SDS, 25 µg/mL proteinase K) and incubated at 37° C. for 1 h. Cell lysates were heated at 85° C. for 15 min to denature proteinase K. For the first PCR, genomic DNA was amplified to the top of the linear range using Phusion Hot Start II DNA polymerase (New England Biolabs) according to the manufacturer's instructions. For all amplicons, the PCR protocol used was an initial heating step for 1 min at 98° C. followed by an optimized number of amplification cycles (10 s at 98° C., 20 s at 68° C., 15 s at 72° C.). qPCR was performed to determine the optimum number of cycles for each amplicon. Amplified DNA was purified using RapidTip2 (Diffinity Genomics) and barcoded with a further PCR. Sequencing adapters and dual-barcoding sequences are based on the TruSeq Indexing Adapters (Illumina). Barcoded samples were pooled and purified by gel extraction (Qiagen) before quantification using the Qubit dsDNA HS Kit (Thermo Fisher) and qPCR (KAPA BioSystems) according to the manufacturer's instructions. Sequencing of pooled samples was performed using a single-end read from 260 to 300 bases on the MiSeq (Illumina) according to the manufacturer's instructions.

Analysis of base-edited sequences. Nucleotide frequencies were analyzed using a previously described MATLAB script 5. Briefly, the reads were aligned to the reference sequence via the Smith-Waterman algorithm. Base calls with Q-scores below 30 were replaced with a placeholder nucleotide (N). This quality threshold results in nucleotide frequencies with an expected theoretical error rate of 1 in 1,000.

To distinguish small molecule-induced inhibition of C+T editing from artefactual C +T editing, Applicants compared the sequencing reads from cells treated with base-editor in the presence of small molecule to the sequencing reads from base-edited cells not exposed to small molecule. A Student's two-tailed t-test was used to determine if inhibition of C+T editing by small-molecule is statistically significant with $P<0.05$ as the threshold.

Figure 78:
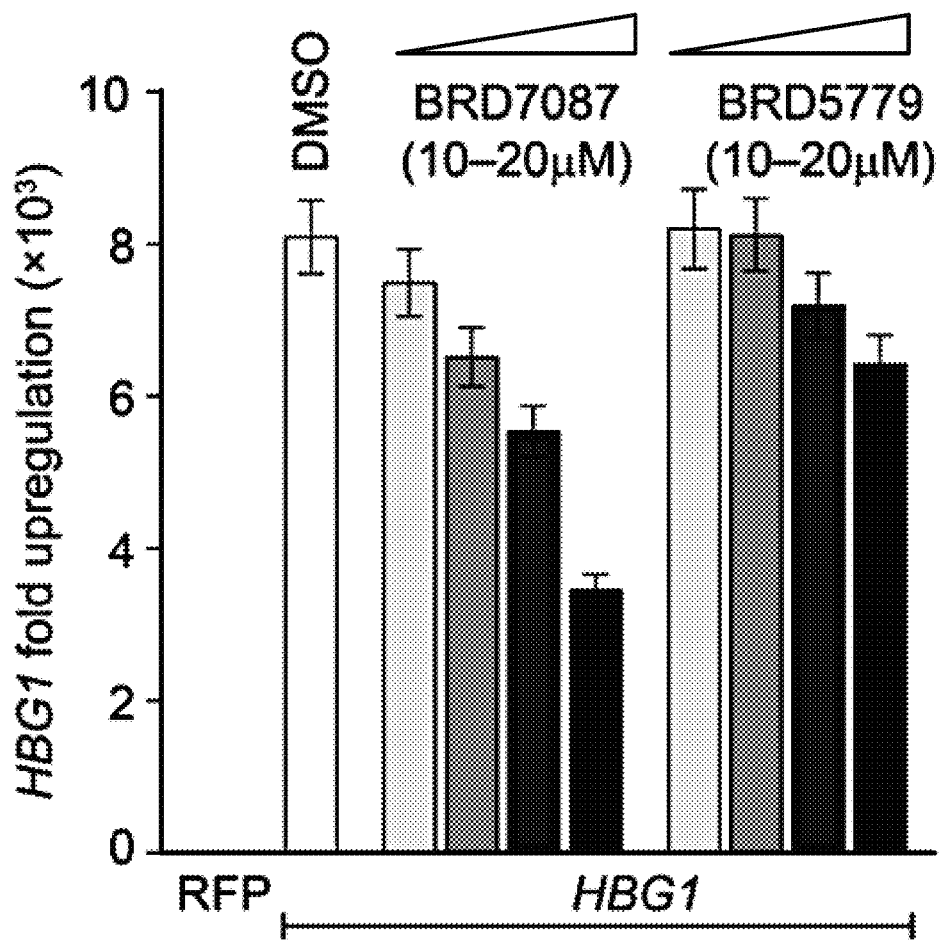
FIG. 78. Dose-dependent inhibition of base-editing activity by compounds. Dose-dependent inhibition of dCas9-based transcriptional activation of HBG1 gene in HEK293FT cells. Cells were transfected with dCas9, MS2.p65.HSF1.GFP plasmids along with either RFP or HBG1 plasmid and incubated in the presence of the compounds at the indicated concentration before processing for RT-qPCR. The experiments were performed in three biological replicates and each biological replicates were processed in six technical replicates. The data are reported as mean±S.E.M. for technical replicates.

Bacterial study. Plasmid pRH248 harboring SpCas9, tracrRNA and a single-spacer array (CGTGTAAAGACAT-ATTAGATCGAGTCAAGG) (SEQ ID NO:38) targeting phage DNM474 was constructed via BsaI cloning onto pDB114 as described in Heler et al[6]. Plate reader growth curves of bacteria infected with phage were conducted as described previously with minor modifications[7]. Overnight cultures were diluted 1:100 into 2 ml of fresh BHI supplemented with appropriate antibiotics and 5 mM $CaCl_2$) and grown to an $OD_{600}$ of ~0.2. Immune cells carrying pRH248 were diluted with cells lacking CRISPR-Cas in a 1:10,000 ratio. Following a 15-minute pre-incubation with DMSO or with varying amounts of inhibitors (5-20 µM), the cultures were infected with DNM474 at an initial MOI of 1. To produce plate reader growth curves, 200 µL of infected cultures, normalized for OD600, were transferred to a 96-well plate in triplicate. $OD_{600}$ measurements were collected every 10 minutes for 16 hours. Similarly, growth curves to evaluate the toxicity of the compounds at 20 µM (FIG. 78) were conducted on cultures lacking CRISPR in the absence of phage.

Example 3

Synthesis and Characterization Data of Compounds

General Procedure A: Microwave-Assisted Suzuki Coupling to Give Hexahydropyrroloquinoline Substrates 13a-h The microwave reactions were performed in a Biotage single-mode microwave reactor with a power of 0 to 400 W. A 10-20 mL Biotage microwave reaction vial was charged with the hexahydropyrroloquinoline substrate 12 (1.0 equiv., >90% ee), 3-fluorophenylboronic acid or 4-methoxyphenylboronic acid (1.2 equiv.), potassium carbonate (2.0 equiv.), XPhos Palladium third generation catalyst (5% mol), and a mixture solvent of THF-$H_2O$ (v/v, 2/1). The vial was sealed with a septum cap, degassed under high vacuum, and backfilled with an argon atmosphere. The degassing step was repeated three times, and the resulting reaction mixture was microwave irradiated for 45 min at 100° C. The reaction mixture was then cooled to room temperature and filtered through a short pad of Celite. The filtrate was evaporated under vacuum to give crude substrate, usually as off-yellow oily substance, which was purified by flash column chromatography on silica gel eluting with hexane and ethyl acetate (or dichloromethane and methanol).

Note: The four isomers of benzyl 8-bromo-4-(hydroxymethyl)-2,3,3a,4,5,9b-hexahydro-1H-pyrrolo[3,2-c]quinoline-1-carboxylate 12a-d were synthesized as described by Jacobsen et al. and Marcaurelle et al. using the chiral urea catalyst 9a or 9b (H. Xu, H. Zhang, E. N. Jacobsen, *Nat. Protoc.* 2014, 9, 1860-1866; B. Gerald, M. W. O'Shea, E. Donckele, S. Kesavan, L. B. Akella, H. Xu, E. N. Jacobsen, L. S. Marcaurelle, *ACS Comb. Sci.* 2012, 14, 621-630). Urea catalysts 9a and 9b were synthesized as described by Jacobsen et al. The obtained NMR spectral data were consistent with those reported in the literature (K. L. Tan, E. N. Jacobsen, *Angew. Chem. Int. Ed.* 2007, 46, 1315-1317.).

General Procedure B: Reductive Amination to Give Pyridinylmethylhexahydropyrroloquinolines 1 to 8

A round-bottom flash was charged with hexahydropyrroloquinoline substrate 13 (1.0 equiv.), palladium on carbon (10% weight), and methanol (0.05 M). The flask was sealed with a rubber septum, degassed under high vacuum, and backfilled with a hydrogen atmosphere. The degassing and hydrogen refilling step was repeated three times, and the resulting reaction mixture was stirred at room temperature for one hour or until the full conversion of the starting material monitored by TLC (methanol in $CH_2C2$). The reaction mixture was filtered through a Celite pad and the filtrate was evaporated under vacuum to give the corresponding Cbz-deprotected hexahydropyrroloquinoline substrate.

A flame-dried round-bottom flash was charged with the Cbz-deprotected hexahydropyrroloquinoline substrate (1.0 equiv.) dissolved in dry $CH_2Cl_2$ (0.05 M), 4-pyridinecarboxaldehyde (1.5 equiv.), and acetic acid (2.0 equiv.). The reaction mixture was stirred at room temperature for one hour before the adding of $NaBH(OAc)_3$ (3.0 equiv.). The reaction mixture was stirred at room temperature for another three hours or until the full conversion of the starting material monitored by TLC (methanol in $CH_2C2$). The reaction mixture was then diluted with $CH_2C2$, quenched with a saturated $NaHCO_3$ aqueous solution, and extracted with $CH_2CL_2$ (three times). Organic layers were combined, washed with brine, dried over anhydrous $Na_2SO_4$, filtered, and concentrated in vacuo to give a crude residue, usually as off-white or light yellow oily substance, which was purified by flash column chromatography on silica gel eluting with hexane and ethyl acetate (or dichloromethane and methanol).

((3aR,4S,9bR)-8-(3-Fluorophenyl)-1-(pyridin-4-ylmethyl)-2,3,3a,4,5,9b-hexahydro-1H-pyrrolo[3,2-c]quinolin-4-yl)methanol (1/BRD7087)

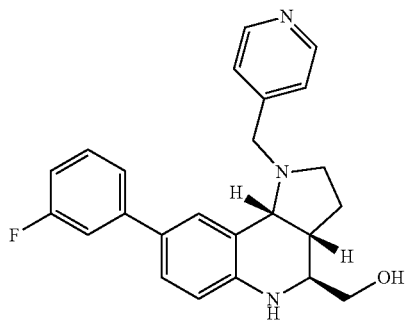 [SMILES: OC[C@H]1Nc2ccc(-c3cccc(F)c3)cc2[C@H]2[C@@H]1CCN2Cc1ccncc1]

Prepared from benzyl (3aR,4S,9bR)-8-(3-fluorophenyl)-4-(hydroxymethyl)-2,3,3a,4,5,9b-hexahydro-1H-pyrrolo[3,2-c]quinoline-1-carboxylate 13a (667 mg, 1.54 mmol) according to General Procedure B. Purification by flash column chromatography eluting with 5% methanol in dichloromethane gave the desired product 3 as a white solid (348 mg, yield 58%).

$R_f$=0.38 (silica gel, 10% methanol in dichloromethane, UV).

$^1$H NMR (400 MHz, $CDCl_3$): δ 8.45 (d, 2H, J=4.8 Hz, aromatic H), 7.35 (d, 2H, J=8.2 Hz, aromatic H), 7.28-7.25 (m, 4H, aromatic H), 7.21 (d, 1H, J=10.5 Hz, aromatic H), 6.97 (t, 1H, J=8.6 Hz, aromatic H), 6.73 (d, 1H, J=8.4 Hz, aromatic H), 4.38 (d, 1H, J=13.8 Hz, $CH_2OH$), 4.01 (d, 1H, J=8.6 Hz, $CH_2NCH$), 3.56-3.53 (m, 2H, NHCHCH and $CH_2NCH$), 3.33 (s, 1H, $CH_2NCH$), 3.27 (d, 1H, J=13.8 Hz, $CH_2OH$), 2.97-2.93 (m, 1H, $NCH_2CH_2$), 2.21-2.19 (m, 1H, $NCH_2CH_2$), 2.10-2.03 (m, 2H, $NCH_2CH_2$ and NHCHCH), 1.65-1.62 (m, 1H, $NCH_2CH_2$).

$^{13}$C NMR (100 MHz, $CDCl_3$): δ 164.5 and 162.1 (d, $^1J_{C, F}$=243.4 Hz, aromatic C), 150.0 (aromatic C), 149.1 (2) (pyridinyl C), 144.7 (pyridinyl C), 143.6 and 143.5 (d, $^3J_{C, F}$=7.8 Hz, aromatic C), 130.3 (aromatic C), 130.1 and 130.0 (d, $^3J_{C,F}$=8.8 Hz, aromatic C), 127.8 (aromatic C), 127.6 (aromatic C), 123.6 (2) (pyridinyl C), 121.7 and 121.7 (d, $^4J_{C, F}$=2.8 Hz, aromatic C), 118.3 (aromatic C), 114.6 (aromatic C), 113.0 and 112.8 (d, $^2J_{C, F}$=21.8 Hz, aromatic C), 112.8 and 112.6 (d, $^2J_{C, F}$=21.0 Hz, aromatic C), 64.7 ($CH_2NCH$), 64.1 ($CH_2NCH$), 56.0 ($CH_2OH$), 54.5 (NHCHCH), 51.4 ($NCH_2CH_2$), 35.8 (NHCHCH), 25.7 ($NCH_2CH_2$).

$^{19}$F NMR (376 MHz, $CDCl_3$): δ−113.5.

$[α]_D^{22}$=+34.4° (c=0.4, $CHCl_3$).

Chiral SFC (AS-H, 1.5 mL/min, MeOH with 0.05% $Et_3N$ in $CO_2$, λ=210 nm): $t_R$(minor)=6.4 min, $t_R$(major)=7.0 min.

IR (thin film, cm$^{-1}$): $v_{max}$ 3413, 2925, 1608, 1522, 1484, 1325, 1261, 1198, 1159, 1077, 869, 819, 782, 752, 693.

LCMS (UV Chromatogram, 210 nm, 2.5 min run): Purity >95% by UV, rt=0.92 min, m/z 390.1 (M+H)$^+$, m/z 434.5 (M+FA−H)$^-$.

HRMS (ESI, m/z): calcd for $C_{24}H_{24}FN_3O$ (M+H)$^+$: 390.1982, found: 390.1976.

((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (2/BRD5779)

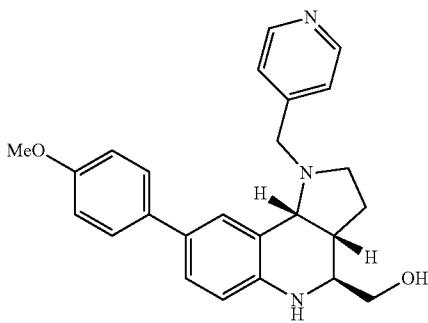 [SMILES: COc1ccc(-c2ccc3c(c2)[C@H]2[C@H](CCN2Cc2ccncc2)[C@@H](CO)N3)cc1]

Prepared from benzyl (3aR,4S,9bR)-4-(hydroxymethyl)-8-(4-methoxyphenyl)-2, 3, 3a, 4, 5, 9b-hexahydro-1H-pyrrolo[3,2-c]quinoline-1-carboxylate 13b (186 mg, 0.42 mmol) according to General Procedure B. Purification by flash column chromatography eluting with 70% ethyl acetate in hexane gave the desired product 2 as an off-white solid (72 mg, yield 43%).

$R_f$=0.69 (silica gel, 10% methanol in dichloromethane, UV).

$^1$H NMR (400 MHz, CDCl$_3$): δ 8.46 (d, 2H, J=4.9 Hz, aromatic H), 7.44 (d, 2H, J=8.2 Hz, aromatic H), 7.33 (d, 1H, J=8.2 Hz, aromatic H), 7.25-7.24 (m, 3H, aromatic H), 6.97 (d, 2H, J=8.2 Hz, aromatic H), 6.74 (d, 1H, J=8.2 Hz, aromatic H), 4.41 (d, 1H, J=13.8 Hz, CH$_2$OH), 3.99 (d, 1H, J=9.6 Hz, CH$_2$NCH), 3.85 (s, 3H, OCH$_3$), 3.59 (d, 1H, J=9.6 Hz, CH$_2$NCH), 3.53-3.51 (m, 1H, NHCHCH), 3.32 (s, 1H, CH$_2$NCH), 3.25 (d, 1H, J=13.8 Hz, CH$_2$OH), 2.97 (t, 1H, J=9.2 Hz, NCH$_2$CH$_2$), 2.20-2.18 (m, 1H, NCH$_2$CH$_2$), 2.10-2.05 (m, 2H, NCH$_2$CH$_2$ and NHCHCH), 1.66-1.62 (m, 1H, NCH$_2$CH$_2$).

$^{13}$C NMR (100 MHz, CDCl$_3$): δ 158.3 (aromatic C), 149.9 (aromatic C), 149.2 (2) (aromatic C), 143.7 (aromatic C), 134.0 (aromatic C), 130.0 (aromatic C), 129.3 (aromatic C), 127.3 (3) (aromatic C), 123.6 (2) (aromatic C), 118.5 (aromatic C), 114.8 (aromatic C), 114.2 (2) (aromatic C), 64.7 (CH$_2$NCH), 64.1 (CH$_2$NCH), 56.1 (CH$_2$OH), 55.4 (OCH$_3$), 54.5 (NHCHCH), 51.4 (NCH$_2$CH$_2$), 35.9 (NHCHCH), 25.7 (NCH$_2$CH$_2$).

[α]$_D^{22}$=+33.1° (c=0.4, CHCl$_3$).

Chiral SFC (AS-H, 1.5 mL/min, MeOH with 0.05% Et$_3$N in CO$_2$, λ=210 nm): t$_R$(minor)=6.1 min, t$_R$(major)=7.3 min.

IR (thin film, cm$^{-1}$): ν$_{max}$ 3402, 2929, 1614, 1499, 1480, 1246, 1180, 1028, 817, 753.

LCMS (UV Chromatogram, 210 nm, 2.5 min run): Purity >95% by UV, rt=0.84 min, m/z 402.2 (M+H)$^+$, m/z 446.5 (M+FA−H)$^−$.

HRMS (ESI, m/z): calcd for C$_{25}$H$_{27}$N$_3$O$_2$ (M+H)$^+$: 402.2182, found: 402.2172.

((3aR,4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161)

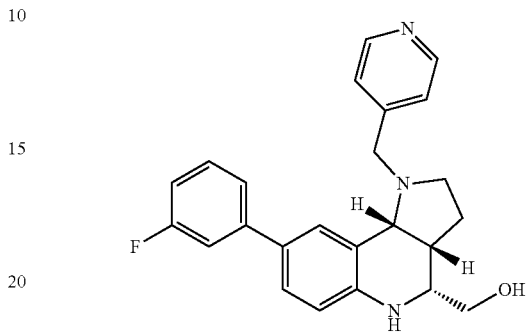

Prepared from benzyl (3aS,4S,9bS)-8-(3-fluorophenyl)-4-(hydroxymethyl)-2,3,3a,4,5,9b-hexahydro-1H-pyrrolo[3,2-c]quinoline-1-carboxylate 13c (276 mg, 0.64 mmol) according to General Procedure B. Purification by flash column chromatography eluting with 5% methanol in dichloromethane gave the desired product 3 as a white solid (66 mg, yield 27%).

$R_f$=0.23 (silica gel, 5% methanol in dichloromethane, UV).

$^1$H NMR (400 MHz, CDCl$_3$): δ 8.55-8.53 (m, 2H, aromatic H), 7.33-7.26 (m, 6H, aromatic H), 7.21 (d, 1H, J=10.8 Hz, aromatic H), 6.97 (t, 1H, J=8.4 Hz, aromatic H), 6.73 (d, 1H, J=8.4 Hz, aromatic H), 4.40 (d, 1H, J=13.5 Hz, CH$_2$OH), 3.90-3.86 (m, 1H, CH$_2$NCH), 3.71-3.65 (m, 2H, NHCHCH and CH$_2$NCH), 3.51-3.47 (m, 2H, CH$_2$NCH and CH$_2$OH), 2.95-2.92 (m, 1H, NCH$_2$CH$_2$), 2.83-2.79 (m, 1H, NCH$_2$CH$_2$), 2.39-2.35 (m, 1H, NCH$_2$CH$_2$), 2.02-1.94 (m, 2H, NHCHCH and NCH$_2$CH$_2$).

$^{13}$C NMR (100 MHz, CDCl$_3$): δ 164.5 and 162.1 (d, $^1J_{C, F}$=244 Hz, aromatic C), 149.5 (2) (pyridinyl C), 148.2 (aromatic C), 145.8 (pyridinyl C), 143.5 and 143.4 (d, $^3J_{C, F}$=7.9 Hz, aromatic C), 130.1 and 130.0 (d, $^3J_{C, F}$=8.2 Hz, aromatic C), 129.4 (aromatic C), 128.8 (aromatic C), 127.5 (aromatic C), 123.9 (2) (pyridinyl C), 121.7 and 121.7 (d, $^4J_{C, F}$=2.3 Hz, aromatic C), 119.4 (aromatic C), 115.2 (aromatic C), 113.0 and 112.8 (d, $^2J_{C, F}$=21.8 Hz, aromatic C), 112.9 and 112.7 (d, $^2J_{C, F}$=21.0 Hz, aromatic C), 64.3 (CH$_2$NCH), 63.3 (CH$_2$NCH), 58.1 (CH$_2$OH), 54.4 (NHCHCH), 51.6 (NCH$_2$CH$_2$), 38.1 (NHCHCH), 23.6 (NCH$_2$CH$_2$).

$^{19}$F NMR (376 MHz, CDCl$_3$): δ−113.4.

[α]$_D^{22}$=−29.8° (c=0.4, CHCl$_3$).

Chiral SFC (AS-H, 1.5 mL/min, MeOH with 0.05% Et$_3$N in CO$_2$, λ=210 nm): t$_R$(minor)=6.2 min, t$_R$(major)=6.9 min.

IR (thin film, cm$^{-1}$): ν$_{max}$ 3364, 2917, 1608, 1516, 1480, 1314, 1262, 1193, 1164, 1076, 869, 822, 788, 752, 691.

LCMS (UV Chromatogram, 210 nm, 2.5 min run): Purity >95% by UV, rt=0.82 min, m/z 390 (M+H)$^+$, m/z 434 (M+FA−H)$^−$.

HRMS (ESI, m/z): calcd for C$_{24}$H$_{24}$FN$_3$O (M+H)$^+$: 390.1982, found: 390.1972.

131
((3aR,4R,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (4/BRD1490)

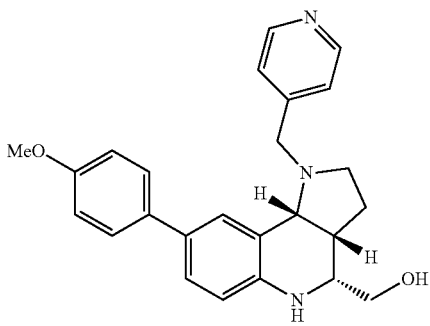 [SMILES: COc1ccc(-c2ccc3c(c2)[C@H]2[C@H](CCN2Cc2ccncc2)[C@H](CO)N3)cc1]

Prepared from benzyl (3aR,4R,9bR)-4-(hydroxymethyl)-8-(4-methoxy-phenyl)-2,3,3a,4,5,9b-hexahydro-1H-pyrrolo[3,2-c]quinoline-1-carboxylate 13d (142 mg, 0.32 mmol) according to General Procedure B. Purification by flash column chromatography eluting with 70% ethyl acetate in hexane gave the desired product 4 as an off-white solid (52 mg, yield 41%).

$R_f$=0.40 (silica gel, 5% methanol in dichloromethane, UV).

$^1$H NMR (400 MHz, CDCl3): δ 8.54 (d, 2H, J=4.9 Hz, aromatic H), 7.44 (d, 2H, J=8.4 Hz, aromatic H), 7.32-7.25 (m, 4H, aromatic H), 6.96 (d, 2H, J=8.4 Hz, aromatic H), 6.73 (d, 1H, J=8.0 Hz, aromatic H), 4.43 (d, 1H, J=13.2 Hz, CH2OH), 3.90-3.89 (m, 1H, CH2NCH), 3.85 (s, 3H, OCH3), 3.71-3.65 (m, 2H, CH2NCH and NHCHCH), 3.49-3.45 (m, 2H, CH2NCH and CH2OH), 2.94-2.80 (m, 2H, NCH2CH2 and NHCHCH), 2.36-2.34 (m, 1H, NCH2CH2), 2.00-1.97 (m, 2H, NCH2CH2).

13C NMR (100 MHz, CDCl3): δ 158.4 (aromatic C), 150.3 (aromatic C), 149.9 (2) (aromatic C), 144.9 (aromatic C), 134.0 (aromatic C), 130.1 (aromatic C), 129.1 (aromatic C), 127.3 (2) (aromatic C), 127.2 (aromatic C), 123.8 (2) (aromatic C), 119.4 (aromatic C), 115.2 (aromatic C), 114.2 (2) (aromatic C), 64.4 (CH2NCH), 63.3 (CH2NCH), 58.1 (CH2OH), 55.4 (OCH3), 54.5 (NHCHCH), 51.6 (NCH2CH2), 38.2 (NHCHCH), 23.6 (NCH2CH2).

$[α]_D^{22}$=−34.1° (c=0.4, CHCl3).

IR (thin film, cm−1): vmax 3364, 2911, 1609, 1495, 1246, 1180, 1045, 1027, 819, 754.

Chiral SFC (AS-H, 1.5 mL/min, MeOH with 0.05% Et3N in CO2, λ=210 nm): tR(minor)=6.8 min, tR(major)=7.1 min.

LCMS (UV Chromatogram, 210 nm, 2.5 min run): Purity >95% by UV, rt=0.79 min, m/z 402.5 (M+H)+, m/z 446.6 (M+FA−H)−.

HRMS (ESI, m/z): calcd for C25H27N3O2 (M+H)+: 402.2182, found: 402.2171.

132
((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (5/BRD0750)

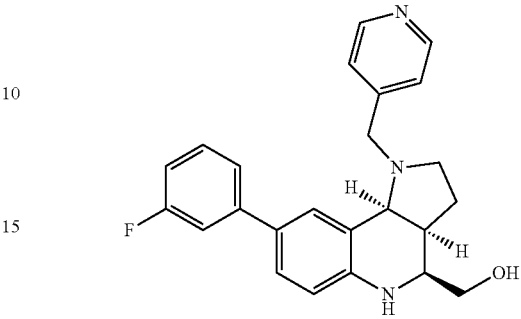

Prepared from benzyl (3aS,4S,9bS)-8-(3-fluorophenyl)-4-(hydroxymethyl)-2,3,3a,4,5,9b-hexahydro-1H-pyrrolo[3,2-c]quinoline-1-carboxylate 13e (168 mg, 0.39 mmol) according to General Procedure B. Purification by flash column chromatography eluting with 80% ethyl acetate in hexane gave the desired product 5 as an off-white solid (71 mg, yield 47%).

$R_f$=0.25 (silica gel, 5% methanol in dichloromethane, UV)

$^1$H NMR (400 MHz, CDCl$_3$): δ 8.53 (d, 2H, J=5.0 Hz, aromatic H), 7.34-7.33 (m, 3H, aromatic H), 7.28-7.26 (m, 3H, aromatic H), 7.21 (d, 1H, J=10.6 Hz, aromatic H), 6.96 (t, 1H, J=8.4 Hz, aromatic H), 6.73 (d, 1H, J=8.4 Hz, aromatic H), 4.39 (d, 1H, J=13.2 Hz, CH$_2$OH), 3.87 (dd, 1H, J=11.6 Hz and 5.0 Hz, CH$_2$NCH), 3.71-3.67 (m, 2H, NHCHCH and CH$_2$NCH), 3.51 (d, 1H, J=13.2 Hz, CH$_2$OH), 3.47-3.45 (m, 1H, CH$_2$NCH), 2.96-2.90 (m, 1H, NCH$_2$CH$_2$), 2.82-2.79 (m, 1H, NCH$_2$CH$_2$), 2.39 (dd, 1H, J=17.8 Hz and 8.8 Hz, NCH$_2$CH$_2$), 1.99-1.96 (m, 2H, NHCHCH and NCH$_2$CH$_2$).

$^{13}$C NMR (100 MHz, CDCl$_3$): δ 164.5 and 162.1 (d, $^1J_{C,F}$=243 Hz, aromatic C), 149.7 (2) (pyridinyl C), 148.0 (aromatic C), 145.9 (pyridinyl C), 143.5 and 143.4 (d, $^3J_{C,F}$=7.5 Hz, aromatic C), 130.1 and 130.0 (d, $^3J_{C,F}$=8.6 Hz, aromatic C), 129.4 (aromatic C), 128.8 (aromatic C), 127.5 (aromatic C), 123.9 (2) (pyridinyl C), 121.8 and 121.7 (d, $^4J_{C,F}$=2.8 Hz, aromatic C), 119.5 (aromatic C), 115.2 (aromatic C), 113.0 and 112.8 (d, $^2J_{C,F}$=21.4 Hz, aromatic C), 112.9 and 112.7 (d, $^2J_{C,F}$=20.9 Hz, aromatic C), 64.2 (CH$_2$NCH), 63.3 (CH$_2$NCH), 58.1 (CH$_2$OH), 54.4 (NHCHCH), 51.6 (NCH$_2$CH$_2$), 38.1 (NHCHCH), 23.6 (NCH$_2$CH$_2$).

$^{19}$F NMR (376 MHz, CDCl$_3$): δ−113.4.

$[α]_D^{22}$=+23.6° (c=0.4, CHCl$_3$).

Chiral SFC (AS-H, 1.5 mL/min, MeOH with 0.05% Et$_3$N in CO$_2$, λ=210 nm): t$_R$(major)=6.2 min, t$_R$(minor)=6.9 min.

IR (thin film, cm$^{-1}$): v$_{max}$ 3332, 2916, 1608, 1517, 1480, 1300, 1262, 1193, 1167, 1077, 867, 821, 784, 753, 692.

LCMS (UV Chromatogram, 210 nm, 2.5 min run): Purity >95% by UV, rt=0.86 min, m/z 390.5 (M+H)$^+$, m/z 434.5 (M+FA−H)$^-$.

HRMS (ESI, m/z): calcd for C$_{24}$H$_{24}$FN$_3$O (M+H)$^+$: 390.1982, found: 390.1973.

((3aS,4S,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (6/BRD6201)

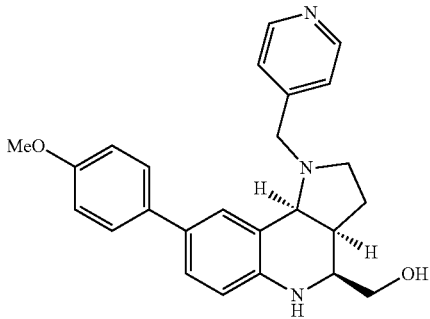 [SMILES: COc1ccc(-c2ccc3c(c2)[C@@H]2[C@@H](CCN2Cc2ccncc2)[C@@H](CO)N3)cc1]

Prepared from benzyl (3aS,4S,9bS)-4-(hydroxymethyl)-8-(4-methoxy-phenyl)-2,3,3a,4,5,9b-hexahydro-1H-pyrrolo[3,2-c]quinoline-1-carboxylate 13f (178 mg, 0.45 mmol) according to General Procedure B. Purification by flash column chromatography eluting with 65% ethyl acetate in hexane gave the desired product 6 as an off-white solid (65 mg, yield 41%).

$R_f$=0.43 (silica gel, 5% methanol in dichloromethane, UV).

$^1$H NMR (400 MHz, CDCl$_3$): δ 8.54 (d, 2H, J=5.0 Hz, aromatic H), 7.44 (d, 2H, J=8.2 Hz, aromatic H), 7.33-7.25 (m, 4H, aromatic H), 6.96 (d, 2H, J=8.2 Hz, aromatic H), 6.73 (d, 1H, J=8.2 Hz, aromatic H), 4.44 (d, 1H, J=13.2 Hz, CH$_2$OH), 3.92-3.86 (m, 1H, CH$_2$NCH), 3.85 (s, 3H, OCH$_3$), 3.71 (dd, 1H, J=11.3 Hz and 3.6 Hz, CH$_2$NCH), 3.65-3.64 (m, 1H, NHCHCH), 3.48-3.44 (m, 2H, CH$_2$NCH and CH$_2$OH), 2.95-2.91 (m, 1H, NCH$_2$CH$_2$), 2.84-2.81 (m, 1H, NCH$_2$CH$_2$), 2.36-2.34 (m, 1H, NCH$_2$CH$_2$), 2.03-1.95 (m, 2H, NCH$_2$CH$_2$).

$^{13}$C NMR (100 MHz, CDCl$_3$): δ 158.4 (aromatic C), 149.8 (2) (aromatic C), 148.0 (aromatic C), 144.9 (aromatic C), 134.0 (aromatic C), 130.1 (aromatic C), 129.1 (aromatic C), 127.3 (2) (aromatic C), 127.3 (aromatic C), 123.8 (2) (aromatic C), 119.3 (aromatic C), 115.2 (aromatic C), 114.2 (2) (aromatic C), 64.4 (CH$_2$NCH), 63.3 (CH$_2$NCH), 58.1 (CH$_2$OH), 55.4 (OCH$_3$), 54.4 (NHCHCH), 51.6 (NCH$_2$CH$_2$), 38.1 (NHCHCH), 23.7 (NCH$_2$CH$_2$).

$[α]_D^{22}$=−24.6° (c=0.4, CHCl$_3$).

Chiral SFC (AS-H, 1.5 mL/min, MeOH with 0.05% Et$_3$N in CO$_2$, λ=210 nm): $t_R$(major)=6.9 min, $t_R$(minor)=7.2 min.

IR (thin film, cm$^{-1}$): $v_{max}$ 3365, 2925, 1610, 1496, 1246, 1180, 1045, 1027, 818, 756.

LCMS (UV Chromatogram, 210 nm, 2.5 min run): Purity >95% by UV, rt=0.80 min, m/z 402.1 (M+H)$^+$, m/z 446.6 (M+FA−H)$^−$.

HRMS (ESI, m/z): calcd for C$_{25}$H$_{27}$N$_3$O$_2$ (M+H)$^+$: 402.2182, found: 402.2180.

((3aS,4R,9bS)-8-(3-Fluorophenyl)-1-(pyridin-4-ylmethyl)-2,3,3a,4,5,9b-hexahydro-1H-pyrrolo[3,2-c]quinolin-4-yl)methanol (7/BRD5039)

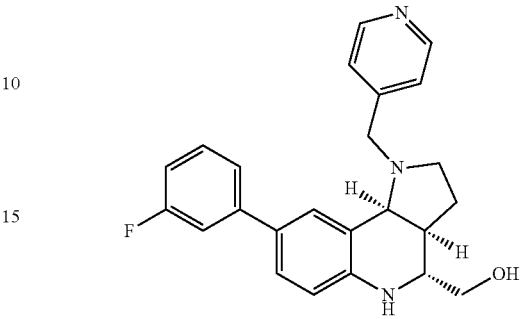

Prepared from benzyl (3aS,4R,9bS)-8-(3-fluorophenyl)-4-(hydroxymethyl)-2,3,3a,4,5,9b-hexahydro-1H-pyrrolo[3,2-c]quinoline-1-carboxylate 13g (168 mg, 0.39 mmol) according to General Procedure B. Purification by flash column chromatography eluting with 80% ethyl acetate in hexane gave the desired product 7 as an off-white solid (83 mg, yield 55%).

$R_f$=0.39 (silica gel, 10% methanol in dichloromethane, UV)

$^1$H NMR (400 MHz, CDCl$_3$): δ 8.46 (d, 2H, J=5.0 Hz, aromatic H), 7.35-7.33 (m, 2H, aromatic H), 7.28-7.25 (m, 4H, aromatic H), 7.21-7.19 (m, 1H, aromatic H), 6.97 (t, 1H, J=8.6 Hz, aromatic H), 6.73 (d, 1H, J=8.4 Hz, aromatic H), 4.37 (d, 1H, J=13.6 Hz, CH$_2$OH), 4.01 (d, 1H, J=9.4 Hz, CH$_2$NCH), 3.57-3.53 (m, 2H, NHCHCH and CH$_2$NCH), 3.37 (s, 1H, CH$_2$NCH), 3.30 (d, 1H, J=13.8 Hz, CH$_2$OH), 2.97-2.93 (m, 1H, NCH$_2$CH$_2$), 2.24-2.21 (m, 1H, NCH$_2$CH$_2$), 2.10-2.04 (m, 2H, NCH$_2$CH$_2$ and NHCHCH), 1.67-1.64 (m, 1H, NCH$_2$CH$_2$).

$^{13}$C NMR (100 MHz, CDCl$_3$): δ 164.5 and 162.1 (d, $^1J_{C,F}$=243.4 Hz, aromatic C), 149.8 (aromatic C), 149.0 (2) (pyridinyl C), 144.6 (pyridinyl C), 143.6 and 143.5 (d, $^3J_{C,F}$=8.4 Hz, aromatic C), 130.3 (aromatic C), 130.1 and 130.0 (d, $^3J_{C,F}$=8.9 Hz, aromatic C), 127.9 (aromatic C), 127.6 (aromatic C), 123.6 (2) (pyridinyl C), 121.7 and 121.7 (d, $^4J_{C,F}$=1.7 Hz, aromatic C), 118.2 (aromatic C), 114.7 (aromatic C), 113.0 and 112.8 (d, $^2J_{C,F}$=21.5 Hz, aromatic C), 112.8 and 112.6 (d, $^2J_{C,F}$=21.0 Hz, aromatic C), 64.7 (CH$_2$NCH), 64.2 (CH$_2$NCH), 56.0 (CH$_2$OH), 54.5 (NHCHCH), 51.4 (NCH$_2$CH$_2$), 35.8 (NHCHCH), 25.7 (NCH$_2$CH$_2$).

$^{19}$F NMR (376 MHz, CDCl$_3$): δ−113.4.

$[α]_D^{22}$=−30.4° (c=0.4, CHCl$_3$).

Chiral SFC (AS-H, 1.5 mL/min, MeOH with 0.05% Et$_3$N in CO$_2$, λ=210 nm): $t_R$(major)=6.4 min, $t_R$(minor)=7.0 min.

IR (thin film, cm$^{-1}$): $v_{max}$ 3334, 2927, 1608, 1522, 1484, 1326, 1261, 1198, 1160, 1076, 868, 819, 782, 752, 694.

LCMS (UV Chromatogram, 210 nm, 2.5 min run): Purity >95% by UV, rt=0.87 min, m/z 390.2 (M+H)*, m/z 434.6 (M+FA−H)$^−$.

HRMS (ESI, m/z): calcd for C$_{24}$H$_{24}$FN$_3$O (M+H)$^+$: 390.1982, found: 390.1976.

((3aS,4R,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (8/BRD0739)

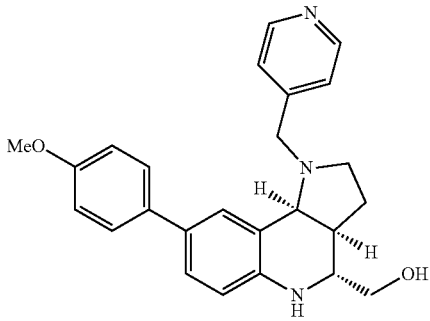 [SMILES: COc1ccc(-c2ccc3c(c2)[C@@H]2[C@@H](CCN2Cc2ccncc2)[C@H](CO)N3)cc1]

Prepared from benzyl (3aS,4R,9bS)-4-(hydroxymethyl)-8-(4-methoxy-phenyl)-2,3,3a,4,5,9b-hexahydro-1H-pyrrolo[3,2-c]quinoline-1-carboxylate 13h (143 mg, 0.32 mmol) according to General Procedure B. Purification by flash column chromatography eluting with 70% ethyl acetate in hexane gave the desired product 8 as an off-white solid (62 mg, yield 48%).

$R_f$=0.67 (silica gel, 10% methanol in dichloromethane, UV)

$^1$H NMR (400 MHz, CDCl$_3$): δ 8.46 (d, 2H, J=4.8 Hz, aromatic H), 7.44-7.43 (d, 2H, J=8.2 Hz, aromatic H), 7.32-7.27 (m, 4H, aromatic H), 6.96 (d, 2H, J=8.2 Hz, aromatic H), 6.73 (d, 1H, J=8.2 Hz, aromatic H), 4.39 (d, 1H, J=13.8 Hz, CH$_2$OH), 3.99 (d, 1H, J=10.0 Hz, CH$_2$NCH), 3.85 (s, 3H, OCH$_3$), 3.58-3.52 (m, 2H, CH$_2$NCH and NHCHCH), 3.37 (s, 1H, CH$_2$NCH), 3.29 (d, 1H, J=13.8 Hz, CH$_2$OH), 2.96 (t, 1H, J=9.0 Hz, NCH$_2$CH$_2$), 2.24-2.18 (m, 1H, NCH$_2$CH$_2$), 2.10-2.07 (m, 2H, NCH$_2$CH$_2$ and NHCHCH), 1.68-1.64 (m, 1H, NCH$_2$CH$_2$).

$^{13}$C NMR (100 MHz, CDCl$_3$): δ 158.3 (aromatic C), 149.8 (aromatic C), 149.1 (2) (aromatic C), 143.7 (aromatic C), 134.0 (aromatic C), 129.9 (aromatic C), 129.3 (aromatic C), 127.4 (aromatic C), 127.3 (2) (aromatic C), 123.7 (2) (aromatic C), 118.2 (aromatic C), 114.8 (aromatic C), 114.2 (2) (aromatic C), 64.6 (CH$_2$NCH), 64.2 (CH$_2$NCH), 56.1 (CH$_2$OH), 55.4 (OCH$_3$), 54.6 (NHCHCH), 51.4 (NCH$_2$CH$_2$), 35.9 (NHCHCH), 25.7 (NCH$_2$CH$_2$).

$[α]_D^{22}$=−23.4° (c=0.4, CHCl$_3$).

Chiral SFC (AS-H, 1.5 mL/min, MeOH with 0.05% Et$_3$N in CO$_2$, λ=210 nm): $t_R$(major)=6.1 min, $t_R$(minor)=7.3 min.

IR (thin film, cm$^{-1}$): $v_{max}$ 3402, 2929, 1614, 1499, 1246, 1180, 1029, 817, 753.

LCMS (UV Chromatogram, 210 nm, 2.5 min run): Purity >95% by UV, rt=0.80 min, m/z 402.2 (M+H)$^+$, m/z 446.6 (M+FA−H)$^-$.

HRMS (ESI, m/z): calcd for C$_{25}$H$_{27}$N$_3$O$_2$ (M+H)$^+$: 402.2182, found: 402.2172.

tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14)

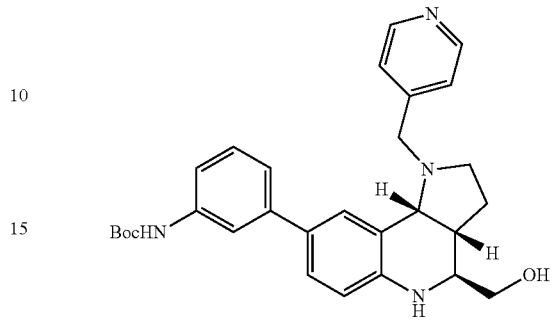

Prepared from benzyl (3aR,4S,9bR)-8-(3-((tert-butoxycarbonyl)amino)-phenyl)-4-(hydroxymethyl)-2, 3, 3a, 4, 5, 9b-hexahydro-1H-pyrrolo[3,2-c]quinoline-1-carboxylate 13i (210 mg, 0.53 mmol) according to General Procedure B. Purification by flash column chromatography eluting with 60% to 90% ethyl acetate in hexane gave the desired product 14 as a white solid (205 mg, yield 79%).

$R_f$=0.28 (silica gel, 10% methanol in dichloromethane, UV).

$^1$H NMR (400 MHz, CDCl$_3$): δ 8.45 (d, 2H, J=5.0 Hz, aromatic H), 7.50 (s, 1H, aromatic H), 7.35-7.29 (m, 5H, aromatic H), 7.18 (d, 1H, J=7.3 Hz, aromatic H), 6.71 (d, 1H, J=8.2 Hz, aromatic H), 4.34 (d, 1H, J=13.8 Hz, CH$_2$OH), 3.98 (d, 1H, J=10.2 Hz, CH$_2$NCH), 3.58 (d, 1H, J=10.2 Hz, CH$_2$NCH), 3.53-3.51 (m, 1H, NHCHCH), 3.36-3.32 (m, 2H, CH$_2$NCH and CH$_2$OH), 2.99-2.97 (m, 1H, NCH$_2$CH$_2$), 2.27-2.25 (m, 1H, NCH$_2$CH$_2$), 2.10-2.03 (m, 2H, NCH$_2$CH$_2$ and NHCHCH), 1.69-1.67 (m, 1H, NCH$_2$CH$_2$), 1.54 (s, 9H, tert-butyl CH$_3$).

$^{13}$C NMR (100 MHz, CDCl$_3$): δ 171.2 (CONH), 152.9 (aromatic C), 148.8 (aromatic C), 144.3 (aromatic C), 142.0 (aromatic C), 138.8 (aromatic C), 130.3 (aromatic C), 129.3 (aromatic C), 127.9 (aromatic C), 123.8 (aromatic C), 121.0 (aromatic C), 116.5 (aromatic C), 116.4 (aromatic C), 114.8 (aromatic C), 80.5 (tert-butyl C), 64.6 (CH$_2$NCH), 64.3 (CH$_2$NCH), 56.0 (CH$_2$OH), 54.4 (NHCHCH), 51.4 (NCH$_2$CH$_2$), 35.8 (NHCHCH), 28.4 (tert-butyl CH$_3$), 25.8 (NCH$_2$CH$_2$).

$[α]_D^{22}$=+57.6° (c=0.5, CHCl$_3$).

Chiral SFC (AS-H, 1.5 mL/min, MeOH with 0.05% Et$_3$N in CO$_2$, λ=210 nm): $t_R$(minor)=6.5 min, $t_R$(major)=6.9 min.

IR (thin film, cm$^{-1}$): $v_{max}$ 3425, 2930, 1706, 1606, 1514, 1366, 1241, 1162, 1065, 788, 754, 699.

LCMS (UV Chromatogram, 210 nm, 2.5 min run): Purity >85% by UV, rt=0.99 min, m/z 487.6 (M+H)$^+$, m/z 531.7 (M+FA−H)$^-$.

HRMS (ESI, m/z): calcd for C$_{29}$H$_{35}$N$_4$O$_3$ (M+H)$^+$: 487.2709, found: 487.2720.

N-(2-(2-(2-(3-((3-((3aR,4S,9bR)-4-(Hydroxymethyl)-1-(pyridin-4-ylmethyl)-2,3,3a,4,5,9b-hexahydro-1H-pyrrolo[3,2-c]quinolin-8-yl)phenyl)amino)-3-oxopropoxy)ethoxy)ethoxy)ethyl)-5-((3aS,4S,6aR)-2-oxohexahydro-1H-thieno[3,4-d]imidazol-4-yl)pentanamide (15).

A 5 mL reaction vial was charged with tert-Butyl (3-((3aR,4S,9bR)-4-(hydroxymethyl)-1-(pyridin-4-ylmethyl)-2,3,3a,4,5,9b-hexahydro-1H-pyrrolo[3,2-c]quinolin-8-yl)phenyl)carbamate (14, 39 mg) and hydrogen chloride solution (4.0 M in dioxane, 0.5 mL). After stirring at room temperature for 30 min, the solvent was removed under vacuum. The residue was re-suspended in dichloromethane and evaporated to dryness. The obtained crude solid was added to a reaction mixture of biotin-PEG3-acid (36 mg, 0.08 mmol), HATU (30 mg, 0.08 mmol), and DIPEA (28 µL, 0.16 mmol) in DMF (1.0 mL), which has been stirred for at room temperature for 2 h before the crude solid addition. The resulting mixture was stirred at room temperature overnight before the removal of solvent under vacuum. The resulting residue was purified through preparative HPLC to afford the desired biotinylated product 15 as a yellow solid (30 mg, 47%).

$R_f$=0.27 (silica gel, 17% methanol in dichloromethane, UV).

$^1$H NMR (400 MHz, D$_2$O): δ 8.70 (d, 2H, J=5.8 Hz), 8.04 (d, 2H, J=5.8 Hz), 7.73 (s, 1H), 7.59 (d, 1H, J=8.4 Hz), 7.51 (t, 1H, J=8.0 Hz), 7.36-7.32 (m, 3H), 6.98 (d, 1H, J=8.4 Hz), 5.02 (d, 1H, J=14.0 Hz), 4.91 (d, 1H, J=6.8 Hz), 4.54 (dd, 1H, J=8.8 and 5.0 Hz), 4.29 (dd, 1H, J=8.8 and 5.0 Hz), 3.94 (t, 2H, J=5.9 Hz), 3.84 (ddd, 1H, J=12.0, 3.0 and 1.5 Hz), 3.75-3.69 (m, 6H), 3.66-3.62 (m, 4H), 3.55-3.53 (m, 2H), 3.47 (t, 2H, J=5.4 Hz), 3.39-3.34 (m, 1H), 3.23 (t, 2H, J=5.2 Hz), 3.18-3.13 (m, 1H), 2.92 (dd, 1H, J=13.2 and 5.0 Hz), 2.81-2.79 (m, 1H), 2.77 (t, 2H, J=5.8 Hz), 2.73 (d, 1H, J=13.2 Hz), 2.67-2.62 (m, 1H), 2.30-2.24 (m, 1H), 2.11 (t, 2H, J=7.2 Hz), 1.61-1.54 (m, 1H), 1.50-1.39 (m, 3H), 1.28-1.20 (m, 2H).

$^{13}$C NMR (100 MHz, D$_2$O): δ 176.6, 173.0, 165.2, 151.0, 145.6, 141.7, 140.0, 137.8, 130.0, 130.0, 129.8, 129.1, 127.7, 122.6, 119.8, 118.6, 116.6, 111.0, 69.8, 69.7, 69.6, 69.4, 68.8, 66.7, 62.3, 62.0, 60.2, 55.4, 55.3, 39.7, 38.8, 36.9, 35.7, 35.3, 27.9, 27.6, 26.5, 25.1.

IR (thin film, cm$^{-1}$): $v_{max}$ 3308, 2872, 2043, 1667, 1556, 1427, 1178, 1126, 796, 719.

LCMS (UV Chromatogram, 210 nm, 2.5 min run): Purity >95% by UV, rt=0.81 min, m/z 816.8 (M+H)$^+$, m/z 861.1 (M+FA–H)$^-$.

HRMS (ESI, m/z): calcd for C$_{43}$H$_{58}$N$_7$O$_7$S (M+H)$^+$: 816.4118, found: 816.4103.

Example 4

Fluorescence polarization-based screening assay exploiting PAM recognition.

Since its discovery, the RNA guided endonuclease cas9 has found a wide variety of applications owing to the ease of targeting it to any genomic locus of interest using a single guide RNA.[1-6] The recognition of the target DNA by Cas9 is based on complementary base-pairing between the target DNA and the guide RNA as well as presence of a protospacer adjacent motif (PAM) sequence adjacent to the target sequence in DNA (Doudna, J. A.; Charpentier, E., Genome editing. The new frontier of genome engineering with CRISPR-Cas9. *Science* 2014, 346 (6213), 1258096; Jinek, M.; Chylinski, K.; Fonfara, I.; Hauer, M.; Doudna, J. A.; Charpentier, E., A programmable dual-RNA-guided DNA endonuclease in adaptive bacterial immunity. *Science* 2012, 337 (6096), 816-21; Jinek, M.; East, A.; Cheng, A.; Lin, S.; Ma, E.; Doudna, J., RNA-programmed genome editing in human cells. *eLife* 2013, 2, e00471; Cong, L.; Ran, F. A.; Cox, D.; Lin, S.; Barretto, R.; Habib, N.; Hsu, P. D.; Wu, X.; Jiang, W.; Marraffini, L. A.; Zhang, F., Multiplex genome engineering using CRISPR/Cas systems. *Science* 2013, 339 (6121), 819-23.; Mali, P.; Yang, L.; Esvelt, K. M.; Aach, J.; Guell, M.; DiCarlo, J. E.; Norville, J. E.; Church, G. M., RNA-guided human genome engineering via Cas9. *Science* 2013, 339 (6121), 823-6; Gasiunas, G.; Barrangou, R.; Horvath, P.; Siksnys, V., Cas9-crRNA ribonucleoprotein complex mediates specific DNA cleavage for adaptive immunity in bacteria. *Proceedings of the National Academy of Sciences of the United States of America* 2012, 109 (39), E2579-86). Till date, several Cas9 based technologies have been developed which lead to knock-in or knock-out of a specific gene (Dahlman, J. E.; Abudayyeh, O. O.; Joung, J.; Gootenberg, J. S.; Zhang, F.; Konermann, S., Orthogonal gene knockout and activation with a catalytically active Cas9 nuclease. *Nat Biotechnol* 2015, 33 (11), 1159-61; Merkle, F. T.; Neuhausser, W. M.; Santos, D.; Valen, E.; Gagnon, J. A.; Maas, K.; Sandoe, J.; Schier, A. F.; Eggan, K., Efficient CRISPR-Cas9-mediated generation of knockin human pluripotent stem cells lacking undesired mutations at the targeted locus. *Cell reports* 2015, 11 (6), 875-883; He, X.; Tan, C.; Wang, F.; Wang, Y.; Zhou, R.; Cui, D.; You, W.; Zhao, H.; Ren, J.; Feng, B., Knock-in of large reporter genes in human cells via CRISPR/Cas9-induced homology-dependent and independent DNA repair. *Nucleic Acids Res* 2016, 44 (9), e85; Lin, S.; Staahl, B. T.; Alla, R. K.; Doudna, J. A., Enhanced homology-directed human genome engineering by controlled timing of CRISPR/Cas9 delivery. *eLife* 2014, 3, e04766; Shalem, O.; Sanjana, N. E.; Hartenian, E.; Shi, X.; Scott, D. A.; Mikkelson, T.; Heckl, D.; Ebert, B. L.; Root, D. E.; Doench, J. G.; Zhang, F., Genome-scale CRISPR-Cas9 knockout screening in human cells. *Science* 2014, 343 (6166), 84-87).

Catalytically inactive Cas9 (dCas9) has been fused to a variety of effectors for applications in transcriptional activation and repression, genome imaging, epigenome editing as well as base editing (Chen, B.; Gilbert, L. A.; Cimini, B. A.; Schnitzbauer, J.; Zhang, W.; Li, G. W.; Park, J.; Blackburn, E. H.; Weissman, J. S.; Qi, L. S.; Huang, B., Dynamic imaging of genomic loci in living human cells by an optimized CRISPR/Cas system. *Cell* 2013, 155 (7), 1479-91; Hilton, I. B.; D'Ippolito, A. M.; Vockley, C. M.; Thakore, P. I.; Crawford, G. E.; Reddy, T. E.; Gersbach, C. A., Epigenome editing by a CRISPR-Cas9-based acetyltransferase activates genes from promoters and enhancers. *Nat Biotechnol* 2015, 33 (5), 510-7; Dominguez, A. A.; Lim, W. A.; Qi, L. S., Beyond editing: repurposing CRISPR-Cas9 for precision genome regulation and interrogation. Nat Rev Mol Cell Biol 2016, 17 (1), 5-15; Shalem, O.; Sanjana, N. E.; Zhang, F., High-throughput functional genomics using CRISPR-Cas9. *Nature reviews. Genetics* 2015, 16 (5), 299-311; Ma, H.; Naseri, A.; Reyes-Gutierrez, P.; Wolfe, S. A.; Zhang, S.; Pederson, T., Multicolor CRISPR labeling of chromosomal loci in human cells. *Proceedings of the National Academy of Sciences of the United States of America* 2015, 112 (10), 3002-7; Fujita, T.; Fujii, H., Efficient isolation of specific genomic regions and identification of associated proteins by engineered DNA-binding molecule-mediated chromatin immunoprecipitation (enChIP) using CRISPR. *Biochemical and biophysical research communications* 2013, 439 (1), 132-6; Komor, A. C.; Kim, Y. B.; Packer, M. S.; Zuris, J. A.; Liu, D. R., Programmable editing of a target base in genomic DNA without double-stranded DNA cleavage. *Nature* 2016, 533 (7603), 420-4). Further, Cas9 based alterations can also be robustly propagated throughout a species population via gene drives (Gantz, V. M.; Bier, E., The dawn of active genetics. BioEssays: news and reviews in molecular, cellular and developmental biology 2016, 38 (1), 50-63; Esvelt, K. M.; Smidler, A.; Catteruccia, F.; Church, G. M., Concerning RNA-guided gene drives for the alteration of wild populations. *Elife* 2014, 3; Champer, J.; Buchman, A.; Akbari, O. S., Cheating evolution: engineering gene drives to manipulate the fate of wild populations. Nature reviews. *Genetics* 2016, 17 (3), 146-59). SpCas9 has been extensively investigated for gene therapy in pathologies such as Duchenne Muscular dystrophy (DMD), HIV, hereditary tyrosinemia and vision disorders (Cox, D. B.; Platt, R. J.; Zhang, F., Therapeutic genome editing: prospects and challenges. *Nat Med* 2015, 21 (2), 121-31; Yin, H.; Xue, W.; Chen, S.; Bogorad, R. L.; Benedetti, E.; Grompe, M.; Koteliansky, V.; Sharp, P. A.; Jacks, T.; Anderson, D. G., Genome editing with Cas9 in adult mice corrects a disease mutation and phenotype. *Nature biotechnology* 2014, 32 (6), 551-3; Doudna, J. A., Genomic engineering and the future of medicine. *Jama* 2015, 313 (8), 791-2; Ding, Q.; Strong, A.; Patel, K. M.; Ng, S. L.; Gosis, B. S.; Regan, S. N.; Cowan, C. A.; Rader, D. J.; Musunuru, K., Permanent alteration of PCSK9 with in vivo CRISPR-Cas9 genome editing. *Circulation research* 2014, 115 (5), 488-92; Saayman, S.; Ali, S. A.; Morris, K. V.; Weinberg, M. S., The therapeutic application of CRISPR/Cas9 technologies for HIV. *Expert Opin Biol Ther* 2015, 15 (6), 819-30; Nelson, C. E.; Hakim, C. H.; Ousterout, D. G.; Thakore, P. I.; Moreb, E. A.; Castellanos Rivera, R. M.; Madhavan, S.; Pan, X.; Ran, F. A.; Yan, W. X.; Asokan, A.; Zhang, F.; Duan, D.; Gersbach, C. A., In vivo genome editing improves muscle function in a mouse model of Duchenne muscular dystrophy. *Science* 2016, 351 (6271), 403-7; Tabebordbar, M.; Zhu, K.; Cheng, J. K. W.; Chew, W. L.; Widrick, J. J.; Yan, W. X.; Maesner, C.; Wu, E. Y.; Xiao, R.; Ran, F. A.; Cong, L.; Zhang, F.; Vandenberghe, L. H.; Church, G. M.; Wagers, A. J., In vivo gene editing in dystrophic mouse muscle and muscle stem cells. *Science* 2016, 351 (6271), 407-411; Long, C.; Amoasii, L.; Mireault, A. A.; McAnally, J. R.; Li, H.; Sanchez-Ortiz, E.; Bhattacharyya, S.; Shelton, J. M.; Bassel-Duby, R.; Olson, E. N., Postnatal genome editing partially restores dystrophin expression in a mouse model of muscular dystrophy. *Science* 2016, 351 (6271), 400-3; Bakondi, B.; Lv, W.; Lu, B.; Jones, M. K.; Tsai, Y.; Kim, K. J.; Levy, R.; Akhtar, A. A.; Breunig, J. J.; Svendsen, C. N.; Wang, S., In Vivo CRISPR/Cas9 Gene Editing Corrects Retinal Dystrophy in the S334ter-3 Rat Model of Autosomal Dominant Retinitis Pigmentosa. *Molecular therapy: the journal of the American Society of Gene Therapy* 2016, 24 (3), 556-63; Wu, W. H.; Tsai, Y. T.; Justus, S.; Lee, T. T.; Zhang, L.; Lin, C. S.; Bassuk, A. G.; Mahajan, V. B.; Tsang, S. H., CRISPR Repair Reveals Causative Mutation in a Preclinical Model of Retinitis Pigmentosa. *Molecular therapy: the journal of the American Society of Gene Therapy* 2016, 24 (8), 1388-94; Zhong, H.; Chen, Y.; Li, Y.; Chen, R.; Mardon, G., CRISPR-engineered mosaicism rapidly reveals that loss of Kcnj13 function in mice mimics human disease phenotypes. *Scientific reports* 2015, 5, 8366).

In order to be effectively used for therapeutic applications, it is essential to have a dosable control of the therapeutic agent. This is an extremely important consideration for gene editing using Cas9, owing to the high off-target effects and chromosomal translocations observed at elevated Cas9 levels (Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat Biotechnol* 2013, 31 (9), 822-6; Hsu, P. D.; Scott, D. A.; Weinstein, J. A.; Ran, F. A.; Konermann, S.; Agarwala, V.; Li, Y.; Fine, E. J.; Wu, X.; Shalem, O.; Cradick, T. J.; Marraffini, L. A.; Bao, G.; Zhang, F., DNA targeting specificity of RNA-guided Cas9 nucleases. *Nat Biotechnol* 2013, 31 (9), 827-32; Pattanayak, V.; Lin, S.; Guilinger, J. P.; Ma, E.; Doudna, J. A.; Liu, D. R., High-throughput profiling of off-target DNA cleavage reveals RNA-programmed Cas9 nuclease specificity. *Nature biotechnology* 2013, 31 (9), 839-43; Pattanayak, V.; Guilinger, J. P.; Liu, D. R., Determining the specificities of TALENs, Cas9, and other genome-editing enzymes. *Methods Enzymol* 2014, 546, 47-78; Frock, R. L.; Hu, J.; Meyers, R. M.; Ho, Y. J.; Kii, E.; Alt, F. W., Genome-wide detection of DNA double-stranded breaks induced by engineered nucleases. *Nature biotechnology* 2015, 33 (2), 179-86; Tsai, S. Q.; Zheng, Z.; Nguyen, N. T.; Liebers, M.; Topkar, V. V.; Thapar, V.; Wyvekens, N.; Khayter, C.; Iafrate, A. J.; Le, L. P.; Aryee, M. J.; Joung, J. K., GUIDE-seq enables genome-wide profiling of off-target cleavage by CRISPR-Cas nucleases. *Nature biotechnology* 2015, 33 (2), 187-97; Davis, K. M.; Pattanayak, V.; Thompson, D. B.; Zuris, J. A.; Liu, D. R., Small molecule-triggered Cas9 protein with improved genome-editing specificity. Nat Chem Biol 2015, 11 (5), 316-8).

Furthermore, the delivery systems used in gene therapy applications deliver constitutively active Cas9 whose activity must be terminated following the desired gene editing activity. From a gene drive perspective, it is important to develop methods to counter the nefarious use of gene drives or to facilitate its dosable, reversible and temporal control. These controls can be achieved through the precise regulation of Cas9 activity. Previous studies to control Cas9 activity have focused on developing fusions of Cas9 to proteins domains that can be regulated by small molecules (Nunez, J. K.; Lee, A. S.; Engelman, A.; Doudna, J. A., Integrase-mediated spacer acquisition during CRISPR-Cas adaptive immunity. *Nature* 2015, 519 (7542), 193-8; Maji, B.; Moore, C. L.; Zetsche, B.; Volz, S. E.; Zhang, F.; Shoulders, M. D.; Choudhary, A., Multidimensional chemical control of CRISPR-Cas9. *Nature chemical biology* 2017, 13 (1), 9-11).

However, such systems will to be difficult to adapt for therapeutic applications, since fitting these large fusion proteins into currently available delivery systems will be challenging (Senis, E.; Fatouros, C.; Grosse, S.; Wiedtke, E.; Niopek, D.; Mueller, A. K.; Borner, K.; Grimm, D., CRISPR/Cas9-mediated genome engineering: an adeno-associated viral (AAV) vector toolbox. *Biotechnol J* 2014, 9 (11), 1402-12). Further, most of these systems act merely as 'turn-on' switches for the Cas9 systems and several are not reversible which hinder temporal control (Nunez, J. K.; Harrington, L. B.; Doudna, J. A., Chemical and Biophysical Modulation of Cas9 for Tunable Genome Engineering. *ACS Chem Biol* 2016, 11 (3), 681-8).

Small molecule inhibitors of Cas9 will allow both dose and temporal control of its activity and aid in the better application of this system in gene therapy. Given that Cas9 is vital to several bacterial processes including immunity, inhibitors of this protein have the potential to afford novel anti-infective agents to counter the ever-growing challenge of antibiotic resistance (Westra, E. R.; Buckling, A.; Fineran, P. C., CRISPR-Cas systems: beyond adaptive immunity. *Nature reviews. Microbiology* 2014, 12 (5), 317-26; Barrangou, R., The roles of CRISPR-Cas systems in adaptive immunity and beyond. *Current opinion in immunology* 2015, 32, 36-41).

Recent studies have described the discovery of certain 'anti-CRISPR' proteins from phages that inhibit SpCas9 in *E. coli* and human cells (Pawluk, A.; Staals, R. H.; Taylor, C.; Watson, B. N.; Saha, S.; Fineran, P. C.; Maxwell, K. L.; Davidson, A. R., Inactivation of CRISPR-Cas systems by anti-CRISPR proteins in diverse bacterial species. *Nature microbiology* 2016, 1 (8), 16085; Pawluk, A.; Amrani, N.; Zhang, Y.; Garcia, B.; Hidalgo-Reyes, Y.; Lee, J.; Edraki, A.;

Shah, M.; Sontheimer, E. J.; Maxwell, K. L.; Davidson, A. R., Naturally Occurring Off-Switches for CRISPR-Cas9. *Cell* 2016, 167 (7), 1829-1838.e9; Shin, J.; Jiang, F.; Liu, J. J.; Bray, N. L.; Rauch, B. J.; Baik, S. H.; Nogales, E.; Bondy-Denomy, J.; Corn, J. E.; Doudna, J. A., Disabling Cas9 by an anti-CRISPR DNA mimic. *Science advances* 2017, 3 (7), e1701620; Rauch, B. J.; Silvis, M. R.; Hultquist, J. F.; Waters, C. S.; McGregor, M. J.; Krogan, N. J.; Bondy-Denomy, J., Inhibition of CRISPR-Cas9 with Bacteriophage Proteins. *Cell* 2017, 168 (1-2), 150-158.e10).

However, development of protein inhibitors of Cas9 for therapeutic purposes may prove tedious since proteins are highly sensitive to pH and temperature making them difficult to produce on a large scale and characterize. Additionally, optimizing the potency of such protein-based inhibitors may involve mutagenesis which can prove to be challenging as well as time-consuming. Further, from a therapeutic standpoint, the immunogenicity of proteins becomes a significant challenge. Small molecules, on the other hand, are quite stable under reasonably small changes in pH, temperature, and humidity as well as to the presence of cellular proteases. They are considerably easier to deliver since most enter cells through passive diffusion. Small molecule inhibitors exhibit their effects rapidly which is in stark contrast to genetic methods. Besides offering efficient dose and temporal control, small molecules are cheaper to synthesize and have little variability amongst batches. Finally, the inhibition resulting from a non-covalent small molecule can be readily reversed. All these attributes make small molecule inhibitors of Cas9 a very attractive avenue to pursue.

Here, Applicants describe a novel fluorescence polarization-based screening assay that exploits the PAM recognition by SpCas9 to identify small molecule inhibitors of SpCas9. Applicants demonstrate the application of this assay in screening multiple compound libraries to identify small-molecule inhibitors of SpCas9. Applicants also illustrate the ability of the identified small molecules to inhibit cas9 activity in mammalian and bacterial cells as well as in flies. Applicants also show that these molecules are capable of inhibiting dSpCas9, thus providing a chemogenic control of dSpCas9 based technologies.

Rationale and Preliminary Studies. As discussed above, an active search is ongoing for "off-switches" of SpCas9. Currently, the best SpCas9 inhibitor is an "Anti-CRISPR" protein with a paltry efficacy of ~25% inhibition in mammalian cells (Rauch, B. J.; Silvis, M. R.; Hultquist, J. F.; Waters, C. S.; McGregor, M. J.; Krogan, N. J.; Bondy-Denomy, J., Inhibition of CRISPR-Cas9 with Bacteriophage Proteins. *Cell* 2017, 168 (1-2), 150-158.e10). Further, this protein is highly-negatively charged with poor PK/PD properties, and has shown delivery and immunogenicity problems. Applicants believe that a small-molecule SpCas9 inhibitor will resolve some of these issues. However, the identification of small molecule inhibitors of SpCas9 poses many challenges. First, inhibitor identification requires robust, orthogonal, sensitive, high-throughput, miniature, and inexpensive assays, which are currently unavailable. Second, SpCas9 is a single turnover enzyme that holds on to its DNA substrate with pM affinity, making the development of such assays challenging (Sternberg, S. H.; Redding, S.; Jinek, M.; Greene, E. C.; Doudna, J. A., DNA interrogation by the CRISPR RNA-guided endonuclease Cas9. *Nature* 2014, 507 (7490), 62-7). Third, the inhibition of SpCas9 activity requires inhibition of two nuclease domains (Jinek, M.; Chylinski, K.; Fonfara, I.; Hauer, M.; Doudna, J. A.; Charpentier, E., A programmable dual-RNA-guided DNA endonuclease in adaptive bacterial immunity. *Science* 2012, 337 (6096), 816-21). Fourth, SpCas9 has many novel protein folds that limit our ability to leverage existing rational design approaches (Nishimasu, H.; Ran, F. A.; Hsu, P. D.; Konermann, S.; Shehata, S. I.; Dohmae, N.; Ishitani, R.; Zhang, F.; Nureki, O., Crystal structure of Cas9 in complex with guide RNA and target DNA. *Cell* 2014, 156 (5), 935-49).

To circumvent these challenges, Applicants focused on targeting the SpCas9-substrate PAM motif interaction as a way to identify novel small molecule inhibitors of Cas9. To this end, Applicants developed a several high-throughput biochemical assays for SpCas9 and performed a preliminary screen large compound libraries to identify small molecules that inhibit >50% of SpCas9 activity. Further, Applicants also found these molecules to inhibit SpCas9 activity in mammalian and bacterial cells at low micromolar concentrations.

Development of High-throughput Primary and Secondary Assays.

Figure 35B:
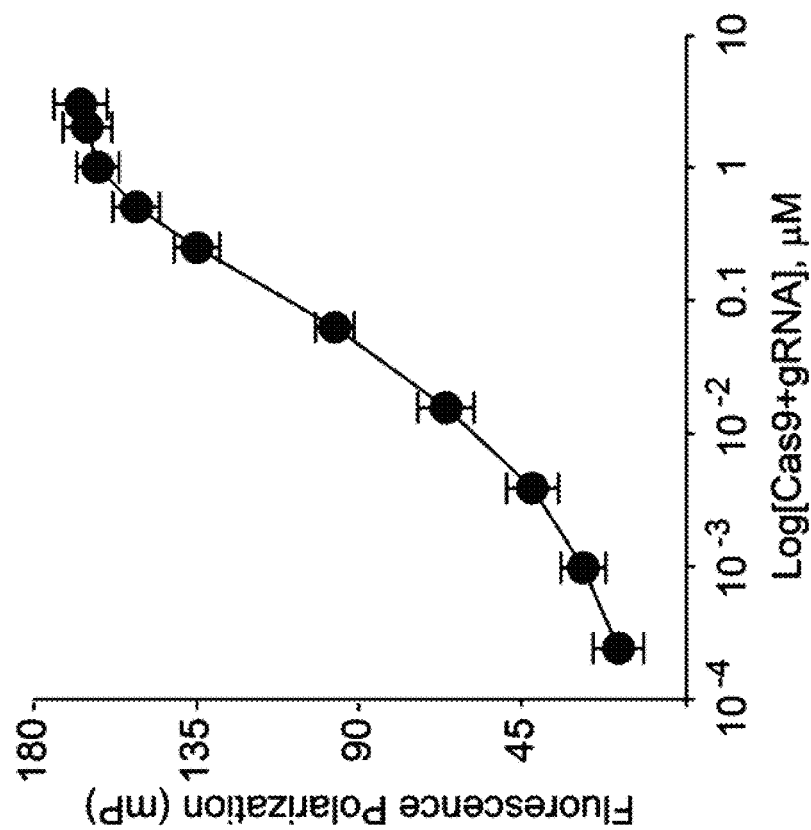
FIGS. 35A-35G. Development of screening pipeline for identifying SpCas9 inhibitor.
Figure 35A:
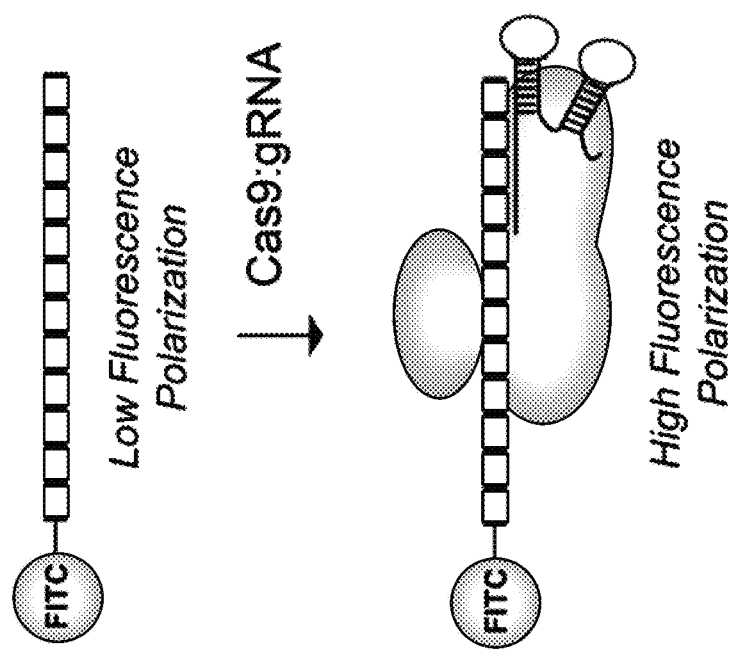

SpCas9-PAM binding assays. Disrupting PAM-sequence binding by SpCas9 (e.g., by mutating SpCas9 or the PAM-site) renders SpCas9 inactive (Kleinstiver, B. P.; Prew, M. S.; Tsai, S. Q.; Topkar, V. V.; Nguyen, N. T.; Zheng, Z.; Gonzales, A. P.; Li, Z.; Peterson, R. T.; Yeh, J. R.; Aryee, M. J.; Joung, J. K., Engineered CRISPR-Cas9 nucleases with altered PAM specificities. *Nature* 2015, 523 (7561), 481-5). Further, SpCas9 has a low affinity for the PAM-sequence, making the SpCas9-PAM interaction an Achilles' heel for inhibitor discovery. However, the low affinity creates a challenge in developing robust SpCas9-PAM binding assays, which Applicants overcame by leveraging the principle of multivalency; a DNA sequence bearing multiple PAM sites will have high affinity for SpCas9. Fluorescence polarization can be used to monitor protein-DNA interaction (Lundblad, J. R.; Laurance, M.; Goodman, R. H., Fluorescence polarization analysis of protein-DNA and protein-protein interactions. *Mol Endocrinol* 1996, 10 (6), 607-12). The binding of this PAM-rich DNA to a much larger SpCas9:gRNA complex will lower DNA's tumbling rate, which can be monitored by fluorescence polarization (FIG. 35A). Applicants developed an assay that measures the change in fluorescence polarization of the fluorophore-labeled PAM-rich target DNA (henceforth called 12PAM-DNA) as it binds to the SpCas9:gRNA complex. As expected, the complexation of SpCas9:gRNA to 12PAM-DNA showed a dose-dependent increase in fluorescence polarization (FIG. 35B). Applicants confirmed that SpCas9:gRNA interaction were PAM dependent and not unspecific DNA binding, and Applicants validated this fluorescence polarization assay using competition experiments, differential scanning fluorimetry (Niesen, F. H.; Berglund, H.; Vedadi, M., The use of differential scanning fluorimetry to detect ligand interactions that promote protein stability. *Nature protocols* 2007, 2 (9), 2212-21) and bio-layer interferometry (Richardson, C. D.; Ray, G. J.; DeWitt, M. A.; Curie, G. L.; Corn, J. E., Enhancing homology-directed genome editing by catalytically active and inactive CRISPR-Cas9 using asymmetric donor DNA. *Nature biotechnology* 2016, 34 (3), 339-44).

Figures 35C, 35D:
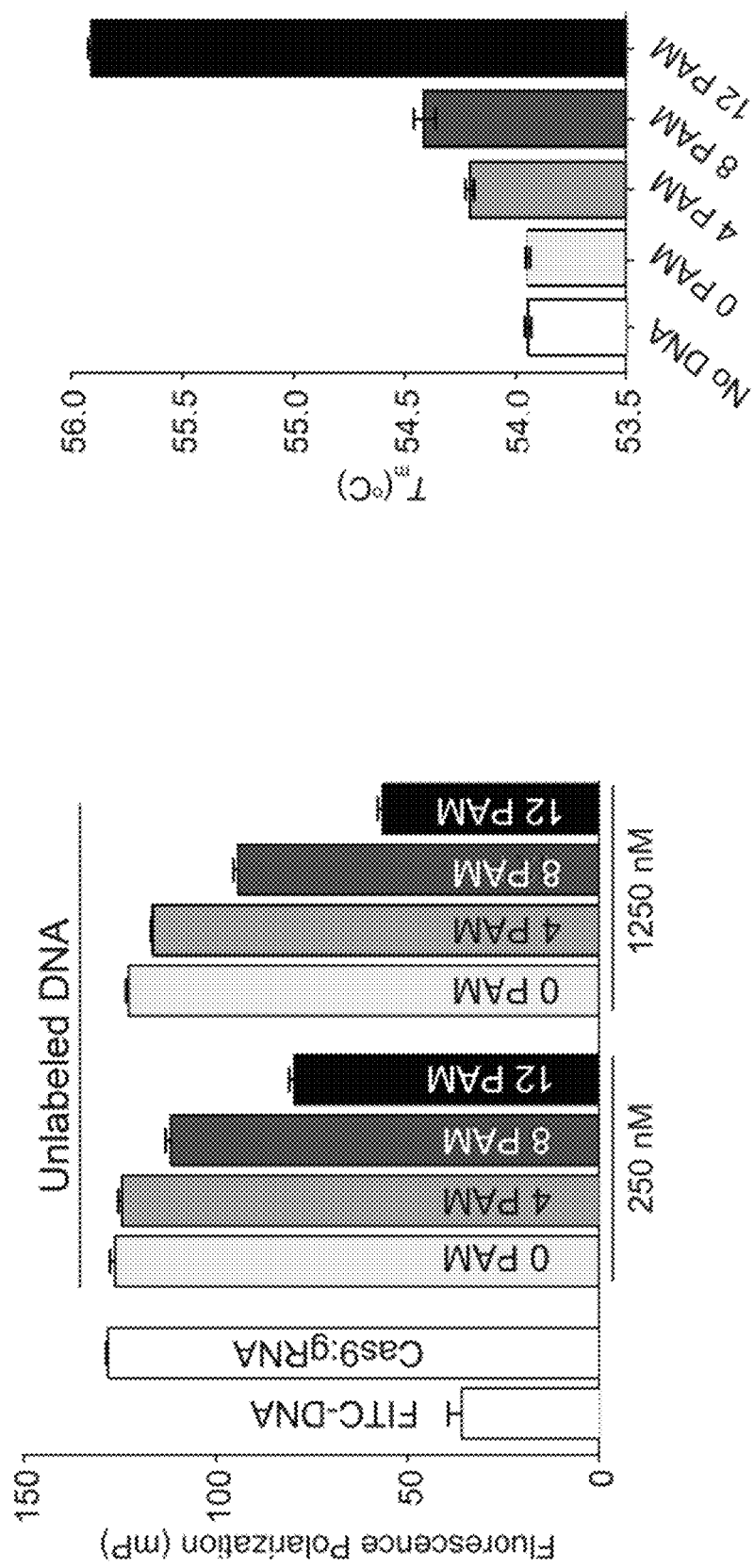
Figure 48:
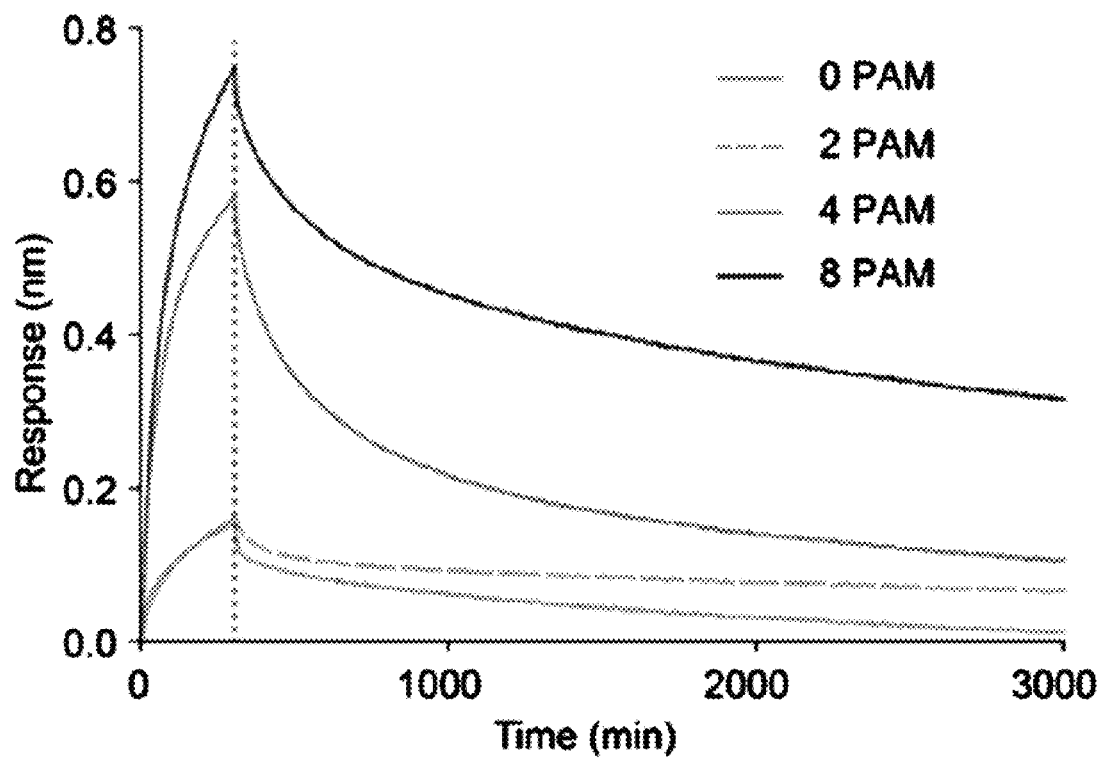
FIG. 48. Interaction of SpCas9 with ds-DNA containing a variable number of PAM sequence. Bio-Layer Interferometry (BLI) study of SpCas9:gRNA complex with ds-DNA with varying PAM sequence. Increase in the PAM number resulted in a concomitant increase in the response signal depicting higher binding affinity.

In the competition experiment, 12PAM-DNA competed with unlabelled DNA sequences containing a varying number of PAM-sites. As expected, the decrease in fluorescence polarization signal of 12PAM-DNA correlated with the number of PAM-sites on the competitor DNA (FIG. 35C) as well as the concentration of the competitor DNA. Next, Applicants used differential scanning fluorimetry, which detects ligand-induced changes in protein stability. Applicants found that the melting temperature of the SpCas9: gRNA complex increases with the number of PAM-sites on the DNA (FIG. 35D) albeit the number of bases in the DNA remained the same. Finally, bio-layer interferometry (BLI) also confirmed higher affinity for SpCas9 toward DNA sequences with more PAM-sites (FIG. 48). All these studies confirm that SpCas9:gRNA interaction with the DNA substrate were PAM specific.

Figure 49:
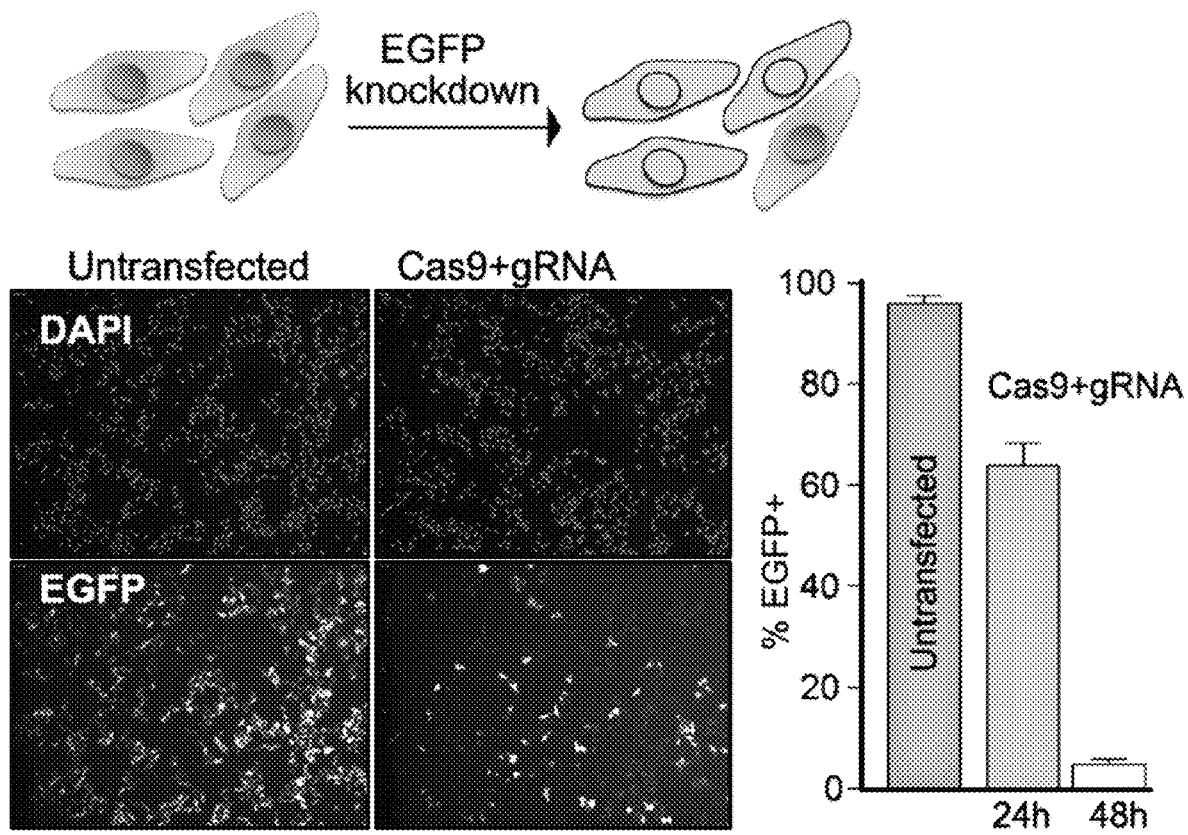
FIG. 49. Schematic representation and validation of EGFP-knockdown assay. (Top) Schematic representation of the EGFP-knockdown by SPCas9 targeting the stably expressing EGFP.PEST gene in U2OS.eGFP.PEST cells. SpCas9 induced knockout of EGFP.PEST results in the GFP fluorescence signal. (Bottom left) Representative images of the EGFP-knockdown assay in U2OS.eGFP.PEST cells. Left panels represent untransfected cells and the right panels represent post-nucleofected U2OS.eGFP.PEST cells with SpCas9 and gRNA expressing plasmids for 48 h. Scale bar=100 µm. (Bottom right) Quantified image analysis of the EGFP-knockdown assay at 24 and 48 h. Error bars represent ±S.D. from technical replicates (n=4).
Figure 50A:
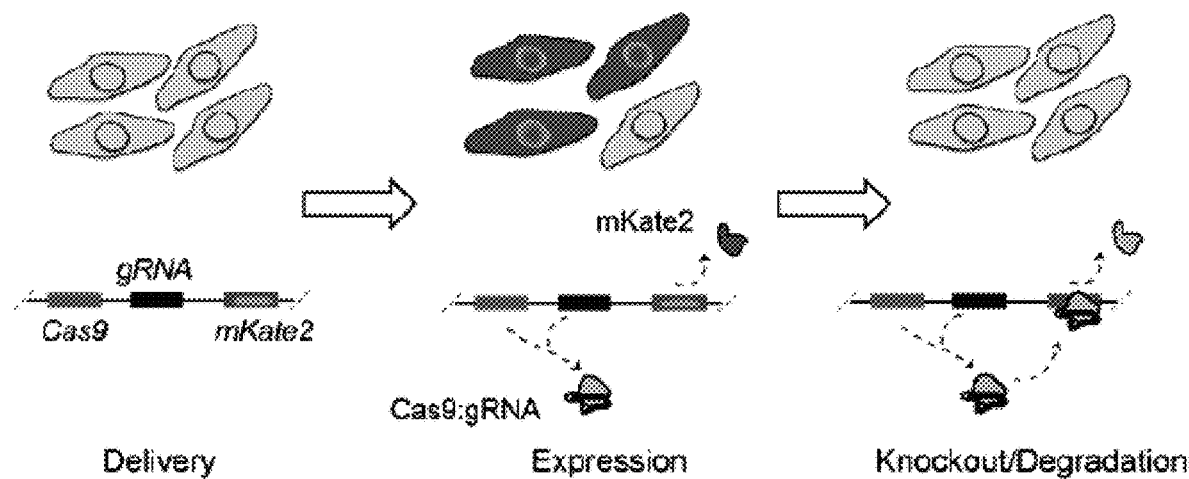
FIGS. 50A-50B. Schematic representation of mKate2 assay.

Cell-based SpCas9 Activity Assays. Applicants have also optimized several cell-based high-throughput assays to measure SpCas9 activity. Recently, Joung and co-workers have reported a U2OS.eGFP.PEST cell-line where eGFP knockout by SpCas9 leads to loss of fluorescence (Kleinstiver, B. P.; Prew, M. S.; Tsai, S. Q.; Topkar, V. V.; Nguyen, N. T.; Zheng, Z.; Gonzales, A. P.; Li, Z.; Peterson, R. T.; Yeh, J. R.; Aryee, M. J.; Joung, J. K., Engineered CRISPR-Cas9 nucleases with altered PAM specificities. *Nature* 2015, 523 (7561), 481-5; Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat. Biotechnol.* 2013, 31 (9), 822-6). By quantifying the percentage of eGFP negative cells using flow cytometry, one can estimate SpCas9 activity. Applicants have modified this assay by replacing the flow-cytometry readout with a more reproducible and high-throughput readout using a high-content, automated microscope and automated image analysis (FIG. 49) using MetaXpress, which allows for high-throughput data analysis. In the mkate2 knockdown assay, the cells are transiently transfected with a single plasmid construct (Cas9-mKate-gRNA) that encodes for both Cas9 and gRNA components along with their target mKate2, a red fluorescent protein (FIG. 50A) (Moore, R.; Spinhirne, A.; Lai, M. J.; Preisser, S.; Li, Y.; Kang, T.; Bleris, L., CRISPR-based self-cleaving mechanism for controllable gene delivery in human cells. *Nucleic Acids Res* 2015, 43 (2), 1297-303).

Figure 50B:
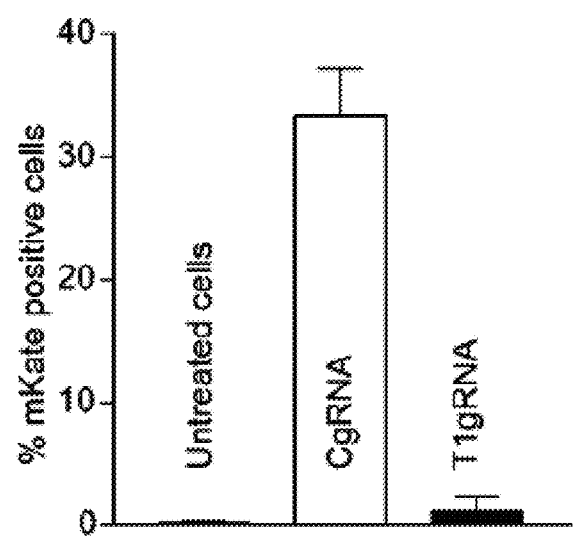

SpCas9-mediated knockdown of mKate2 expression level results in a loss of mKate signal that can be quantified using high-content imaging and automated data analysis using MetaXpress (FIG. 50B). Applicants also optimized a fluorescence-based non-homologous end joining (NHEJ) measurement was employed to determine SpCas9 nuclease activity (Nguyen, D. P.; Miyaoka, Y.; Gilbert, L. A.; Mayerl, S. J.; Lee, B. H.; Weissman, J. S.; Conklin, B. R.; Wells, J. A., Ligand-binding domains of nuclear receptors facilitate tight control of split CRISPR activity. *Nat Commun* 2016, 7, 12009).

Figures 35E, 35F:
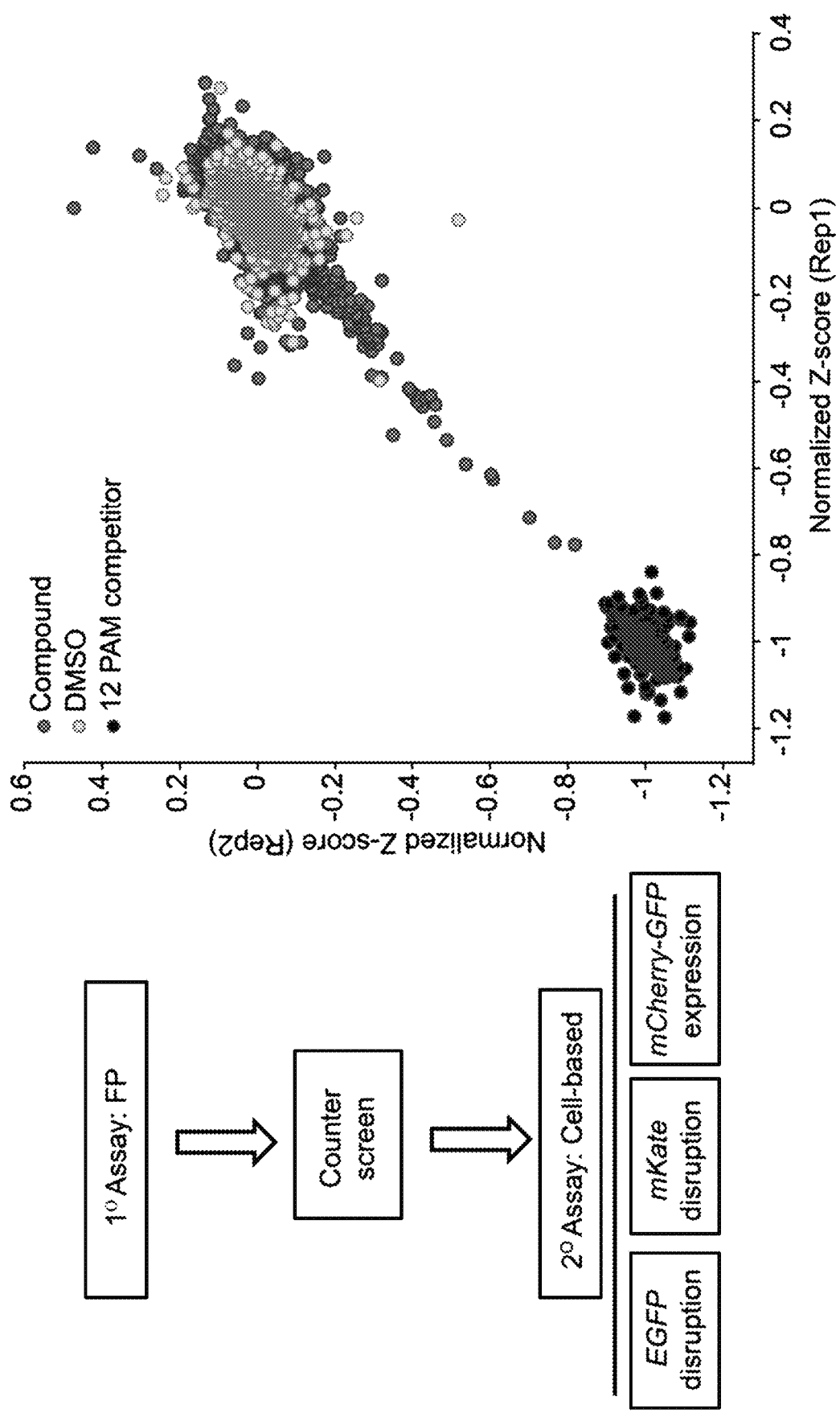
Figure 51:
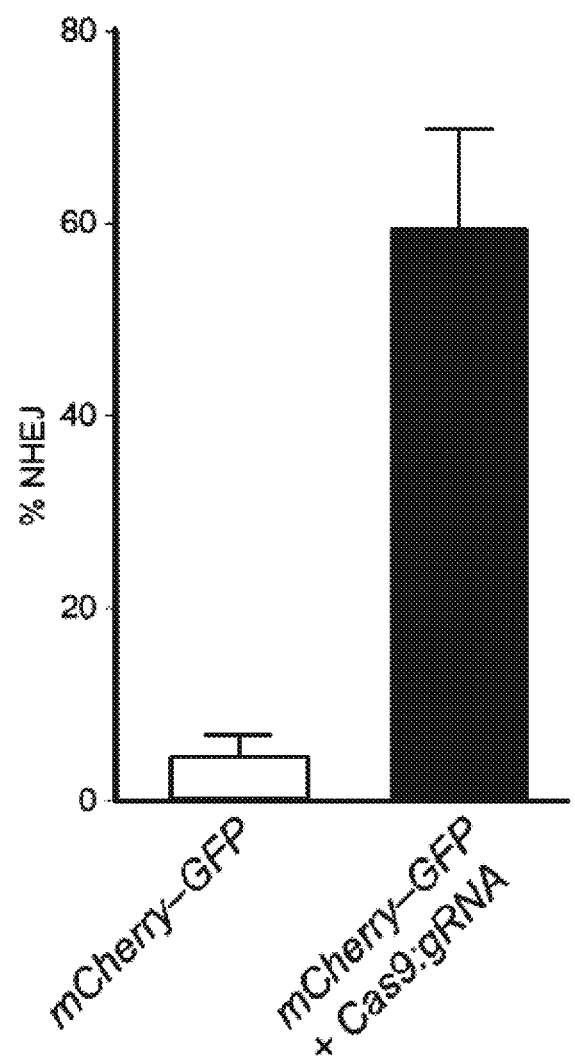
FIG. 51. Validation of mCherry-GFP expression NHEJ assay. Quantification of Cas9 induced NHEJ as measured by mCherry-GFP expression assay in HEK293T cells. The reporter construct DN66 (mCherry-TAG-GFP) alone gave a basal level of NHEJ after 24 h. However, Cas9:gRNA induced GFP expression increased the NHEJ significantly. Error bars represent ±S.D. from technical replicates (n=4).

In this assay, cells are transfected with two plasmids in an equimolar ratio, where one plasmid has an out-of-frame reporter eGFP gene downstream of mCherry gene separated by a stop codon, while the other plasmid has SpCas9 and gRNA genes that can target the stop codon linker and make the eGFP gene in-frame. Thus, SpCas9 mediated DNA cleavage induces eGFP expression which can be quantified by a high-content imaging and automated data analysis (FIG. 51). Applicants note that both eGFP-disruption and mKate2 expression assays, when deployed to identify inhibitors, are gain-of-signal assays which have much lower probability of false positives and these assays are complementary to the loss-of-signal NHEJ assay. All of these assays have been optimized to be conducted in 384-well plate format and have good Z-scores (FIG. 35E). In summary, Applicants have built up a screening pipeline with FP-based primary screening assay followed by a counter screening and subsequent cell-based secondary screening for identifying and validating SpCas9 inhibitors.

Small Molecule Screening and Hit Validation.

Figure 52:
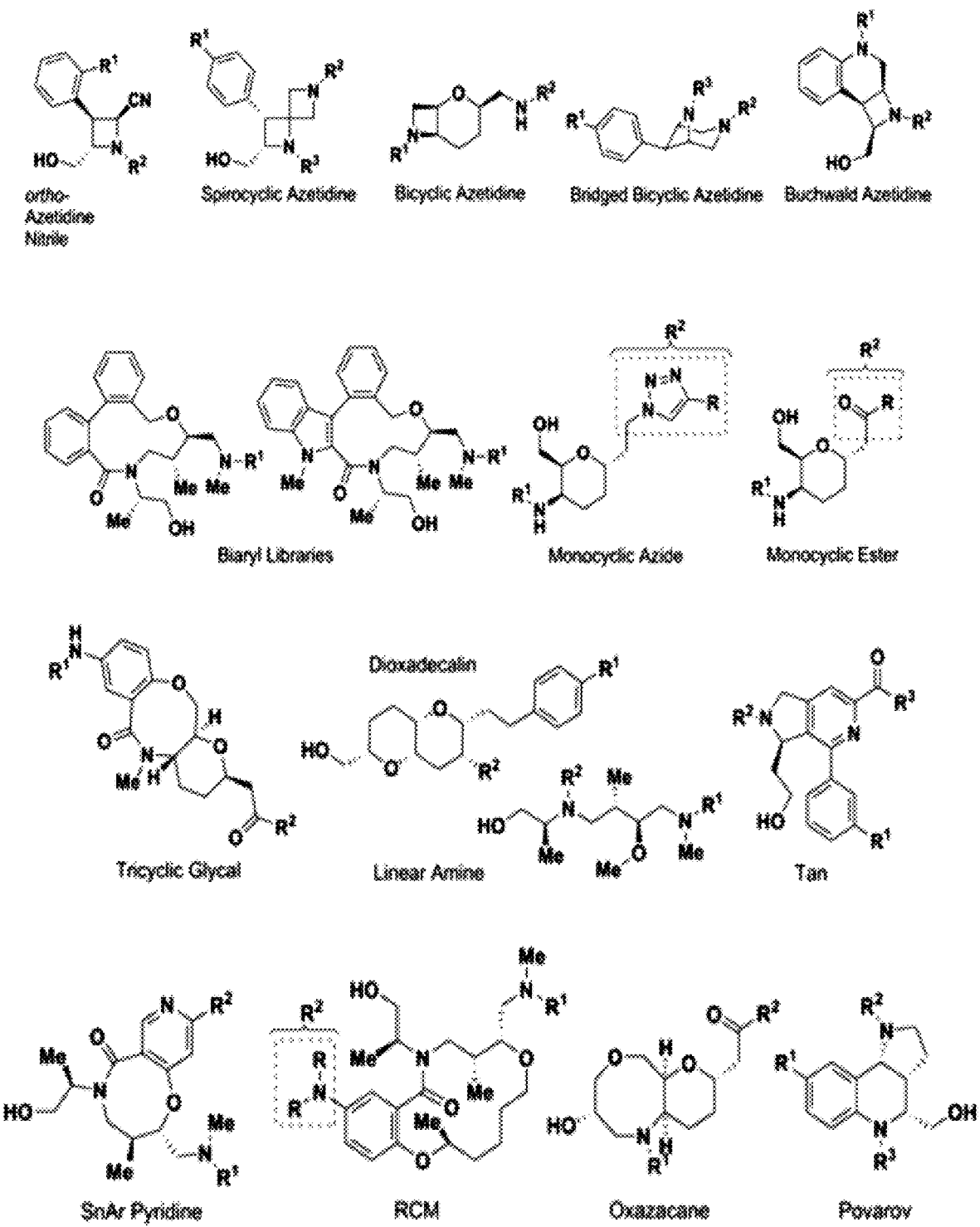
FIG. 52. Structural diversity of the DOS informer library set of compounds. Structures are the core-scaffold corresponding to each of the library and the R-groups represents the different functional moieties.

Applicants decided to leverage Broad Institute's performance diverse set as well as ~100,000 diversity-oriented synthetic (DOS) compound library as these natural-product like molecules have proved effective against microbial proteins (Burke, M. D.; Schreiber, S. L., A planning strategy for diversity-oriented synthesis. *Angew Chem Int Ed Engl* 2004, 43 (1), 46-58). However, screening all of these compounds will be inefficient as compounds within a single library are relatively similar to each other, and may perform similarly in assays. The Computational Chemical Biology group at the Broad Institute has established a list of ~10,000 compounds, called the "Informer set," that maximally represent the diversity across all DOS compounds. For the pilot screening, Applicants decided to use this "informer set" (FIG. 52) that consists of 10,000 compounds. Using fluorescence polarization-based primary assay, Applicants screened ~1x,000 compounds (informer set and performance diverse set) in two replicates (FIG. 35F) considering 12PAM-DNA without fluorophore as a positive control.

Figure 35G:
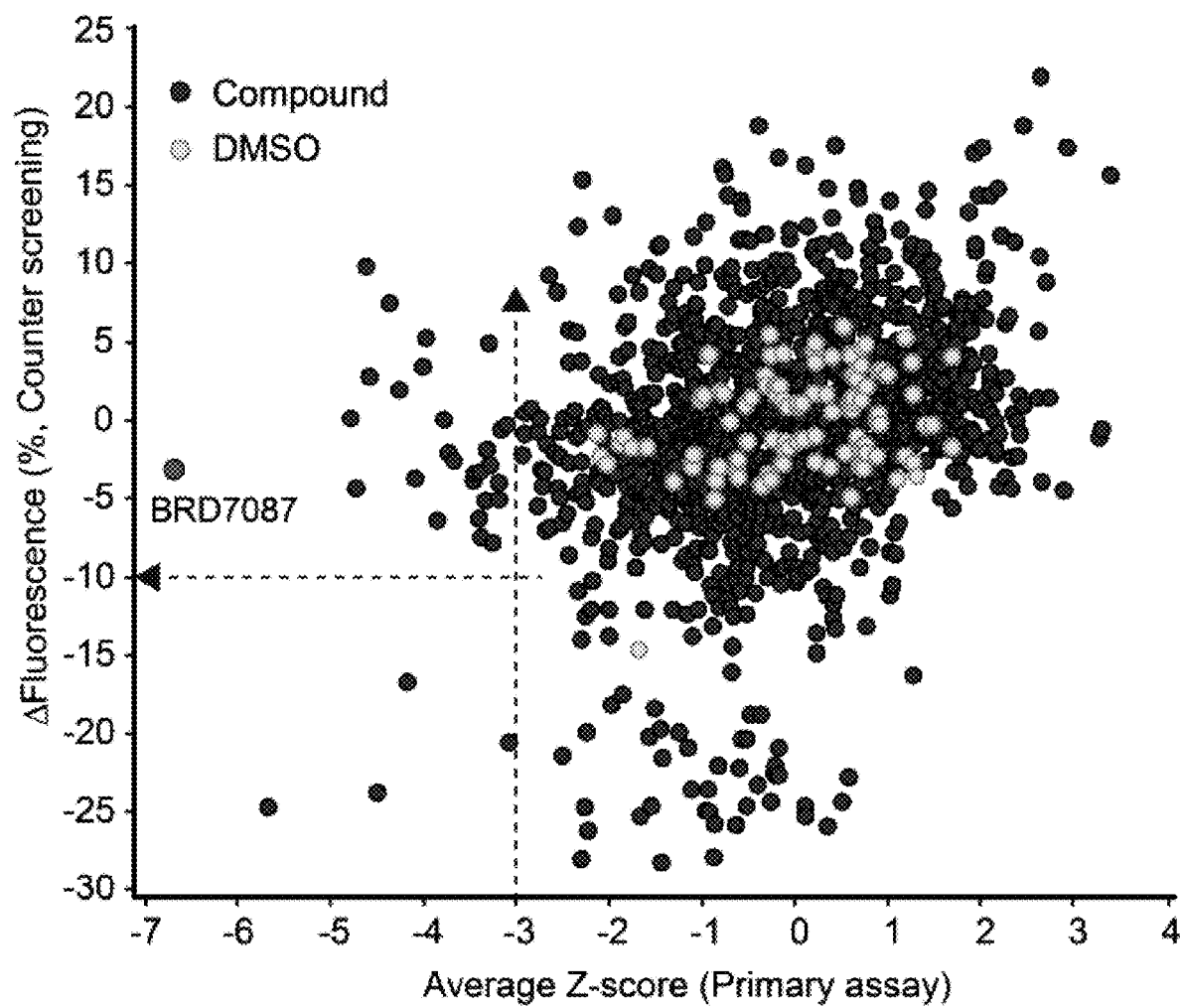
Figure 53:
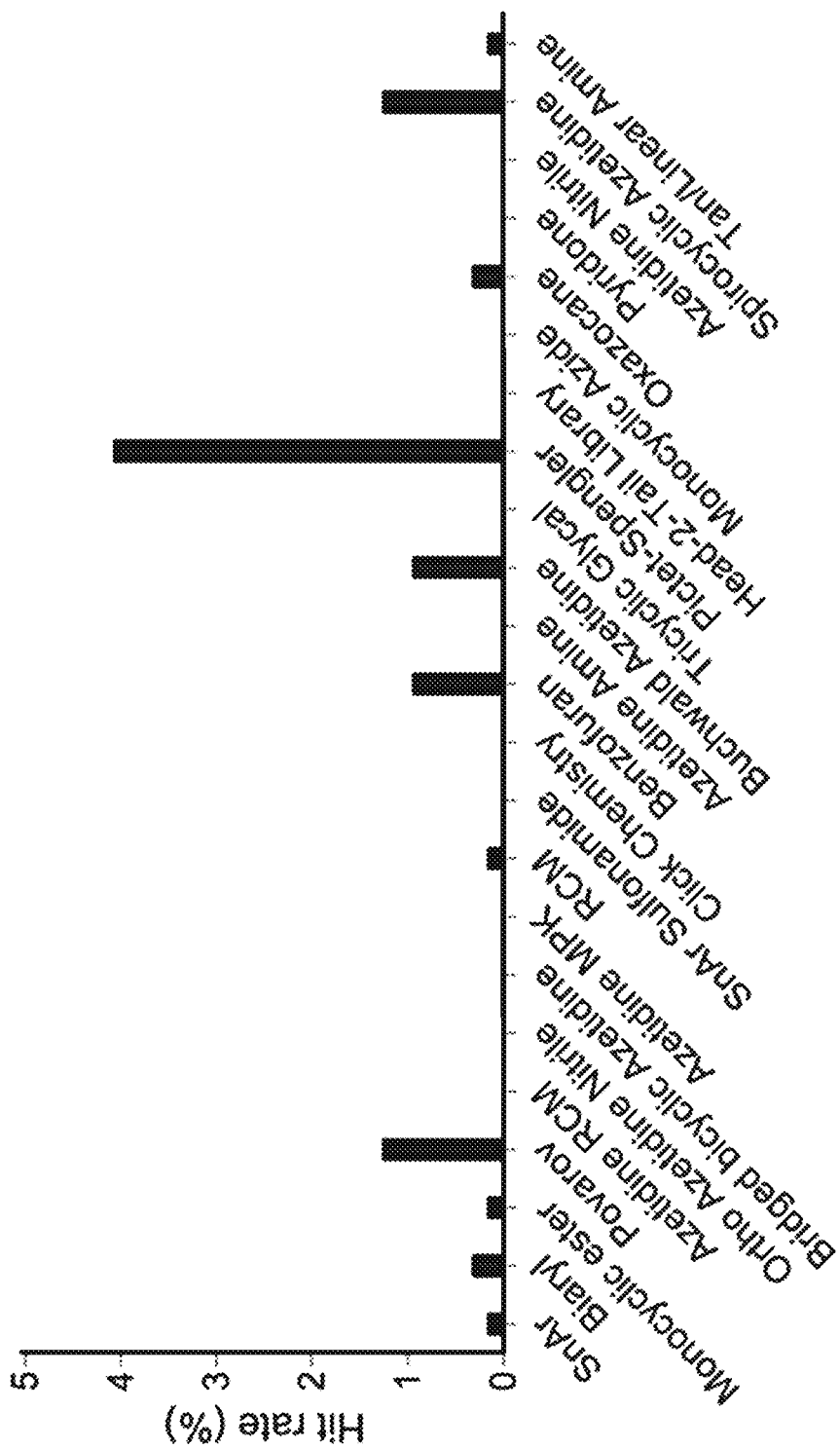
FIG. 53. Hit rate distribution of FP-based primary assay. Enrichment plot of the sub-libraries in the FP-assay emphasizing the higher hit-rate of specific libraries (% hit rate ≥1) Povarov, Pictet-Spengler, and Spirocyclic Azetidine.
Figure 54:
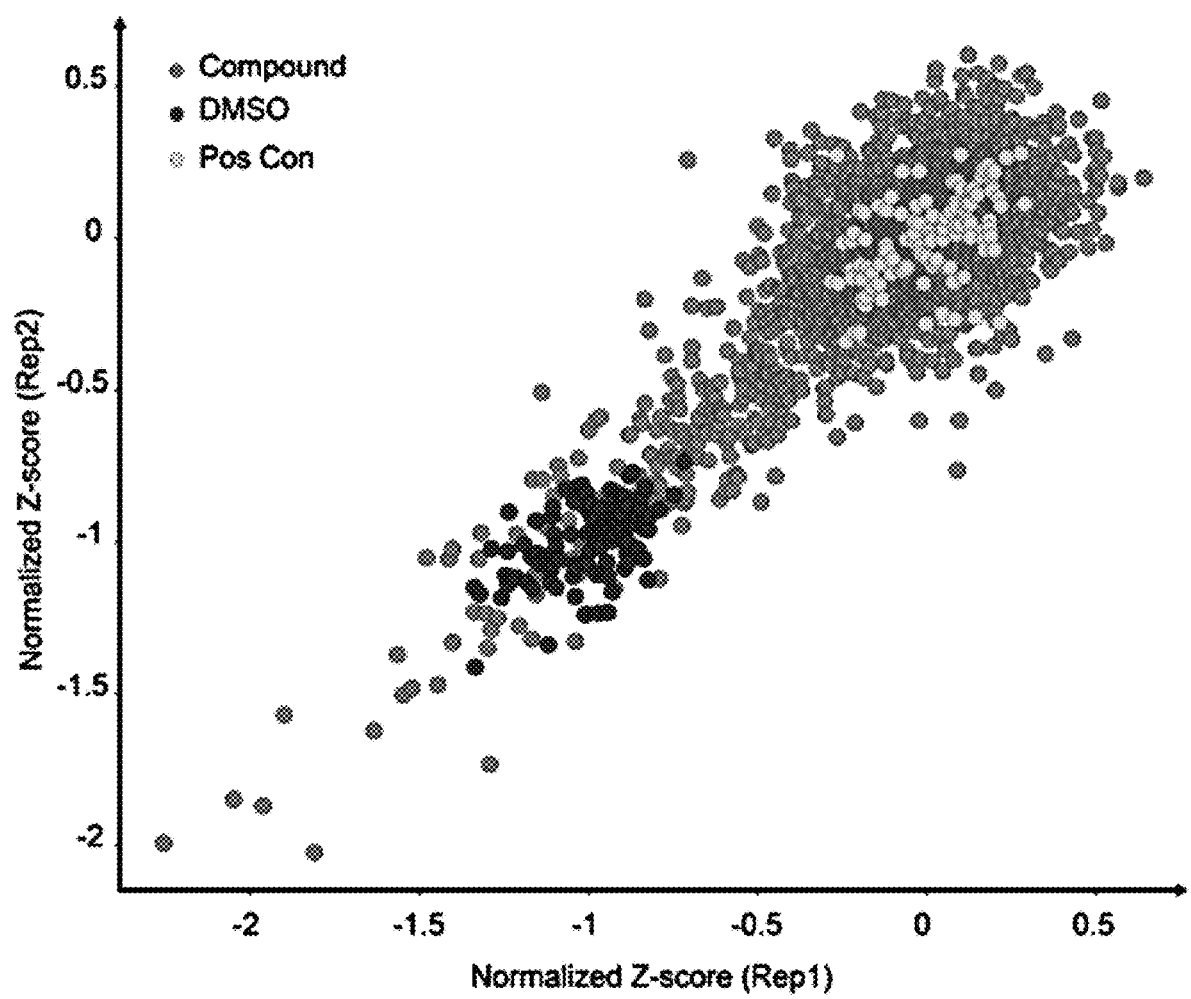
FIG. 54. Primary assay screening of Specific library. Primary screening assay results of specific library Pictet-Spengler in an FP-based assay. The assay was performed in duplicate and the each of the replicate data was plotted on two different axes.
Figure 55:
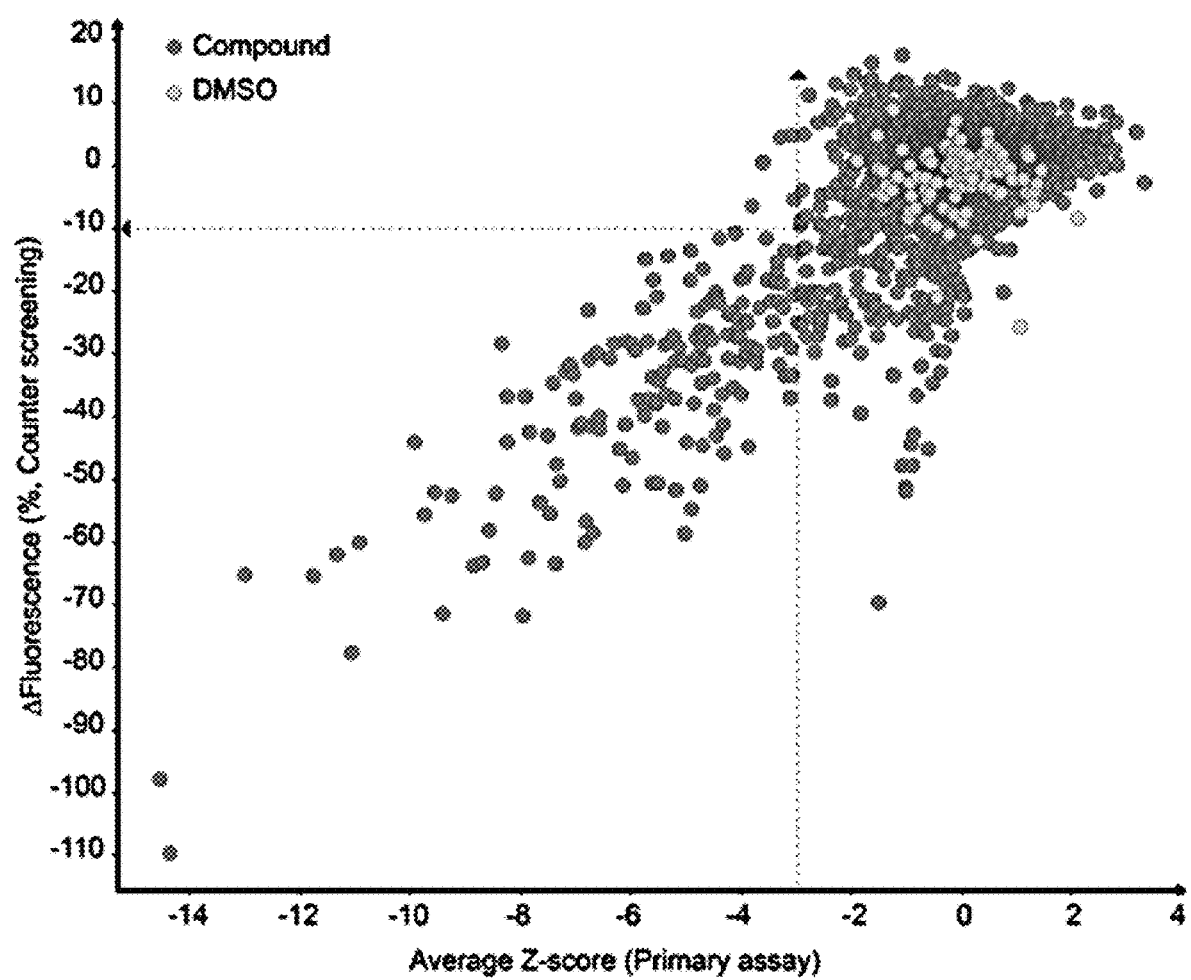
FIG. 55. Counter-screening data for specific library Pictet-Spengler. FP-assay results of specific library Pictet-Spengler in the primary assay and counter-screening assay. The screening assay was performed in duplicate and the counter-screening assay was performed in singlicate. The average Z-score value from two-replicate screening data was plotted along the X-axis while the counter-screening data was plotted along the Y-axis.
Figure 56:
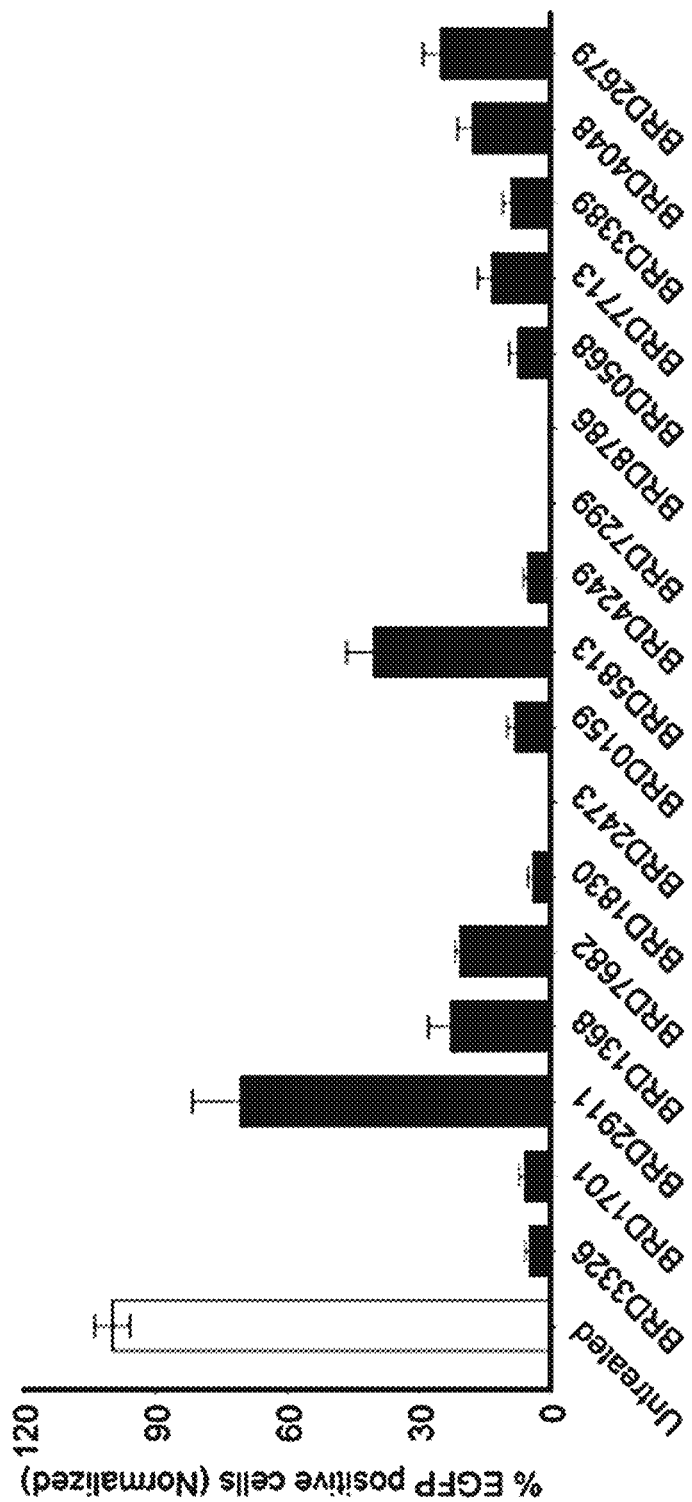
FIG. 56. Testing of counter-screened Pictet-Spengler hit compounds in EGFP-knockdown based secondary assay. Recovery of EGFP signal by compounds in the Cas9-mediated EGFP-knockdown assay. U2OS.eGFP.PEST cells were Nucleofected with SpCas9 and gRNA plasmids and incubated either in the presence of vehicle or 20 µM compounds for 48 h. Error bars represent ±S.D. from technical replicates (n=4).
Figure 57:
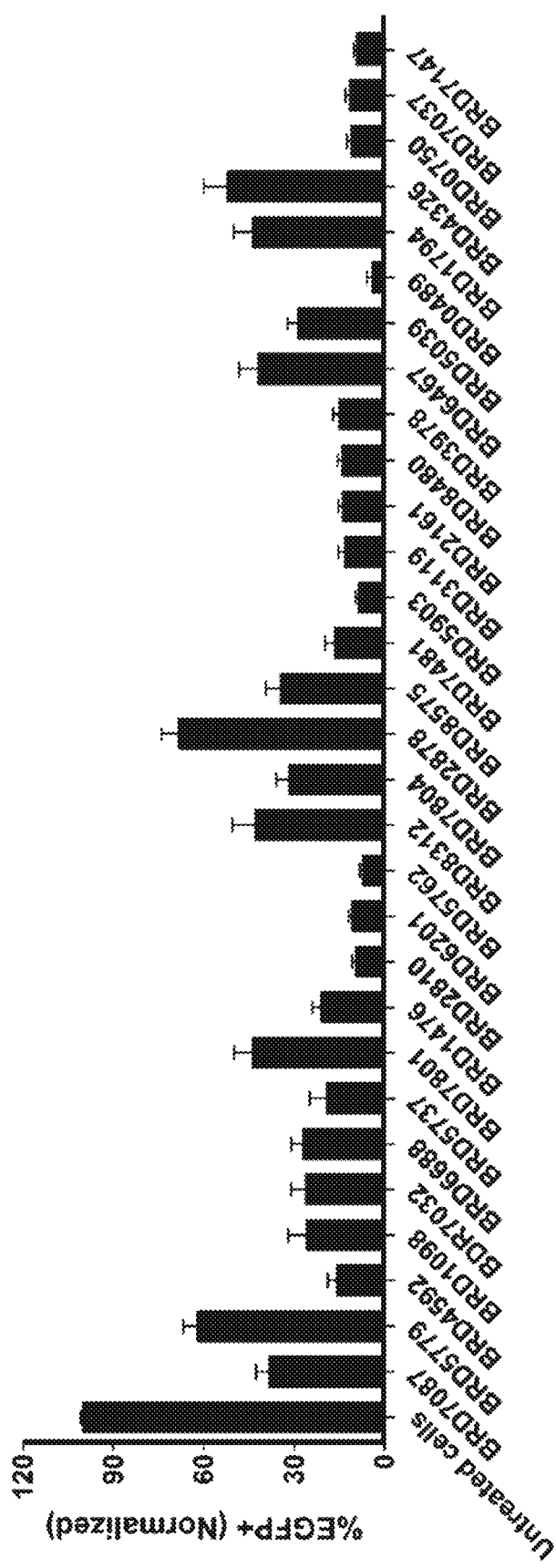
FIG. 57. Testing of counter-screened Povarov hit compounds in EGFP-knockdown based secondary assay. Recovery of EGFP signal by compounds in the Cas9-mediated EGFP-knockdown assay. U2OS.eGFP.PEST cells were Nucleofected with SpCas9 and gRNA plasmids and incubated either in the presence of vehicle or 20 µM compounds for 48 h. Error bars represent ±S.D. from technical replicates (n=4).
Figure 58:
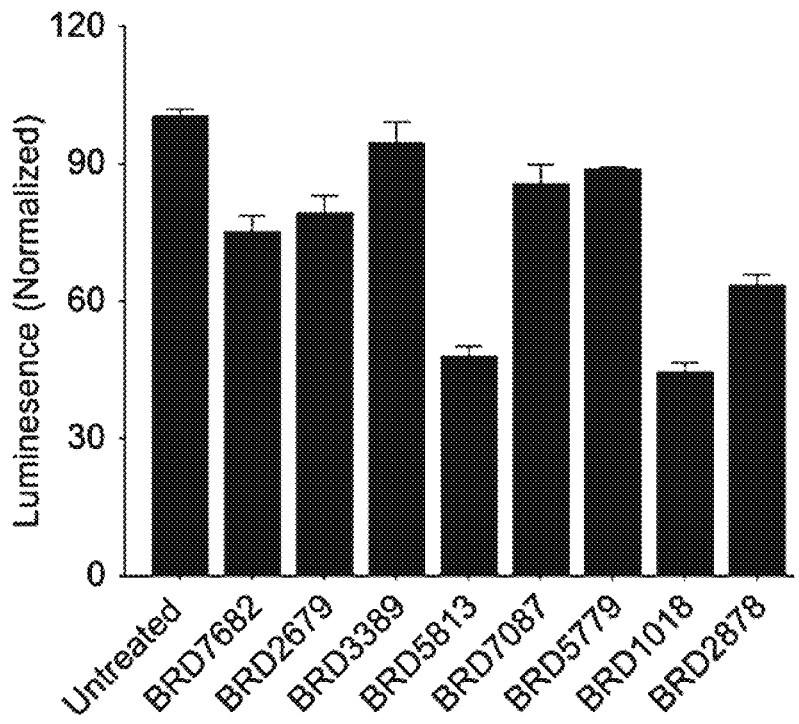
FIG. 58. Cell viability assay (ATP content) of U2OS.eGFP.PEST cells in the presence of compounds. Measurement of ATP content of U2OS.eGFP.PEST cells upon incubating with 20 µM compound for 48 h. Error bars represent ±S.D. from technical replicates (n=3).

Following the conventional norm, Applicants selected small molecules that lowered the fluorescence polarization signal by >3a of that of DMSO as "candidates" and categorized them according to their compound-class to generate an enrichment plot (FIG. 53). The majority of the candidates belonged to two compound libraries, Povarov and Pictet-Spengler, suggesting a strong structure-activity relationship. Applicants initiated the structure-activity studies to identify the key pharmacophore required for SpCas9 inhibition by these candidates. Traditionally, this process involves synthesis and potency evaluation of the structural analogs of the candidate compounds iteratively and is low throughput, tedious, labor-intensive, expensive, and time-consuming. Conveniently, >5,000 analogs of our candidate compounds already existed at the Broad Institute as a part of their compound library, and Applicants tested all of these specific library analogs in our FP-based screening assay (FIG. 54). Moreover, Applicants also tested the compounds by a counter-screen assay that measures the inherent fluorescence of these compounds to eliminate false positives (FIG. 35G and FIG. 55). Subsequently, Applicants performed a structure based computational similarity search to widen the pharmacological scope. Applicants then tested all the hit compounds and their similar analogs (Tables 6 and 7) in cell-based secondary assays. Applicants tested the short-listed compounds in a cell-based eGFP-disruption assay and identified the most potent candidates based on both eGFP signal recovery (FIGS. 56 and 57) and cytotoxicity (FIG. 58). Applicants resynthesized and thoroughly characterized the most potent and non-toxic compounds, BRD7087 and BRD5779 (FIG. 36A), by $^1$H and $^{13}$C NMR, $^{19}$F NMR, HRMS, Chiral SFC, and IR to validate the analytical integrity (FIG. 46B-46E). Applicants determined the solubilities of the synthesized compounds by mass spectroscopy and found that both the compounds showed no detectable aggregation up to ~75 μM concentration in PBS (FIG. 58).

TABLE 6

List of hit compounds from the counter-screening assay of
Pictet-Spengler library and their structurally similar analogs.

| Index | Compound ID | Structure |
|-------|-------------|-----------|
| 1 | BRD3326 | |
| 2 | BRD1701 | 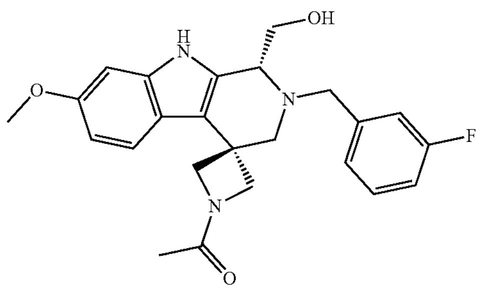 |
| 3 | BRD2911 | 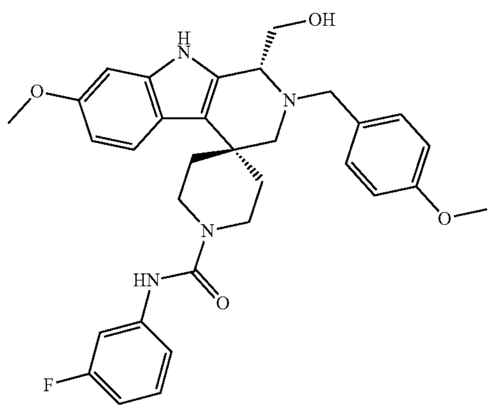 |
| 4 | BRD1368 | 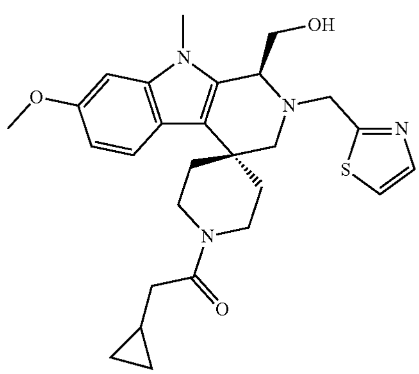 |
| 5 | BRD7682 | 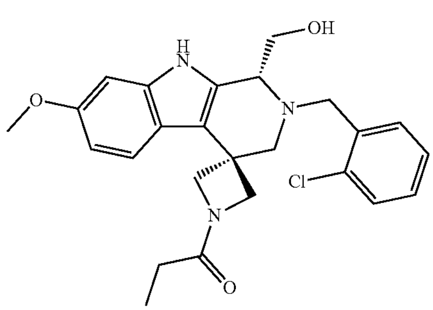 |

TABLE 6-continued

List of hit compounds from the counter-screening assay of
Pictet-Spengler library and their structurally similar analogs.

| Index | Compound ID | Structure |
|-------|-------------|-----------|
| 6 | BRD1830 | 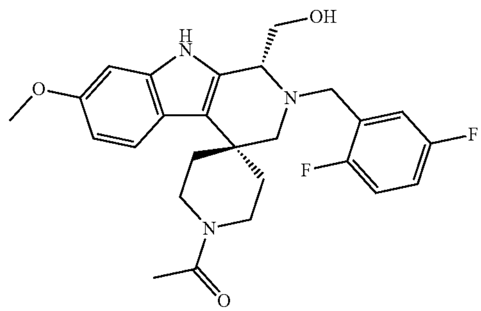 |
| 7 | BRD2473 | 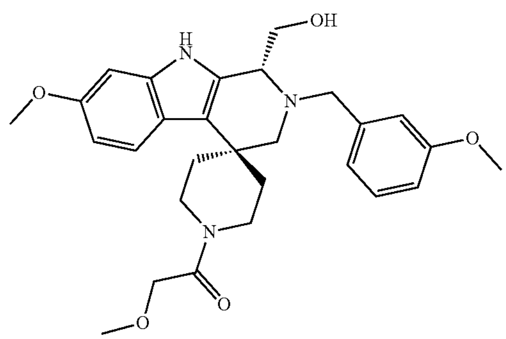 |
| 8 | BRD0159 | |
| 9 | BRD5813 | 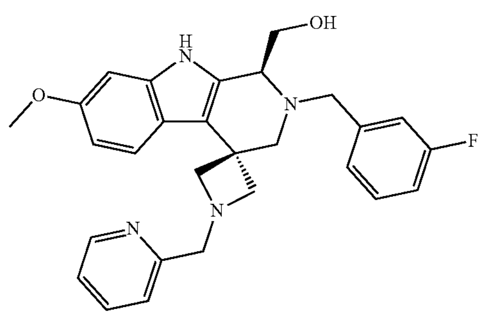 |
| 10 | BRD4249 | |
| 11 | BRD7299 | |
| 12 | BRD8786 | 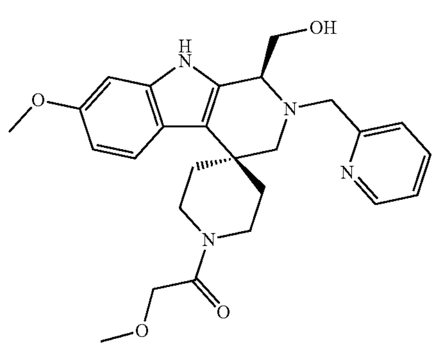 |

TABLE 6-continued

List of hit compounds from the counter-screening assay of
Pictet-Spengler library and their structurally similar analogs.

| Index | Compound ID | Structure |
|-------|-------------|-----------|
| 13 | BRD0568 | |
| 14 | BRD7713 | 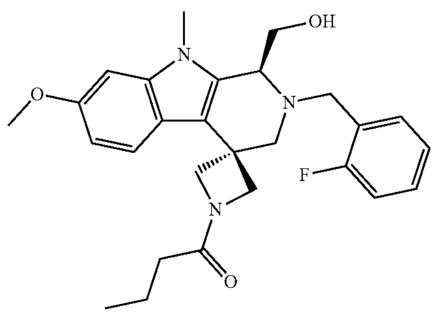 |
| 15 | BRD3389 | 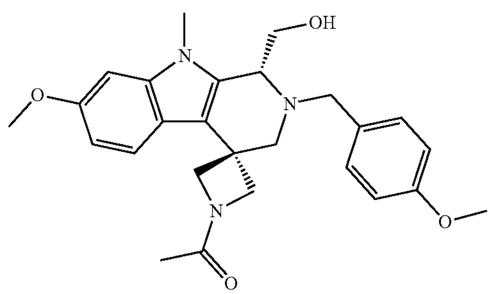 |
| 16 | BRD4048 | 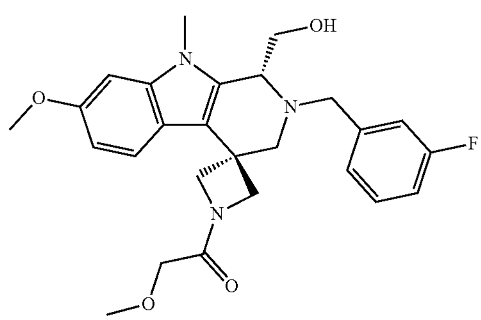 |
| 17 | BRD2679 | 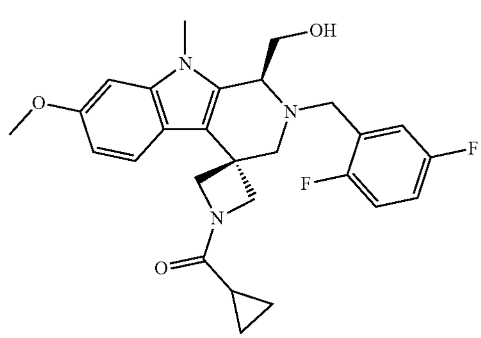 |
| 18 | BRD3326 | |

TABLE 7
List of hit compounds from the counter-screening assay of Povarov library and their structurally similar analogs.
Table 7
| Index | Compound ID | Structure |
|---|---|---|
| 1 | BRD7087 | 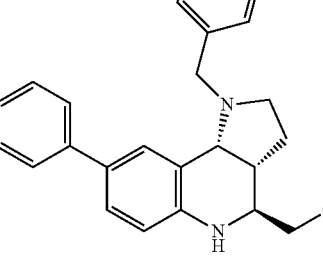 |
| 2 | BRD5779 | 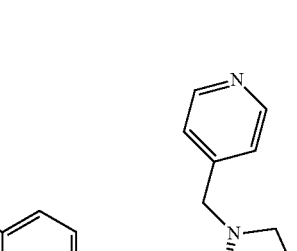 |
| 3 | BRD4592 | 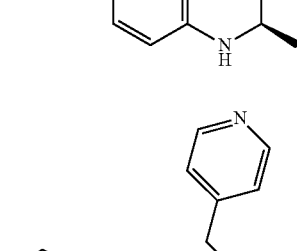 |
| 4 | BRD1098 | 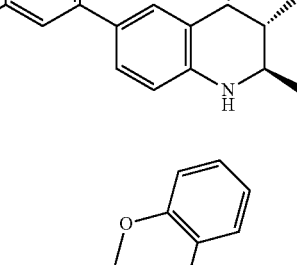 |

TABLE 7-continued

List of hit compounds from the counter-screening assay
of Povarov library and their structurally similar analogs.
Table 7

| Index | Compound ID | Structure |
|-------|-------------|-----------|
| 5 | BRD7032 | 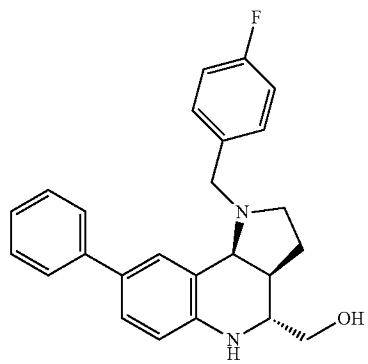 [SMILES: OC[C@@H]1Nc2ccc(-c3ccccc3)cc2[C@@H]2[C@H]1CCN2Cc1ccc(F)cc1] |
| 6 | BRD6688 | 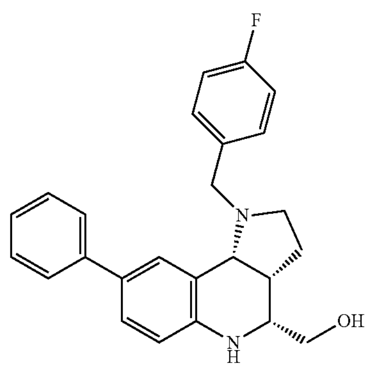 [SMILES: OC[C@@H]1Nc2ccc(-c3ccccc3)cc2[C@H]2[C@@H]1CCN2Cc1ccc(F)cc1] |
| 7 | BRD5737 | 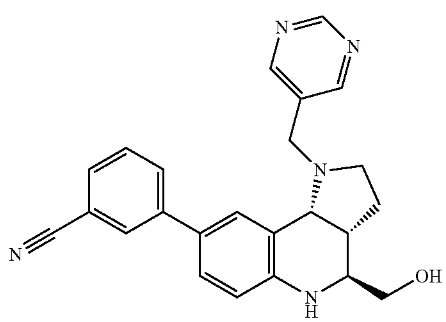 [SMILES: N#Cc1cccc(-c2ccc3c(c2)[C@H]2[C@H](CCN2Cc2cncnc2)[C@@H](CO)N3)c1] |
| 8 | BRD7801 | 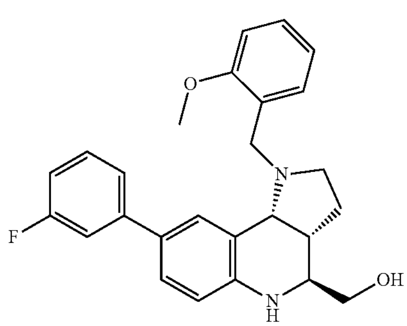 [SMILES: COc1ccccc1CN1CC[C@@H]2[C@@H](CO)Nc3ccc(-c4cccc(F)c4)cc3[C@@H]21] |

TABLE 7-continued

List of hit compounds from the counter-screening assay
of Povarov library and their structurally similar analogs.
Table 7

| Index | Compound ID | Structure |
|-------|-------------|-----------|
| 9 | BRD1476 | 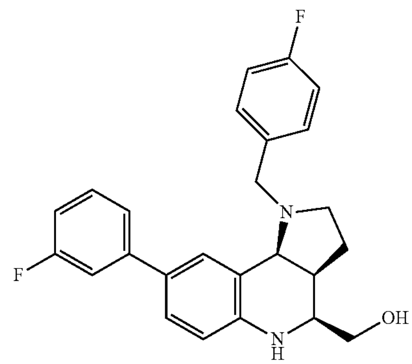 [SMILES: OC[C@H]1Nc2ccc(-c3cccc(F)c3)cc2[C@@H]2[C@H]1CCN2Cc1ccc(F)cc1] |
| 10 | BRD2810 | |
| 11 | BRD6201 | 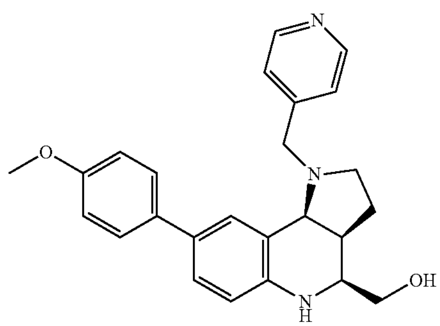 [SMILES: COc1ccc(-c2ccc3c(c2)[C@@H]2[C@@H](CCN2Cc2ccncc2)[C@@H](CO)N3)cc1] |
| 12 | BRD5762 | 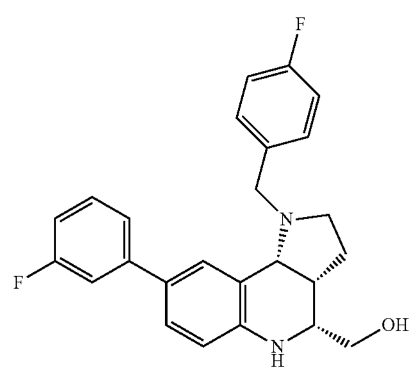 [SMILES: OC[C@@H]1Nc2ccc(-c3cccc(F)c3)cc2[C@H]2[C@@H]1CCN2Cc1ccc(F)cc1] |
| 13 | BRD8312 | 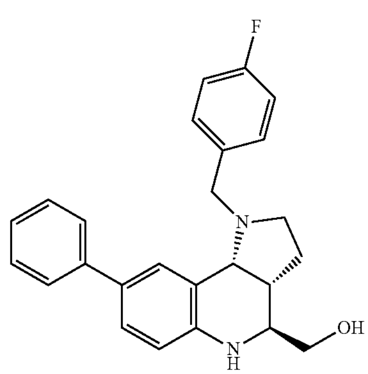 [SMILES: OC[C@H]1Nc2ccc(-c3ccccc3)cc2[C@H]2[C@@H]1CCN2Cc1ccc(F)cc1] |

TABLE 7-continued

List of hit compounds from the counter-screening assay
of Povarov library and their structurally similar analogs.
Table 7

| Index | Compound ID | Structure |
|-------|-------------|-----------|
| 14 | BRD7804 | 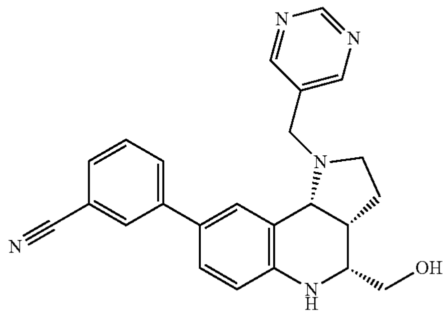 [SMILES: N#Cc1cccc(-c2ccc3c(c2)[C@H]2[C@H](CCN2Cc2cncnc2)[C@H](CO)N3)c1] |
| 15 | BRD2878 | 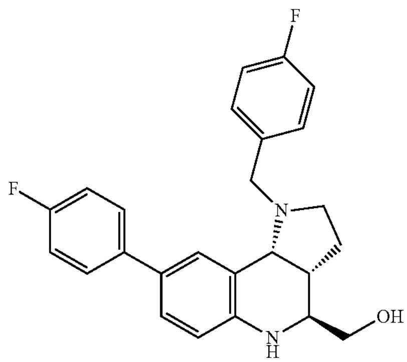 [SMILES: OC[C@H]1Nc2ccc(-c3ccc(F)cc3)cc2[C@H]2[C@@H]1CCN2Cc1ccc(F)cc1] |
| 16 | BRD8575 | 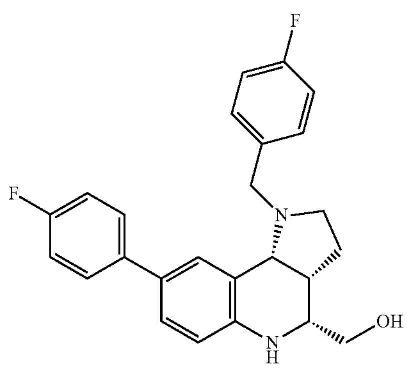 [SMILES: OC[C@@H]1Nc2ccc(-c3ccc(F)cc3)cc2[C@H]2[C@@H]1CCN2Cc1ccc(F)cc1] |
| 17 | BRD7481 | 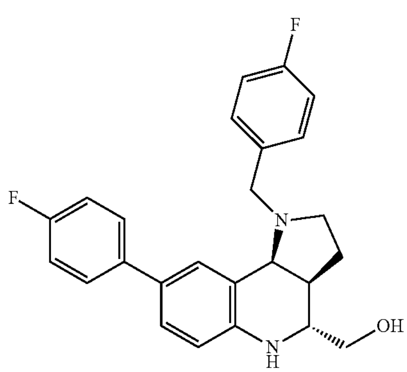 [SMILES: OC[C@@H]1Nc2ccc(-c3ccc(F)cc3)cc2[C@@H]2[C@H]1CCN2Cc1ccc(F)cc1] |

TABLE 7-continued
List of hit compounds from the counter-screening assay of Povarov library and their structurally similar analogs.
Table 7
| Index | Compound ID | Structure |
|---|---|---|
| 18 | BRD5903 | 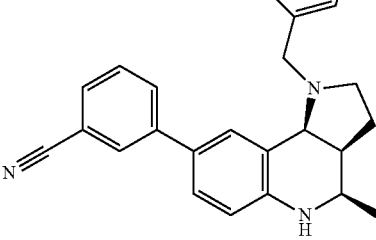 |
| 19 | BRD3119 | 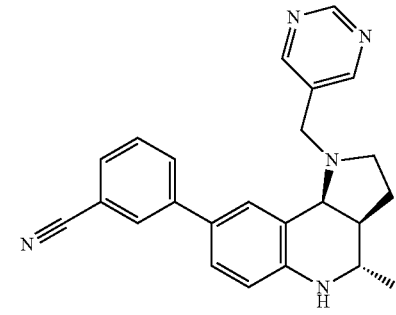 |
| 20 | BRD2161 | 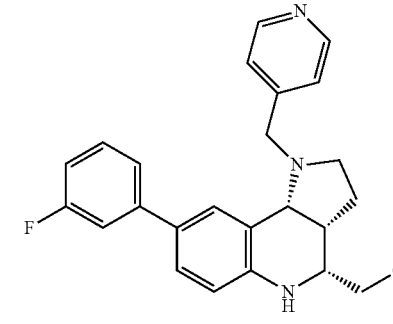 |
| 21 | BRD8480 | 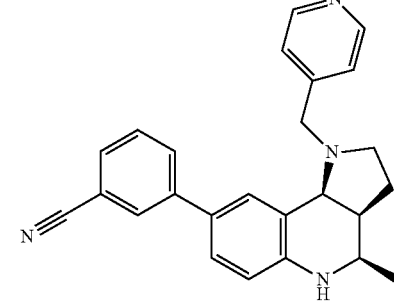 |

TABLE 7-continued

List of hit compounds from the counter-screening assay
of Povarov library and their structurally similar analogs.
Table 7

| Index | Compound ID | Structure |
|---|---|---|
| 22 | BRD3978 | 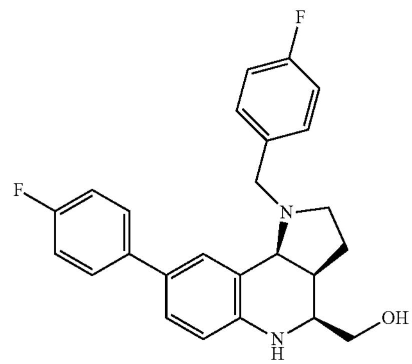 [SMILES: OC[C@H]1Nc2ccc(-c3ccc(F)cc3)cc2[C@@H]2[C@H]1CCN2Cc1ccc(F)cc1] |
| 23 | BRD6467 | 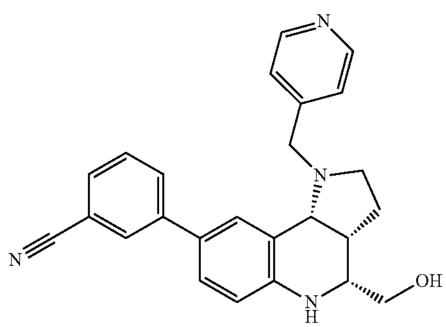 [SMILES: N#Cc1cccc(-c2ccc3c(c2)[C@H]2[C@H](CCN2Cc2ccncc2)[C@H](CO)N3)c1] |
| 24 | BRD5039 | 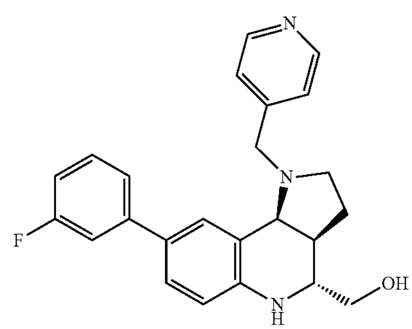 [SMILES: OC[C@@H]1Nc2ccc(-c3cccc(F)c3)cc2[C@@H]2[C@H]1CCN2Cc1ccncc1] |
| 25 | BRD0489 | 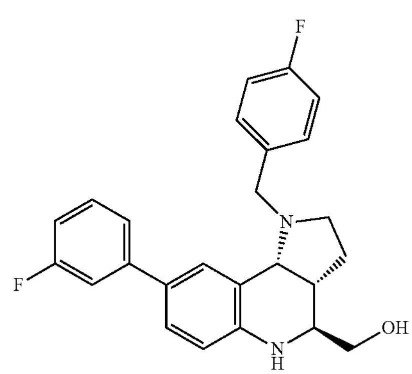 [SMILES: OC[C@H]1Nc2ccc(-c3cccc(F)c3)cc2[C@H]2[C@@H]1CCN2Cc1ccc(F)cc1] |

TABLE 7-continued

List of hit compounds from the counter-screening assay
of Povarov library and their structurally similar analogs.
Table 7

| Index | Compound ID | Structure |
|-------|-------------|-----------|
| 26 | BRD1794 | 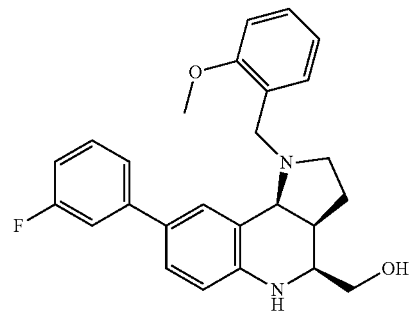 [SMILES: COc1ccccc1CN1CC[C@@H]2[C@H]1c1cc(-c3cccc(F)c3)ccc1N[C@@H]2CO] |
| 27 | BRD4326 | 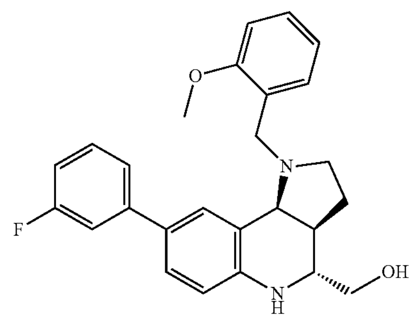 [SMILES: COc1ccccc1CN1CC[C@H]2[C@H](CO)Nc3ccc(-c4cccc(F)c4)cc3[C@H]21] |
| 28 | BRD0750 | 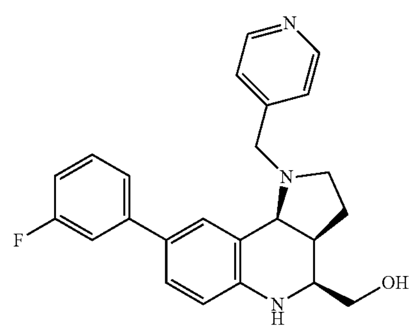 [SMILES: OC[C@H]1Nc2ccc(-c3cccc(F)c3)cc2[C@@H]2[C@H]1CCN2Cc1ccncc1] |
| 29 | BRD7037 | 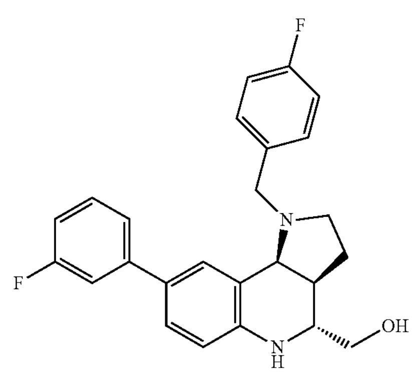 [SMILES: OC[C@@H]1Nc2ccc(-c3cccc(F)c3)cc2[C@@H]2[C@H]1CCN2Cc1ccc(F)cc1] |
| 30 | BRD7147 | |

Figures 36A, 36B, 36C:
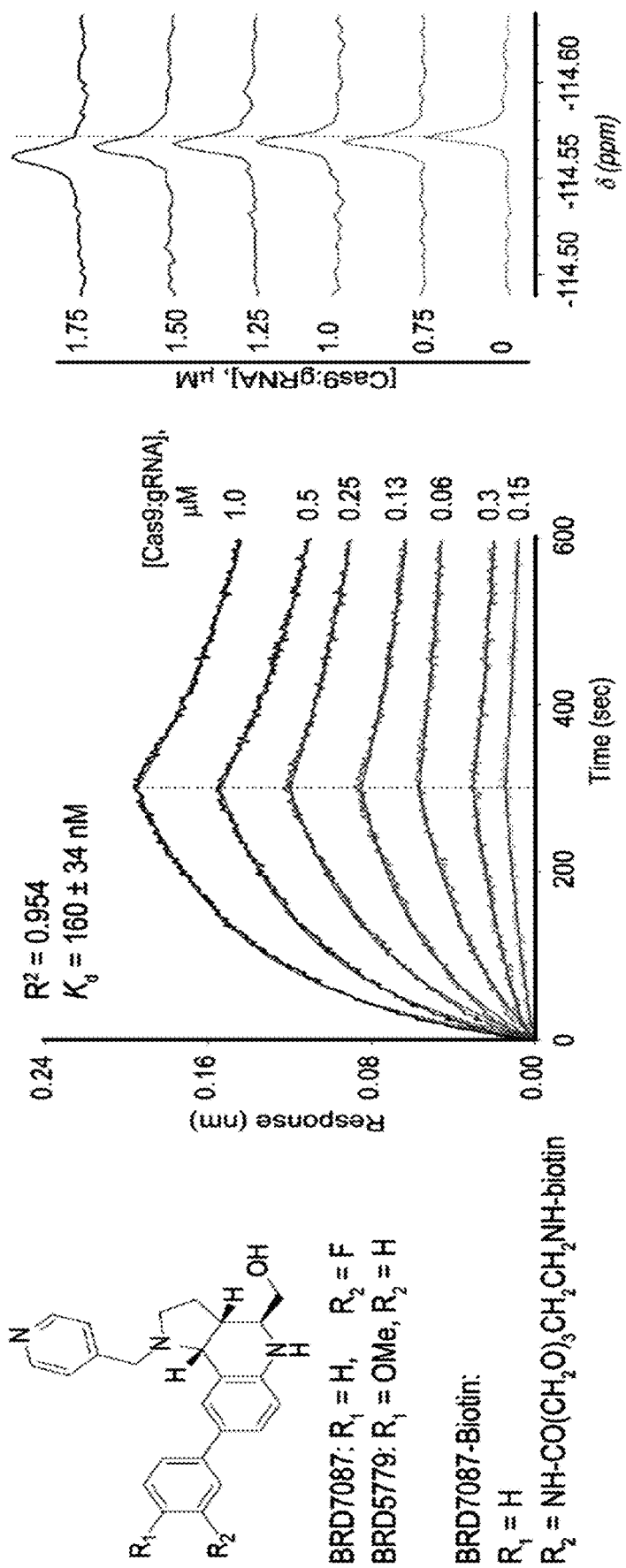
FIGS. 36A-36C. Biochemical characterization of small molecule-SpCas9 binding.
Figure 59:
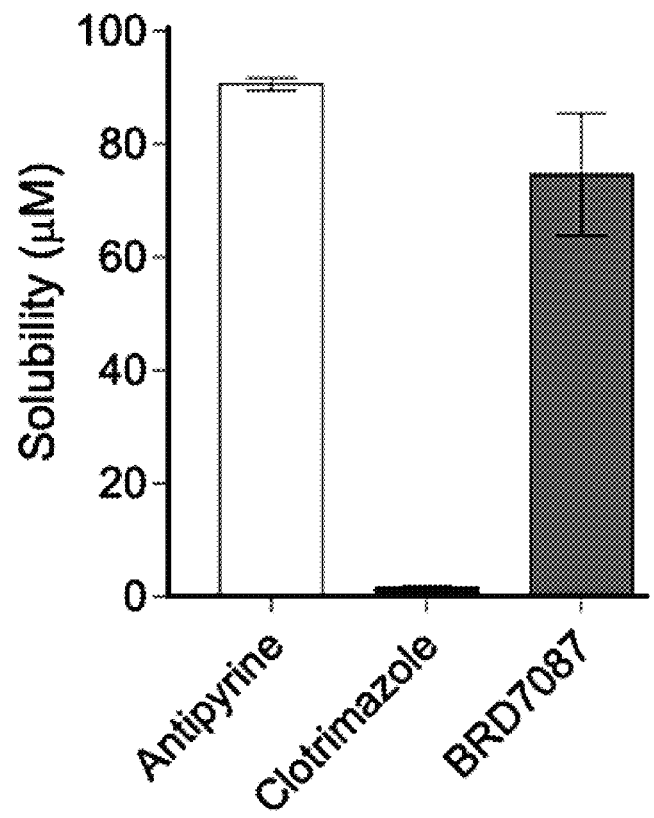
FIG. 59. The solubility of BRD7087 compound in PBS as determined by Mass spectroscopy after 24 h of incubation at room temperature. Compounds Antipyrine and Clotrimazole have been used as the positive controls.
Figure 60A:
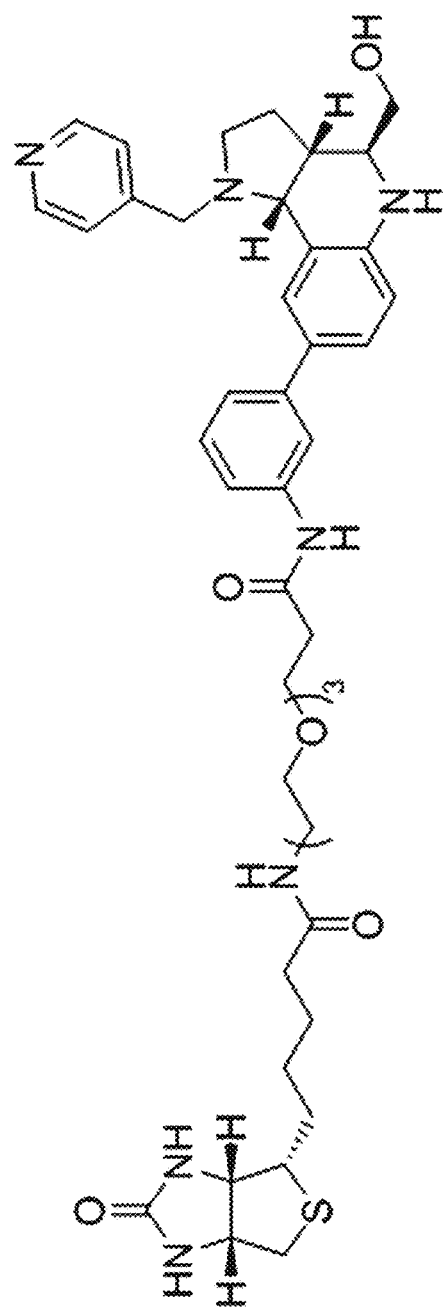
FIGS. 60A-60B. Structure of compound (FIG. 60A) BRD7087-Biotin conjugate and (FIG. 60B) Biotin-Linker.
Figure 60B:
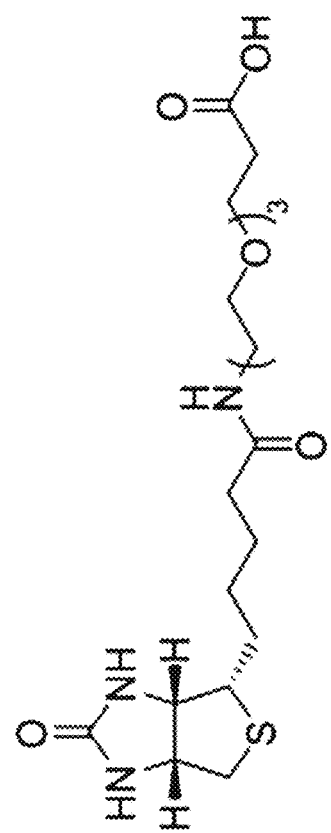
Figure 61:
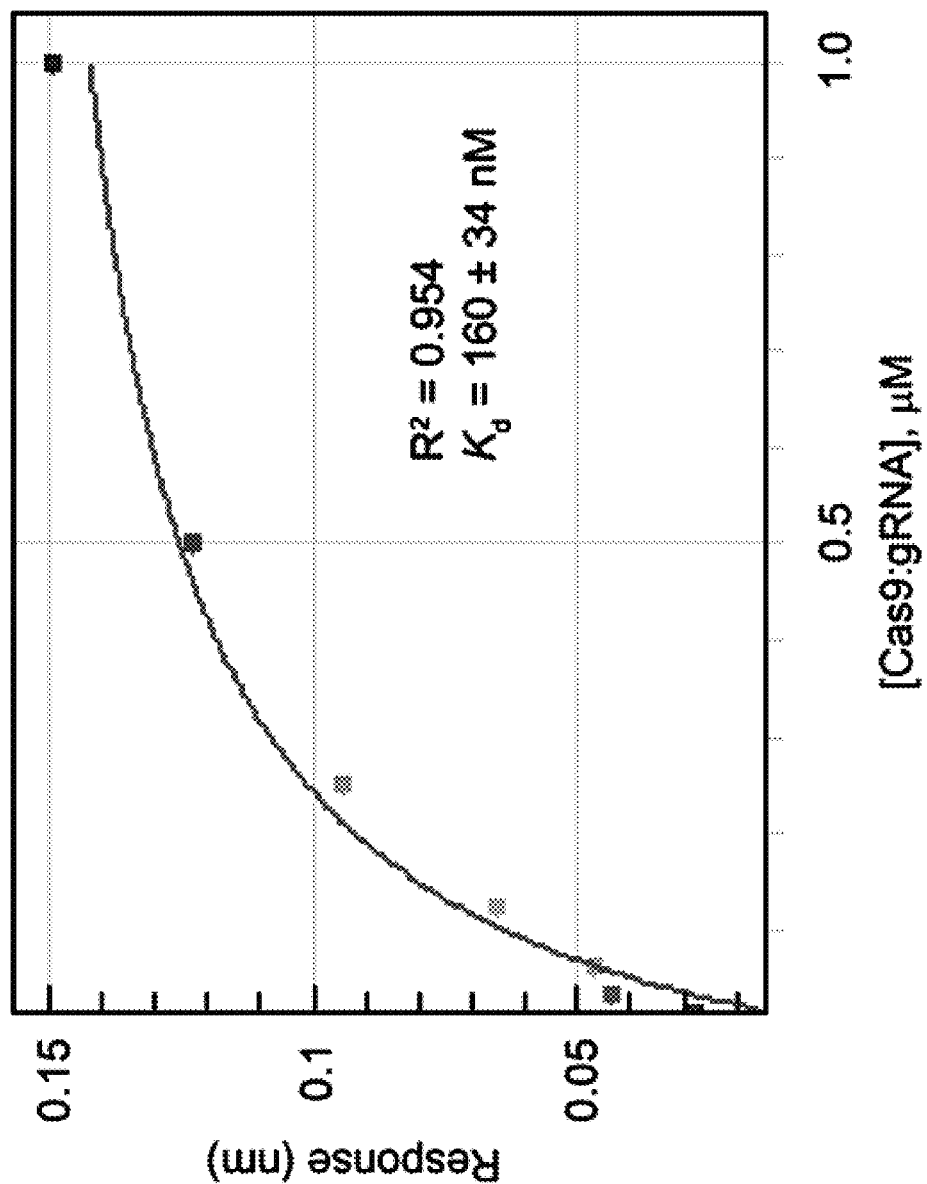
FIG. 61. Binding isotherm of BRD7087-Biotin and SpCas9:gRNA complex in BLI. The steady-state plot for BLI binding study of BRD7087-Biotin and SpCas9:gRNA complex. BLI experiment was performed using 1 µM BRD7087-Biotin onto streptavidin sensors followed by association with different concentration of SpCas9:gRNA complex and subsequent dissociation. Response data were plotted along X-axis and concentration of SpCas9:gRNA complex was plotted along Y-axis. A global 2:1 (small molecule:protein) model was used to plot the steady state and determine the binding constant.
Figure 62:
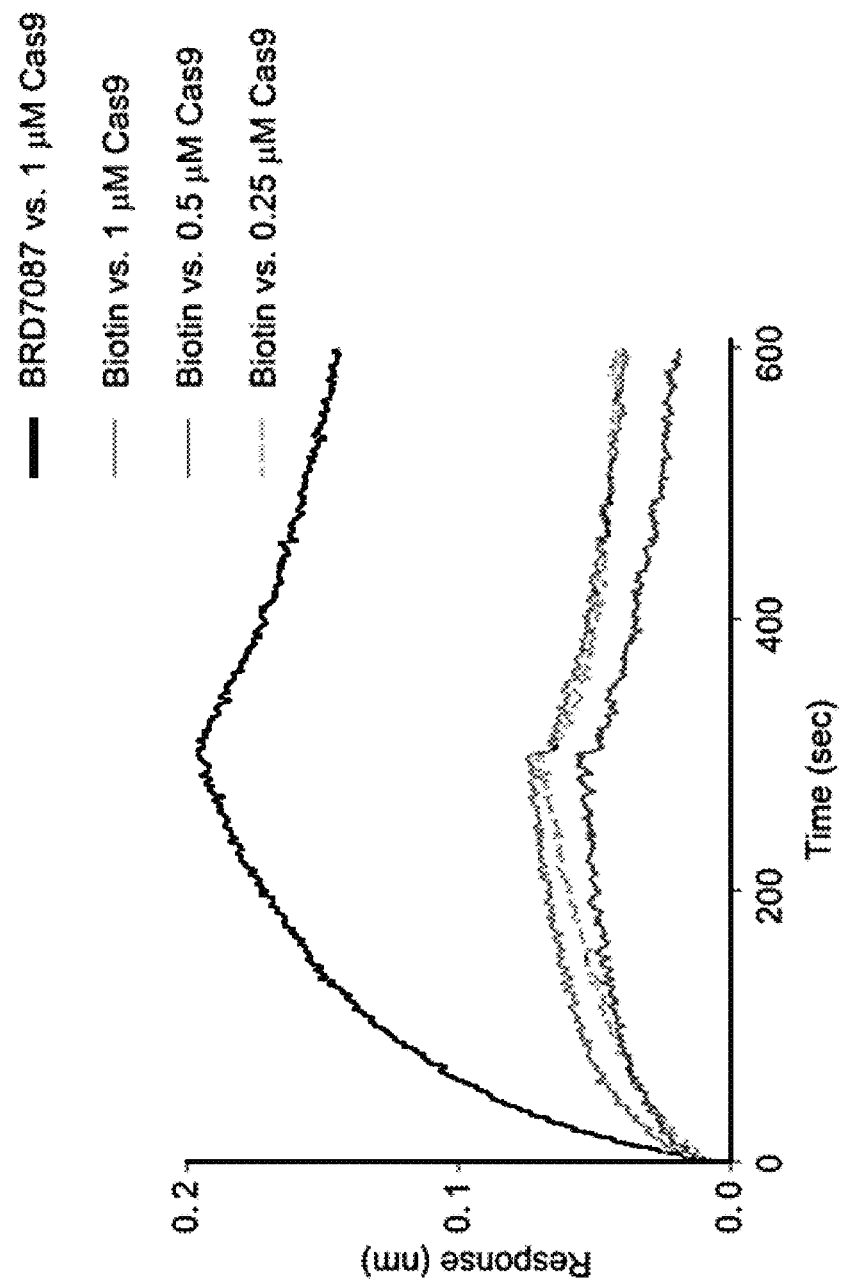
FIG. 62. BLI study of Biotin loaded streptavidin sensors with SpCas9:gRNA complex. Bio-Layer Interferometry study of streptavidin sensors loaded either with 1 µM BRD7087-Biotin or 10 µM of Biotin in 20 mM Tris buffer of pH 7.4, 100 mM KCl, 5 mM MgCl$_2$, 1 mM DTT, 0.01% Tween®. SpCas9:gRNA complex concentration was varied from 1-0.25 µM.
Figure 63:
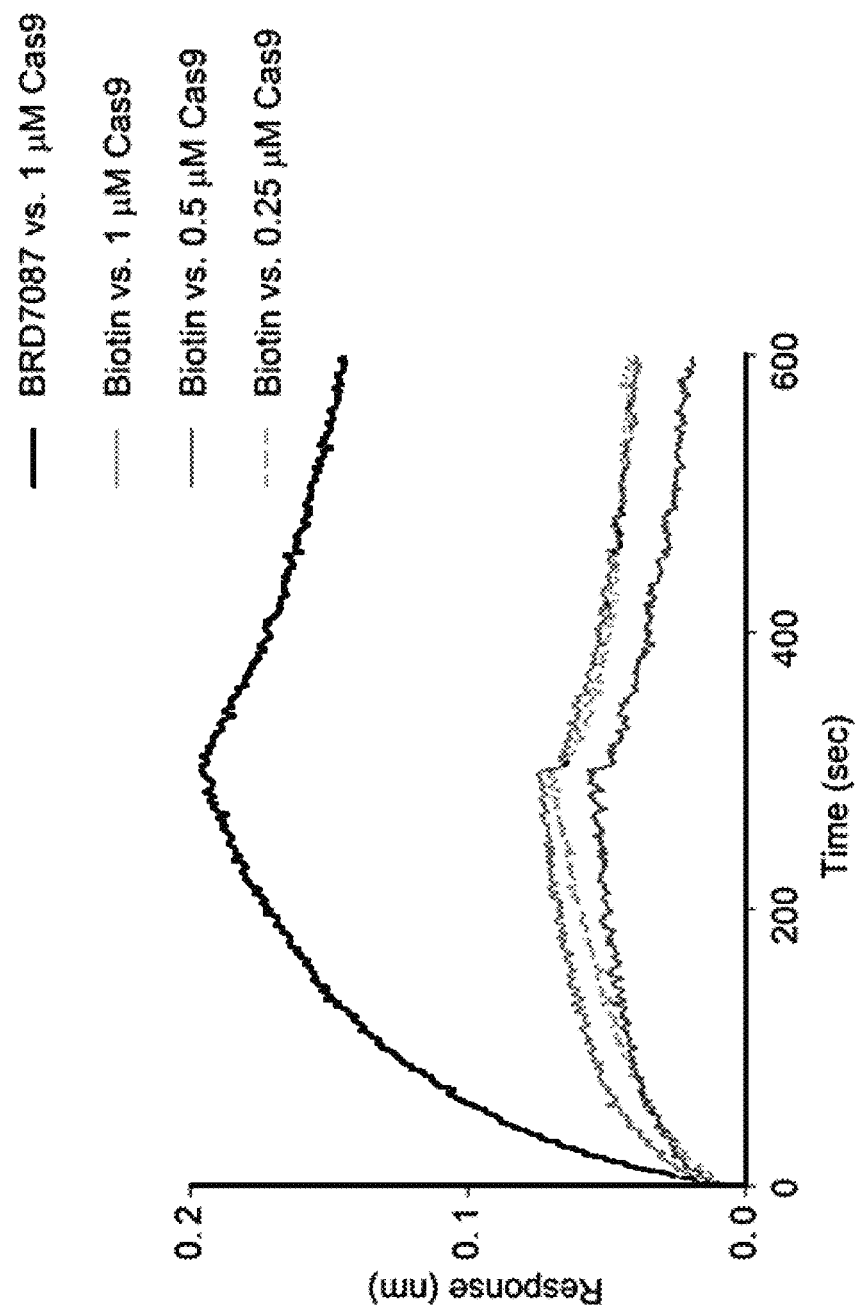
FIG. 63. Competitive BLI study of BRD7087-Biotin in the presence of 10-fold excess of Biotin. Bio-Layer Interferometry study of streptavidin sensors loaded with either with 1 µM BRD7087-Biotin or 10 µM of Biotin or Biotin as a competitor in 20 mM Tris buffer of pH 7.4, 100 mM KCl, 5 mM MgCl$_2$, 1 mM DTT, 0.01% Tween®. In the competition assay, streptavidin sensors were pre-loaded with 10 µM of Biotin followed by loading of 1 µM BRD7087-Biotin. SpCas9:gRNA complex concentration was varied from 1-0.25 µM.
Figure 64:
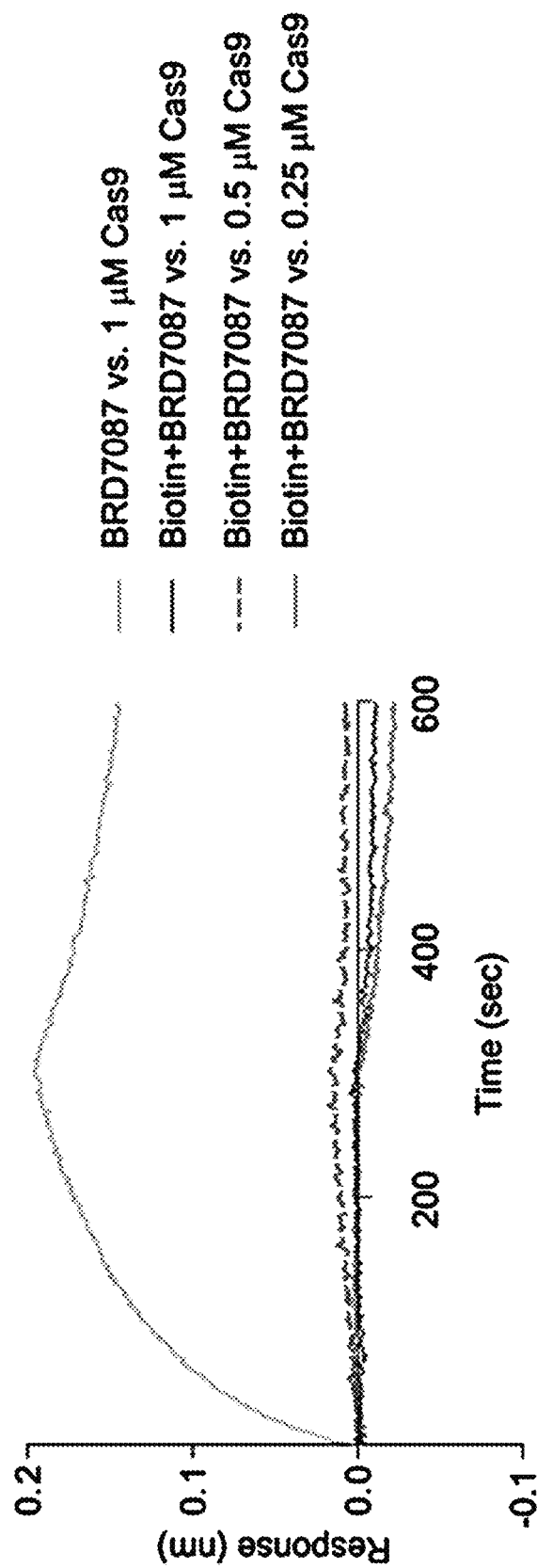
FIG. 64. Competitive BLI study of BRD7087-Biotin in the presence of 10-fold excess of Biotin. Background subtracted BLI responses of BRD7087-Biotin with SpCas9: gRNA in the presence of 10-fold excess Biotin as the competitor in 20 mM Tris buffer of pH 7.4, 100 mM KCl, 5 mM MgCl$_2$, 1 mM DTT, 0.01% Tween®. SpCas9:gRNA complex concentration was varied from 1-0.25 µM.

Applicants deployed biolayer interferometry (BLI) to determine the binding affinity of BRD7087 and SpCas9:gRNA complex by tethering the compound onto the sensor. Towards this end, Applicants synthesized a biotin-conjugate of BRD7087 (FIG. 59) and loaded this compound on the streptavidin sensors of BLI. The compound loaded sensors were allowed to interact with SpCas9:gRNA complex generating the response curves (FIG. 36B). A 2:1 compound to Cas9 binding isotherm indicated a dissociation constant of ~160 nM (FIGS. 60A-60B). In a competitive experiment performed in the presence of excess (10×) of biotin to BRD7087 loading, Applicants observed no substantial response signal upon incubation with the SpCas9:gRNA solution, confirming the specific nature of BRD7087 and SpCas9:gRNA interaction (FIGS. 61-63). Furthermore, the BRD7087 has a fluorine moiety which allowed us to investigate the interaction of compound and SpCas9:gRNA by $^{19}F$ NMR. Binding of BRD7087 was confirmed using differential line broadening of $^{19}F$ signal upon titration of SpCas9:gRNA; the signal corresponding to 50 μM ligand broadens in a dose-dependent manner as expected (Table 7). While small amounts of protein showed a negligible effect, significant broadening is observed with SpCas9:gRNA concentrations as low as 0.75 μM (67-fold excess of ligand), indicating relatively tight binding. Using peak intensities obtained by fitting for these datapoints, the method of Shortridge et. al. indicates a binding constant $K_d$-2.2 μM (Shortridge, M. D.; Hage, D. S.; Harbison, G. S.; Powers, R., Estimating protein-ligand binding affinity using high-throughput screening by NMR. *J Comb Chem* 2008, 10 (6), 948-58). Allowing for the inclusion of a nonspecific binding term does not alter the binding constant value but slightly improves the fit (FIG. 64).

TABLE 8

Table containing data that was used to estimate the ligand binding affinity based on the method described by Shortridge et. al. The linewidth (LW) increases with increasing protein concentration, as expected. Peak intensity values were used to measure the Fractional Occupancy using the relationship given in the paper ($1-I_{bound}/I_0$), where $I_0$ is the intensity of the peak with no protein in the sample. The peak area remains relatively constant, as expected for a fixed concentration of ligand. The value of $K_d$ was estimated by nonlinear least-squares fitting of expression from the reference.
RAW DATA EXTRACTED FROM SPECTRA

| [Ligand], (μM) | [Protein:gRNA], (μM) | LW (Hz) | Peak Intensity | Peak Area | Fractional Occupancy |
|---|---|---|---|---|---|
| 50 | 0 | 4.1 | 572470.95 | 3151271.718 | 0 |
| 50 | 0.75 | 4.3 | 497630.81 | 2968891.536 | 0.130731769 |
| 50 | 1.0 | 4.6 | 468481.06 | 2999269.636 | 0.181650947 |
| 50 | 1.25 | 5.3 | 398322.72 | 2964107.303 | 0.304204484 |
| 50 | 1.5 | 5.9 | 375769.97 | 3176044.761 | 0.343599933 |
| 50 | 1.75 | 6.3 | 342640.49 | 3020022.312 | 0.401470957 |

Figure 37B:
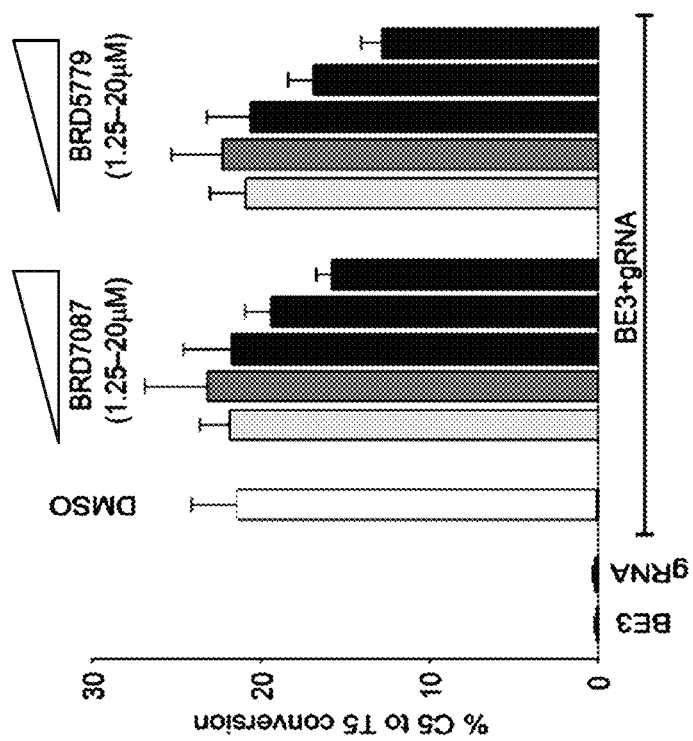
FIGS. 37A-37E. Cellular activity of small molecule inhibitors of SpCas9.
Figure 37A:
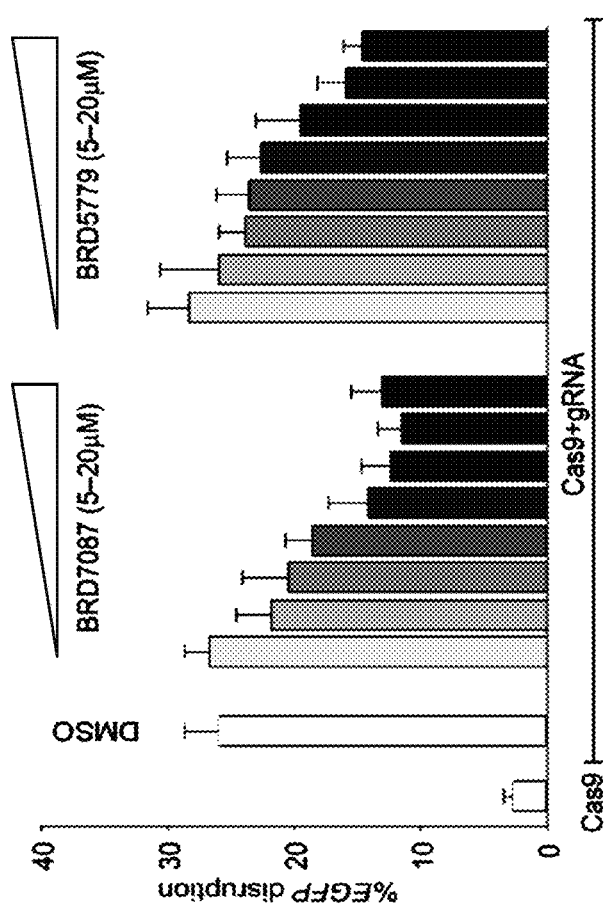
Figure 65:
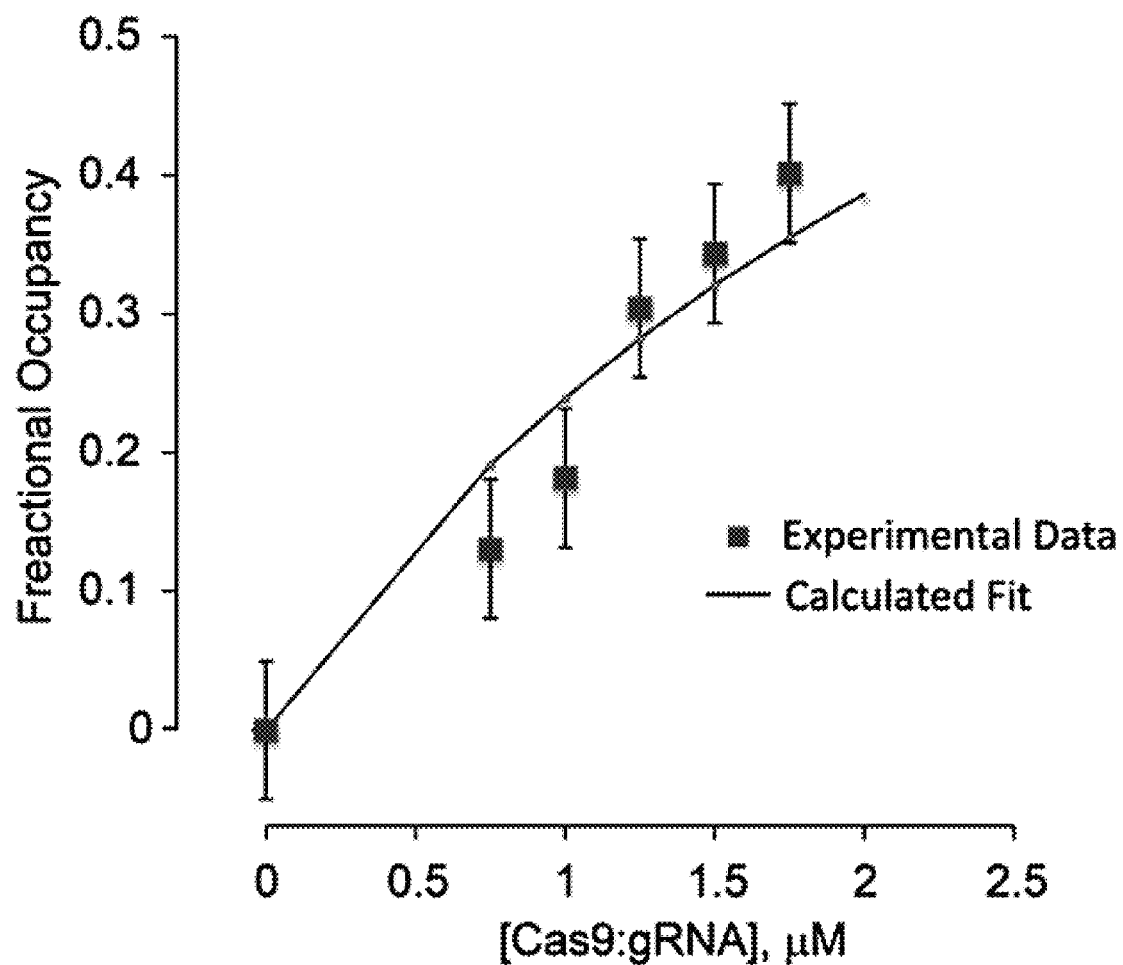
FIG. 65. NMR binding data of BRD7087 and SpCas9: gRNA complex. 19F NMR titration data were fitted following a reported protocol to calculate the binding constant of BRD7087 with SpCas9:gRNA complex in 20 mM Tris buffer of pH 7.4, 100 mM KCl, 5 mM MgCl$_2$, 1 mM DTT. A 50 µM Compound BRD7087 was titrated against increasing amount of SpCas9:gRNA ribonucleoprotein complex.
Figure 66:
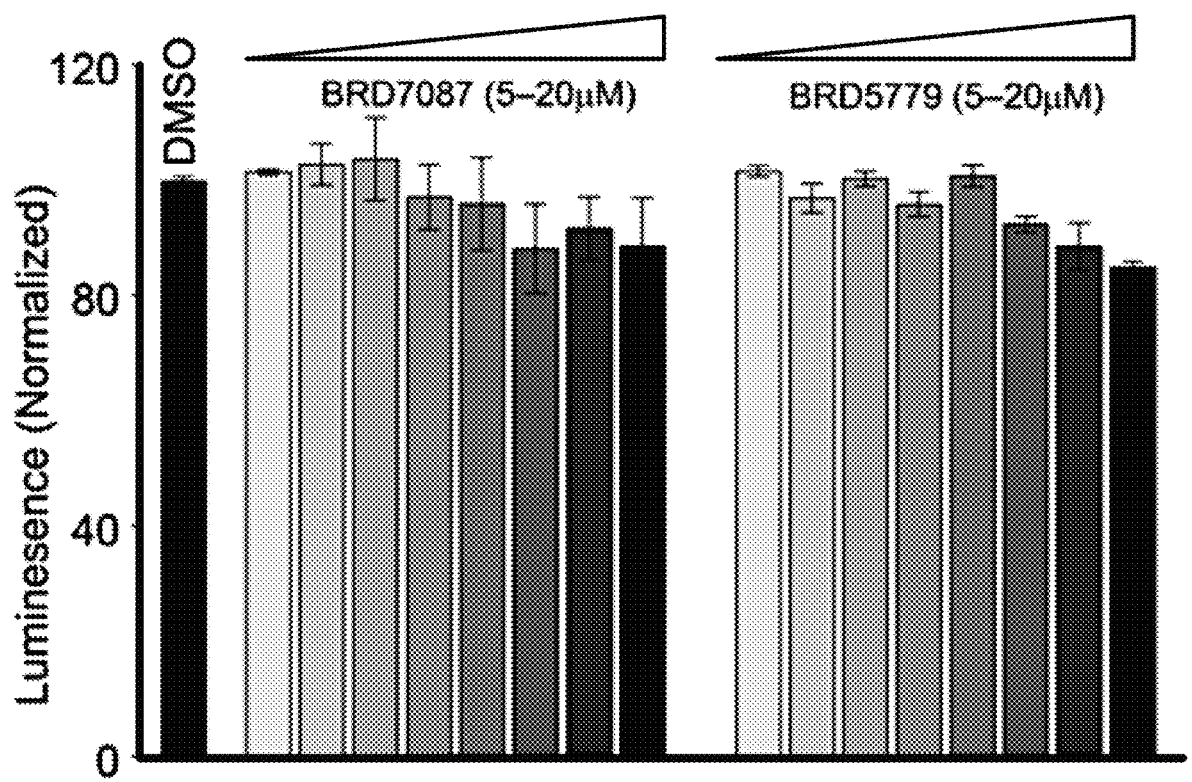
FIG. 66. Cell viability assay (ATP content) of U2OS.eGFP.PEST cells in the presence of compounds. Measurement of ATP content of U2OS.eGFP.PEST cells upon incubating with BRD7087 and BRD5779 (5-20 µM) for 24 h. Error bars represent ±S.D. from technical replicates (n=3).
Figure 67:
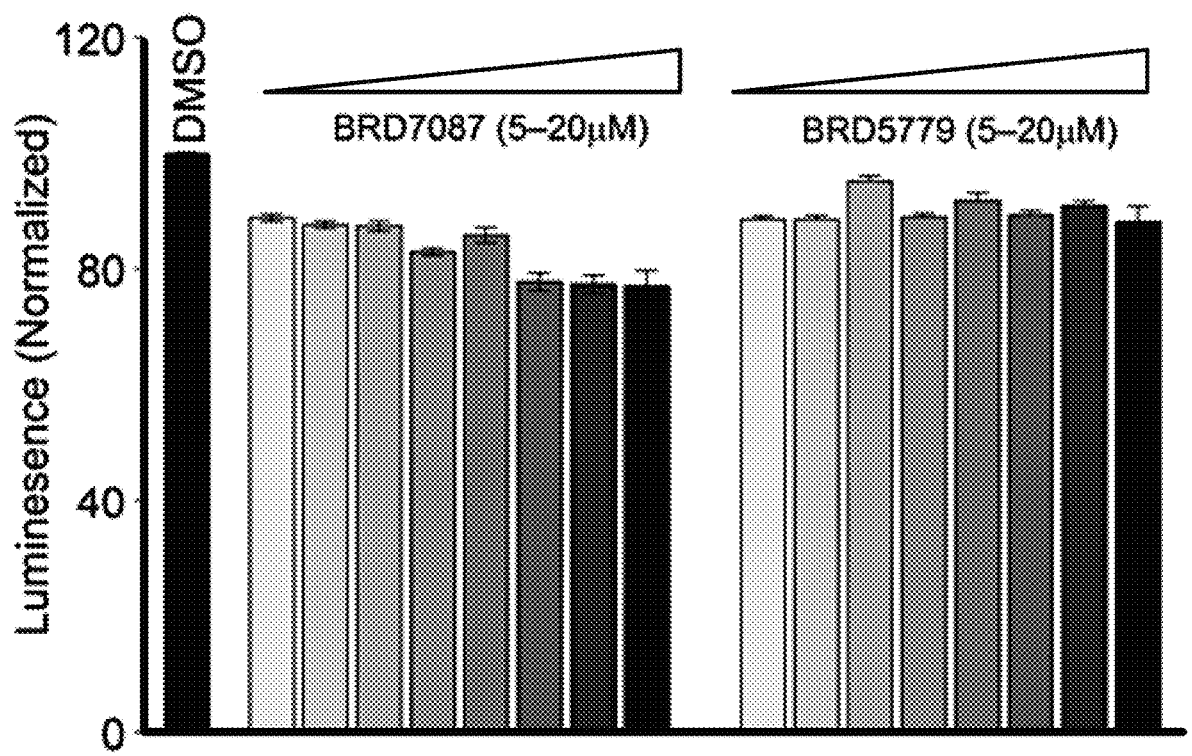
FIG. 67. Cell viability assay (ATP content) of HEK293T cells in the presence of compounds. Measurement of ATP content of HEK293T cells upon incubating with BRD7087 and BRD5779 (5-20 µM) for 24 h. Error bars represent ±S.D. from technical replicates (n=3).
Figure 68:
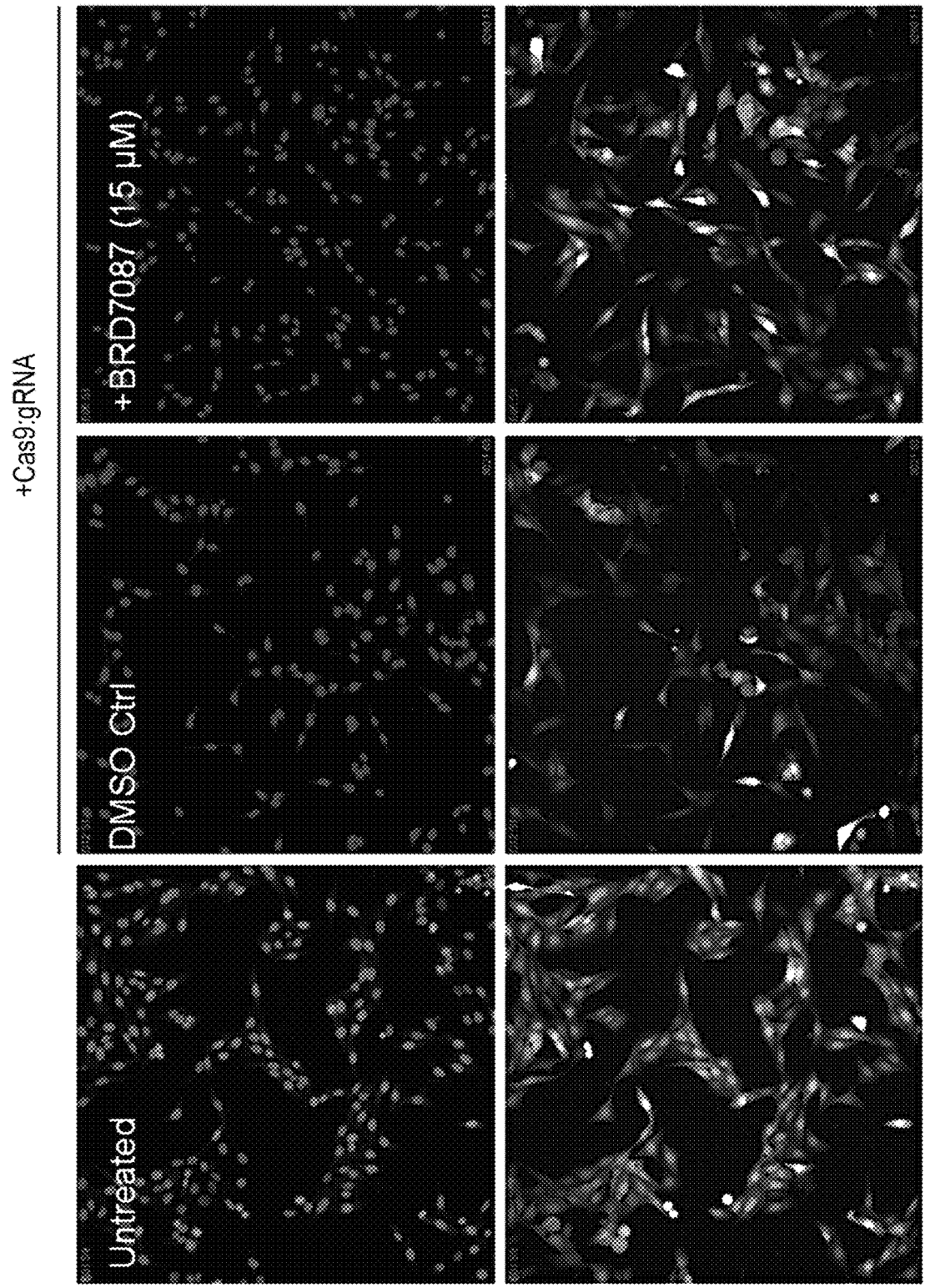
FIG. 68. Representative images of the EGFP-knockdown assay. Representative images of U2OS.eGFP.PESt cells nucleofected with either SpCas9 expressing plasmid alone or SpCas9 and gRNA plasmids treated with vehicle or compound. Left panel represents cells nucleofected with SpCas9 expressing plasmid alone. Middle panel represents cells nucleofected with SpCas9 and gRNA expressing plasmids and treated with vehicle. Right panel represents cells nucleofected with SpCas9 and gRNA expressing plasmids and treated with 15 µM BRD7087 for 24 h. Scale bar=100 µm.
Figure 69:
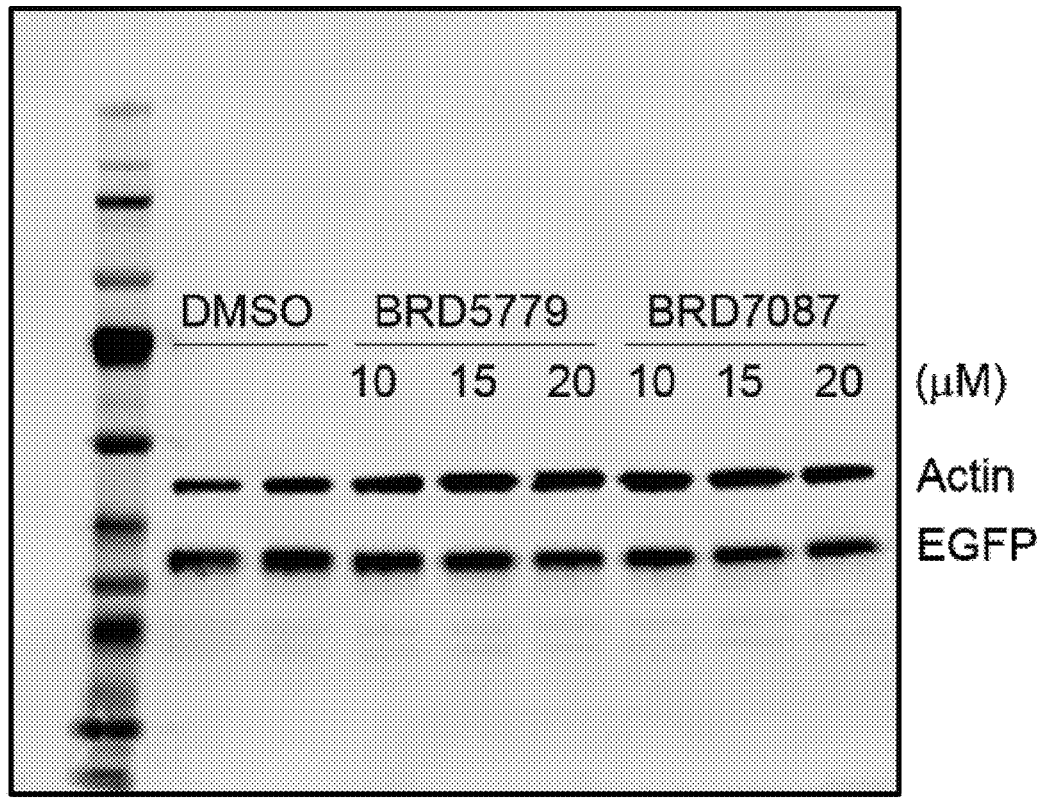
FIG. 69. Western blot analysis of EGFP protein in U2OS.eGFP.PEST cells in presence of compound. Western Blot analysis of EGFP gene expression in U2OS.eGFP.PEST cells in the presence of DMSO and compound. Cells were incubated with compound BRD5779 and BRD7087 with an indicated concentration for 24 h before harvesting and processing for Western Blot analysis.
Figure 70:
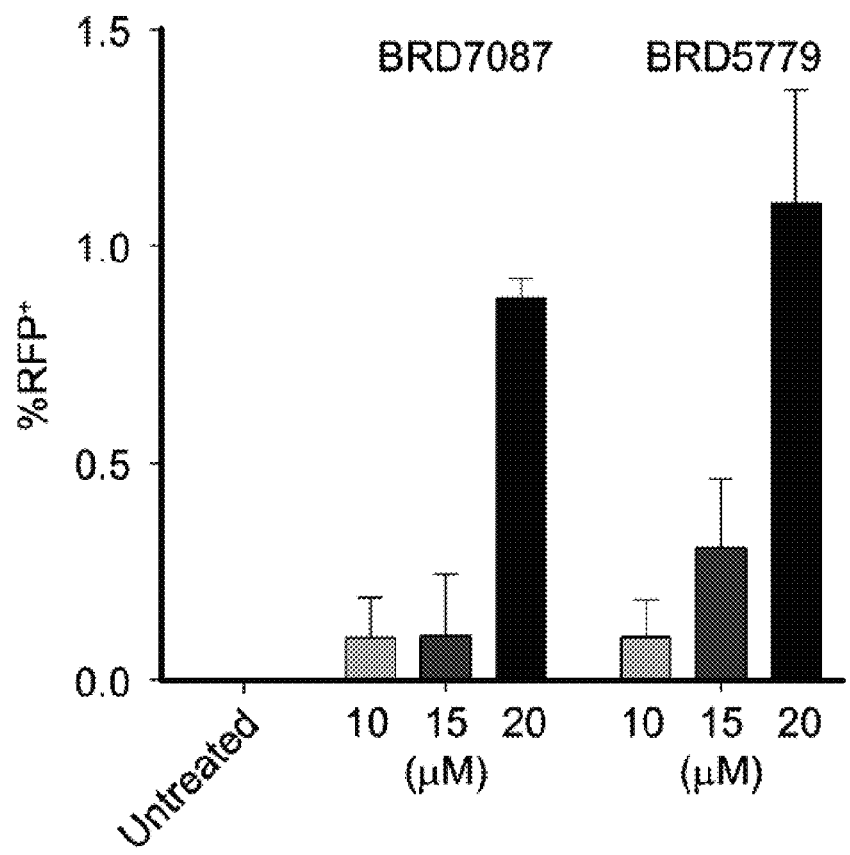
FIG. 70. Auto-fluorescence of cells treated with the compound in the EGFP-knockdown assay. Measurement of the auto-fluorescence level of compound-treated U2OS.eGFP.PEST cells. Cells were imaged in RFP channel with a same exposure time that has been used in the EGFP-knockdown assay for measuring compound mediated recovery of GFP signal. Compound-treated cells showed maximum 1% auto-fluorescence population indicating no significant contribution of auto-fluorescence in compound mediated GFP recovery. Error bars represent ±S.D. from technical replicates (n=4).
Figure 71:
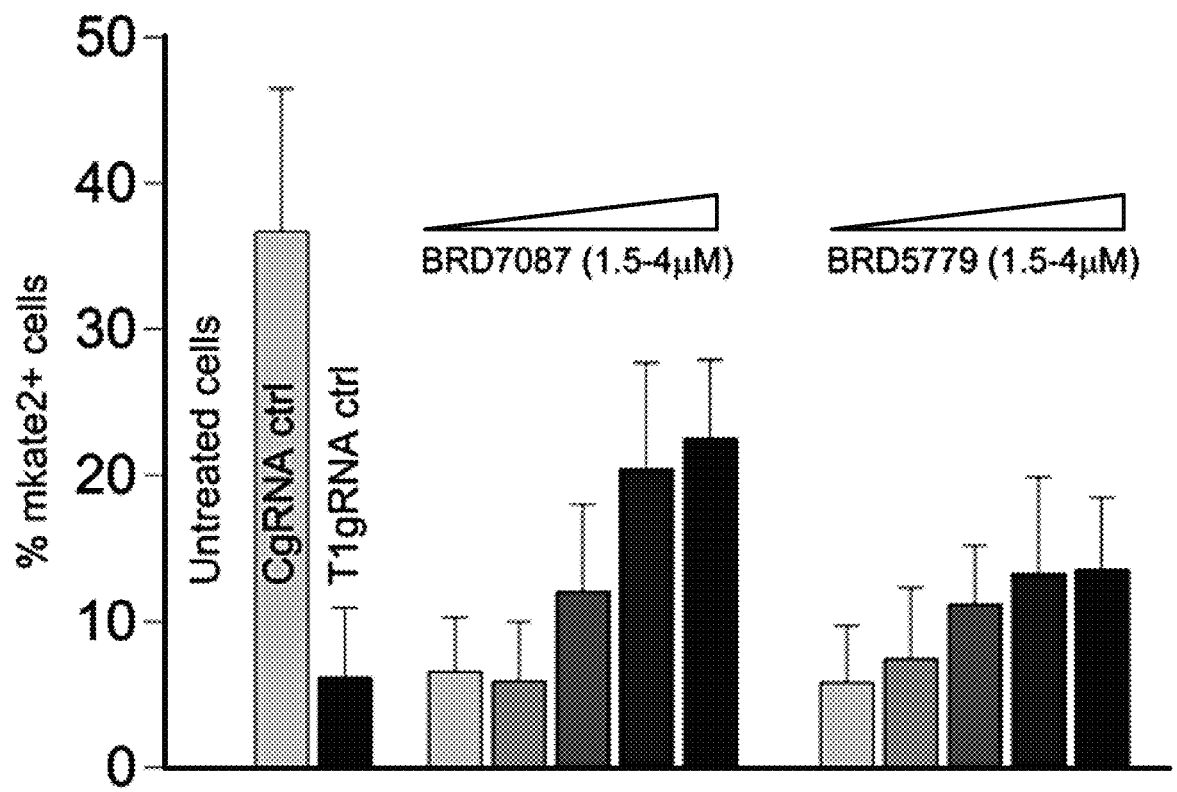
FIG. 71. Dose-dependent inhibition of SpCas9 by the compound in mKate2 expression assay. Dose-dependent recovery of the mKate2 signal by compound BRD7087 and BRD5779 in the mKate2-knockdown assay. HEK293 cells were transfected with a single plasmid containing SpCas9, gRNA, and mKate2 expressing genes. Plasmid without a non-targeting gRNA (CgRNA) was used as the positive control. Cells transfected with the targeting guide plasmid (T1gRNA) was incubated either in presence of DMSO or compound (1.5-5 µM) for 24 h. Error bars represent ±S.D. from technical replicates (n=3).
Figure 72:
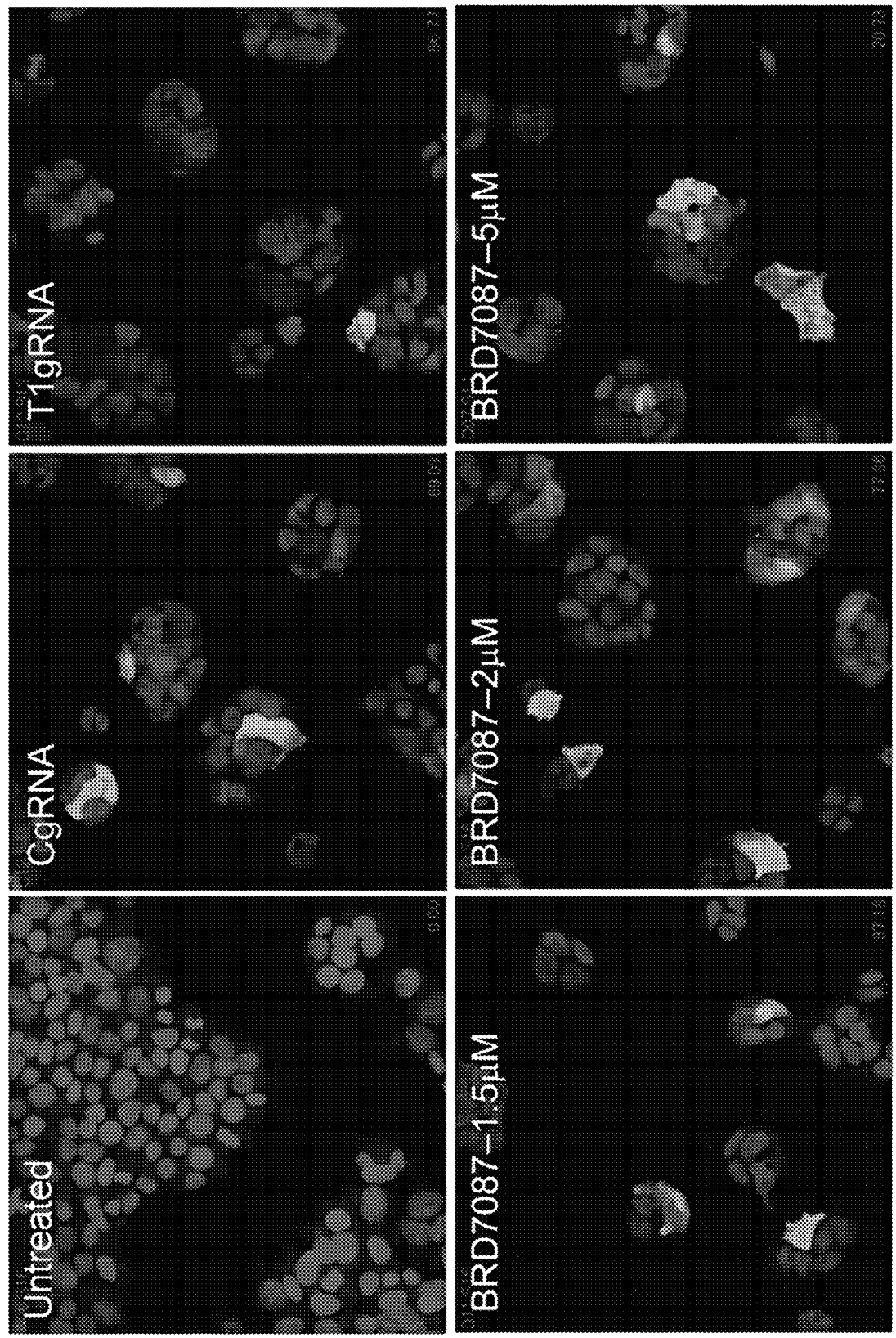
FIG. 72. Representative images of the mKate2-knockdown assay. Representative images of HEK293 cells transfected with a single plasmid containing SpCas9, gRNA, and mKate2 expressing genes. The Nuclei are counter-stained with DAPI and the red channel represents the expression level of mKate2. While control panel (CgRNA) was transfected with a plasmid with a non-targeting gRNA. Other panels represent cells transfected with targeting gRNA (T1gRNA) incubated with either DMSO or compound BRD7087 with indicated concentration. Error bars represent S.D. from technical replicates (n=3). Scale bar=100 µm.
Figure 73:
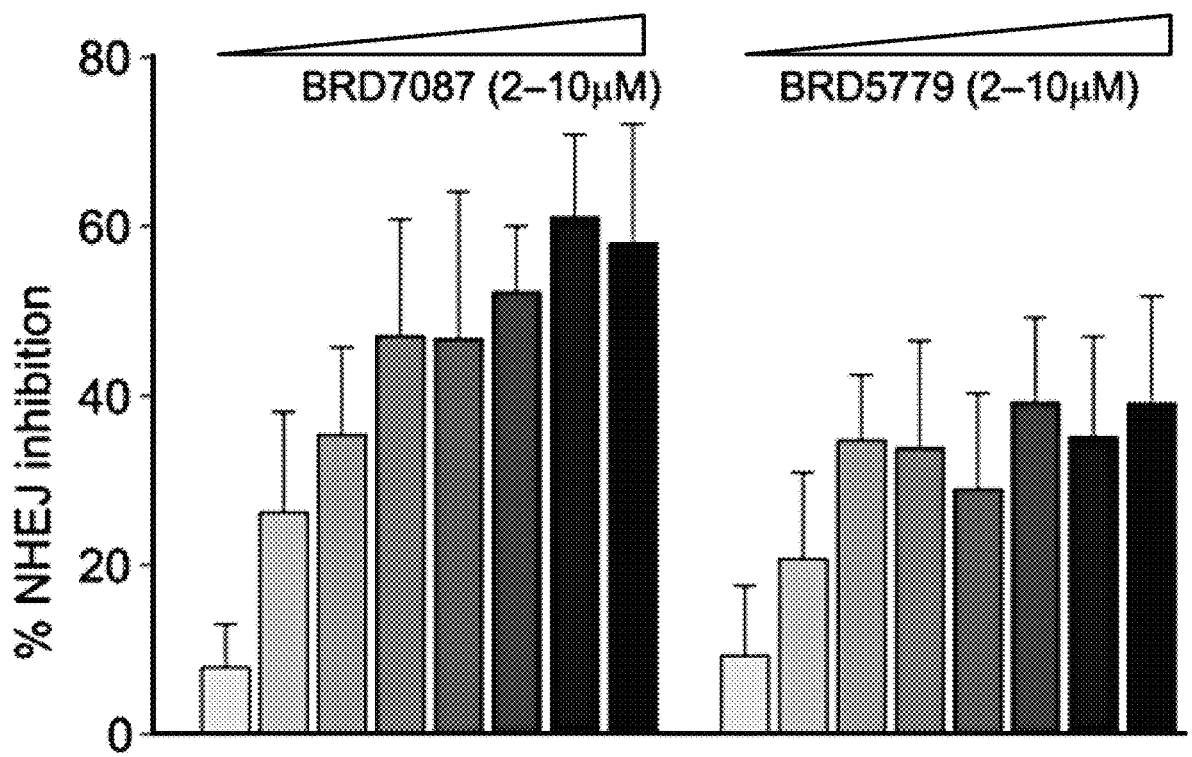
FIG. 73. Dose-dependent inhibition of SpCas9 mediated NHEJ by compounds. Dose-dependent inhibition of SpCas9-mediated NHEJ by compound BRD7087 and BRD5779 in HEK293T cells. HEK293 cells were transfected with a plasmid containing SpCas9, gRNA and another plasmid containing reporter gene mCherry-GFP. Transfected cells were incubated with either DMSO or compound (2-10 µM) for 24 h. Error bars represent ±S.D. from technical replicates (n=3).
Figure 74:
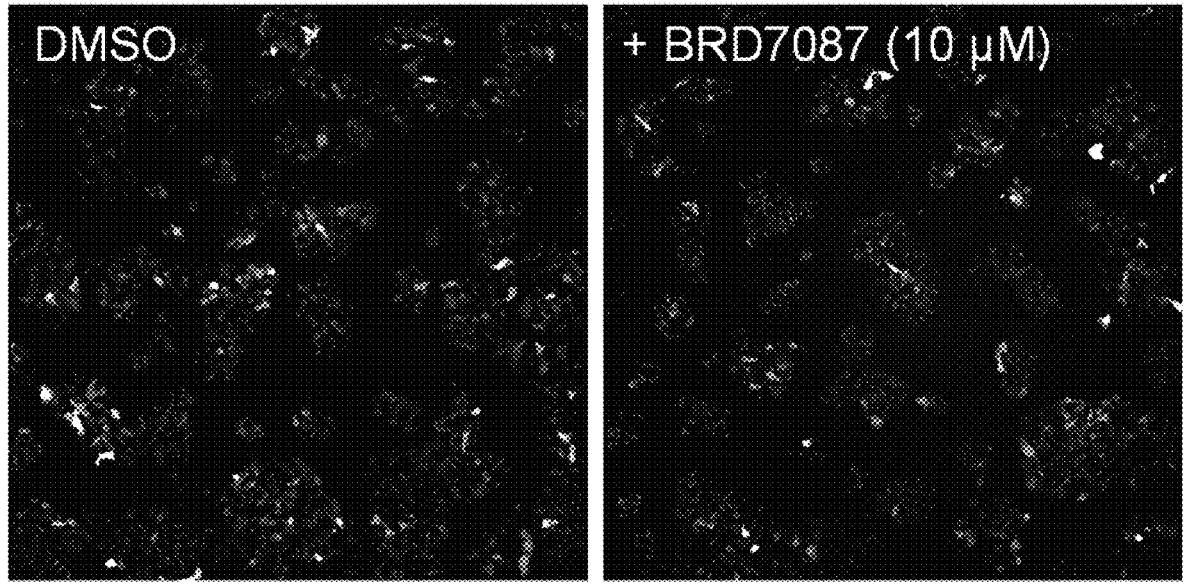
FIG. 74. Representative images of HEK293 cells transfected with a reporter plasmid containing mCherry and GFP genes and another plasmid with SpCas9 and gRNA genes. The Nuclei are counter-stained with DAPI and the red and green channels represent the expression level of mCherry and GFP respectively. Cells were incubated either with DMSO or compound BRD7087 with the indicated concentration. Error bars represent ±S.D. from technical replicates (n=3). Scale bar=100 µm.
Figure 75:
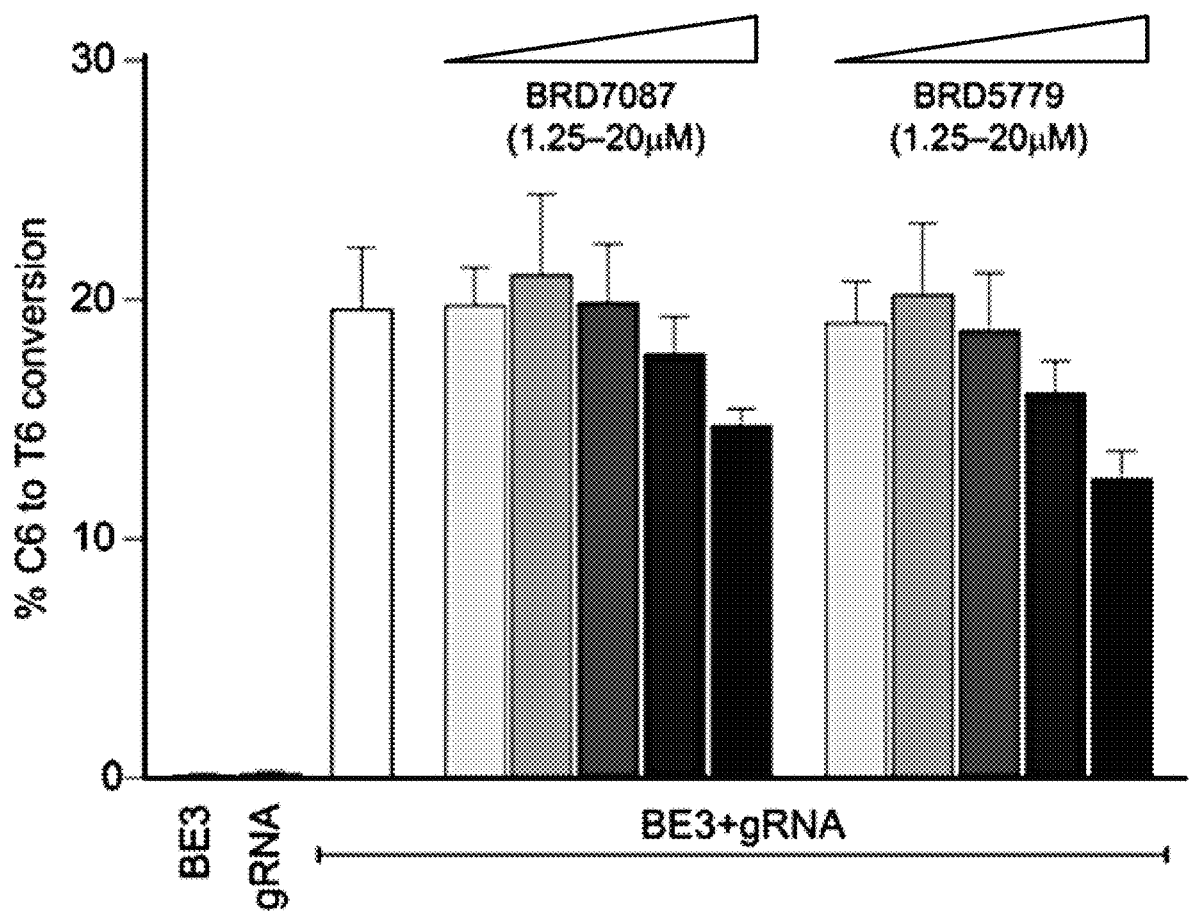
FIG. 75. Dose-dependent inhibition of base-editing activity by compounds. Dose-dependent inhibition of the dCas9-based base-editing activity of cytidine deaminase (BE3) targeting EMX1 gene in HEK293T cells. Ribonucleoprotein BE3:gRNA preincubated with small molecule was delivered into the adhered HEK293T cells and incubated in the presence of either DMSO or compound at the indicated concentration for 72 h. The cells were then harvested and processed for DNA sequencing to evaluate the extent of C6+T6 conversion. Error bars represent ±S.D. from technical replicates (n=3).
Figure 76:
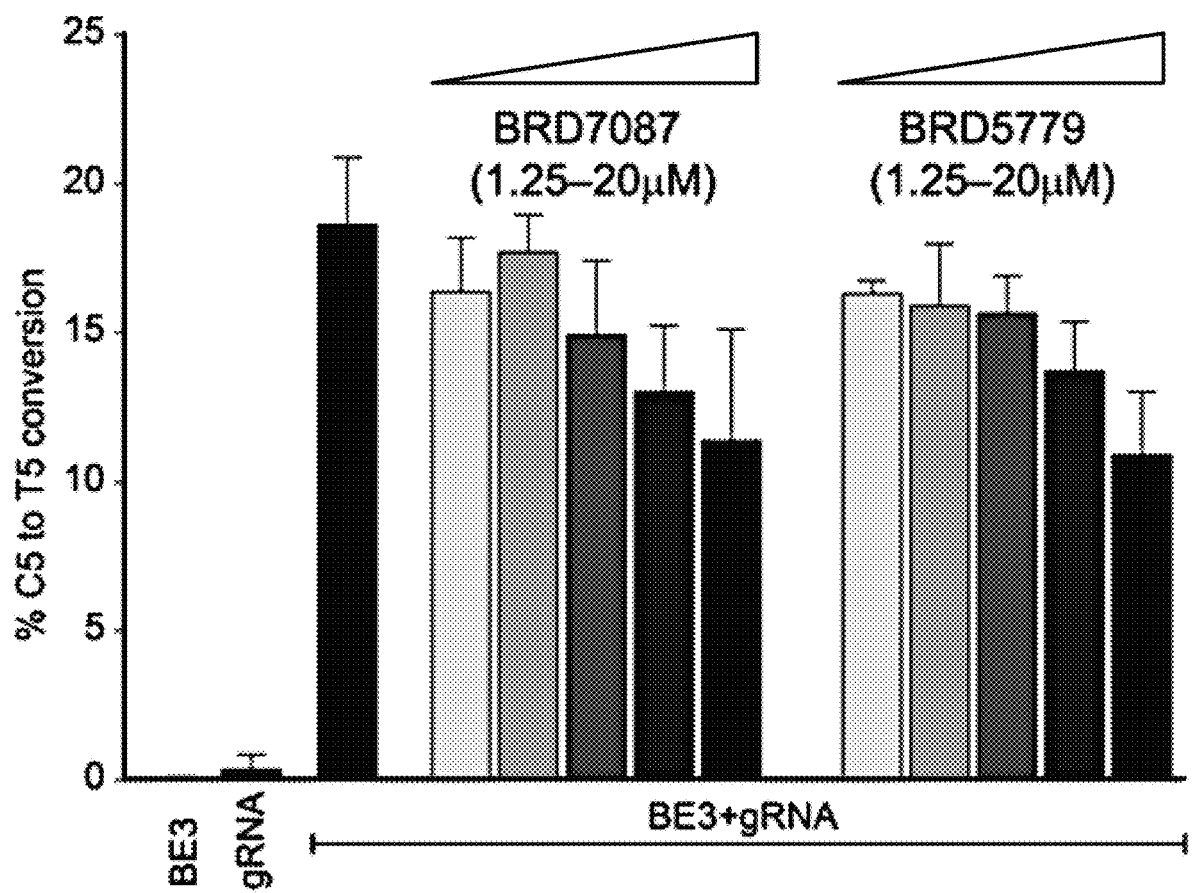
FIG. 76. Dose-dependent inhibition of base-editing by compounds. Dose-dependent inhibition of the dCas9-based base-editing activity of cytidine deaminase (BE3) targeting EMX1 gene in HEK293T cells. Ribonucleoprotein BE3: gRNA preincubated with small molecule was delivered into the adhered HEK293T cells and incubated in the presence of either DMSO or compound at the indicated concentration for 72 h. The cells were then harvested and processed for DNA sequencing to evaluate the extent of C5+T5 conversion. Error bars represent ±S.D. from biological replicates (n=3).

After biophysical validation of the interaction of BRD7087 with SpCas9, Applicants performed cellular studies with this compound. First, Applicants determined if BRD7087 and BRD5779 were cytotoxic. Treatment of U2OS and HEK293T cells with these compounds did not significantly alter the cellular ATP-levels upon incubation up to 20 μM concentration for 24 h (FIGS. 65-66). Applicants then tested the compounds at different doses in EGFP-disruption assay in U2OS.eGFP.PEST cell and measured the recovery of EGFP signal. Both the compounds showed a dose-dependent SpCas9 inhibition activity as quantified by the recovery of the EGFP signal (FIGS. 37A and 67). Compound BRD7087 showed an inhibition of SpCas9 activity by 44% (exact numbers here and below) at 10 μM. Applicants also confirmed that these compounds do not alter proteasomal degradation of EGFP when incubated with U2OS.eGFP.PEST cells (FIG. 68). The compounds also did not induce any notable auto-fluorescence in cells (FIG. 69). Applicants further employed both the mKate2 expression assay and NHEJ assay to validate the activity of the compounds BRD7087 and BRD5779. Compound BRD7087 was found to be more active than BRD5779 with a 50% inhibition activity at ~5 μM in mKate2 disruption assay (FIGS. 70-71). Both compounds were also active in the NHEJ assay (FIGS. 72-73).

Figures 37C, 37D, 37E:
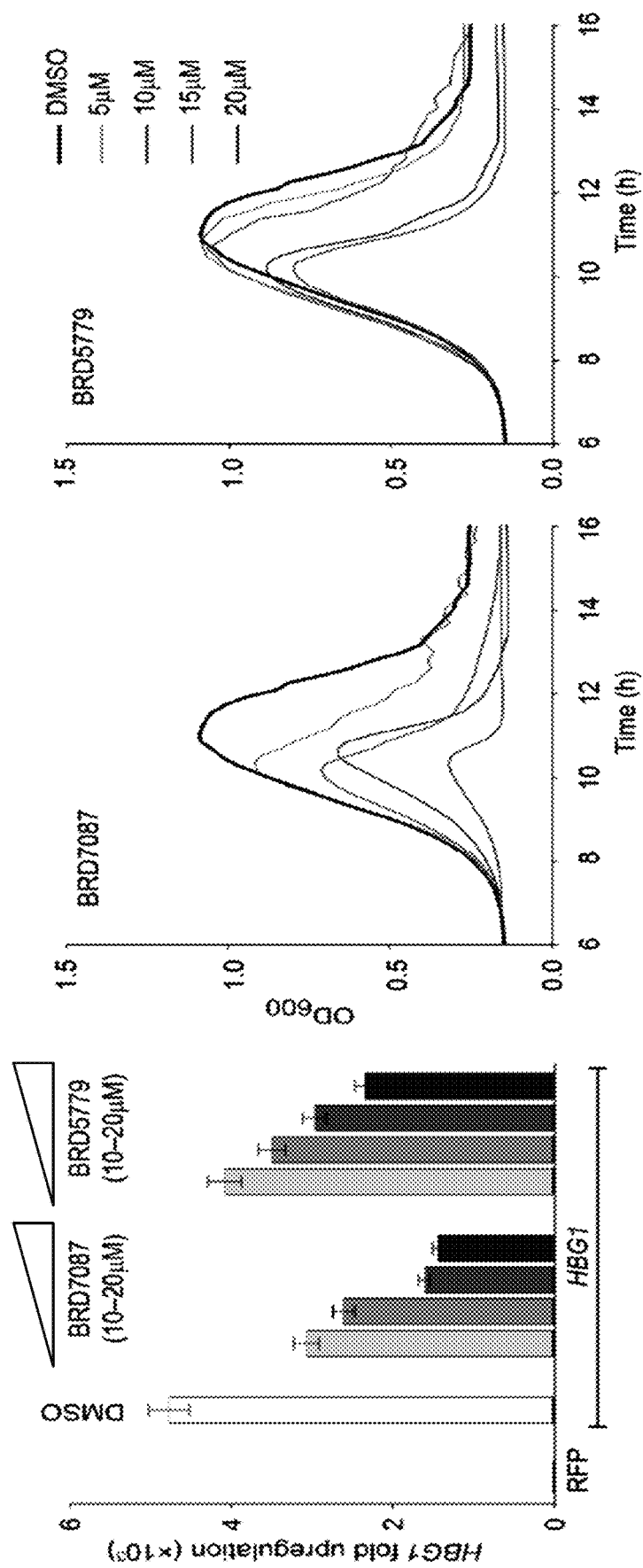
Figure 77:
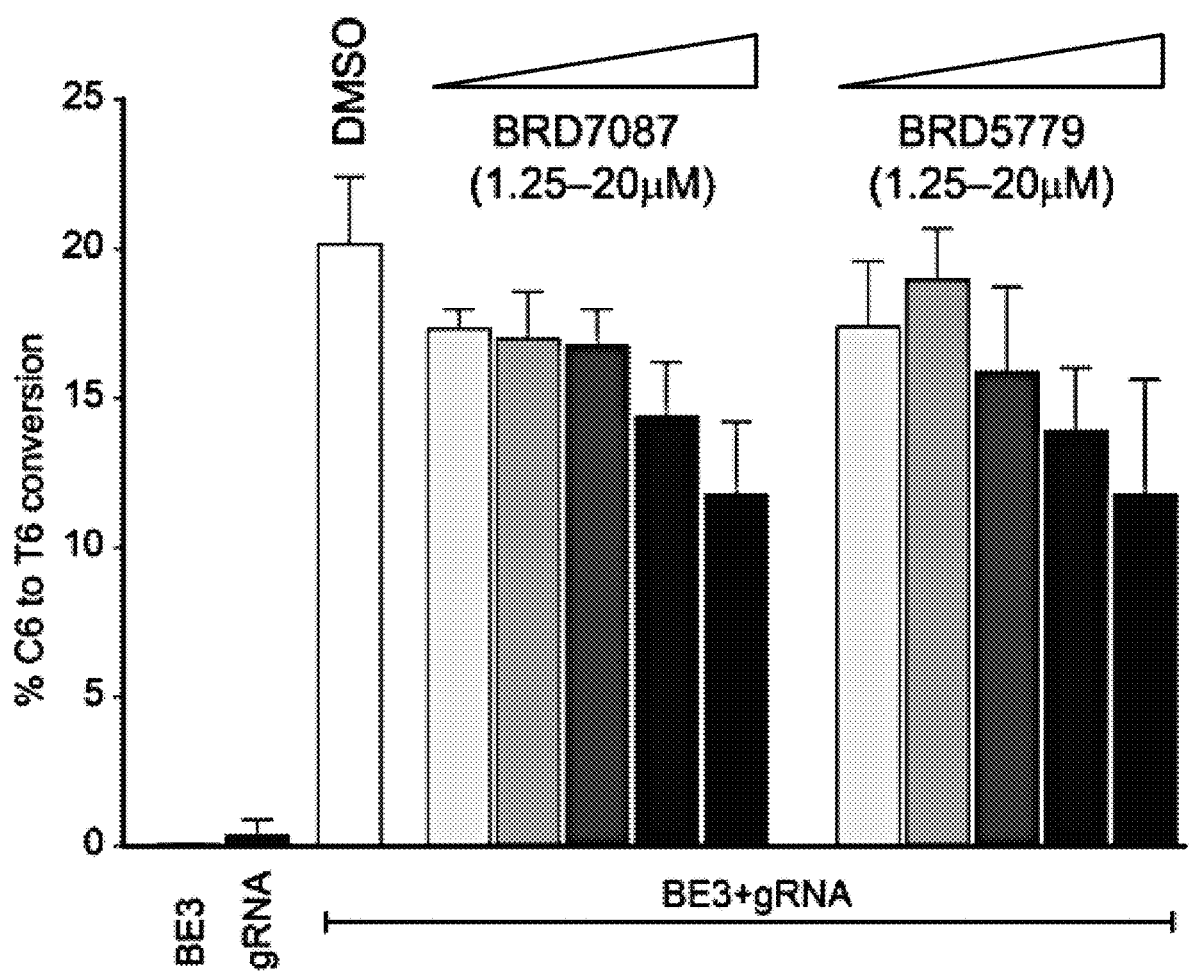
FIG. 77. Dose-dependent inhibition of base-editing activity by compounds. Dose-dependent inhibition of the dCas9-based base-editing activity of cytidine deaminase (BE3) targeting EMX1 gene in HEK293T cells. Ribonucleoprotein BE3:gRNA preincubated with small molecule was delivered into the adhered HEK293T cells and incubated in the presence of either DMSO or compound at the indicated concentration for 72 h. The cells were then harvested and processed for DNA sequencing to evaluate the extent of C6→T6 conversion. Error bars represent ±S.D. from biological replicates (n=3).

Since BRD7087 and BRD5779 alter PAM-binding, they should inhibit dCas9-based technologies, including base-editing and transcriptional activation technologies. Applicants undertook the dCas9-cytidine deaminase conjugate (BE3)19 targeting the EMX1 gene toward cytosine to thymine (C→T) conversion in the presence and absence of inhibitors at different concentrations. In this assay a ribonucleoprotein complex (BE3:gRNA) was incubated with either DMSO or compound at the specified concentration and delivered into HEK239T cells maintaining the corresponding compound concentration in the media. The base-editing efficiency was determined by isolating the genomic DNA followed by two-step barcoding the EMX1 gene and running on the MiSeq (Illumina) sequencer. Both the compounds BRD7087 and BRD5779 showed an efficient and dose-dependent inhibition of BE3-mediated base-editing (FIG. 37B and FIGS. 74-76). Applicants observed similar inhibition of base editing when plasmid transfection was used in place of protein delivery. Next, Applicants tested BRD7087 and BRD5779 in a dCas9-based transcriptional activation assay targeting the HBG1 gene. A dose-dependent inhibition of the HBG1 transcriptional activation further corroborated the inhibitory activity of BRD7087 and BRD5779 (FIG. 37C and FIG. 77). Compound BRD7087 showed >60% inhibition of transcriptional activation at 10 μM concentration (FIG. 37C).

After demonstrating inhibition of Cas9 and dCas9-based technologies, Applicants determined if BRD7087 and BRD5779 can block CRISPR-immunity of bacteria from phages. Applicants anticipated that SpCas9 inhibitors will disrupt the bacterial immunity and trigger lysis in the presence of phage. To test this hypothesis, Applicants exposed the immune bacterial cell *S. aureus* RN4220 strain (Heler, R.; Samai, P.; Modell, J. W.; Weiner, C.; Goldberg, G. W.; Bikard, D.; Marraffini, L. A., Cas9 specifies functional viral targets during CRISPR-Cas adaptation. *Nature* 2015, 519 (7542), 199-202) to CRISPR targeting lytic phage #NM4Y4 in the presence and absence of SpCas9 inhibitor BRD7087 and BRD5779 at different concentrations. Bacterial cell lysis, which was followed by OD600 measurements, was observed in the presence of our SpCas9 inhibitors and phage (FIG. 37D), but not in the presence of inhibitor alone (FIG. 78), suggesting that the inhibitors disrupt CRISPR-immunity and are non-toxic in the absence of phage. Both the compounds BRD7087 and BRD5779 were able to sensitize the immune bacterial cells against target phage in a dose-dependent manner, however, BRD7087 showed higher activity as was observed in the mammalian cells.

Figure 79:
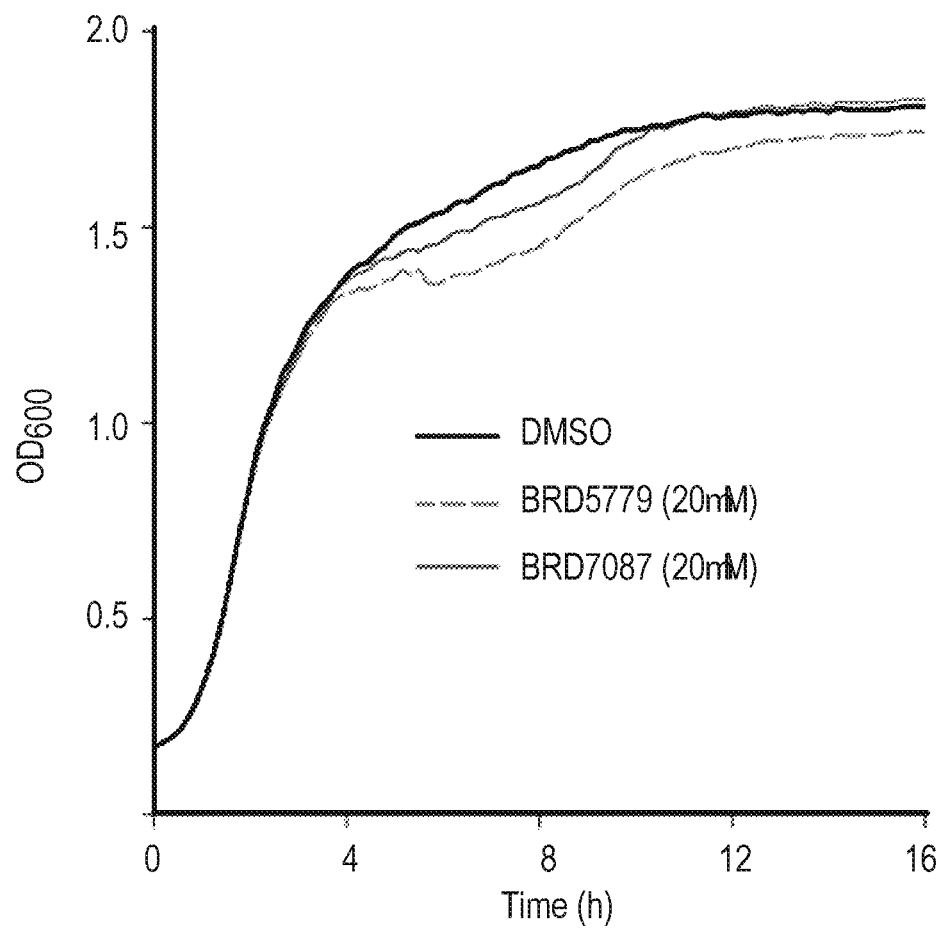
FIG. 79. Toxicity study of compounds in bacterial culture. Bacterial growth study in the presence of the compound. Bacterial cell S. aureus RN4220 strain was allowed to grow either in the presence of DMSO or 20 µM of compound BRD7087 or BRD5779 over 16 h. The experiment was performed in three technical replicates.
Figure 80:
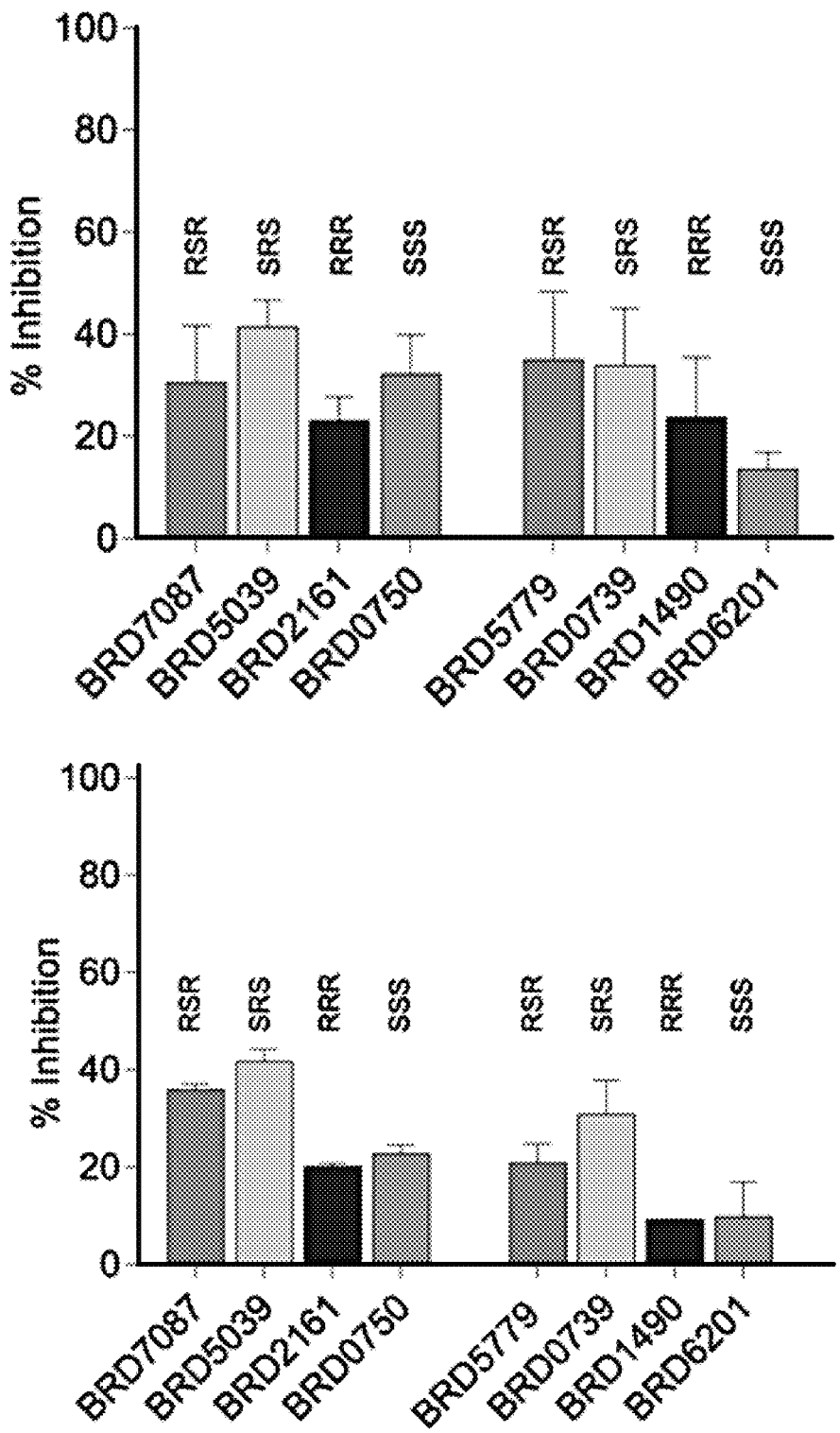
FIG. 80. Effect of stereo-isomers in Cas9 inhibition activity. Evaluation of the SpCas9 activity of compound BRD7087 and BRD5779 and their stereo-isomers in the EGFP-knockdown assay in U2OS.eGFP.PEST cells. Cells were Nucleofected with SpCas9 and gRNA expressing plasmids and incubated with either DMSO or 10 µM of the compound for 24 h before processing for imaging and analysis. Error bars represent ±S.D. from biological replicates (n=2).
Figure 82:
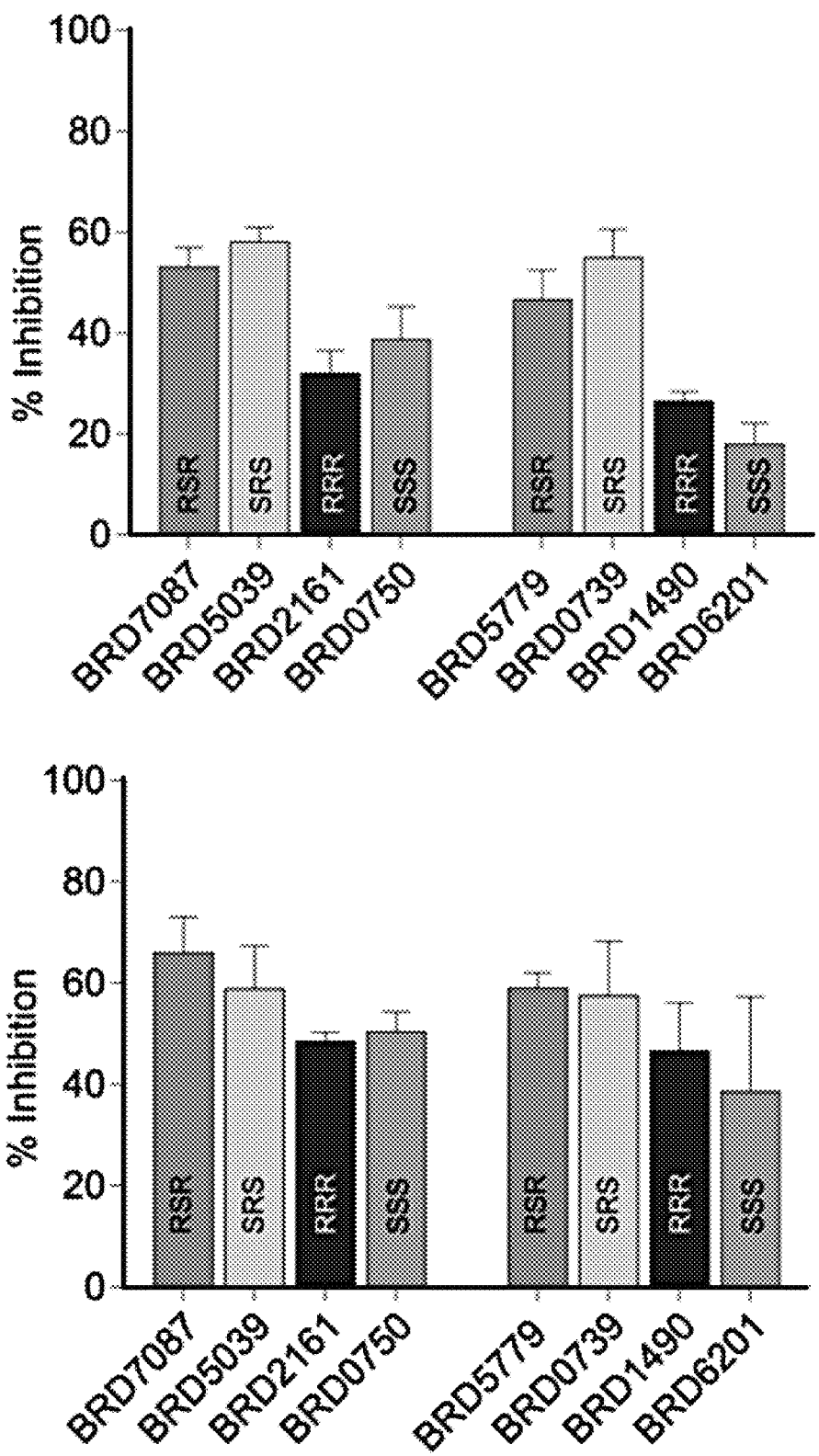
FIG. 82. Effect of stereo-isomers in Cas9 inhibition activity. Evaluation of the SpCas9 activity of compound BRD7087 and BRD5779 and their stereo-isomers in the EGFP-knockdown assay in U2OS.eGFP.PEST cells. Cells were Nucleofected with SpCas9 and gRNA expressing plasmids and incubated with either DMSO or 20 µM of the compound for 24 h before processing for imaging and analysis. Error bars represent ±S.D. from biological replicates (n=2).

BRD7087 and BRD5779 possess three chiral centers (3aR,4S,9bR) and Applicants wished to determine if different stereoisomers have similar nuclease inhibition activity. Applicants tested four isomers of each compound BRD7087 and BRD5779 in EGFP-disruption assay (FIGS. 79-81). Strikingly, the enantiomer of BRD7087 (3aR,4S,9bR), that is BRD5039 (3aS,4R,9bS), was equipotent as BRD7087 in EGFP-disruption assay. However, the other two diastereomers BRD2161 (3aR,4R,9bR) and BRD0750 (3aS,4S,9bS) were less potent (FIGS. 79-81). Similar trend was observed for BRD5779 and its stereoisomers (FIGS. 79-81).

Small molecule inhibitors of CRISPR-Cas9 will find multifactorial use in basic, biomedical, and defense research. Applicants report a suite of assays and workflow for discovery of small molecule inhibitors of SpCas9, and demonstrate the utility of these assays by identifying small molecule inhibitors of SpCas9. The availability of such workflow will catalyze discovery of inhibitors for not only SpCas9 but also several other next-generation CRISPR-associated nucleases. Our screening strategy involved disrupting PAM-binding by SpCas9 and Applicants were able to demonstrate >60% inhibition of nuclease activity of SpCas9 in mammalian and bacterial cells, as well as inhibition of dCas9 based transcriptional and base editing technologies. Thus, Applicants envision our SpCas9 inhibitors to find utility in wide variety of applications. Our future studies will involve identification of binding sites of our inhibitors and structure-guided potency optimization. Further, Applicants are interested in determining if the disruption of CRISPR-immunity by our SpCas9 inhibitors will propel bacteria to evolve CRISPR system.

REFERENCES

1. Doudna, J. A.; Charpentier, E., Genome editing. The new frontier of genome engineering with CRISPR-Cas9. *Science* 2014, 346 (6213), 1258096.
2. Hsu, P. D.; Lander, E. S.; Zhang, F., Development and applications of CRISPR-Cas9 for genome engineering. *Cell* 2014, 157 (6), 1262-78.
3. Jinek, M.; Chylinski, K.; Fonfara, I.; Hauer, M.; Doudna, J. A.; Charpentier, E., A programmable dual-RNA-guided DNA endonuclease in adaptive bacterial immunity. *Science* 2012, 337 (6096), 816-21.
4. Jinek, M.; East, A.; Cheng, A.; Lin, S.; Ma, E.; Doudna, J., RNA-programmed genome editing in human cells. *eLife* 2013, 2, e00471.
5. Cong, L.; Ran, F. A.; Cox, D.; Lin, S.; Barretto, R.; Habib, N.; Hsu, P. D.; Wu, X.; Jiang, W.; Marraffini, L. A.; Zhang, F., Multiplex genome engineering using CRISPR/Cas systems. *Science* 2013, 339 (6121), 819-23.
6. Mali, P.; Yang, L.; Esvelt, K. M.; Aach, J.; Guell, M.; DiCarlo, J. E.; Norville, J. E.; Church, G. M., RNA-guided human genome engineering via Cas9. *Science* 2013, 339 (6121), 823-6.
7. Gasiunas, G.; Barrangou, R.; Horvath, P.; Siksnys, V., Cas9-crRNA ribonucleoprotein complex mediates specific DNA cleavage for adaptive immunity in bacteria. *Proceedings of the National Academy of Sciences of the United States of America* 2012, 109 (39), E2579-86.
8. Dahlman, J. E.; Abudayyeh, O. O.; Joung, J.; Gootenberg, J. S.; Zhang, F.; Konermann, S., Orthogonal gene knockout and activation with a catalytically active Cas9 nuclease. *Nat Biotechnol* 2015, 33 (11), 1159-61.
9. Merkle, F. T.; Neuhausser, W. M.; Santos, D.; Valen, E.; Gagnon, J. A.; Maas, K.; Sandoe, J.; Schier, A. F.; Eggan, K., Efficient CRISPR-Cas9-mediated generation of knockin human pluripotent stem cells lacking undesired mutations at the targeted locus. *Cell reports* 2015, 11 (6), 875-883.
10. He, X.; Tan, C.; Wang, F.; Wang, Y.; Zhou, R.; Cui, D.; You, W.; Zhao, H.; Ren, J.; Feng, B., Knock-in of large reporter genes in human cells via CRISPR/Cas9-induced homology-dependent and independent DNA repair. *Nucleic Acids Res* 2016, 44 (9), e85.
11. Lin, S.; Staahl, B. T.; Alla, R. K.; Doudna, J. A., Enhanced homology-directed human genome engineering by controlled timing of CRISPR/Cas9 delivery. *eLife* 2014, 3, e04766.
12. Shalem, O.; Sanjana, N. E.; Hartenian, E.; Shi, X.; Scott, D. A.; Mikkelson, T.; Heckl, D.; Ebert, B. L.; Root, D. E.; Doench, J. G.; Zhang, F., Genome-scale CRISPR-Cas9 knockout screening in human cells. *Science* 2014, 343 (6166), 84-87.
13. Chen, B.; Gilbert, L. A.; Cimini, B. A.; Schnitzbauer, J.; Zhang, W.; Li, G. W.; Park, J.; Blackburn, E. H.; Weissman, J. S.; Qi, L. S.; Huang, B., Dynamic imaging of genomic loci in living human cells by an optimized CRISPR/Cas system. *Cell* 2013, 155 (7), 1479-91.
14. Hilton, I. B.; D'Ippolito, A. M.; Vockley, C. M.; Thakore, P. I.; Crawford, G. E.; Reddy, T. E.; Gersbach, C. A., Epigenome editing by a CRISPR-Cas9-based acetyltransferase activates genes from promoters and enhancers. *Nat Biotechnol* 2015, 33 (5), 510-7.
15. Dominguez, A. A.; Lim, W. A.; Qi, L. S., Beyond editing: repurposing CRISPR-Cas9 for precision genome regulation and interrogation. *Nat Rev Mol Cell Biol* 2016, 17 (1), 5-15.
16. Shalem, O.; Sanjana, N. E.; Zhang, F., High-throughput functional genomics using CRISPR-Cas9. *Nature reviews. Genetics* 2015, 16 (5), 299-311.
17. Ma, H.; Naseri, A.; Reyes-Gutierrez, P.; Wolfe, S. A.; Zhang, S.; Pederson, T., Multicolor CRISPR labeling of chromosomal loci in human cells. *Proceedings of the National Academy of Sciences of the United States of America* 2015, 112 (10), 3002-7.
18. Fujita, T.; Fujii, H., Efficient isolation of specific genomic regions and identification of associated proteins by engineered DNA-binding molecule-mediated chromatin immunoprecipitation (enChIP) using CRISPR. *Biochemical and biophysical research communications* 2013, 439 (1), 132-6.
19. Komor, A. C.; Kim, Y. B.; Packer, M. S.; Zuris, J. A.; Liu, D. R., Programmable editing of a target base in genomic DNA without double-stranded DNA cleavage. *Nature* 2016, 533 (7603), 420-4.
20. Gantz, V. M.; Bier, E., The dawn of active genetics. *BioEssays: news and reviews in molecular, cellular and developmental biology* 2016, 38 (1), 50-63.
21. Esvelt, K. M.; Smidler, A. L.; Catteruccia, F.; Church, G. M., Concerning RNA-guided gene drives for the alteration of wild populations. *Elife* 2014, 3.
22. Champer, J.; Buchman, A.; Akbari, O. S., Cheating evolution: engineering gene drives to manipulate the fate of wild populations. *Nature reviews. Genetics* 2016, 17 (3), 146-59.
23. Cox, D. B.; Platt, R. J.; Zhang, F., Therapeutic genome editing: prospects and challenges. *Nat Med* 2015, 21 (2), 121-31.
24. Yin, H.; Xue, W.; Chen, S.; Bogorad, R. L.; Benedetti, E.; Grompe, M.; Koteliansky, V.; Sharp, P. A.; Jacks, T.; Anderson, D. G., Genome editing with Cas9 in adult mice corrects a disease mutation and phenotype. *Nature biotechnology* 2014, 32 (6), 551-3.
25. Doudna, J. A., Genomic engineering and the future of medicine. *Jama* 2015, 313 (8), 791-2.
26. Ding, Q.; Strong, A.; Patel, K. M.; Ng, S. L.; Gosis, B. S.; Regan, S. N.; Cowan, C. A.; Rader, D. J.; Musunuru, 27. Saayman, S.; Ali, S. A.; Morris, K. V.; Weinberg, M. S., The therapeutic application of CRISPR/Cas9 technologies for HIV. *Expert Opin Biol Ther* 2015, 15 (6), 819-30.
28. Nelson, C. E.; Hakim, C. H.; Ousterout, D. G.; Thakore, P. I.; Moreb, E. A.; Castellanos Rivera, R. M.; Madhavan, S.; Pan, X.; Ran, F. A.; Yan, W. X.; Asokan, A.; Zhang, F.; Duan, D.; Gersbach, C. A., In vivo genome editing improves muscle function in a mouse model of Duchenne muscular dystrophy. *Science* 2016, 351 (6271), 403-7.
29. Tabebordbar, M.; Zhu, K.; Cheng, J. K. W.; Chew, W. L.; Widrick, J. J.; Yan, W. X.; Maesner, C.; Wu, E. Y.; Xiao, R.; Ran, F. A.; Cong, L.; Zhang, F.; Vandenberghe, L. H.; Church, G. M.; Wagers, A. J., In vivo gene editing in dystrophic mouse muscle and muscle stem cells. *Science* 2016, 351 (6271), 407-411.
30. Long, C.; Amoasii, L.; Mireault, A. A.; McAnally, J. R.; Li, H.; Sanchez-Ortiz, E.; Bhattacharyya, S.; Shelton, J. M.; Bassel-Duby, R.; Olson, E. N., Postnatal genome editing partially restores dystrophin expression in a mouse model of muscular dystrophy. *Science* 2016, 351 (6271), 400-3.
31. Bakondi, B.; Lv, W.; Lu, B.; Jones, M. K.; Tsai, Y.; Kim, K. J.; Levy, R.; Akhtar, A. A.; Breunig, J. J.; Svendsen, C. N.; Wang, S., In Vivo CRISPR/Cas9 Gene Editing Corrects Retinal Dystrophy in the S334ter-3 Rat Model of Autosomal Dominant Retinitis Pigmentosa. *Molecular therapy: the journal of the American Society of Gene Therapy* 2016, 24 (3), 556-63.
32. Wu, W. H.; Tsai, Y. T.; Justus, S.; Lee, T. T.; Zhang, L.; Lin, C. S.; Bassuk, A. G.; Mahajan, V. B.; Tsang, S. H., CRISPR Repair Reveals Causative Mutation in a Preclinical Model of Retinitis Pigmentosa. *Molecular therapy: the journal of the American Society of Gene Therapy* 2016, 24 (8), 1388-94.
33. Zhong, H.; Chen, Y.; Li, Y.; Chen, R.; Mardon, G., CRISPR-engineered mosaicism rapidly reveals that loss of Kcnj13 function in mice mimics human disease phenotypes. *Scientific reports* 2015, 5, 8366.
34. Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat Biotechnol* 2013, 31 (9), 822-6.
35. Hsu, P. D.; Scott, D. A.; Weinstein, J. A.; Ran, F. A.; Konermann, S.; Agarwala, V.; Li, Y.; Fine, E. J.; Wu, X.; Shalem, O.; Cradick, T. J.; Marraffini, L. A.; Bao, G.; Zhang, F., DNA targeting specificity of RNA-guided Cas9 nucleases. *Nat Biotechnol* 2013, 31 (9), 827-32.
36. Pattanayak, V.; Lin, S.; Guilinger, J. P.; Ma, E.; Doudna, J. A.; Liu, D. R., High-throughput profiling of off-target DNA cleavage reveals RNA-programmed Cas9 nuclease specificity. *Nature biotechnology* 2013, 31 (9), 839-43.
37. Pattanayak, V.; Guilinger, J. P.; Liu, D. R., Determining the specificities of TALENs, Cas9, and other genome-editing enzymes. *Methods Enzymol* 2014, 546, 47-78.
38. Frock, R. L.; Hu, J.; Meyers, R. M.; Ho, Y. J.; Kii, E.; Alt, F. W., Genome-wide detection of DNA double-stranded breaks induced by engineered nucleases. *Nature biotechnology* 2015, 33 (2), 179-86.
39. Tsai, S. Q.; Zheng, Z.; Nguyen, N. T.; Liebers, M.; Topkar, V. V.; Thapar, V.; Wyvekens, N.; Khayter, C.; Iafrate, A. J.; Le, L. P.; Aryee, M. J.; Joung, J. K., GUIDE-seq enables genome-wide profiling of off-target cleavage by CRISPR-Cas nucleases. *Nature biotechnology* 2015, 33 (2), 187-97.
40. Davis, K. M.; Pattanayak, V.; Thompson, D. B.; Zuris, J. A.; Liu, D. R., Small molecule-triggered Cas9 protein with improved genome-editing specificity. *Nat Chem Biol* 2015, 11 (5), 316-8.
41. Nunez, J. K.; Lee, A. S.; Engelman, A.; Doudna, J. A., Integrase-mediated spacer acquisition during CRISPR-Cas adaptive immunity. *Nature* 2015, 519 (7542), 193-8.
42. Maji, B.; Moore, C. L.; Zetsche, B.; Volz, S. E.; Zhang, F.; Shoulders, M. D.; Choudhary, A., Multidimensional chemical control of CRISPR-Cas9. *Nature chemical biology* 2017, 13 (1), 9-11.
43. Senis, E.; Fatouros, C.; Grosse, S.; Wiedtke, E.; Niopek, D.; Mueller, A. K.; Borner, K.; Grimm, D., CRISPR/Cas9-mediated genome engineering: an adeno-associated viral (AAV) vector toolbox. *Biotechnol J* 2014, 9 (11), 1402-12.
44. Nunez, J. K.; Harrington, L. B.; Doudna, J. A., Chemical and Biophysical Modulation of Cas9 for Tunable Genome Engineering. *ACS Chem Biol* 2016, 11 (3), 681-8.
45. Westra, E. R.; Buckling, A.; Fineran, P. C., CRISPR-Cas systems: beyond adaptive immunity. *Nature reviews. Microbiology* 2014, 12 (5), 317-26.
46. Barrangou, R., The roles of CRISPR-Cas systems in adaptive immunity and beyond. *Current opinion in immunology* 2015, 32, 36-41.
47. Pawluk, A.; Staals, R. H.; Taylor, C.; Watson, B. N.; Saha, S.; Fineran, P. C.; Maxwell, K. L.; Davidson, A. R., Inactivation of CRISPR-Cas systems by anti-CRISPR proteins in diverse bacterial species. Nature microbiology 2016, 1 (8), 16085.
48. Pawluk, A.; Amrani, N.; Zhang, Y.; Garcia, B.; Hidalgo-Reyes, Y.; Lee, J.; Edraki, A.; Shah, M.; Sontheimer, E. J.; Maxwell, K. L.; Davidson, A. R., Naturally Occurring Off-Switches for CRISPR-Cas9. *Cell* 2016, 167 (7), 1829-1838.e9.
49. Shin, J.; Jiang, F.; Liu, J. J.; Bray, N. L.; Rauch, B. J.; Baik, S. H.; Nogales, E.; Bondy-Denomy, J.; Corn, J. E.; Doudna, J. A., Disabling Cas9 by an anti-CRISPR DNA mimic. *Science advances* 2017, 3 (7), e1701620.
50. Rauch, B. J.; Silvis, M. R.; Hultquist, J. F.; Waters, C. S.; McGregor, M. J.; Krogan, N. J.; Bondy-Denomy, J., Inhibition of CRISPR-Cas9 with Bacteriophage Proteins. *Cell* 2017, 168 (1-2), 150-158.e10.
51. Sternberg, S. H.; Redding, S.; Jinek, M.; Greene, E. C.; Doudna, J. A., DNA interrogation by the CRISPR RNA-guided endonuclease Cas9. *Nature* 2014, 507 (7490), 62-7.
52. Nishimasu, H.; Ran, F. A.; Hsu, P. D.; Konermann, S.; Shehata, S. I.; Dohmae, N.; Ishitani, R.; Zhang, F.; Nureki, O., Crystal structure of Cas9 in complex with guide RNA and target DNA. *Cell* 2014, 156 (5), 935-49.
53. Kleinstiver, B. P.; Prew, M. S.; Tsai, S. Q.; Topkar, V. V.; Nguyen, N. T.; Zheng, Z.; Gonzales, A. P.; Li, Z.; Peterson, R. T.; Yeh, J. R.; Aryee, M. J.; Joung, J. K., Engineered CRISPR-Cas9 nucleases with altered PAM specificities. *Nature* 2015, 523 (7561), 481-5.
54. Lundblad, J. R.; Laurance, M.; Goodman, R. H., Fluorescence polarization analysis of protein-DNA and protein-protein interactions. *Mol Endocrinol* 1996, 10 (6), 607-12.
55. Niesen, F. H.; Berglund, H.; Vedadi, M., The use of differential scanning fluorimetry to detect ligand interactions that promote protein stability. *Nature protocols* 2007, 2 (9), 2212-21.
56. Richardson, C. D.; Ray, G. J.; DeWitt, M. A.; Curie, G. L.; Corn, J. E., Enhancing homology-directed genome editing by catalytically active and inactive CRISPR-Cas9 using asymmetric donor DNA. *Nature biotechnology* 2016, 34 (3), 339-44.
57. Fu, Y.; Foden, J. A.; Khayter, C.; Maeder, M. L.; Reyon, D.; Joung, J. K.; Sander, J. D., High-frequency off-target mutagenesis induced by CRISPR-Cas nucleases in human cells. *Nat. Biotechnol.* 2013, 31 (9), 822-6.
58. Moore, R.; Spinhirne, A.; Lai, M. J.; Preisser, S.; Li, Y.; Kang, T.; Bleris, L., CRISPR-based self-cleaving mechanism for controllable gene delivery in human cells. *Nucleic Acids Res* 2015, 43 (2), 1297-303.
59. Nguyen, D. P.; Miyaoka, Y.; Gilbert, L. A.; Mayerl, S. J.; Lee, B. H.; Weissman, J. S.; Conklin, B. R.; Wells, J. A., Ligand-binding domains of nuclear receptors facilitate tight control of split CRISPR activity. *Nat Commun* 2016, 7, 12009.
60. Burke, M. D.; Schreiber, S. L., A planning strategy for diversity-oriented synthesis. *Angew Chem Int Ed Engl* 2004, 43 (1), 46-58.
61. Shortridge, M. D.; Hage, D. S.; Harbison, G. S.; Powers, R., Estimating protein-ligand binding affinity using high-throughput screening by NMR. *J Comb Chem* 2008, 10 (6), 948-58.
62. Heler, R.; Samai, P.; Modell, J. W.; Weiner, C.; Goldberg, G. W.; Bikard, D.; Marraffini, L. A., Cas9 specifies functional viral targets during CRISPR-Cas adaptation. *Nature* 2015, 519 (7542), 199-202.

Example 5—Methods for Cas9 Nuclease Assays

Materials Instruments: All oligos were purchased from IDT, and were either purified by HPLC for use in strand displacement assays or by desalting for use in in vitro transcription experiments. Single time point fluorescence measurements were taken using an Envision plate reader with a FITC top mirror (403), FITC 485 excitation filter (102), and BODIPY TMP FP 531 emission filter (105). Gel images were acquired with an Azure Biosystems C400 or C600.

Oligonucleotide and plasmid cleavage assays. Oligonucleotides were annealed by heating to 95° C. for 5 minutes, followed by slow cooling to 25° C. at a rate of 0.1° C./sec to produce a double stranded oligo (DS-oligo). Oligo-annealing solutions were prepared by mixing 10 μM of each complementary strand together in the presence of 1×Cas9 assay buffer (20 mM Tris-HCl, pH=7.5, 150 mM KCl, 1 mM EDTA, 50 mM MgCl$_2$). A T7-promoter spinach sequence cloned into pUC57-Kan and linearized with AsiS1 was used as the plasmid substrate for Cas9 cleavage.

A Cas9:gRNA complex was first preformed by mixing each component at a ratio of 1:1.2 (Cas9:gRNA) and incubating at room temperature for 15 minutes. Cas9:gRNA complexes (500 nM) were mixed with either 100 nM of oligonucleotide or 5 nM (100 ng) of linearized plasmid in 1×assay buffer, and incubated at 37° C. for 1 hour. For oligonucleotide cleavage assays, Proteinase K (Qiagen) and RNAse (Qiagen) were added to final concentrations of 200 μg/μL and 100 μg/μL, respectively, and incubated at 37° C. for at least 30 minutes. Samples were boiled in loading buffer and 50 mM EDTA for 10 min, and run on a 15% TBE-Urea gel (ThermoFisher EC68855) for 70 minutes at 200 V. FAM fluorescence was measured prior to staining with SYBR gold (ThermoFisher) to visualize total nucleotide content. For plasmid cleavage assays, loading buffer was directly added to reactions and run on 1.6-2% agarose gels with 0.01% ethidium bromide.

Fluorescence strand displacement assays (SDA). All assay components and solutions were prepared at 10× working stocks prior to mixing. Concentrations are given as the final concentrations. In a typical assay, a Cas9:gRNA complex was first formed as described above. Cas9 without gRNA (ApoCas9) was treated similarly. DS-oligo (1 nM) was mixed with quencher oligo (Q-oligo, 5 nM) in 1×Cas9 assay buffer. Reactions were initiated by addition of Cas9: gRNA (5 nM), distributed among a 384-well plate (Corning 3575) (3 technical replicates per experiment), and incubated at 37° C. for 2-3 hours. Fluorescence was read on an Envision plate reader, using 485 nm emission and 535 nm excitation wavelengths. Typical controls included replacing Cas9:gRNA with ApoCas9 (maximum possible fluorescence), replacing DS-oligo with the single stranded FAM-labeled oligo (SS-oligo, maximum possible quenching), and omitting FAM labeled oligos altogether (background fluorescence from ApoCas9 and Q-oligo). Fraction cleaved was calculated by subtracting SS-oligo controls from matched Apo-Cas9+DS-oligo and Cas9/gRNA+DS-oligo samples and normalizing to ApoCas9+DS-oligo samples.

Cas nuclease binding in vitro transcription Spinach assay: HiScribe T7 High Yield RNA in vitro transcription kits were purchased from NEB (E2040S). The Spinach aptamer template and non-template oligonucleotides were annealed as described above. In a typical assay, a Cas9/Cpf1:gRNA complex was first formed as described above. Cas9/Cpf1 without gRNA (ApoCas9/ApCpf1) was treated similarly. A typical assay was performed by mixing the following components together from the 10× stocks to get the indicated final concentrations: NTPs (6.7 mM), 10× T7 reaction buffer (0.67×), murine RNase inhibitor (M0314L) (1.3 U), DFHBI (1 mM), DNA template (0.1 nM), and water to a final volume of 25 mL. ApoCas9 or Cas9:gRNA complexes (10×) were added to initiate cleavage and incubated at 37° C. for 30 minutes. Transcription was initiated by adding 2 mL of T7 RNA polymerase, or was omitted to assess background fluorescence. Reactions (27 μL) were transferred to a 384-well plate and the fluorescence was monitored at 37° C.

Figure 38A:
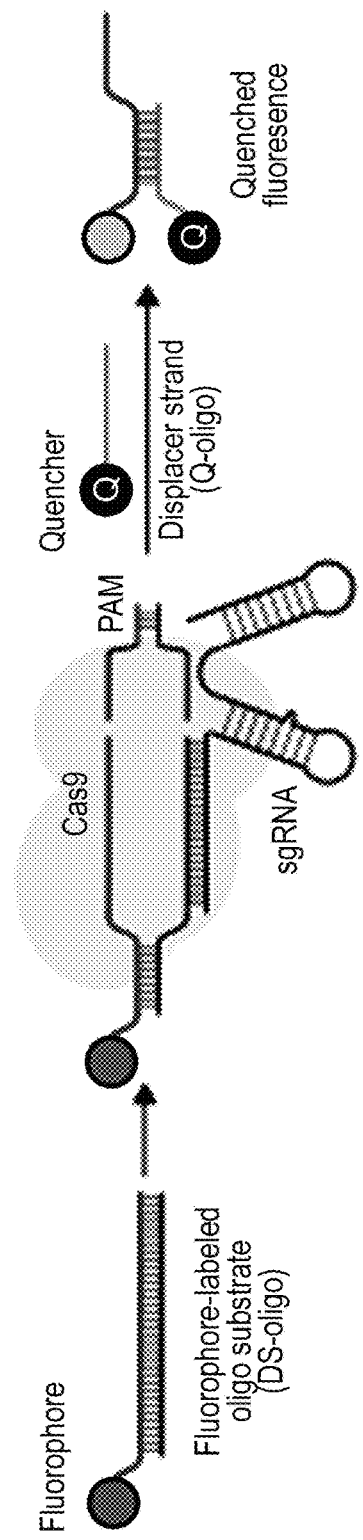
FIGS. 38A-38E.
Figure 38B:
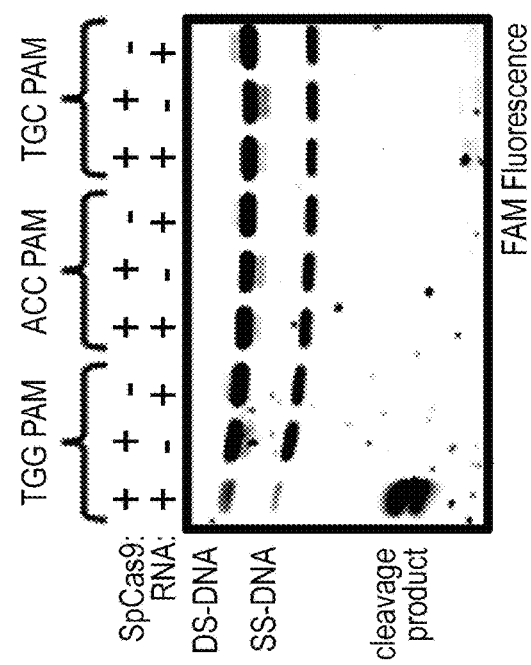

Although SpCas9 binds to its DNA substrate with nano-molar affinity, even following double stranded cleavage, it was discovered that of the 4 resulting DNA fragments, the distal non-target strand is weakly held, and can be displaced upon addition of excess complementary single stranded DNA (Richardson et al., Enhancing homology-directed genome editing by catalytically active and inactive CRISPR-Cas9 using asymmetric donor DNA. *Nature biotechnology* 2016, 34 (3), 339-44)) (FIG. 38A). Applications envisioned a system wherein by fluorescently labeling the 5' end of the non-target strand, Applicants could quench the fluorescence in a cleavage-dependent manner by adding in excess a complementary DNA strand labeled with a 3' quencher. Upon displacement and annealing of the two strands, fluorescence would be quenched by a FRET mechanism, and Applicants would have a proxy measurement for Cas9 activity at the RuvC domain based on the extent of fluorescence loss. Applicants generated 6-carboxyfluorescein-labeled double stranded oligos (DS-oligo) containing either a TGG PAM motif for recognition by SpCas9, or ACC and TGC PAMs that should not be recognized by SpCas9. Applicants verified cleavage of our DS-oligo substrate oligos by SpCas9:gRNA by monitoring the FAM fluorescence in a denaturing gel (FIG. 38B), validating the PAM dependence on our activity.

Figures 38C, 38D, 38E:
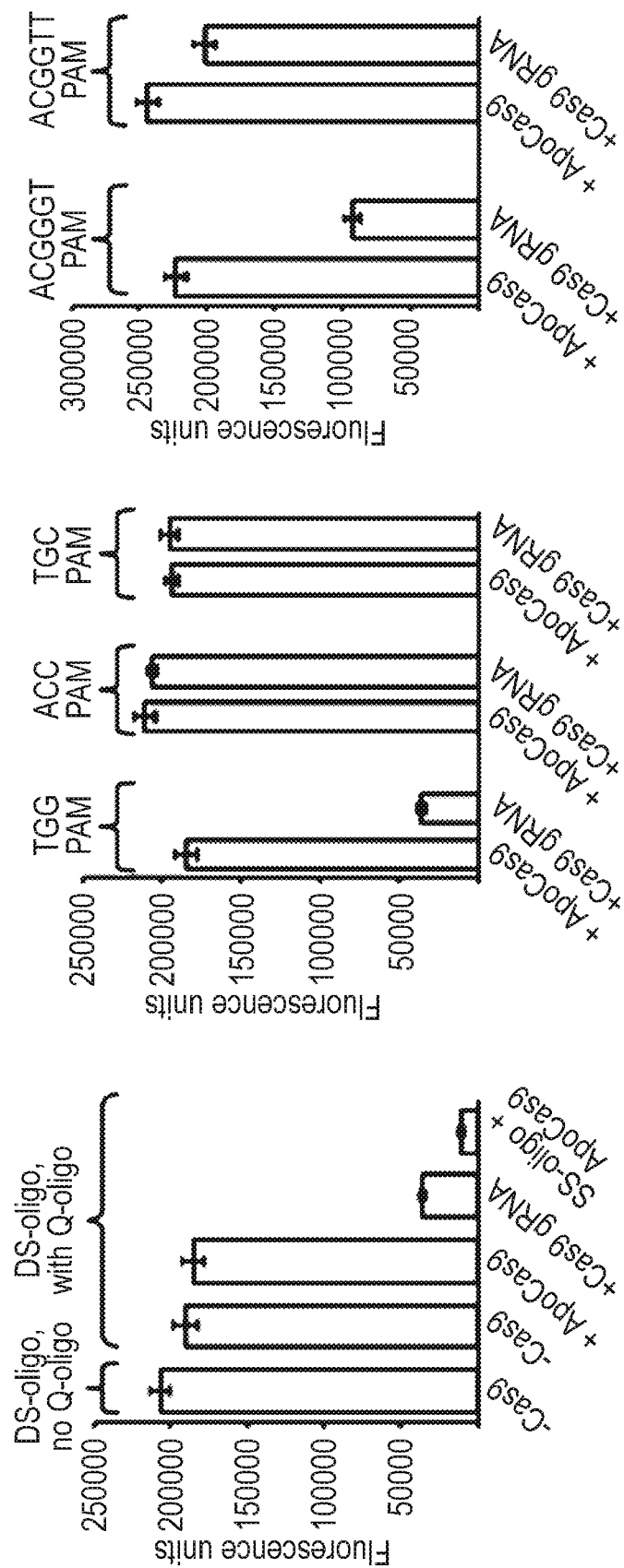

Next, Applicants generated an oligo complementary to the 5'-end of the non-target strand and containing an Iowa-Black FQ quencher on the 3' terminus (Q-oligo). Applicants verified that excess Q-oligo (5 nM) could not disrupt the fluorescence of duplex DS-oligo (1 nM), but was capable of quenching the FAM-labeled strand outside of a duplex (SS-oligo, 1 nM). Applicants then added 5 nM of a SpCas9: gRNA complex and observed a significant loss of fluorescence. This activity was dependent on gRNA-mediated cleavage of DNA and not local DNA melting caused by Cas9 binding to the PAM motif, as addition of ApoCas9 to DS-oligo and Q-oligo did not result in fluorescence loss (FIG. 38C). In agreement with the substrate cleavage observed via denaturing gel, strand displacement was dependent on the correct TGG PAM motif, as no quenching was observed with the ACC or TGC PAM oligos (FIG. 38D).

Figure 39B:
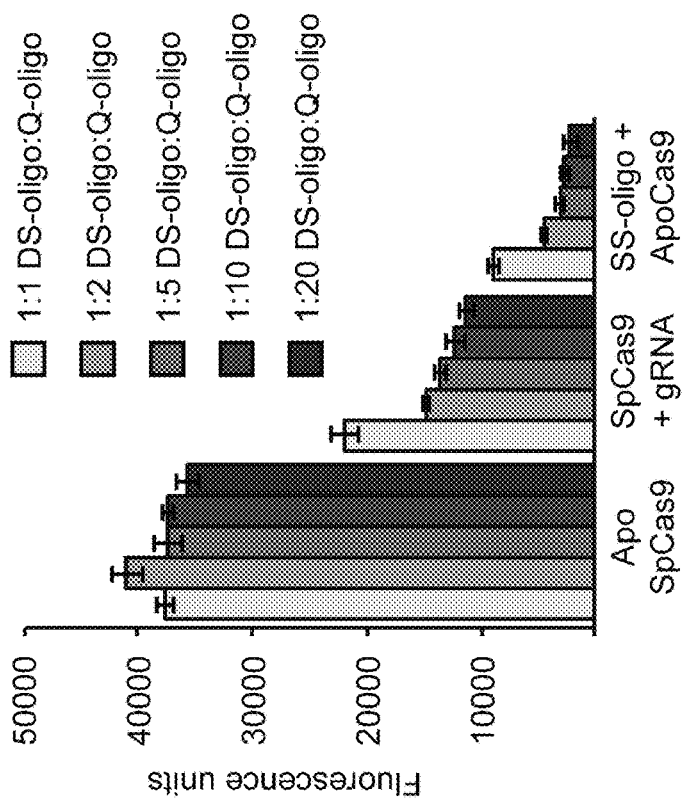
FIGS. 39A-39D.
Figure 39A:
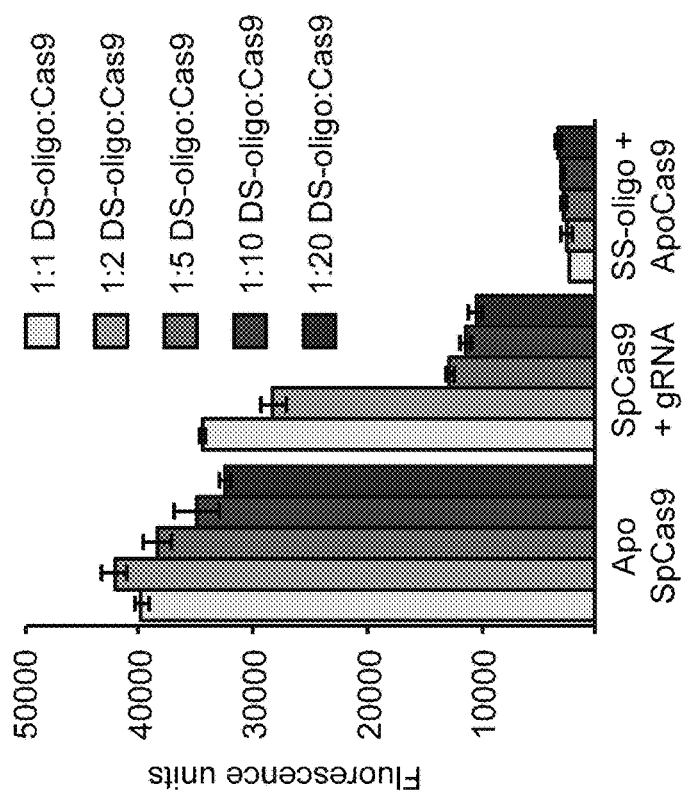
Figure 39D:
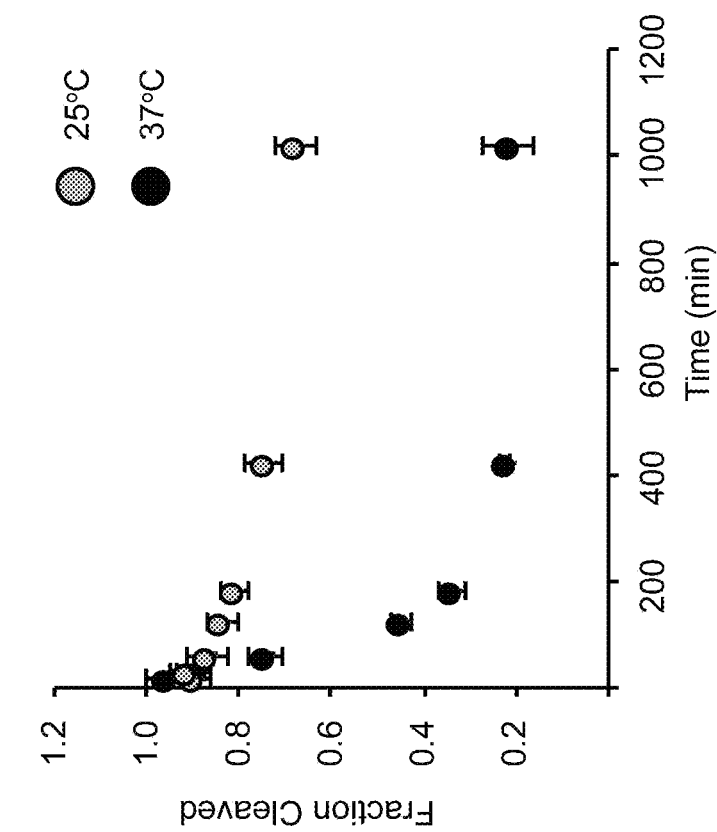
Figure 39C:
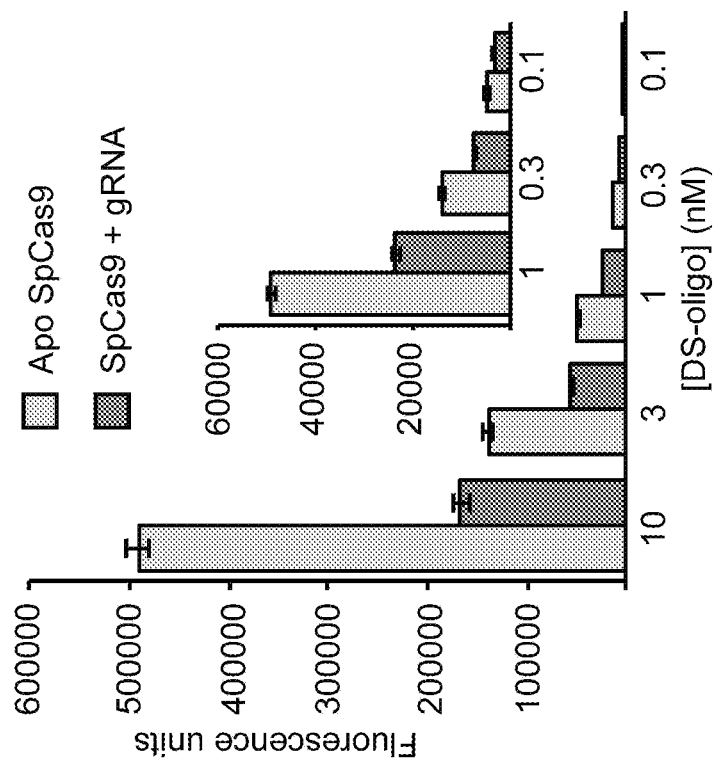

Applicants optimized the ratio of Q-oligo and Cas9: gRNA to the DS-oligo substrate by testing relative ratios of 1:1, 1:2, 1:5, 1:10, and 1:20, and found that a 5-fold excess of each reagent relative to DS-oligo is sufficient to yield maximum quenching (FIGS. 39A and 39B). Using these optimized conditions, Applicants determined that our assay was capable of detecting low (<5 nM) nanomolar quantities of SpCas9 (FIG. 39C). Applicants further optimized the kinetics of this assay, and found that 2.5 hours was sufficient to see >80% quenching at 37° C. (FIG. 39D). In agreement with previous reports, SpCas9 activity at room temperature was very weak although observable using our strand displacement assay (FIG. 39D). Thus, our assay provides a sensitive, specific, and potentially high-throughput readout of SpCas9 nuclease activity, at least as it pertains to the RuvC nuclease domain.

Generalization of the Strand Displacement Assay to SaCas9 and FnCpf1:

Encouraged by our success at assessing SpCas9 activity, Applicants wondered whether such a scheme would be amenable to other CRISPR nucleases. Such generalizability is hindered by lack of detailed studies on the catalytic mechanisms of Cas9-nucleases from other classes and bacterial species. However, given the similarities between *Staphylococcus aureus* Cas9 (SaCas9) and SpCas9 protein fold and modes of DNA substrate binding, Applicants wondered if SaCas9 strand displacement would precede in the same manner. Using FAM-labeled oligos containing an SaCas9-recognizable ACGGGT PAM and a ACGGTT non-target PAM with the appropriate Q-oligo, Applicants again observed PAM- and Cas9:gRNA-dependent loss of fluorescence (FIG. 38E) with similar efficiencies and detection limits as SpCas9. Similar Results were observed with Cas nucleases of the Cpf1 family, particularly FnCpf1.

Figure 40A:
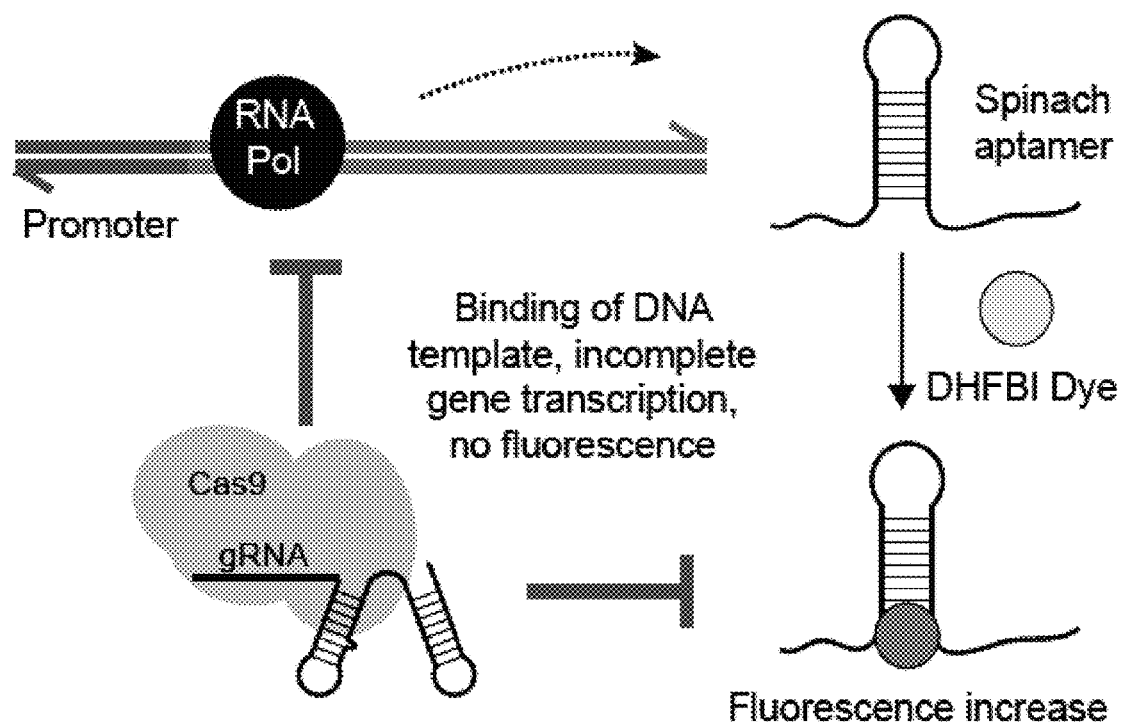
FIGS. 40A-40E. Proof of principle of a spinach assay for detecting Cas9 binding.

Discussion of Spinach IVT:

Development of an In Vitro Transcription Spinach Assay for Measuring Cas9 Activity:

Applicants wished to design a mechanism-independent assay to assess any Cas9 nuclease activity in vitro. Applicants turned to the coupling of an in vitro transcription (IVT) reaction that produces the RNA aptamer Spinach which, upon binding to the small molecule DFHBI, produces a fluorescent complex. A synthetic gene-like construct was designed to use the bacteriophage T7 RNA Polymerase (T7 RNAP) to drive the production of the Spinach RNA aptamer. This dsDNA construct, which Applicants call a 'genelet,' consists of a T7 RNAP promoter upstream of the region that codes for the spinach RNA. By designing Cas9 gRNAs that can bind to and/or cleave PAM-containing sites within the Spinach DNA template (FIG. 40B), Applicants would be able to interfere with T7 RNAP transcription and inhibit production of a functional DFHBI-binding RNA, and hence decrease fluorescence (FIG. 40A).

Figure 40B:
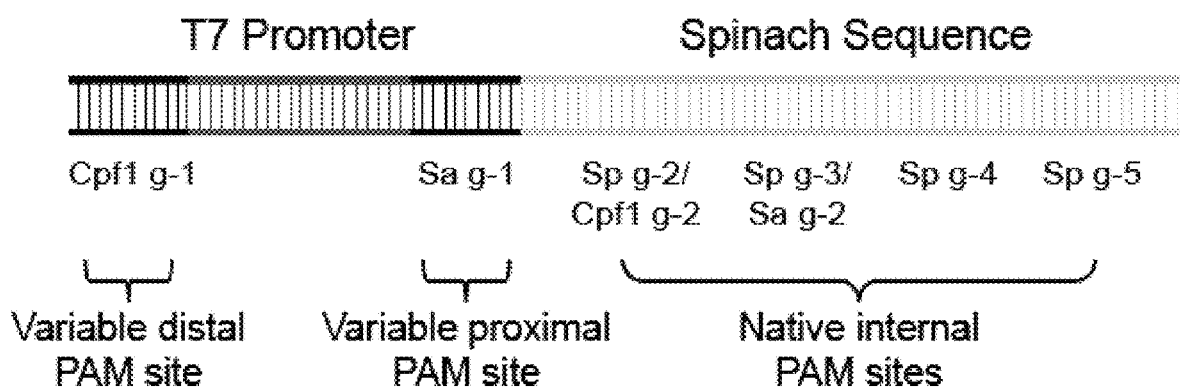
Figure 40C:
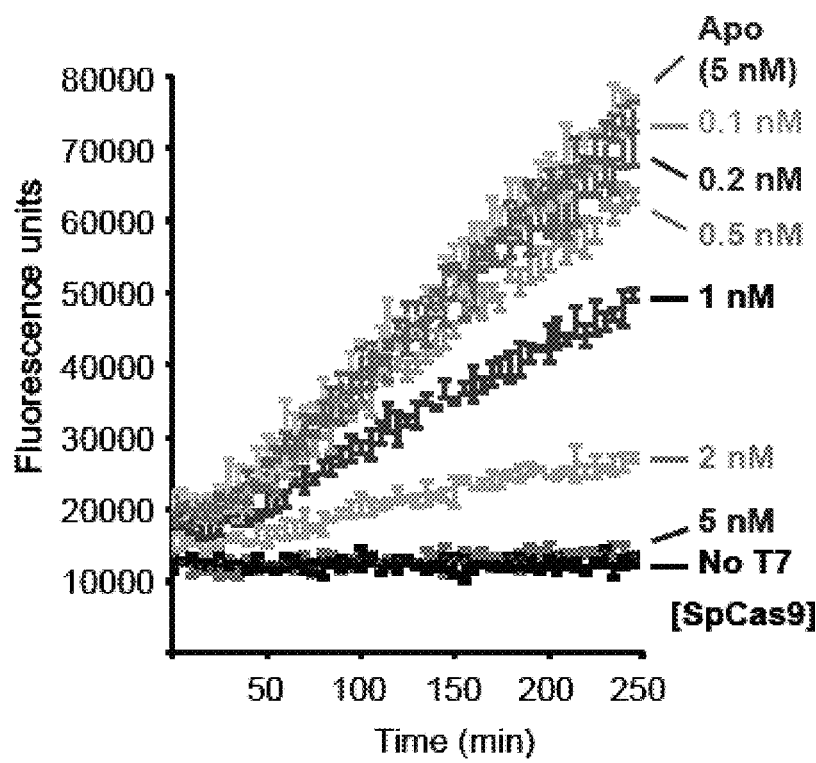
Figure 40D:
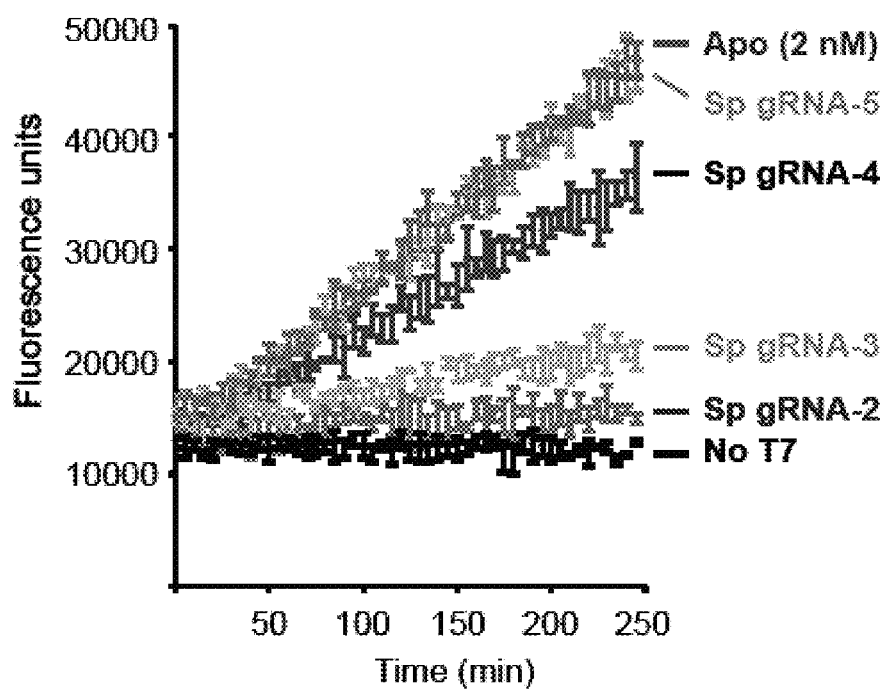

As long as the correct PAM sequence is present in the DNA template, it should be possible to use any Cas nuclease with the appropriate gRNA. Analysis of the Spinach sequence revealed a number of NGG sites evenly distributed throughout the sequence, allowing for preliminary optimization of the assay with SpCas9. Indeed, Applicants were able to titer the amount of DNA template used (0.1 nM) to detect nanomolar levels of SpCas9 activity using a guide RNA that targeted site Sp-g1 (FIG. 40C). This activity was dependent on the SpCas9 concentration and was highly dependent on the site of cleavage—scanning the length of the spinach sequence with 4 different SpCas9 guides (Sp-g1 through g4) revealed that binding events 5' to the DFHBI-binding Lu loop resulted in fluorescence loss, while binding after this loop produced fluorescence (FIG. 40D).

Figure 40E:
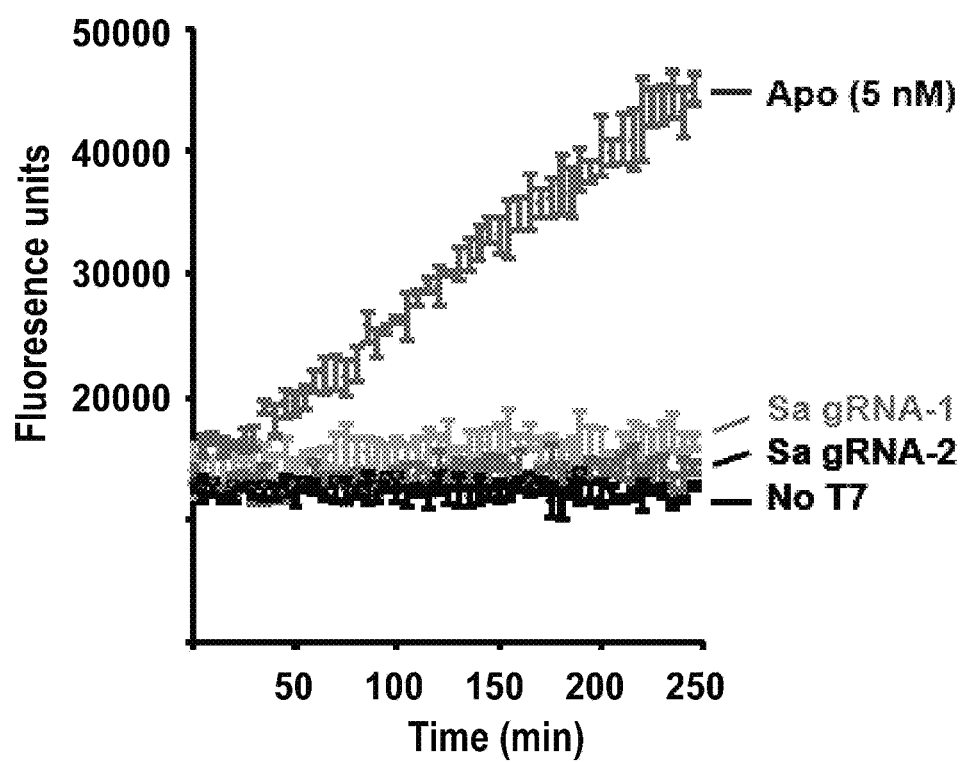

While this indicated that no modifications would be needed to assess this assay in the context of SpCas9, it hindered the generalizability of the assay to include Cas9 nucleases with more complex PAM recognitions. Indeed, the spinach gene only contained only one NNGGGT and TTTN site each, which are the PAM recognition sequences for SaCas9 and AsCpf1/LbCpf1, respectively. To overcome this limitation, Applicants inserted additional nucleotides that could accommodate arbitrary PAM sites—one between the T7 promoter and the spinach gene (proximal site, intended for 3'-PAM binding Cas enzymes), and one upstream of the T7 promoter (distal site, intended for 5'-PAM binding Cas enzymes like Cpf1. Our proximal site contained a TAGGGT SaCas9 PAM, and the distal site contained a TTTC Cpf1 PAM (FIG. 40B). Because early termination of spinach transcription resulted in optimal fluorescence loss, Applicants reasoned that these sites would allow direct targeting of the T7 promoter to completely abolish transcription. When comparing the activity of SaCas9 with a guide RNA targeting an internal spinach site (Sa-g1) and the proximal variable site (Sa-g2), Applicants observed comparable loss of DFHBI fluorescence with nanomolar levels of SaCas9 (FIG. 40E).

Figure 41A:
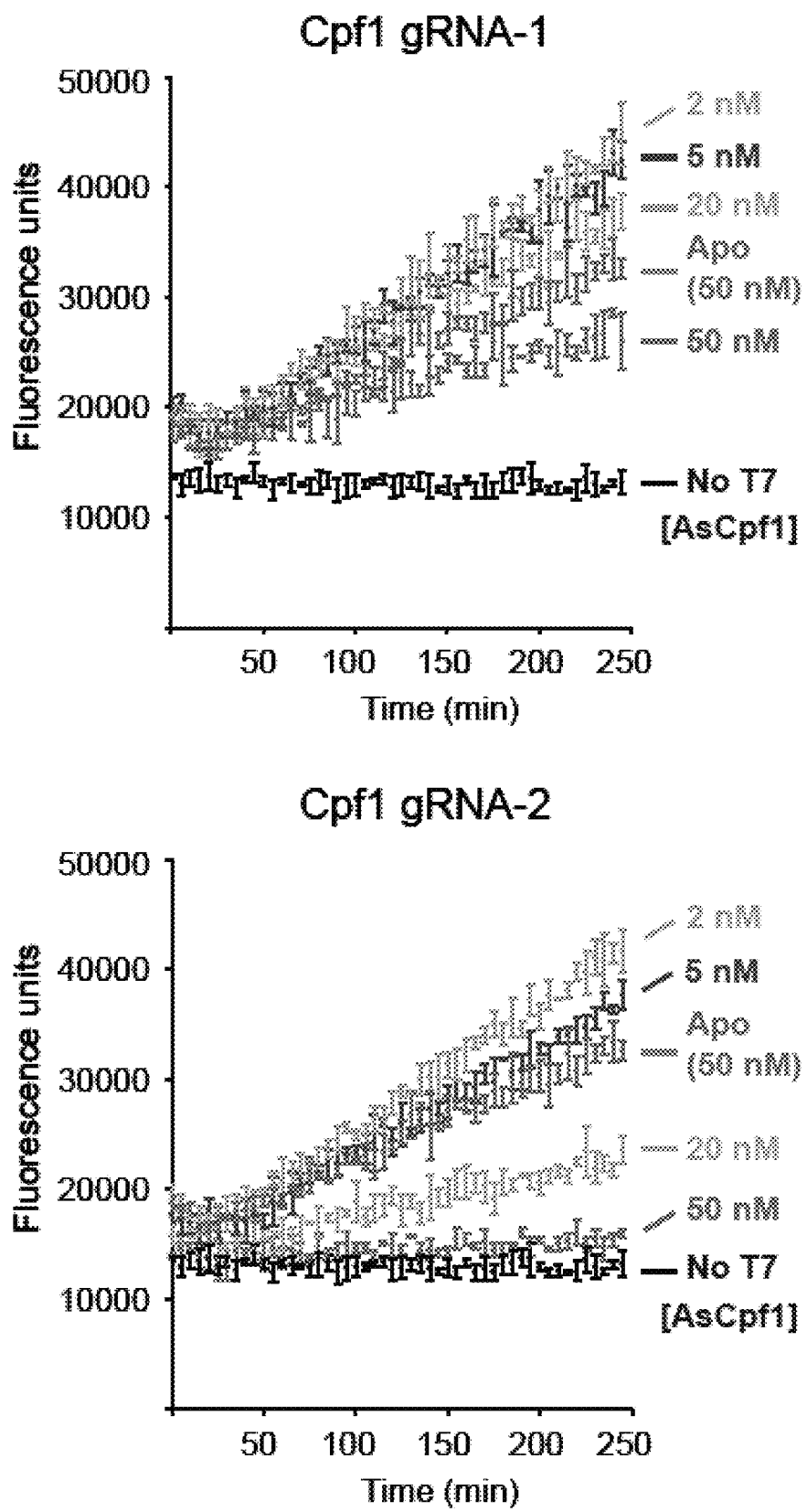
FIGS. 41A-41C. Comparison of Cpf1 binding activities using the Spinach assay.
Figure 41B:
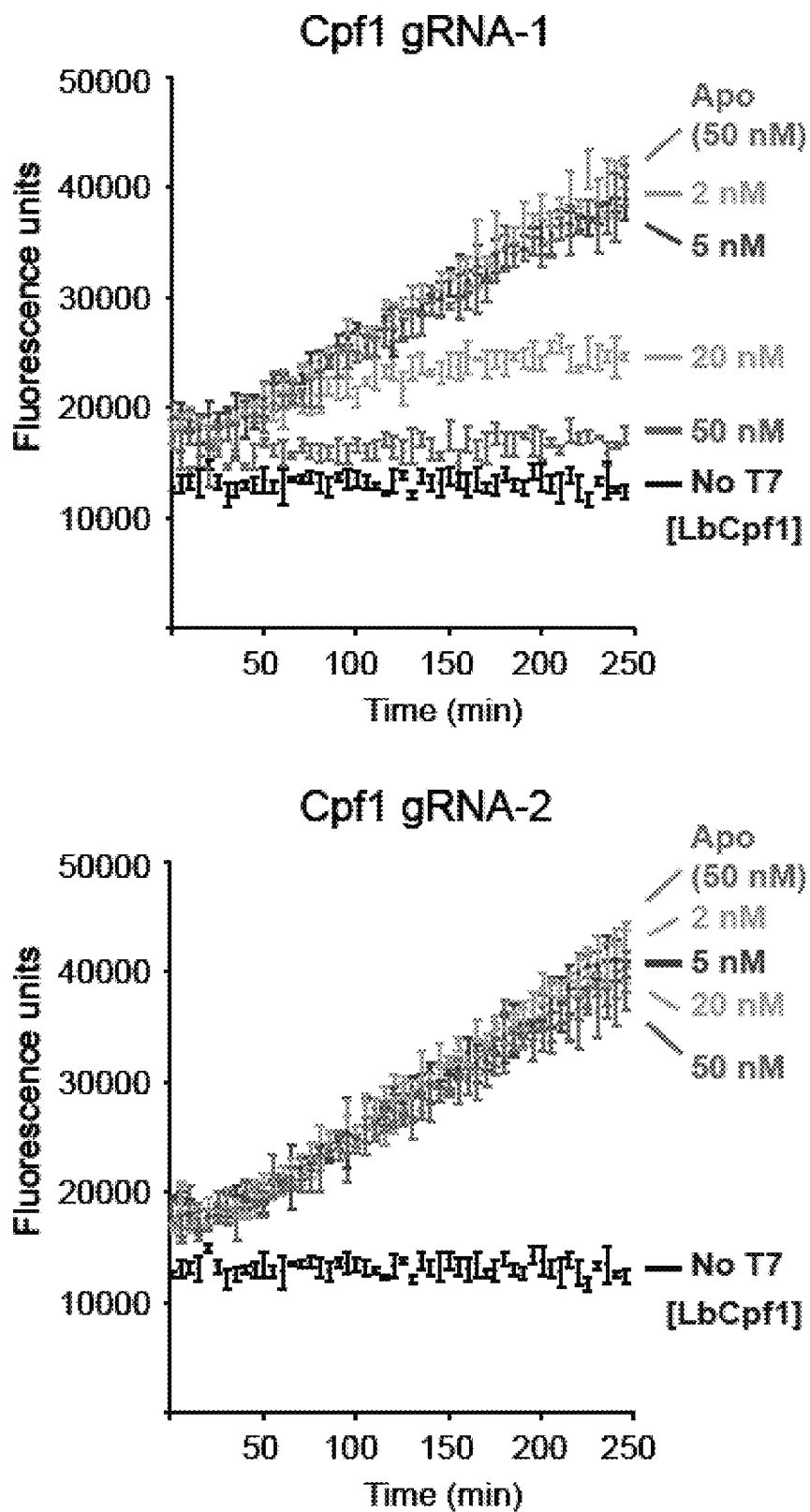
Figure 41C:
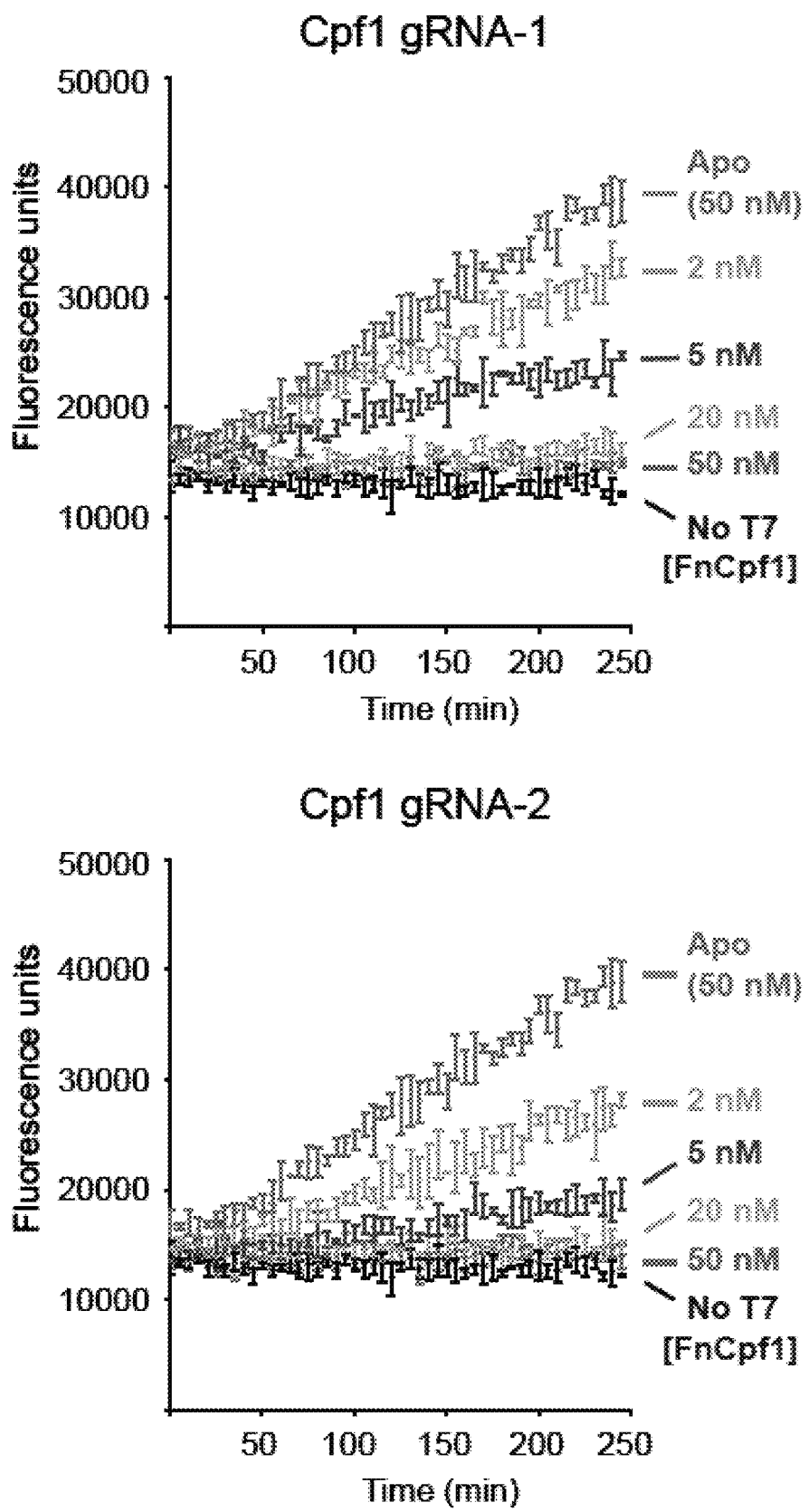
Figure 42B:
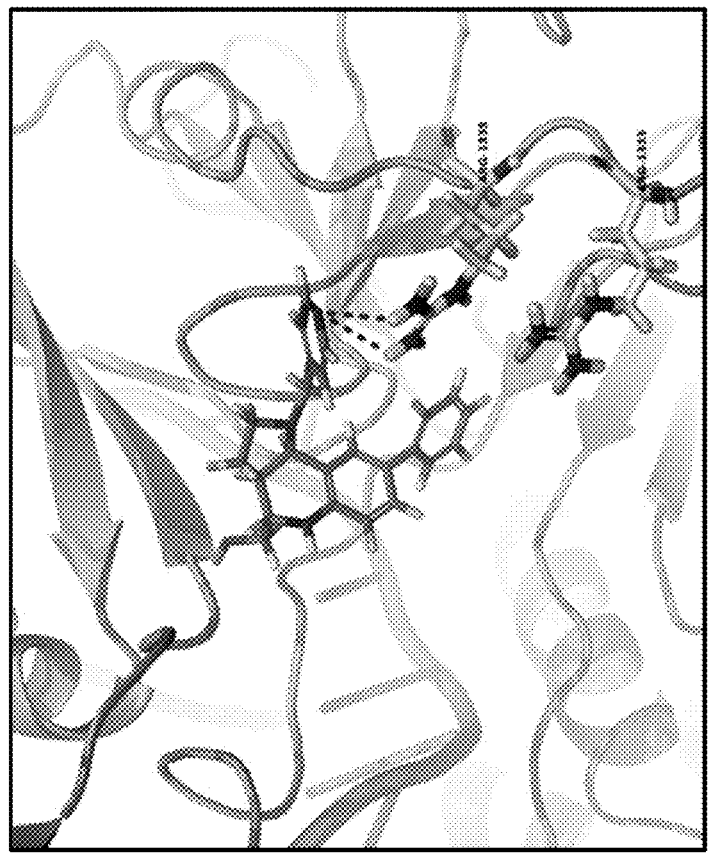
FIGS. 42A-42B. Docking complex of BRD7087 and SpCas9-RNA complex. The pyridine nitrogen forms key hydrogen-bond interactions with the guanidine group of Arg1335. The phenyl-1-(pyridin-4-ylmethyl)-2,3,3a,4,5,9b-hexahydro-1H-pyrrolo[3,2-c]quinolone scaffold of BRD7087 occupies a cavity, surrounded by residues such as Arg1333, Arg 1335, Lys1107, which accommodates the PAM region upon DNA-binding (Jiang, F., Zhou, K., Ma, L., Gressel, S., and Doudna, J. A. (2015). A Cas9-guide RNA complex preorganized for target DNA recognition. Science 348, 1477-1481; Jiang, F., Zhou, K., Ma, L., Gressel, S., and Doudna, J. A. (2015). A Cas9-guide RNA complex preorganized for target DNA recognition. Science 348, 1477-1481).
Figure 42A:
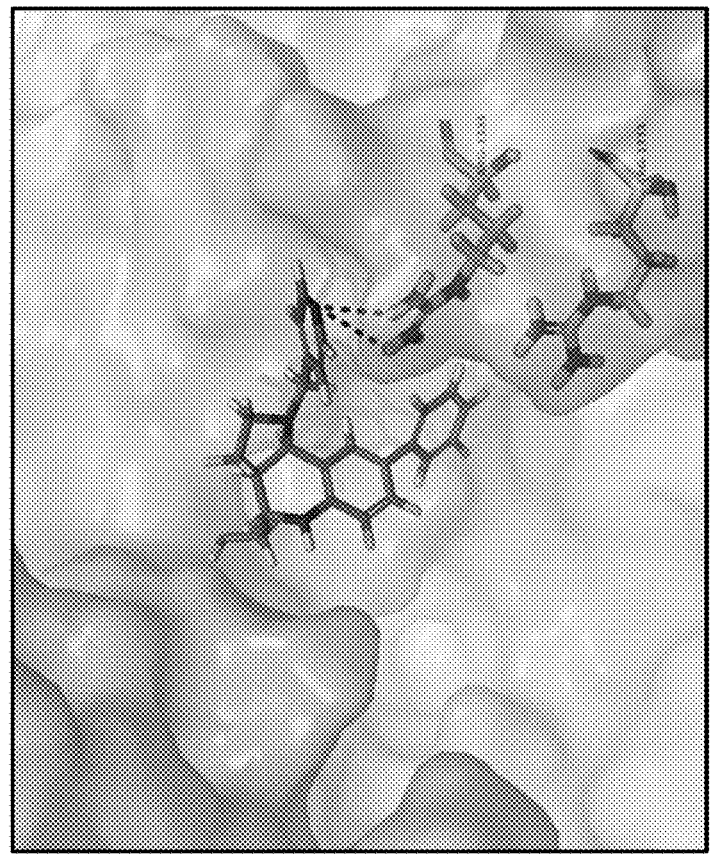
Figure 43:
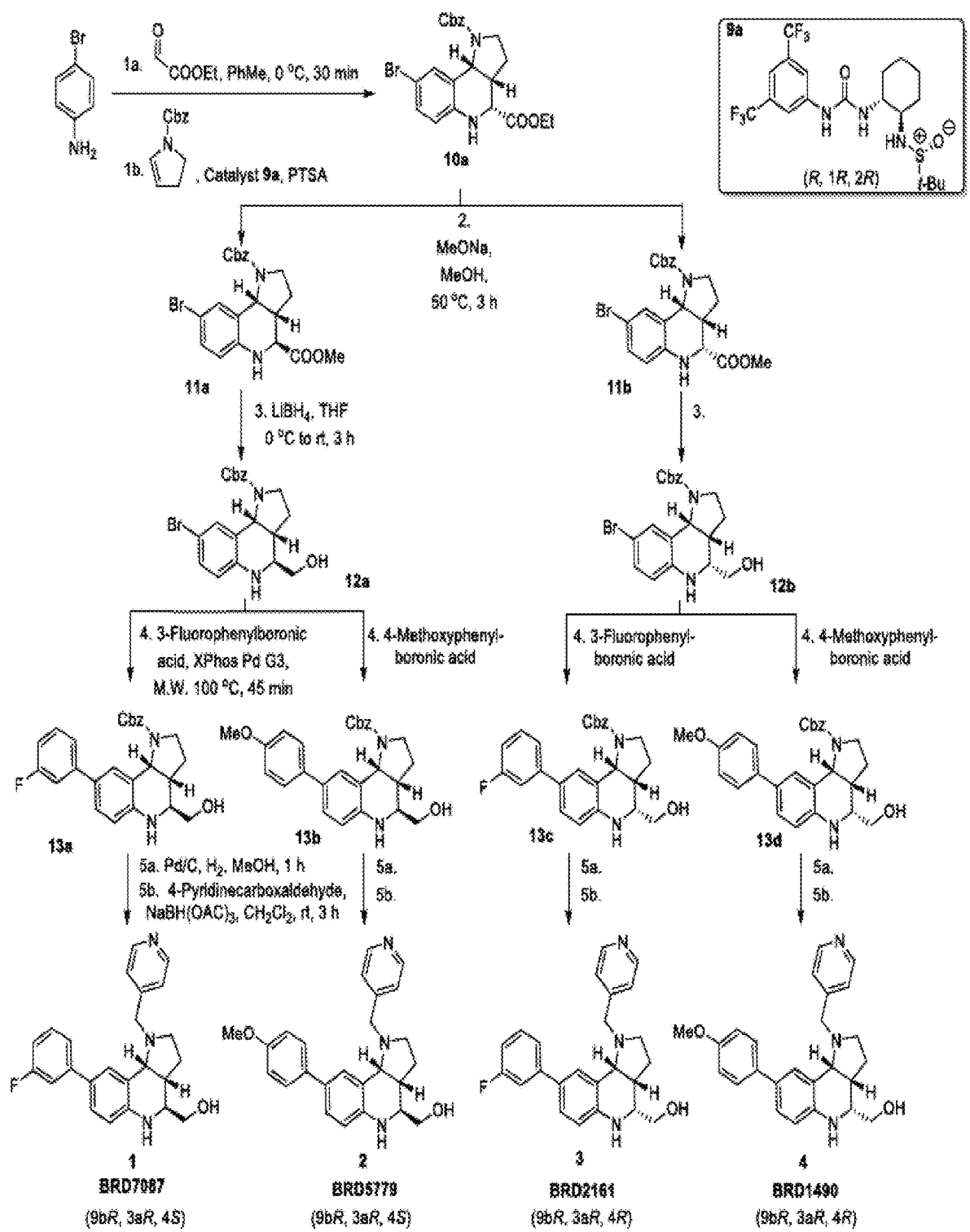
FIG. 43. Synthetic scheme for the ((3aR, 9bR)-1-(pyridin-4-ylmethyl)-2,3,3a,4,5,9b-hexahydro-1H-pyrrolo[3,2-c]quinolin-4-yl)methanols 1-4.
Figure 44:
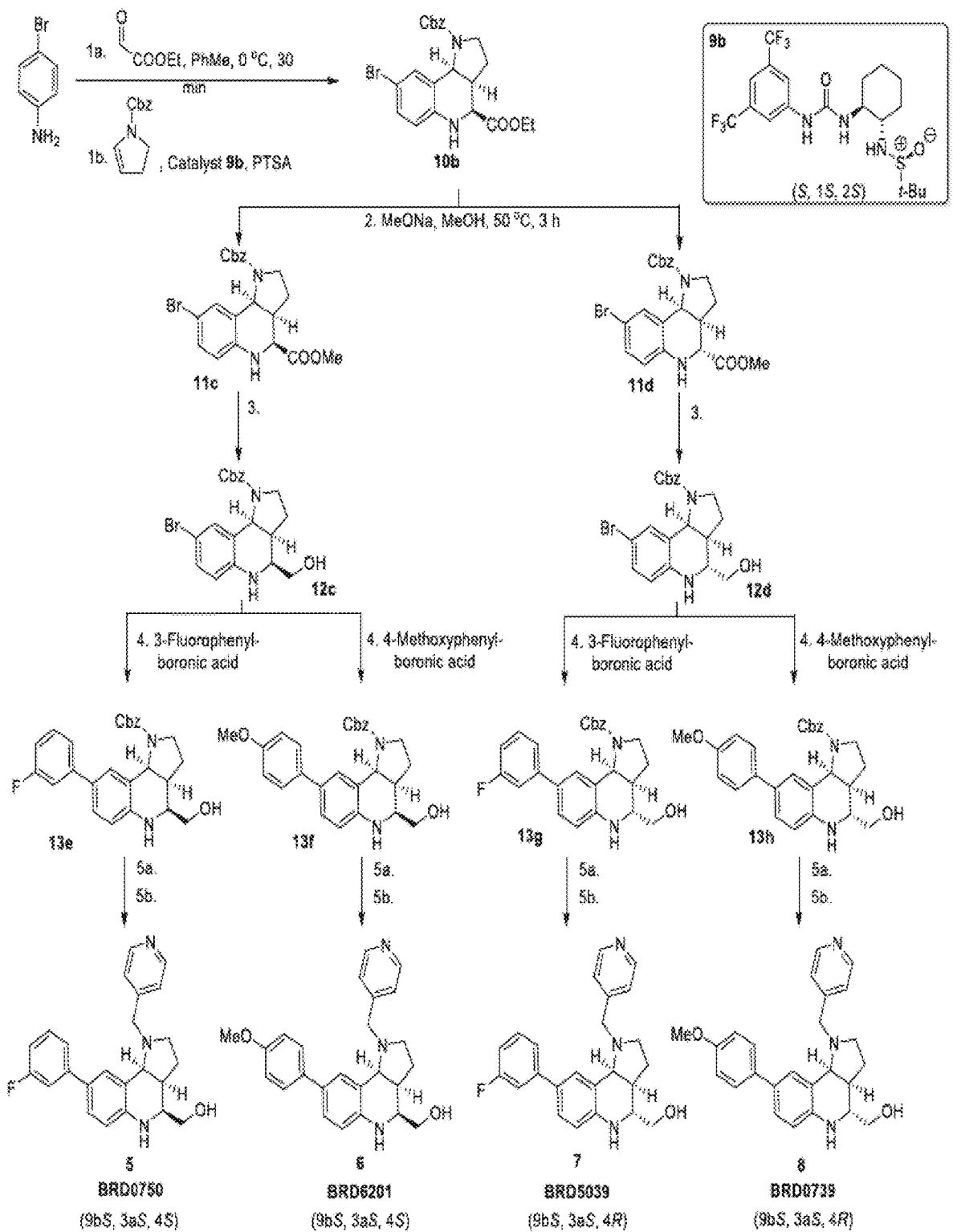
FIG. 44. Synthetic scheme for the ((3aS, 9bS)-1-(pyridin-4-ylmethyl)-2,3,3a,4,5,9b-hexahydro-1H-pyrrolo[3,2-c]quinolin-4-yl)methanols 5-8.
Figure 45:
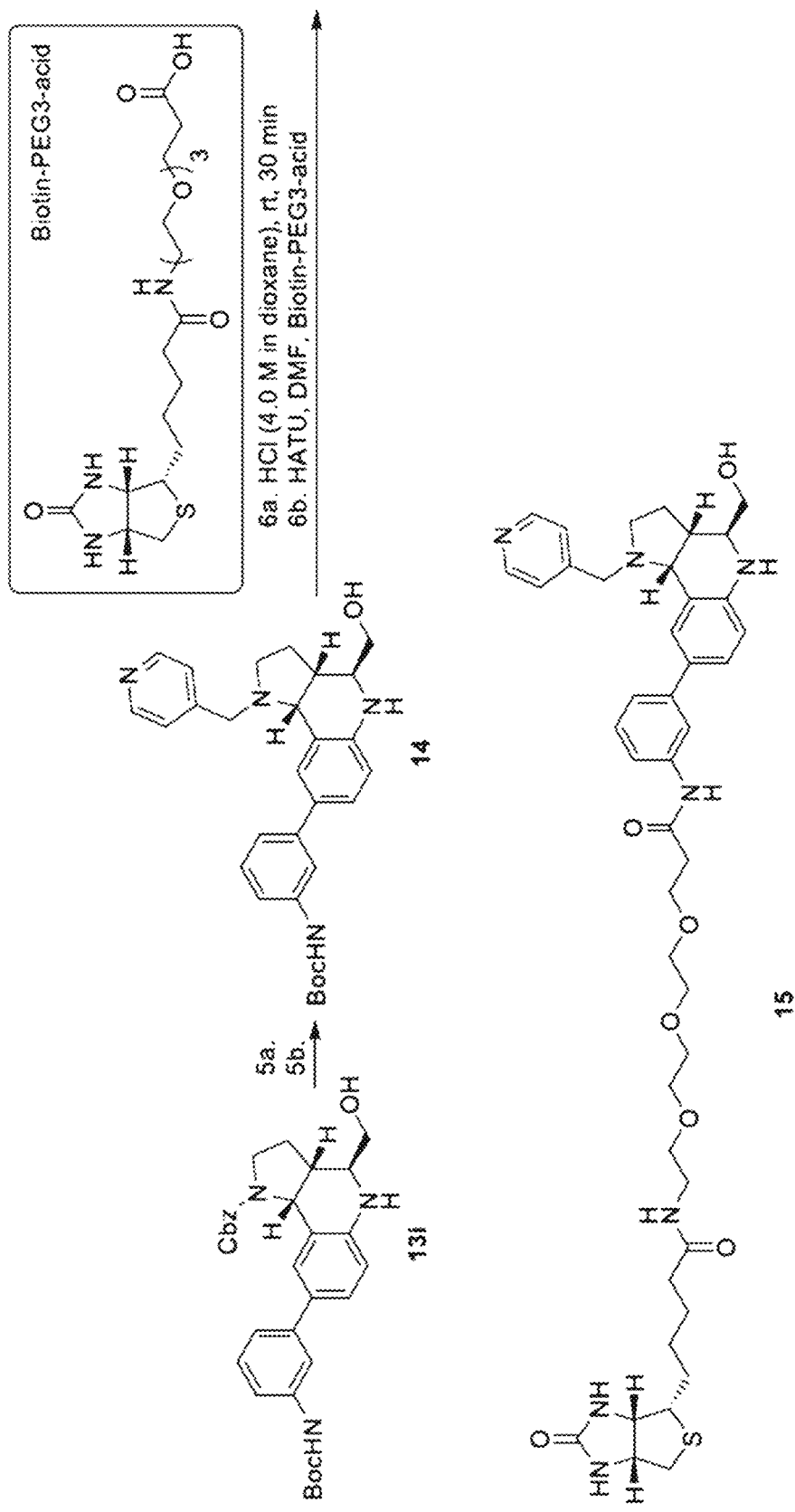
FIG. 45. Synthetic scheme for the biotinylated ((3aR, 9bR)-1-(pyridin-4-ylmethyl)-2,3,3a,4,5,9b-hexahydro-1H-pyrrolo[3,2-c]quinolin-4-yl)methanol 15.
Figure 46A:
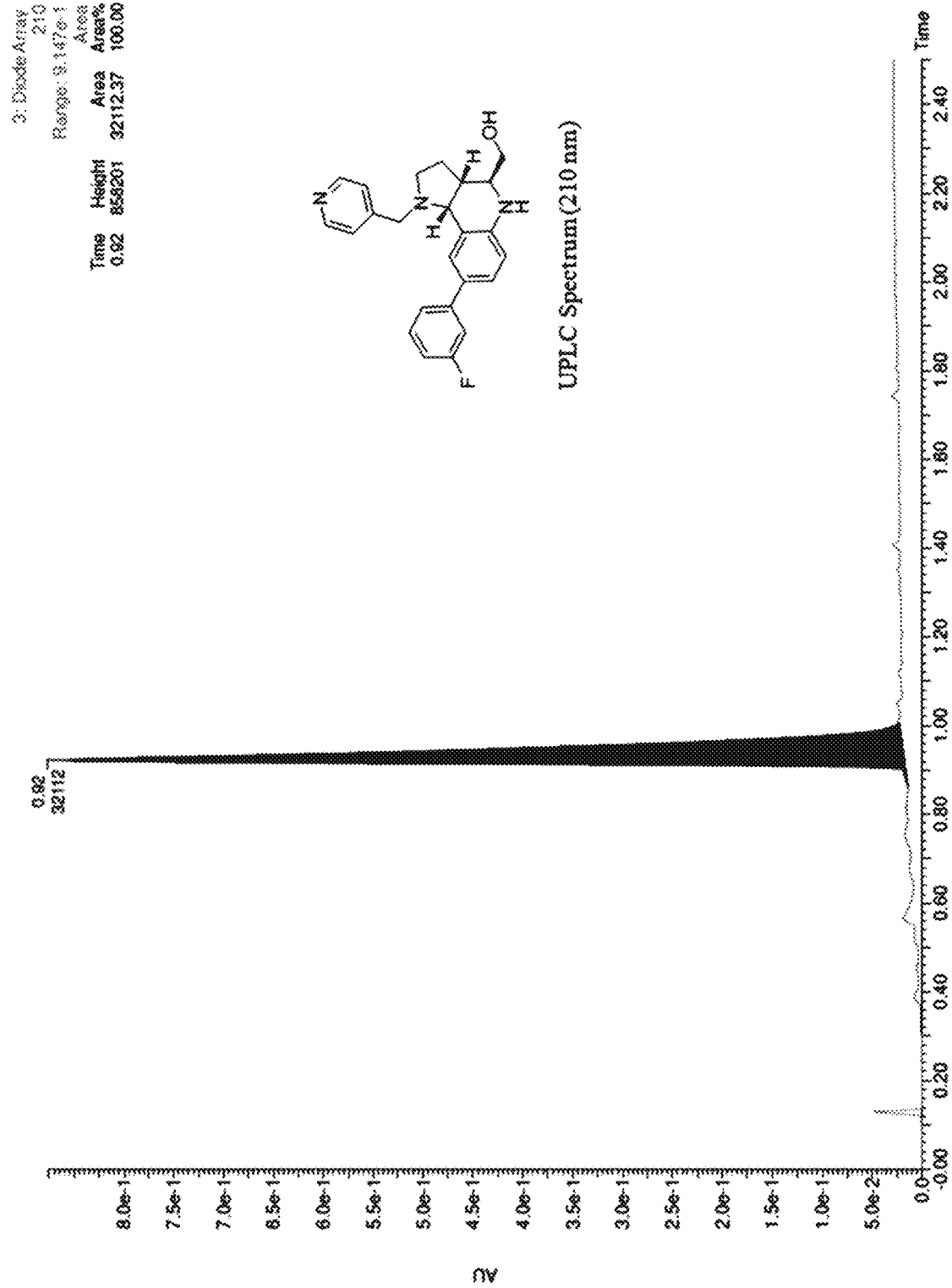
FIGS. 46A-46AJ. Characterization spectra of compounds 1-8.
Figure 46C:
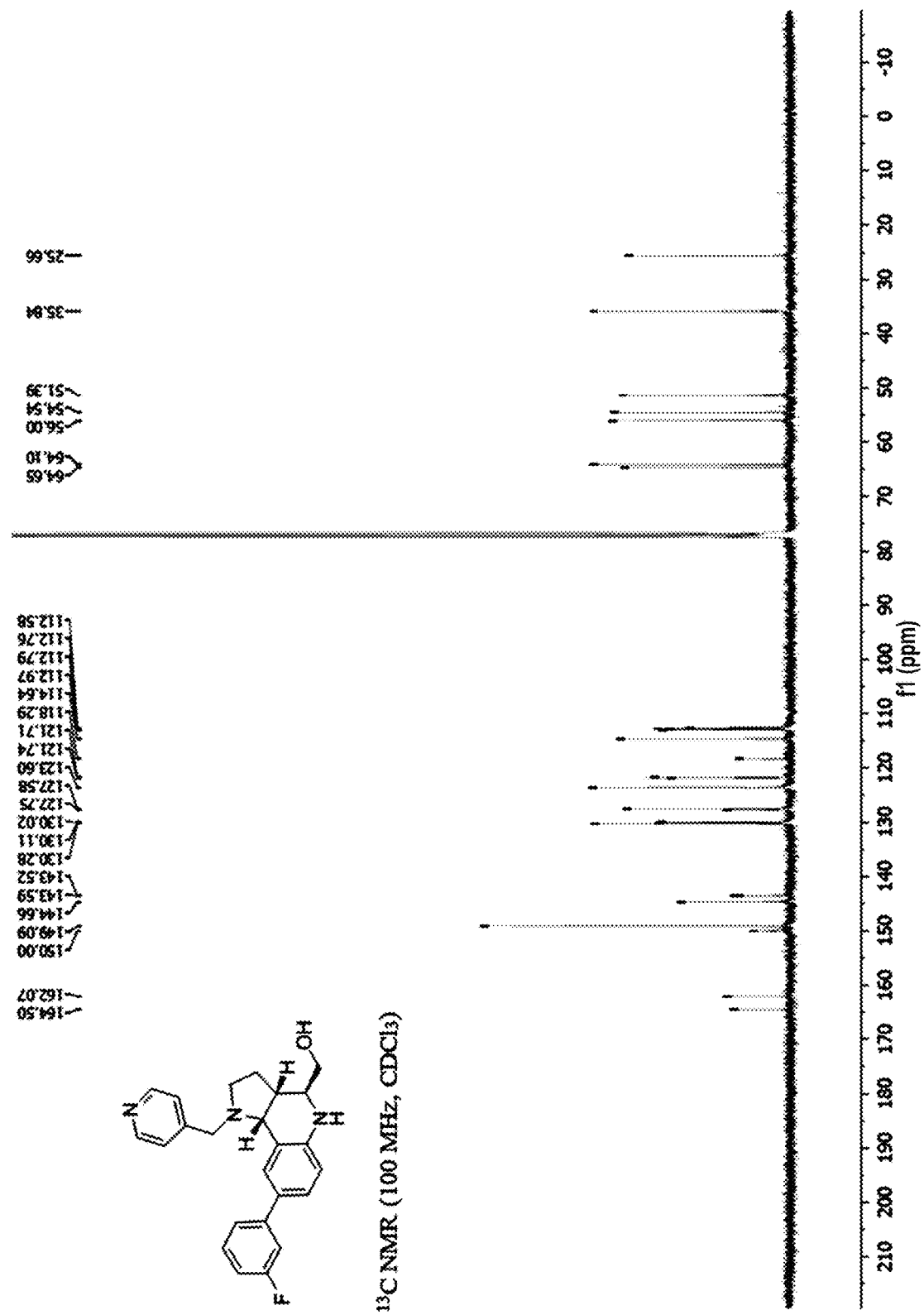
(FIG. 46C). ((3aR, 4S, 9bR)-8-(3-Fluorophenyl)-1-(pyridin-4-ylmethyl)-2,3,3a,4,5,9b-hexahydro-1H-pyrrolo[3,2-c]quinolin-4-yl)methanol (BRD7087)$^{13}$C NMR (100 MHz, CDCl$_3$).
Figure 46D:
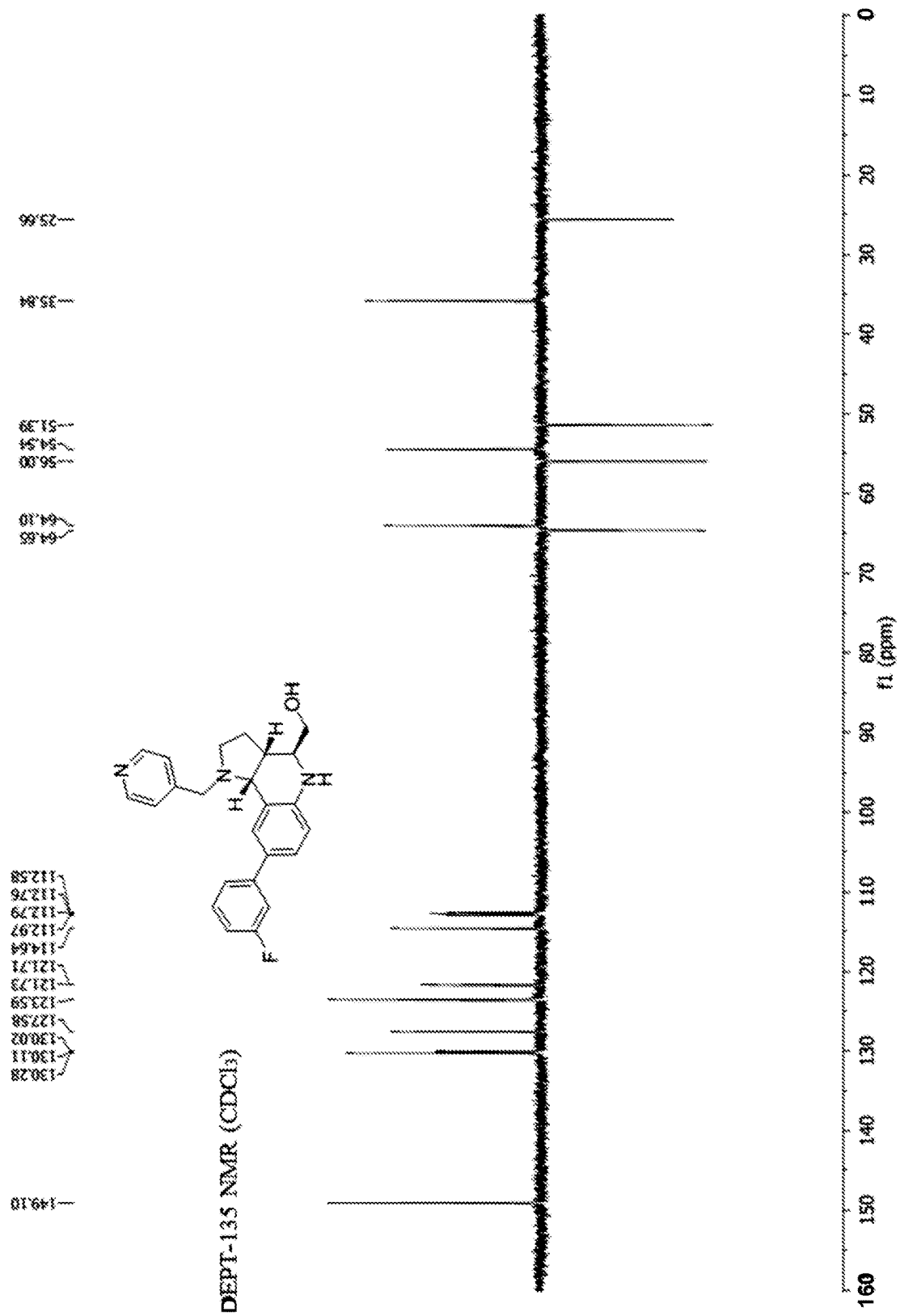
(FIG. 46D). ((3aR, 4S, 9bR)-8-(3-Fluorophenyl)-1-(pyridin-4-ylmethyl)-2,3,3a,4,5,9b-hexahydro-1H-pyrrolo[3,2-c]quinolin-4-yl)methanol (BRD7087) DEPT-135 NMR (CDCl$_3$).
Figure 46F:
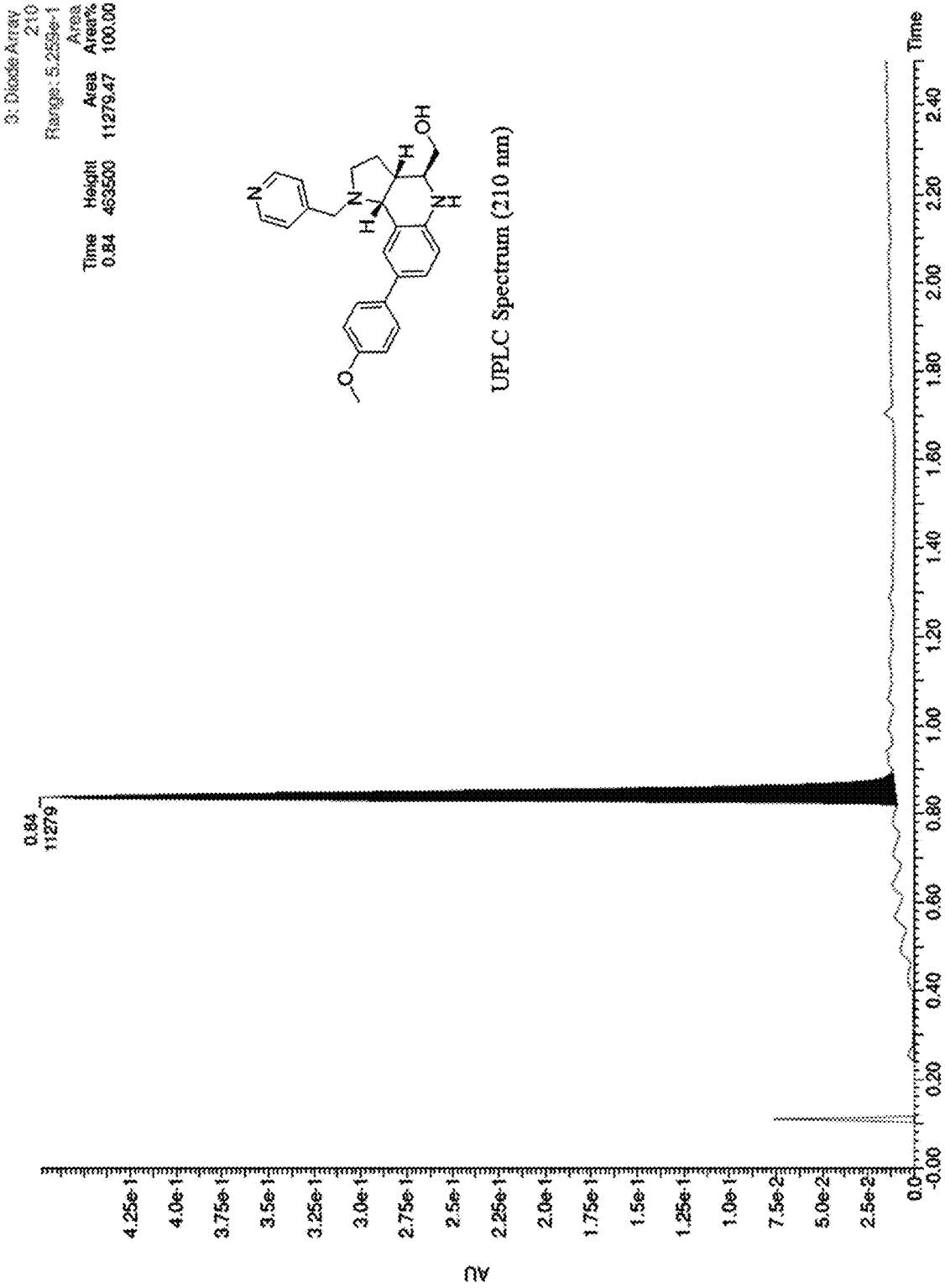
(FIG. 46F). ((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD5779) UPLC Spectrum (210 nm).
Figure 46G:
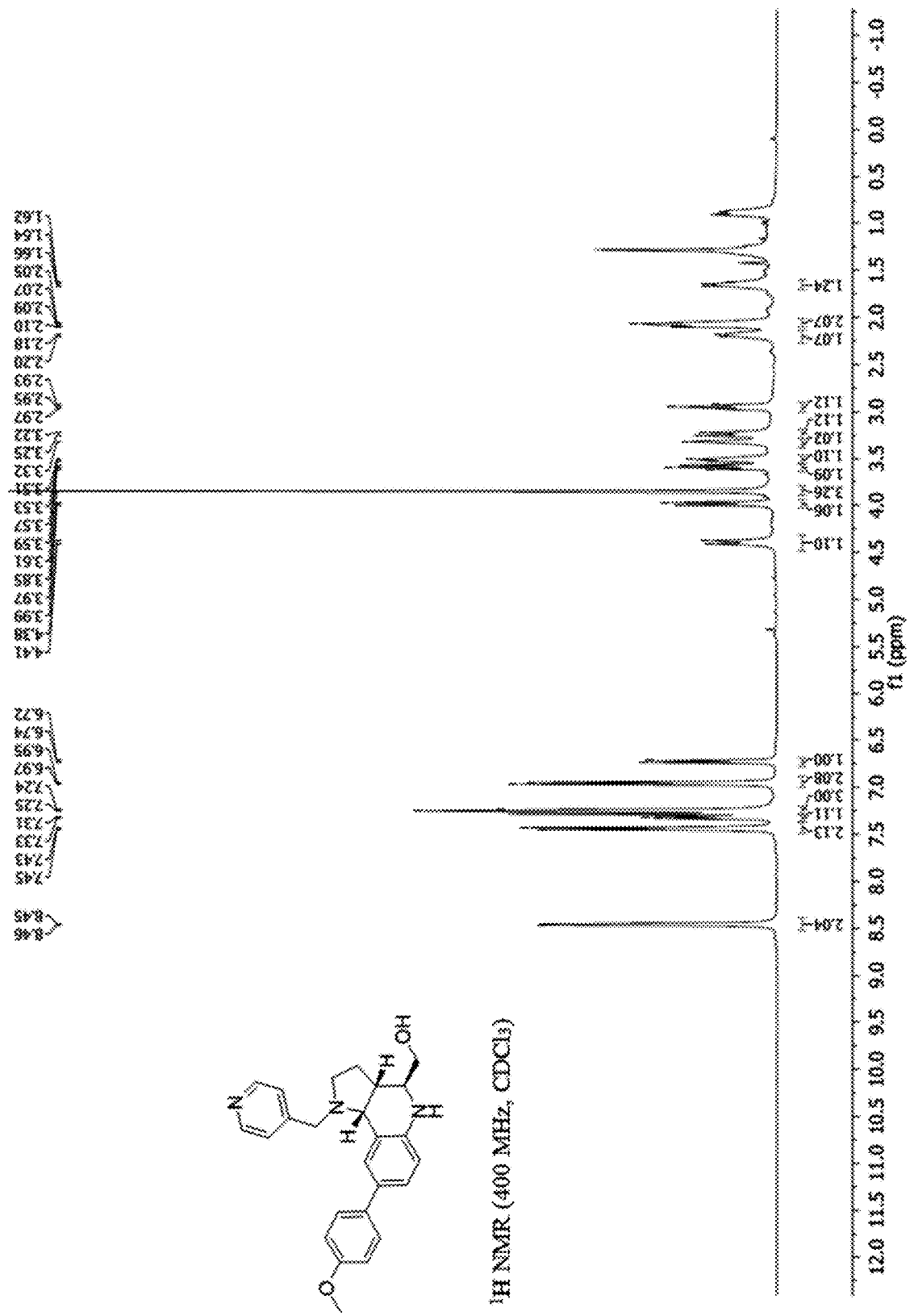
(FIG. 46G). ((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD5779)$^1$H NMR (400 MHz, CDCl$_3$).
Figure 46H:
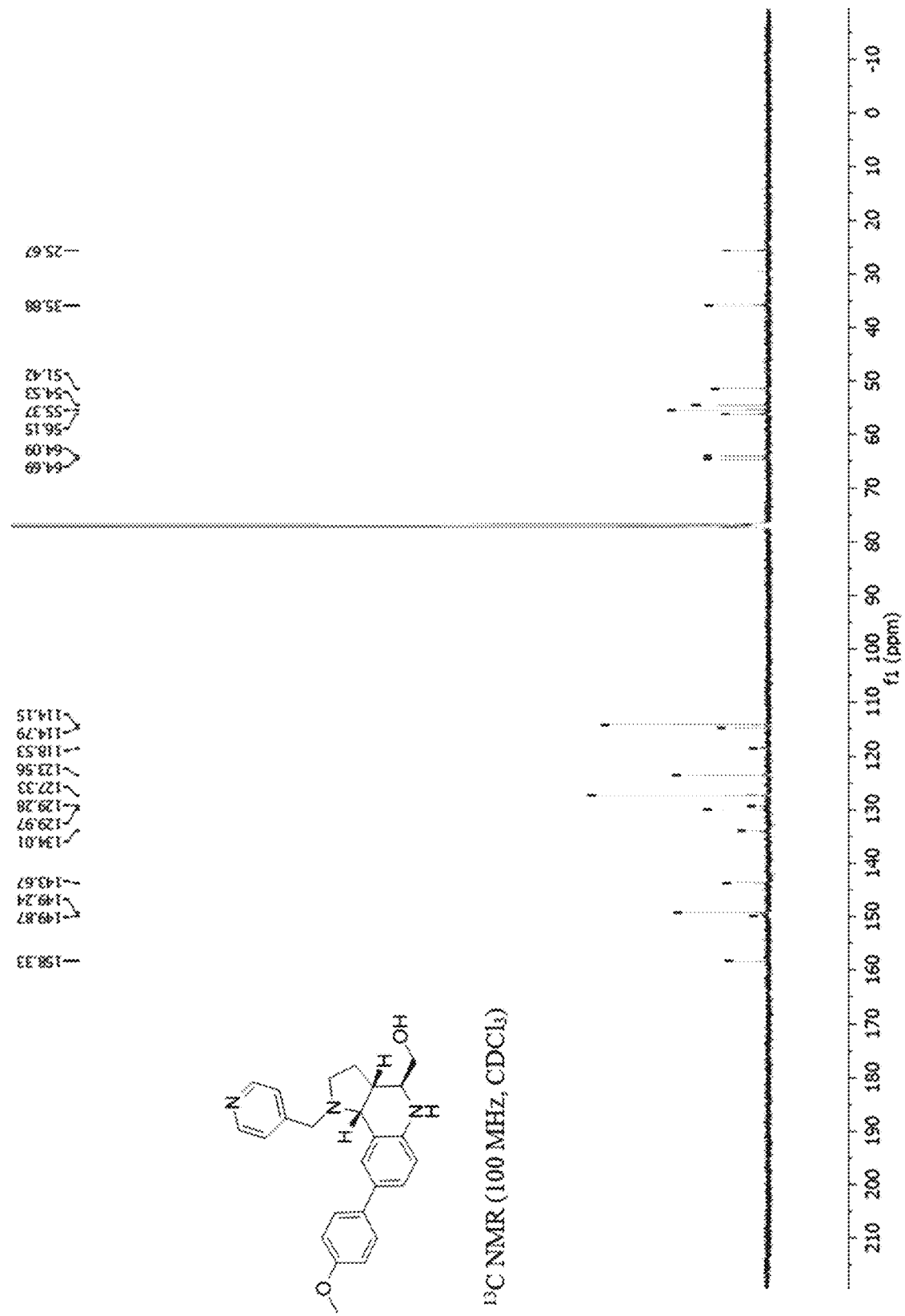
(FIG. 46H). ((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD5779)$^{13}$C NMR (100 MHz, CDCl$_3$).
Figure 46I:
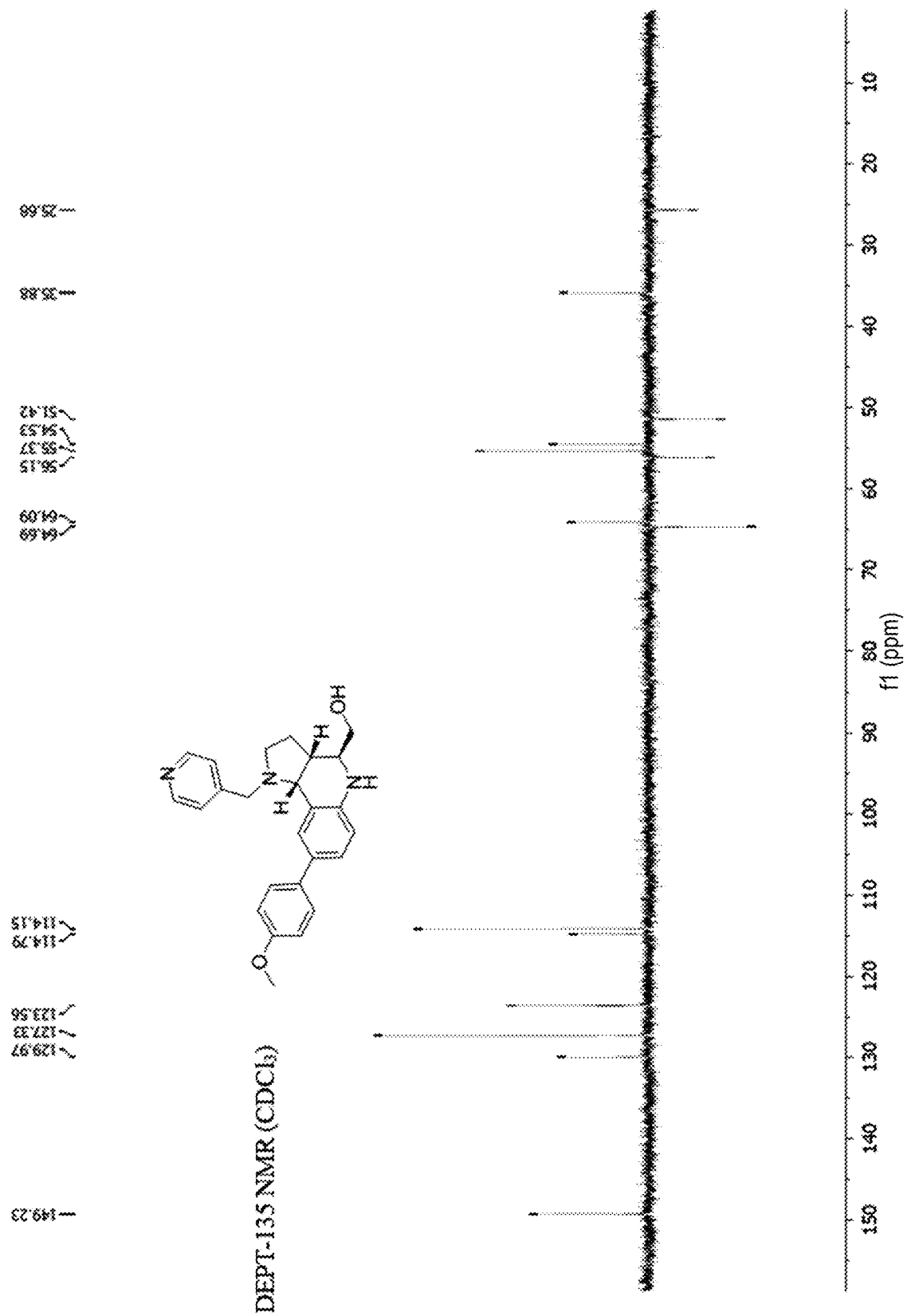
(FIG. 46I). ((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD5779) DEPT-135 NMR (CDCl$_3$).
Figure 46J:
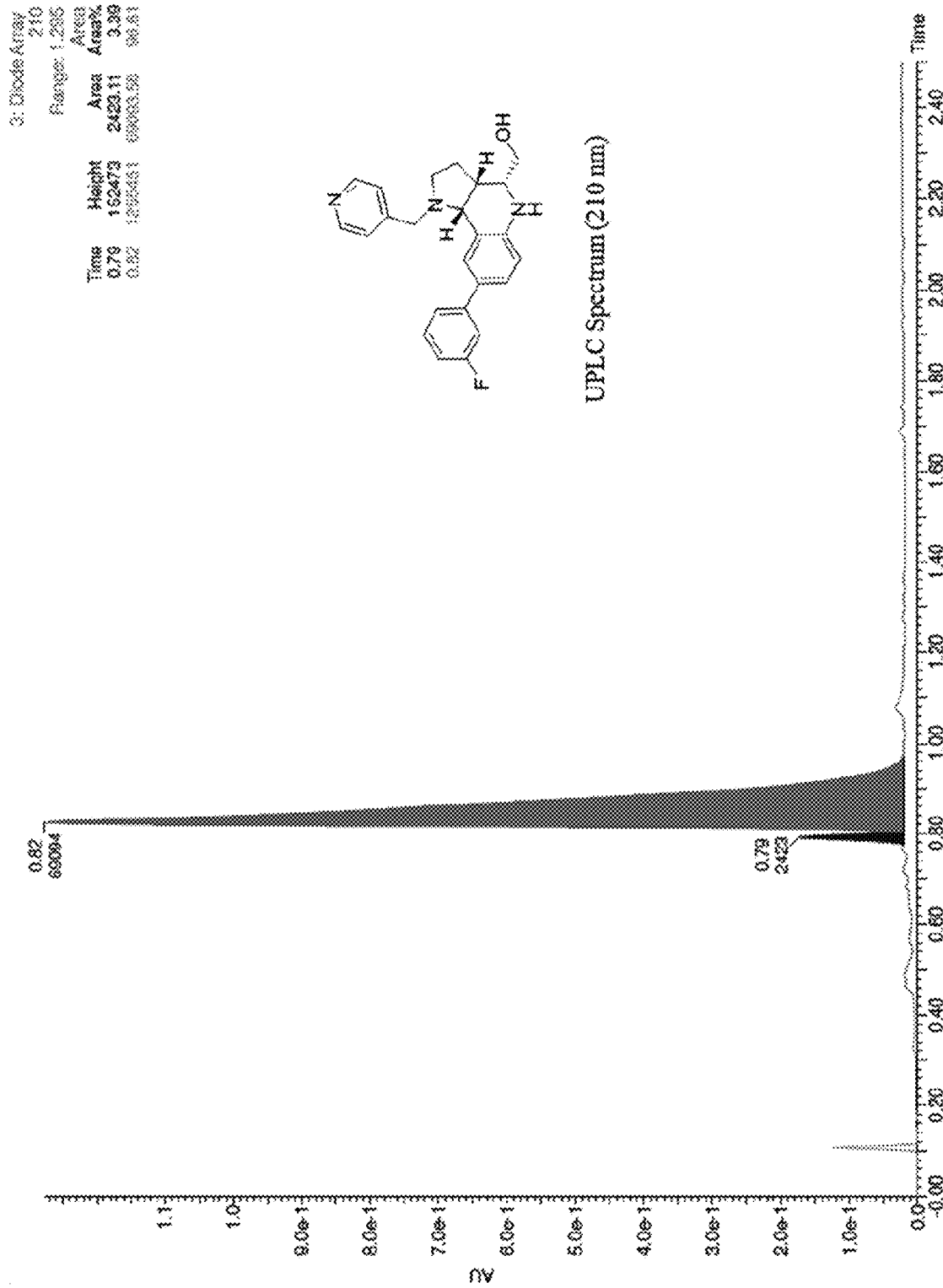
(FIG. 46J). ((3aR, 4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161) UPLC Spectrum (210 nm).
Figure 46K:
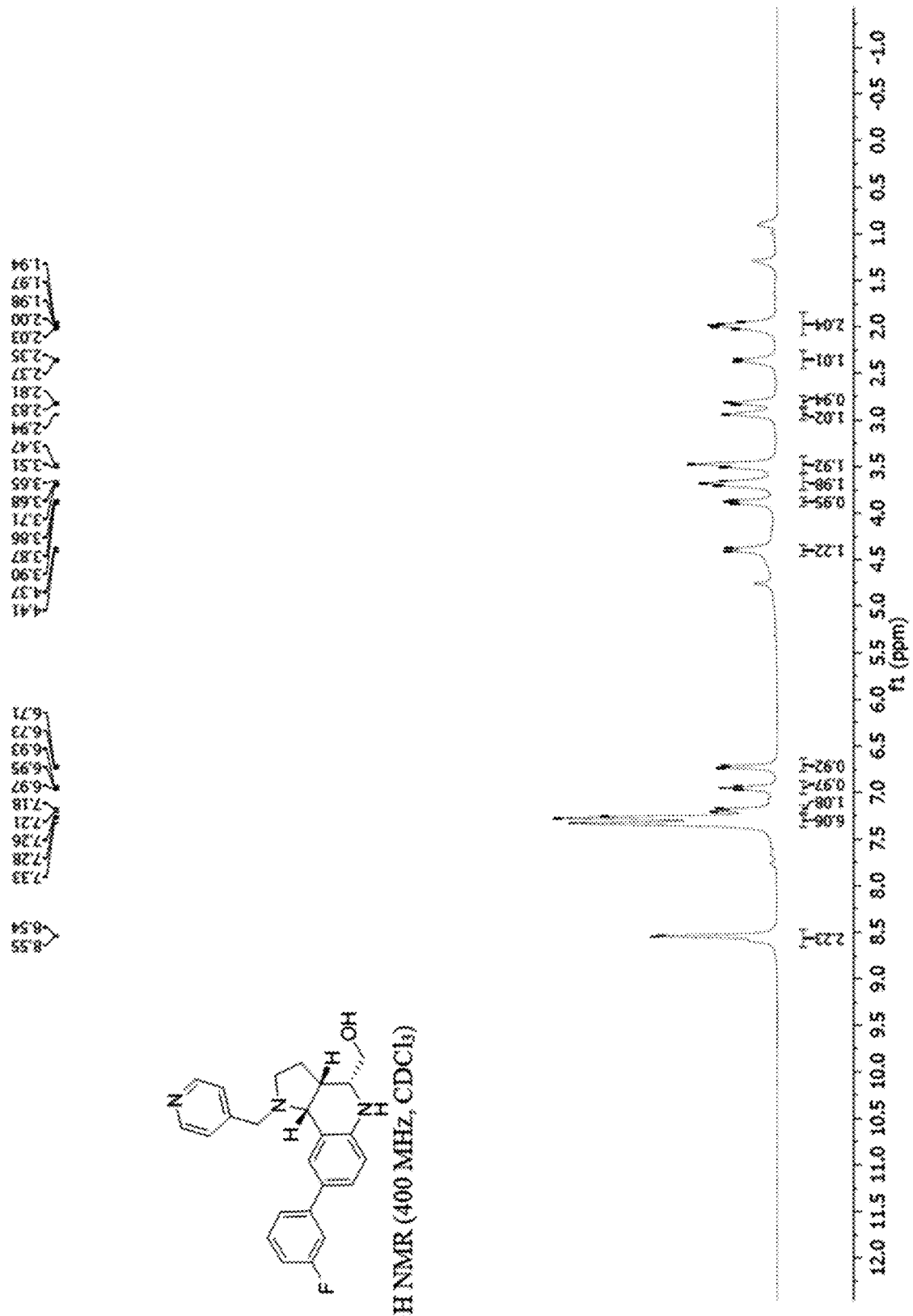
(FIG. 46K). ((3aR, 4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161)$^1$H NMR (400 MHz, CDCl$_3$).
Figure 46L:
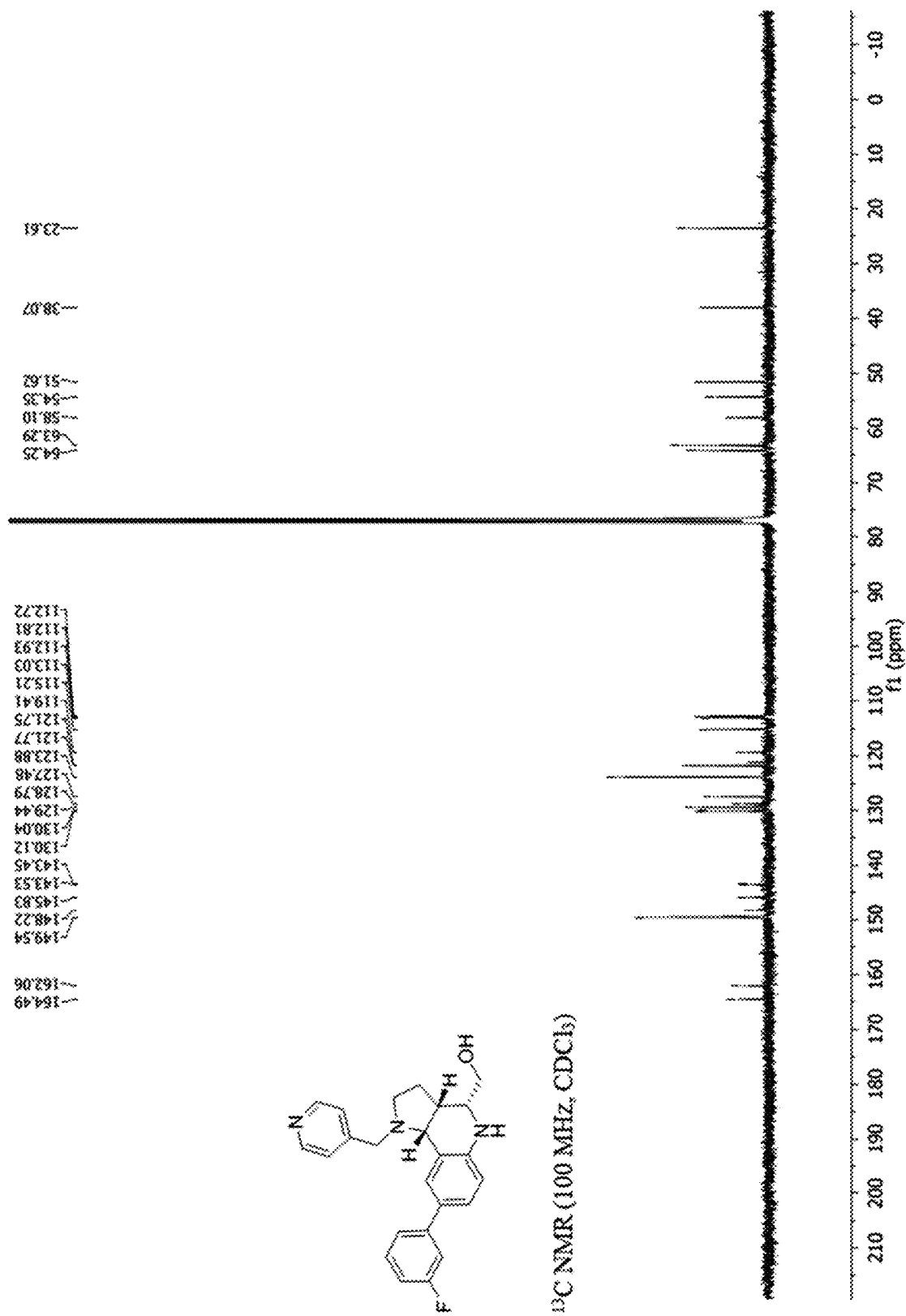
(FIG. 46L). ((3aR,4R,9bR)-8-(3-Fluorophenyl)-1-(pyridin-4-ylmethyl)-2,3,3a,4,5,9b-hexahydro-1H-pyrrolo[3,2-c]quinolin-4-yl) methanol (3/BRD2161)$^{13}$C NMR (100 MHz, CDCl$_3$).
Figure 46M:
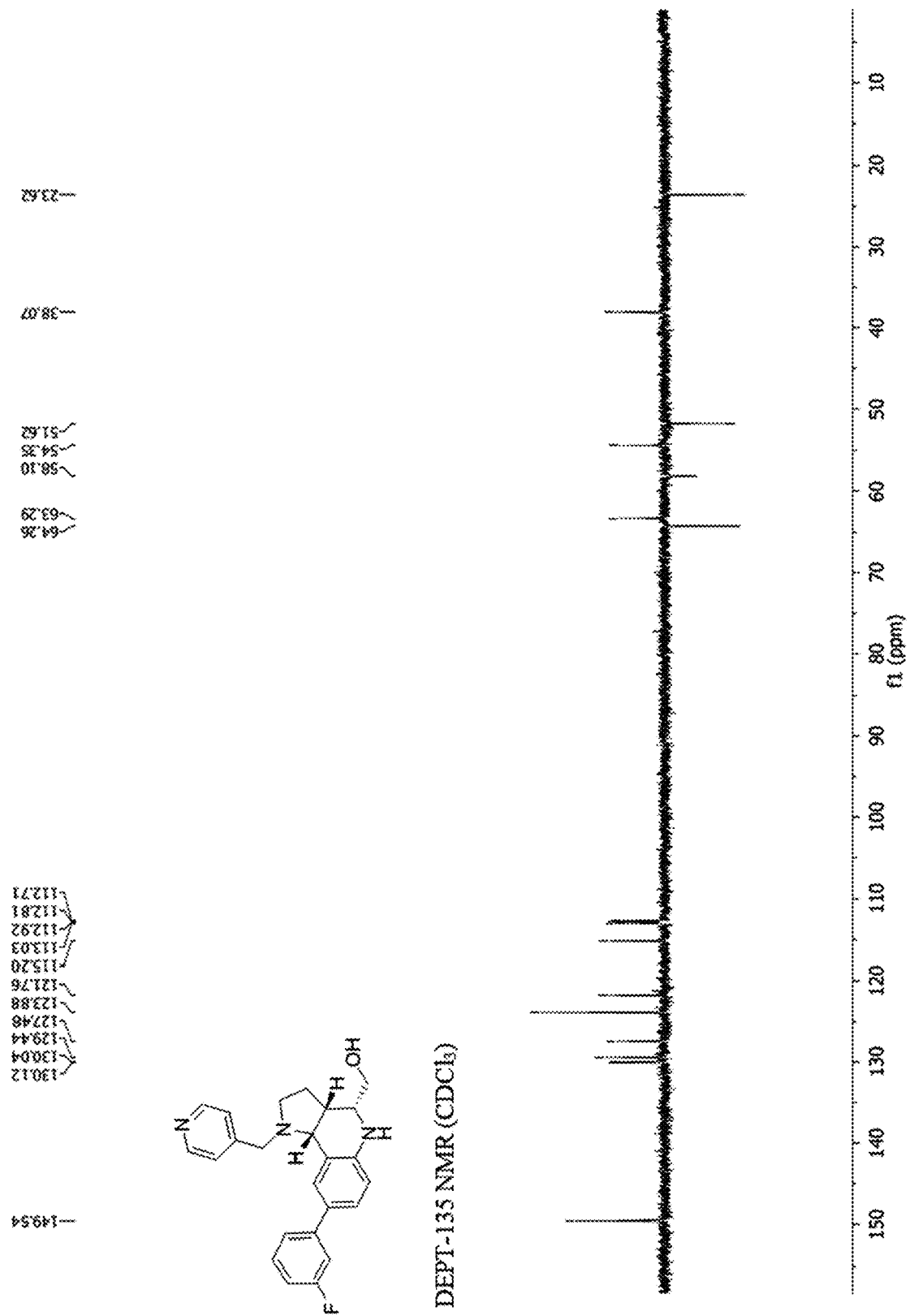
(FIG. 46M). ((3aR,4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161) DEPT-135 NMR (CDCl$_3$) (FIG. 46N). ((3aR,4R,9bR)-8-(3-Fluorophenyl)-1-(pyridin-4-ylmethyl)-2,3,3a,4,5,9b-hexahydro-1H-pyrrolo[3,2-c]quinolin-4-yl)methanol (3/BRD2161)$^{19}$F NMR (376 MHz, CDCl$_3$).
Figure 46O:
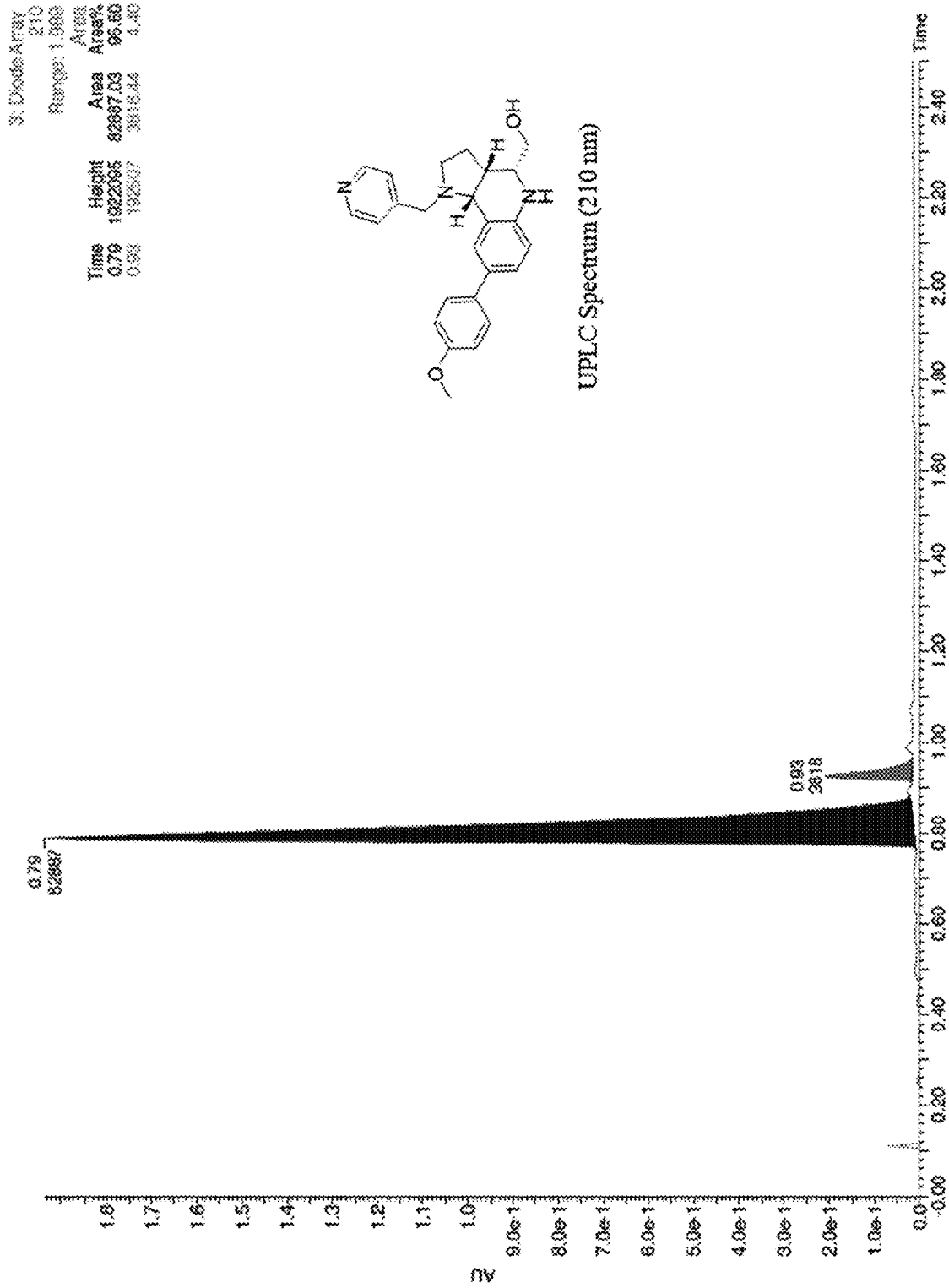
(FIG. 46O). ((3aR,4R,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD1490) UPLC Spectrum (210 nm).
Figure 46P:
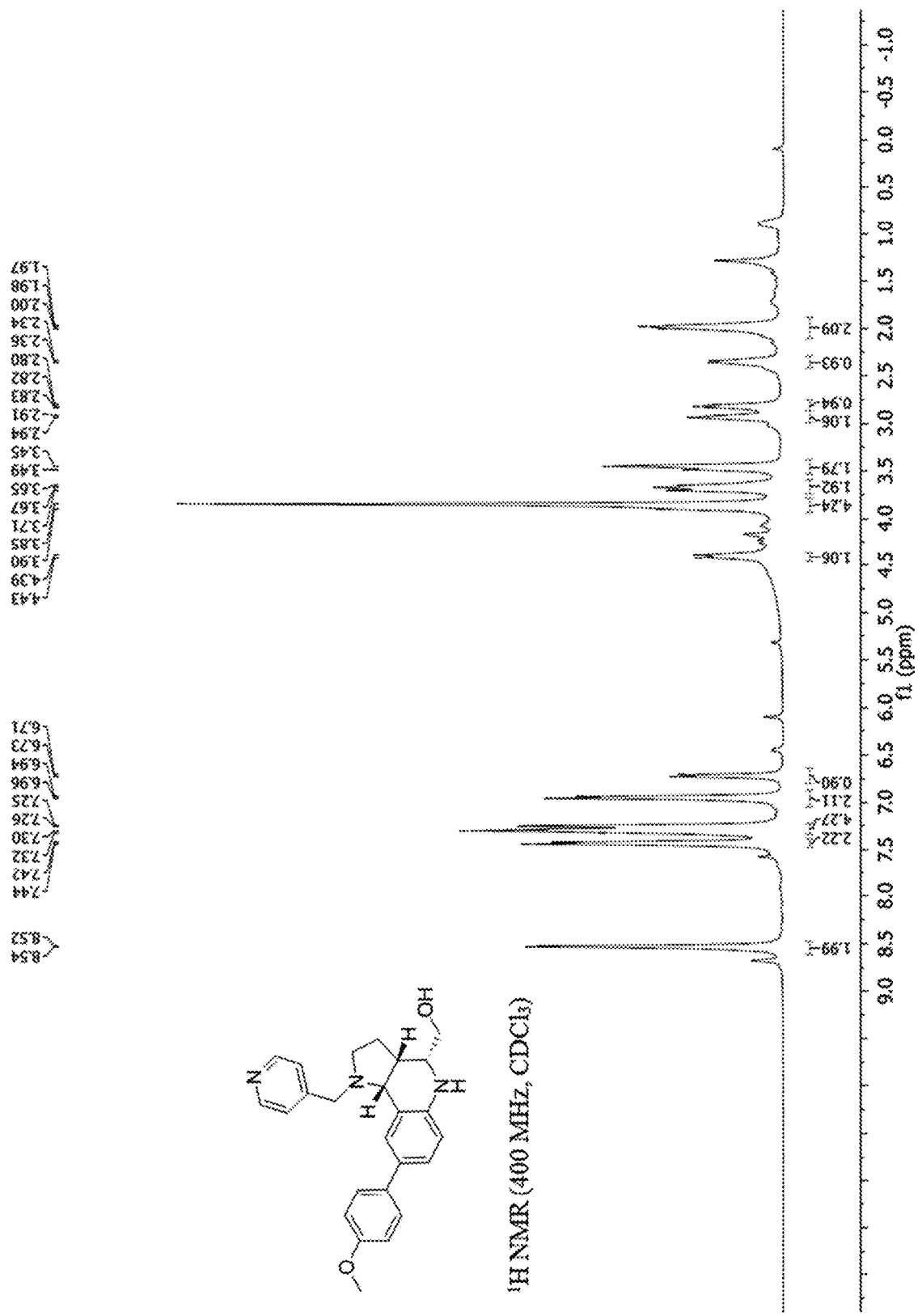
(FIG. 46P). ((3aR,4R,9bR)-8-(4-Methoxyphenyl)-1-(pyridin-4-ylmethyl)-2,3,3a,4,5,9b-hexahydro-1H-pyrrolo[3,2-c]quinolin-4-yl)methanol (BRD1490)$^1$H NMR (400 MHz, CDCl$_3$).
Figure 46Q:
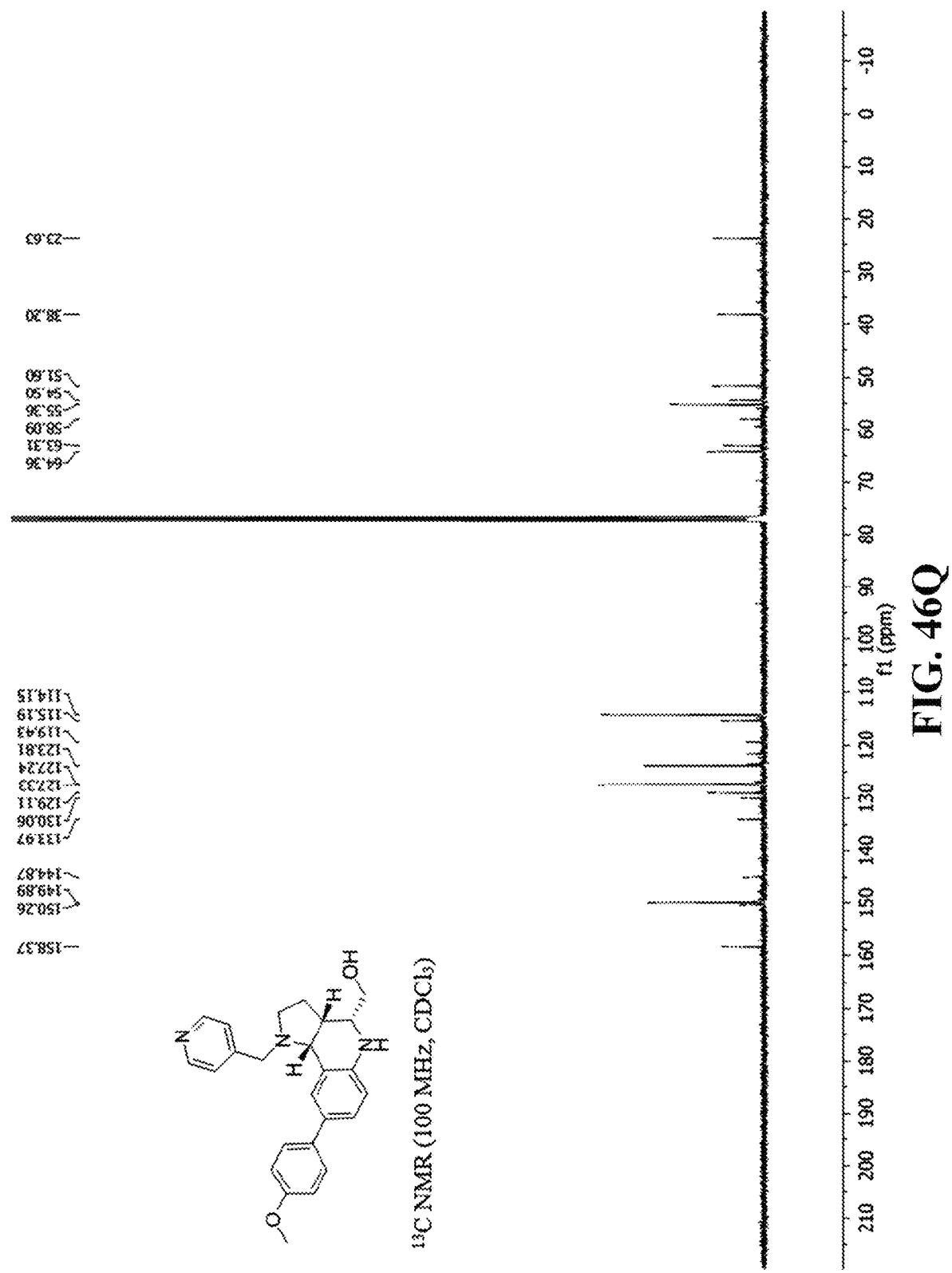
(FIG. 46Q). ((3aR, 4R,9bR)-8-(4-Methoxyphenyl)-1-(pyridin-4-ylmethyl)-2,3, 3a,4,5,9b-hexahydro-1H-pyrrolo[3,2-c]quinolin-4-yl) methanol (BRD1490)$^{13}$C NMR (100 MHz, CDCl$_3$).
Figure 46S:
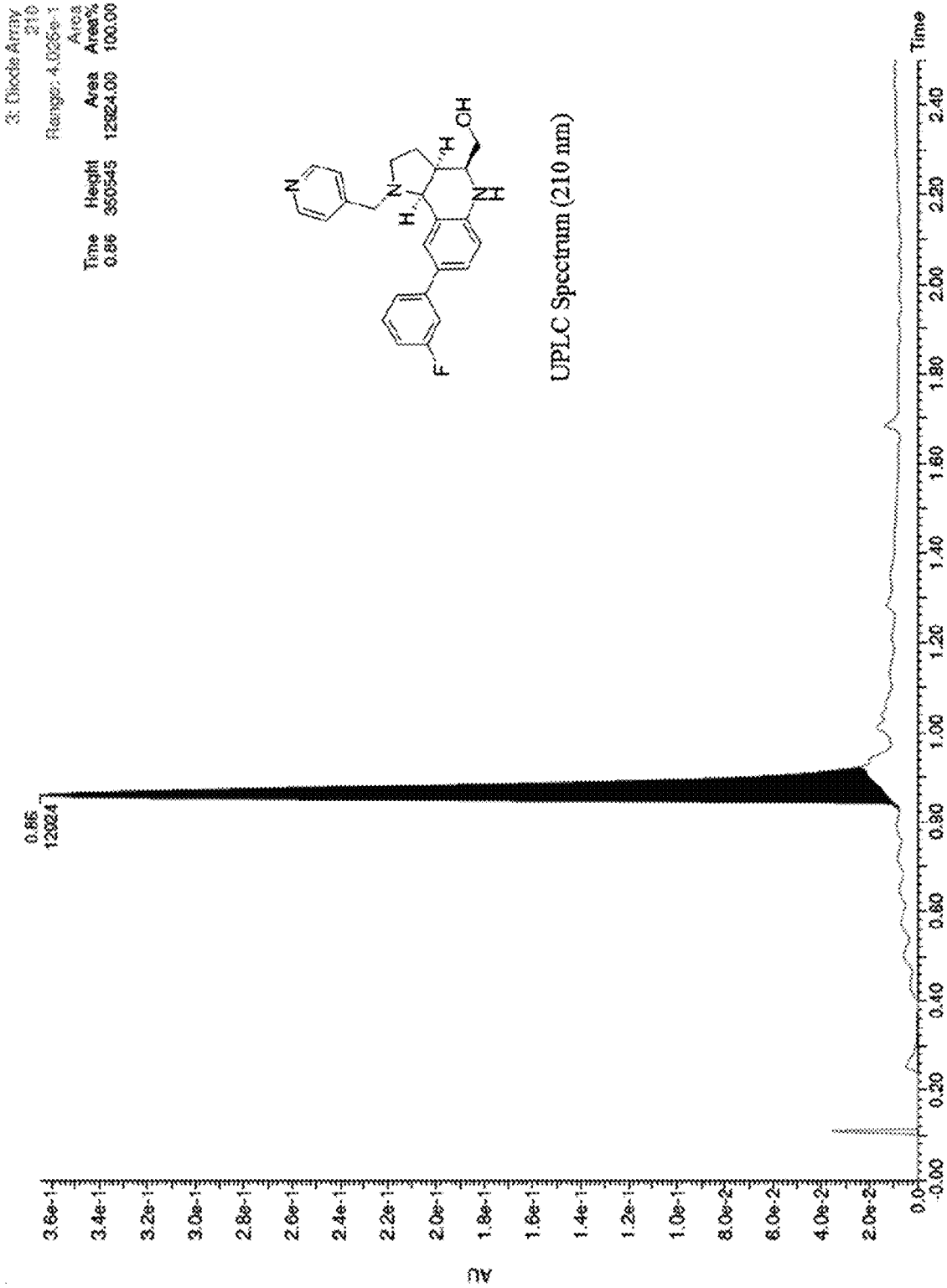
(FIG. 46S). ((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD 0750) UPLC Spectrum (210 nm).
Figure 46T:
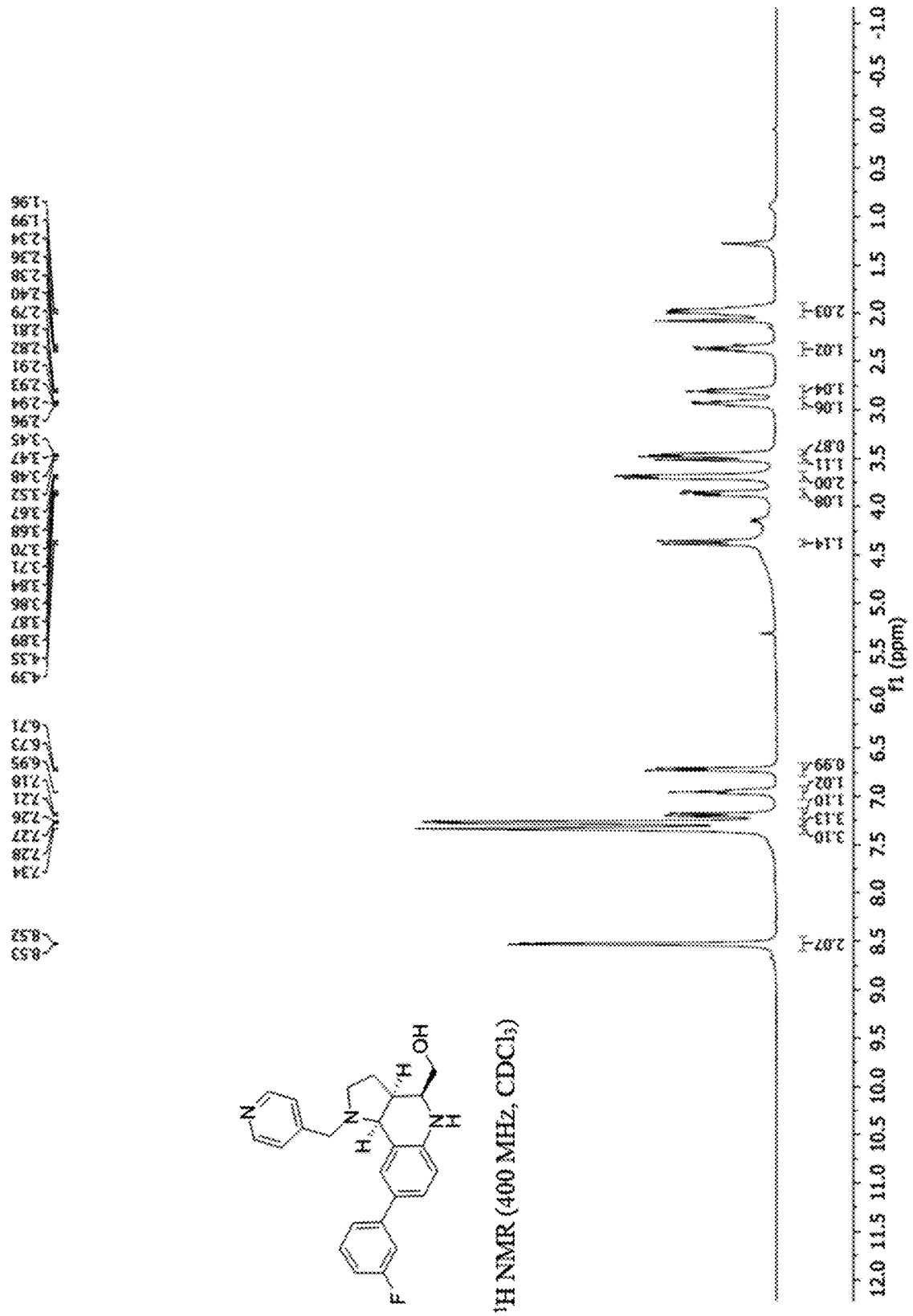
(FIG. 46T). ((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD 0750)$^1$H NMR (400 MHz, CDCl$_3$).
Figure 46U:
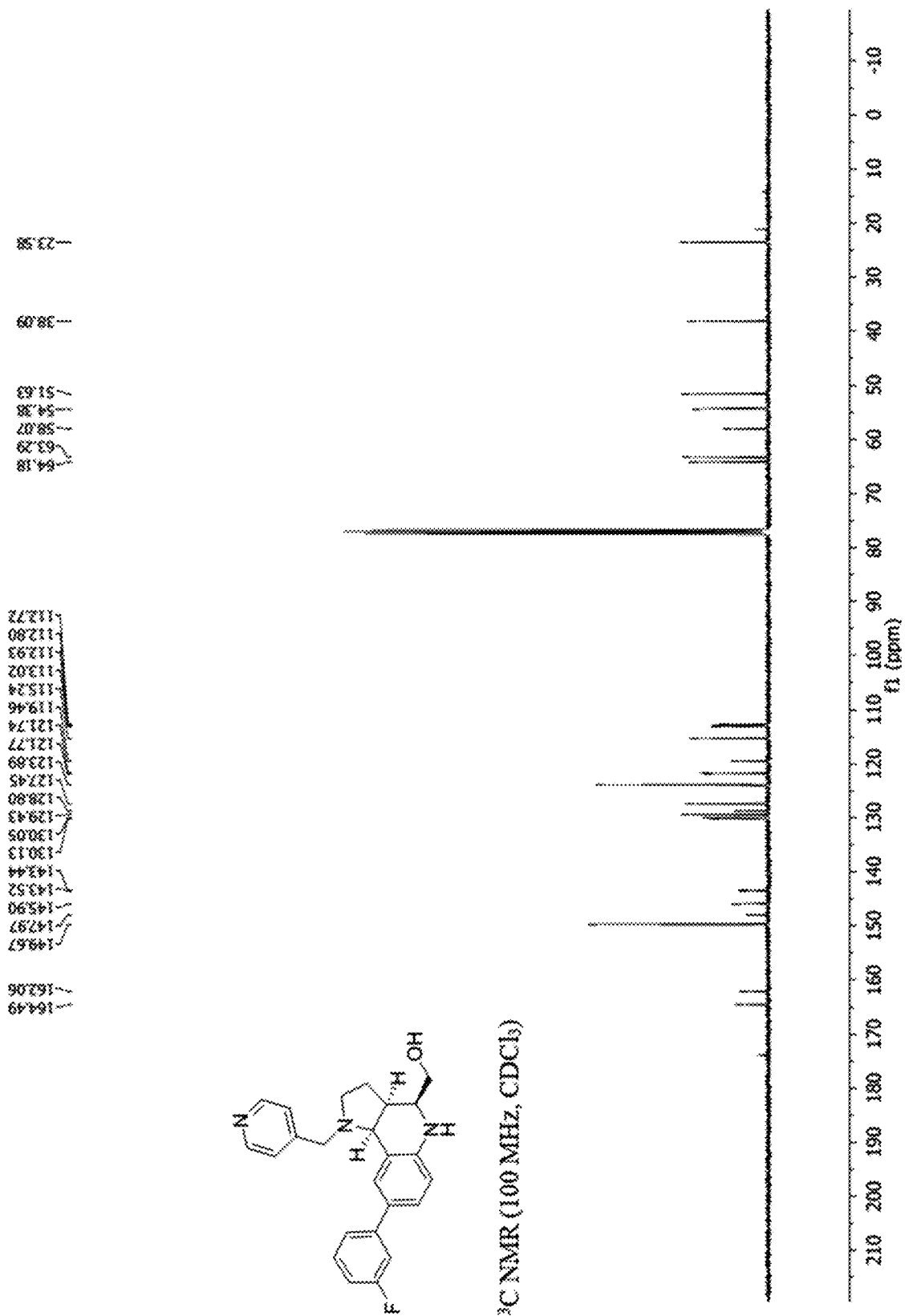
(FIG. 46U). ((3aS,4S,9bS)-8-(3-Fluorophenyl)-1-(pyridin-4-ylmethyl)-2,3,3a,4,5,9b-hexahydro-1H-pyrrolo [3,2-c]quinolin-4-yl)methanol (BRD 0750)$^{13}$C NMR (100 MHz, CDCl$_3$).
Figure 46V:
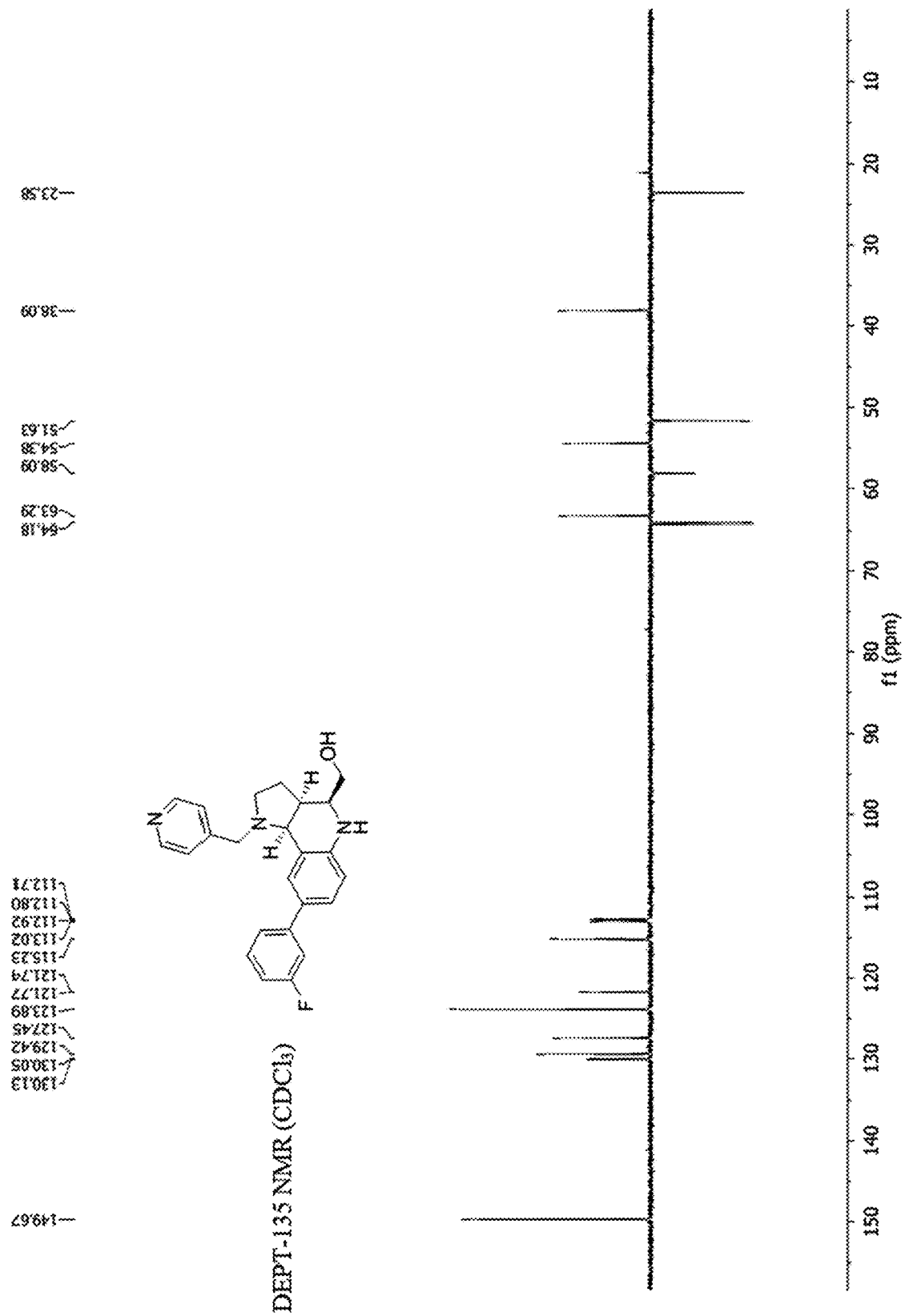
(FIG. 46V). ((3aS,4S,9bS)-8-(3-Fluorophenyl)-1-(pyridin-4-ylmethyl)-2,3,3a,4,5,9b-hexahydro-1H-pyrrolo[3,2-c]quinolin-4-yl)methanol (BRD 0750) DEPT-135 NMR (CDCl$_3$).
Figure 46X:
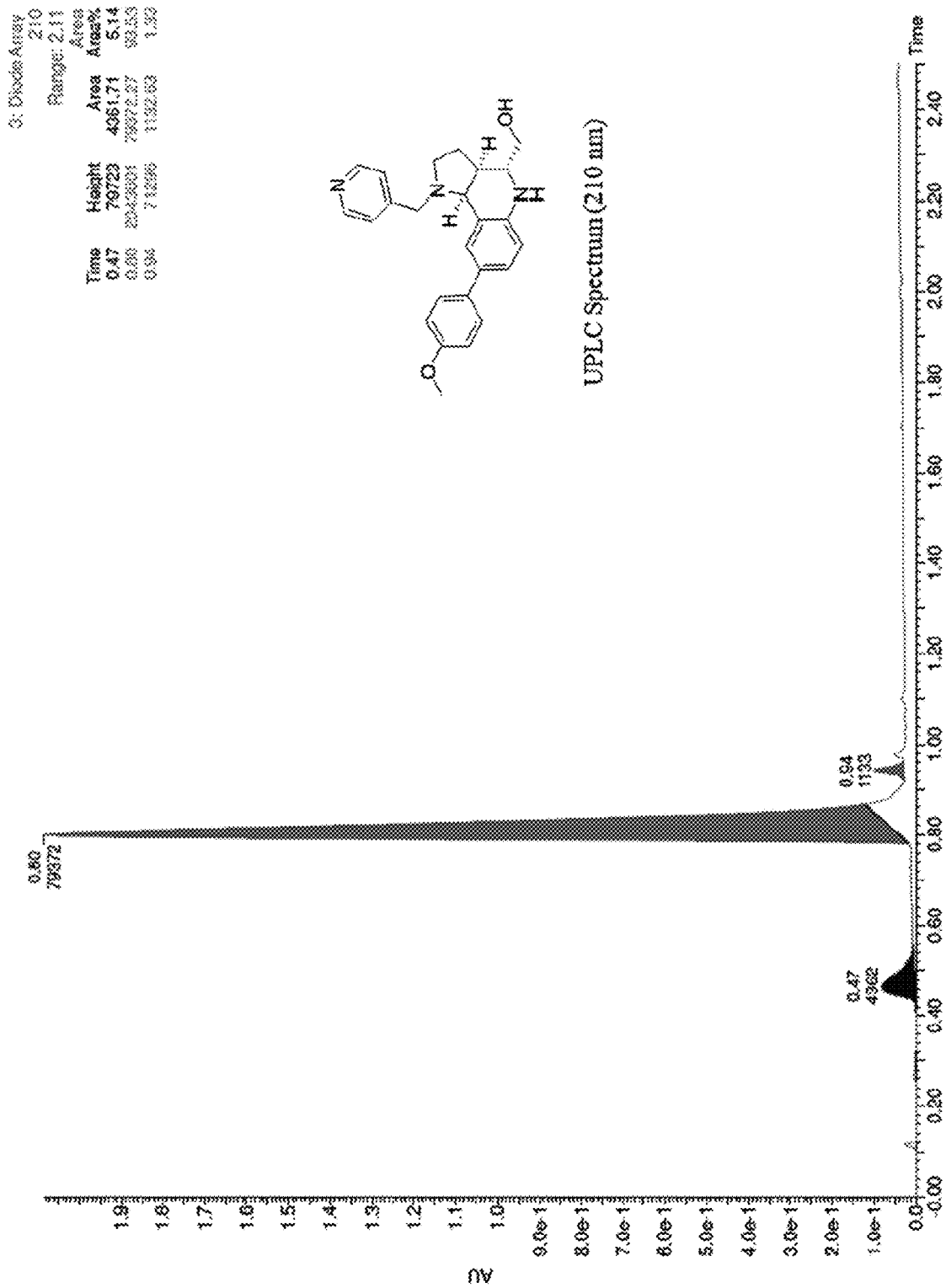
(FIG. 46X). ((3aS,4R, 9bS)-8-(4-Methoxyphenyl)-1-(pyridin-4-ylmethyl)-2,3,3a, 4,5,9b-hexahydro-1H-pyrrolo[3,2-c]quinolin-4-yl)methanol (BRD0739) UPLC Spectrum (210 nm).
Figure 46Y:
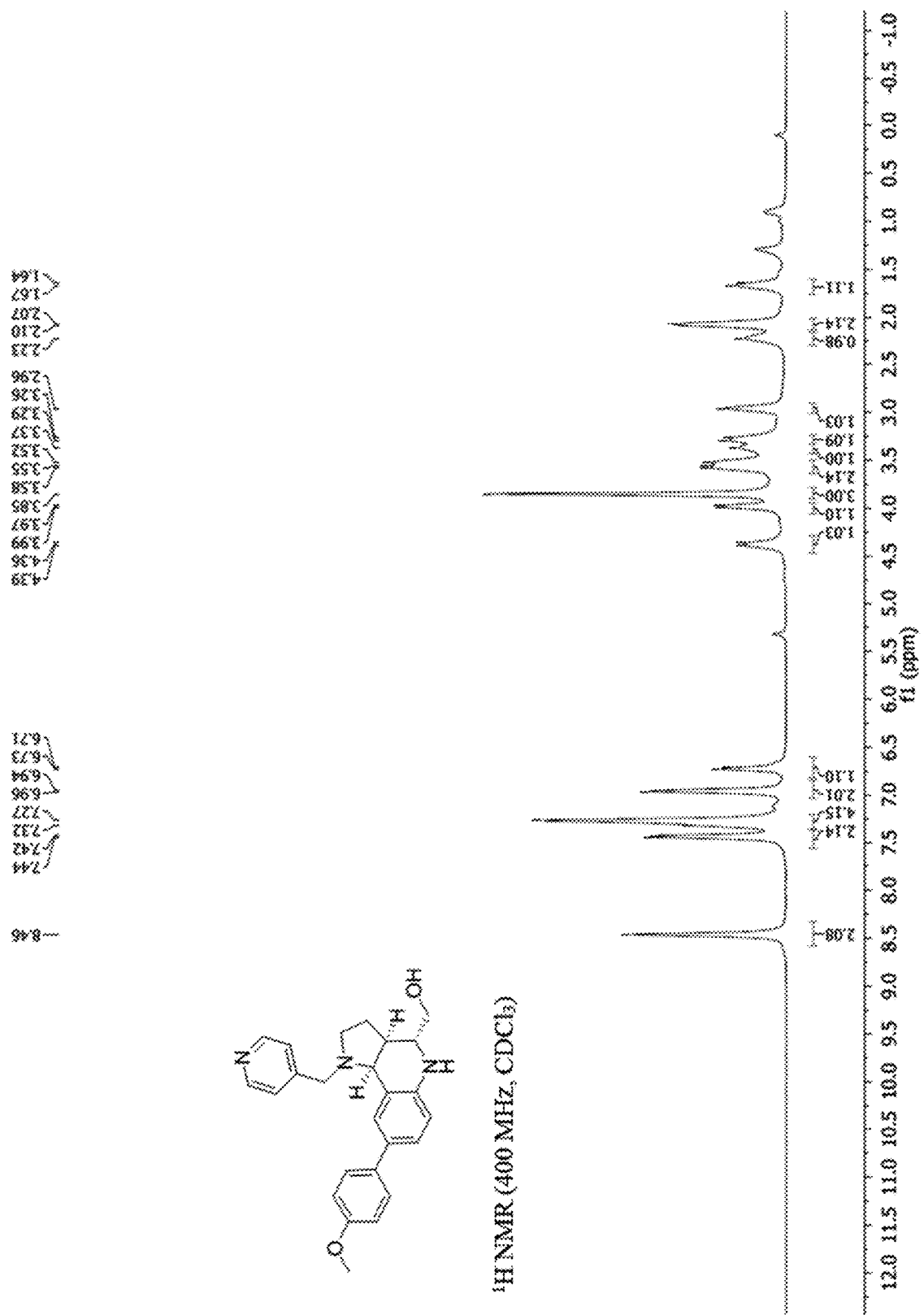
(FIG. 46Y). ((3aS, 4R,9bR)-8-(4-Methoxyphenyl)-1-(pyridin-4-ylmethyl)-2,3, 3a,4,5,9b-hexahydro-1H-pyrrolo[3,2-c]quinolin-4-yl) methanol (BRD0739)$^1$H NMR (400 MHz, CDCl$_3$).
Figure 46Z:
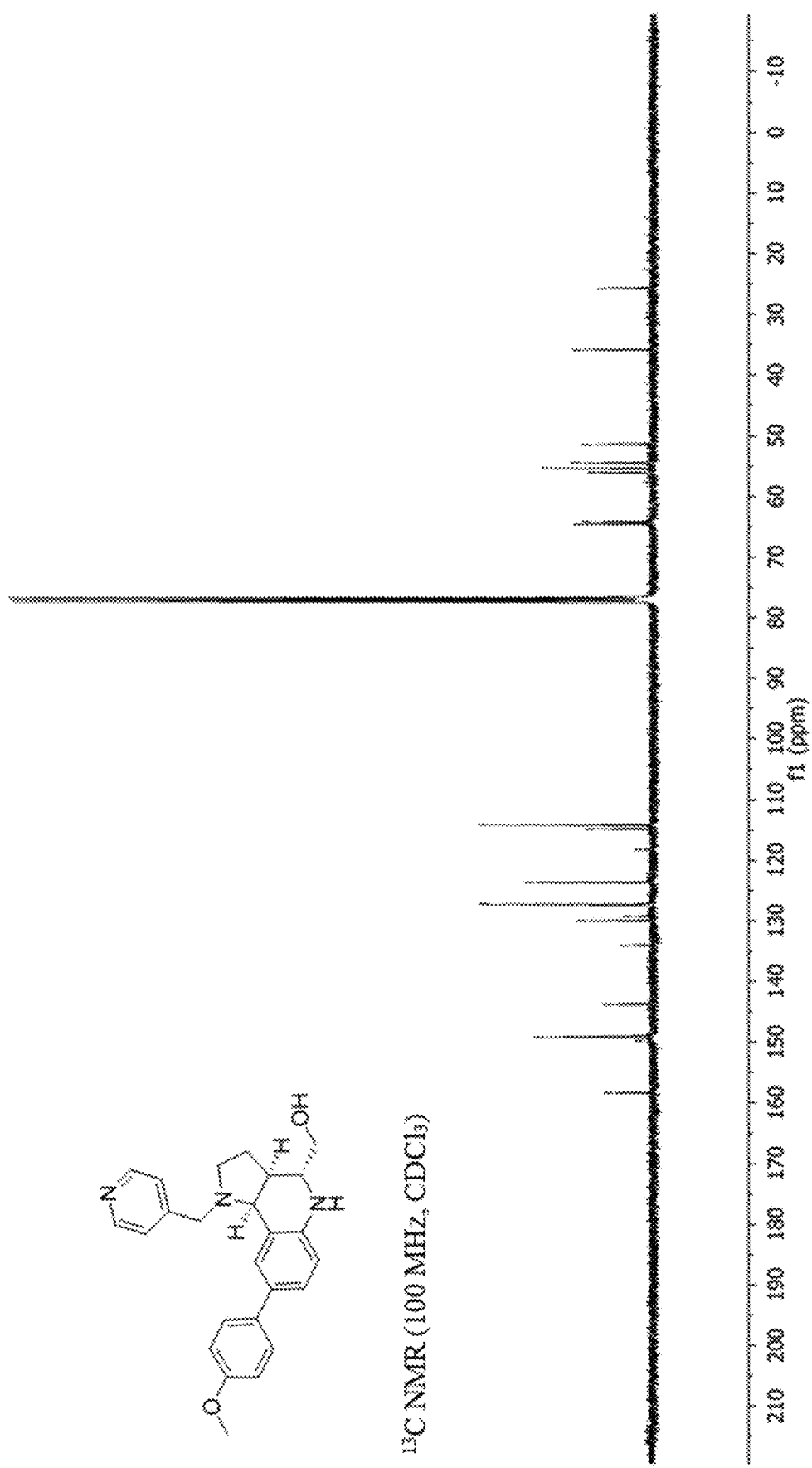
(FIG. 46Z). ((3aS,4R,9bS)-8-(4-Methoxyphenyl)-1-(pyridin-4-ylmethyl)-2,3,3a,4,5,9b-hexahydro-1H-pyrrolo[3,2-c]quinolin-4-yl)methanol (BRD0739)$^{13}$C NMR (100 MHz, CDCl$_3$).
Figure 46A:
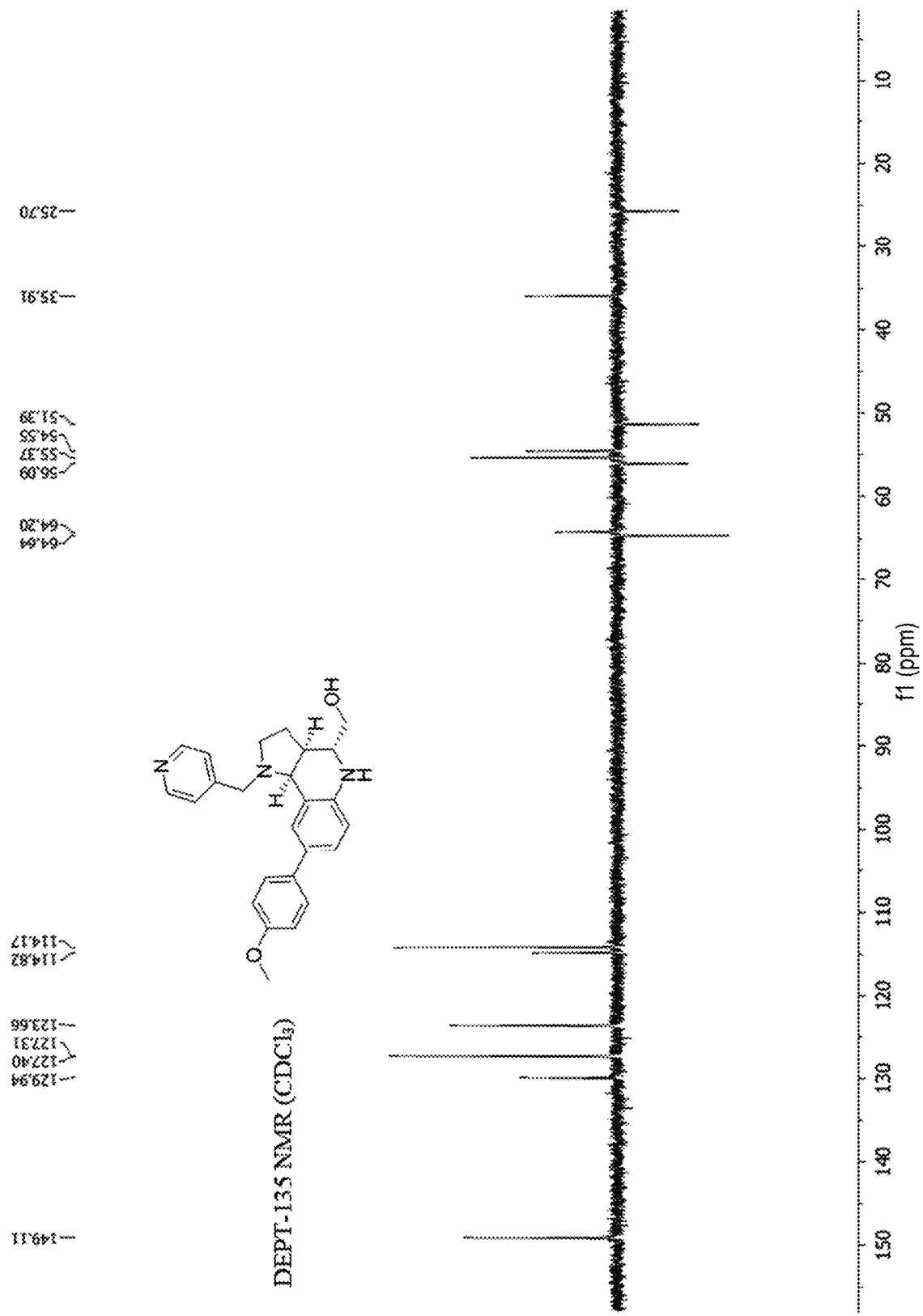
Figure 46A:
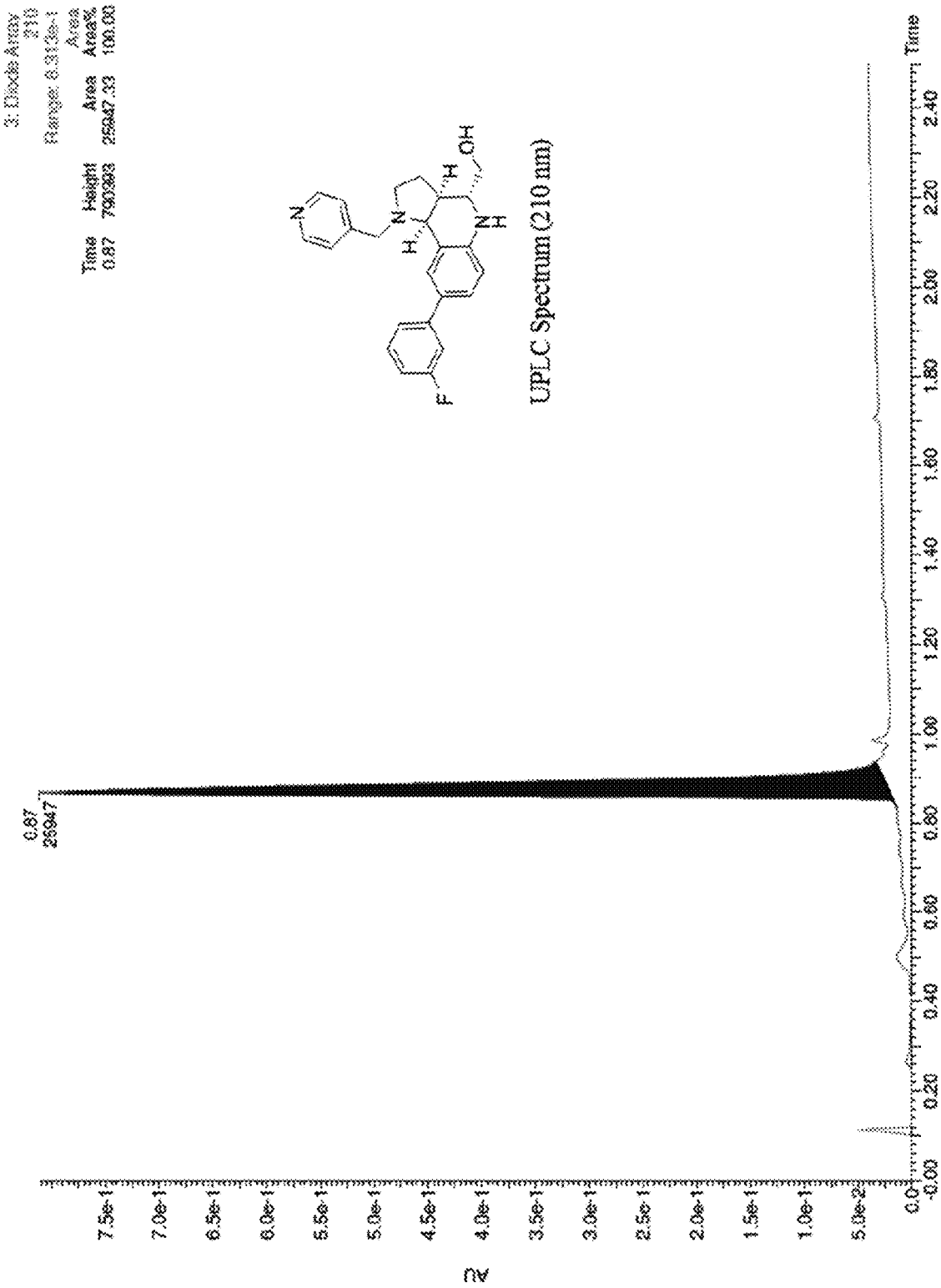
Figure 46A:
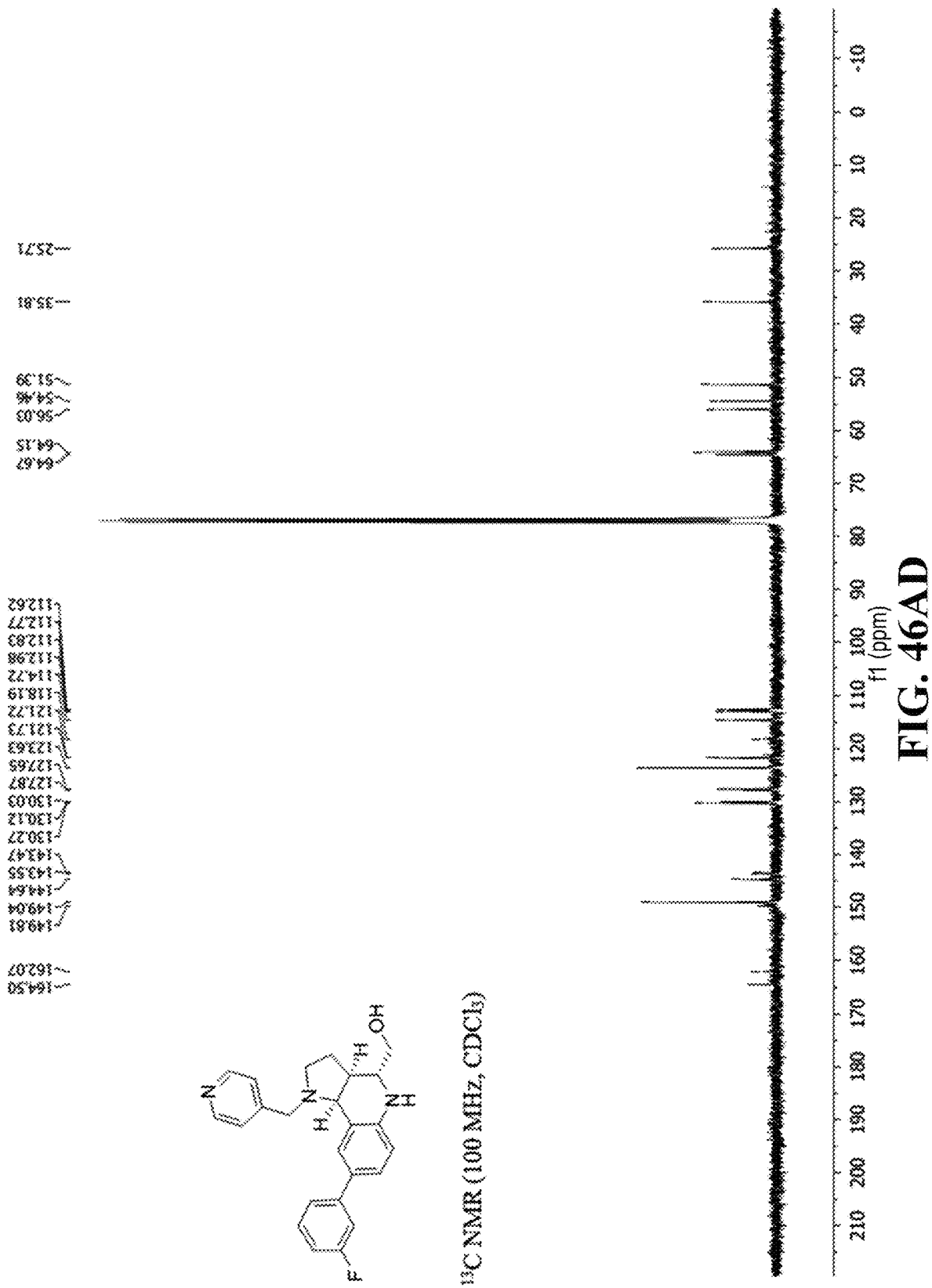
Figure 46A:
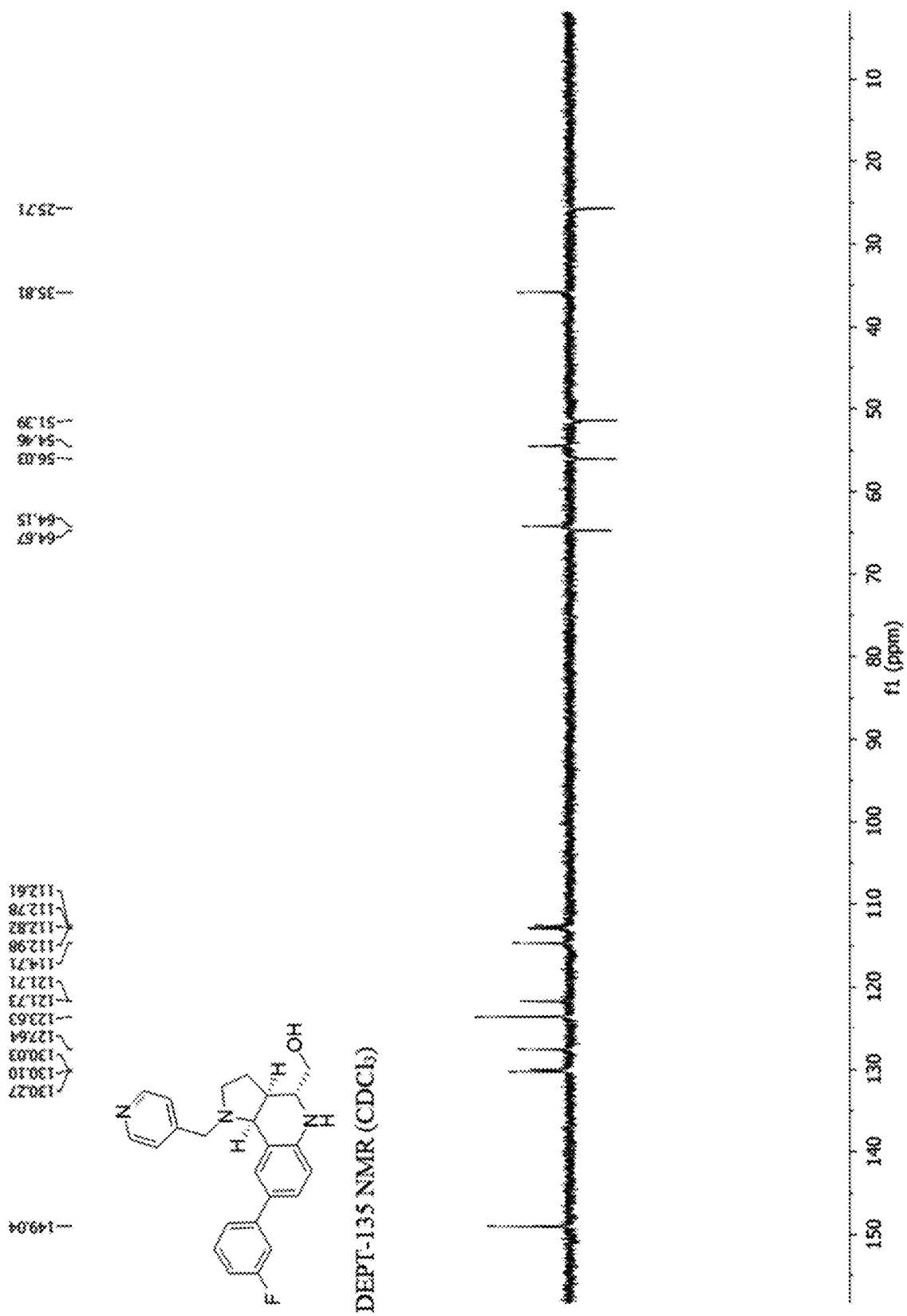
Figure 46A:
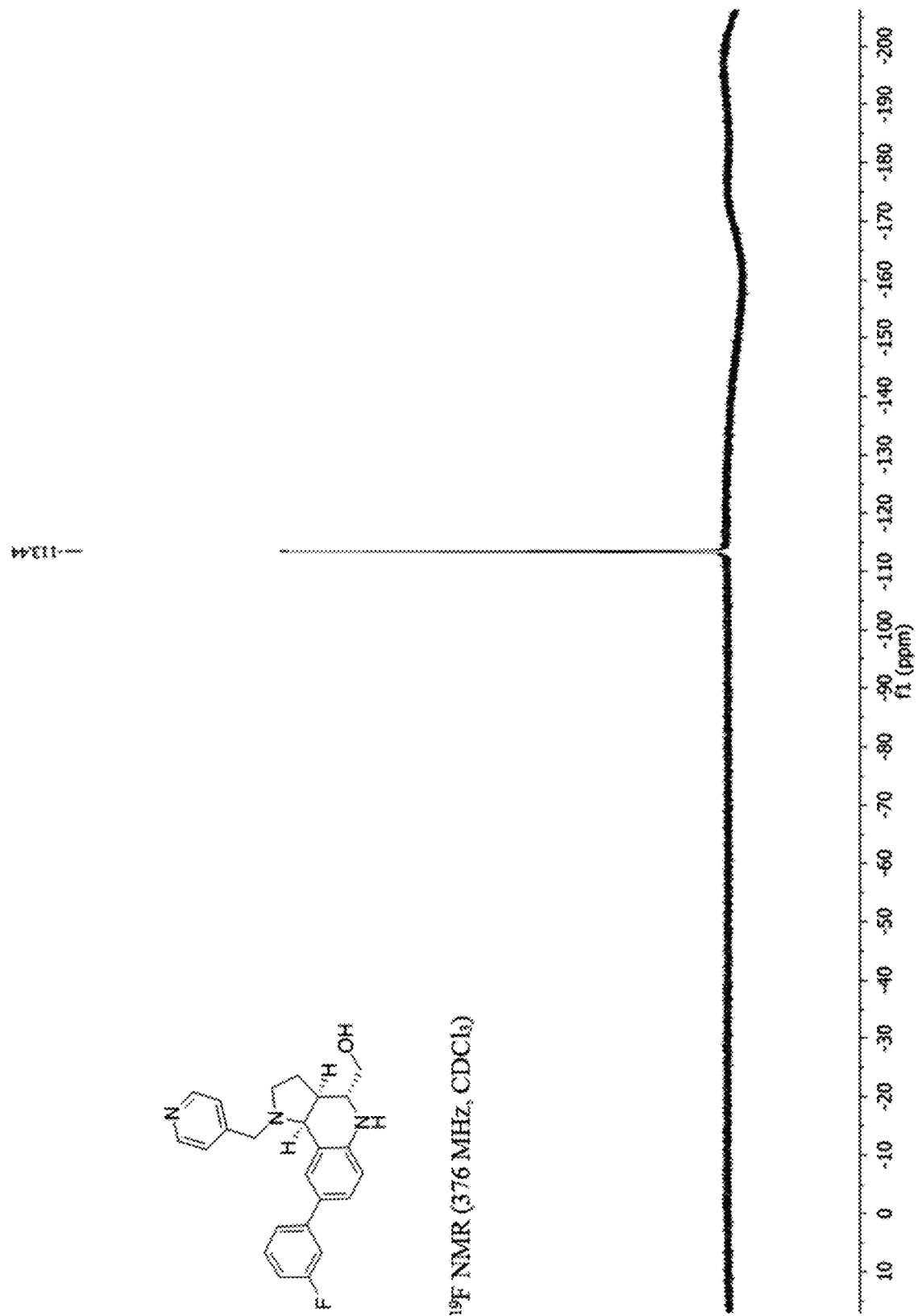
Figure 46A:
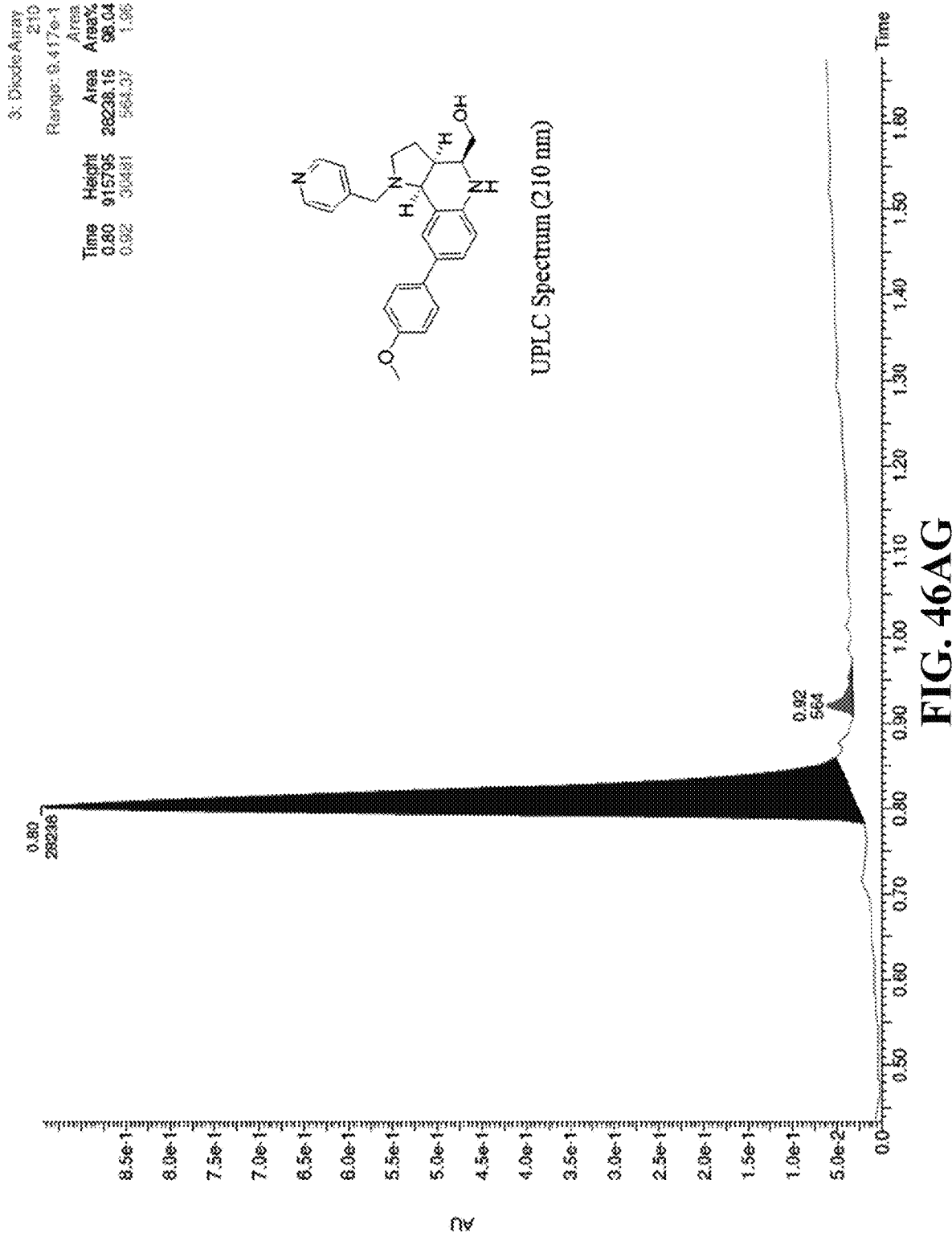
Figure 46A:
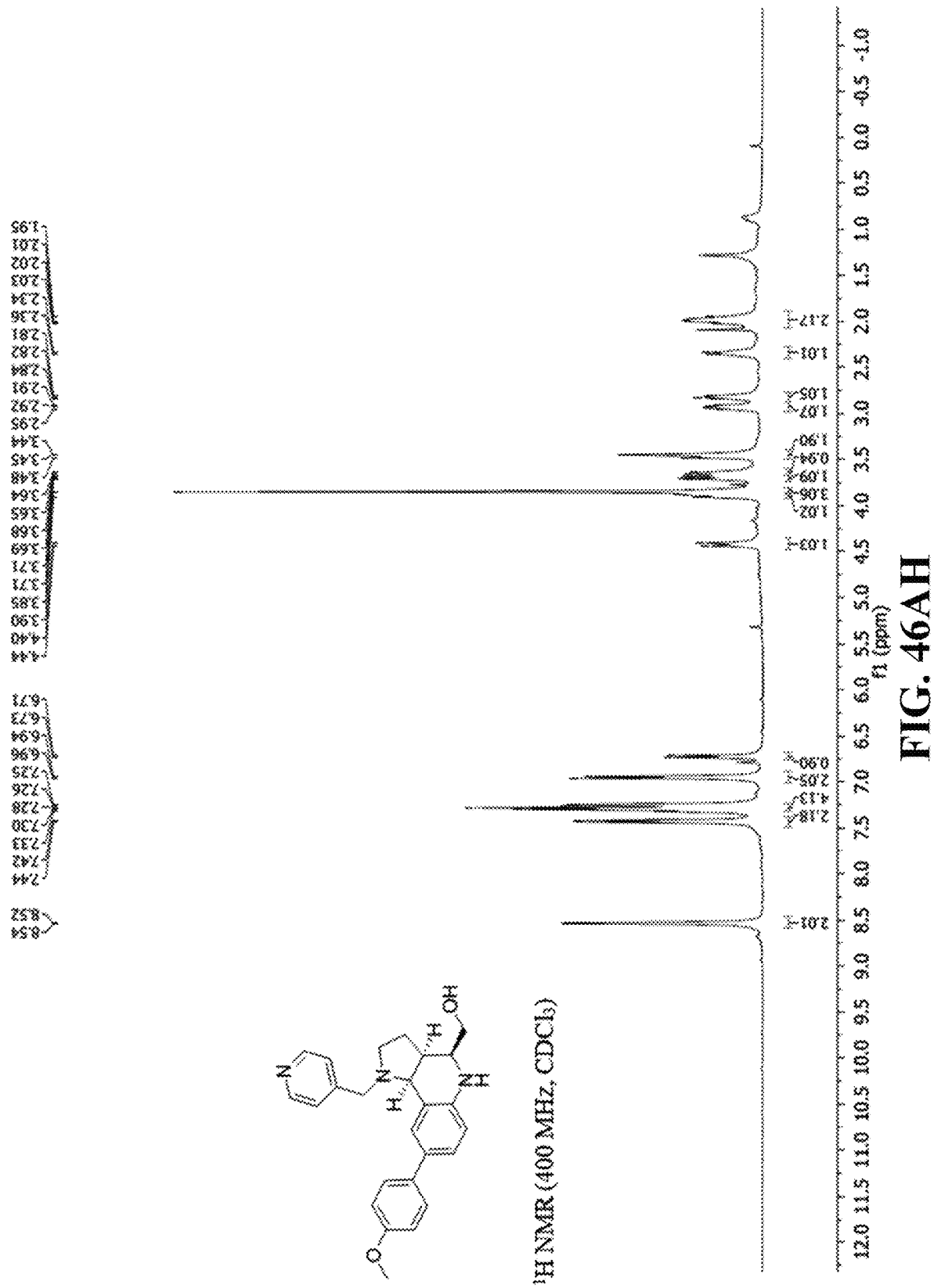
Figure 46A:
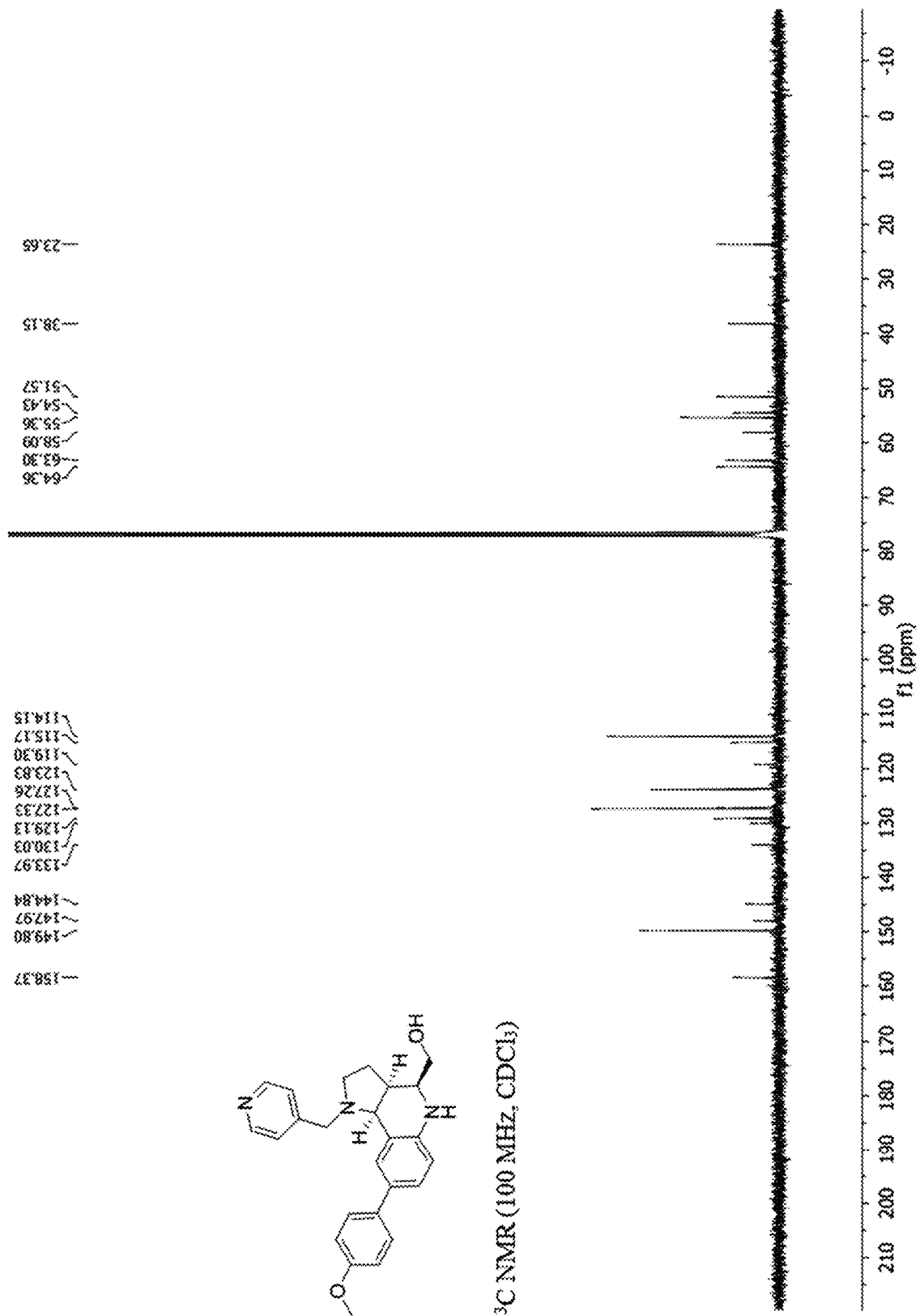
Figure 46A:
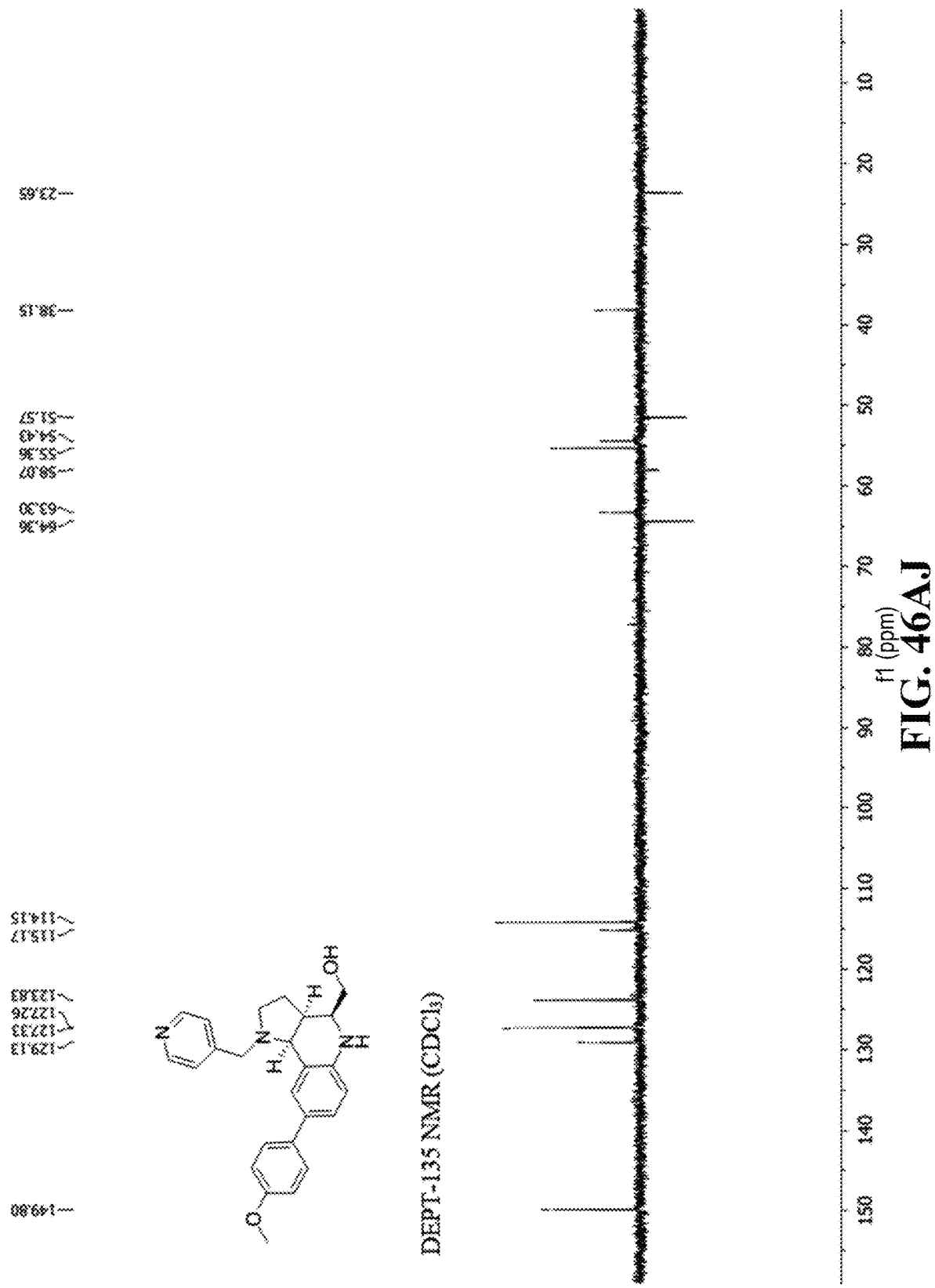
Figure 47A:
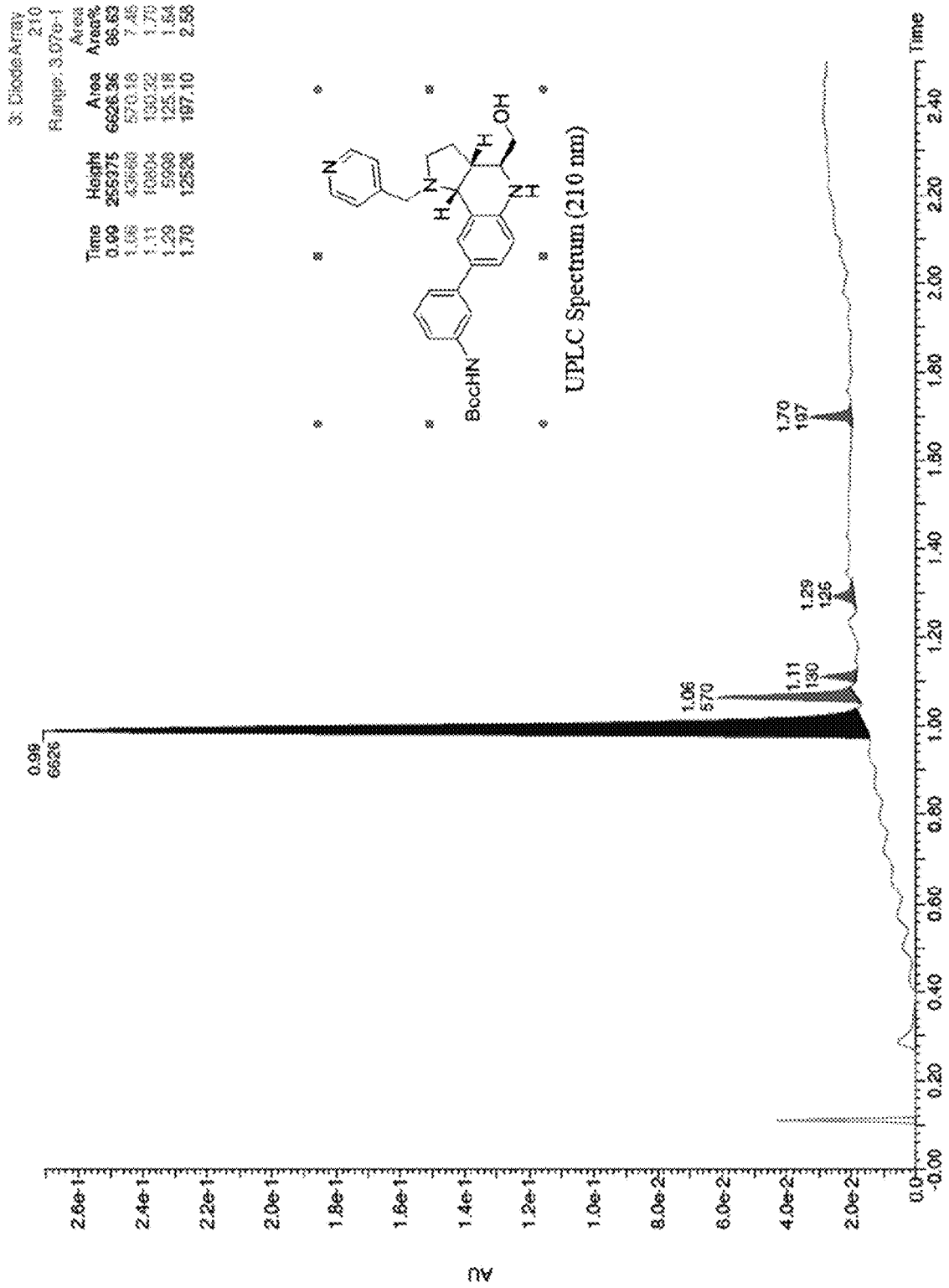
FIGS. 47A-47H. Characterization spectra of compounds 14-15.
Figure 47B:
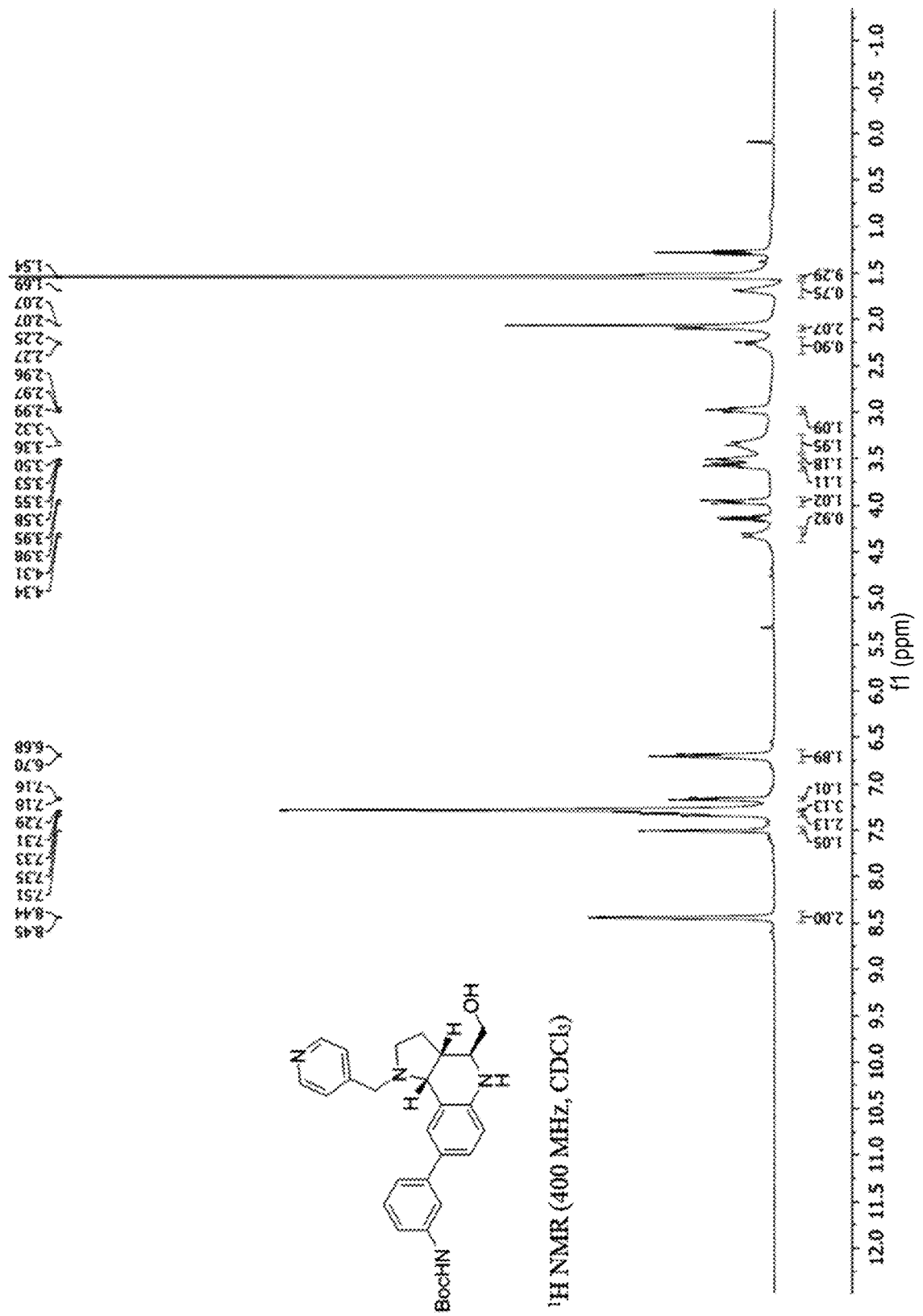
Figure 47C:
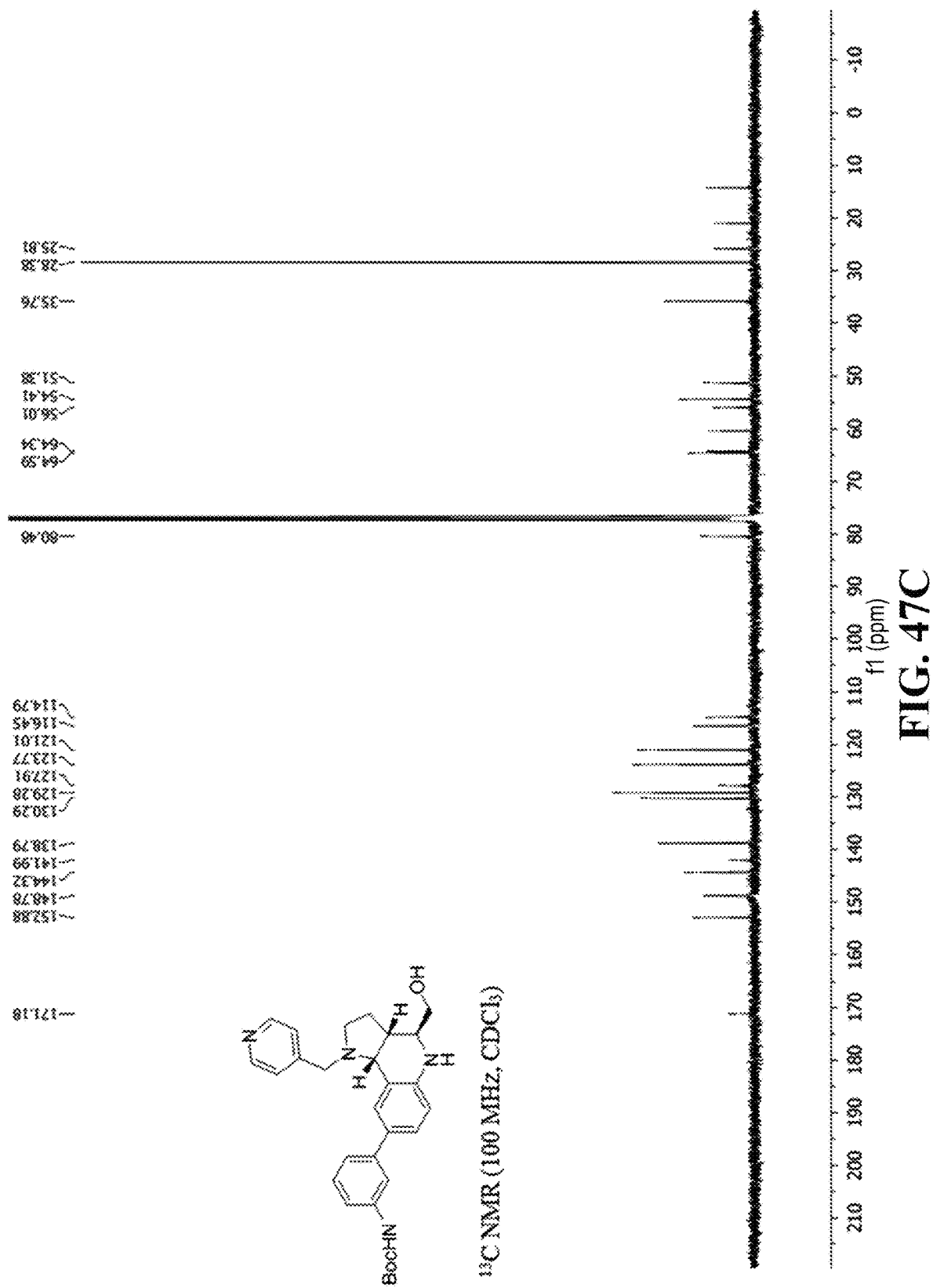
Figure 47D:
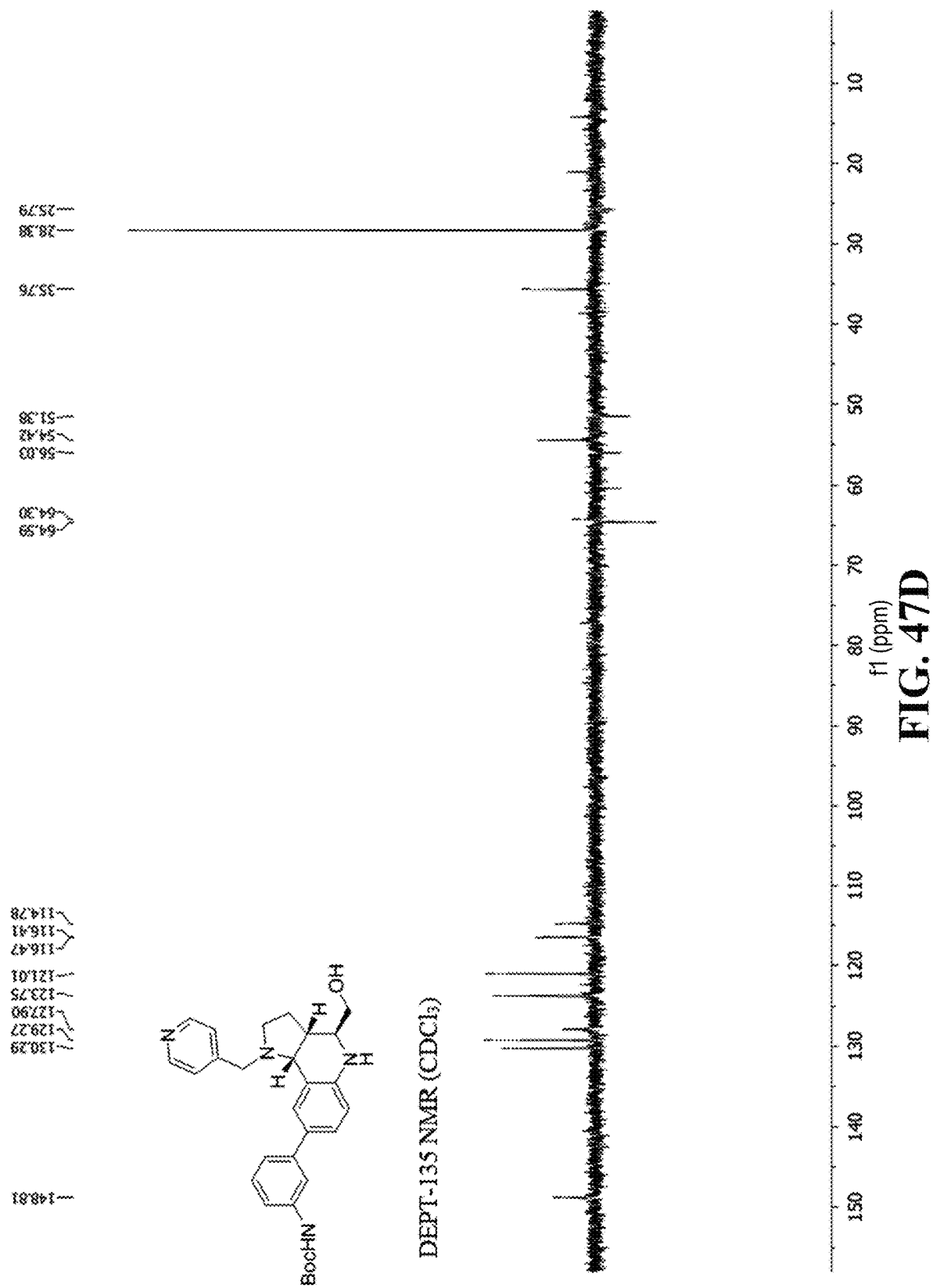
Figure 47E:
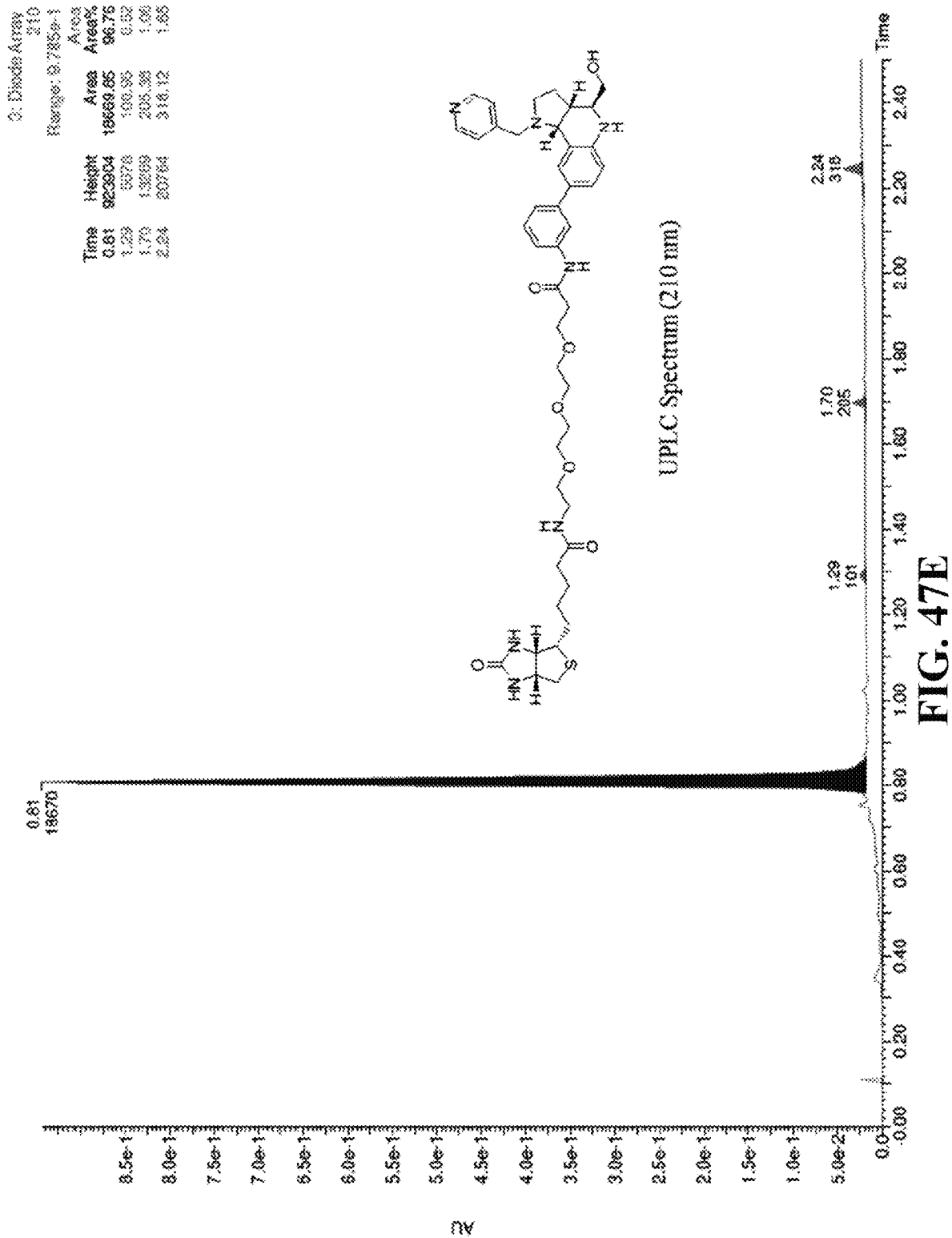
Figure 47F:
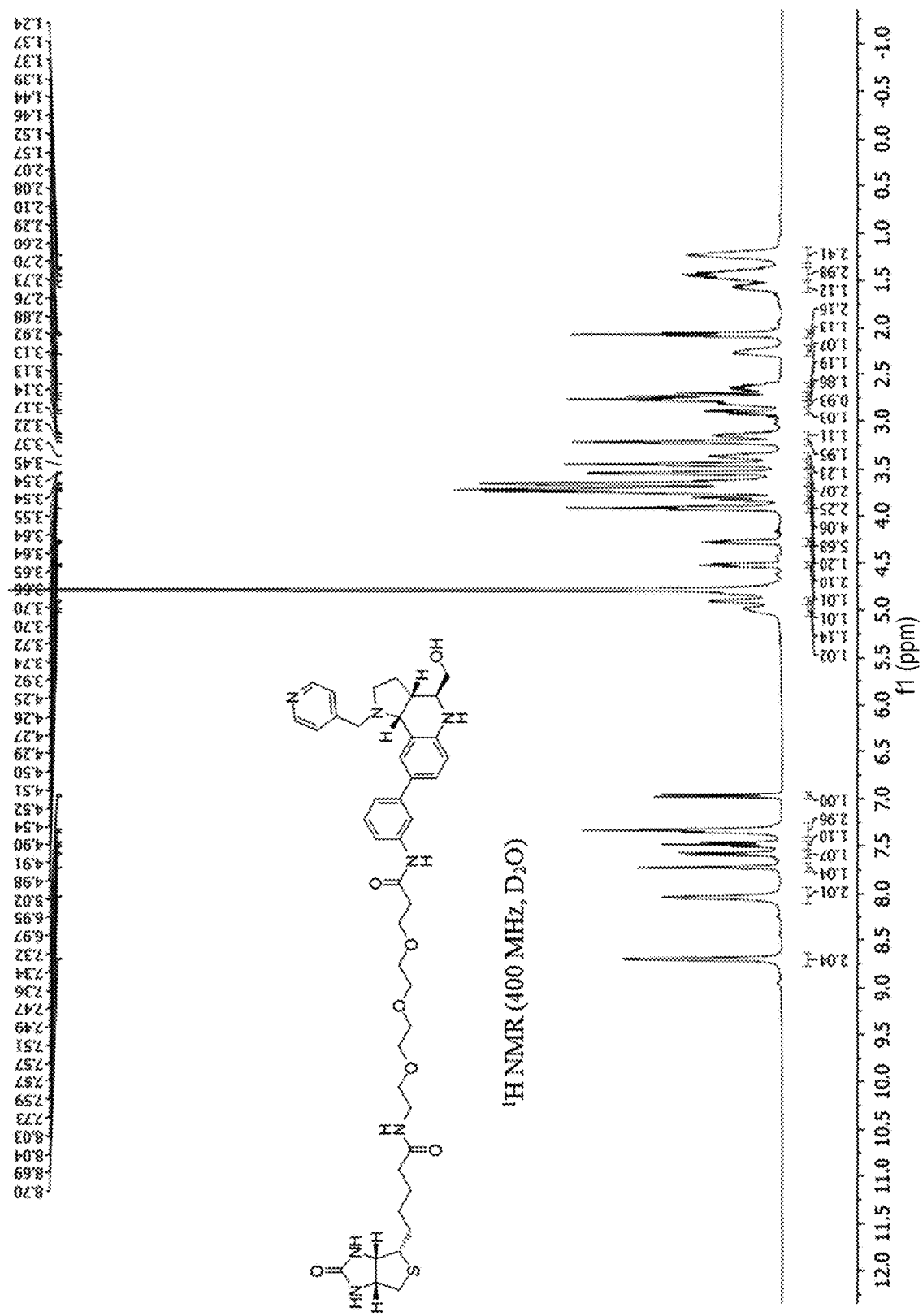
Figure 47G:
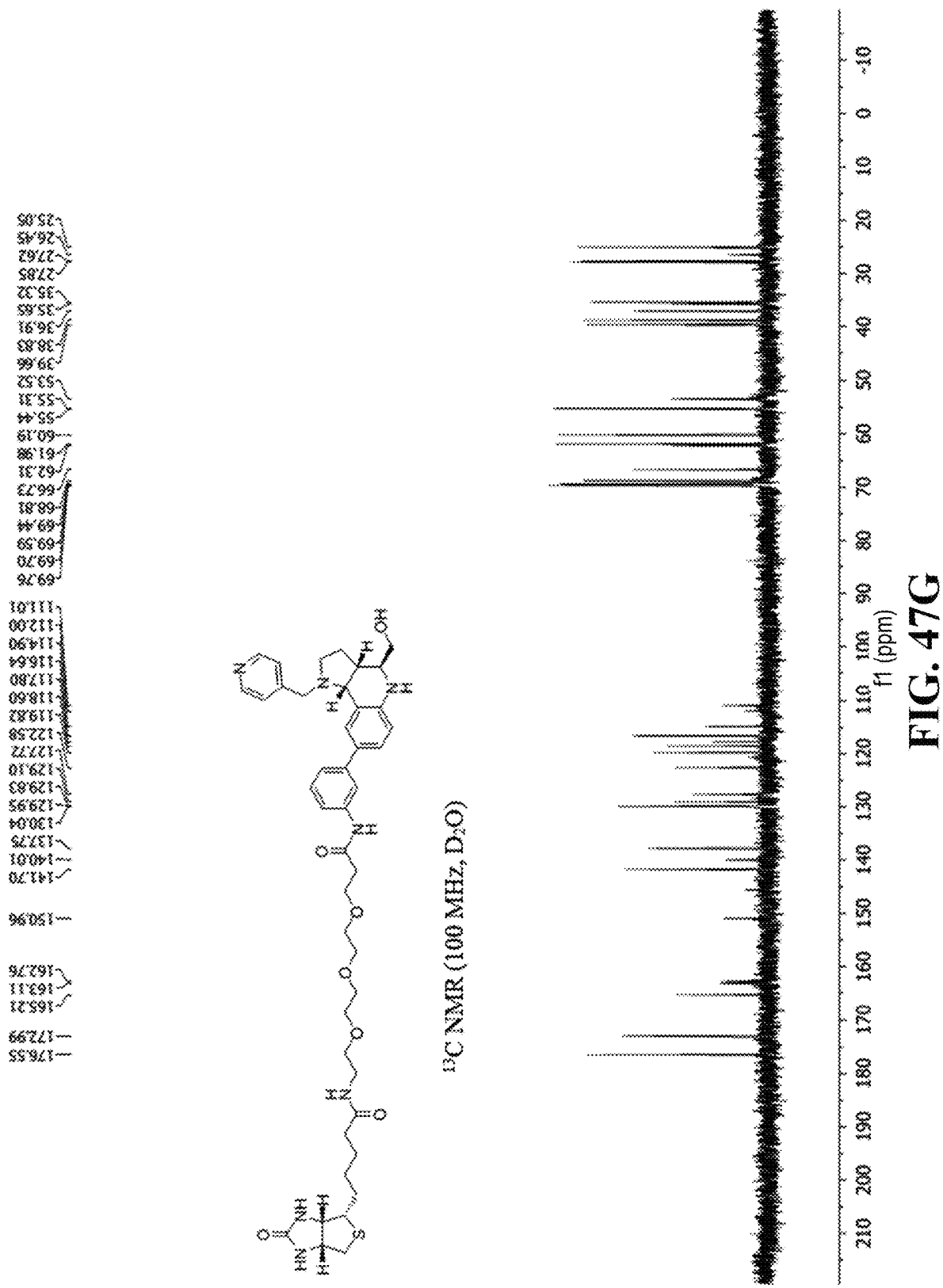
Figure 47H:
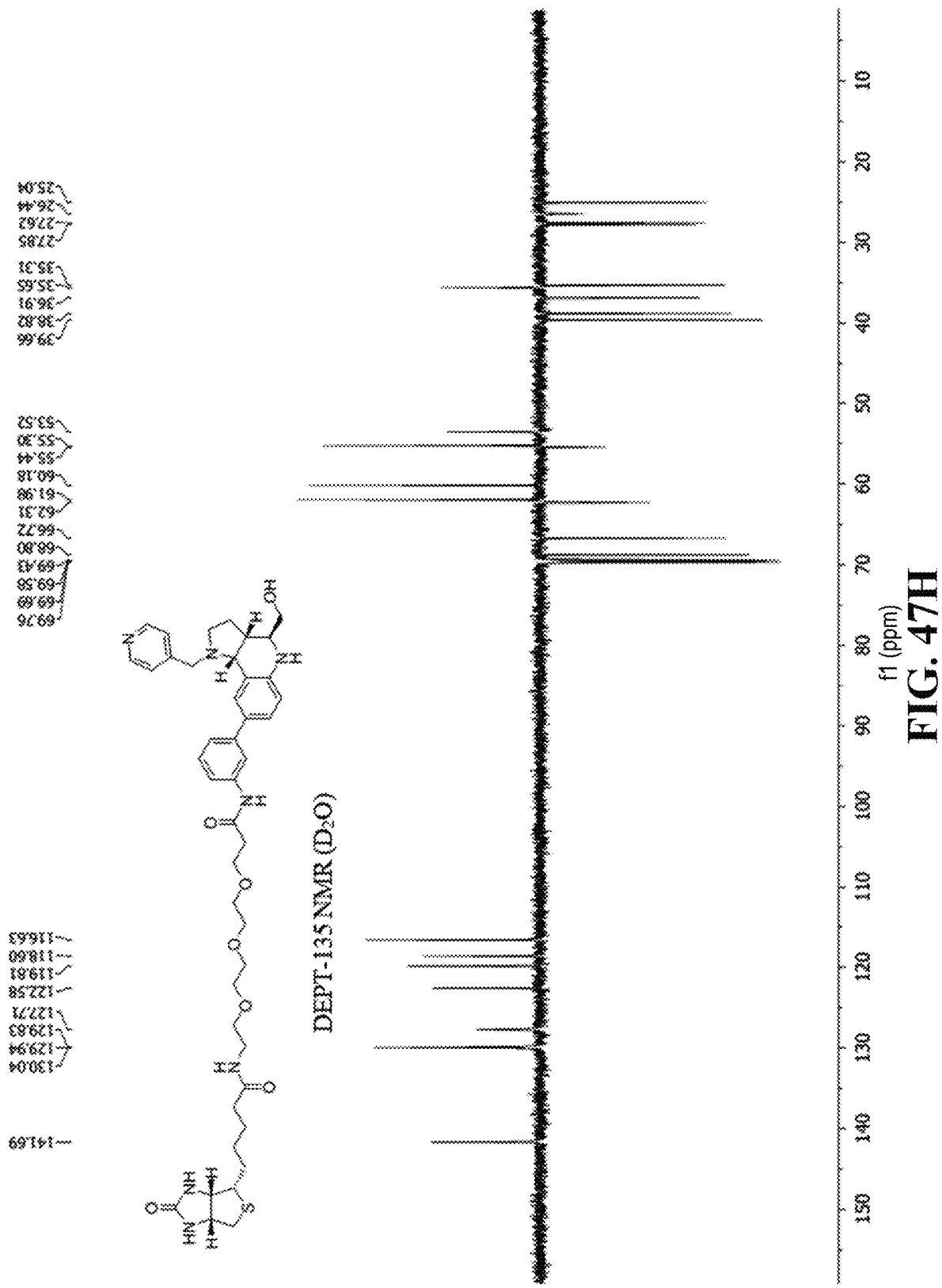

To assess the generalizability of our assay, Applicants decided to assess whether Applicants could sensitively detect the activities 3 different Cpf1 orthologs—*Acidaminococcus* sp. Cpf1 (AsCpf1), *Lachnospiraceae bacterium* ND2006 Cpf1 (LbCpf1), or *Francisella tularensis* subsp. *novicida* Cpf1 (FnCpf1). In general, the Cpf1 orthologs had lower cleavage efficiency compared to the Cas9 nucleases, as was previously reported, although nanomolar detection was observed (FIGS. 41A-41C). Of the orthologs tested, FnCpf1 exhibited the widest dose response range with similar activity for the two target sites tested (FIG. 41C). While successful inhibition of fluorescence was observed for both AsCpf1 and LbCpf1, their efficiencies were much lower than FnCpf1, SpCas9, or SaCas9, and required >200 fold excess protein to detect cleavage of 0.1 nM DNA (FIG. 41A, FIG. 41B). Interestingly, each Cpf1 ortholog yielded different activity depending on the gRNA site, with the installed distal PAM site generally being active toward all Cpf1s tested. LbCpf1 was not able to cleave the endogenous TTTC PAM site, but was very active toward the distal site PAM (FIG. 41B). This trend of activity was reversed for AsCpf1, although it was capable of cleaving both targets (FIG. 41A). In all cases, denaturing gels confirmed the expected sizes of gRNAs and crRNAs.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for screening inhibitors of CRISPR-Cas systems comprising:
   incubating a set of candidate inhibitors in individual discrete volumes, each individual discrete volume comprising (i) a different candidate inhibitor, different concentration of a inhibitor, different combination of inhibitors, or different concentrations of the combination of inhibitors, and (ii) a labeled PAM-rich target oligonucleotide, a CRISPR-Cas effector protein, and a guide molecule, wherein the guide molecule targets binding of the CRISPR-Cas effector protein to the labeled PAM-rich target oligonucleotide, wherein the PAM-rich target oligonucleotide comprises between 2 and 40 PAM sites per molecule;
   selecting one or more putative inhibitors from the set of candidate inhibitors at least in part by detecting change in fluorescence polarization of the labeled PAM-rich target oligonucleotide, wherein inhibition of formation of a complex of the CRISPR-Cas and the guide molecule by the one or more of the candidate inhibitors leads to a decrease in fluorescence polarization of the labeled PAM-rich target oligonucleotide;
   validating the one or more putative inhibitors by performing a cell-based knockdown assay and a cell-based nuclease activity assay comprising use of a frame-shift reporter.

2. The method of claim 1, further comprising a counter-screen of the one or more putative inhibitors comprising measuring change in fluorescence polarization of the labeled PAM-rich target oligonucleotide in presence of the one or more putative inhibitors alone, wherein candidate inhibitors that increase fluorescence polarization beyond a defined cut-off value are excluded from the one or more putative inhibitors.

3. The method of claim 1, wherein the cell-based knockdown assay is performed by:
   delivering the CRISPR-Cas effector protein, a nucleotide sequence encoding a polypeptide reporter, and a guide sequence targeting the nucleotide sequence encoding the polypeptide reporter to a population of cells in the individual discrete volumes, each individual discrete volume comprising the one or more putative inhibitors; and
   detecting inhibitor activity by measuring changes in fluorescence, wherein an increase in fluorescence relative to a control indicates inhibition of CRISPR-Cas mediated knockdown of the polypeptide reporter.

4. The method of claim 1, wherein the cell-based nuclease activity assay comprises:
   delivering a first construct and a second construct to a population of cells in individual discrete volumes, each individual discrete volume comprising the one or more putative inhibitors, wherein the first construct encodes an out-of-frame first reporter and a downstream in-frame second reporter separated by a linker comprising a stop codon, and the second construct encodes the CRISPR-Cas effector protein and a guide molecule targeting the linker, wherein the CRJSPR-Cas effector protein introduces a frameshift edit at the stop codon that shifts the first reporter in-frame; and
   detecting inhibitor activity by measuring changes in expression of the first reporter, wherein decreased expression of the first reporter relative to a control indicates inhibition of CRISPR-Cas mediated nuclease activity.

5. The method of claim 2, wherein detecting inhibitor activity is performed using high-content imaging and automated data analysis.

6. The method of claim 3, wherein the polypeptide reporter is a fluorescent protein.

7. The method of claim 6, wherein the fluorescent protein is mKate2.

8. The method of claim 4, wherein the first construct and the second construct are delivered in equimolar ratios.

9. The method of claim 4, wherein the first reporter is a first fluorescent polypeptide detectable at a first wavelength or range of wavelengths, and the second reporter is a second fluorescent polypeptide detectable at a second wavelength or range of wavelengths.

10. The method of claim 3, wherein the CRISPR-Cas effector protein, the nucleotide sequence encoding the polypeptide reporter, and the guide sequence targeting the nucleotide sequence encoding the polypeptide reporter are all encoded on a single construct.

11. The method of claim 1, wherein the labeled PAM-rich target molecule comprises between 2 and 20 PAM regions per oligonucleotide.

12. The method of claim 11, wherein the labeled PAM-rich target oligonucleotide comprises 12 PAM regions per molecule.

13. The method of claim 1, wherein the individual discrete volumes are droplets or wells of a multi-well plate.

14. The method of claim 1, further comprising performing a transcription assay and/or a strand displacement assay to identify one or more final inhibitors.

\* \* \* \* \*

UNITED STATES PATENT AND TRADEMARK OFFICE
CERTIFICATE OF CORRECTION

PATENT NO. : 11,760,984 B2
APPLICATION NO. : 16/760425
DATED : September 19, 2023
INVENTOR(S) : Amit Choudhary et al.

It is certified that error appears in the above-identified patent and that said Letters Patent is hereby corrected as shown below:

In the Specification

In Column 1, Line 22, delete "No. DE-SC0010595and" and insert -- Nos. DE-SC0010595 and --.

In Column 40, Line 30, delete "S.D." and insert -- ±S.D. --.

In Column 40, Line 58, delete "C6+T6" and insert -- C6→T6 --.

In Column 41, Line 1, delete "C5+T5" and insert -- C5→T5 --.

In Column 48, Line 66, delete "8100," and insert -- 81%, --.

In Column 56, Line 5, delete "R" and insert -- β --.

In Column 65, Line 32, delete "of:" and insert -- of. --.

In Column 68, Line 2, delete "J Med." and insert -- J. Med. --.

In Column 74, Line 56, delete "100 s" and insert -- 100 μs --.

In Column 79, Line 24, delete "216" and insert -- 2016 --.

In Column 87, Line 45, delete "thereof," and insert -- thereof; --.

In Column 90, Line 24, delete "201," and insert -- 20 μl, --.

In Column 106, Line 1, delete "ϕNM4ɣ" and insert -- ΦNM4γ4 --.

In Column 107, Line 32, delete "20 l" and insert -- 20 μl --.

Signed and Sealed this
Fifth Day of March, 2024

Katherine Kelly Vidal
*Director of the United States Patent and Trademark Office*

CERTIFICATE OF CORRECTION (continued)
U.S. Pat. No. 11,760,984 B2

In Column 113, Line 50, delete "(DNM4γ4" and insert -- ΦNM4γ4 --.

In Column 113, Line 60, delete "<DNM4γ4" and insert -- ΦNM4γ4 --.

In Column 120, Line 15, delete "20 l" and insert -- 20 µl --.

In Column 121, Line 49, delete "a >3a" and insert -- a >3σ --.

In Column 121, Line 55, delete "BLL" and insert -- BLI. --.

In Column 126, Line 38, delete "C+T" and insert -- C→T --.

In Column 126, Line 39, delete "C +T" and insert -- C→T --.

In Column 126, Line 43, delete "C+T" and insert -- C→T --.

In Column 126, Line 50, delete "DNM4γ4" and insert -- ΦNM4γ4 --.

In Column 126, Line 60, delete "DNM4γ4" and insert -- ΦNM4γ4 --.

In Column 127, Line 5, delete "Substrates" and insert -- substrates --.

In Column 127, Line 48, delete "CH$_2$C2)." and insert -- CH$_2$Cl$_2$). --.

In Column 127, Line 61, delete "CH$_2$C2)." and insert -- CH$_2$Cl$_2$). --.

In Column 127, Line 62, delete "CH$_2$C2," and insert -- CH$_2$Cl$_2$, --.

In Column 128, Line 49, delete "$^3J_{C,F}=$" and insert -- $^3J_{C,\,F}=$ --.

In Column 131, Line 56, delete "$[\alpha]_D 22$" and insert -- $[\alpha]_D^{22}$ --.

In Column 134, Line 45, delete "3J$_{C,\,F}=$" and insert -- $^3J_{C,\,F}=$ --.

In Column 134, Line 46, delete "$^3J_{C,F}=$" and insert -- $^3J_{C,\,F}=$ --.

In Column 134, Line 64, delete "(M+H)*," and insert -- (M+H)$^+$, --.

In Column 144, Line 30, delete ">3a" and insert -- >3σ --.

In Column 166, Line 50, delete "#NM4Y4" and insert -- ΦNM4γ4 --.

In Column 174, Line 8, delete "Lu" and insert -- L$_{12}$ --.

CERTIFICATE OF CORRECTION (continued)
U.S. Pat. No. 11,760,984 B2

In the Claims

In Column 188, Line 25, in Claim 4, delete "CRJSPR-Cas" and insert -- CRISPR-Cas --.

SEQUENCE LISTING

```
<160> NUMBER OF SEQ ID NOS: 38

<210> SEQ ID NO 1
<211> LENGTH: 4
<212> TYPE: RNA
<213> ORGANISM: Artificial Sequence
<220> FEATURE:
<223> OTHER INFORMATION: Synthetic

<400> SEQUENCE: 1 ucuu                                                                        4

<210> SEQ ID NO 2
<211> LENGTH: 4
<212> TYPE: RNA
<213> ORGANISM: Artificial Sequence
<220> FEATURE:
<223> OTHER INFORMATION: Synthetic

<400> SEQUENCE: 2 uuuu                                                                        4

<210> SEQ ID NO 3
<211> LENGTH: 4
<212> TYPE: RNA
<213> ORGANISM: Artificial Sequence
<220> FEATURE:
<223> OTHER INFORMATION: Synthetic

<400> SEQUENCE: 3 uauu                                                                        4

<210> SEQ ID NO 4
<211> LENGTH: 4
<212> TYPE: RNA
<213> ORGANISM: Artificial Sequence
<220> FEATURE:
<223> OTHER INFORMATION: Synthetic

<400> SEQUENCE: 4 uguu                                                                        4

<210> SEQ ID NO 5
<211> LENGTH: 6
<212> TYPE: DNA
<213> ORGANISM: Staphylococcus aureus

<400> SEQUENCE: 5 ttgaat                                                                      6

<210> SEQ ID NO 6
<211> LENGTH: 6
<212> TYPE: DNA
<213> ORGANISM: Staphylococcus aureus

<400> SEQUENCE: 6 ttgggt                                                                      6

<210> SEQ ID NO 7
<211> LENGTH: 58
<212> TYPE: DNA
<213> ORGANISM: Artificial Sequence
<220> FEATURE:
<223> OTHER INFORMATION: Synthetic

<400> SEQUENCE: 7
```

```
ggctggacca cgcgggaaaa tccacctagg tggttcctct tcggatgttc catcctttt        58
```

<210> SEQ ID NO 8
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 8

```
aaaggatgga acatccgaag aggaaccacc taggtggatt ttcccgcgtg gtccagcc         58
```

<210> SEQ ID NO 9
<211> LENGTH: 80
<212> TYPE: DNA
<213> ORGANISM: Artificial Sequence
<220> FEATURE:
<223> OTHER INFORMATION: Synthetic primer

<400> SEQUENCE: 9

```
aaaagcaccg actcggtgcc acttttttcaa gttgataacg gactagcctt attttaactt     60
gctatttcta gctctaaaac                                                  80
```

<210> SEQ ID NO 10
<211> LENGTH: 54
<212> TYPE: DNA
<213> ORGANISM: Artificial Sequence
<220> FEATURE:
<223> OTHER INFORMATION: Synthetic primer

<400> SEQUENCE: 10

```
taatacgact cactatagct ataggacgcg accgaaagtt ttagagctag aaat            54
```

<210> SEQ ID NO 11
<211> LENGTH: 60
<212> TYPE: DNA
<213> ORGANISM: Artificial Sequence
<220> FEATURE:
<223> OTHER INFORMATION: Synthetic primer

<400> SEQUENCE: 11

```
taatacgact cactataggg agtccgagca gaagaagaag ttttagagct agaaatagca     60
```

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12

```
aaaaaaagca ccgactcggt gccac                                            25
```

<210> SEQ ID NO 13
<211> LENGTH: 30
<212> TYPE: DNA
<213> ORGANISM: Artificial Sequence
<220> FEATURE:
<223> OTHER INFORMATION: Synthetic array

<400> SEQUENCE: 13

```
cgtgtaaaga catattagat cgagtcaagg                                       30
```

<210> SEQ ID NO 14

```
<211> LENGTH: 106
<212> TYPE: RNA
<213> ORGANISM: Artificial Sequence
<220> FEATURE:
<223> OTHER INFORMATION: Spinach aptamer

<400> SEQUENCE: 14
gggagacgca acugaaugaa auggugaagg acgggaccag guguggcugc uucggcagug    60
cagcuuguug aguagagugu gagcuccgcg uaacuagucg cgucac                  106

<210> SEQ ID NO 15
<211> LENGTH: 100
<212> TYPE: RNA
<213> ORGANISM: Artificial Sequence
<220> FEATURE:
<223> OTHER INFORMATION: Synthetic

<400> SEQUENCE: 15
gcuauaggac gcgaccgaaa guuuuagagc uagaaauagc aaguuaaaau aaggcuaguc    60
cguuaucaac uugaaaaagu ggcaccgagu cggugcuuuu                         100

<210> SEQ ID NO 16
<211> LENGTH: 111
<212> TYPE: DNA
<213> ORGANISM: Artificial Sequence
<220> FEATURE:
<223> OTHER INFORMATION: Synthetic

<400> SEQUENCE: 16
gcgcgctttc taatacgact cactataggg tgacgcgacc gaaatggtga aggacgggtc    60
cagtgcttcg gcactgttga gtagagtgtg agctccgtaa ctggtcgcgt c            111

<210> SEQ ID NO 17
<211> LENGTH: 83
<212> TYPE: RNA
<213> ORGANISM: Artificial Sequence
<220> FEATURE:
<223> OTHER INFORMATION: Spinach RNA aptamer

<400> SEQUENCE: 17
ggugacgcga ccgaaauggu gaaggacggg uccagugcuu cggcacuguu gaguagagug    60
ugagcuccgu aacuggucgc guc                                           83

<210> SEQ ID NO 18
<211> LENGTH: 114
<212> TYPE: DNA
<213> ORGANISM: Artificial Sequence
<220> FEATURE:
<223> OTHER INFORMATION: Spinach IVT
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 18
gcgcgcnnnn taatacgact cactataggg nnnngacgcg accgaaatgg tgaaggacgg    60
gtccagtgct tcggcactgt tgagtagagt gtgagctccg taactggtcg cgtc         114

<210> SEQ ID NO 19
<211> LENGTH: 86
```

```
<212> TYPE: RNA
<213> ORGANISM: Artificial Sequence
<220> FEATURE:
<223> OTHER INFORMATION: Spinach RNA aptamer
<220> FEATURE:
<221> NAME/KEY: misc_feature
<222> LOCATION: (3)..(6)
<223> OTHER INFORMATION: n is a, c, g, or u

<400> SEQUENCE: 19
ggnnnngacg cgaccgaaau ggugaaggac ggguccagug cuucggcacu guugaguaga      60
gugugagcuc cguaacuggu cgcguc                                          86

<210> SEQ ID NO 20
<211> LENGTH: 46
<212> TYPE: DNA
<213> ORGANISM: Artificial Sequence
<220> FEATURE:
<223> OTHER INFORMATION: Synthetic

<400> SEQUENCE: 20
taatacgact cactatagga cgcgaccgaa atggtgaagg acgggt                    46

<210> SEQ ID NO 21
<211> LENGTH: 52
<212> TYPE: DNA
<213> ORGANISM: Artificial Sequence
<220> FEATURE:
<223> OTHER INFORMATION: Synthetic

<400> SEQUENCE: 21
actcactata gggacgcgac cgaaatggtg aaggacgggt ccagtgcttc gg             52

<210> SEQ ID NO 22
<211> LENGTH: 51
<212> TYPE: DNA
<213> ORGANISM: Artificial Sequence
<220> FEATURE:
<223> OTHER INFORMATION: Synthetic

<400> SEQUENCE: 22
cgtccttcac catttcggtc gcgtccctat agtgagtcgt attagttcca t              51

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
atggaactaa tacgactcac tagggacg cgaccgaaat ggtgaaggac g                51

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
atagtgagtc gtatta                                                     16

<210> SEQ ID NO 25
<211> LENGTH: 16
<212> TYPE: DNA
```

```
<213> ORGANISM: Artificial Sequence
<220> FEATURE:
<223> OTHER INFORMATION: Synthetic

<400> SEQUENCE: 25
cgtccctata gtgagt                                                      16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
atggaactaa tacgac                                                      16

<210> SEQ ID NO 27
<211> LENGTH: 16
<212> TYPE: DNA
<213> ORGANISM: Artificial Sequence
<220> FEATURE:
<223> OTHER INFORMATION: Synthetic

<400> SEQUENCE: 27
gtcgtattag ttccat                                                      16

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 28

Thr Tyr Cys Asn
1

<210> SEQ ID NO 29
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 29

Thr Thr Thr Asn
1

<210> SEQ ID NO 30
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 30

Thr Gly Tyr Val
1

<210> SEQ ID NO 31
<211> LENGTH: 4
<212> TYPE: PRT
<213> ORGANISM: Artificial Sequence
<220> FEATURE:
<223> OTHER INFORMATION: Synthetic Peptide
```

<400> SEQUENCE: 31

Thr Tyr Cys Val
1

<210> SEQ ID NO 32
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 32

Val Tyr Cys Val
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 33

Thr Tyr Thr Val
1

<210> SEQ ID NO 34
<211> LENGTH: 80
<212> TYPE: DNA
<213> ORGANISM: Artificial Sequence
<220> FEATURE:
<223> OTHER INFORMATION: Synthetic Primer

<400> SEQUENCE: 34
aaaagcaccg actcggtgcc acttttttcaa gttgataacg gactagcctt attttaactt    60
gctatttcta gctctaaaac                                                80

<210> SEQ ID NO 35
<211> LENGTH: 54
<212> TYPE: DNA
<213> ORGANISM: Artificial Sequence
<220> FEATURE:
<223> OTHER INFORMATION: Synthetic Primer

<400> SEQUENCE: 35
taatacgact cactatagct ataggacgcg accgaaagtt ttagagctag aaat           54

<210> SEQ ID NO 36
<211> LENGTH: 60
<212> TYPE: DNA
<213> ORGANISM: Artificial Sequence
<220> FEATURE:
<223> OTHER INFORMATION: Synthetic Primer

<400> SEQUENCE: 36
taatacgact cactataggg agtccgagca gaagaagaag ttttagagct agaaatagca    60

<210> SEQ ID NO 37
<211> LENGTH: 25
<212> TYPE: DNA
<213> ORGANISM: Artificial Sequence
<220> FEATURE:
<223> OTHER INFORMATION: Synthetic Primer

<400> SEQUENCE: 37

```
aaaaaaagca ccgactcggt gccac                                      25

<210> SEQ ID NO 38
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 38
cgtgtaaaga catattagat cgagtcaagg                                 30
```